(12) United States Patent
Cha et al.

(10) Patent No.: US 11,306,060 B2
(45) Date of Patent: Apr. 19, 2022

(54) COMPOUND AND ORGANIC ELECTRONIC ELEMENT COMPRISING SAME

(71) Applicant: LG CHEM, LTD., Seoul (KR)

(72) Inventors: Yongbum Cha, Daejeon (KR); Sang Duk Suh, Daejeon (KR); Jungbum Kim, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 287 days.

(21) Appl. No.: 16/085,547

(22) PCT Filed: Sep. 8, 2017

(86) PCT No.: PCT/KR2017/009879
§ 371 (c)(1),
(2) Date: Sep. 14, 2018

(87) PCT Pub. No.: WO2018/048247
PCT Pub. Date: Mar. 15, 2018

(65) Prior Publication Data
US 2019/0152919 A1    May 23, 2019

(30) Foreign Application Priority Data
Sep. 9, 2016 (KR) .................. 10-2016-0116524
Sep. 6, 2017 (KR) .................. 10-2017-0113862

(51) Int. Cl.
*H01L 51/50* (2006.01)
*C07D 221/20* (2006.01)
(Continued)

(52) U.S. Cl.
CPC .......... *C07D 221/20* (2013.01); *C07C 211/54* (2013.01); *C07D 219/02* (2013.01); *C07D 307/91* (2013.01); *C07D 333/76* (2013.01); *C07D 401/12* (2013.01); *C07D 401/14* (2013.01); *C07D 405/12* (2013.01); *C07D 405/14* (2013.01); *C07D 471/06* (2013.01); *C07D 471/10* (2013.01); *C07F 7/0812* (2013.01); *C09K 11/06* (2013.01); *H01L 51/006* (2013.01); *H01L 51/0052* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/5012* (2013.01);
(Continued)

(58) Field of Classification Search
None
See application file for complete search history.

(56) References Cited

U.S. PATENT DOCUMENTS

2003/0137239 A1*  7/2003  Matsuura ............ H01L 51/5016
                                                            313/503
2004/0251816 A1  12/2004  Leo et al.
(Continued)

FOREIGN PATENT DOCUMENTS

CN    101405255 A    4/2009
CN    101489961 A    7/2009
(Continued)

*Primary Examiner* — Gregory D Clark
(74) *Attorney, Agent, or Firm* — Dentons US LLP

(57) ABSTRACT

The present specification relates to a compound and an organic electronic device comprising the same.

12 Claims, 2 Drawing Sheets

(51) Int. Cl.
| | |
|---|---|
| *H01L 51/00* | (2006.01) |
| *C07D 401/14* | (2006.01) |
| *C07D 405/14* | (2006.01) |
| *C07D 401/12* | (2006.01) |
| *C07D 405/12* | (2006.01) |
| *C07C 211/54* | (2006.01) |
| *C09K 11/06* | (2006.01) |
| *C07D 471/06* | (2006.01) |
| *C07F 7/08* | (2006.01) |
| *C07D 307/91* | (2006.01) |
| *C07D 219/02* | (2006.01) |
| *C07D 333/76* | (2006.01) |
| *C07D 471/10* | (2006.01) |

(52) U.S. Cl.
CPC ...... *H01L 51/5092* (2013.01); *H01L 51/5096* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *H01L 51/5056* (2013.01)

(56) References Cited

U.S. PATENT DOCUMENTS

| | | |
|---|---|---|
| 2009/0134781 A1 | 5/2009 | Jang et al. |
| 2009/0318625 A1 | 12/2009 | Busing et al. |
| 2015/0333277 A1* | 11/2015 | Kim ............... H01L 51/006 257/40 |
| 2016/0005980 A1 | 1/2016 | Ito et al. |
| 2017/0062729 A1 | 3/2017 | Cha et al. |

FOREIGN PATENT DOCUMENTS

| | | |
|---|---|---|
| EP | 2796529 A1 | 10/2014 |
| EP | 3020782 A1 | 5/2016 |
| EP | 3048654 A2 | 7/2016 |
| KR | 10-2012-0135501 A | 12/2012 |
| KR | 10-2013-0110347 A | 10/2013 |
| KR | 10-2014-0115636 A | 10/2014 |
| KR | 10-2014-0135117 A | 11/2014 |
| KR | 10-2015-0095545 A | 8/2015 |
| KR | 10-2015-0130206 A | 11/2015 |
| KR | 10-2016-0005196 A | 1/2016 |
| WO | 03/012890 A2 | 2/2003 |
| WO | 2006/080640 A1 | 8/2006 |

* cited by examiner

[FIG. 1]
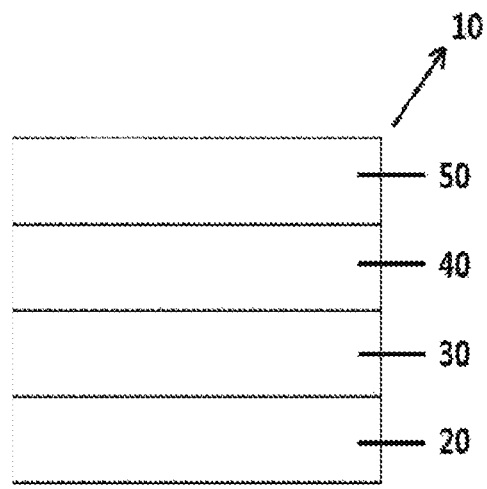

[FIG. 2]
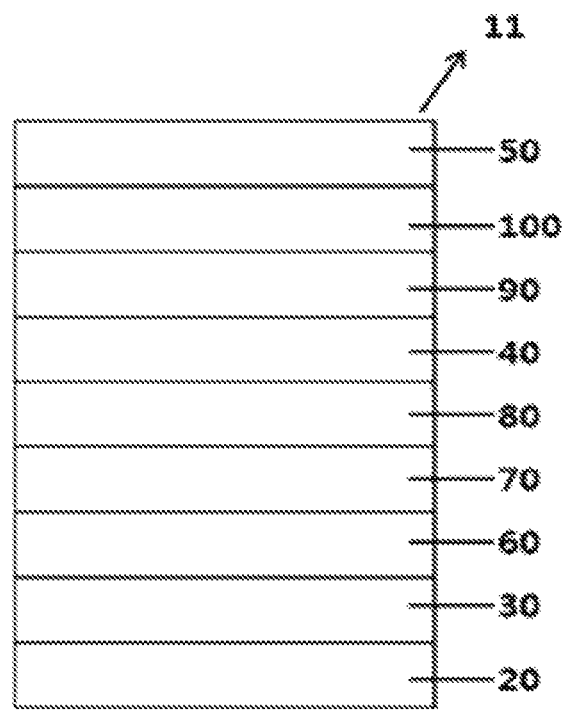

COMPOUND AND ORGANIC ELECTRONIC ELEMENT COMPRISING SAME

TECHNICAL FIELD

This application is a National Stage Application of International Application No. PCT/KR2017/009879 filed Sep. 8, 2017, and claims the benefit of Korean Patent Application No. 10-2016-0116524 filed Sep. 9, 2016 and Korean Patent Application No. 10-2017-0113862 filed Sep. 6, 2017, all of which are hereby incorporated by reference in their entirety for all purposes as if fully set forth herein.

The present specification relates to a compound and an organic electronic device comprising the same.

BACKGROUND ART

Typical examples of an organic electronic device include an organic light emitting device. An organic light emission phenomenon generally refers to a phenomenon converting electrical energy to light energy using an organic material. An organic light emitting device using an organic light emission phenomenon normally has a structure comprising an negative electrode, a positive electrode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the negative electrode and the positive electrode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

International Patent Application Laid-Open Publication No. 2003-012890

DISCLOSURE

Technical Problem

The present specification is directed to providing a compound and an organic electronic device comprising the same.

Technical Solution

The present specification provides a compound represented by the following Chemical Formula 1.

[Chemical Formula 1]

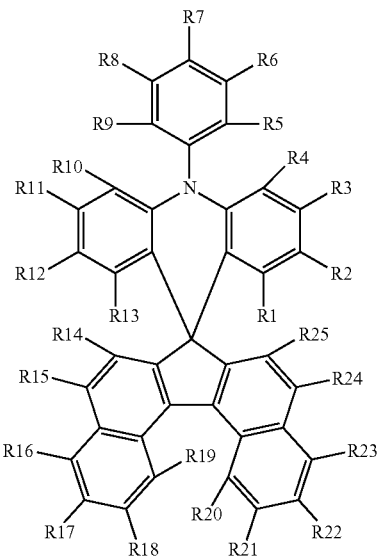

In Chemical Formula 1,
at least one of R1 to R25 is

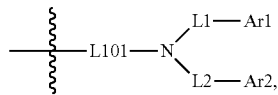

L101, L1, and L2 are the same as or different from each other, and each independently a direct bond; a substituted or unsubstituted arylene group; or a substituted or unsubstituted divalent heterocyclic group, Ar1 and Ar2 are the same as or different from each other, and each independently hydrogen; deuterium; a halogen group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, groups that are not

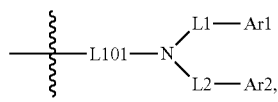

among R1 to R25 are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, or may bond to adjacent groups to form a substituted or unsubstituted ring, and

means a site bonding to other substituents or bonding sites.

Further, the present specification provides an organic electronic device comprising: a first electrode; a second electrode disposed to face the first electrode; and an organic material layer having one or more layers disposed between the first electrode and the second electrode, in which one or more layers of the organic material layer comprise the above-described compound.

Advantageous Effects

The compound according to an exemplary embodiment of the present specification is used in an organic electronic device including an organic light emitting device, and is capable of lowering a driving voltage of the organic electronic device.

In addition, the compound according to an exemplary embodiment of the present specification is used in an organic electronic device including an organic light emitting device, and is capable of enhancing light efficiency.

Furthermore, the compound according to an exemplary embodiment of the present specification is used in an organic electronic device comprising an organic light emitting device, and is capable of enhancing a device lifespan property by thermal stability of the compound.

DESCRIPTION OF DRAWINGS

FIG. 1 illustrates an organic light emitting device (10) according to an exemplary embodiment of the present specification.

FIG. 2 illustrates an organic light emitting device (11) according to another exemplary embodiment of the present specification.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Blocking Layer
90: Electron Transfer Layer
100: Electron Injection Layer

MODE FOR DISCLOSURE

Hereinafter, the present specification will be described in more detail.

The present specification provides a compound represented by the following Chemical Formula 1.

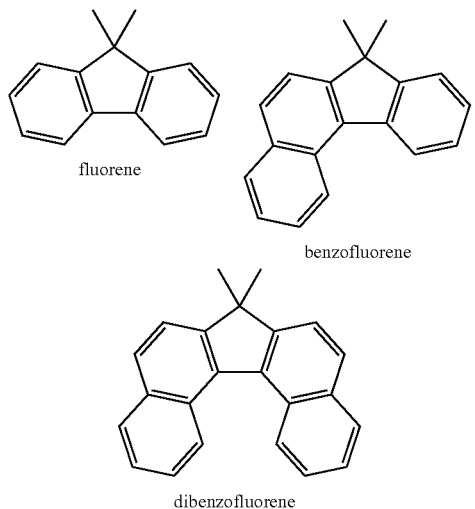

A core structure of the compound of Chemical Formula 1 is a spiro-type compound, and specifically, includes a dibenzofluorene structure. The dibenzofluorene structure has an electron-rich form compared to fluorene and benzofluorene structures. In addition, by including N or having a fused-ring structure including N, the compound represented by Chemical Formula 1 of the present specification has a structure of bigger skeleton compared to a spirobifluorene structure, and therefore, is excellent in terms of compound stability. Particularly, when using the compound represented by Chemical Formula 1 of the present specification as a dopant of a light emitting layer in which a lifespan property is important, a significantly excellent effect is obtained.

Examples of the substituents in the present specification are described below, however, the substituents are not limited thereto.

In the present specification,

and ------ means a site bonding to other substituents or binding sites.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of hydrogen; deuterium; a halogen group; a nitrile group; a nitro group; a hydroxyl group; an imide group; an amide group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a phosphine oxide group; an amine group; an aryl group; and a heterocyclic group including one or more of N, O, S, Se and Si atoms, or being substituted with a substituent linking two or more substituents among the substituents illustrated above, or having no substituents.

In the present specification, examples of the halogen group may include fluorine, chlorine, bromine or iodine.

In the present specification, the number of carbon atoms of the imide group is not particularly limited, but is preferably from 1 to 50. Specifically, compounds having structures as below may be included, however, the imide group is not limited thereto.

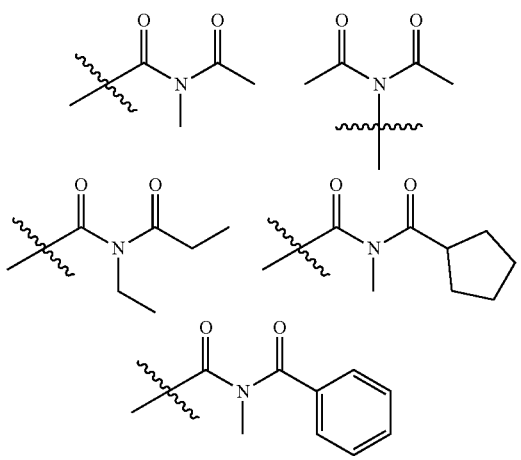

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, however, the amide group is not limited thereto.

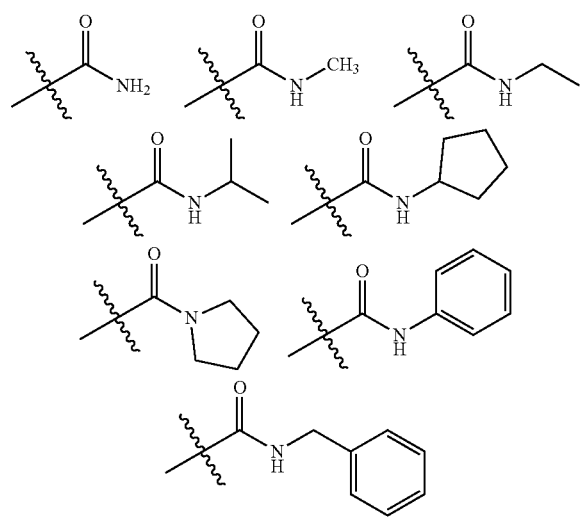

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methyl-pentyl, 2-methylpentyl, 4-methyl-2-pentyl, 3,3-dimethyl-butyl, 2-ethylbutyl, heptyl, n-heptyl, 1-methylhexyl, cyclo-pentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 60 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the silyl group is a substituent including Si with the Si atom being directly linked as a radical, and is represented by —$SiR_{201}R_{202}R_{203}$. $R_{201}$ to $R_{203}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, when the aryl group is a monocyclic aryl group, the number of carbon atoms is not particularly limited, but is preferably from 6 to 50. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 50. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

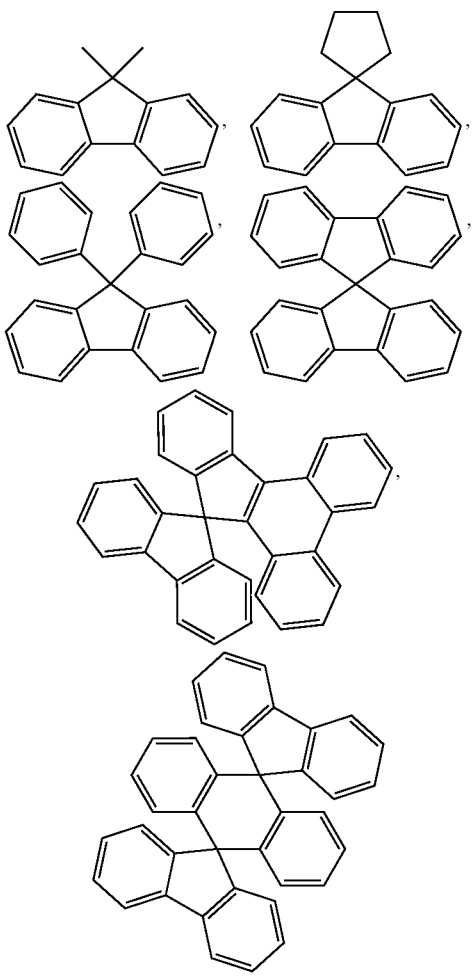

and the like may be included. However, the structure is not limited thereto.

In the present specification, the heterocyclic group is a group including one or more of N, O, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridine group, a pyridazine group, a pyrazine group, a quinolinyl group, a quinazoline group, a quinoxalinyl group, a phthalazinyl group, a pyridopyrimidine group, a pyridopyrazine group, a pyrazinopyrazine group, an isoquinoline group, an indole group, a carbozole group, a benzoxazole group, a benzimidazole group, a benzothiazole group, a benzocarbazole group, a benzothiophene group, a dibenzothiophene group, a benzofuran group, a phenanthroline group, a pteridine group, a thiazolyl group, an isoxazolyl group, an oxadiazolyl group, a thiadiazolyl group, a dibenzofuran group and the like, but are not limited thereto.

In the present specification, the heteroaryl group may be selected from among the examples of the heterocyclic group except for being an aromatic group, but is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the meaning of adjacent groups bonding to each other to form a ring means, as described above, adjacent groups bonding to each other to form a 5-membered to 8-membered hydrocarbon ring or a 5-membered to 8-membered heteroring. The ring may be monocyclic or multicyclic, may be aliphatic, aromatic, or a fused form thereof, but is not limited thereto.

In the present specification, the hydrocarbon ring or the heteroring may be selected from among the examples of the cycloalkyl group, the aryl group or the heteroaryl group described above except for being a monovalent. The hydrocarbon ring or the heteroring may be monocyclic or multicyclic, may be aliphatic, aromatic, or a fused form thereof, but is not limited thereto.

In the present specification, the aromatic ring group may be monocyclic or multicyclic, and may be selected from among the examples of the aryl group except for not being a monovalent.

In the present specification, the divalent to tetravalent aromatic ring group may be monocyclic or multicyclic, and means having 2 to 4 bonding sites in the aryl group, that is, a divalent to tetravalent group. The descriptions on the aryl group provided above may be applied except that these are each a divalent to tetravalent group.

In the present specification, the amine group is represented by —NR$_{206}$R$_{207}$, and R$_{206}$ and R$_{207}$ are the same as or different from each other, and may be each independently a substituent formed with at least one of hydrogen, deuterium, a halogen group, an alkyl group, an alkenyl group, an alkoxy group, a cycloalkyl group, an aryl group and a heterocyclic group. For example, the amine group may be selected from the group consisting of —NH$_2$, a monoalkylamine group, a dialkylamine group, an N-alkylarylamine group, a monoarylamine group, a diarylamine group, an N-arylheteroarylamine group, an N-alkylheteroarylamine group, a monoheteroarylamine group and a diheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, Specific examples of the phosphine oxide group may include a diphenylphosphine oxide group, a dinaphthylphosphine oxide group and the like, but are not limited thereto.

In the present specification, the alkyl group in the alkylamine group, the N-alkylarylamine group, the alkylthioxy group, the alkylsulfoxy group and the N-alkylheteroarylamine group is the same as the examples of the alkyl group described above. Specific examples of the alkylthioxy group may include a methylthioxy group, an ethylthioxy group, a tert-butylthioxy group, a hexylthioxy group, an octylthioxy group and the like, and specific example of the alkylsulfoxy group may include mesyl, an ethylsulfoxy group, a propylsulfoxy group, a butylsulfoxy group and the like, however, the alkylthioxy group and the alkylsulfoxy group are not limited thereto.

In the present specification, the aryl group in the aryloxy group, the arylthioxy group, the arylsulfoxy group, the N-arylalkylamine group and the N-arylheteroarylamine group is the same as the examples of the aryl group described above. Specific examples of the aryloxy group may include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthryloxy group, a 3-phenanthryloxy group, a 9-phenanthryloxy group and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the aryloxy group, the arylthioxy group and the arylsulfoxy group are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, the arylene group means an aryl group having two bonding sites, that is, a divalent group. The descriptions on the aryl group provided above may be applied except that these are each a divalent.

According to an exemplary embodiment of the present specification, at least one of R1 to R25 is

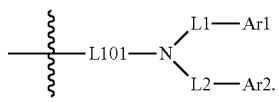

According to an exemplary embodiment of the present specification, L101, L1, and L2 are the same as or different from each other, and each independently a direct bond; a substituted or unsubstituted arylene group; or a substituted or unsubstituted divalent heterocyclic group.

According to an exemplary embodiment of the present specification, L101 is a direct bond.

According to an exemplary embodiment of the present specification, L101 is a substituted or unsubstituted arylene group.

According to an exemplary embodiment of the present specification, L101 is a substituted or unsubstituted phenylene group, a substituted or unsubstituted biphenylene group, a substituted or unsubstituted naphthylene group, or a substituted or unsubstituted fluorenylene group.

According to an exemplary embodiment of the present specification, L101 is a substituted or unsubstituted divalent heterocyclic group.

According to an exemplary embodiment of the present specification, L1 is a direct bond.

According to an exemplary embodiment of the present specification, L1 is a substituted or unsubstituted arylene group.

According to an exemplary embodiment of the present specification, L1 is a substituted or unsubstituted phenylene group, a substituted or unsubstituted biphenylene group, a substituted or unsubstituted terphenylene group, a substituted or unsubstituted naphthylene group, a substituted or unsubstituted phenanthrene group, or a substituted or unsubstituted fluorenylene group.

According to an exemplary embodiment of the present specification, L1 is a phenylene group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, L1 is a phenylene group unsubstituted or substituted with a methyl group, an ethyl group, an isopropyl group, a tert-butyl group, a cyclohexyl group, fluorine, a nitrile group, —$OCF_3$, —$CF_3$, —$C_2F_5$ or a trimethylsilyl group.

According to an exemplary embodiment of the present specification, L1 is a phenylene group.

According to an exemplary embodiment of the present specification, L1 is a biphenylene group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, L1 is a biphenylene group unsubstituted or substituted with a methyl group, an ethyl group, an isopropyl group, a tert-butyl group, a cyclohexyl group, fluorine, a nitrile group, —$OCF_3$, —$CF_3$, —$C_2F_5$ or a trimethylsilyl group.

According to an exemplary embodiment of the present specification, L1 is a biphenylene group.

According to an exemplary embodiment of the present specification, L1 is a terphenylene group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, L1 is a terphenylene group unsubstituted or substituted with a methyl group, an ethyl group, an isopropyl group, a tert-butyl group, a cyclohexyl group, fluorine, a nitrile group, —$OCF_3$, —$CF_3$, —$C_2F_5$ or a trimethylsilyl group.

According to an exemplary embodiment of the present specification, L1 is a terphenylene group.

According to an exemplary embodiment of the present specification, L1 is a naphthylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L1 is a naphthylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L1 is a naphthylene group.

According to an exemplary embodiment of the present specification, L1 is a phenanthrene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L1 is a phenanthrene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L1 is a phenanthrene group.

According to an exemplary embodiment of the present specification, L1 is a fluorenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L1 is a fluorenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L1 is a fluorenylene group.

According to an exemplary embodiment of the present specification, L1 is a substituted or unsubstituted divalent heterocyclic group.

According to an exemplary embodiment of the present specification, L1 is a substituted or unsubstituted divalent carbazole group, a substituted or unsubstituted divalent dibenzofuran group, or a substituted or unsubstituted divalent dibenzothiophene group.

According to an exemplary embodiment of the present specification, L1 is a divalent carbazole group unsubstituted or substituted with an alkyl group, a cycloalkyl group, a halogen group, a halogenated alkyl group, a nitrile group, a silyl group, an aryl group or a heterocyclic group.

According to an exemplary embodiment of the present specification, L1 is a divalent carbazole group unsubstituted or substituted with a phenyl group.

According to an exemplary embodiment of the present specification, L1 is a divalent dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L1 is a divalent dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L1 is a divalent dibenzofuran group.

According to an exemplary embodiment of the present specification, L1 is a divalent dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L1 is a divalent dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L1 is a divalent dibenzothiophene group.

According to an exemplary embodiment of the present specification, L2 is a direct bond.

According to an exemplary embodiment of the present specification, L2 is a substituted or unsubstituted arylene group.

According to an exemplary embodiment of the present specification, L2 is a substituted or unsubstituted phenylene group, a substituted or unsubstituted biphenylene group, a substituted or unsubstituted terphenylene group, a substituted or unsubstituted naphthylene group, a substituted or unsubstituted phenanthrene group, or a substituted or unsubstituted fluorenylene group.

According to an exemplary embodiment of the present specification, L2 is a phenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a phenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a phenylene group.

According to an exemplary embodiment of the present specification, L2 is a biphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a biphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a biphenylene group.

According to an exemplary embodiment of the present specification, L2 is a terphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a terphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a terphenylene group.

According to an exemplary embodiment of the present specification, L2 is a naphthylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a naphthylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a naphthylene group.

According to an exemplary embodiment of the present specification, L2 is a phenanthrene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a phenanthrene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a phenanthrene group.

According to an exemplary embodiment of the present specification, L2 is a fluorenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a fluorenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L2 is a fluorenylene group.

According to an exemplary embodiment of the present specification, L2 is a substituted or unsubstituted divalent heterocyclic group.

According to an exemplary embodiment of the present specification, L2 is a substituted or unsubstituted divalent carbazole group, a substituted or unsubstituted divalent dibenzofuran group, or a substituted or unsubstituted divalent dibenzothiophene group.

According to an exemplary embodiment of the present specification, L2 is a divalent carbazole group unsubstituted or substituted with an alkyl group, a cycloalkyl group, a halogen group, a halogenated alkyl group, a nitrile group, a silyl group, an aryl group or a heterocyclic group.

According to an exemplary embodiment of the present specification, L2 is a divalent carbazole group unsubstituted or substituted with a phenyl group.

According to an exemplary embodiment of the present specification, L2 is a divalent dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a divalent dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L2 is a divalent dibenzofuran group.

According to an exemplary embodiment of the present specification, L2 is a divalent dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L2 is a divalent dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L2 is a divalent dibenzothiophene group.

According to an exemplary embodiment of the present specification, Ar1 and Ar2 are the same as or different from each other, and each independently hydrogen; deuterium; a halogen group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group.

According to an exemplary embodiment of the present specification, Ar1 is hydrogen.

According to an exemplary embodiment of the present specification, Ar1 is a halogen group.

According to an exemplary embodiment of the present specification, Ar1 is fluorine.

According to an exemplary embodiment of the present specification, Ar1 is a substituted or unsubstituted alkyl group.

According to an exemplary embodiment of the present specification, Ar1 is a substituted or unsubstituted methyl group, a substituted or unsubstituted ethyl group, a substituted or unsubstituted isopropyl group, or a substituted or unsubstituted tert-butyl group.

According to an exemplary embodiment of the present specification, Ar1 is a methyl group.

According to an exemplary embodiment of the present specification, Ar1 is an ethyl group.

According to an exemplary embodiment of the present specification, Ar1 is an isopropyl group.

According to an exemplary embodiment of the present specification, Ar1 is a tert-butyl group.

According to an exemplary embodiment of the present specification, Ar1 is a substituted or unsubstituted cycloalkyl group.

According to an exemplary embodiment of the present specification, Ar1 is a substituted or unsubstituted cyclopentyl group, or a substituted or unsubstituted cyclohexyl group.

According to an exemplary embodiment of the present specification, Ar1 is a cyclohexyl group.

According to an exemplary embodiment of the present specification, Ar1 is a substituted or unsubstituted silyl group.

According to an exemplary embodiment of the present specification, Ar1 is a silyl group unsubstituted or substituted with an alkyl group.

According to an exemplary embodiment of the present specification, Ar1 is a trimethylsilyl group.

According to an exemplary embodiment of the present specification, Ar1 is a substituted or unsubstituted aryl group having 6 to 40 carbon atoms.

According to an exemplary embodiment of the present specification, Ar1 is a substituted or unsubstituted phenyl group, a substituted or unsubstituted biphenyl group, a substituted or unsubstituted terphenyl group, a substituted or unsubstituted triphenyl group, a substituted or unsubstituted quaterphenyl group, a substituted or unsubstituted naphthyl group, a substituted or unsubstituted anthracenyl group, a substituted or unsubstituted phenanthryl group, or a substituted or unsubstituted fluorenyl group.

According to an exemplary embodiment of the present specification, Ar1 is a phenyl group unsubstituted or substituted with deuterium, an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar1 is a phenyl group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group, a biphenyl group, a naphthyl group, a phenanthryl group, a triphenyl group or a dimethylfluorenyl group.

According to an exemplary embodiment of the present specification, Ar1 is a phenyl group.

According to an exemplary embodiment of the present specification, Ar1 is a biphenyl group unsubstituted or substituted with an alkyl group or an aryl group.

According to an exemplary embodiment of the present specification, Ar1 is a biphenyl group unsubstituted or substituted with a methyl group, a phenyl group or a naphthyl group.

According to an exemplary embodiment of the present specification, Ar1 is a biphenyl group.

According to an exemplary embodiment of the present specification, Ar1 is a terphenyl group unsubstituted or substituted with an alkyl group or an aryl group.

According to an exemplary embodiment of the present specification, Ar1 is a terphenyl group unsubstituted or substituted with a methyl group, a phenyl group or a naphthyl group.

According to an exemplary embodiment of the present specification, Ar1 is a terphenyl group.

According to an exemplary embodiment of the present specification, Ar1 is a triphenyl group unsubstituted or substituted with an alkyl group or an aryl group.

According to an exemplary embodiment of the present specification, Ar1 is a triphenyl group unsubstituted or substituted with a methyl group, a phenyl group or a naphthyl group.

According to an exemplary embodiment of the present specification, Ar1 is a triphenyl group.

According to an exemplary embodiment of the present specification, Ar1 is a naphthyl group unsubstituted or substituted with an alkyl group or an aryl group.

According to an exemplary embodiment of the present specification, Ar1 is a naphthyl group unsubstituted or substituted with a methyl group, a phenyl group or a naphthyl group.

According to an exemplary embodiment of the present specification, Ar1 is a naphthyl group.

According to an exemplary embodiment of the present specification, Ar1 is an anthracenyl group unsubstituted or substituted with an alkyl group or an aryl group.

According to an exemplary embodiment of the present specification, Ar1 is an anthracenyl group unsubstituted or substituted with a methyl group, a phenyl group or a naphthyl group.

According to an exemplary embodiment of the present specification, Ar1 is an anthracenyl group.

According to an exemplary embodiment of the present specification, Ar1 is a phenanthryl group unsubstituted or substituted with an alkyl group or an aryl group.

According to an exemplary embodiment of the present specification, Ar1 is a phenanthryl group unsubstituted or substituted with a methyl group, a phenyl group or a naphthyl group.

According to an exemplary embodiment of the present specification, Ar1 is a phenanthryl group.

According to an exemplary embodiment of the present specification, Ar1 is a fluorenyl group unsubstituted or substituted with an alkyl group or an aryl group.

According to an exemplary embodiment of the present specification, Ar1 is a fluorenyl group unsubstituted or substituted with a methyl group, a phenyl group or a naphthyl group.

According to an exemplary embodiment of the present specification, Ar1 is a fluorenyl group.

According to an exemplary embodiment of the present specification, Ar1 is a spirobifluorenyl group.

According to an exemplary embodiment of the present specification, Ar1 is a substituted or unsubstituted heterocyclic group having 2 to 40 carbon atoms.

According to an exemplary embodiment of the present specification, Ar1 is a substituted or unsubstituted carbazole group, a substituted or unsubstituted dibenzocarbazole group, a substituted or unsubstituted dibenzofuran group, or a substituted or unsubstituted dibenzothiophene group.

According to an exemplary embodiment of the present specification, Ar1 is a carbazole group unsubstituted or substituted with an aryl group.

According to an exemplary embodiment of the present specification, Ar1 is a carbazole group unsubstituted or substituted with a phenyl group or a biphenyl group.

According to an exemplary embodiment of the present specification, Ar1 is a dibenzocarbazole group unsubstituted or substituted with an aryl group.

According to an exemplary embodiment of the present specification, Ar1 is a dibenzocarbazole group unsubstituted or substituted with a phenyl group or a biphenyl group.

According to an exemplary embodiment of the present specification, Ar1 is a dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar1 is a dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group or a naphthyl group.

According to an exemplary embodiment of the present specification, Ar1 is a benzonaphthofuran group.

According to an exemplary embodiment of the present specification, Ar1 is a dibenzofuran group.

According to an exemplary embodiment of the present specification, Ar1 is a dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar1 is a dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group or a naphthyl group.

According to an exemplary embodiment of the present specification, Ar1 is a benzonaphthothiophene group.

According to an exemplary embodiment of the present specification, Ar1 is a dibenzothiophene group.

According to an exemplary embodiment of the present specification, Ar2 is hydrogen.

According to an exemplary embodiment of the present specification, Ar2 is a halogen group.

According to an exemplary embodiment of the present specification, Ar2 is fluorine.

According to an exemplary embodiment of the present specification, Ar2 is a substituted or unsubstituted alkyl group.

According to an exemplary embodiment of the present specification, Ar2 is a substituted or unsubstituted methyl group, a substituted or unsubstituted ethyl group, a substituted or unsubstituted isopropyl group, or a substituted or unsubstituted tert-butyl group.

According to an exemplary embodiment of the present specification, Ar2 is a methyl group.

According to an exemplary embodiment of the present specification, Ar2 is an ethyl group.

According to an exemplary embodiment of the present specification, Ar2 is an isopropyl group.

According to an exemplary embodiment of the present specification, Ar2 is a tert-butyl group.

According to an exemplary embodiment of the present specification, Ar2 is a substituted or unsubstituted cycloalkyl group.

According to an exemplary embodiment of the present specification, Ar2 is a substituted or unsubstituted cyclopentyl group, or a substituted or unsubstituted cyclohexyl group According to an exemplary embodiment of the present specification, Ar2 is a cyclohexyl group.

According to an exemplary embodiment of the present specification, Ar2 is a substituted or unsubstituted silyl group.

According to an exemplary embodiment of the present specification, Ar2 is a silyl group unsubstituted or substituted with an alkyl group.

According to an exemplary embodiment of the present specification, Ar2 is a trimethylsilyl group.

According to an exemplary embodiment of the present specification, Ar2 is a substituted or unsubstituted aryl group having 6 to 40 carbon atoms.

According to an exemplary embodiment of the present specification, Ar2 is a substituted or unsubstituted phenyl group, a substituted or unsubstituted biphenyl group, a substituted or unsubstituted terphenyl group, a substituted or unsubstituted triphenyl group, a substituted or unsubstituted quaterphenyl group, a substituted or unsubstituted naphthyl group, a substituted or unsubstituted anthracenyl group, a substituted or unsubstituted phenanthryl group, or a substituted or unsubstituted fluorenyl group.

According to an exemplary embodiment of the present specification, Ar2 is a phenyl group unsubstituted or substituted with deuterium, an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar2 is a phenyl group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group, a biphenyl group, a naphthyl group, a phenanthryl group, a triphenyl group or a dimethylfluorenyl group.

According to an exemplary embodiment of the present specification, Ar2 is a phenyl group.

According to an exemplary embodiment of the present specification, Ar2 is a biphenyl group unsubstituted or substituted with an alkyl group or an aryl group.

According to an exemplary embodiment of the present specification, Ar2 is a biphenyl group unsubstituted or substituted with a methyl group, a phenyl group or a naphthyl group.

According to an exemplary embodiment of the present specification, Ar2 is a biphenyl group.

According to an exemplary embodiment of the present specification, Ar2 is a terphenyl group unsubstituted or substituted with an alkyl group or an aryl group.

According to an exemplary embodiment of the present specification, Ar2 is a terphenyl group unsubstituted or substituted with a methyl group, a phenyl group or a naphthyl group.

According to an exemplary embodiment of the present specification, Ar2 is a terphenyl group.

According to an exemplary embodiment of the present specification, Ar2 is a triphenyl group unsubstituted or substituted with an alkyl group or an aryl group.

According to an exemplary embodiment of the present specification, Ar2 is a triphenyl group unsubstituted or substituted with a methyl group, a phenyl group or a naphthyl group.

According to an exemplary embodiment of the present specification, Ar2 is a triphenyl group.

According to an exemplary embodiment of the present specification, Ar2 is a naphthyl group unsubstituted or substituted with an alkyl group or an aryl group.

According to an exemplary embodiment of the present specification, Ar2 is a naphthyl group unsubstituted or substituted with a methyl group, a phenyl group or a naphthyl group.

According to an exemplary embodiment of the present specification, Ar2 is a naphthyl group.

According to an exemplary embodiment of the present specification, Ar2 is an anthracenyl group unsubstituted or substituted with an alkyl group or an aryl group.

According to an exemplary embodiment of the present specification, Ar2 is an anthracenyl group unsubstituted or substituted with a methyl group, a phenyl group or a naphthyl group.

According to an exemplary embodiment of the present specification, Ar2 is an anthracenyl group.

According to an exemplary embodiment of the present specification, Ar2 is a phenanthryl group unsubstituted or substituted with an alkyl group or an aryl group.

According to an exemplary embodiment of the present specification, Ar2 is a phenanthryl group unsubstituted or substituted with a methyl group, a phenyl group or a naphthyl group.

According to an exemplary embodiment of the present specification, Ar2 is a phenanthryl group.

According to an exemplary embodiment of the present specification, Ar2 is a fluorenyl group unsubstituted or substituted with an alkyl group or an aryl group.

According to an exemplary embodiment of the present specification, Ar2 is a fluorenyl group unsubstituted or substituted with a methyl group, a phenyl group or a naphthyl group.

According to an exemplary embodiment of the present specification, Ar2 is a fluorenyl group.

According to an exemplary embodiment of the present specification, Ar2 is a spirobifluorenyl group.

According to an exemplary embodiment of the present specification, Ar2 is a substituted or unsubstituted heterocyclic group having 2 to 40 carbon atoms.

According to an exemplary embodiment of the present specification, Ar2 is a substituted or unsubstituted carbazole group, a substituted or unsubstituted dibenzocarbazole group, a substituted or unsubstituted dibenzofuran group, or a substituted or unsubstituted dibenzothiophene group.

According to an exemplary embodiment of the present specification, Ar2 is a carbazole group unsubstituted or substituted with an aryl group.

According to an exemplary embodiment of the present specification, Ar2 is a carbazole group unsubstituted or substituted with a phenyl group or a biphenyl group.

According to an exemplary embodiment of the present specification, Ar2 is a dibenzocarbazole group unsubstituted or substituted with an aryl group.

According to an exemplary embodiment of the present specification, Ar2 is a dibenzocarbazole group unsubstituted or substituted with a phenyl group or a biphenyl group.

According to an exemplary embodiment of the present specification, Ar2 is a dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar2 is a dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group or a naphthyl group.

According to an exemplary embodiment of the present specification, Ar2 is a benzonaphthofuran group.

According to an exemplary embodiment of the present specification, Ar2 is a dibenzofuran group.

According to an exemplary embodiment of the present specification, Ar2 is a dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar2 is a dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group or a naphthyl group.

According to an exemplary embodiment of the present specification, Ar2 is a benzonaphthothiophene group.

According to an exemplary embodiment of the present specification, Ar2 is a dibenzothiophene group.

According to an exemplary embodiment of the present specification, Ar1 and Ar2 are the same as or different from each other, and may be each independently any one selected from among the following substituents.

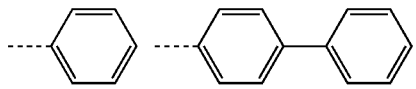

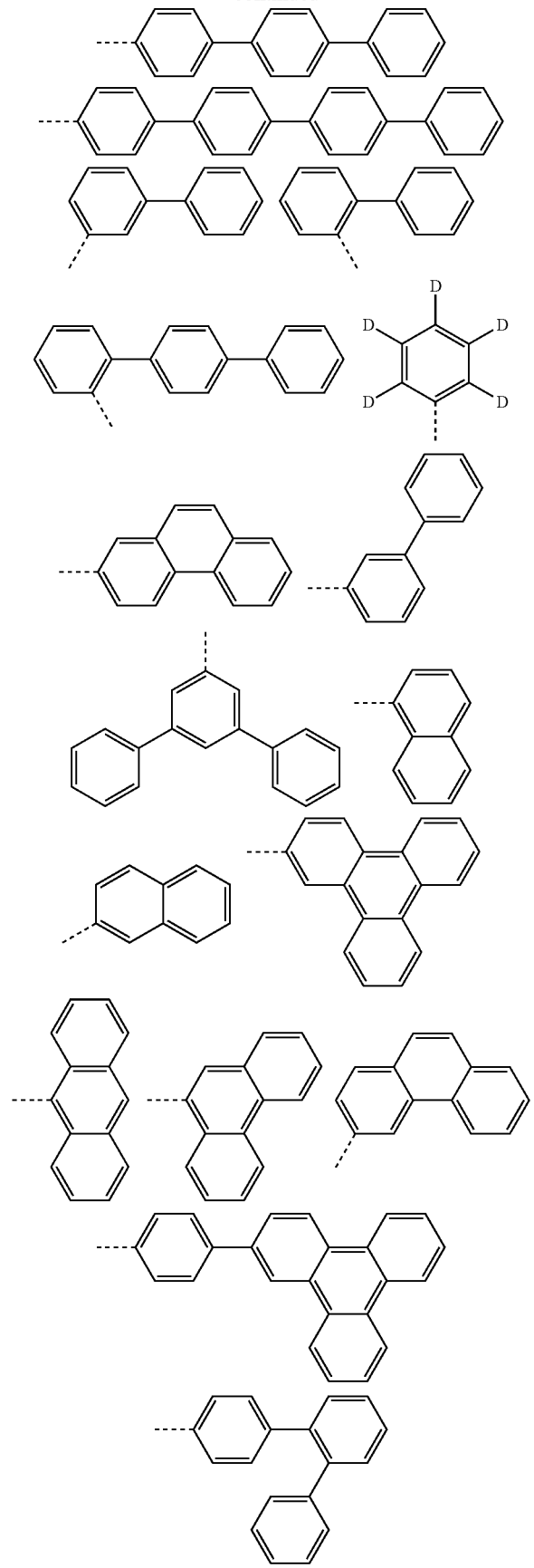

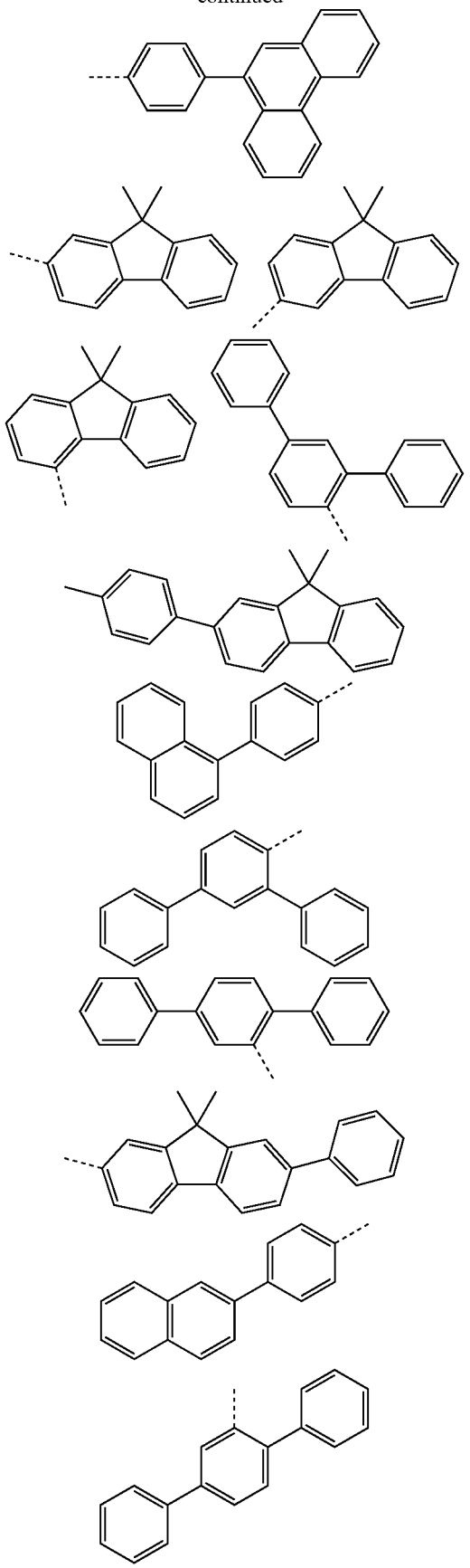
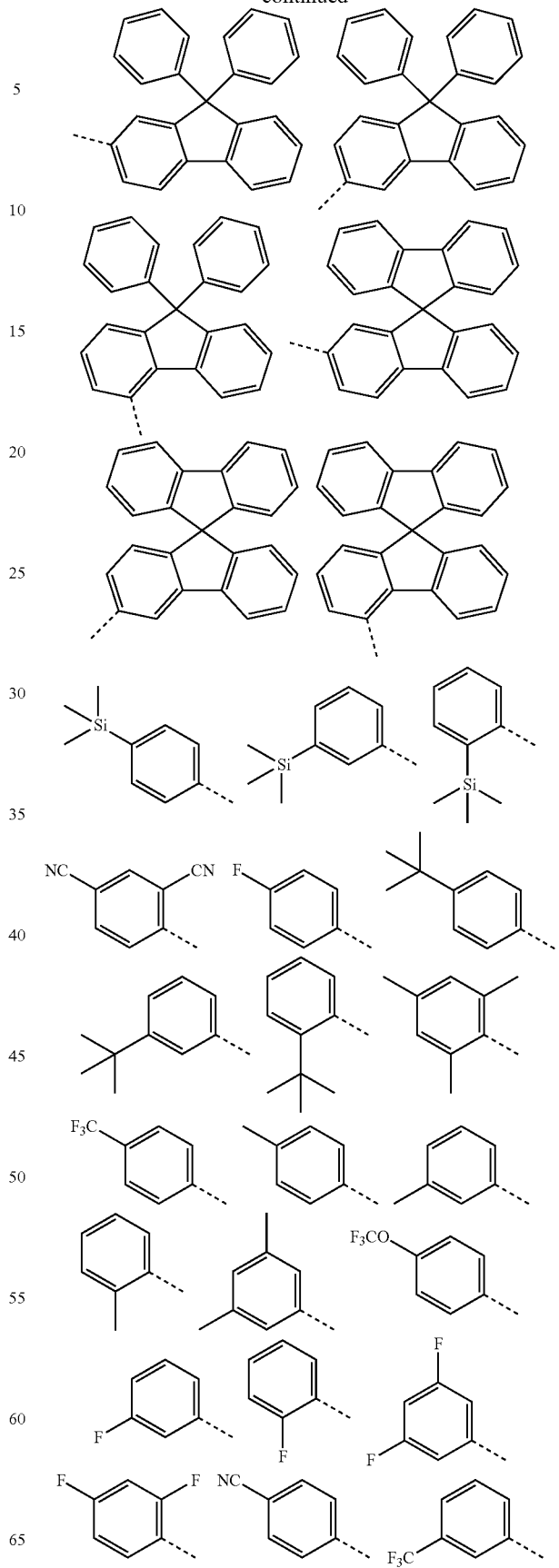

-continued
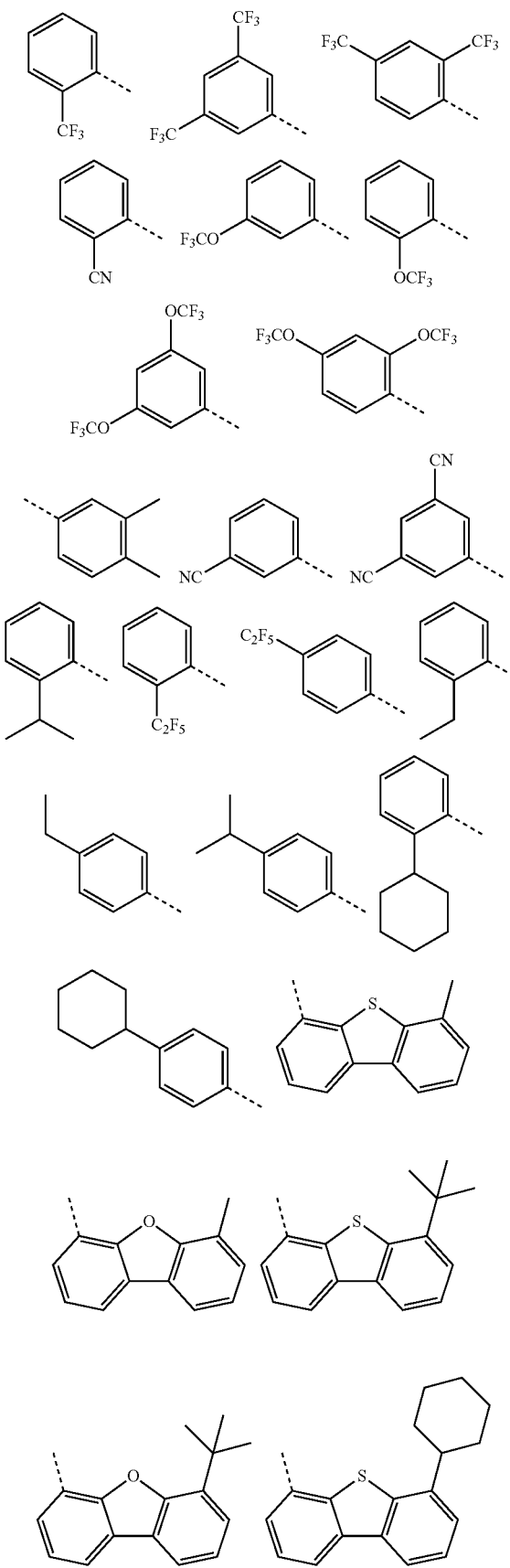
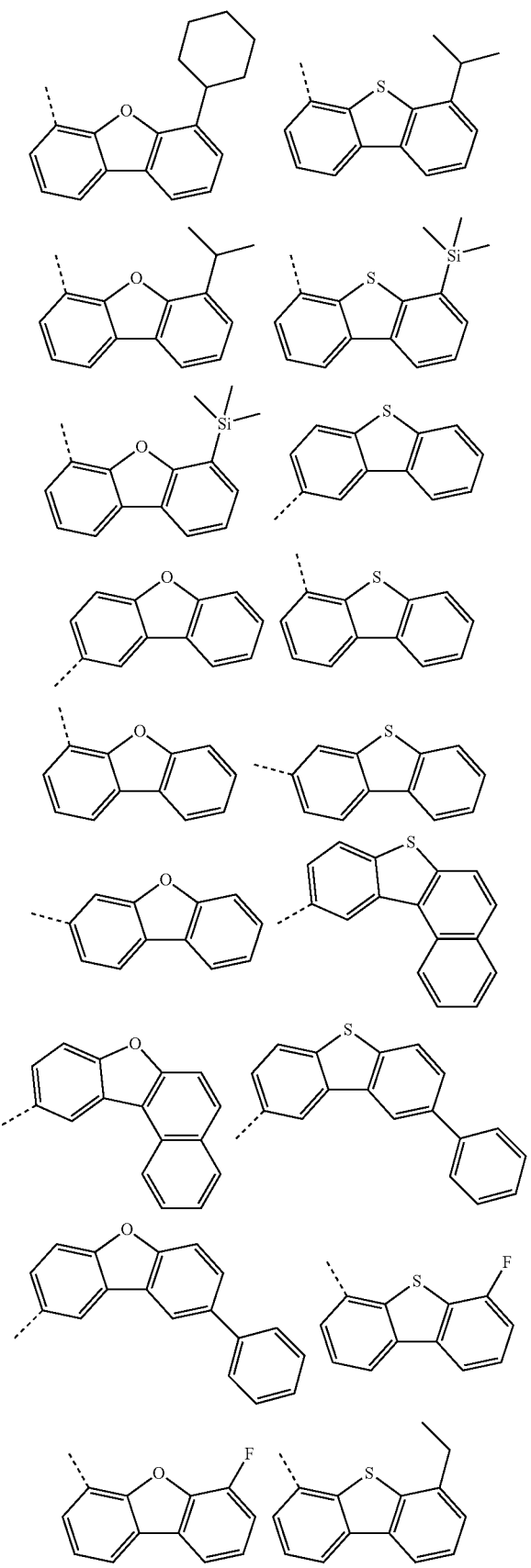

-continued

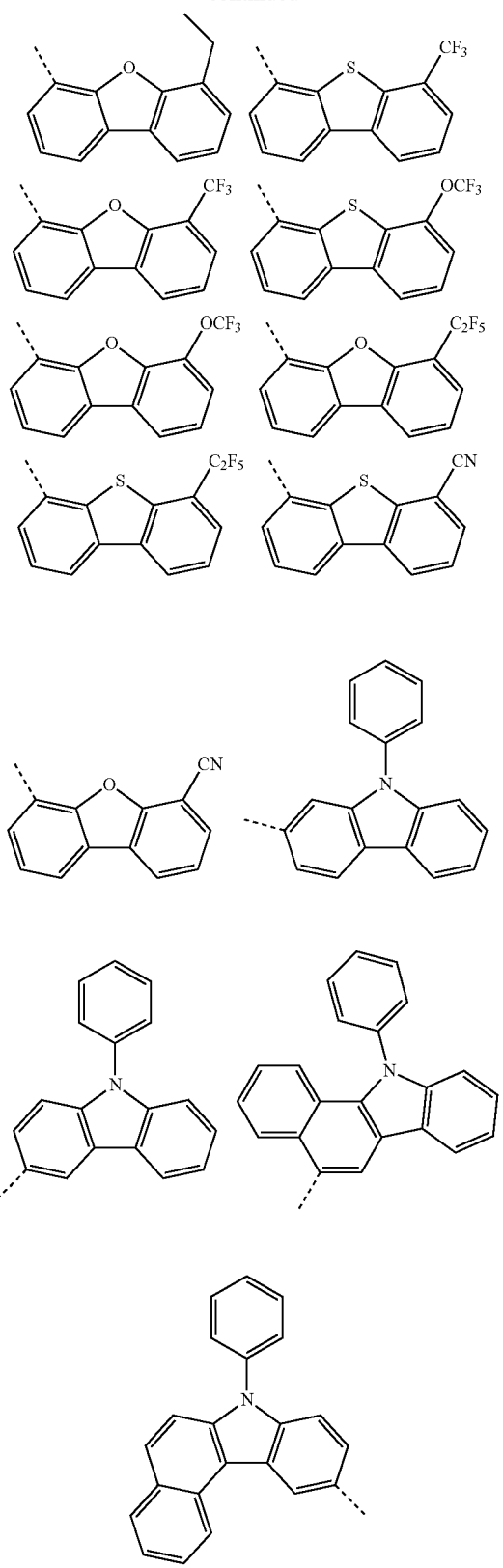

According to an exemplary embodiment of the present specification, any one or more of Ar1 and Ar2 may be represented by the following Chemical Formula 1A.

[Chemical Formula 1A]

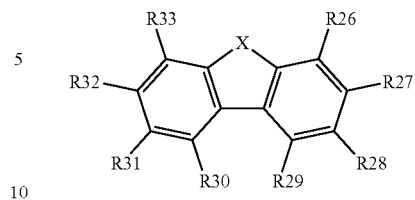

According to an exemplary embodiment of the present specification, X is S, O, CRR' or NR.

According to an exemplary embodiment of the present specification, X is S.

According to an exemplary embodiment of the present specification, X is O.

According to an exemplary embodiment of the present specification, X is CRR'.

According to an exemplary embodiment of the present specification, X is NR.

According to an exemplary embodiment of the present specification, R, R', and R26 to R29 are the same as or different from each other, and each independently hydrogen; deuterium; a halogen group; a nitrile group; a nitro group; a substituted or unsubstituted alkoxy group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, or may bond to adjacent groups to form a substituted or unsubstituted ring.

According to an exemplary embodiment of the present specification, any one of R30 to R33 bonds to L1 or L2 of Chemical Formula 1, and groups that do not bond to L1 or L2 of Chemical Formula 1 among R30 to R33 are the same as or different from each other, and each independently hydrogen; deuterium; a halogen group; a nitrile group; a nitro group; a substituted or unsubstituted alkoxy group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, or may bond to adjacent groups to form a substituted or unsubstituted ring.

According to an exemplary embodiment of the present specification, R is a substituted or unsubstituted aryl group having 6 to 20 carbon atoms.

According to an exemplary embodiment of the present specification, R is a phenyl group.

According to an exemplary embodiment of the present specification, R is a biphenyl group.

According to an exemplary embodiment of the present specification, R26 is a methyl group.

According to an exemplary embodiment of the present specification, R26 is an ethyl group.

According to an exemplary embodiment of the present specification, R26 is an isopropyl group.

According to an exemplary embodiment of the present specification, R26 is a tert-butyl group.

According to an exemplary embodiment of the present specification, R26 is a cyclohexyl group.

According to an exemplary embodiment of the present specification, R26 is fluorine.

According to an exemplary embodiment of the present specification, R26 is a nitrile group.

According to an exemplary embodiment of the present specification, R26 is a phenyl group.

According to an exemplary embodiment of the present specification, R26 is a trimethylsilyl group.

According to an exemplary embodiment of the present specification, R26 is —OCF$_3$.

According to an exemplary embodiment of the present specification, R26 is —CF$_3$.

According to an exemplary embodiment of the present specification, R26 is —C$_2$F$_5$.

According to an exemplary embodiment of the present specification, R28 is a phenyl group.

According to an exemplary embodiment of the present specification, R28 and R29 may bond to each other to form a ring.

According to an exemplary embodiment of the present specification, R32 and R33 may bond to each other to form a ring.

According to an exemplary embodiment of the present specification, R27 and R29 to R33 are hydrogen.

According to an exemplary embodiment of the present specification, R26 to R33 are each hydrogen.

According to an exemplary embodiment of the present specification,

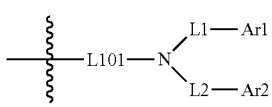

may be any one selected from among the following substituents.

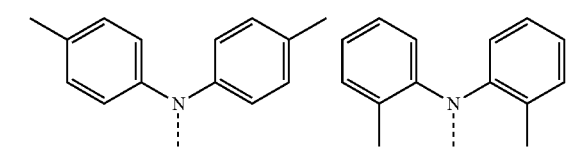

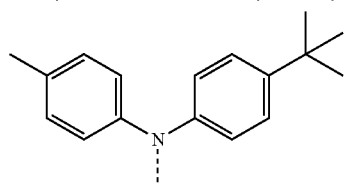

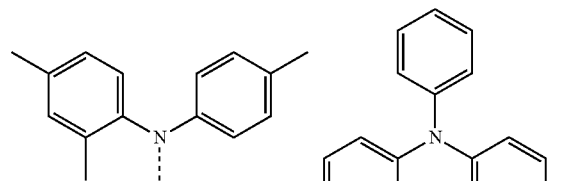

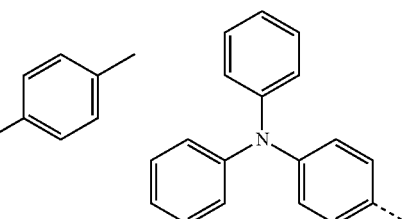

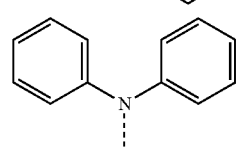

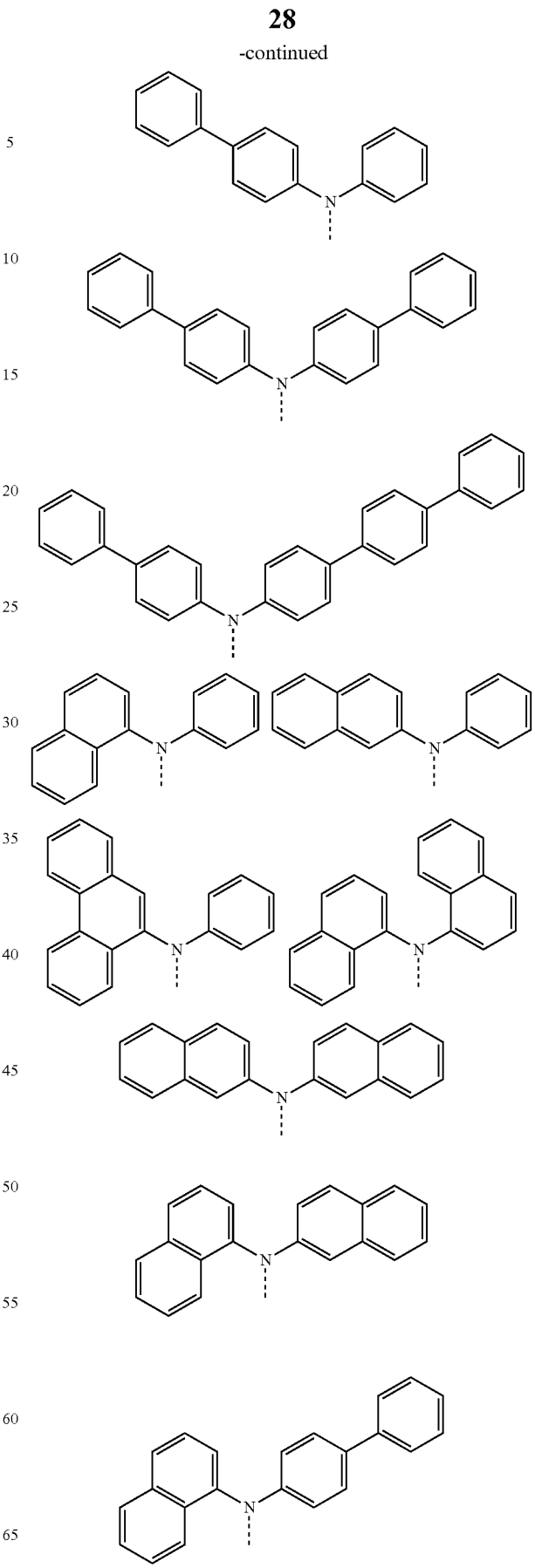

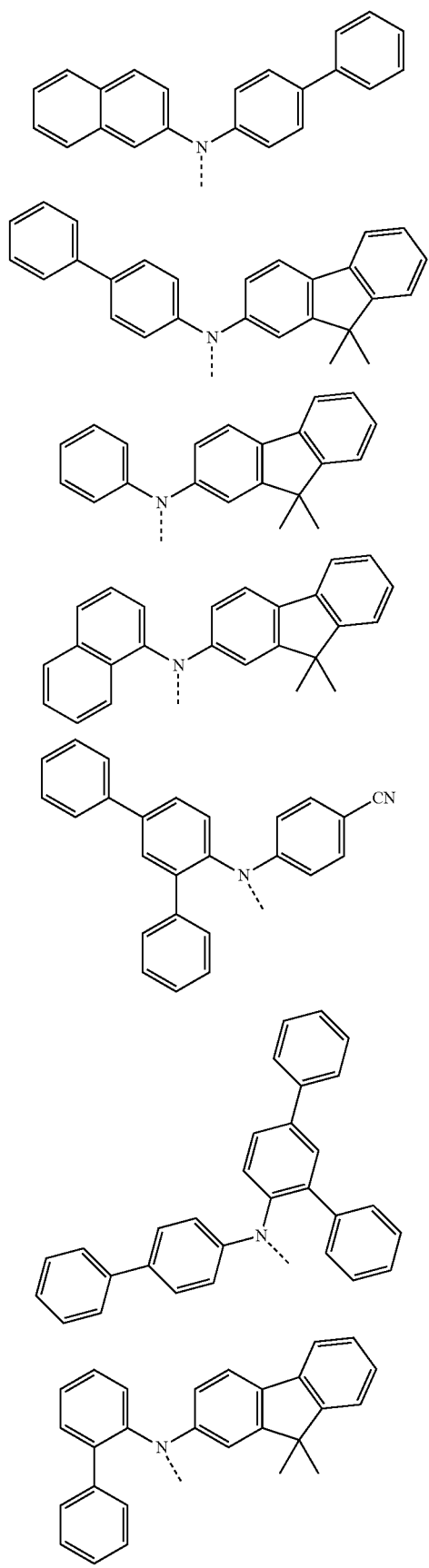
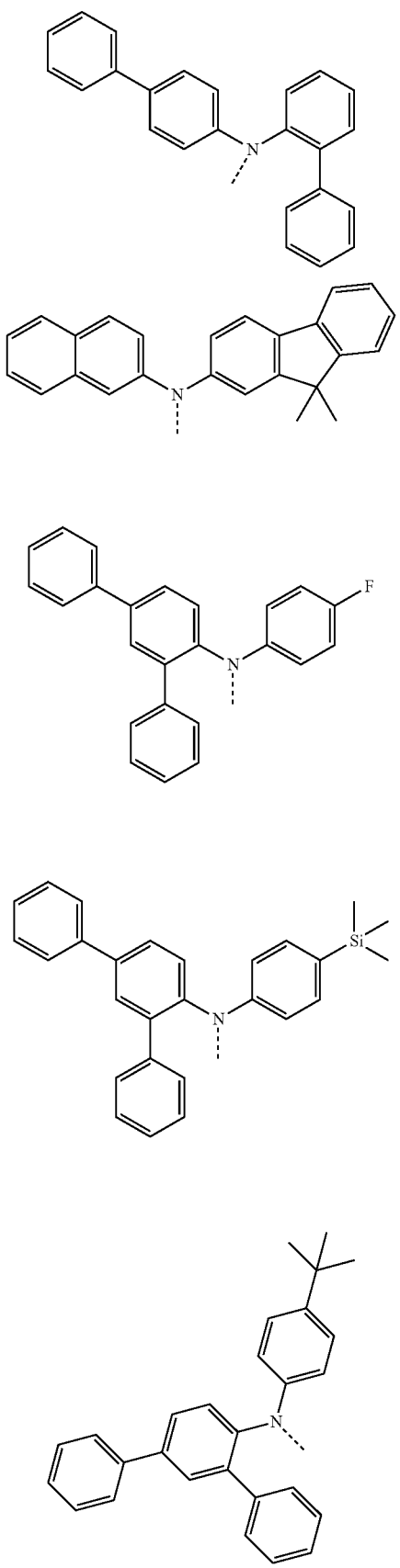

-continued
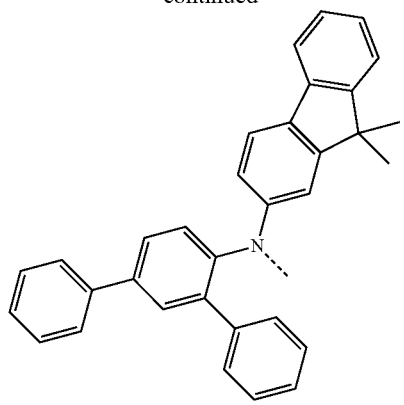
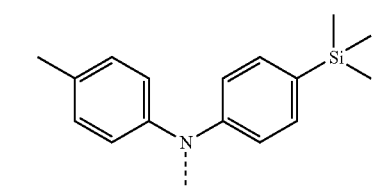
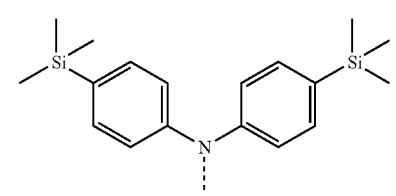
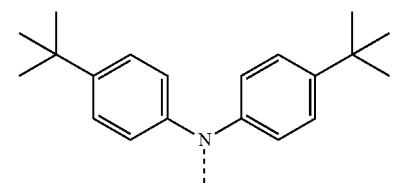
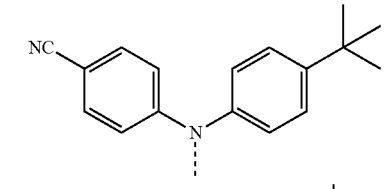
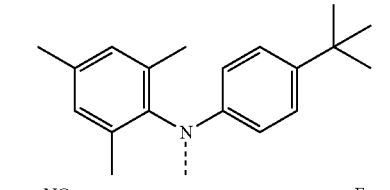
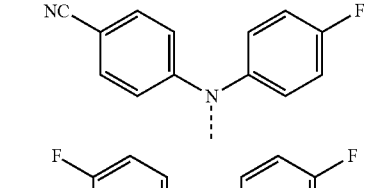
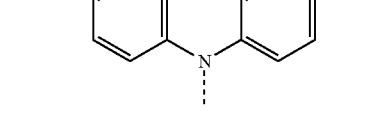
-continued
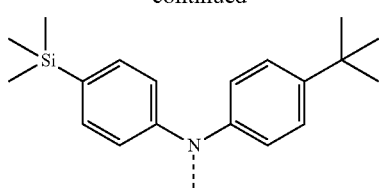
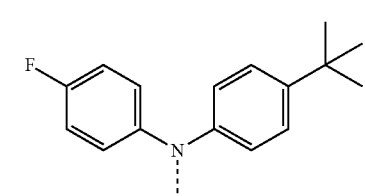
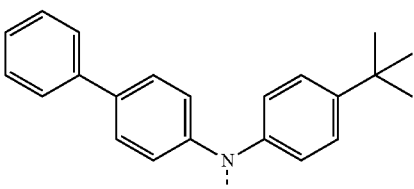
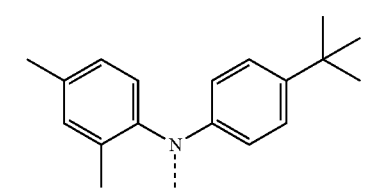
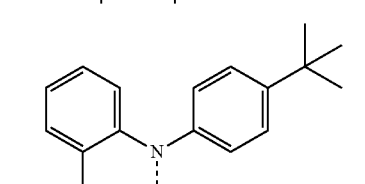
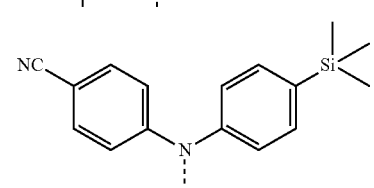
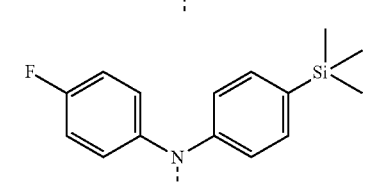
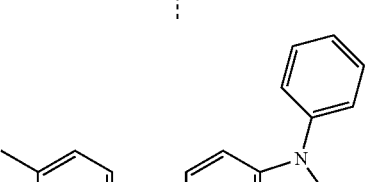
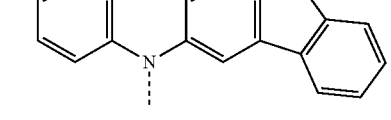

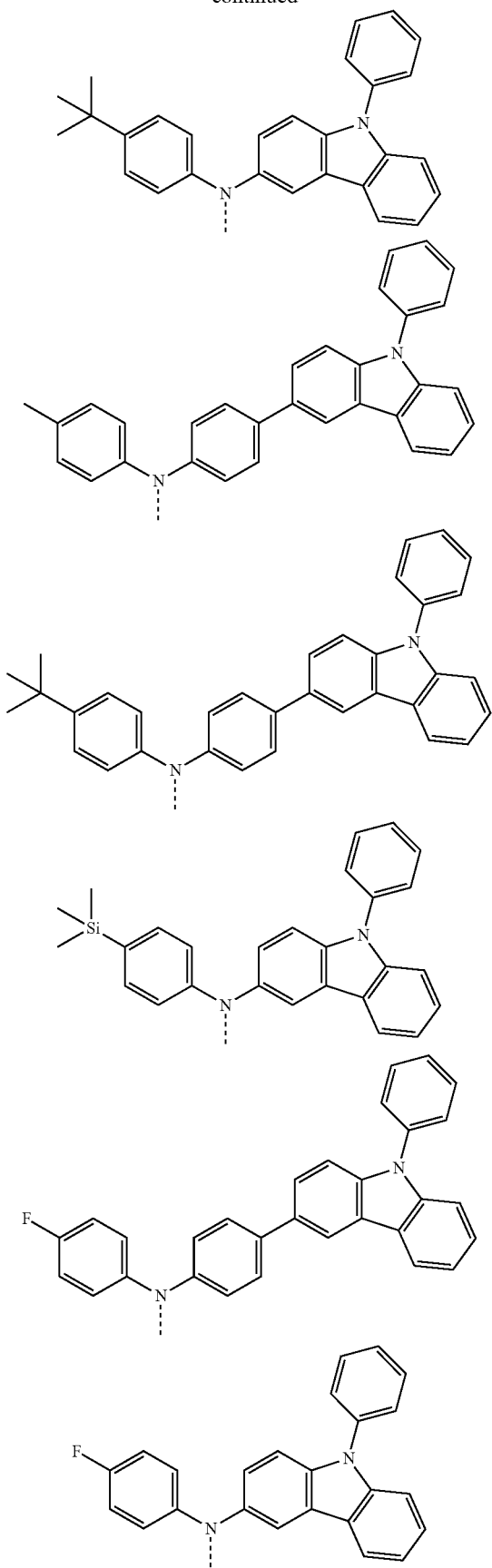
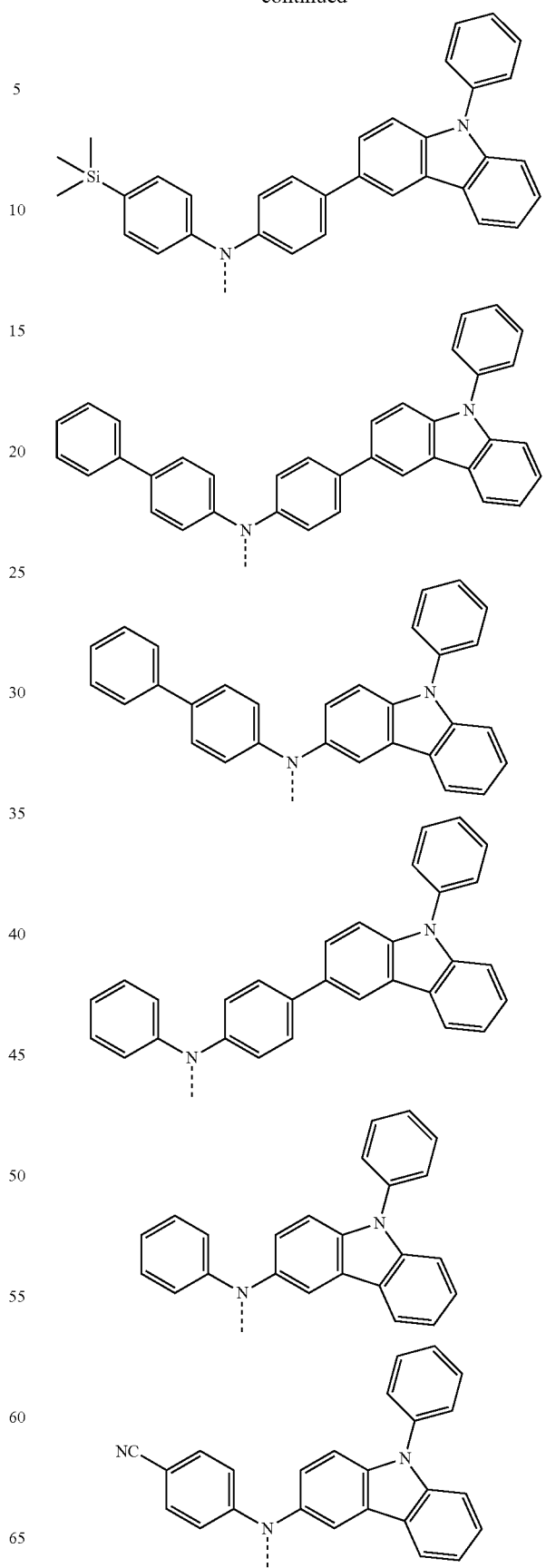

-continued
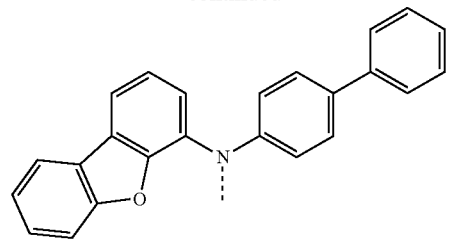
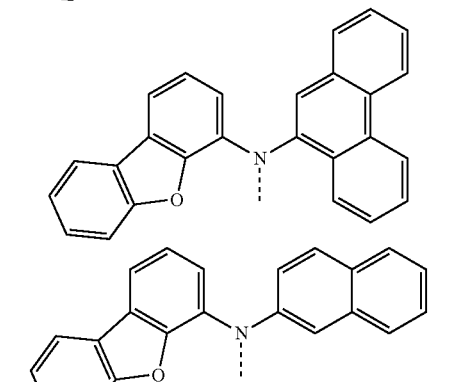
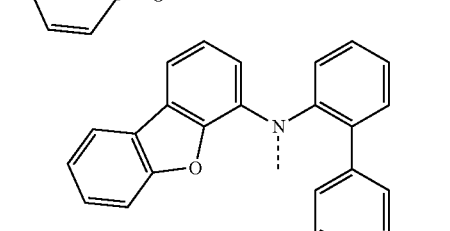
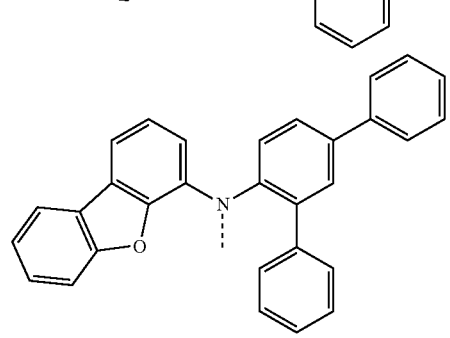
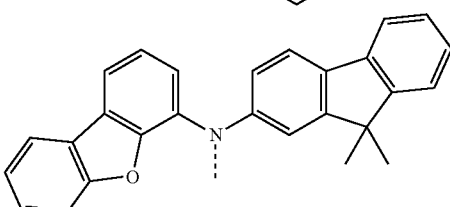
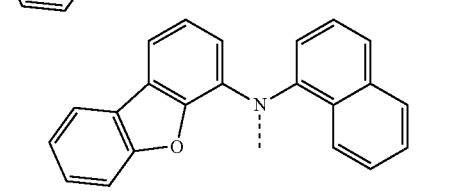
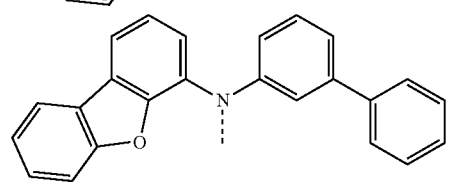
-continued
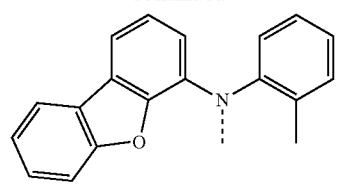
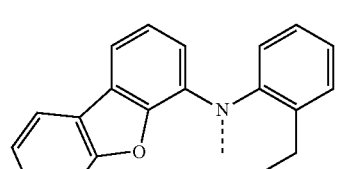
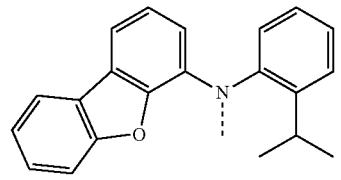
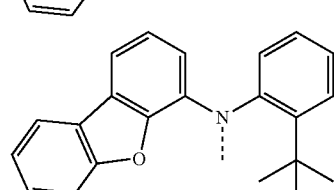
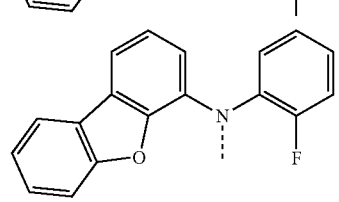
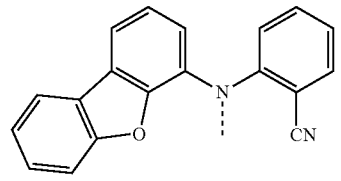
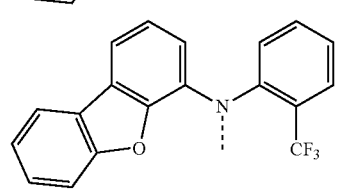
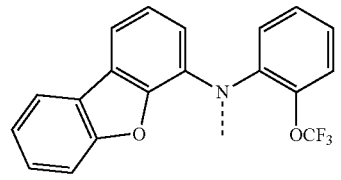
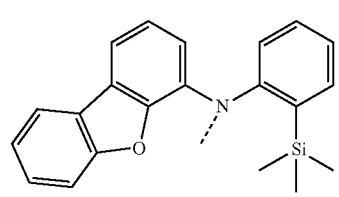

-continued

-continued
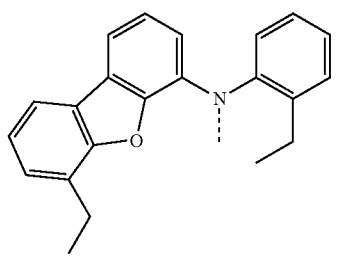
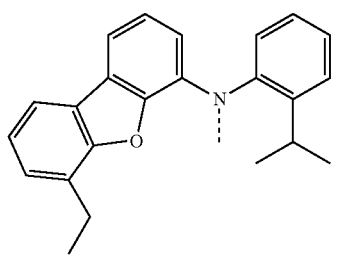
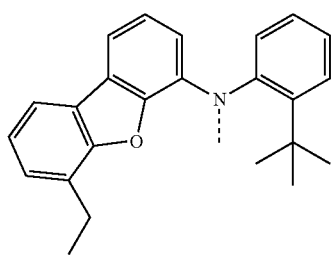
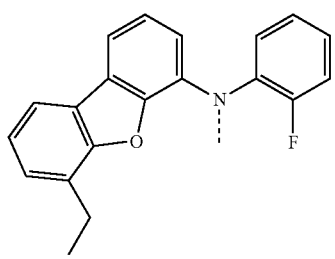
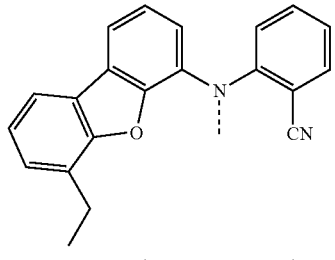
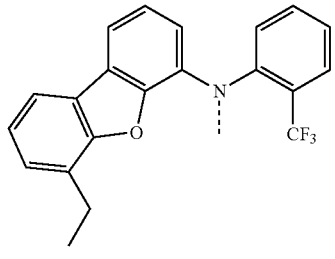
-continued
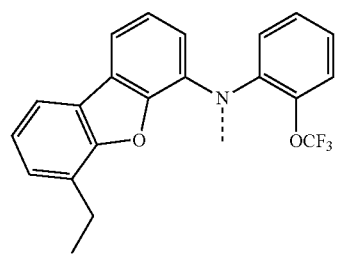
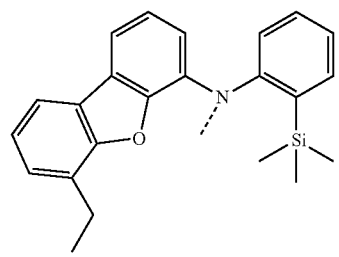
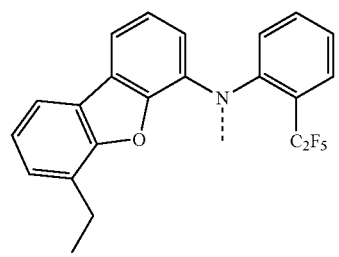
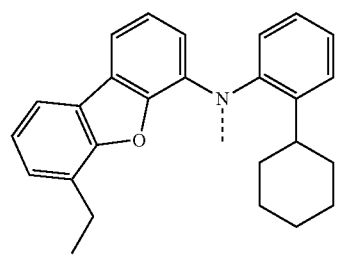
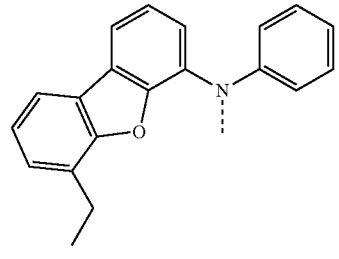
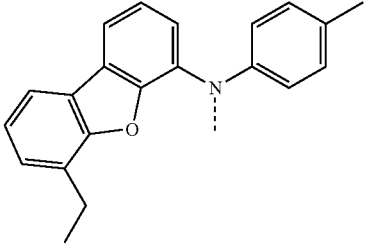

-continued
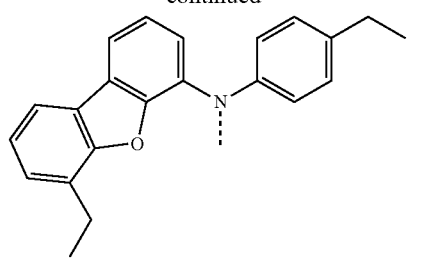
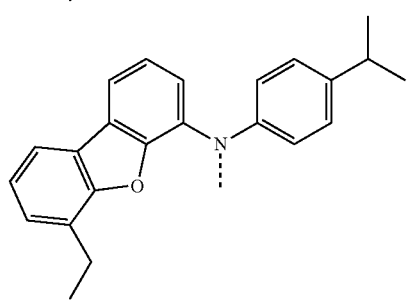
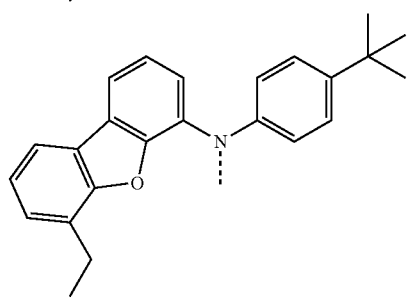
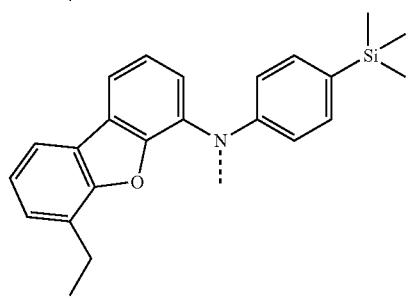
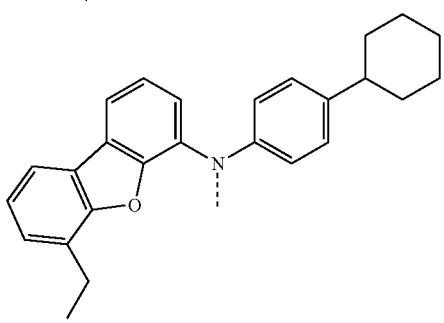
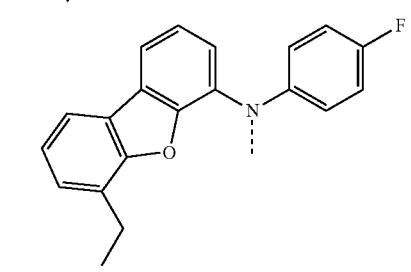
-continued
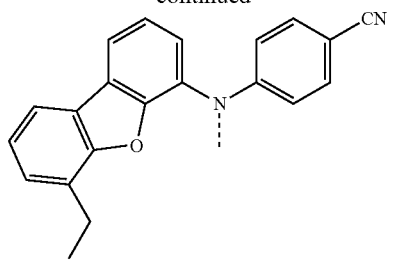
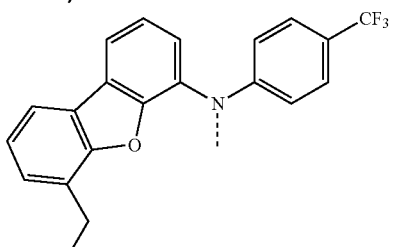
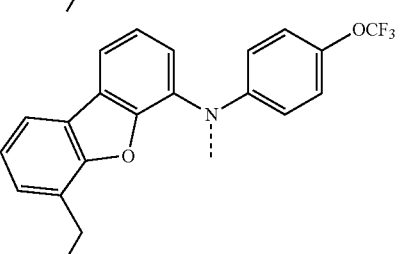
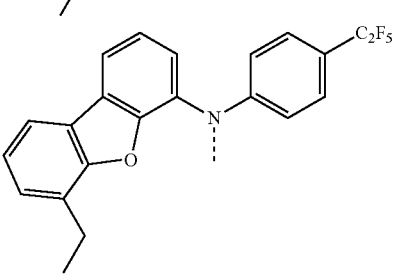
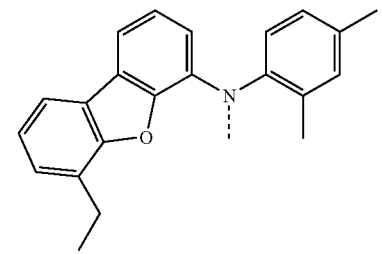
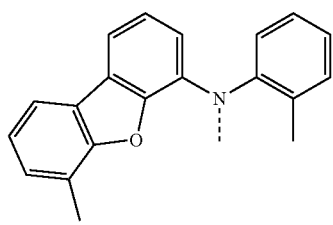
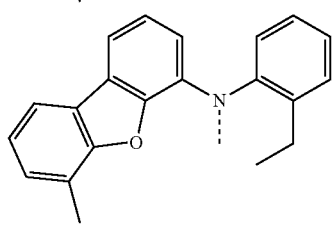

-continued
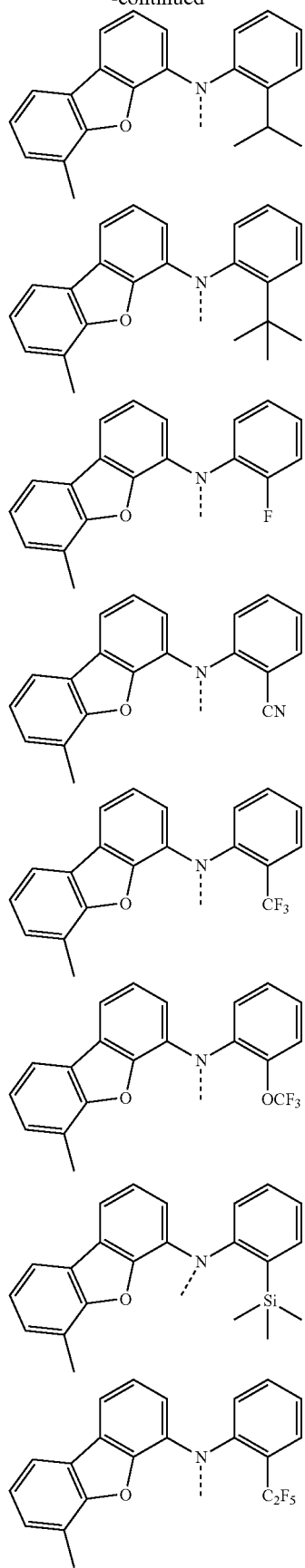
-continued
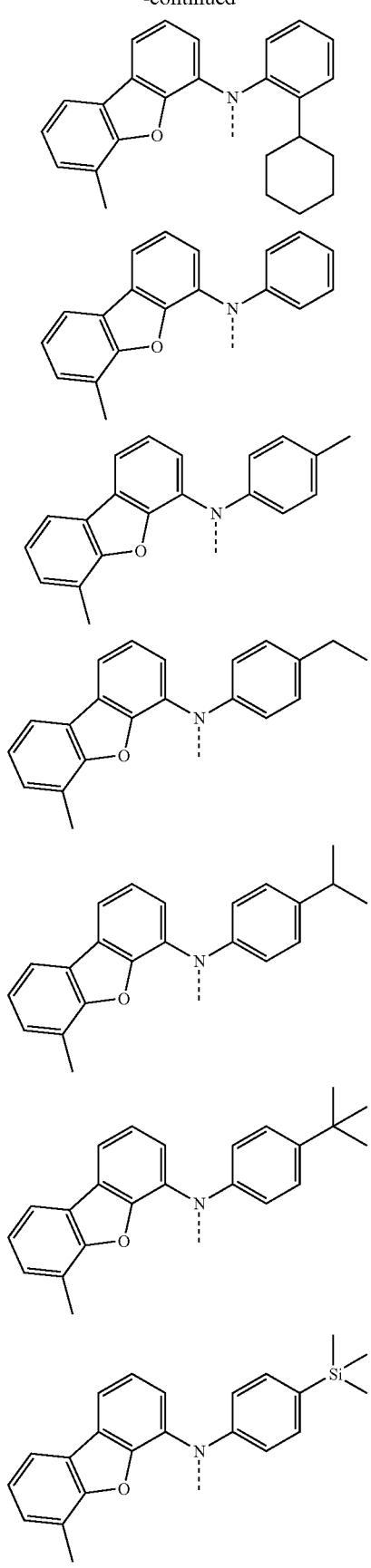

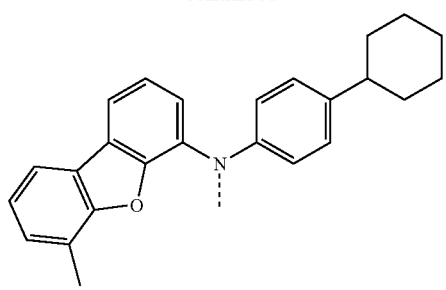
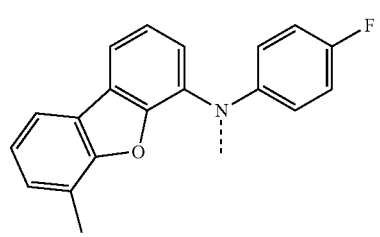
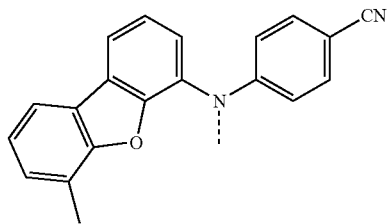
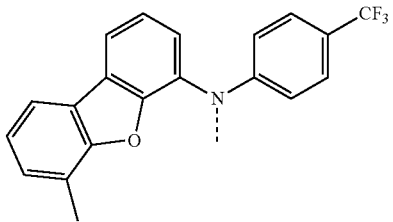
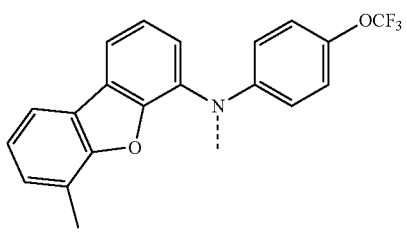
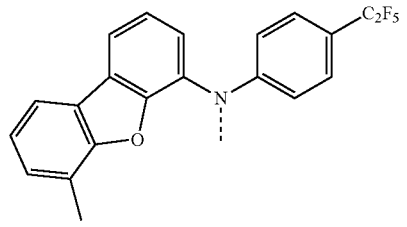
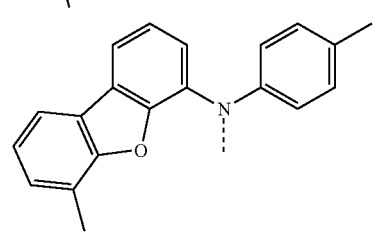
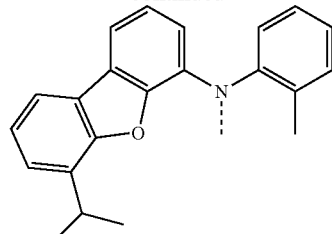
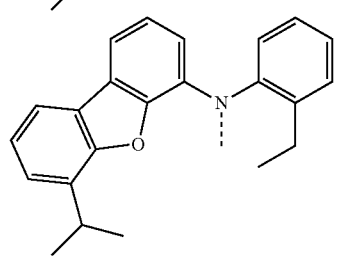
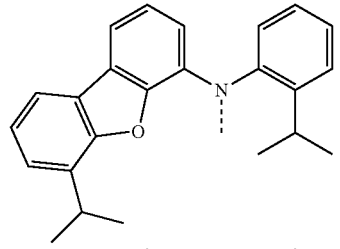
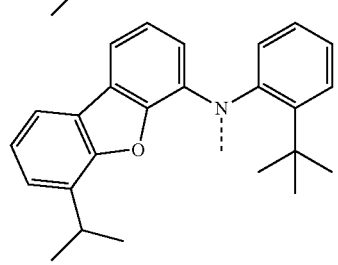
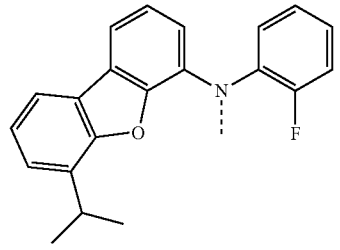
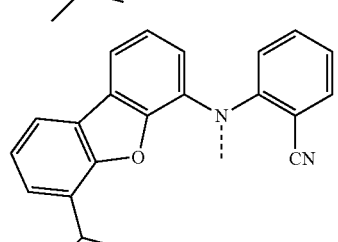
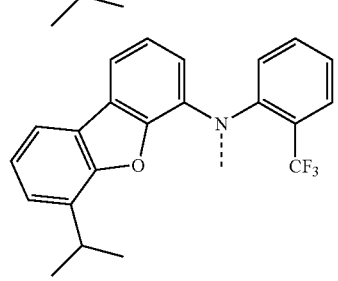

-continued
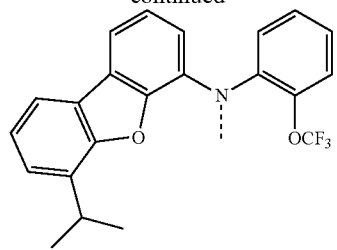
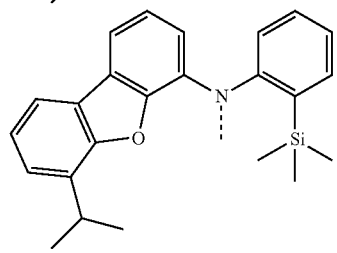
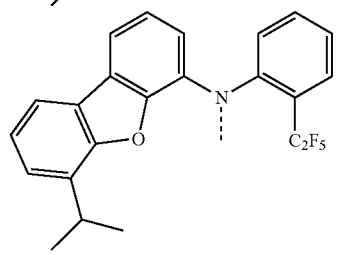
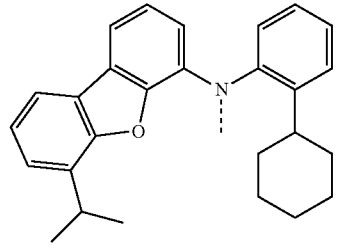
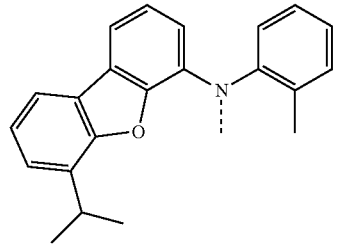
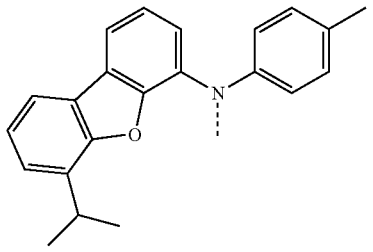
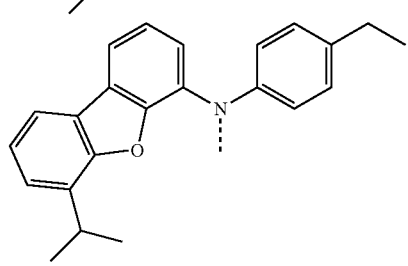
-continued
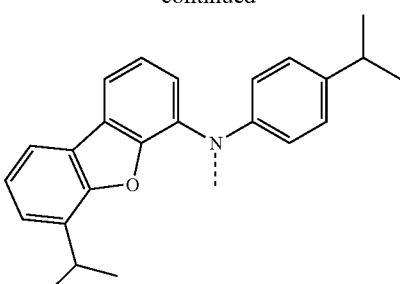
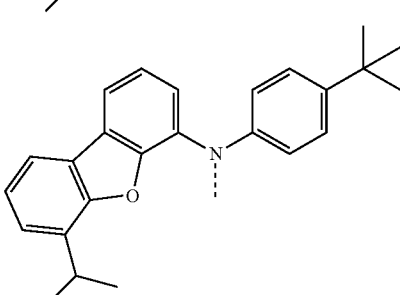
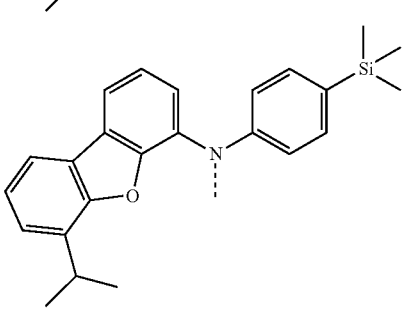
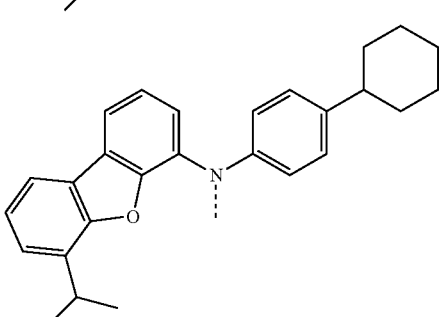
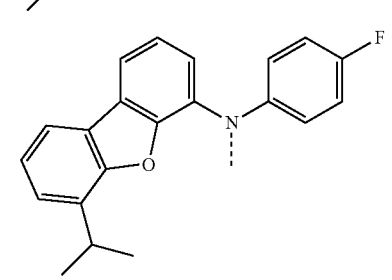
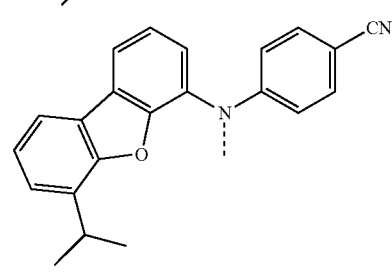

49
-continued
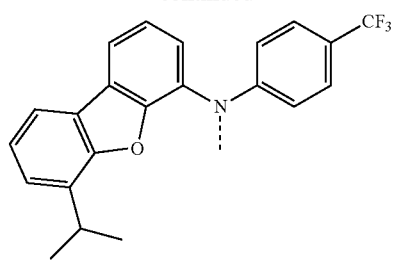
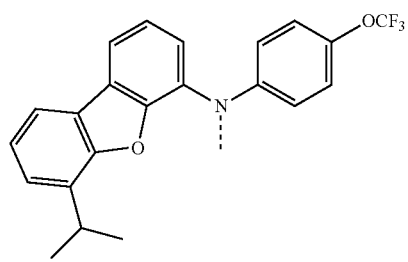
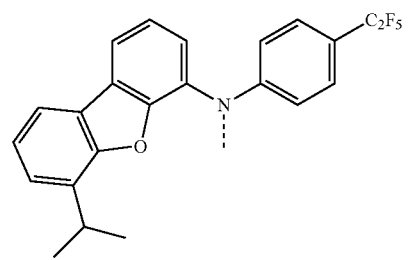
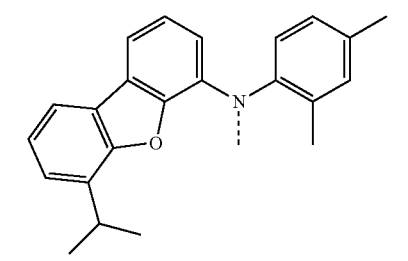
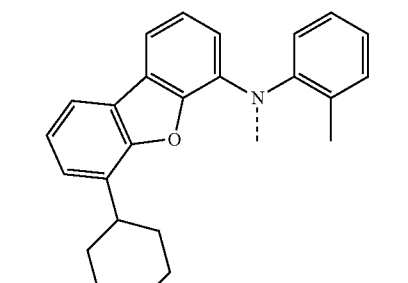
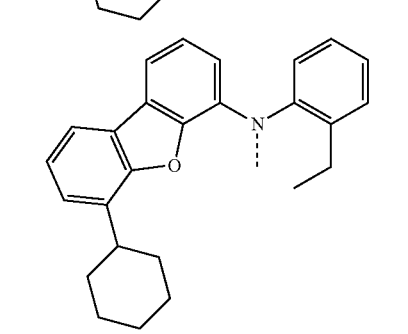
50
-continued
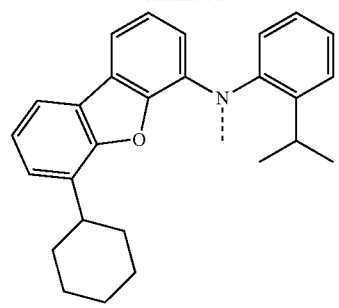
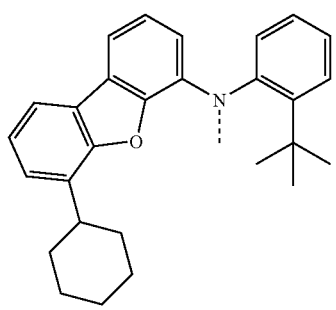
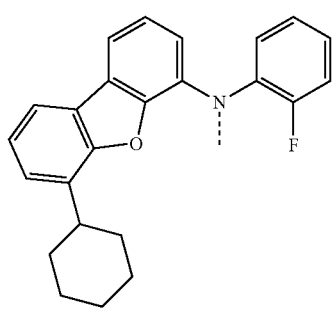
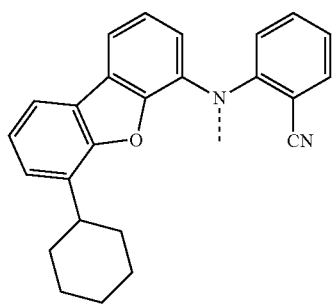
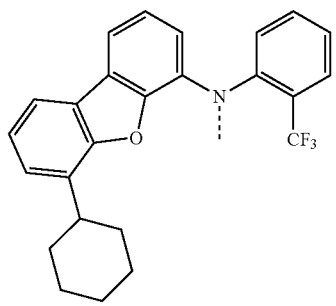

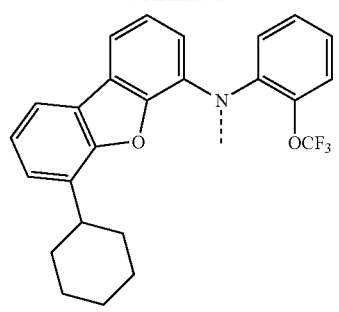
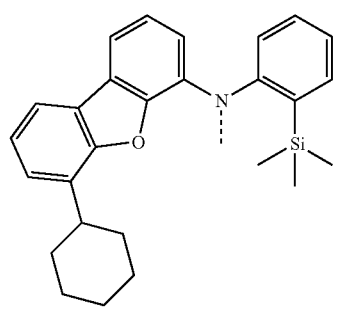
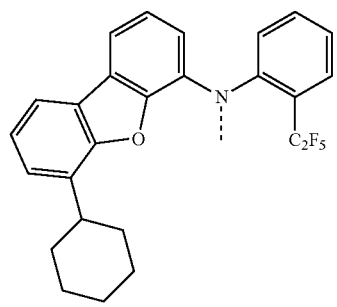
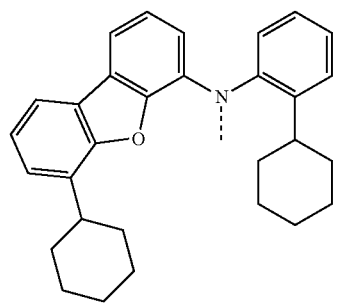
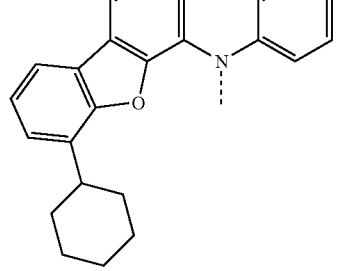
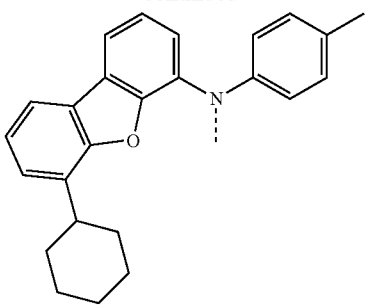
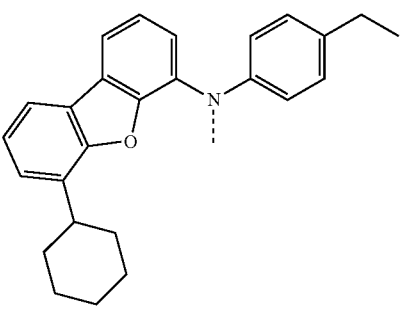
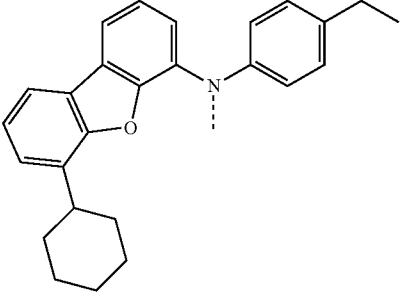
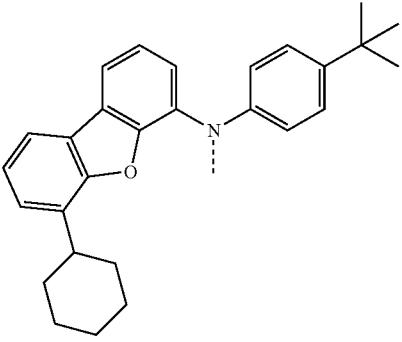
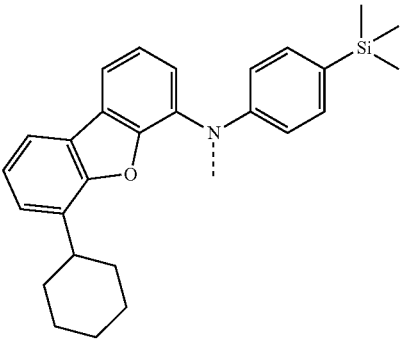

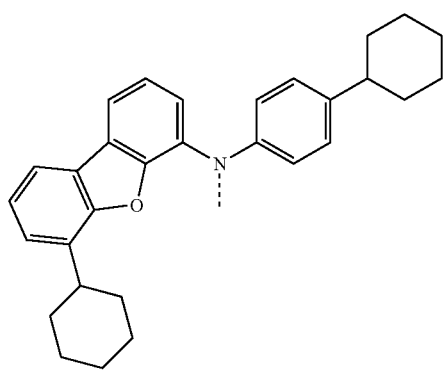
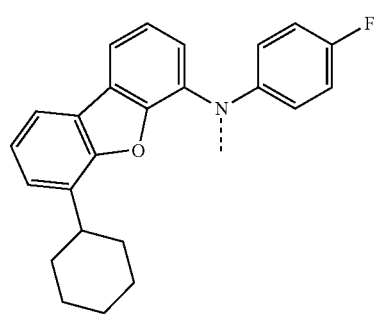
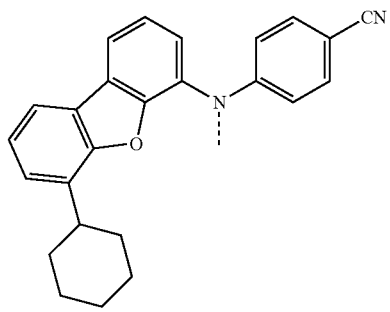
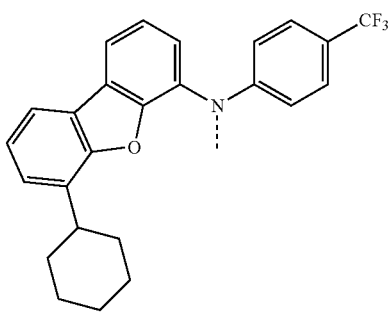
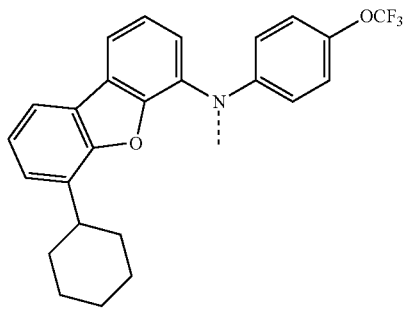
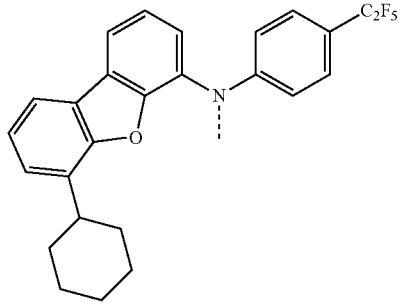
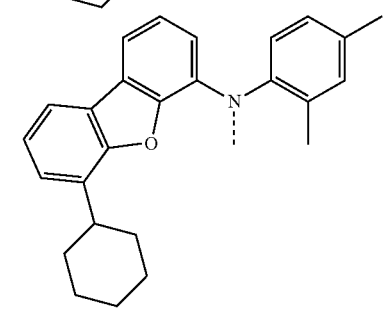
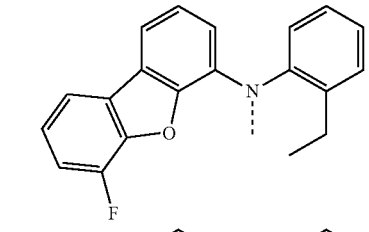
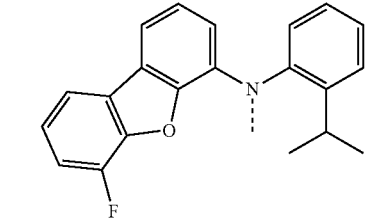
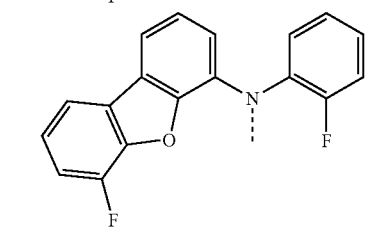
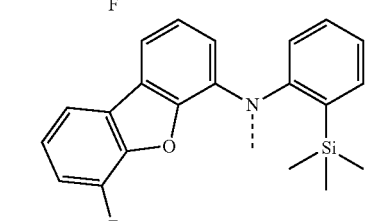
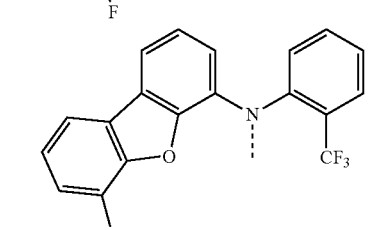

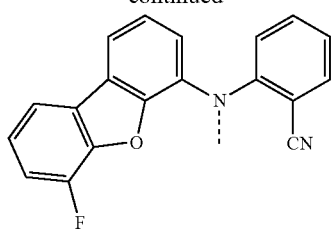
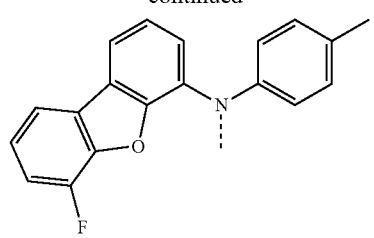
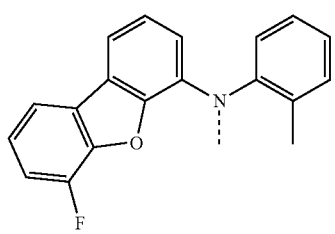
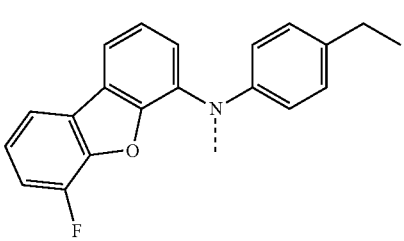
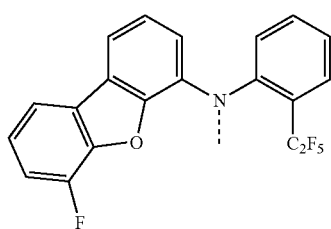
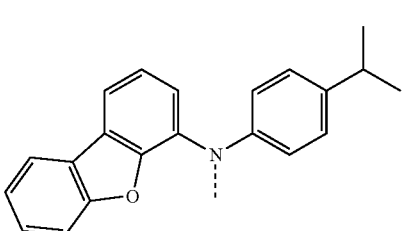
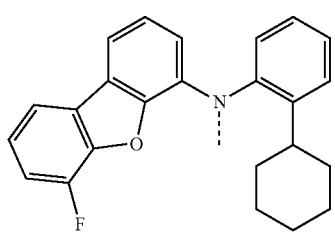
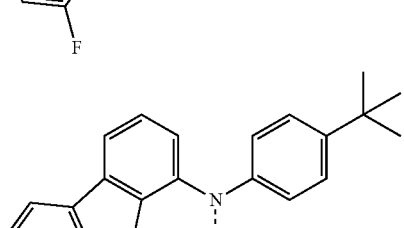
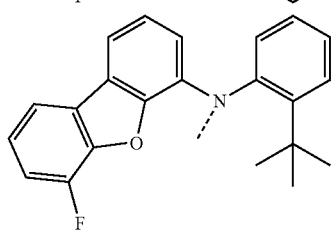
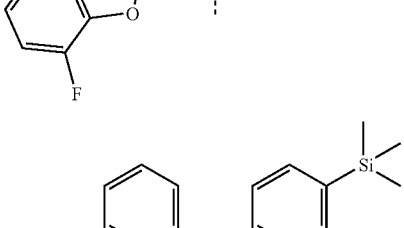
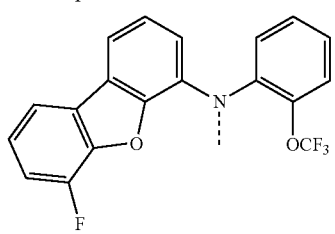
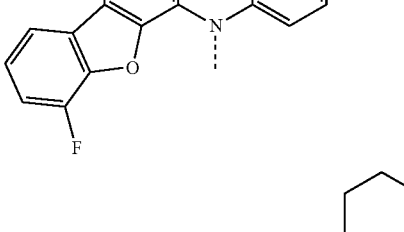
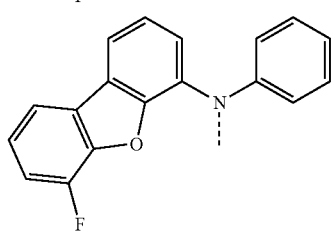
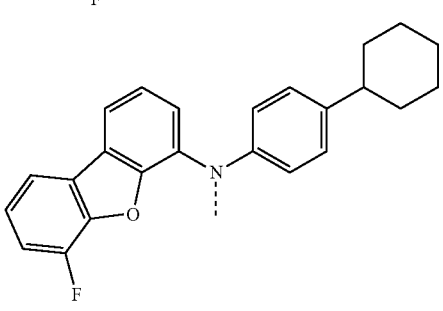

-continued
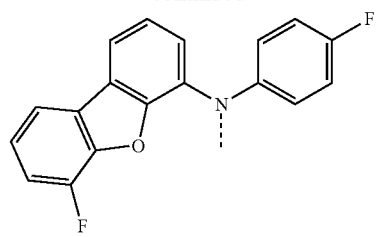
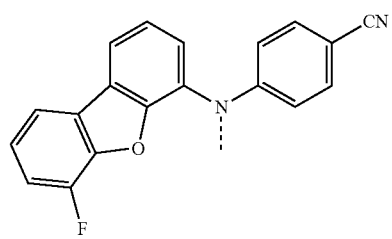
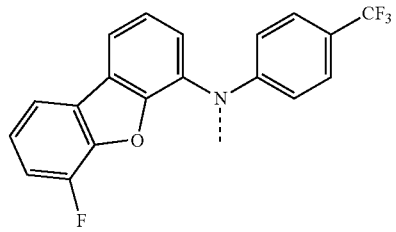
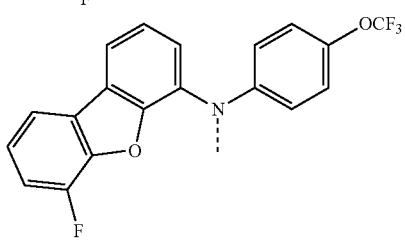
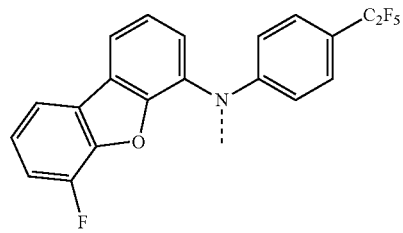
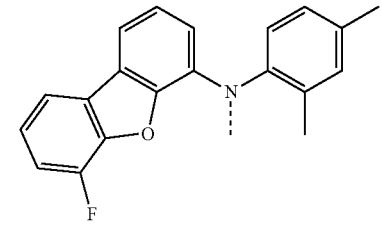
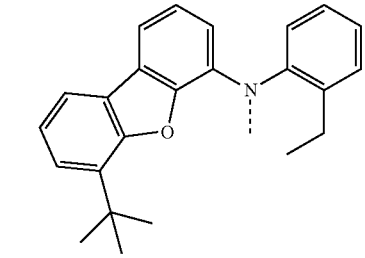
-continued
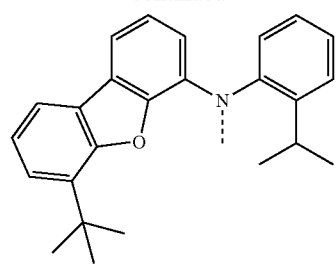
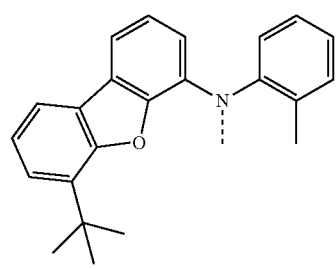
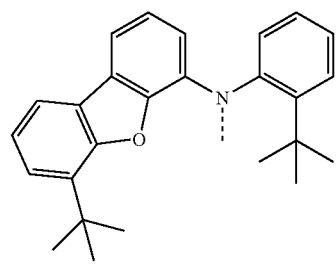
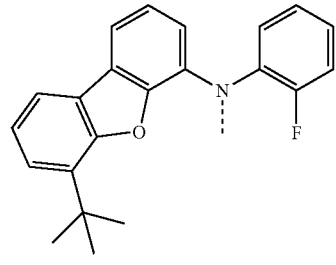
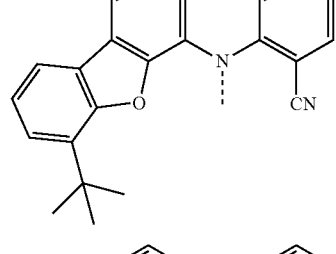
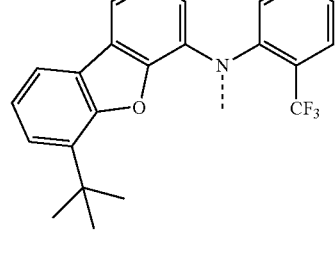

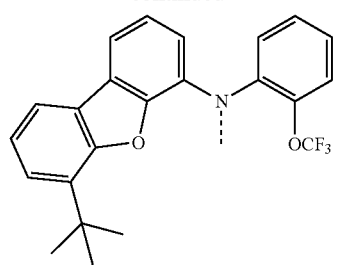
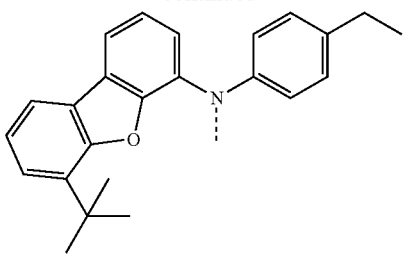
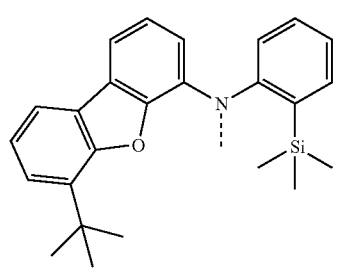
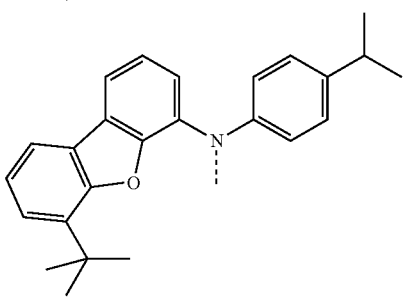
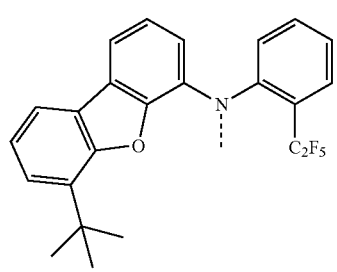
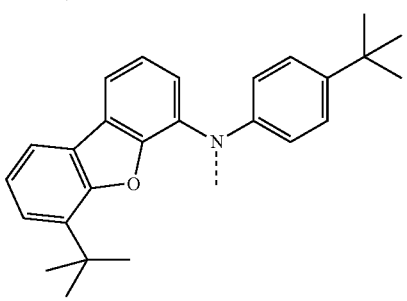
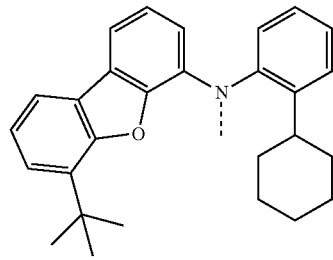
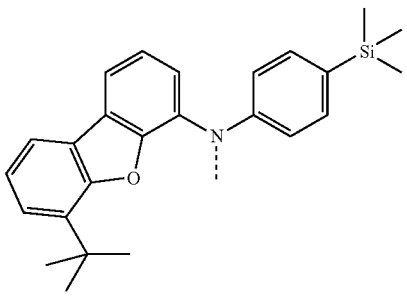
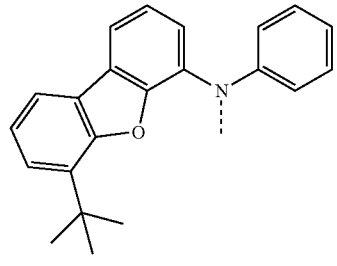
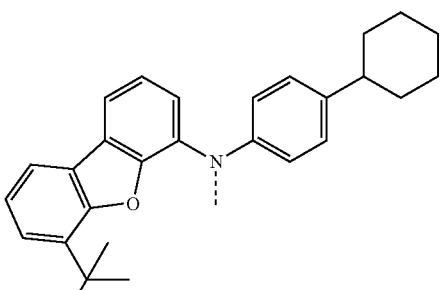
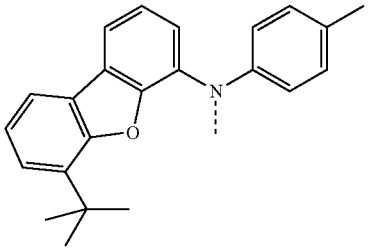
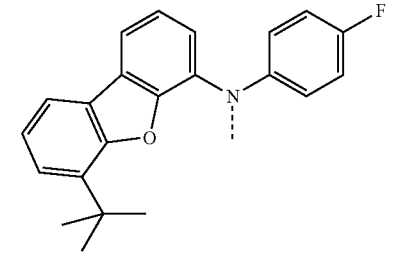

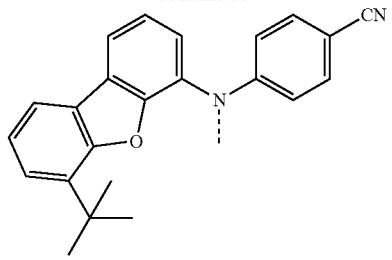
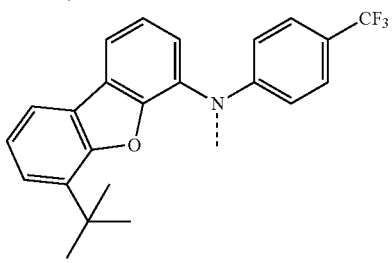
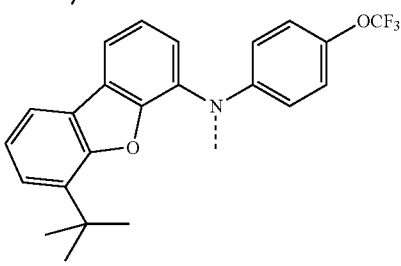
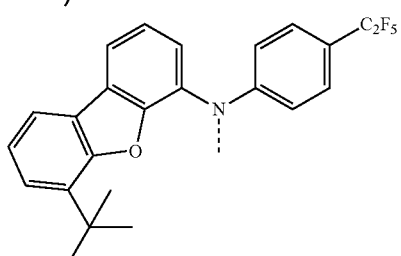
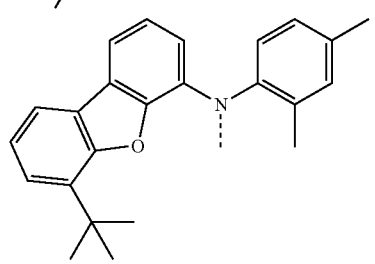
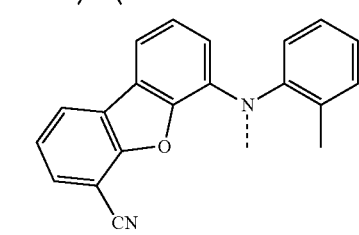
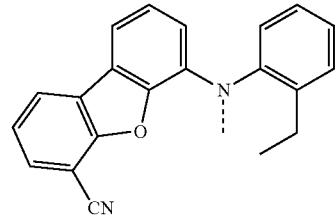
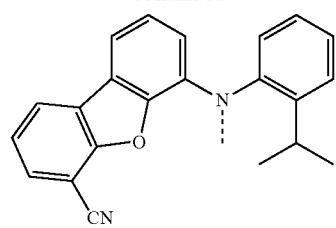
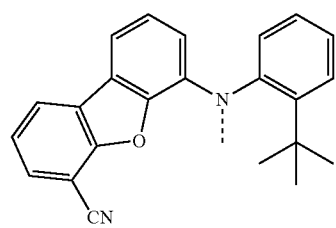
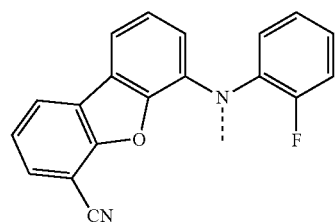
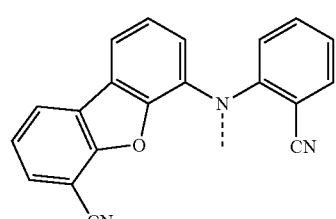
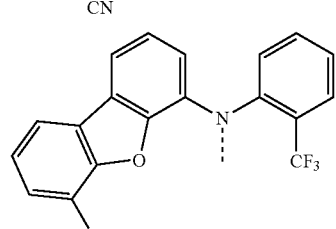
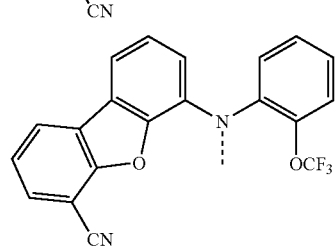
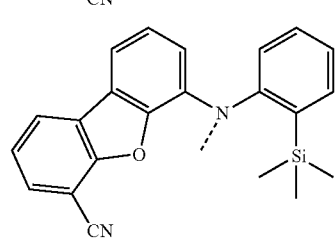

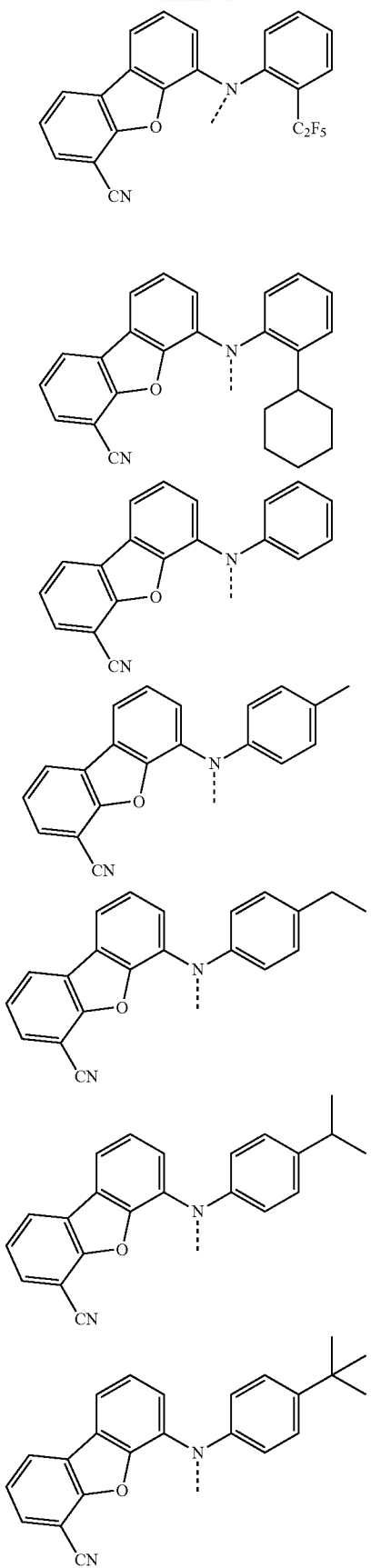
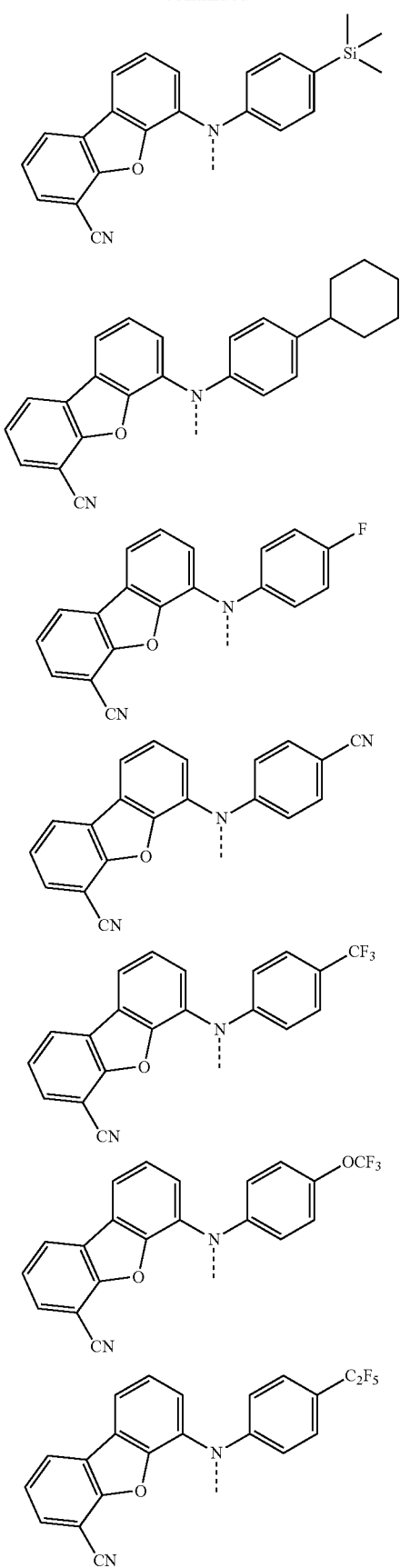

-continued
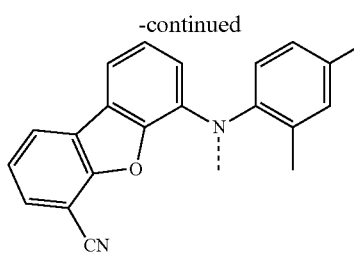
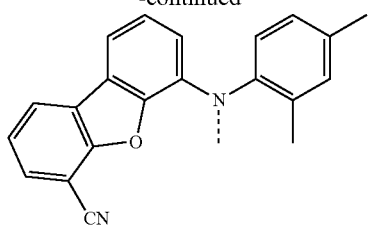
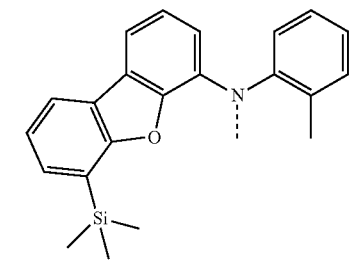
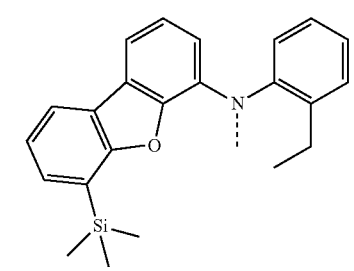
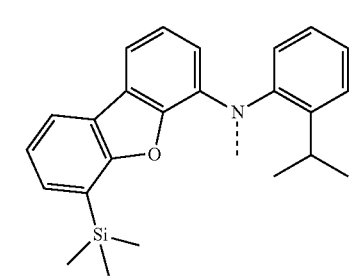
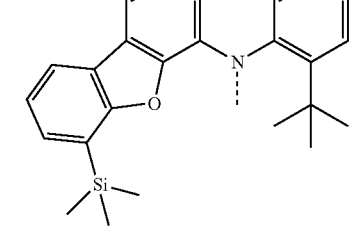
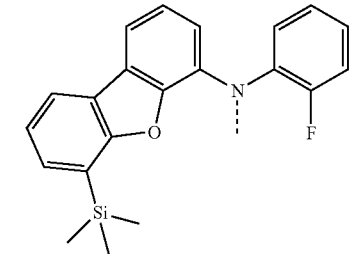
-continued
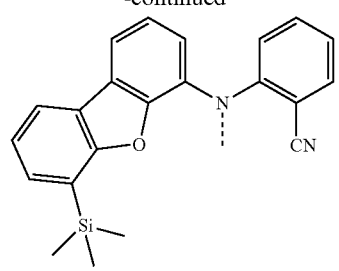
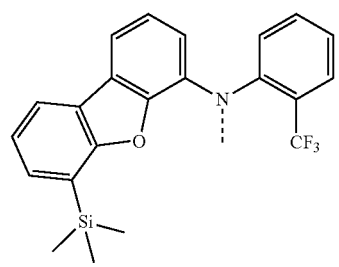
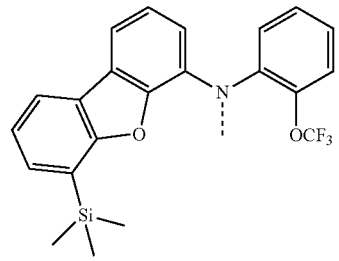
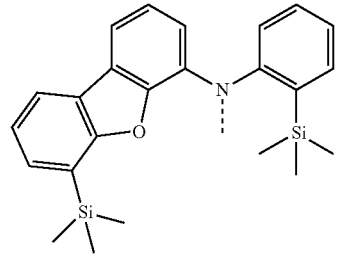
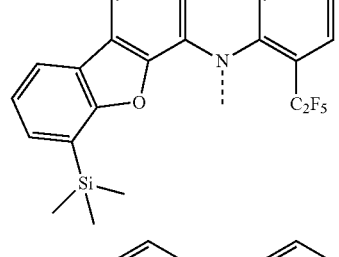
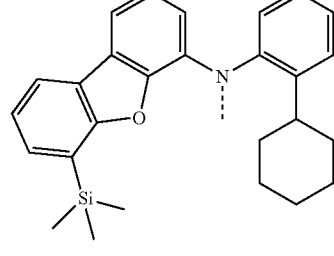

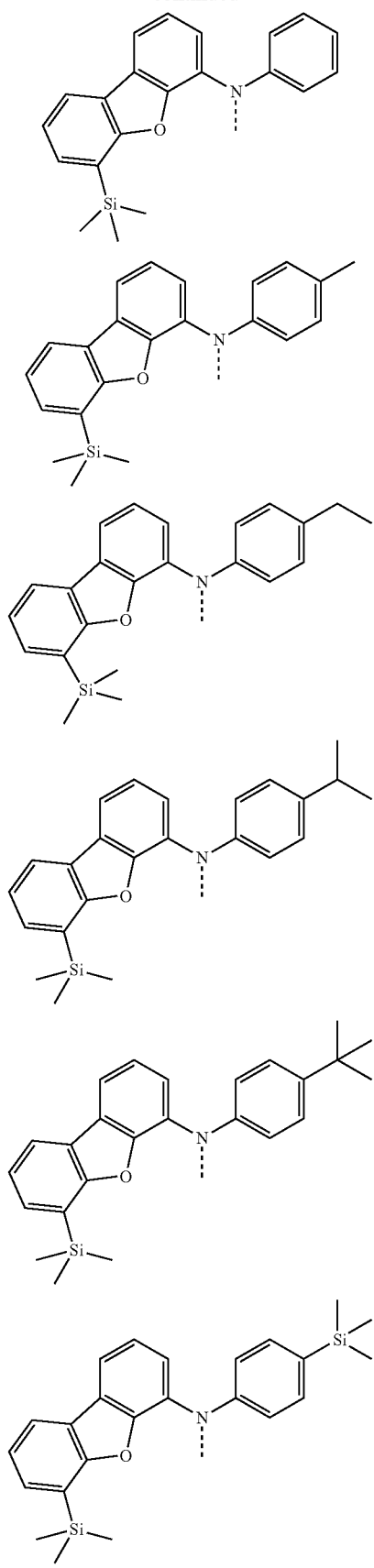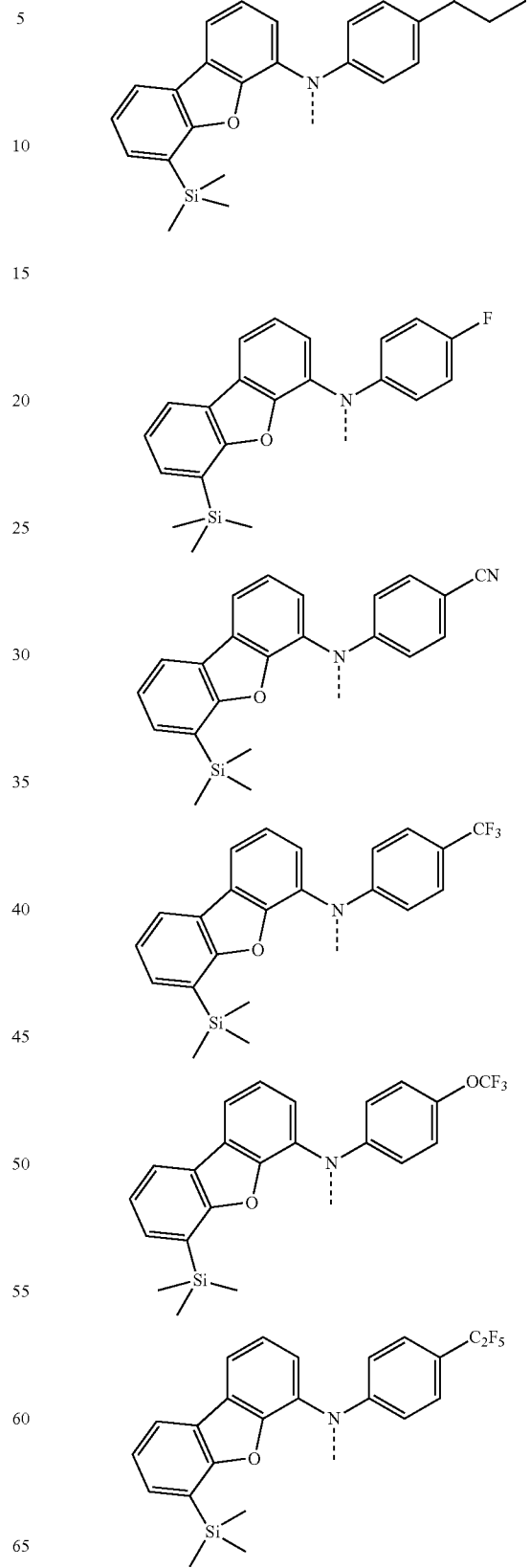

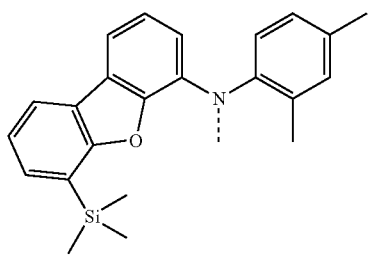
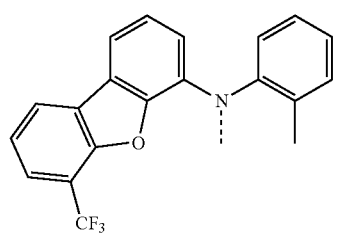
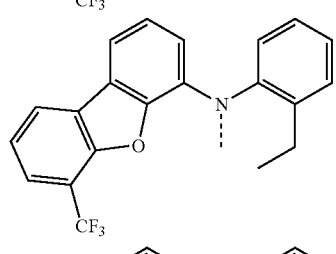
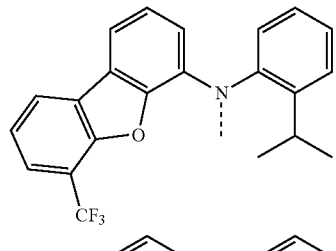
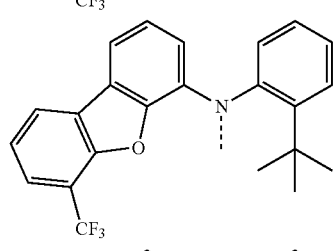
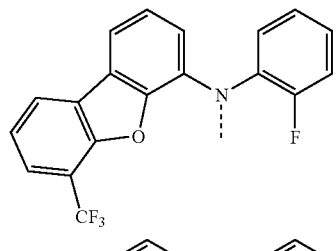
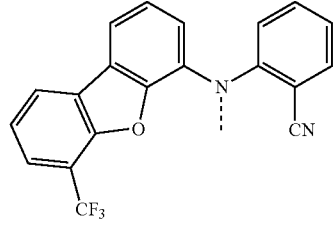
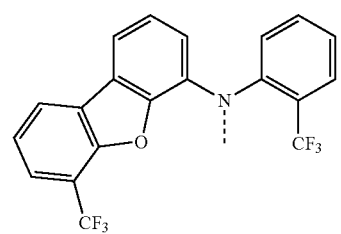
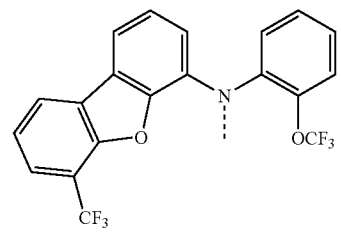
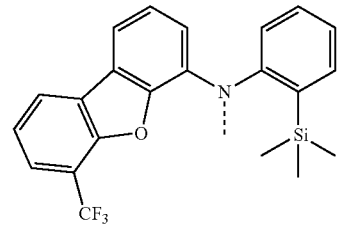
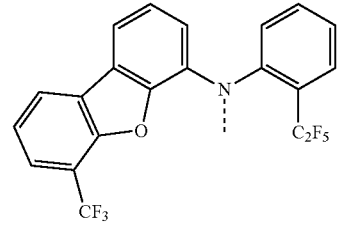
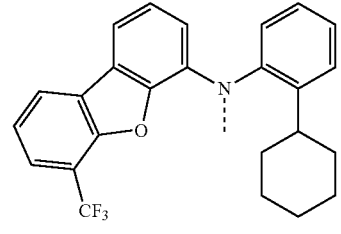
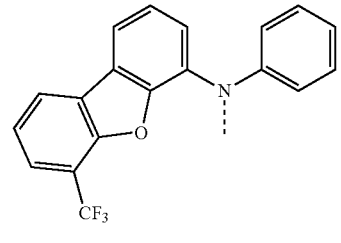
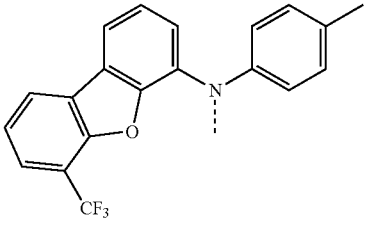

71
-continued
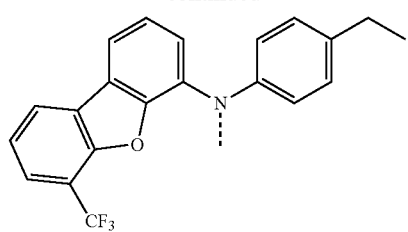
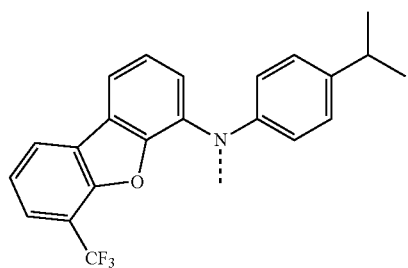
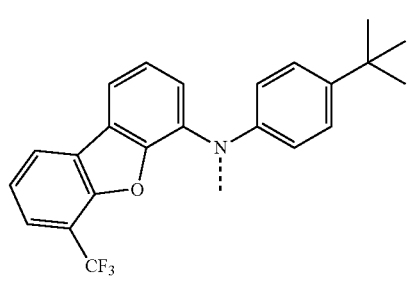
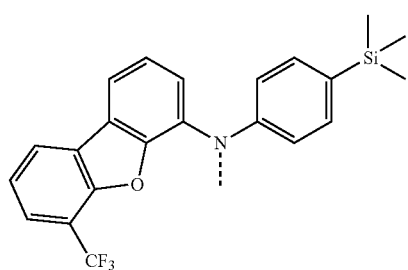
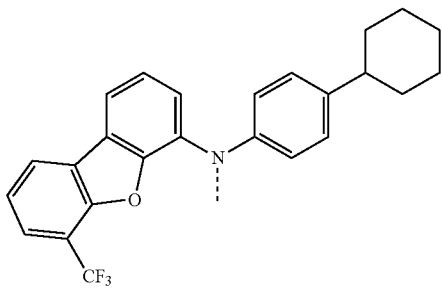
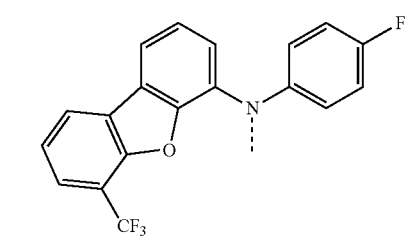
72
-continued
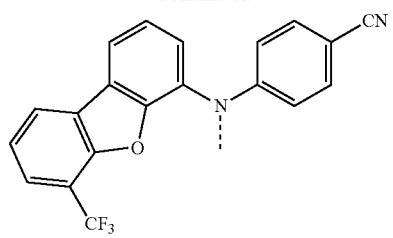
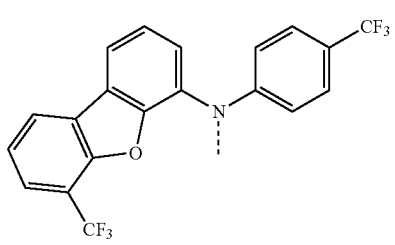
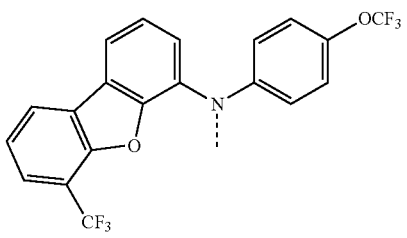
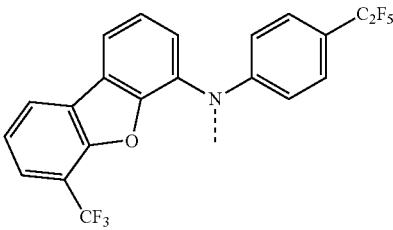
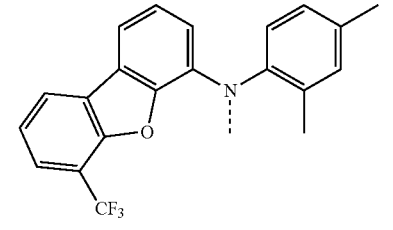
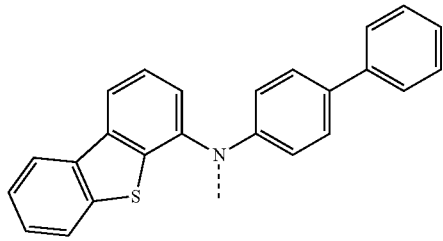
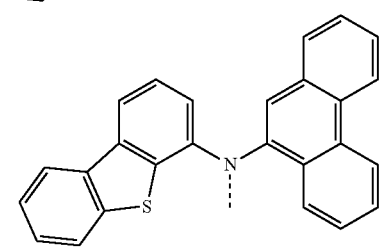

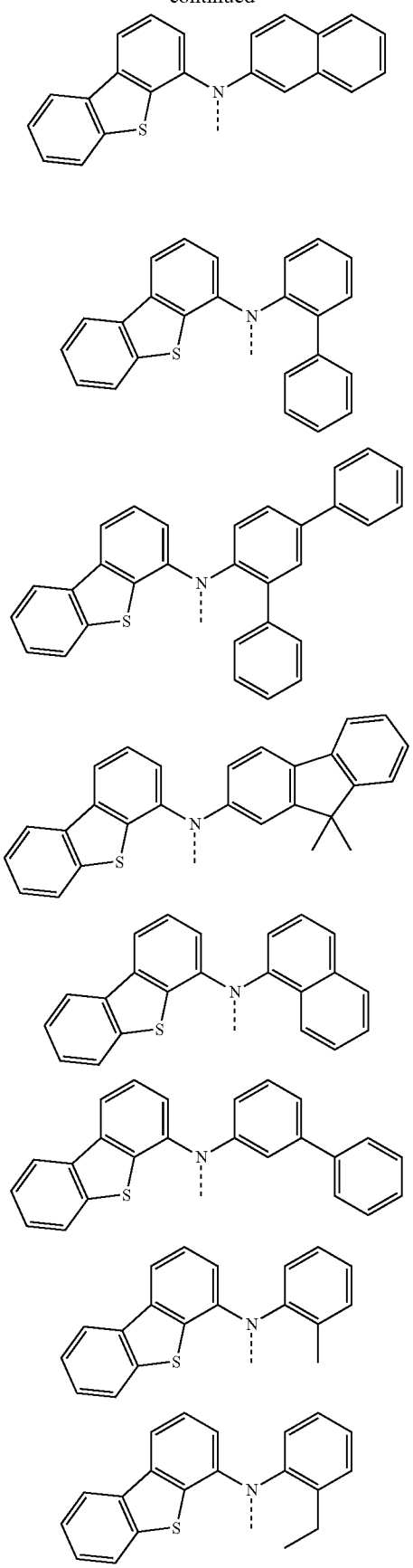
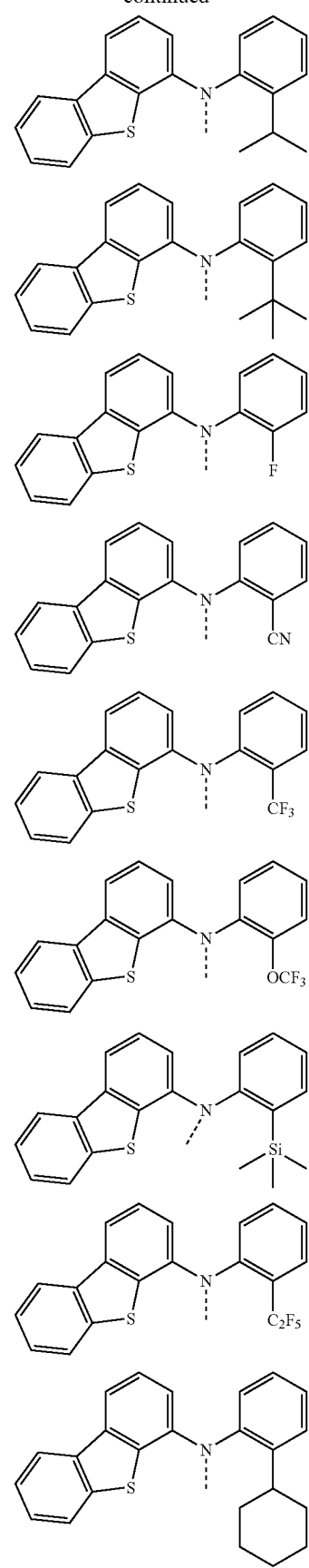

-continued
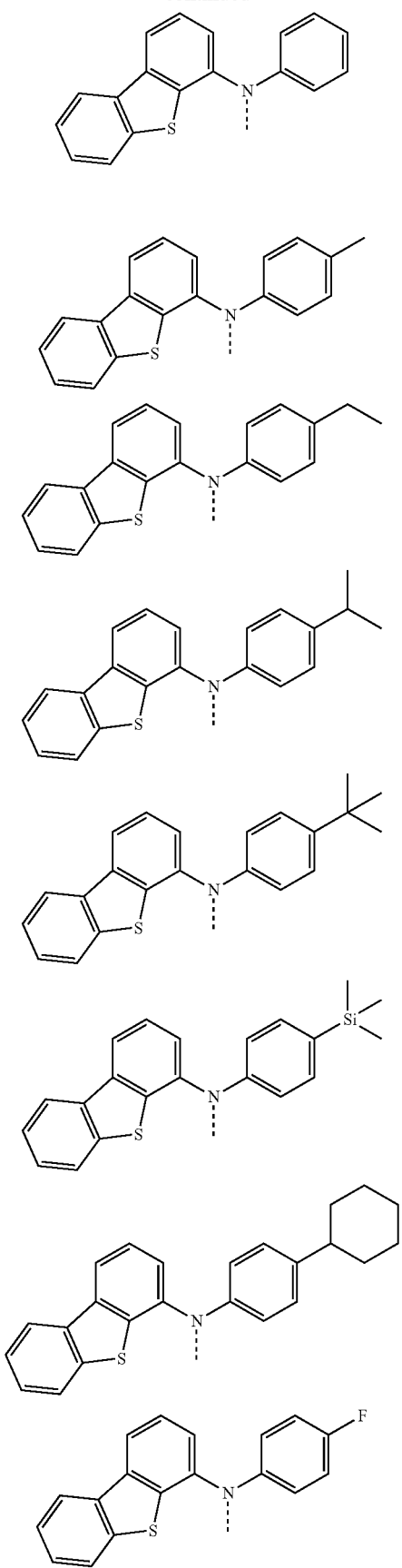
-continued
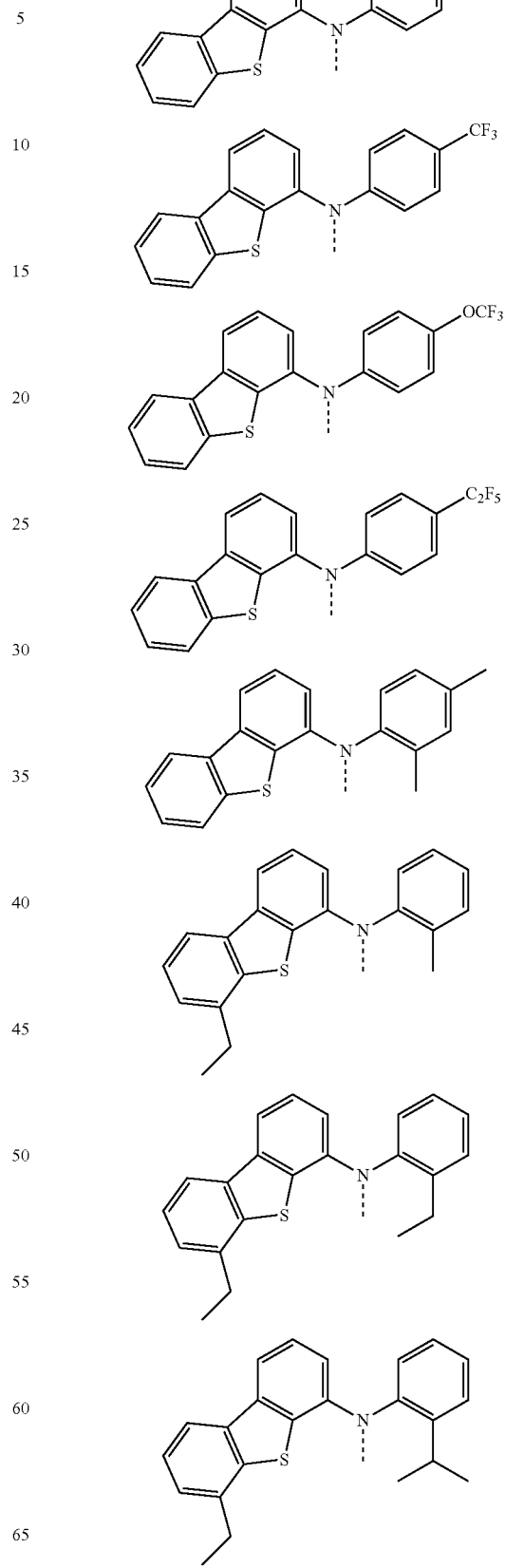

-continued
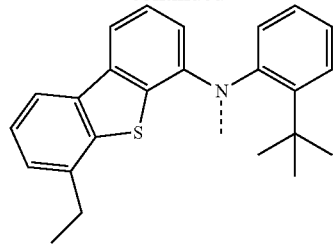
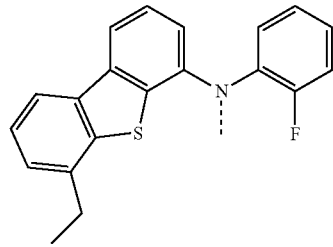
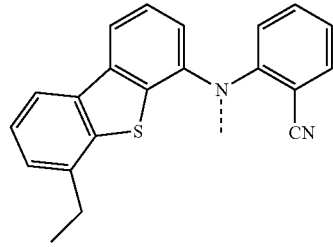
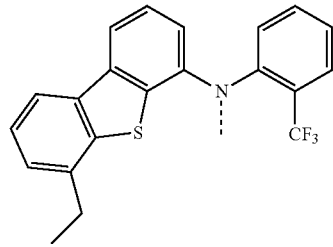
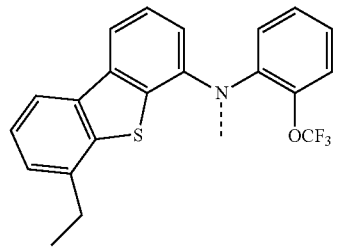
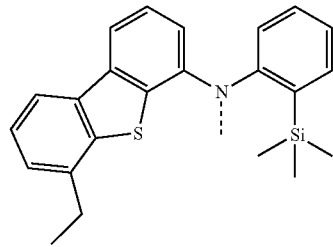
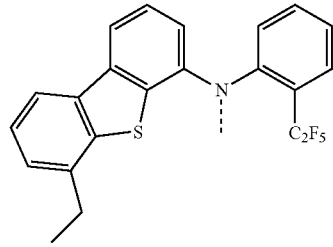
-continued
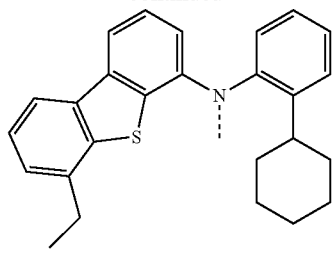
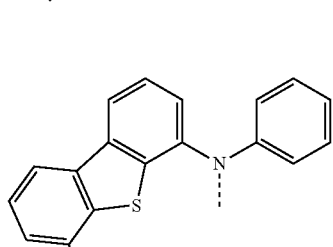
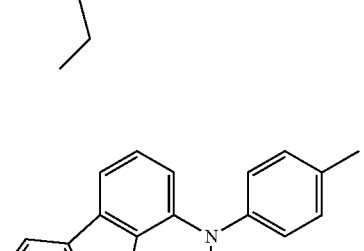
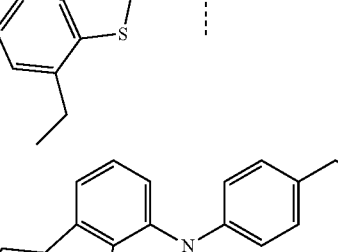
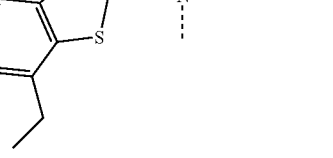
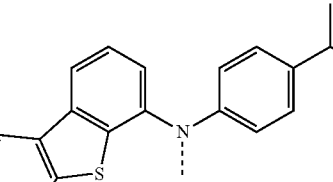
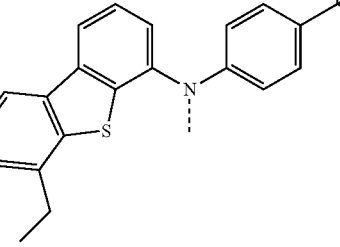

79 -continued
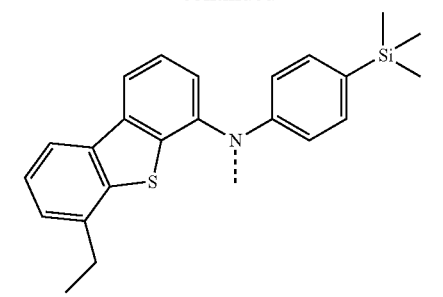
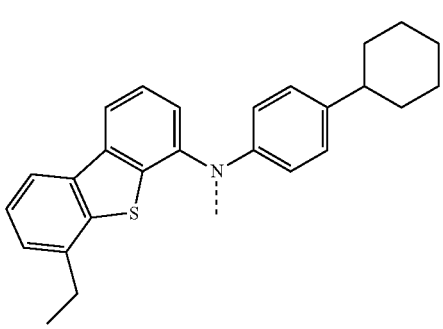
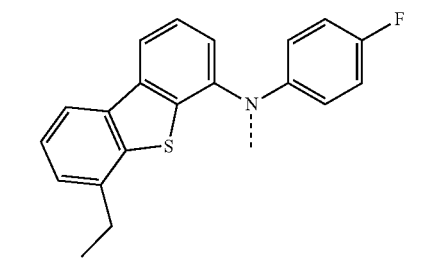
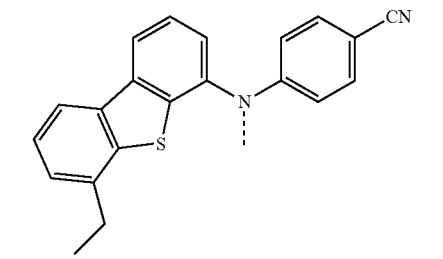
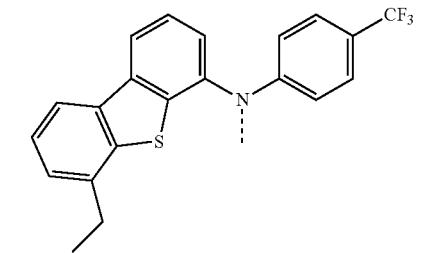
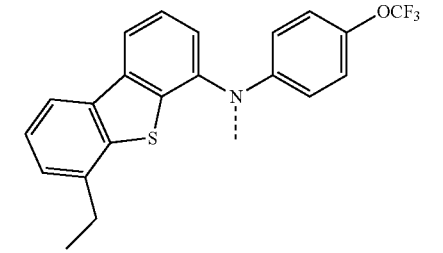
80 -continued
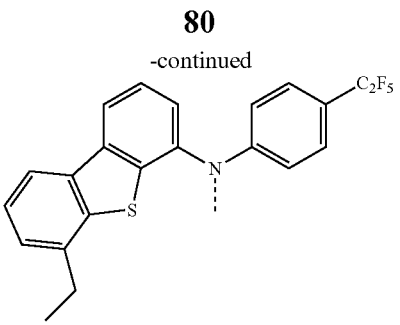
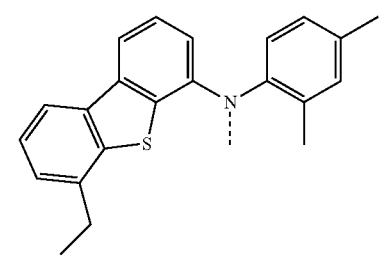
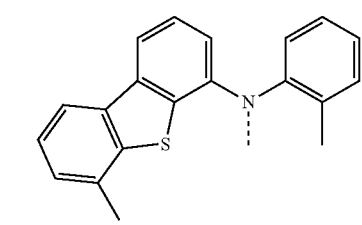
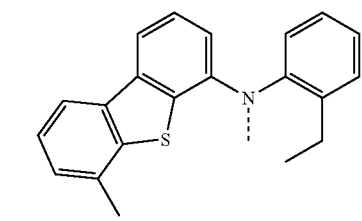
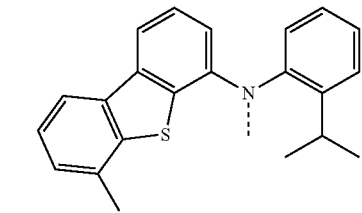
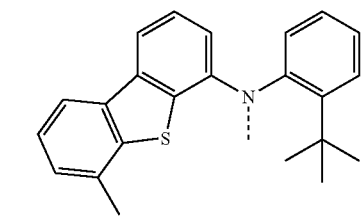
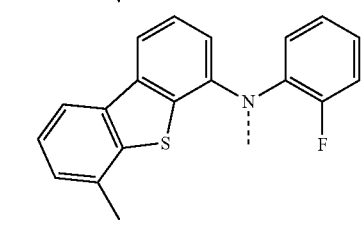

81
-continued
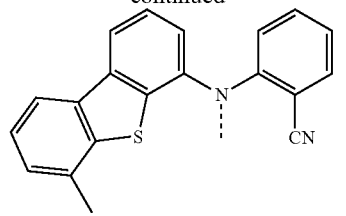
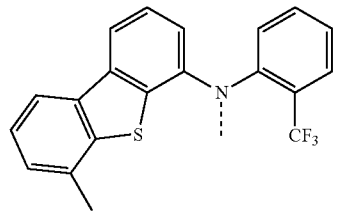
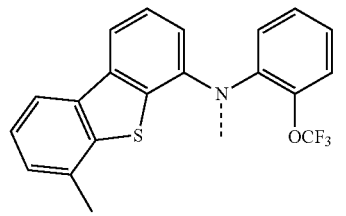
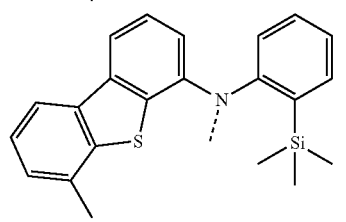
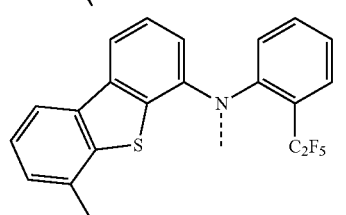
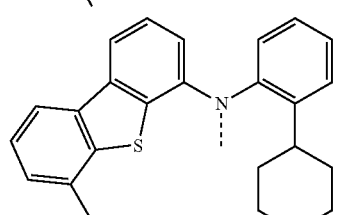
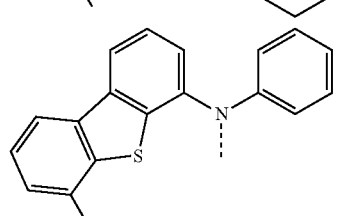
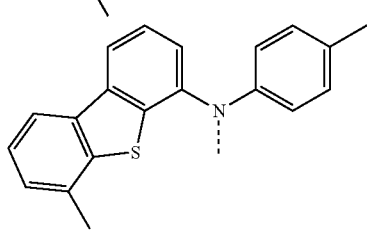
82
-continued
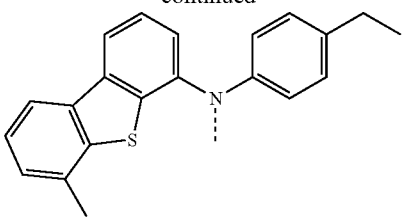
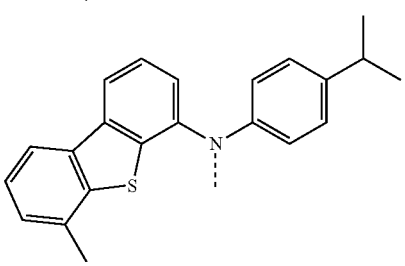
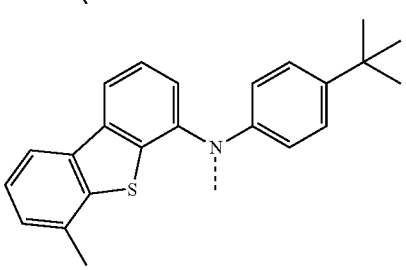
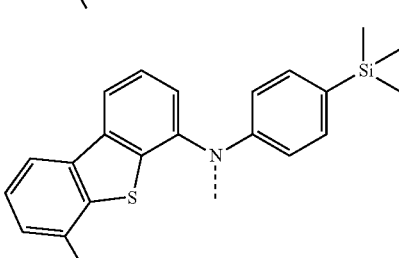
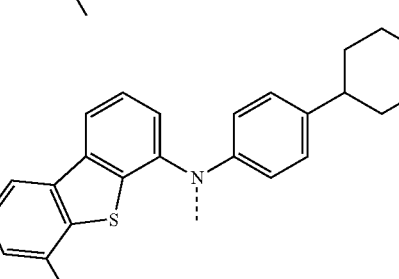
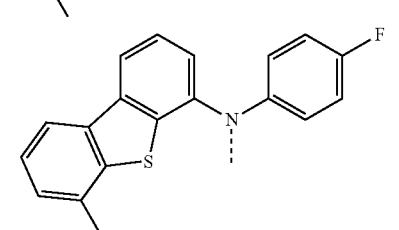
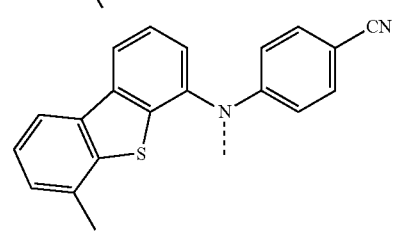

-continued
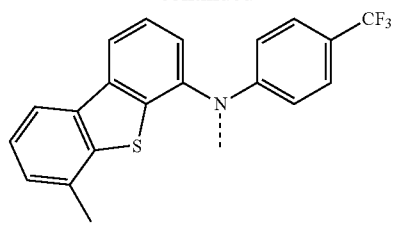
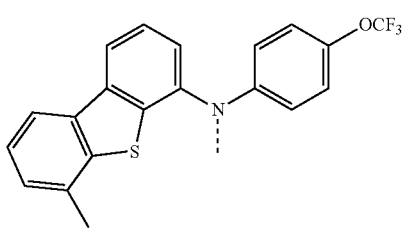
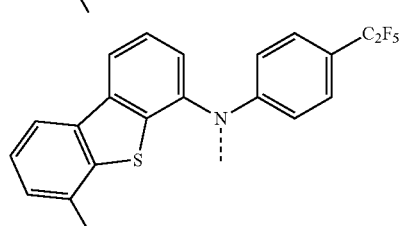
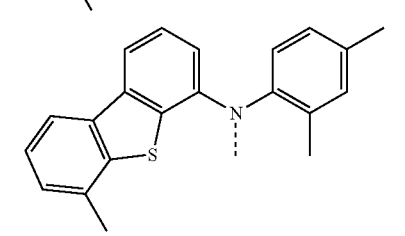
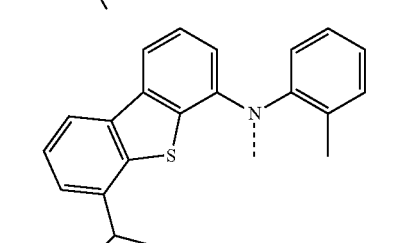
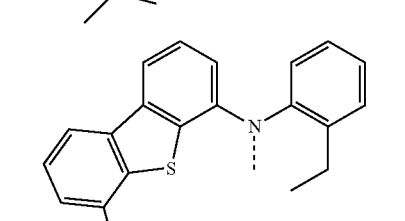
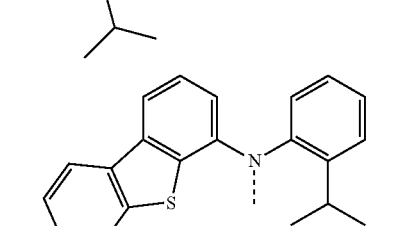
-continued
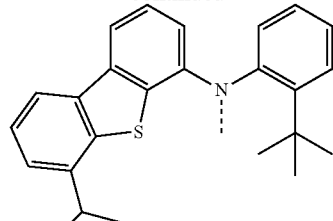
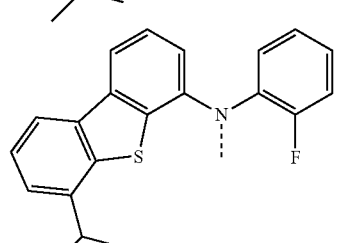
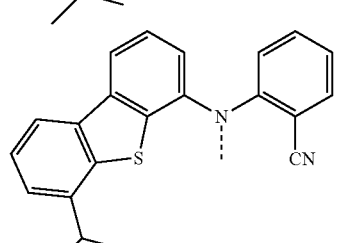
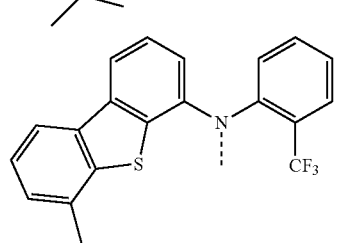
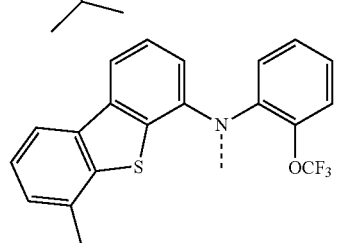
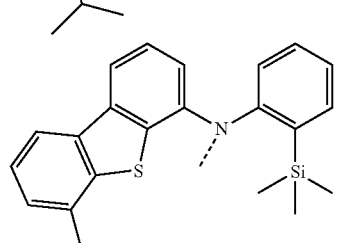
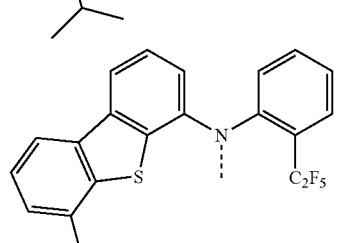

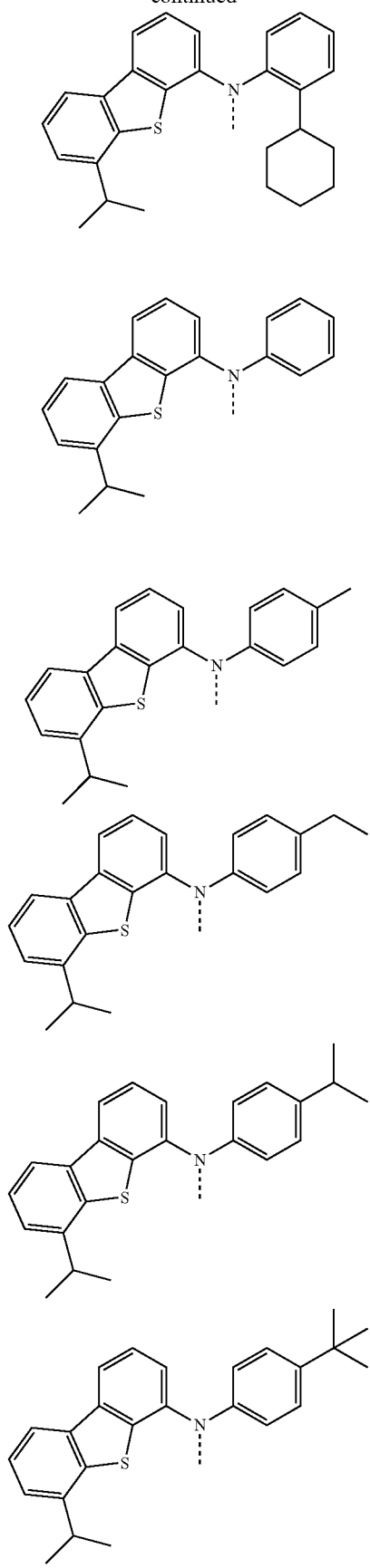
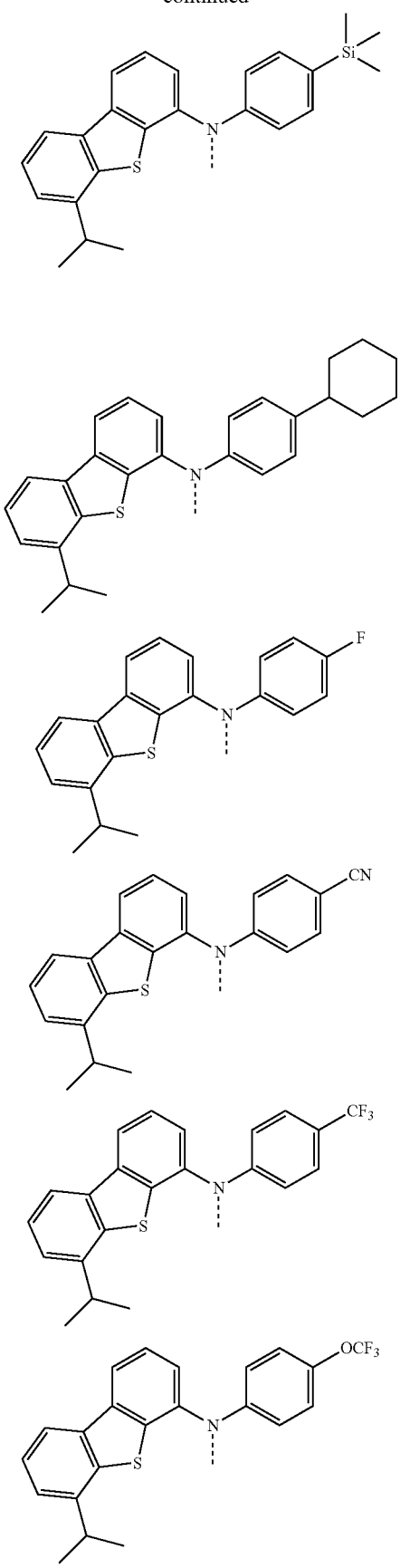

87
-continued
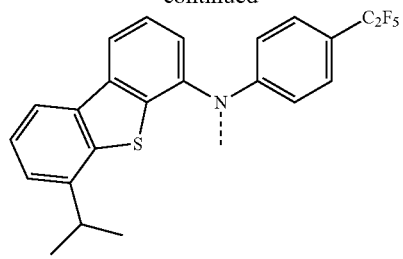
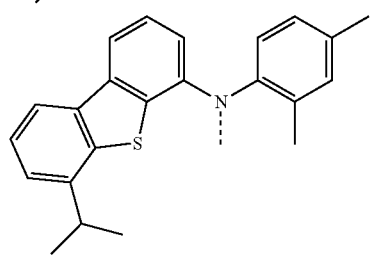
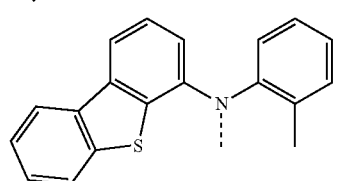
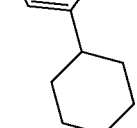
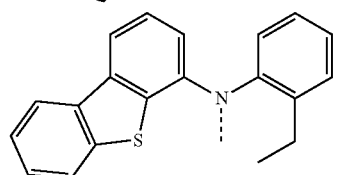
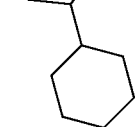
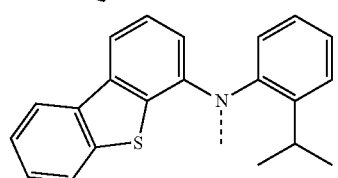
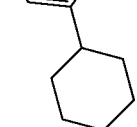
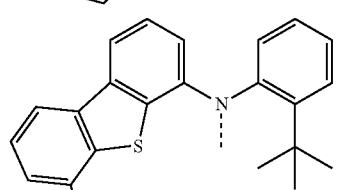
88
-continued
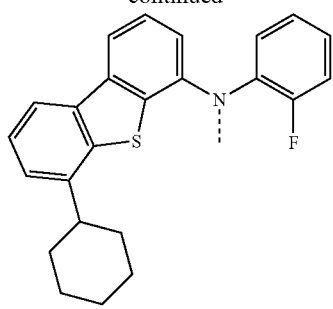
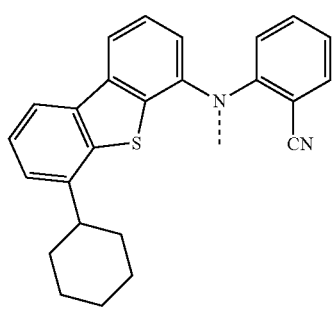
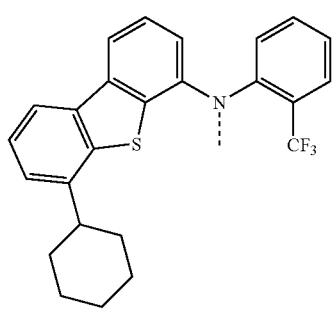
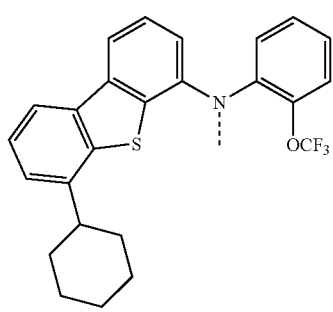
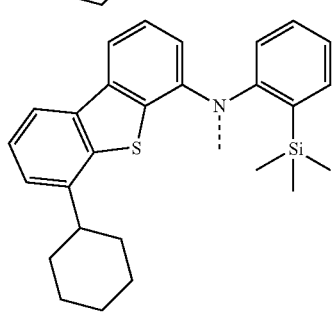

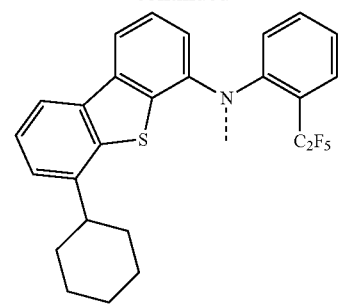
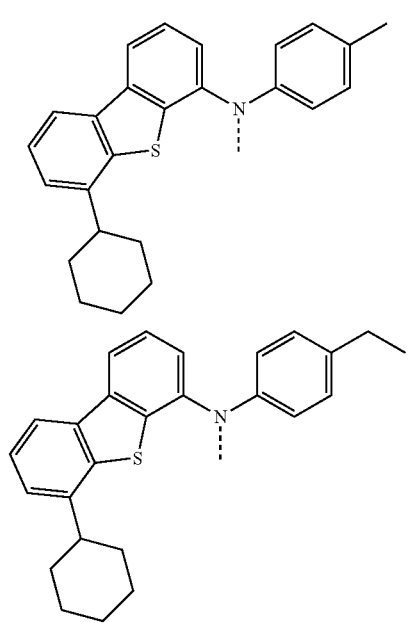
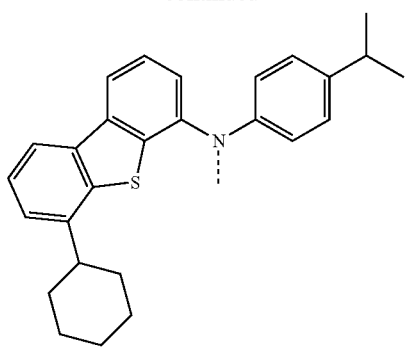
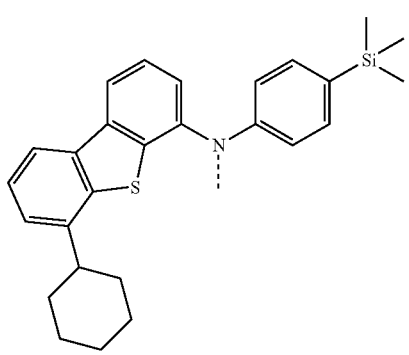
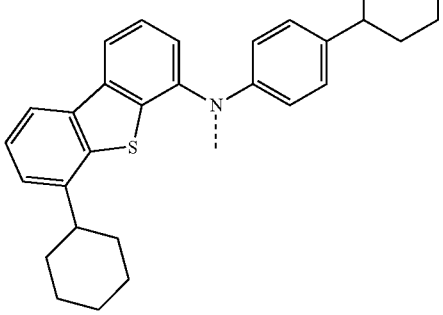
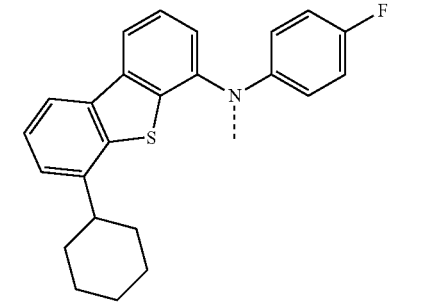

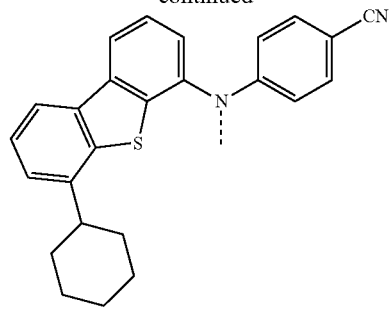
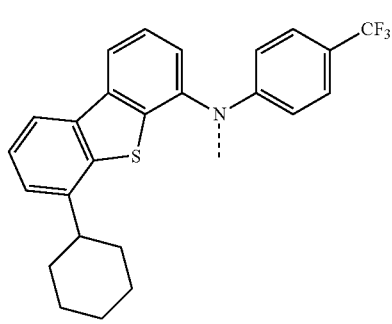
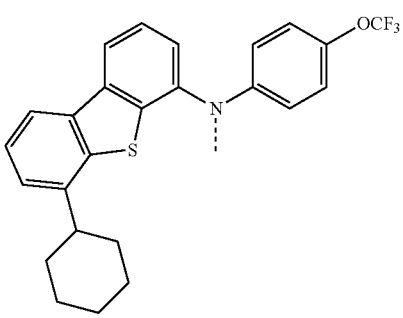
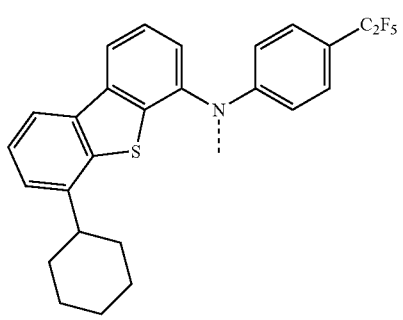
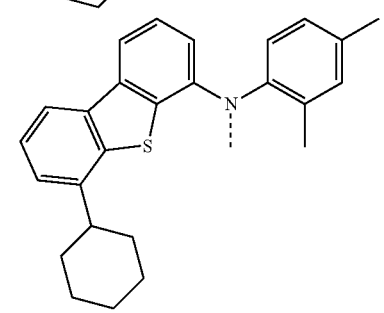
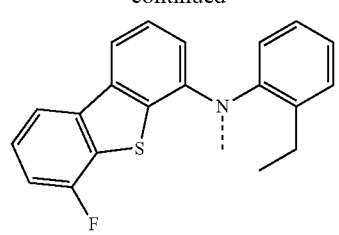
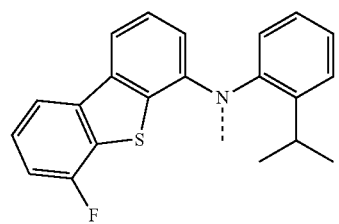
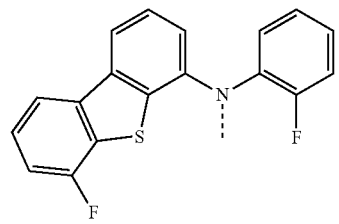
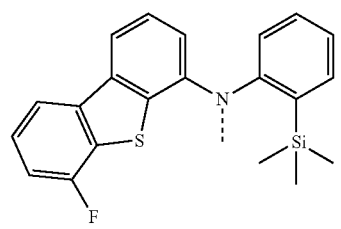
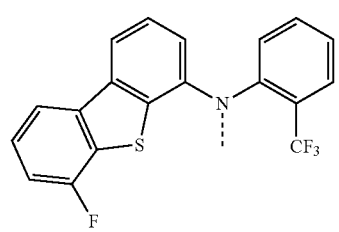
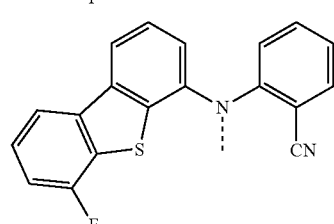
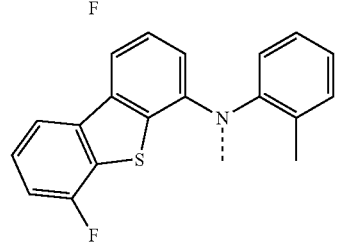

93
-continued
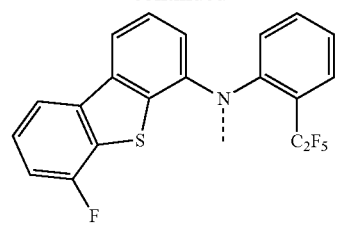
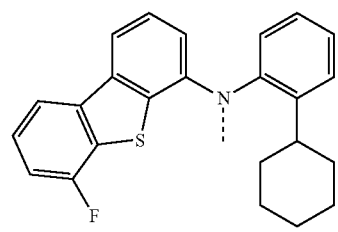
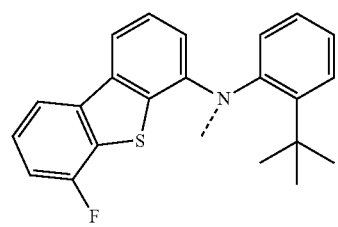
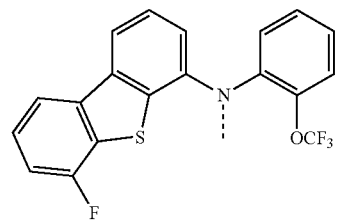
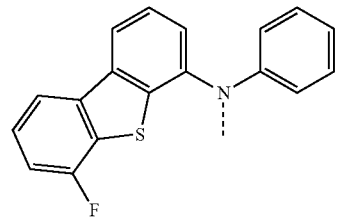
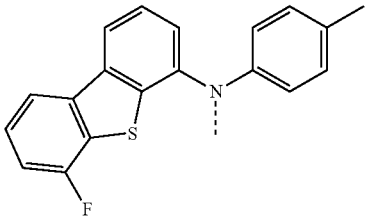
94
-continued
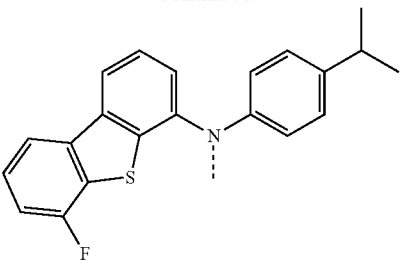
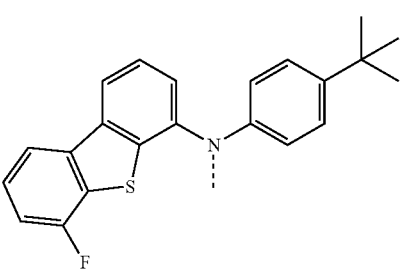
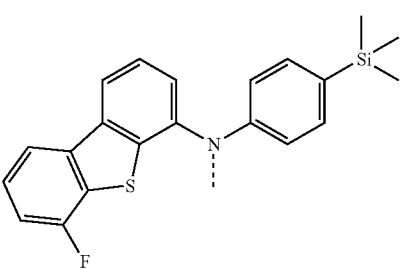
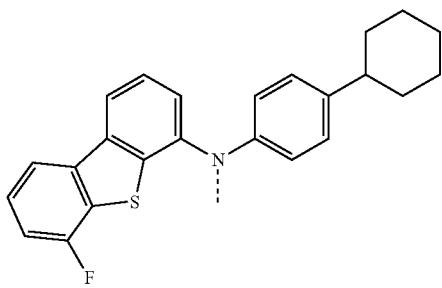
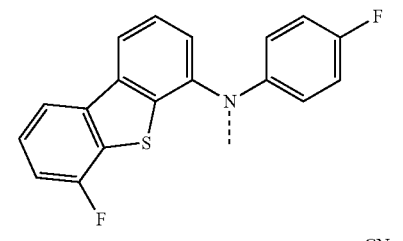
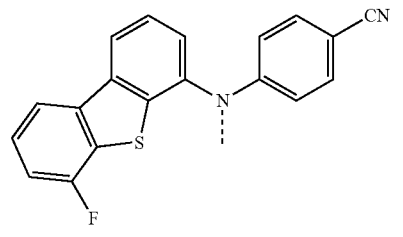

-continued
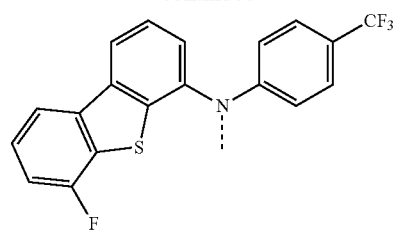
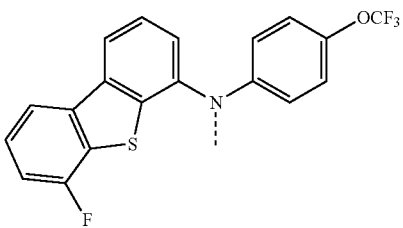
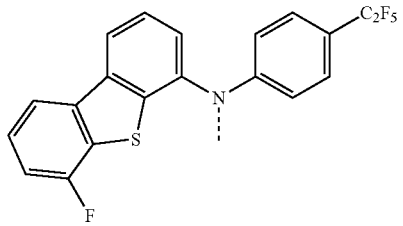
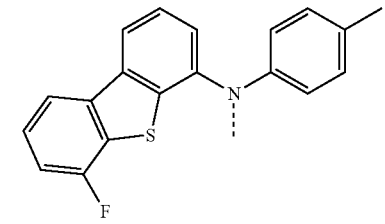
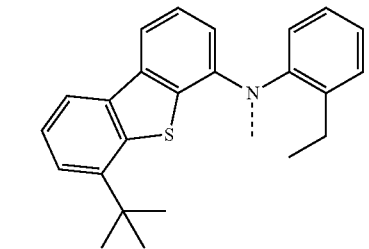
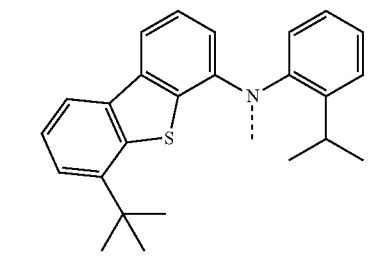
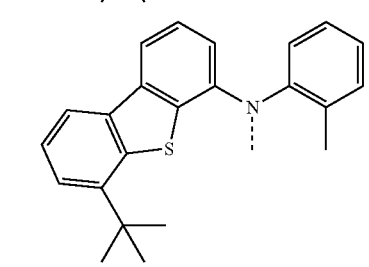
-continued
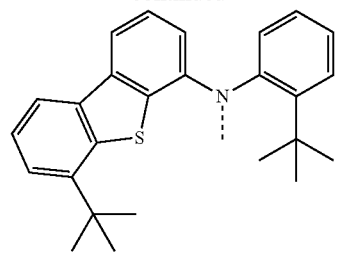
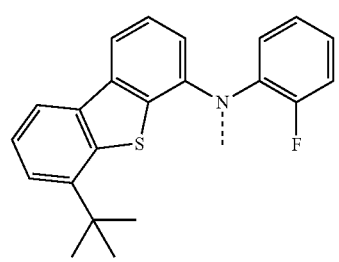
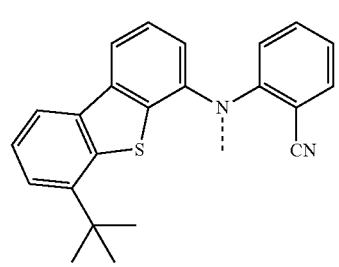
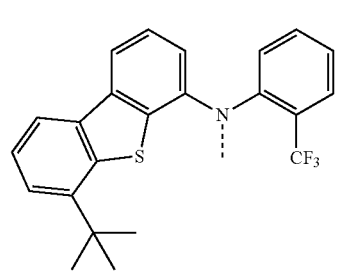
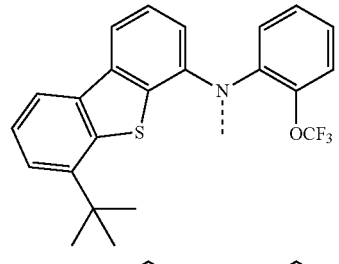
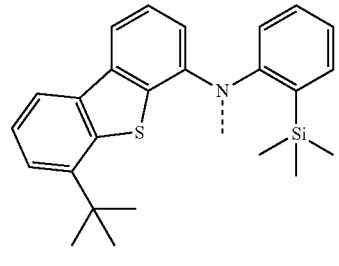

-continued
97
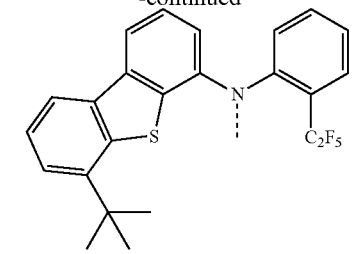
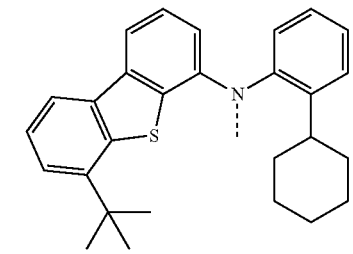
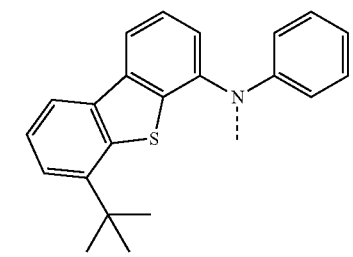
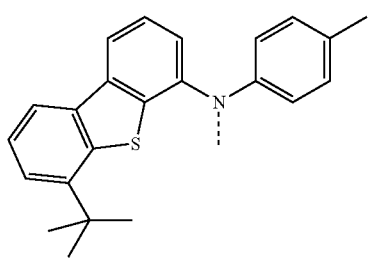
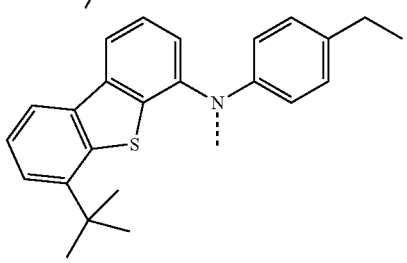
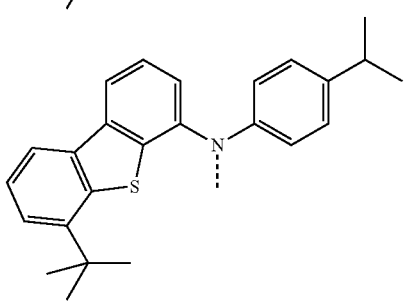
-continued
98
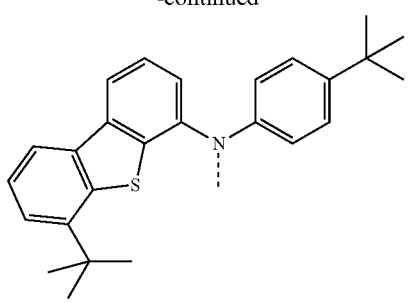
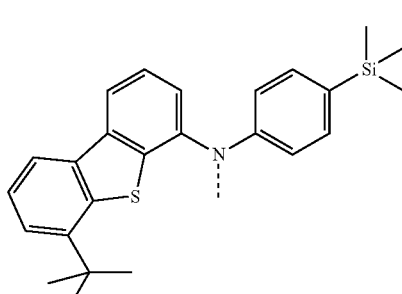
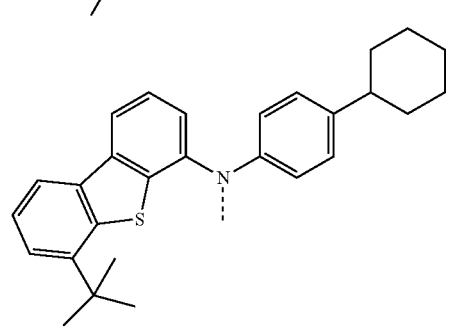
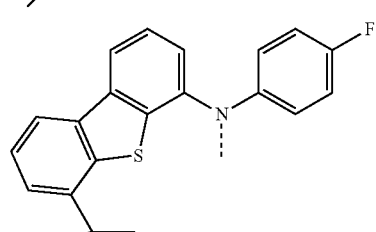
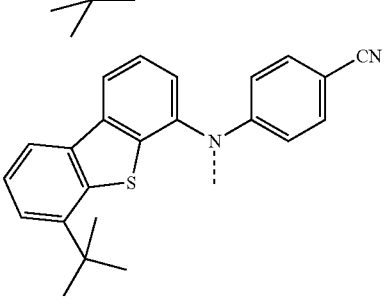
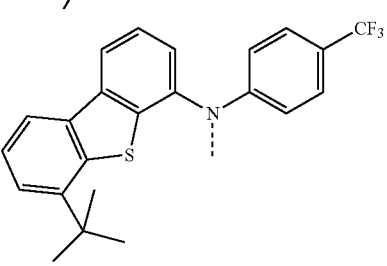

99
-continued
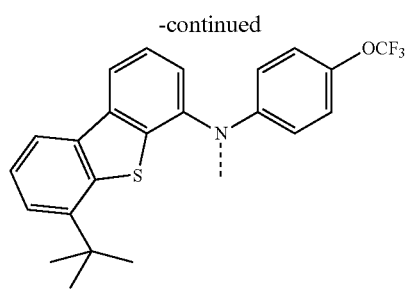
100
-continued
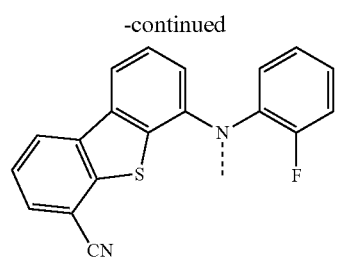

101
-continued
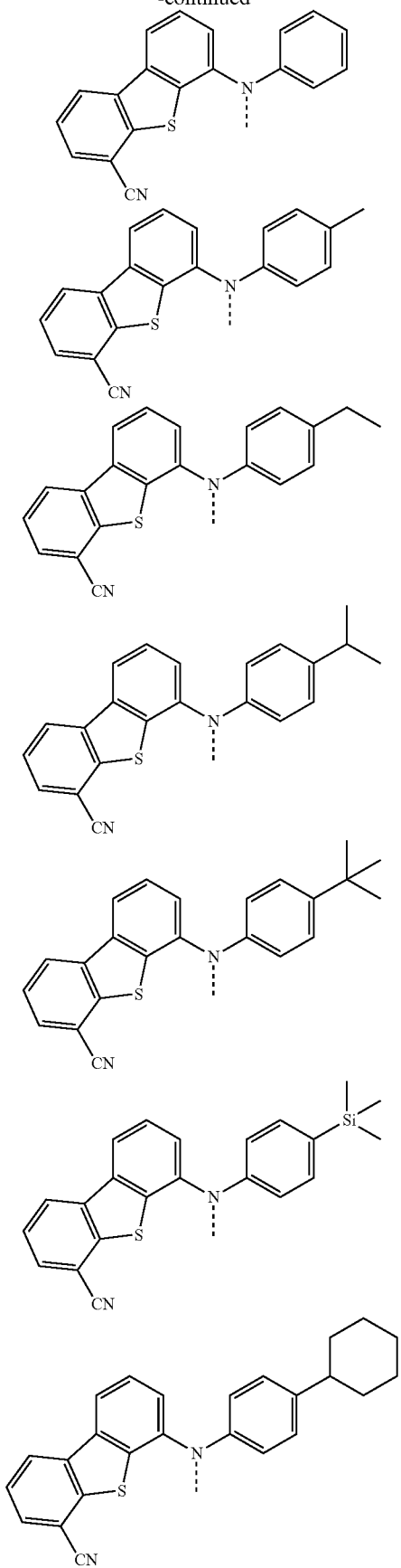
102
-continued
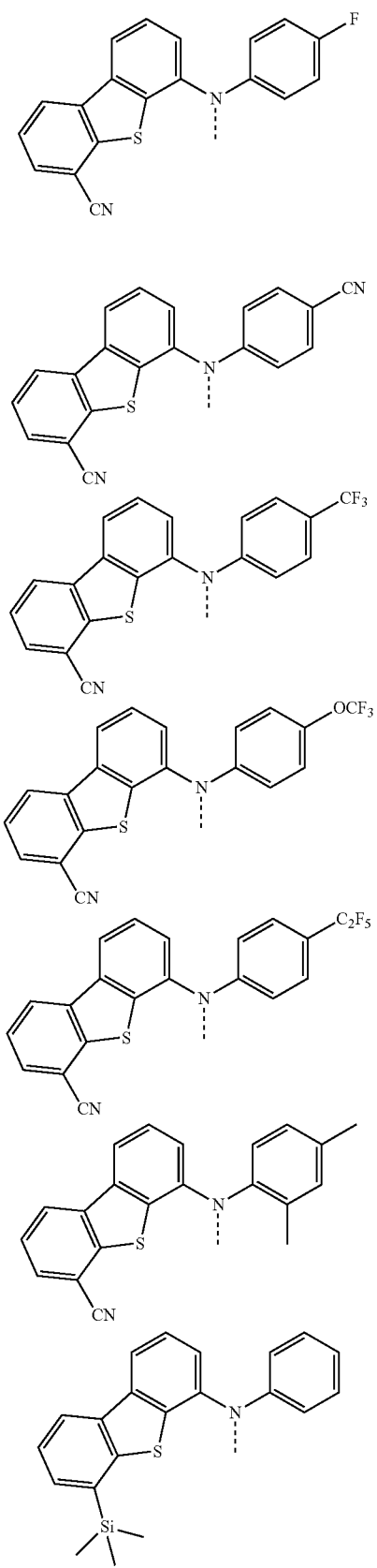

103
-continued

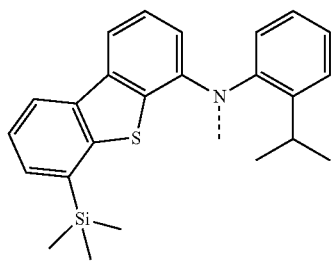
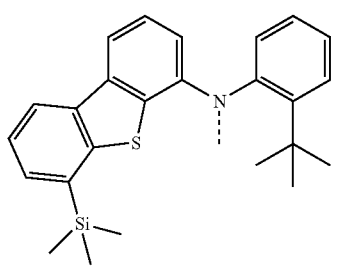
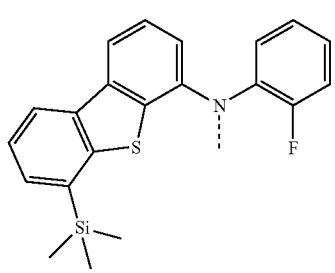
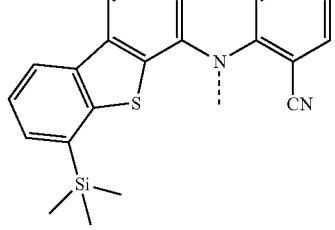
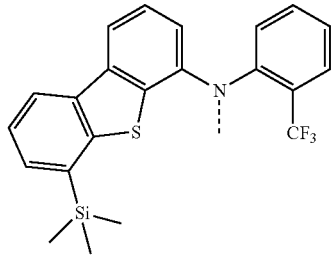
104
-continued
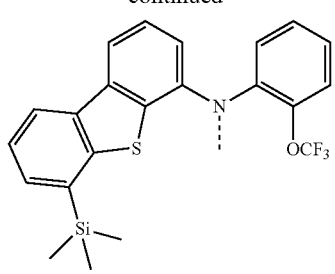
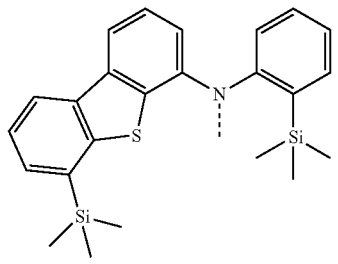
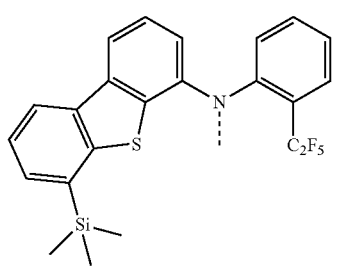
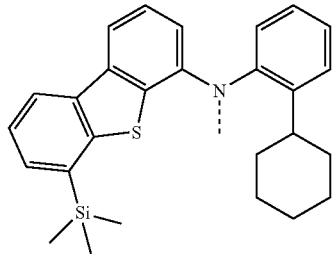
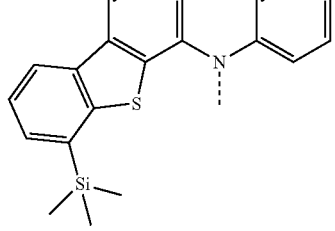
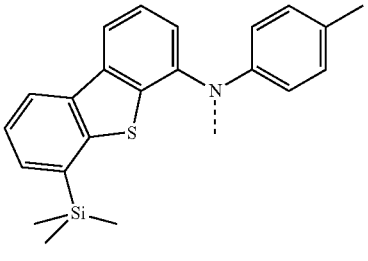

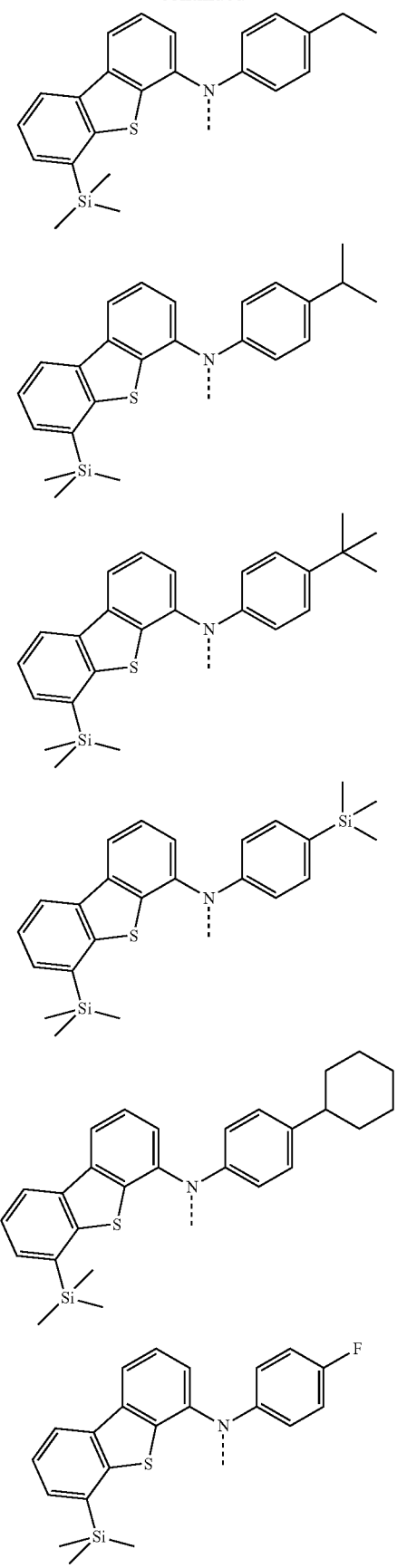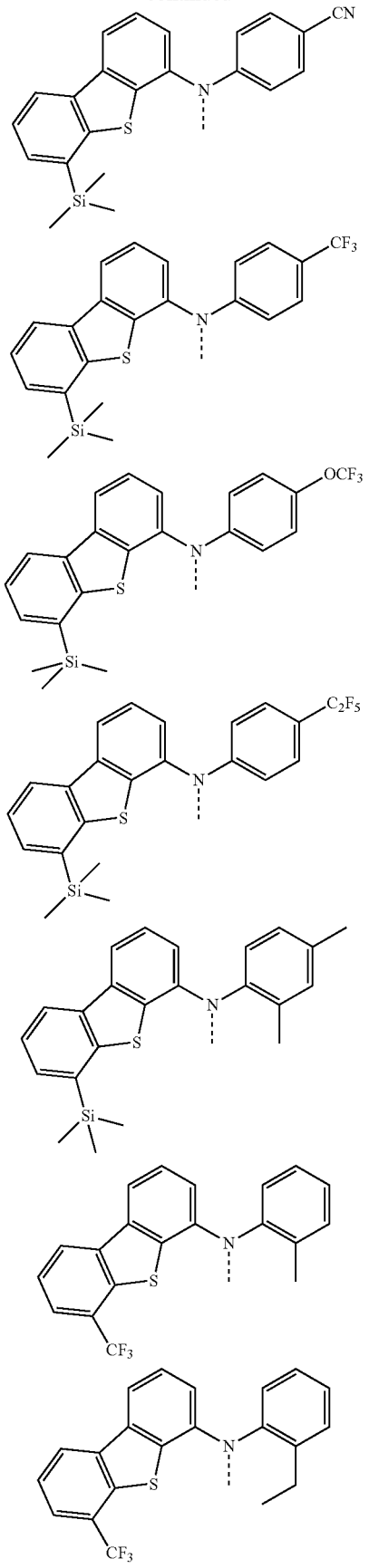

107
-continued

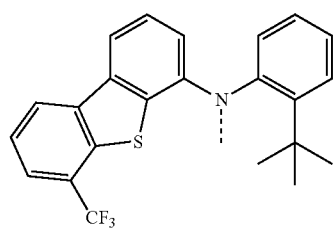
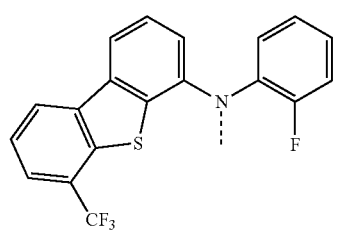
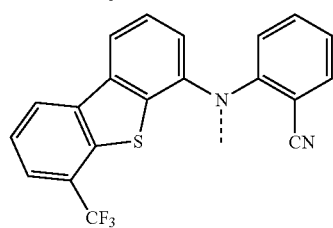
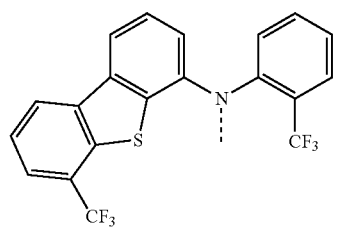
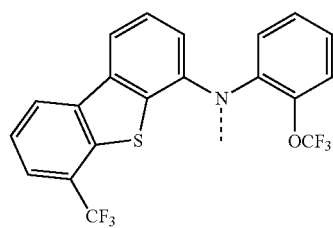
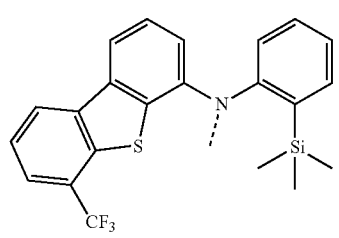
108
-continued
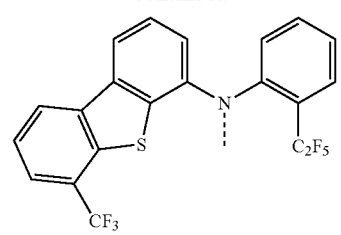
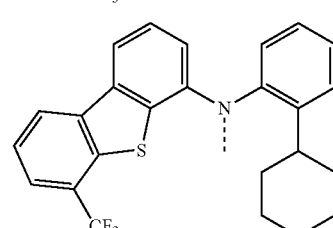
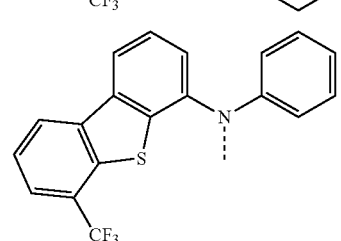
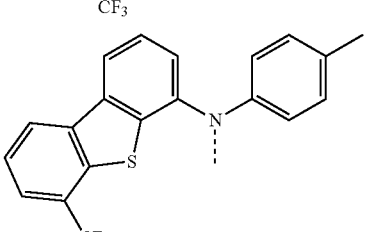
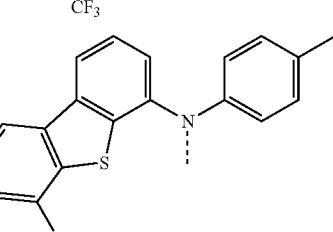

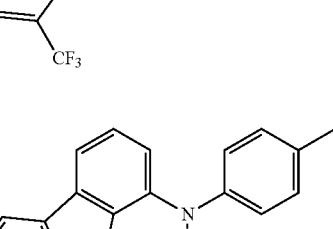
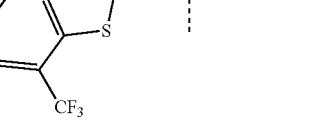

-continued

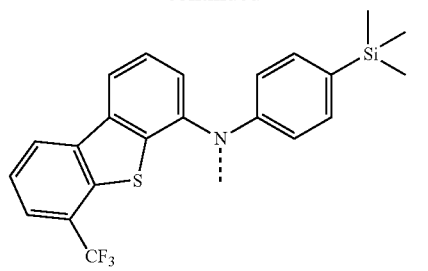
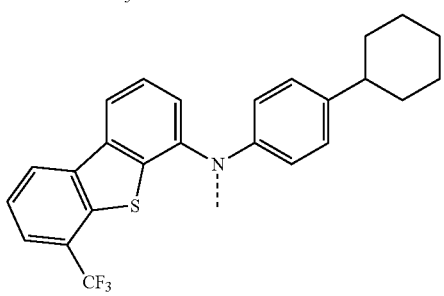
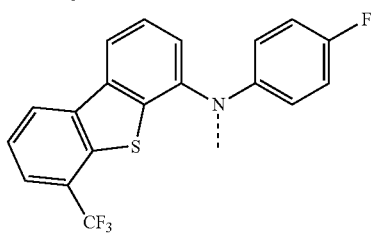
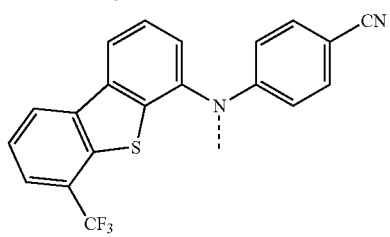
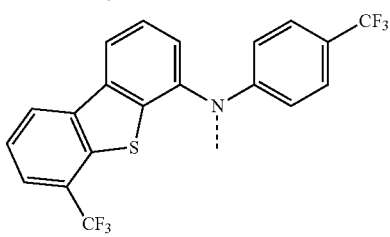
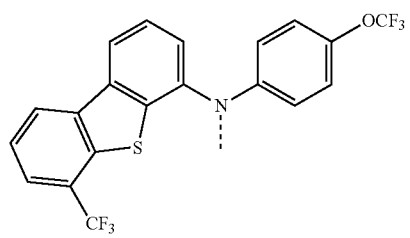
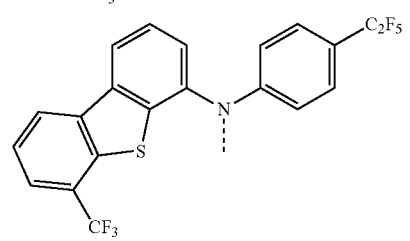

-continued

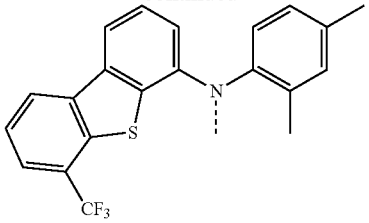

According to an exemplary embodiment of the present specification, groups that are not

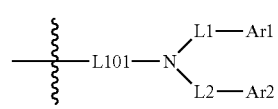

among R1 to R25 are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, or may bond to adjacent groups to form a substituted or unsubstituted ring.

According to an exemplary embodiment of the present specification, groups that are not

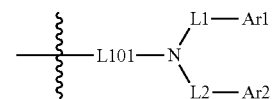

among R1 to R25 are each hydrogen.

According to an exemplary embodiment of the present specification, Chemical Formula 1 may be represented by any one of the following Chemical Formulae 2 to 8.

[Chemical Formula 2]

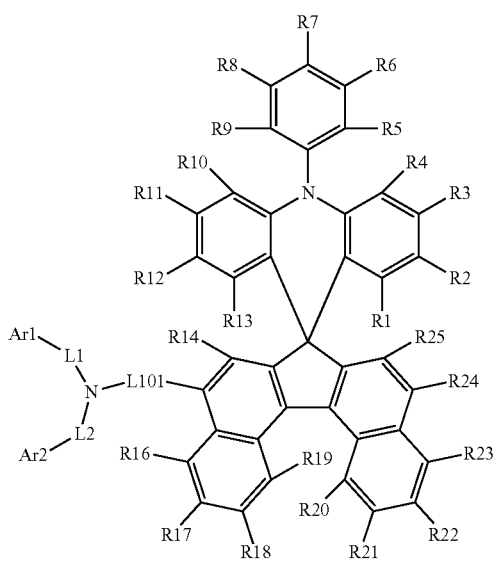

-continued
[Chemical Formula 3]
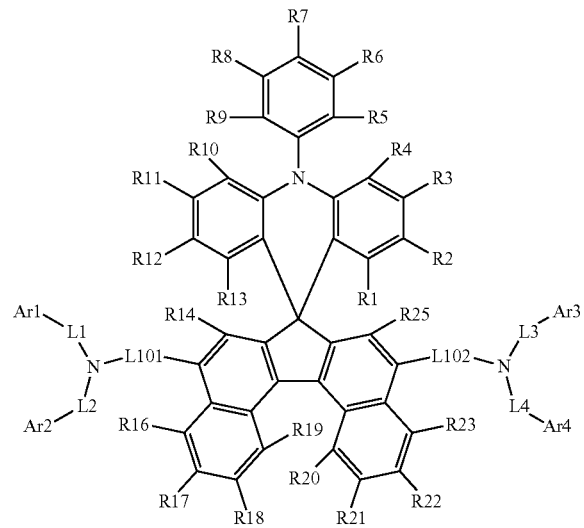
[Chemical Formula 4]
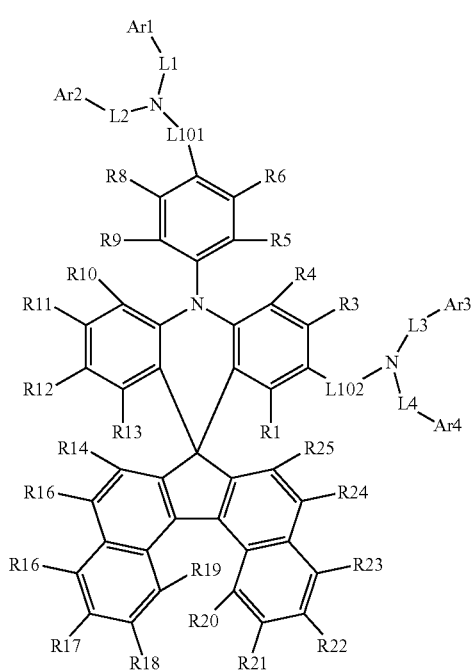
-continued
[Chemical Formula 5]
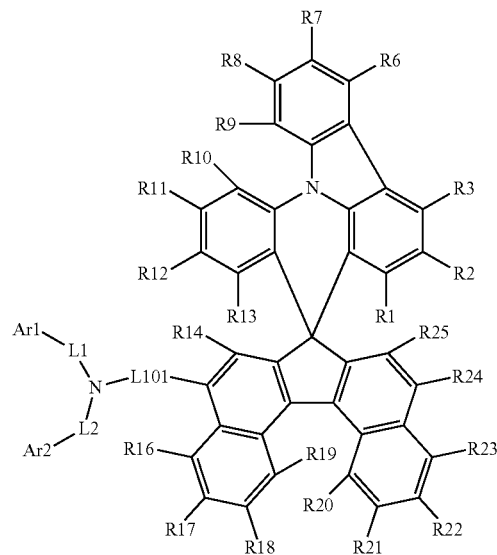
[Chemical Formula 6]
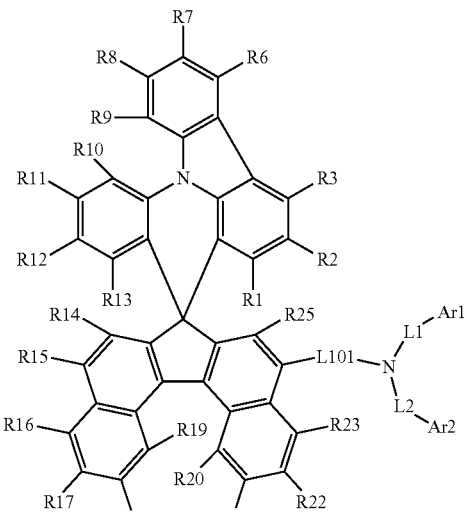
[Chemical Formula 7]
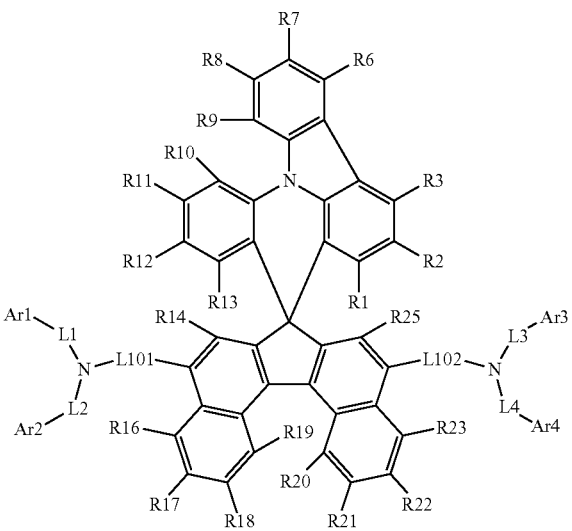

[Chemical Formula 8]

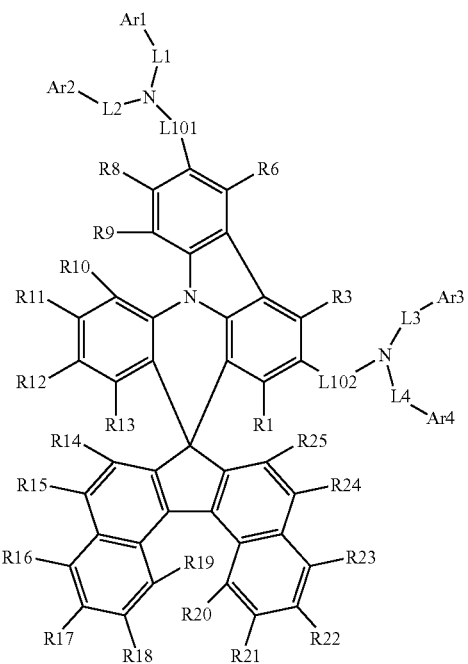

In Chemical Formulae 2 to 8, R1 to R25, L101, L1, L2, Ar1, and Ar2 have the same definitions as in Chemical Formula 1.

According to an exemplary embodiment of the present specification, L102, L3 and L4 are the same as or different from each other, and each independently a direct bond; a substituted or unsubstituted arylene group; or a substituted or unsubstituted divalent heterocyclic group.

According to an exemplary embodiment of the present specification, L102 is a direct bond.

According to an exemplary embodiment of the present specification, L102 is a substituted or unsubstituted arylene group.

According to an exemplary embodiment of the present specification, L102 is a substituted or unsubstituted phenylene group, a substituted or unsubstituted biphenylene group, a substituted or unsubstituted naphthylene group, or a substituted or unsubstituted fluorenylene group.

According to an exemplary embodiment of the present specification, L102 is a substituted or unsubstituted divalent heterocyclic group.

According to an exemplary embodiment of the present specification, L3 is a direct bond.

According to an exemplary embodiment of the present specification, L3 is a substituted or unsubstituted arylene group.

According to an exemplary embodiment of the present specification, L3 is a substituted or unsubstituted phenylene group, a substituted or unsubstituted biphenylene group, a substituted or unsubstituted terphenylene group, a substituted or unsubstituted naphthylene group, a substituted or unsubstituted phenanthrene group, or a substituted or unsubstituted fluorenylene group.

According to an exemplary embodiment of the present specification, L3 is a phenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a phenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a phenylene group.

According to an exemplary embodiment of the present specification, L3 is a biphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a biphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a biphenylene group.

According to an exemplary embodiment of the present specification, L3 is a terphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a terphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a terphenylene group.

According to an exemplary embodiment of the present specification, L3 is a naphthylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a naphthylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a naphthylene group.

According to an exemplary embodiment of the present specification, L3 is a phenanthrene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a phenanthrene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a phenanthrene group.

According to an exemplary embodiment of the present specification, L3 is a fluorenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a fluorenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L3 is a fluorenylene group.

According to an exemplary embodiment of the present specification, L3 is a substituted or unsubstituted divalent heterocyclic group.

According to an exemplary embodiment of the present specification, L3 is a substituted or unsubstituted divalent carbazole group, a substituted or unsubstituted divalent dibenzofuran group, or a substituted or unsubstituted divalent dibenzothiophene group.

According to an exemplary embodiment of the present specification, L3 is a divalent carbazole group unsubstituted or substituted with an alkyl group, a cycloalkyl group, a halogen group, a halogenated alkyl group, a nitrile group, a silyl group, an aryl group or a heterocyclic group.

According to an exemplary embodiment of the present specification, L3 is a divalent carbazole group unsubstituted or substituted with a phenyl group.

According to an exemplary embodiment of the present specification, L3 is a divalent dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a divalent dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L3 is a divalent dibenzofuran group.

According to an exemplary embodiment of the present specification, L3 is a divalent dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L3 is a divalent dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L3 is a divalent dibenzothiophene group.

According to an exemplary embodiment of the present specification, L4 is a direct bond.

According to an exemplary embodiment of the present specification, L4 is a substituted or unsubstituted arylene group.

According to an exemplary embodiment of the present specification, L4 is a substituted or unsubstituted phenylene group, a substituted or unsubstituted biphenylene group, a substituted or unsubstituted terphenylene group, a substituted or unsubstituted naphthylene group, a substituted or unsubstituted phenanthrene group, or a substituted or unsubstituted fluorenylene group.

According to an exemplary embodiment of the present specification, L4 is a phenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a phenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a phenylene group.

According to an exemplary embodiment of the present specification, L4 is a biphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a biphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a biphenylene group.

According to an exemplary embodiment of the present specification, L4 is a terphenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a terphenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a terphenylene group.

According to an exemplary embodiment of the present specification, L4 is a naphthylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a naphthylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a naphthylene group.

According to an exemplary embodiment of the present specification, L4 is a phenanthrene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a phenanthrene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a phenanthrene group.

According to an exemplary embodiment of the present specification, L4 is a fluorenylene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a fluorenylene group unsubstituted or substituted with a methyl group, an ethyl group, an isopropyl group, a tert-butyl group, a cyclohexyl group, fluorine, a nitrile group, —OCF$_3$, —CF$_3$, —C$_2$F$_5$ or a trimethylsilyl group.

According to an exemplary embodiment of the present specification, L4 is a fluorenylene group.

According to an exemplary embodiment of the present specification, L4 is a substituted or unsubstituted divalent heterocyclic group.

According to an exemplary embodiment of the present specification, L4 is a substituted or unsubstituted divalent carbazole group, a substituted or unsubstituted divalent dibenzofuran group, or a substituted or unsubstituted divalent dibenzothiophene group.

According to an exemplary embodiment of the present specification, L4 is a divalent carbazole group unsubstituted or substituted with an alkyl group, a cycloalkyl group, a halogen group, a halogenated alkyl group, a nitrile group, a silyl group, an aryl group or a heterocyclic group.

According to an exemplary embodiment of the present specification, L4 is a divalent carbazole group unsubstituted or substituted with a phenyl group.

According to an exemplary embodiment of the present specification, L4 is a divalent dibenzofuran group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a divalent dibenzofuran group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L4 is a divalent dibenzofuran group.

According to an exemplary embodiment of the present specification, L4 is a divalent dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, L4 is a divalent dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group or a trimethylsilyl group.

According to an exemplary embodiment of the present specification, L4 is a divalent dibenzothiophene group.

According to an exemplary embodiment of the present specification, Ar3 and Ar4 are the same as or different from each other, and each independently hydrogen; deuterium; a halogen group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group.

According to an exemplary embodiment of the present specification, Ar3 is hydrogen.

According to an exemplary embodiment of the present specification, Ar3 is a halogen group.

According to an exemplary embodiment of the present specification, Ar3 is fluorine.

According to an exemplary embodiment of the present specification, Ar3 is a substituted or unsubstituted alkyl group.

According to an exemplary embodiment of the present specification, Ar3 is a substituted or unsubstituted methyl group, a substituted or unsubstituted ethyl group, a substituted or unsubstituted isopropyl group, or a substituted or unsubstituted tert-butyl group.

According to an exemplary embodiment of the present specification, Ar3 is a methyl group.

According to an exemplary embodiment of the present specification, Ar3 is an ethyl group.

According to an exemplary embodiment of the present specification, Ar3 is an isopropyl group.

According to an exemplary embodiment of the present specification, Ar3 is a tert-butyl group.

According to an exemplary embodiment of the present specification, Ar3 is a substituted or unsubstituted cycloalkyl group.

According to an exemplary embodiment of the present specification, Ar3 is a substituted or unsubstituted cyclopentyl group, or a substituted or unsubstituted cyclohexyl group.

According to an exemplary embodiment of the present specification, Ar3 is a cyclohexyl group.

According to an exemplary embodiment of the present specification, Ar3 is a substituted or unsubstituted silyl group.

According to an exemplary embodiment of the present specification, Ar3 is a silyl group unsubstituted or substituted with an alkyl group.

According to an exemplary embodiment of the present specification, Ar3 is a trimethylsilyl group.

According to an exemplary embodiment of the present specification, Ar3 is a substituted or unsubstituted aryl group having 6 to 40 carbon atoms.

According to an exemplary embodiment of the present specification, Ar3 is a substituted or unsubstituted phenyl group, a substituted or unsubstituted biphenyl group, a substituted or unsubstituted terphenyl group, a substituted or unsubstituted triphenyl group, a substituted or unsubstituted quaterphenyl group, a substituted or unsubstituted naphthyl group, a substituted or unsubstituted anthracenyl group, a substituted or unsubstituted phenanthryl group, or a substituted or unsubstituted fluorenyl group.

According to an exemplary embodiment of the present specification, Ar3 is a phenyl group unsubstituted or substituted with deuterium, an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar3 is a phenyl group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group, a biphenyl group, a naphthyl group, a phenanthryl group, a triphenyl group or a dimethylfluorenyl group.

According to an exemplary embodiment of the present specification, Ar3 is a phenyl group.

According to an exemplary embodiment of the present specification, Ar3 is a biphenyl group unsubstituted or substituted with an alkyl group or an aryl group.

According to an exemplary embodiment of the present specification, Ar3 is a biphenyl group unsubstituted or substituted with a methyl group, a phenyl group or a naphthyl group.

According to an exemplary embodiment of the present specification, Ar3 is a biphenyl group.

According to an exemplary embodiment of the present specification, Ar3 is a terphenyl group unsubstituted or substituted with an alkyl group or an aryl group.

According to an exemplary embodiment of the present specification, Ar3 is a terphenyl group unsubstituted or substituted with a methyl group, a phenyl group or a naphthyl group.

According to an exemplary embodiment of the present specification, Ar3 is a terphenyl group.

According to an exemplary embodiment of the present specification, Ar3 is a triphenyl group unsubstituted or substituted with an alkyl group or an aryl group.

According to an exemplary embodiment of the present specification, Ar3 is a triphenyl group unsubstituted or substituted with a methyl group, a phenyl group or a naphthyl group.

According to an exemplary embodiment of the present specification, Ar3 is a triphenyl group.

According to an exemplary embodiment of the present specification, Ar3 is a naphthyl group unsubstituted or substituted with an alkyl group or an aryl group.

According to an exemplary embodiment of the present specification, Ar3 is a naphthyl group unsubstituted or substituted with a methyl group, a phenyl group or a naphthyl group.

According to an exemplary embodiment of the present specification, Ar3 is a naphthyl group.

According to an exemplary embodiment of the present specification, Ar3 is an anthracenyl group unsubstituted or substituted with an alkyl group or an aryl group.

According to an exemplary embodiment of the present specification, Ar3 is an anthracenyl group unsubstituted or substituted with a methyl group, a phenyl group or a naphthyl group.

According to an exemplary embodiment of the present specification, Ar3 is an anthracenyl group.

According to an exemplary embodiment of the present specification, Ar3 is a phenanthryl group unsubstituted or substituted with an alkyl group or an aryl group.

According to an exemplary embodiment of the present specification, Ar3 is a phenanthryl group unsubstituted or substituted with a methyl group, a phenyl group or a naphthyl group.

According to an exemplary embodiment of the present specification, Ar3 is a phenanthryl group.

According to an exemplary embodiment of the present specification, Ar3 is a fluorenyl group unsubstituted or substituted with an alkyl group or an aryl group.

According to an exemplary embodiment of the present specification, Ar3 is a fluorenyl group unsubstituted or substituted with a methyl group, a phenyl group or a naphthyl group.

According to an exemplary embodiment of the present specification, Ar3 is a fluorenyl group.

According to an exemplary embodiment of the present specification, Ar3 is a spirobifluorenyl group.

According to an exemplary embodiment of the present specification, Ar3 is a substituted or unsubstituted heterocyclic group having 2 to 40 carbon atoms.

According to an exemplary embodiment of the present specification, Ar3 is a substituted or unsubstituted carbazole group, a substituted or unsubstituted dibenzocarbazole group, a substituted or unsubstituted dibenzofuran group, or a substituted or unsubstituted dibenzothiophene group.

According to an exemplary embodiment of the present specification, Ar3 is a carbazole group unsubstituted or substituted with an aryl group.

According to an exemplary embodiment of the present specification, Ar3 is a carbazole group unsubstituted or substituted with a phenyl group or a biphenyl group.

According to an exemplary embodiment of the present specification, Ar3 is a dibenzocarbazole group unsubstituted or substituted with an aryl group.

According to an exemplary embodiment of the present specification, Ar3 is a dibenzocarbazole group unsubstituted or substituted with a phenyl group or a biphenyl group.

According to an exemplary embodiment of the present specification, Ar3 is a dibenzofuran group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, Ar3 is a dibenzofuran group unsubstituted or substituted with a methyl group, an ethyl group, an isopropyl group, a tert-butyl group, a cyclohexyl group, fluorine, —$OCF_3$, —$CF_3$, —$C_2F_5$, a nitrile group, a trimethylsilyl group, a phenyl group or a naphthyl group.

According to an exemplary embodiment of the present specification, Ar3 is a benzonaphthofuran group.

According to an exemplary embodiment of the present specification, Ar3 is a dibenzofuran group.

According to an exemplary embodiment of the present specification, Ar3 is a dibenzothiophene group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, Ar3 is a dibenzothiophene group unsubstituted or substituted with a methyl group, an ethyl group, an isopropyl group, a tert-butyl group, a cyclohexyl group, fluorine, —$OCF_3$, —$CF_3$, —$C_2F_5$, a nitrile group, a trimethylsilyl group, a phenyl group or a naphthyl group.

According to an exemplary embodiment of the present specification, Ar3 is a benzonaphthothiophene group.

According to an exemplary embodiment of the present specification, Ar3 is a dibenzothiophene group.

According to an exemplary embodiment of the present specification, Ar4 is hydrogen.

According to an exemplary embodiment of the present specification, Ar4 is a halogen group.

According to an exemplary embodiment of the present specification, Ar4 is fluorine.

According to an exemplary embodiment of the present specification, Ar4 is a substituted or unsubstituted alkyl group.

According to an exemplary embodiment of the present specification, Ar4 is a substituted or unsubstituted methyl group, a substituted or unsubstituted ethyl group, a substituted or unsubstituted isopropyl group, or a substituted or unsubstituted tert-butyl group.

According to an exemplary embodiment of the present specification, Ar4 is a methyl group.

According to an exemplary embodiment of the present specification, Ar4 is an ethyl group.

According to an exemplary embodiment of the present specification, Ar4 is an isopropyl group.

According to an exemplary embodiment of the present specification, Ar4 is a tert-butyl group.

According to an exemplary embodiment of the present specification, Ar4 is a substituted or unsubstituted cycloalkyl group.

According to an exemplary embodiment of the present specification, Ar4 is a substituted or unsubstituted cyclopentyl group, or a substituted or unsubstituted cyclohexyl group.

According to an exemplary embodiment of the present specification, Ar4 is a cyclohexyl group.

According to an exemplary embodiment of the present specification, Ar4 is a substituted or unsubstituted silyl group.

According to an exemplary embodiment of the present specification, Ar4 is a silyl group unsubstituted or substituted with an alkyl group.

According to an exemplary embodiment of the present specification, Ar4 is a trimethylsilyl group.

According to an exemplary embodiment of the present specification, Ar4 is a substituted or unsubstituted aryl group having 6 to 40 carbon atoms.

According to an exemplary embodiment of the present specification, Ar4 is a substituted or unsubstituted phenyl group, a substituted or unsubstituted biphenyl group, a substituted or unsubstituted terphenyl group, a substituted or unsubstituted triphenyl group, a substituted or unsubstituted quaterphenyl group, a substituted or unsubstituted naphthyl group, a substituted or unsubstituted anthracenyl group, a substituted or unsubstituted phenanthryl group, or a substituted or unsubstituted fluorenyl group.

According to an exemplary embodiment of the present specification, Ar4 is a phenyl group unsubstituted or substituted with deuterium, an alkyl group, a cycloalkyl group, a halogen group, a halogenated alkyl group, a nitrile group, a silyl group, —$OCF_3$, an aryl group or a heterocyclic group.

According to an exemplary embodiment of the present specification, Ar4 is a phenyl group unsubstituted or substituted with a methyl group, an ethyl group, an isopropyl group, a tert-butyl group, a cyclohexyl group, fluorine, —$OCF_3$, —$CF_3$, —$C_2F_5$, a nitrile group, a trimethylsilyl group, a phenyl group, a biphenyl group, a naphthyl group, a phenanthryl group, a triphenyl group or a dimethylfluorenyl group.

According to an exemplary embodiment of the present specification, Ar4 is a phenyl group.

According to an exemplary embodiment of the present specification, Ar4 is a biphenyl group unsubstituted or substituted with an alkyl group or an aryl group.

According to an exemplary embodiment of the present specification, Ar4 is a biphenyl group unsubstituted or substituted with a methyl group, a phenyl group or a naphthyl group.

According to an exemplary embodiment of the present specification, Ar4 is a biphenyl group.

According to an exemplary embodiment of the present specification, Ar4 is a terphenyl group unsubstituted or substituted with an alkyl group or an aryl group.

According to an exemplary embodiment of the present specification, Ar4 is a terphenyl group unsubstituted or substituted with a methyl group, a phenyl group or a naphthyl group.

According to an exemplary embodiment of the present specification, Ar4 is a terphenyl group.

According to an exemplary embodiment of the present specification, Ar4 is a triphenyl group unsubstituted or substituted with an alkyl group or an aryl group.

According to an exemplary embodiment of the present specification, Ar4 is a triphenyl group unsubstituted or substituted with a methyl group, a phenyl group or a naphthyl group.

According to an exemplary embodiment of the present specification, Ar4 is a triphenyl group.

According to an exemplary embodiment of the present specification, Ar4 is a naphthyl group unsubstituted or substituted with an alkyl group or an aryl group.

According to an exemplary embodiment of the present specification, Ar4 is a naphthyl group unsubstituted or substituted with a methyl group, a phenyl group or a naphthyl group.

According to an exemplary embodiment of the present specification, Ar4 is a naphthyl group.

According to an exemplary embodiment of the present specification, Ar4 is an anthracenyl group unsubstituted or substituted with an alkyl group or an aryl group.

According to an exemplary embodiment of the present specification, Ar4 is an anthracenyl group unsubstituted or substituted with a methyl group, a phenyl group or a naphthyl group.

According to an exemplary embodiment of the present specification, Ar4 is an anthracenyl group.

According to an exemplary embodiment of the present specification, Ar4 is a phenanthryl group unsubstituted or substituted with an alkyl group or an aryl group.

According to an exemplary embodiment of the present specification, Ar4 is a phenanthryl group unsubstituted or substituted with a methyl group, a phenyl group or a naphthyl group.

According to an exemplary embodiment of the present specification, Ar4 is a phenanthryl group.

According to an exemplary embodiment of the present specification, Ar4 is a fluorenyl group unsubstituted or substituted with an alkyl group or an aryl group.

According to an exemplary embodiment of the present specification, Ar4 is a fluorenyl group unsubstituted or substituted with a methyl group, a phenyl group or a naphthyl group.

According to an exemplary embodiment of the present specification, Ar4 is a fluorenyl group.

According to an exemplary embodiment of the present specification, Ar4 is a spirobifluorenyl group.

According to an exemplary embodiment of the present specification, Ar4 is a substituted or unsubstituted heterocyclic group having 2 to 40 carbon atoms.

According to an exemplary embodiment of the present specification, Ar4 is a substituted or unsubstituted carbazole group, a substituted or unsubstituted dibenzocarbazole group, a substituted or unsubstituted dibenzofuran group, or a substituted or unsubstituted dibenzothiophene group.

According to an exemplary embodiment of the present specification, Ar4 is a carbazole group unsubstituted or substituted with an aryl group.

According to an exemplary embodiment of the present specification, Ar4 is a carbazole group unsubstituted or substituted with a phenyl group or a biphenyl group.

According to an exemplary embodiment of the present specification, Ar4 is a dibenzocarbazole group unsubstituted or substituted with an aryl group.

According to an exemplary embodiment of the present specification, Ar4 is a dibenzocarbazole group unsubstituted or substituted with a phenyl group or a biphenyl group.

According to an exemplary embodiment of the present specification, Ar4 is a dibenzofuran group unsubstituted or substituted with an alkyl group, a cycloalkyl group, a halogen group, a halogenated alkyl group, a nitrile group, a silyl group, —$OCF_3$, an aryl group or a heterocyclic group.

According to an exemplary embodiment of the present specification, Ar4 is a dibenzofuran group unsubstituted or substituted with a methyl group, an ethyl group, an isopropyl group, a tert-butyl group, a cyclohexyl group, fluorine, —$OCF_3$, —$CF_3$, —$C_2F_5$, a nitrile group, a trimethylsilyl group, a phenyl group or a naphthyl group.

According to an exemplary embodiment of the present specification, Ar4 is a benzonaphthofuran group.

According to an exemplary embodiment of the present specification, Ar4 is a dibenzofuran group.

According to an exemplary embodiment of the present specification, Ar4 is a dibenzothiophene group unsubstituted or substituted with an alkyl group, a cycloalkyl group, a halogen group, a halogenated alkyl group, a nitrile group, a silyl group, —OCF$_3$, an aryl group or a heterocyclic group.

According to an exemplary embodiment of the present specification, Ar4 is a dibenzothiophene group unsubstituted or substituted with a methyl group, an ethyl group, an isopropyl group, a tert-butyl group, a cyclohexyl group, fluorine, —OCF$_3$, —CF$_3$, —C$_2$F$_5$, a nitrile group, a trimethylsilyl group, a phenyl group or a naphthyl group.

According to an exemplary embodiment of the present specification, Ar4 is a benzonaphthothiophene group.

According to an exemplary embodiment of the present specification, Ar4 is a dibenzothiophene group.

According to an exemplary embodiment of the present specification, the compound represented by Chemical Formula 1 is any one selected from among the following compounds.

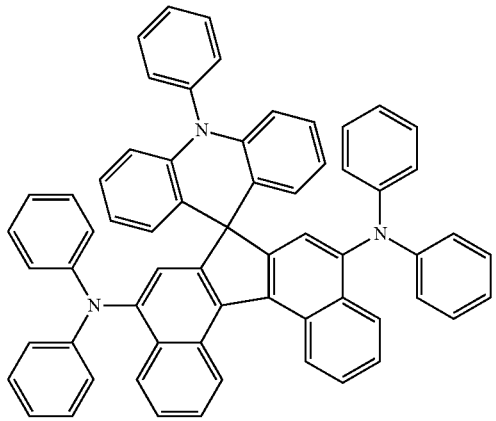

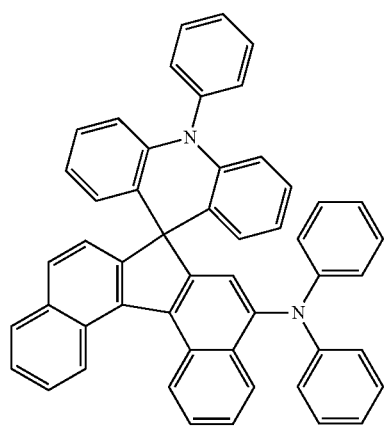

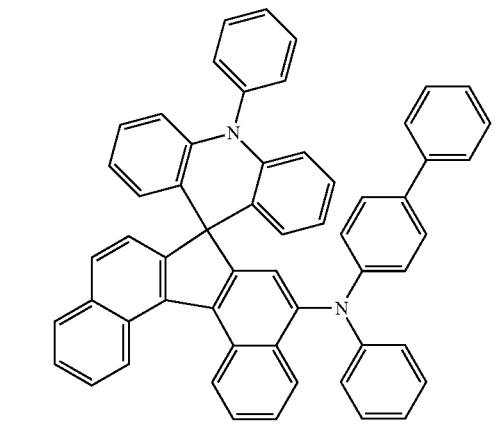

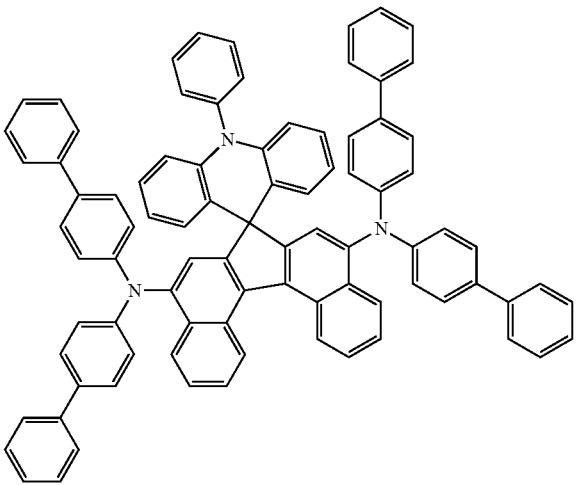

125
-continued
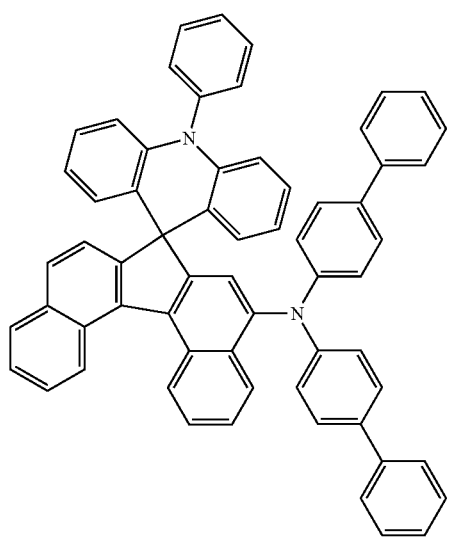
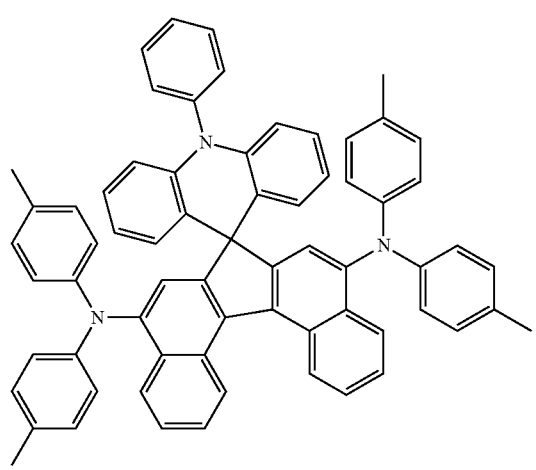
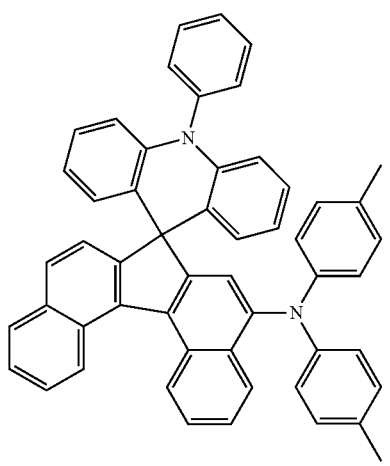
126
-continued
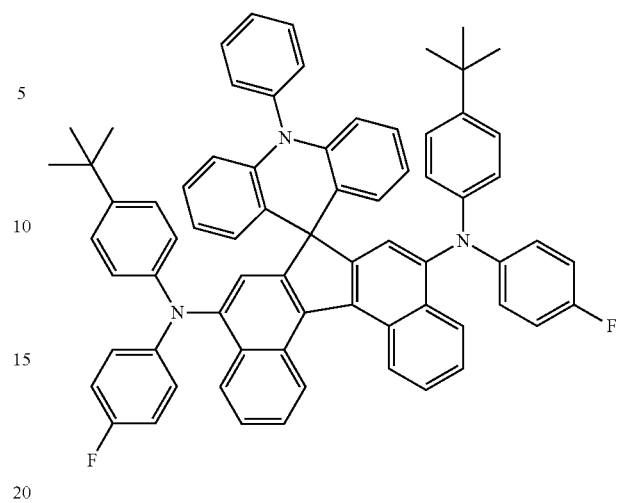
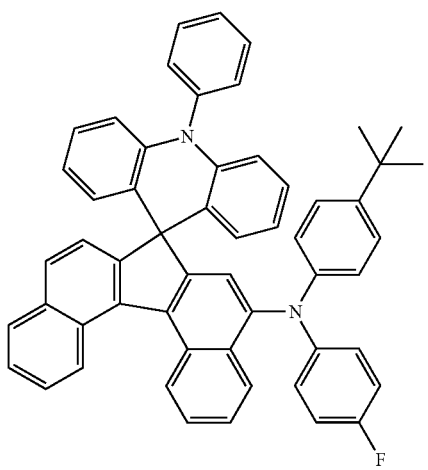
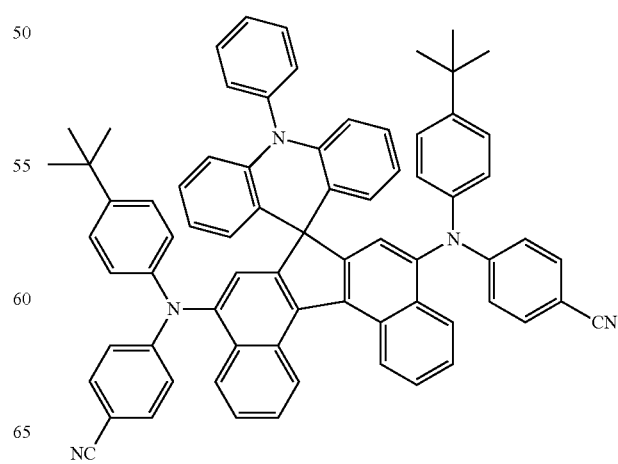

127
-continued
128
-continued
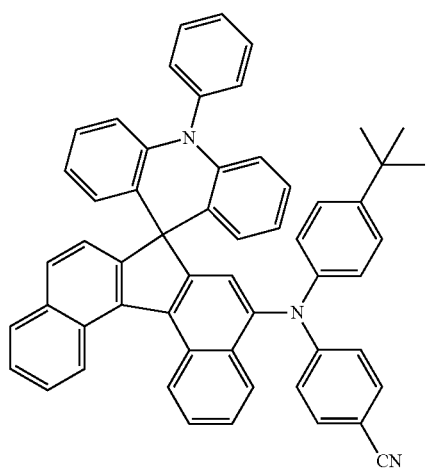
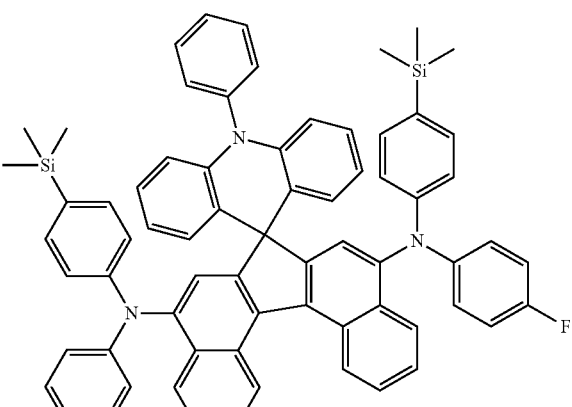
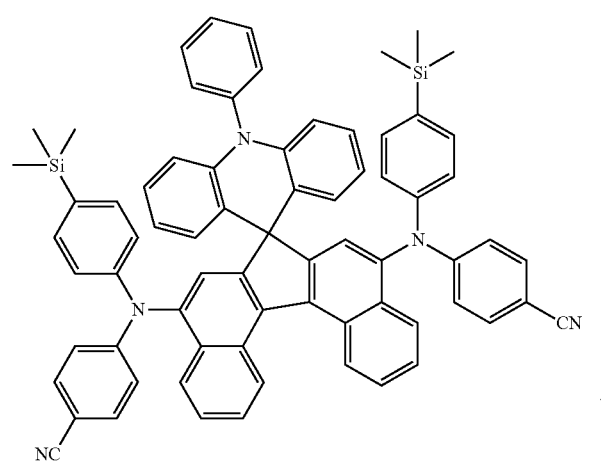
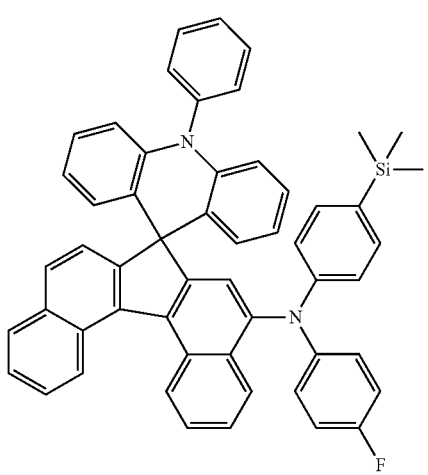
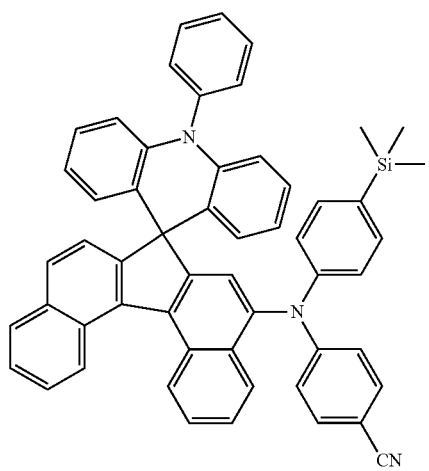

129
-continued
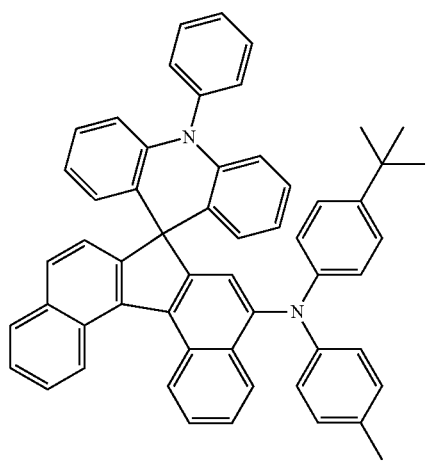
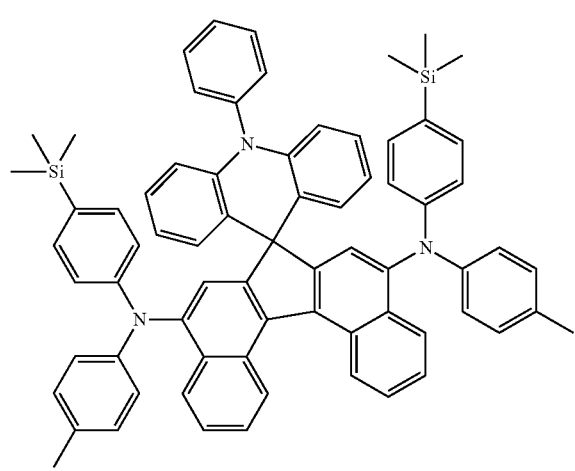
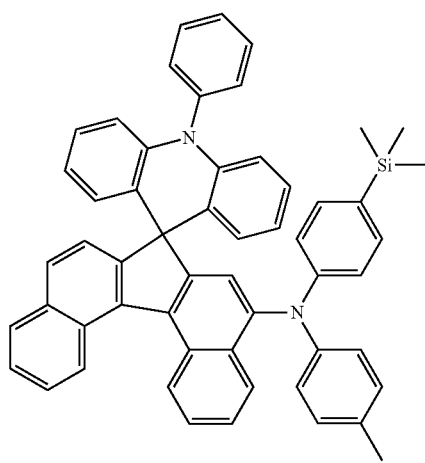
130
-continued
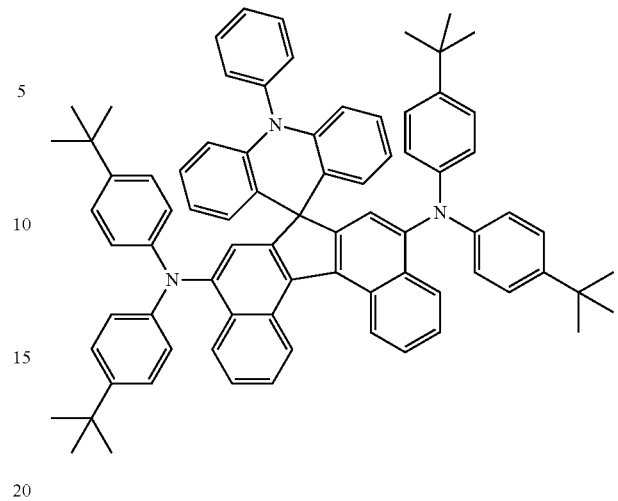
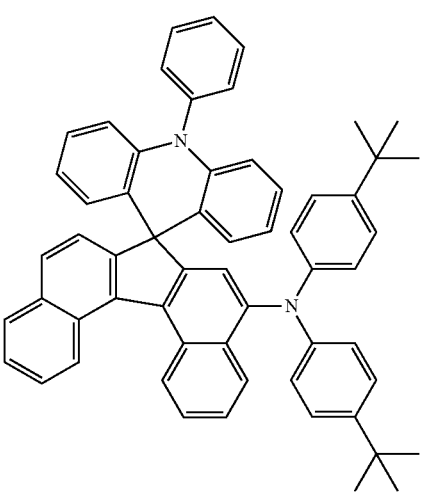
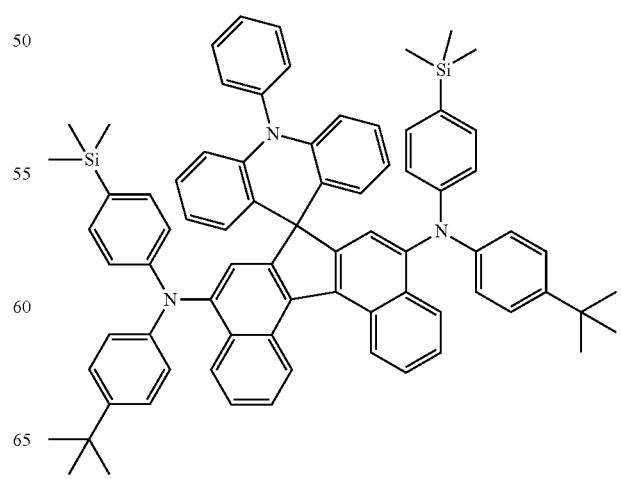

131
-continued
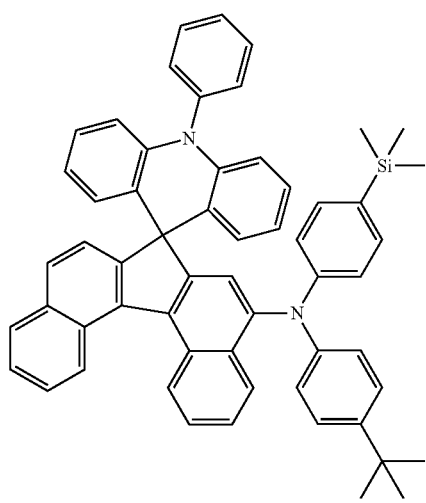
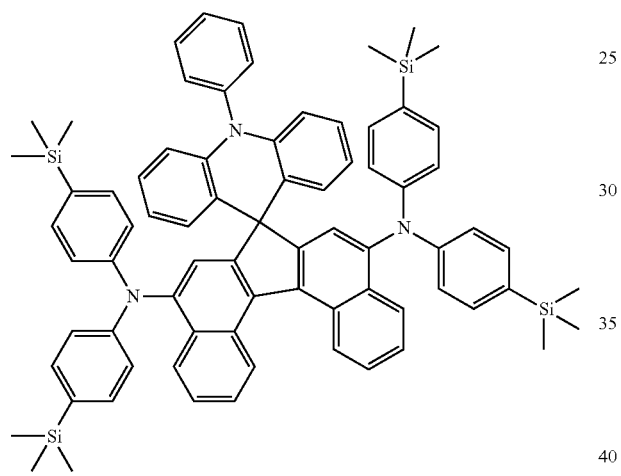
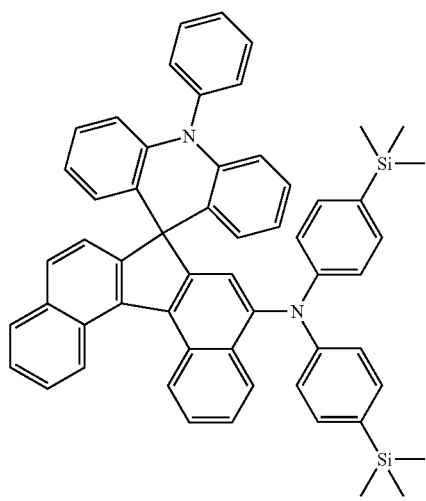
132
-continued
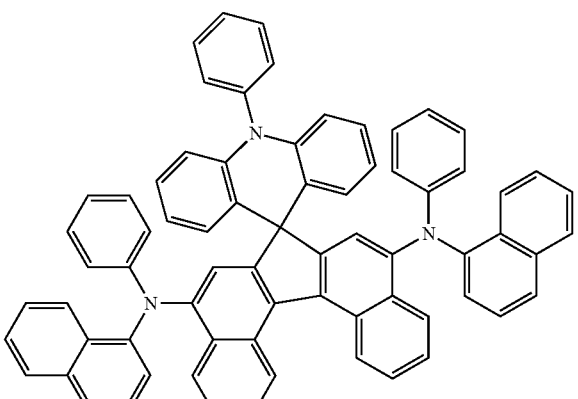
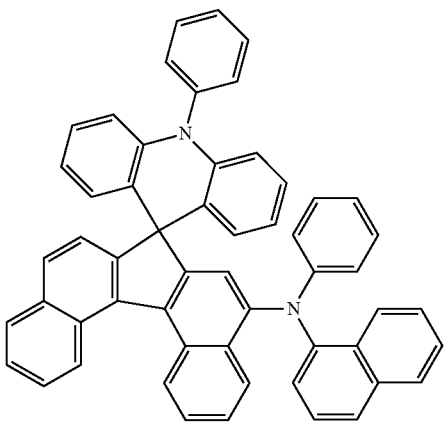
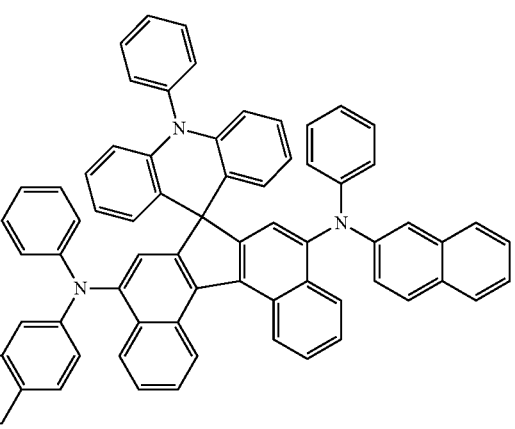

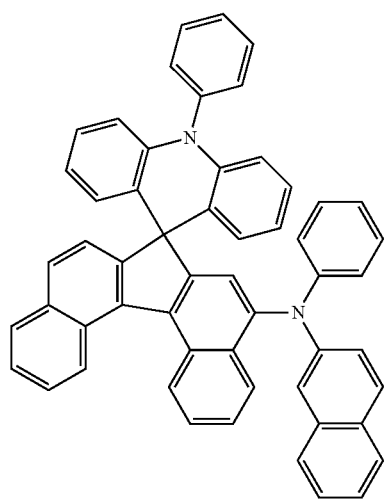
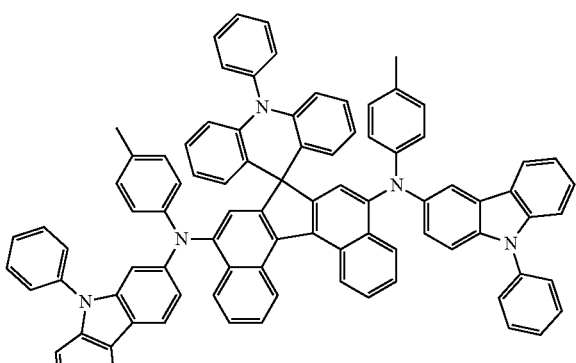
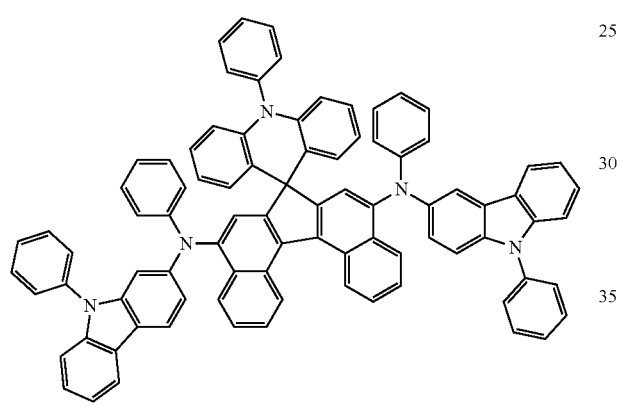
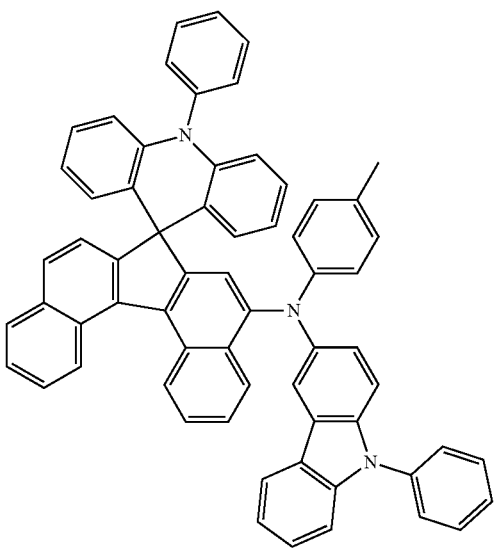
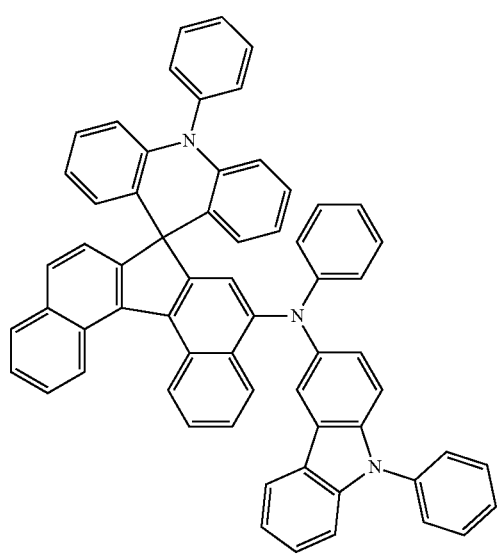
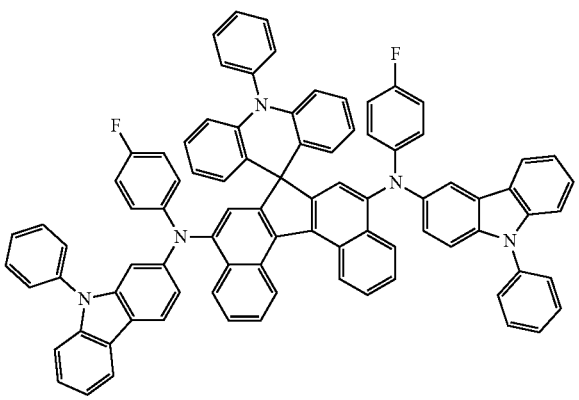

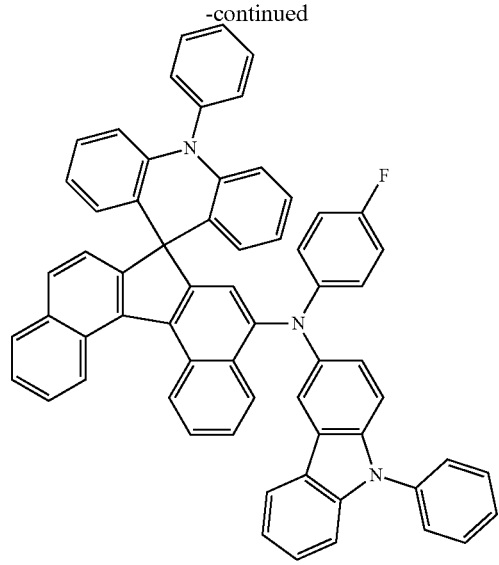
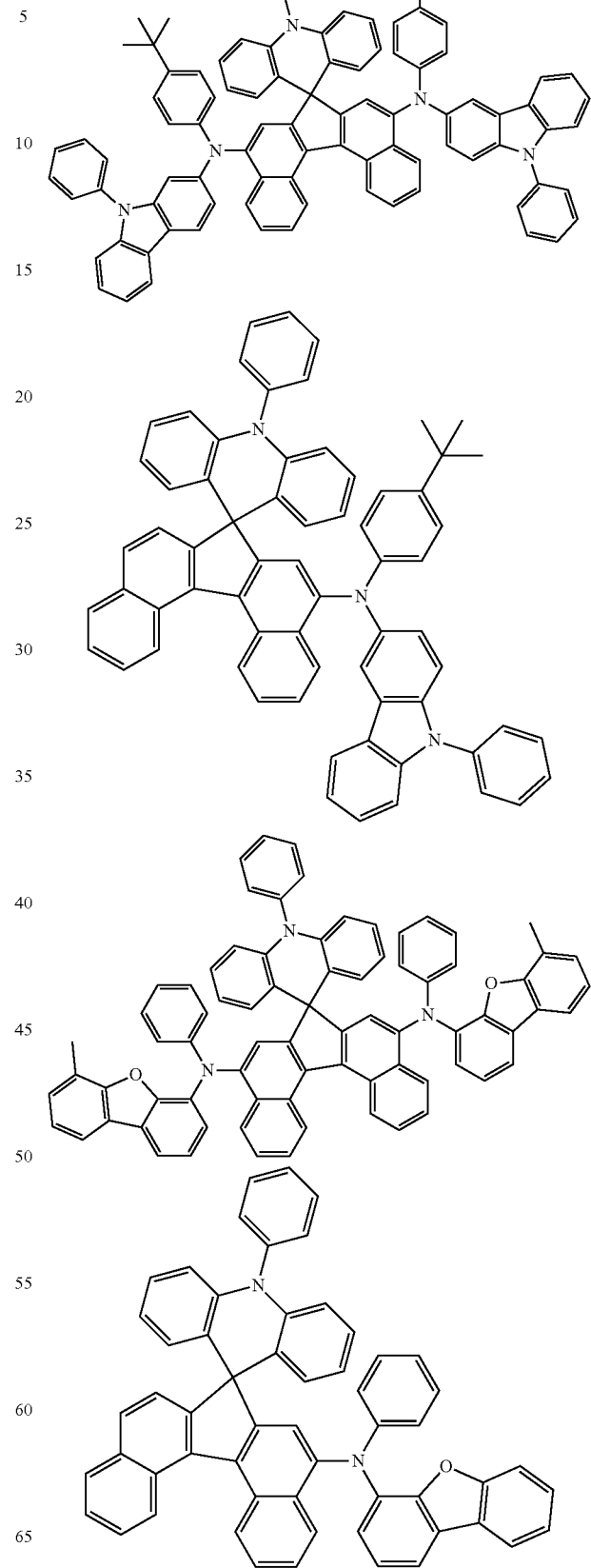

137
-continued
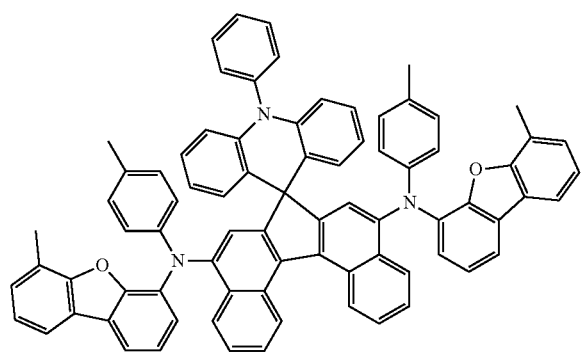
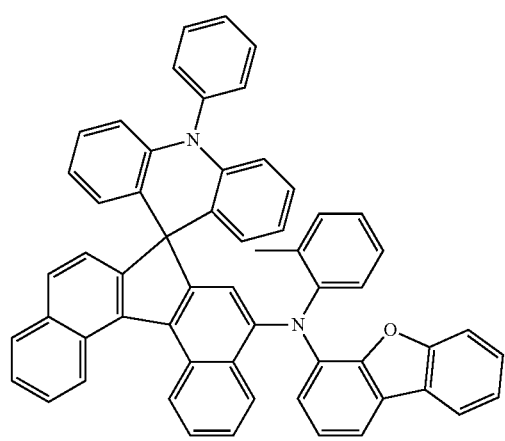
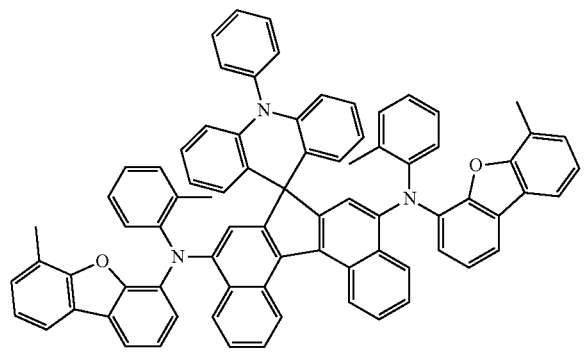
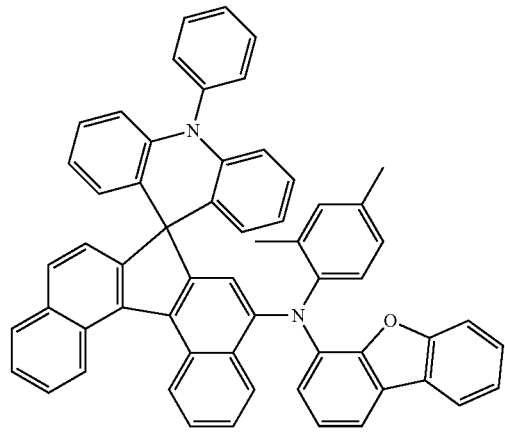
138
-continued
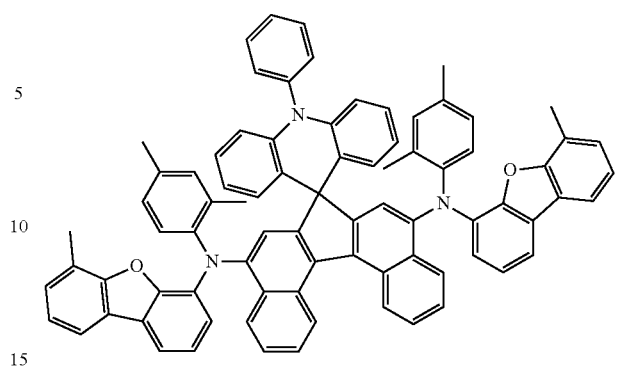
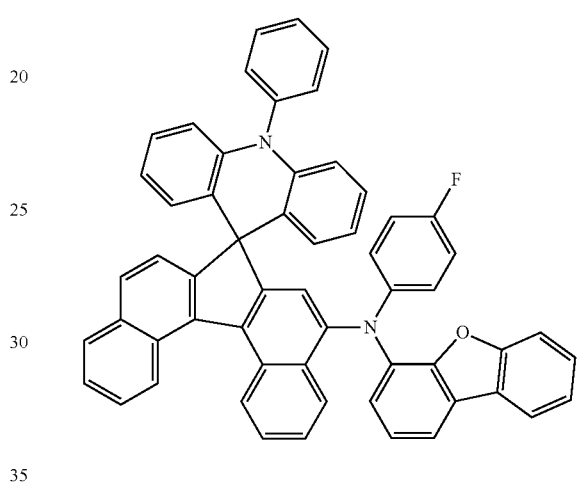
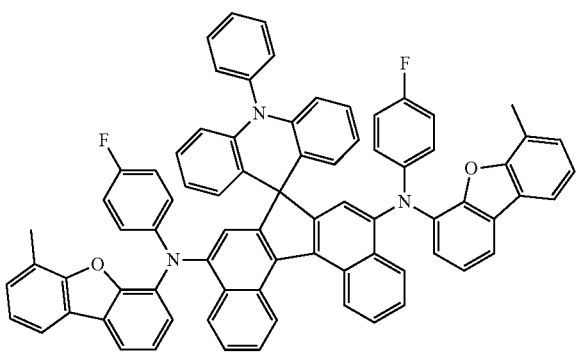
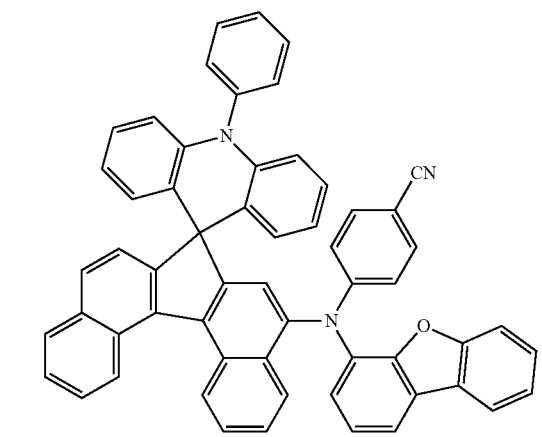

139
-continued
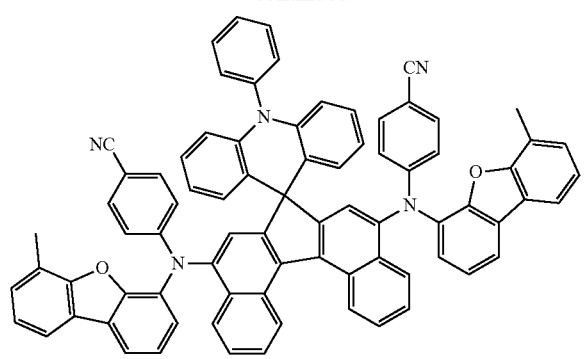
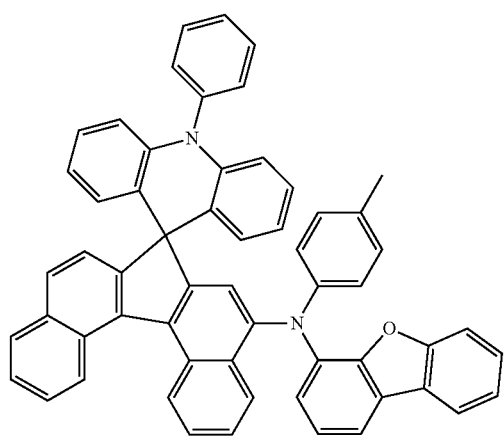
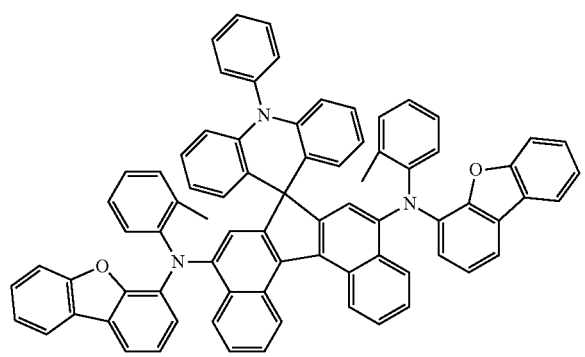
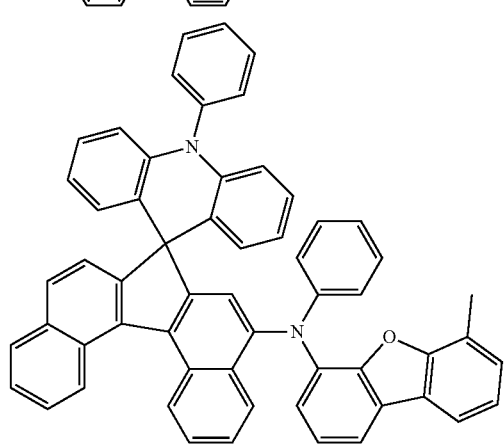
140
-continued
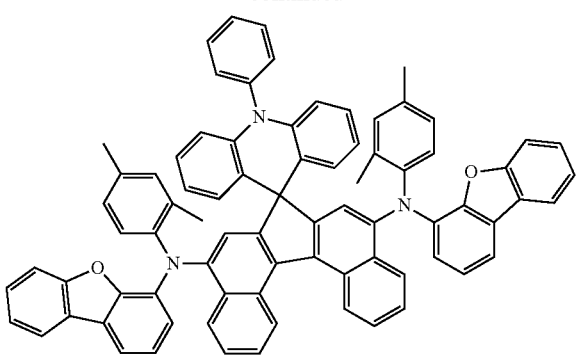
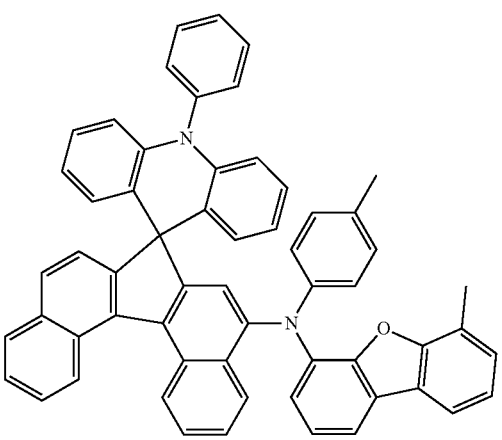
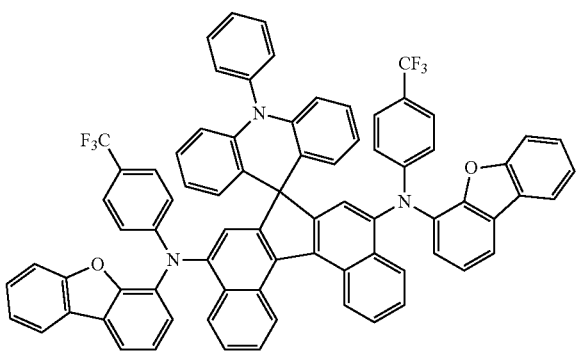
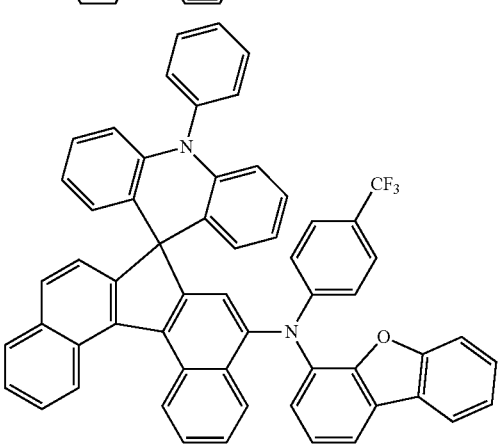

141
-continued
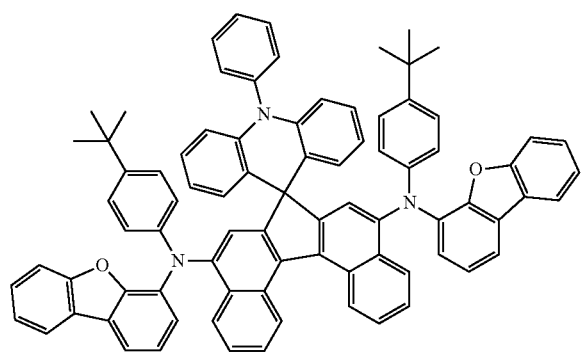
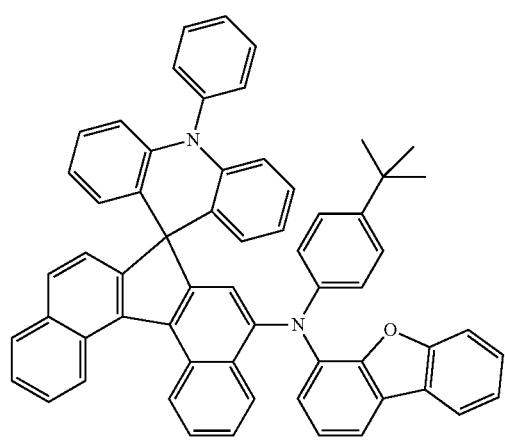
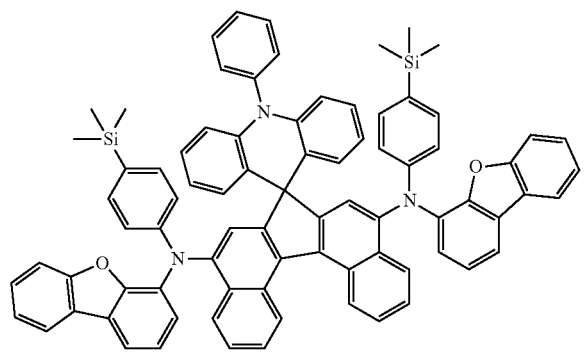
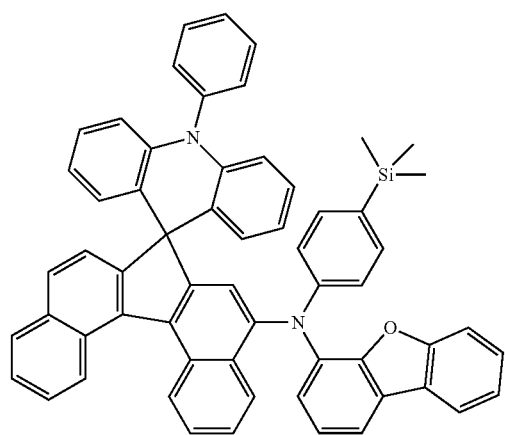
142
-continued
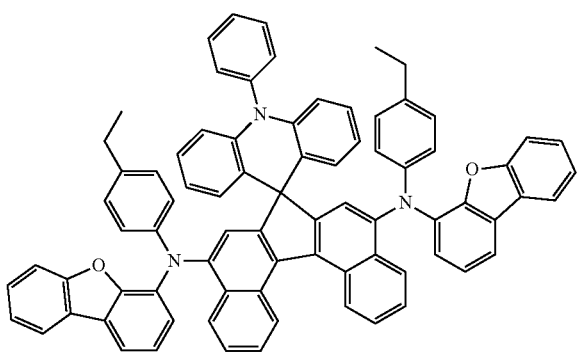
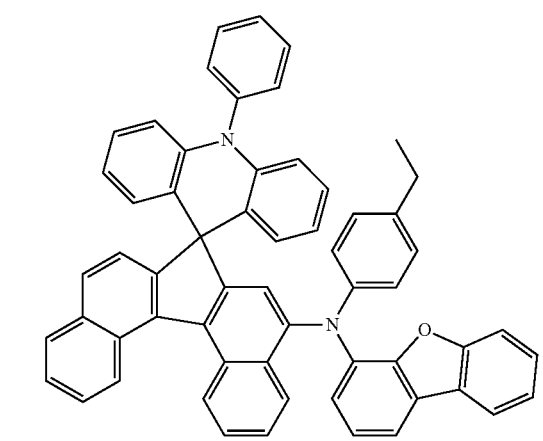
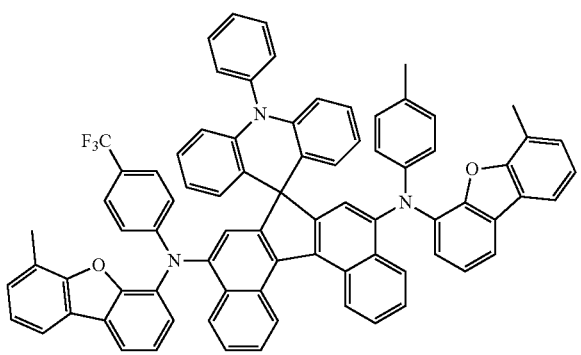
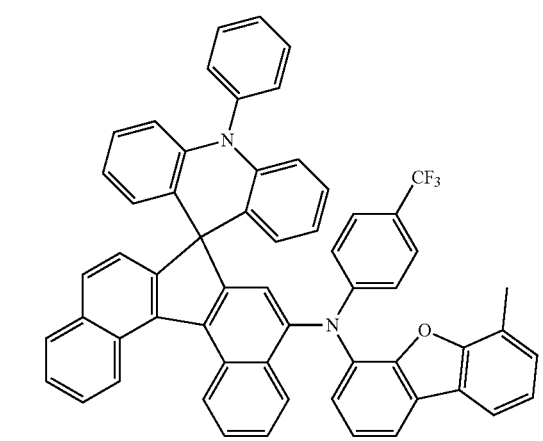

143
-continued
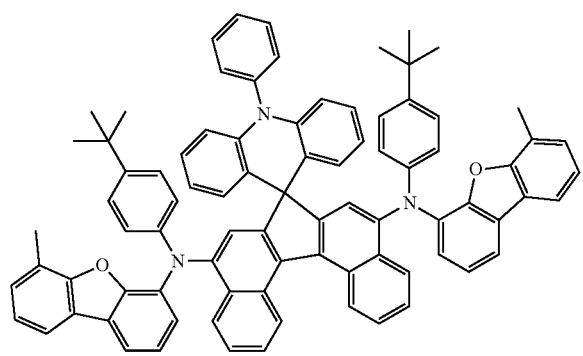
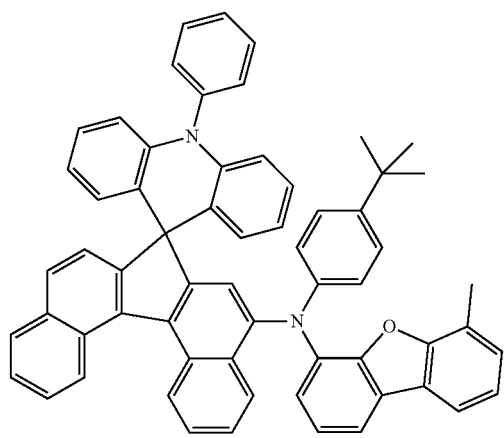
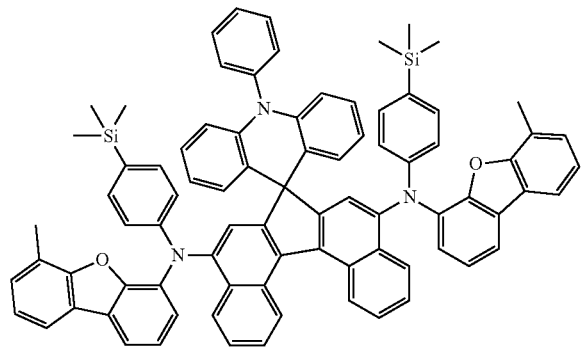
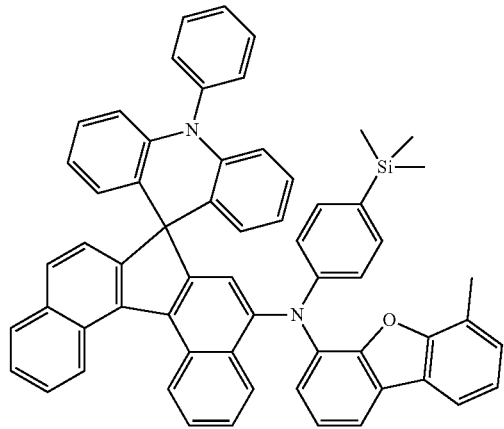
144
-continued
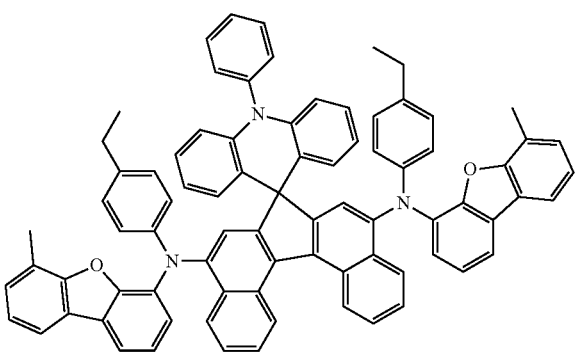
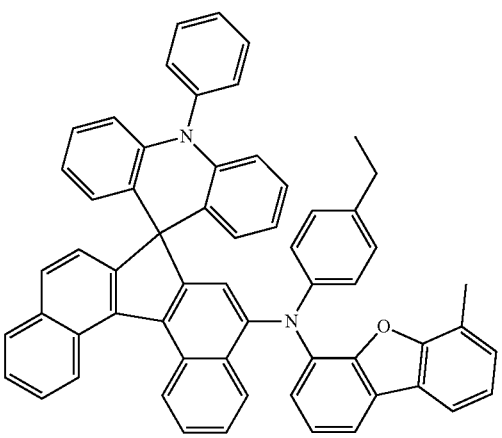
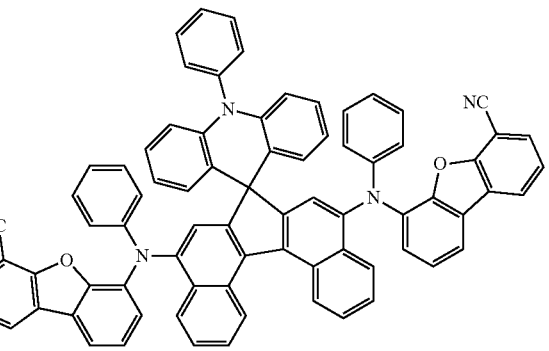
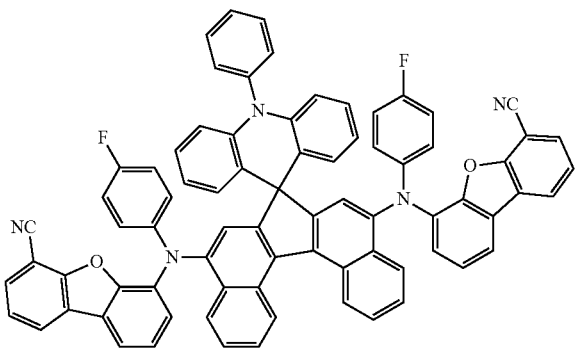

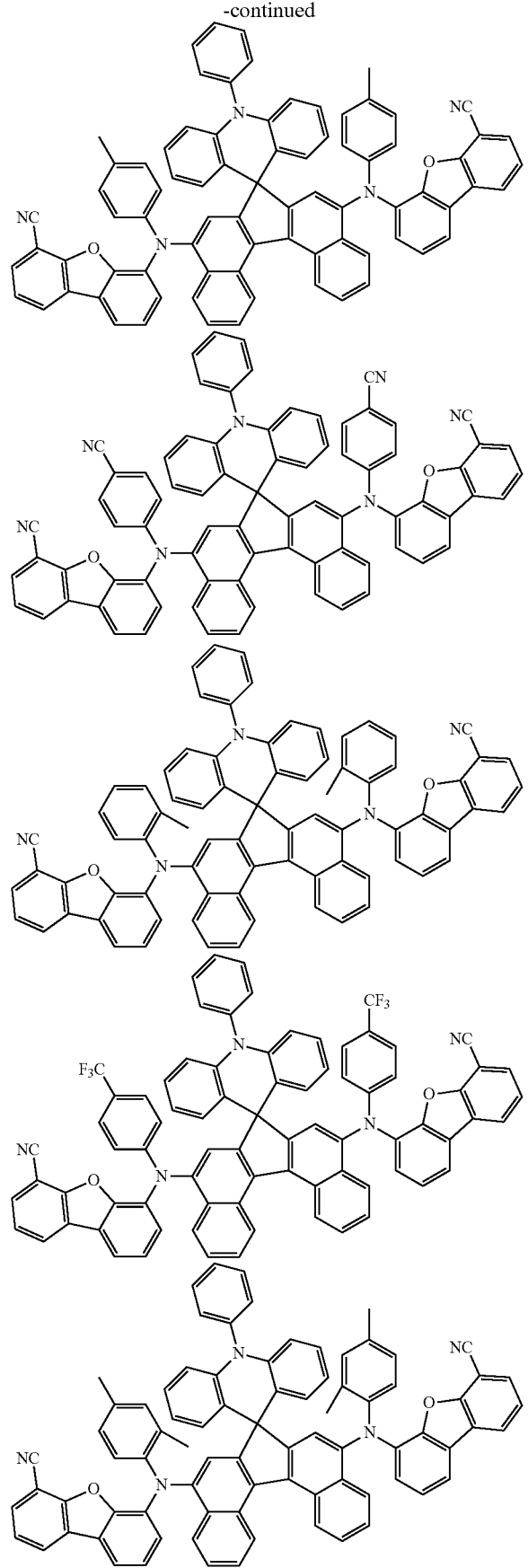
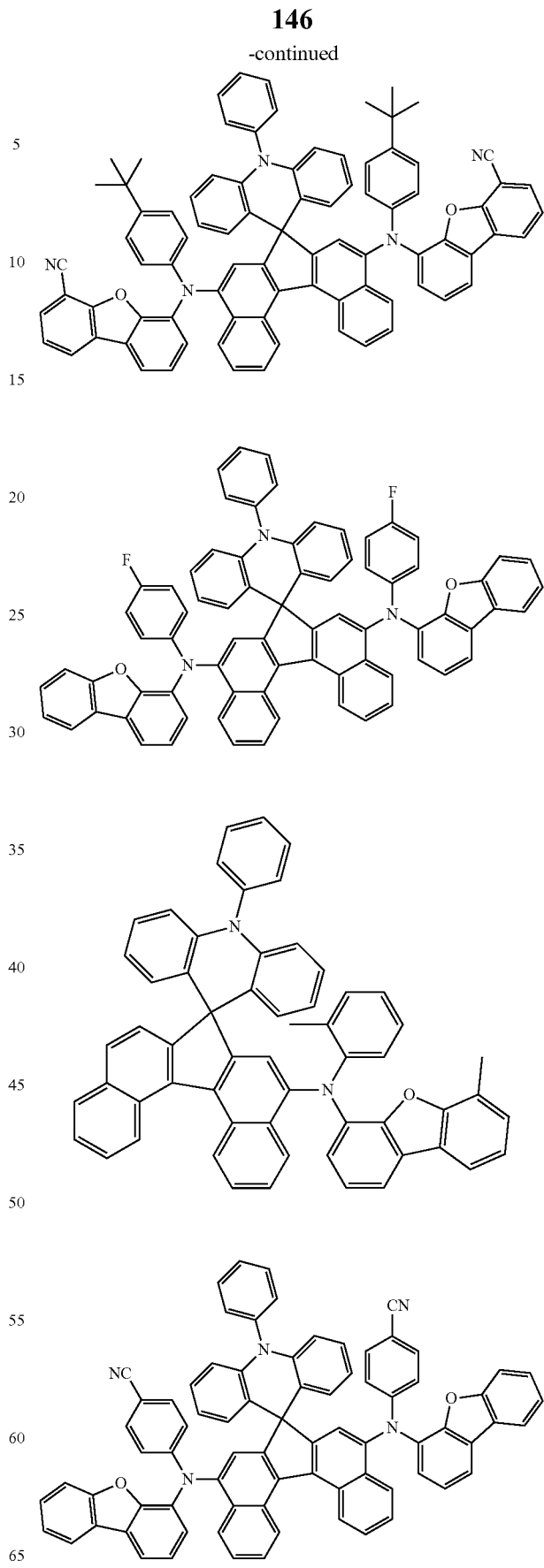

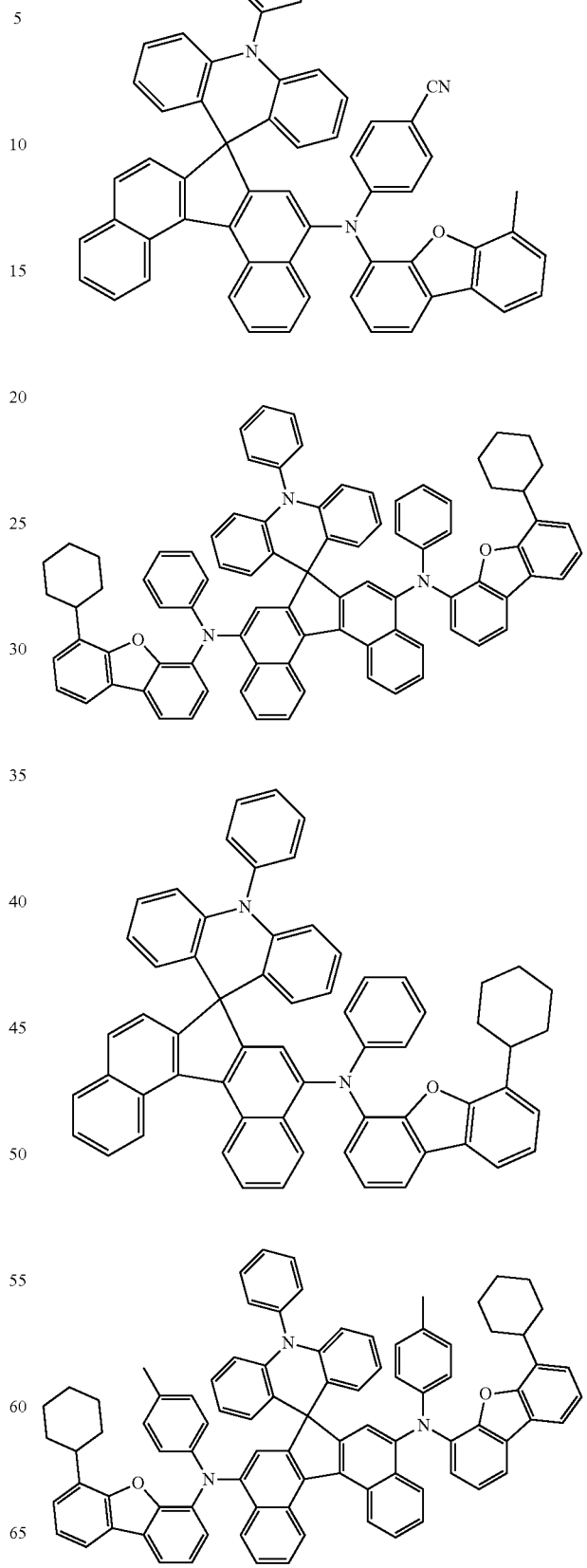

149
-continued
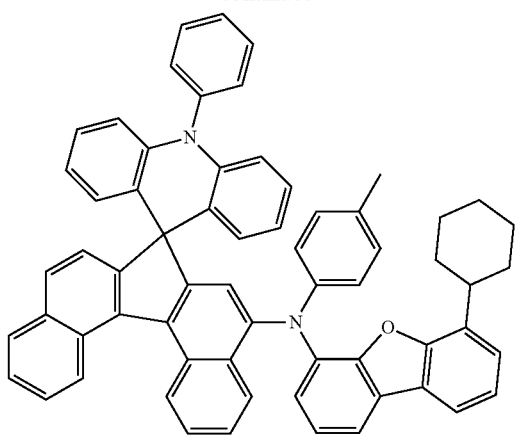
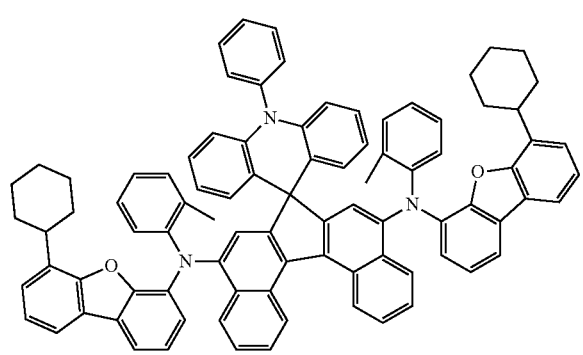
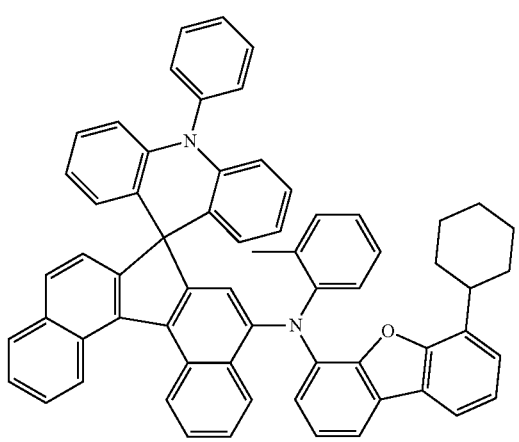
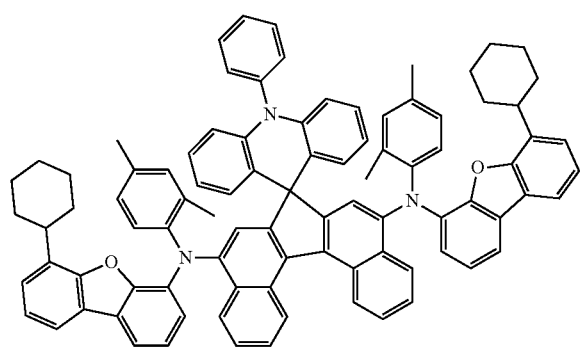
150
-continued
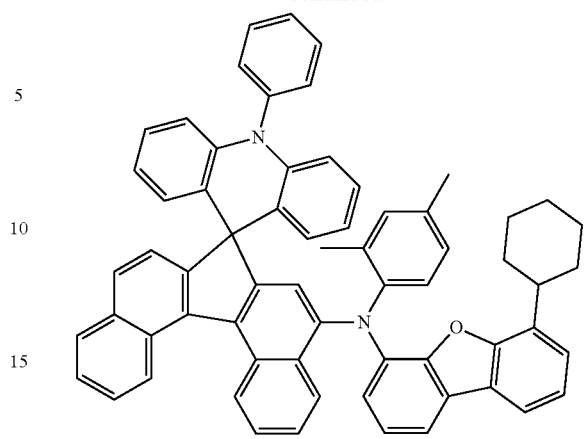
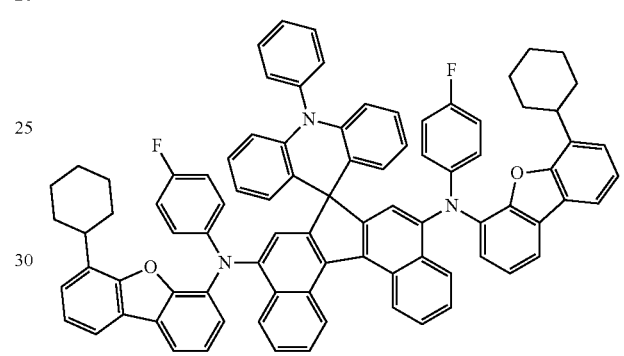
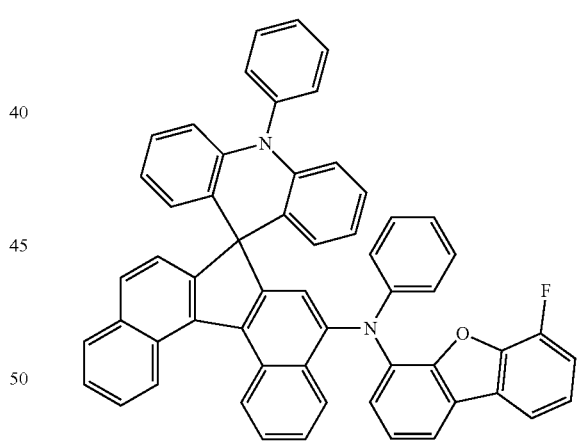
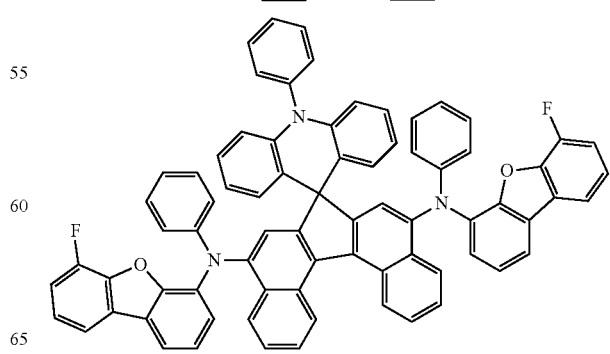

151
-continued
152
-continued
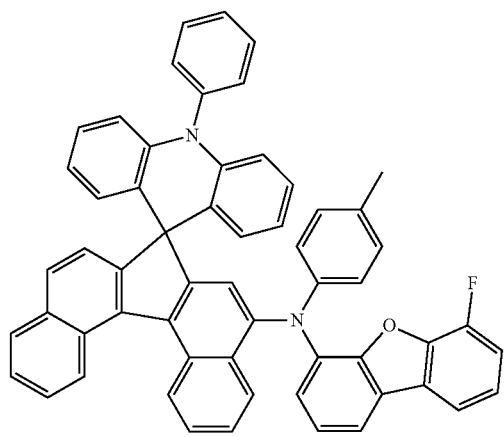
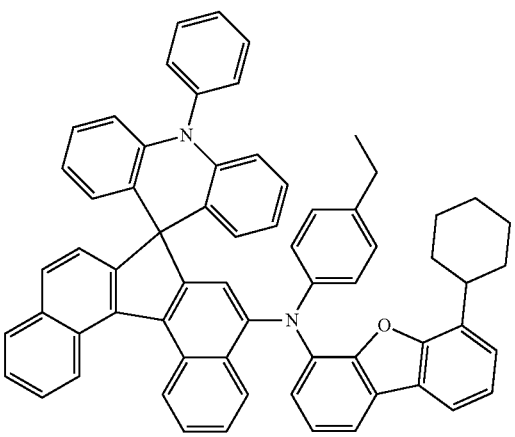
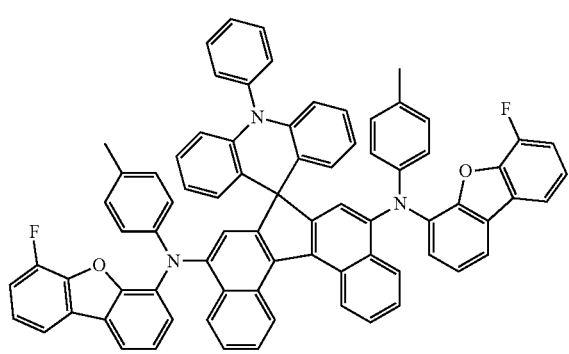
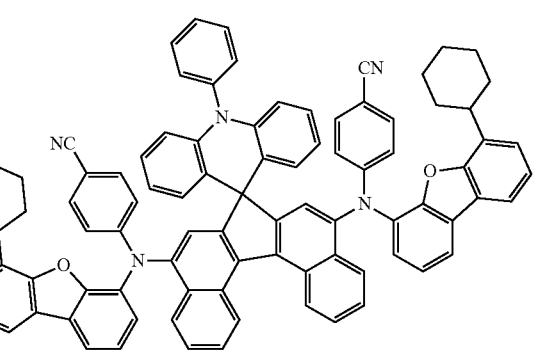
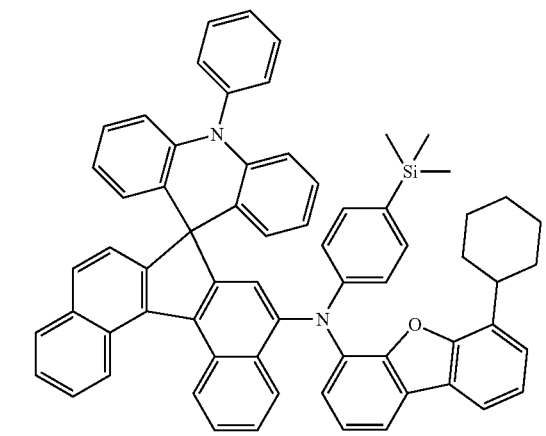
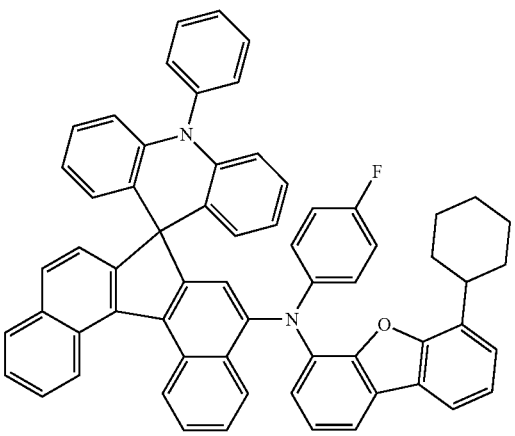
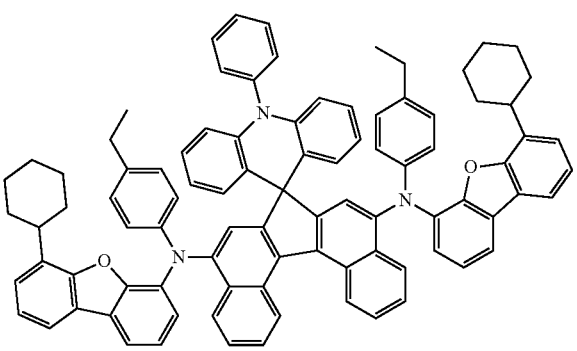
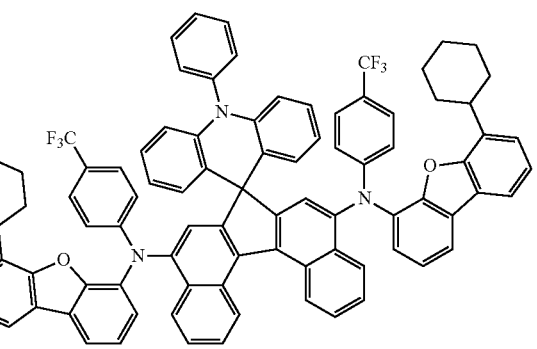

153
-continued
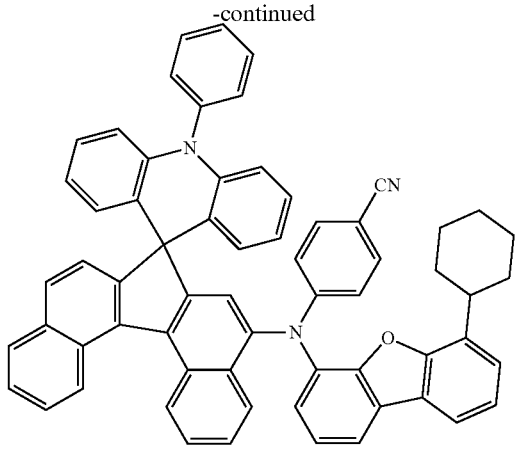
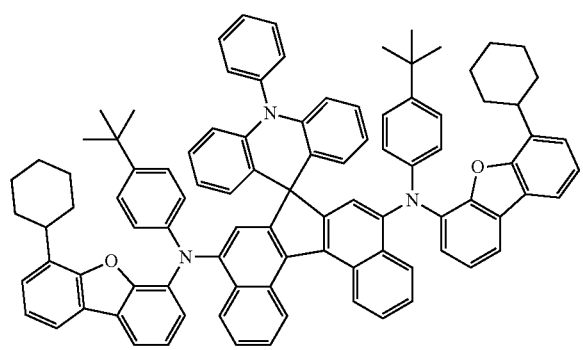
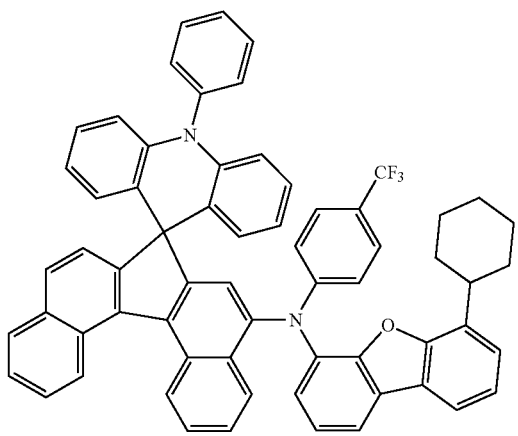
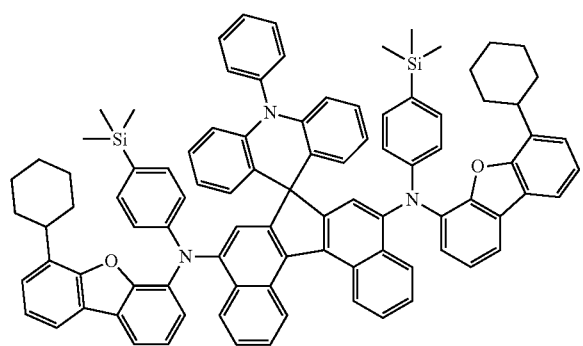
154
-continued
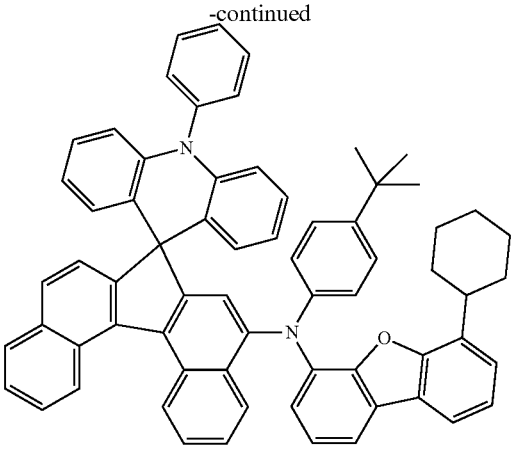
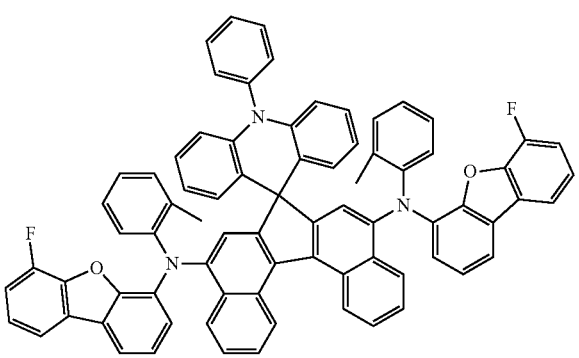
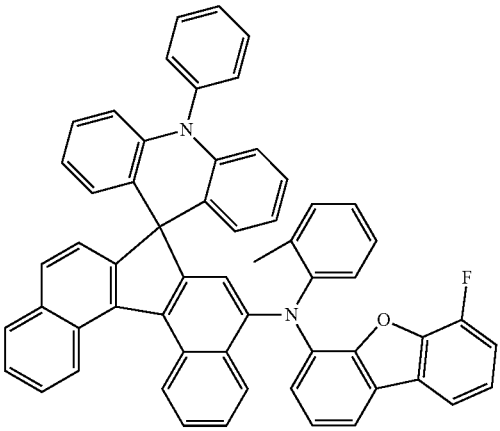
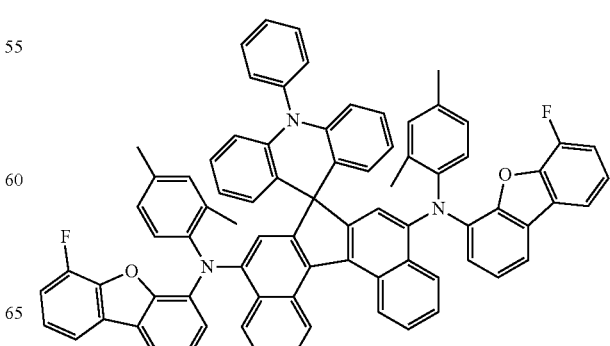

155 156
-continued -continued
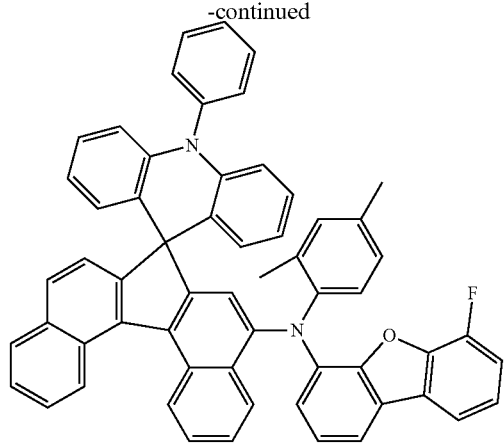
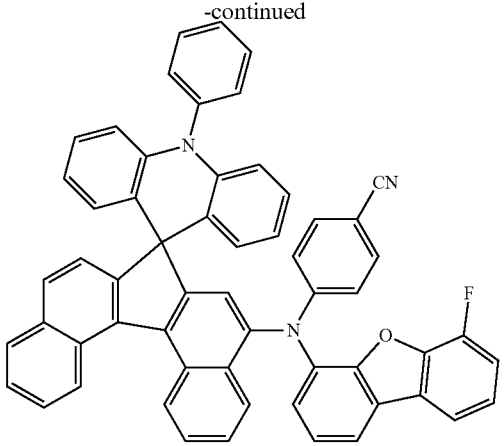
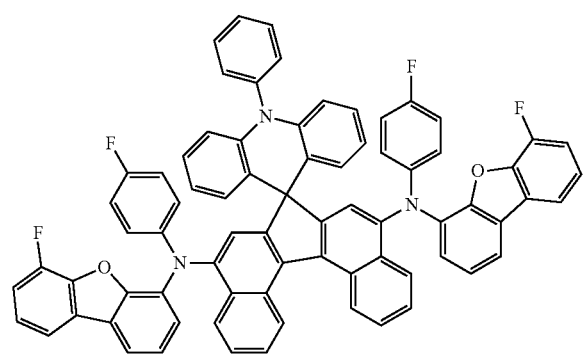
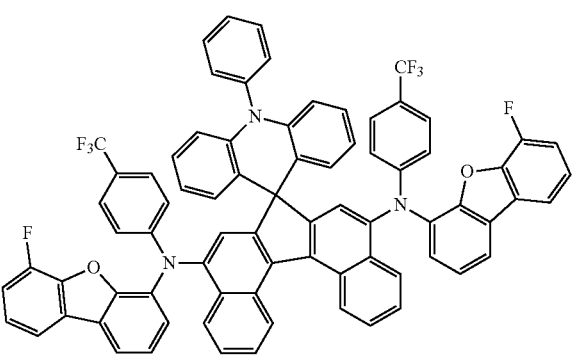
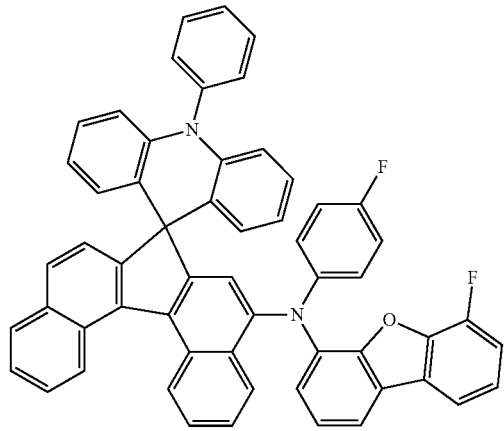
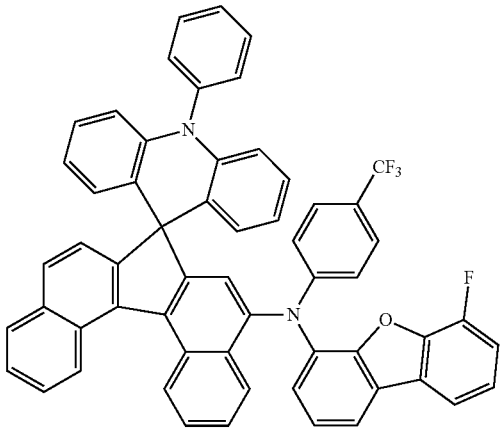
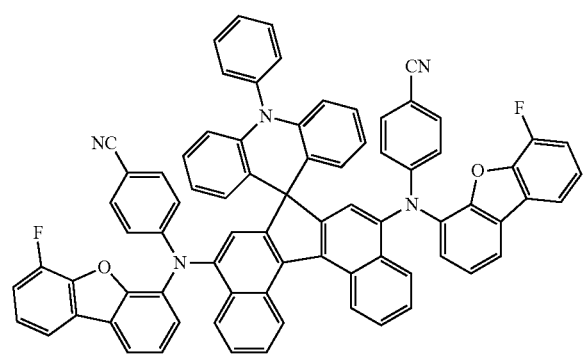
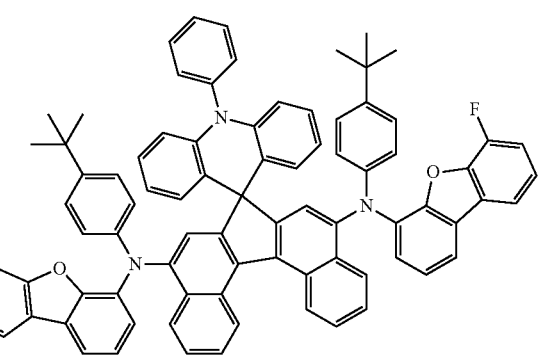

157
-continued
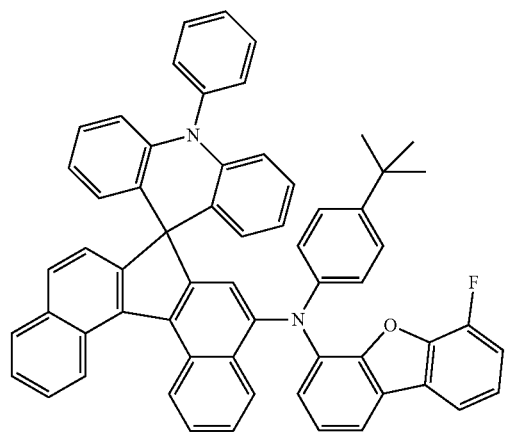
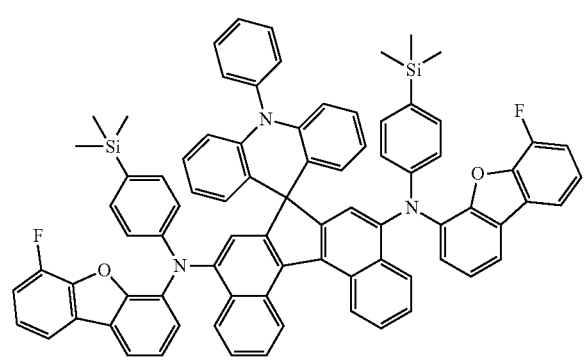
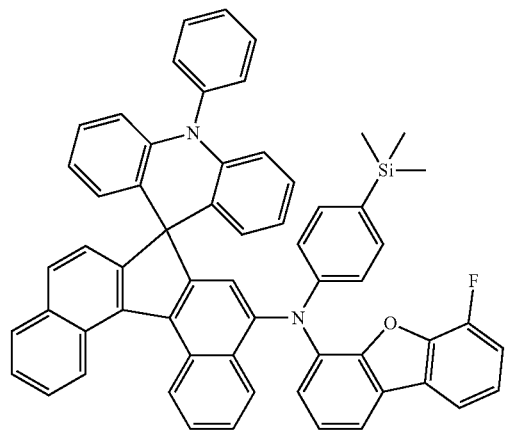
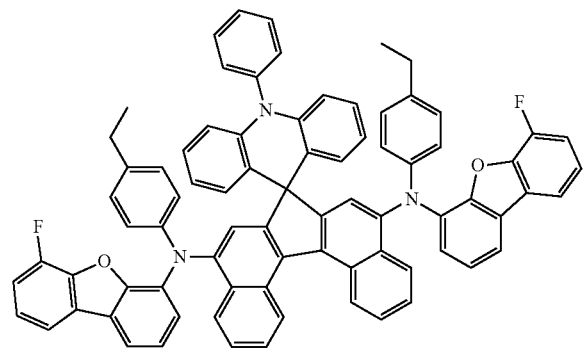
158
-continued
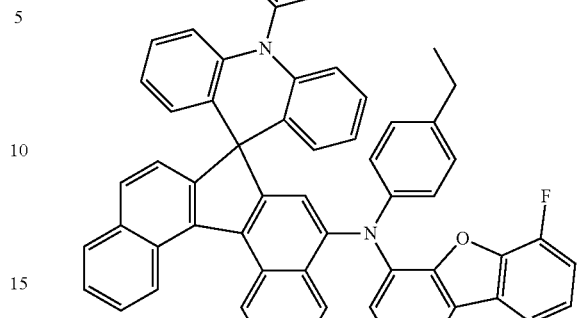
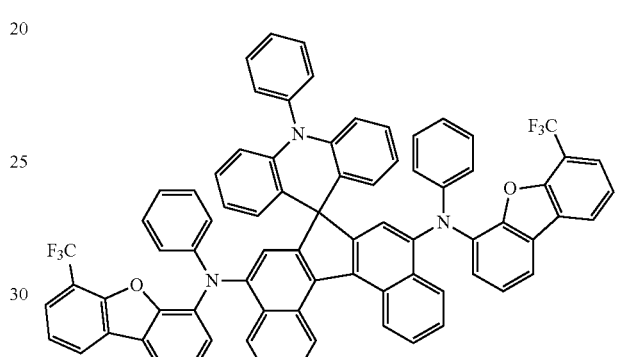
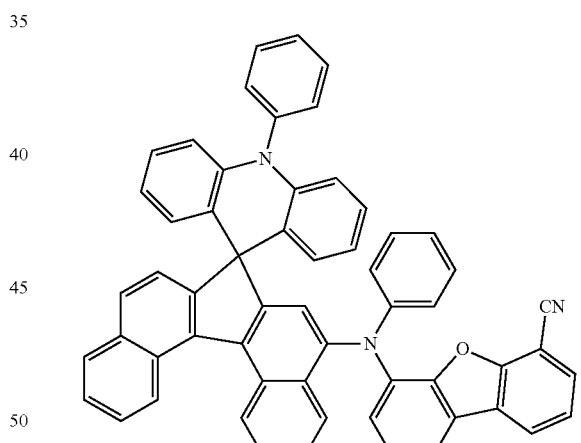
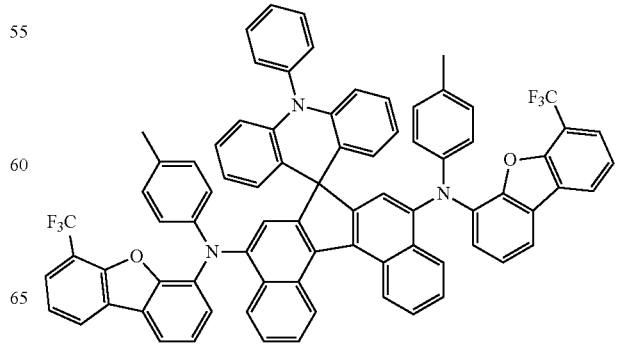

159
-continued
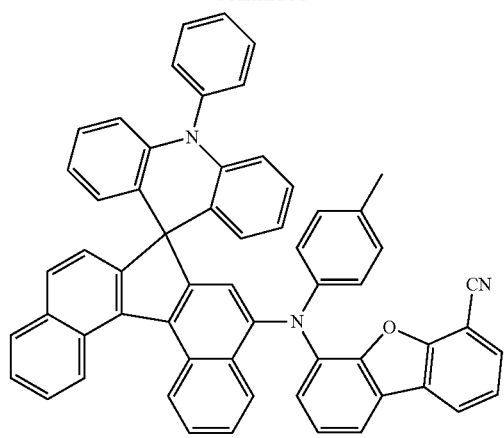
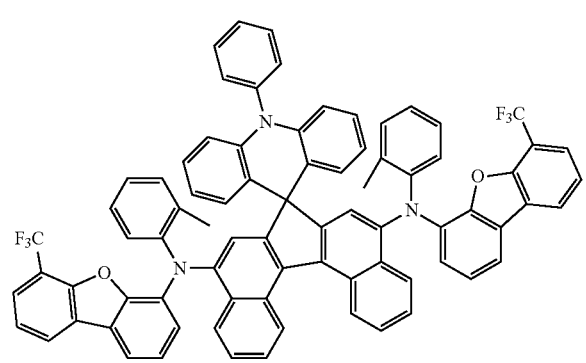
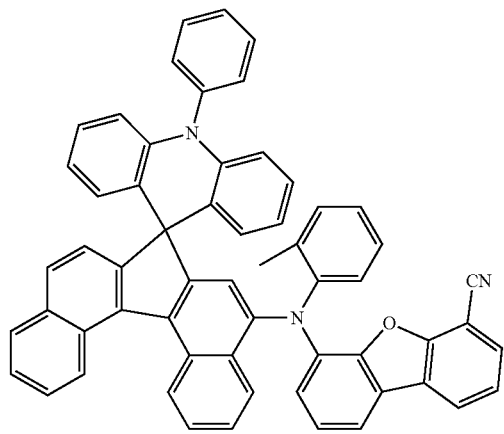
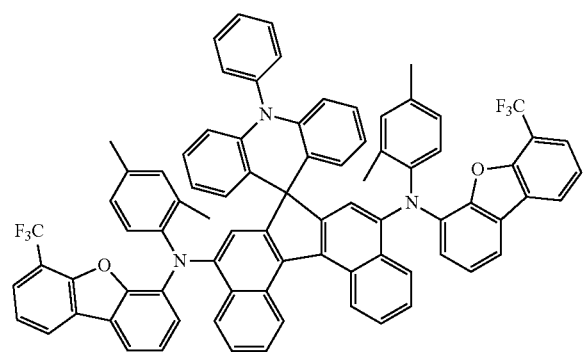
160
-continued
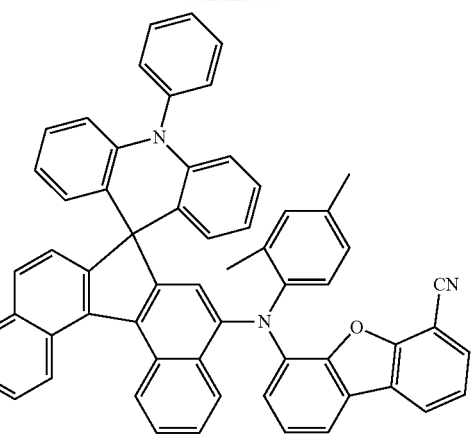
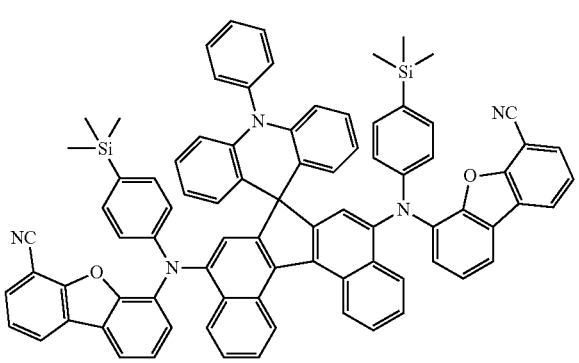
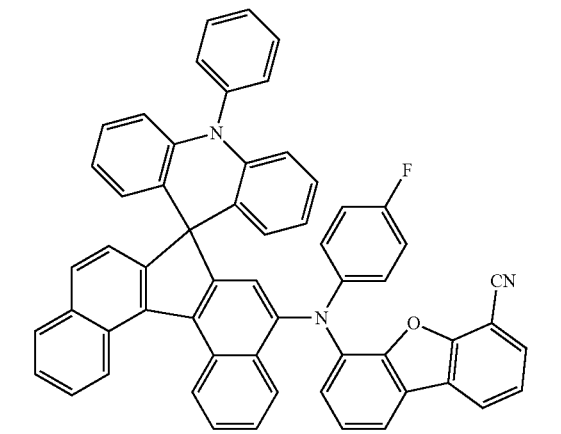
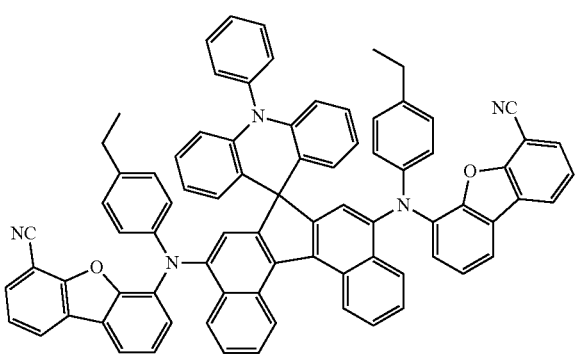

161
-continued
162
-continued
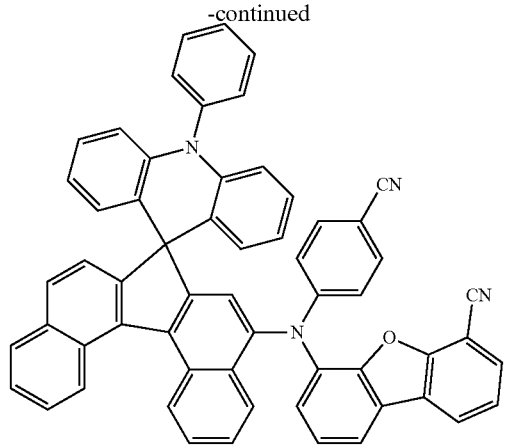
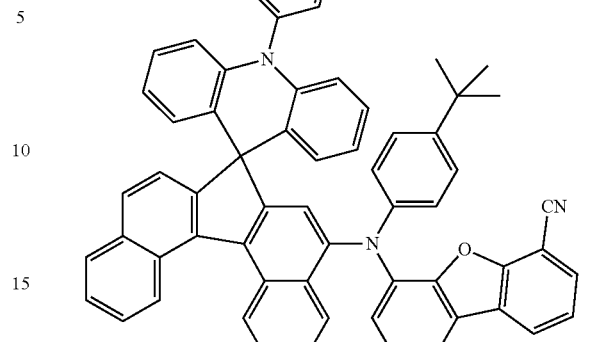
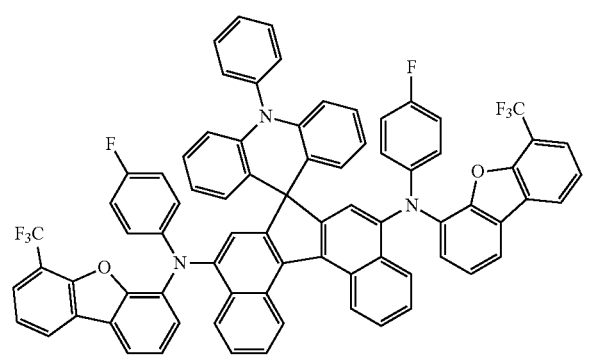
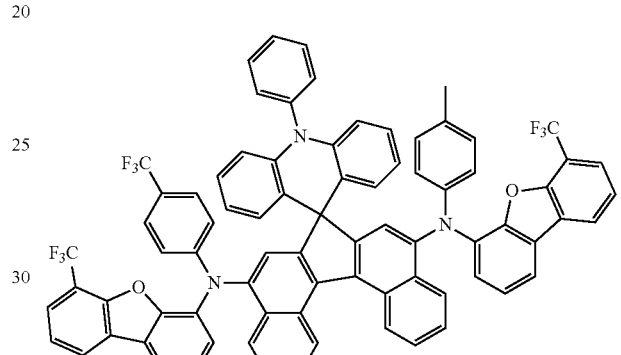
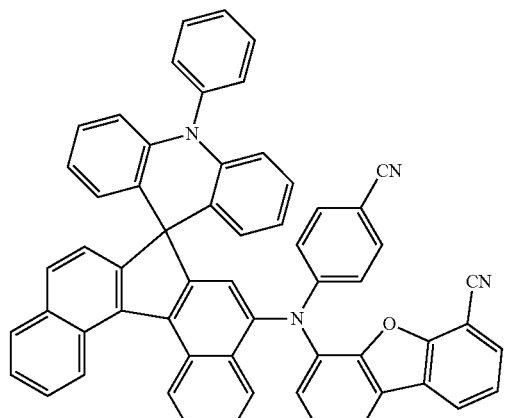
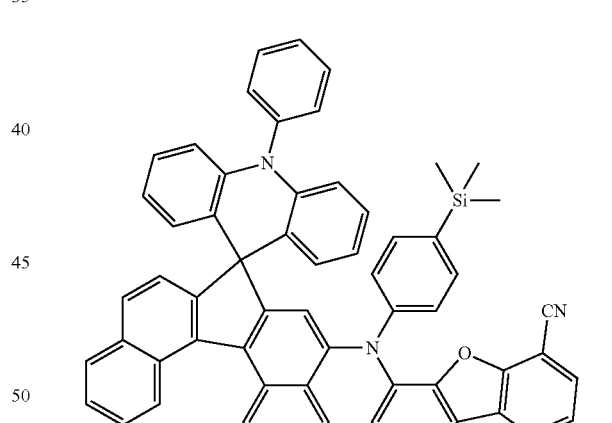
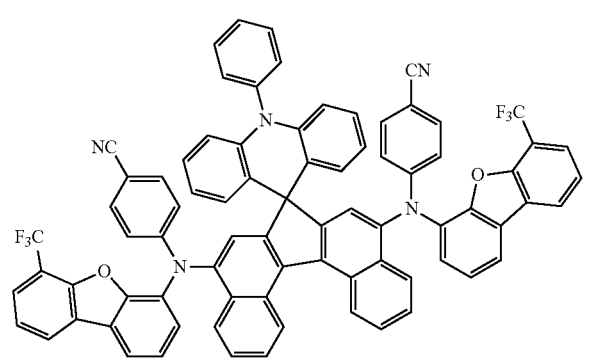
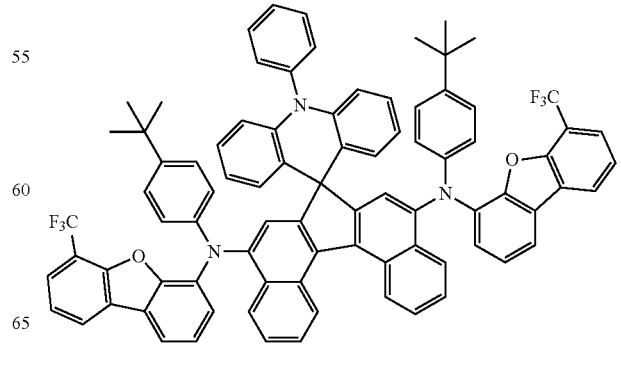

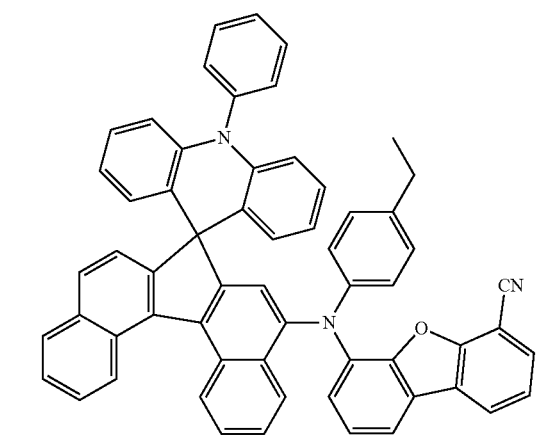
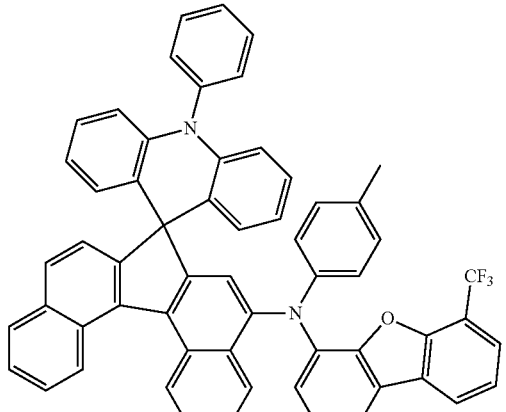
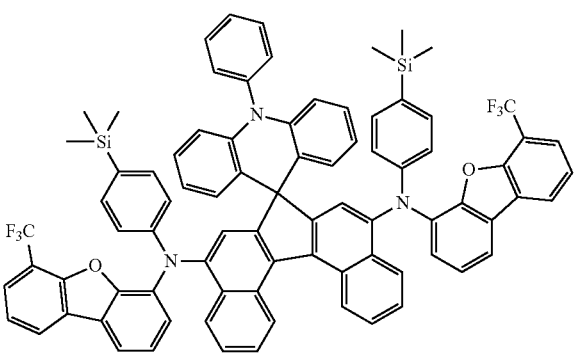
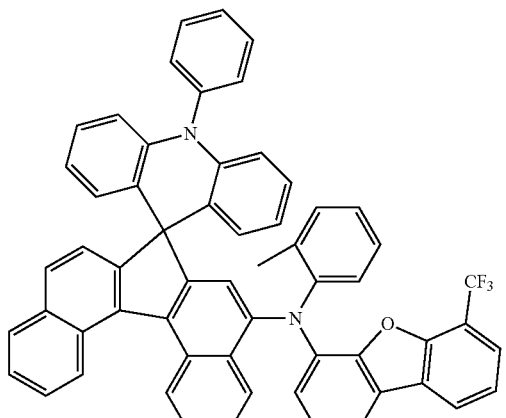
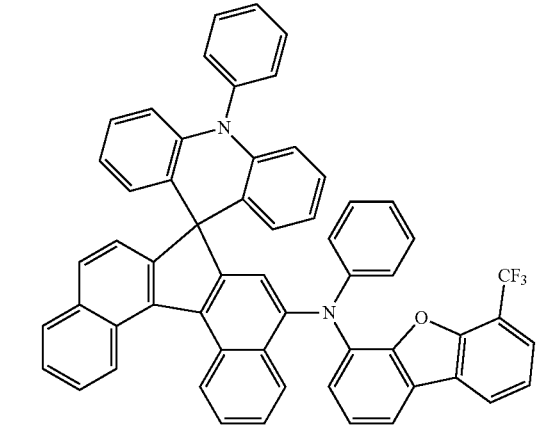
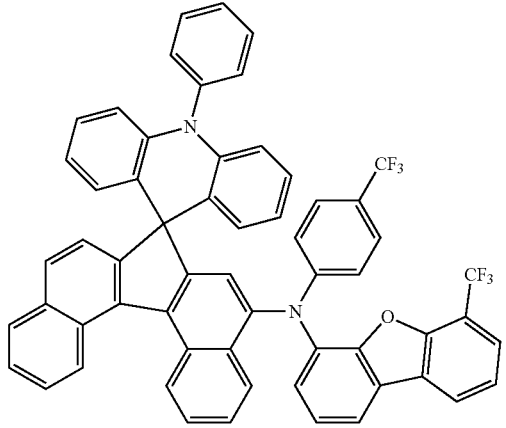
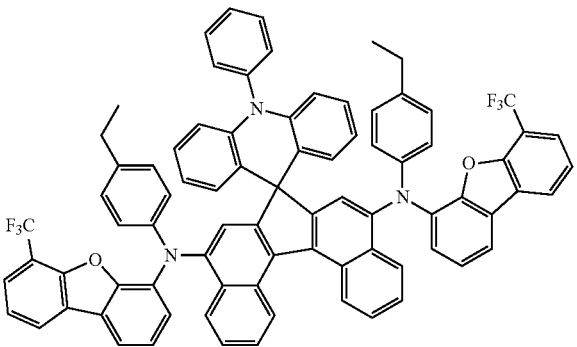
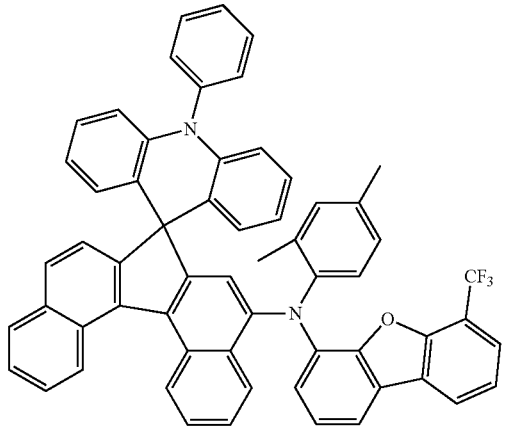

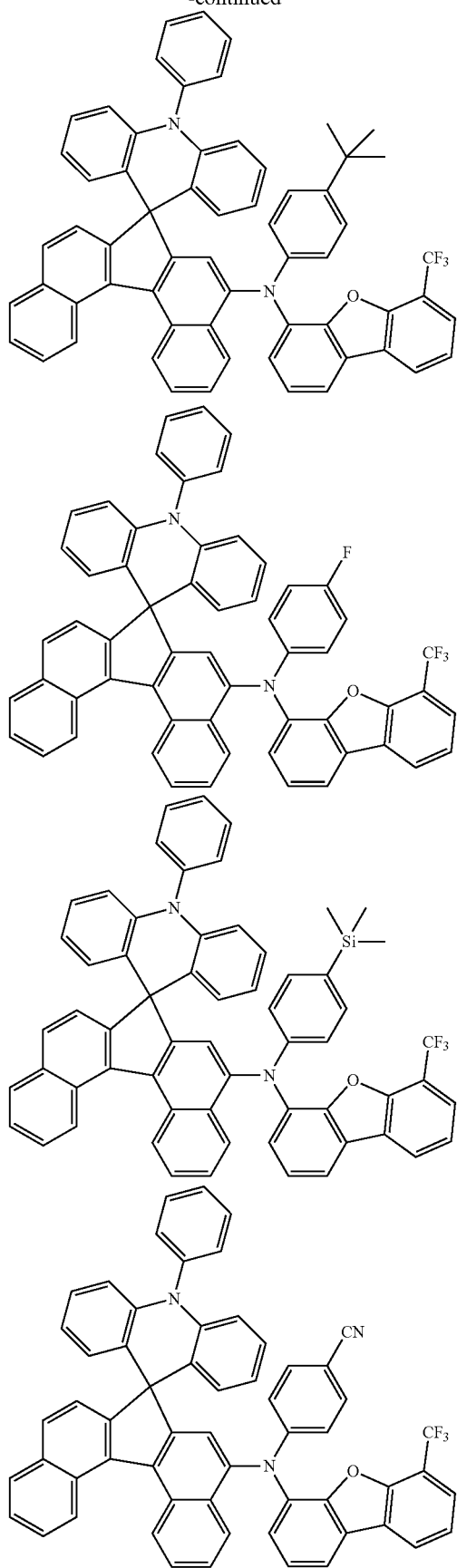
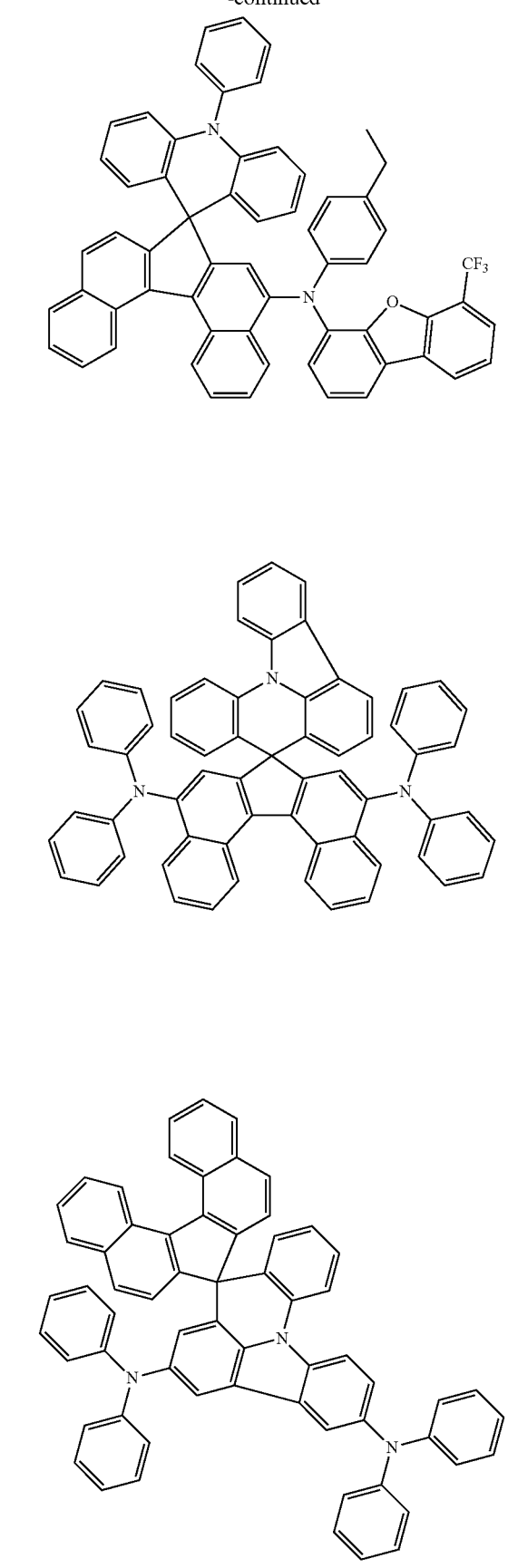

-continued
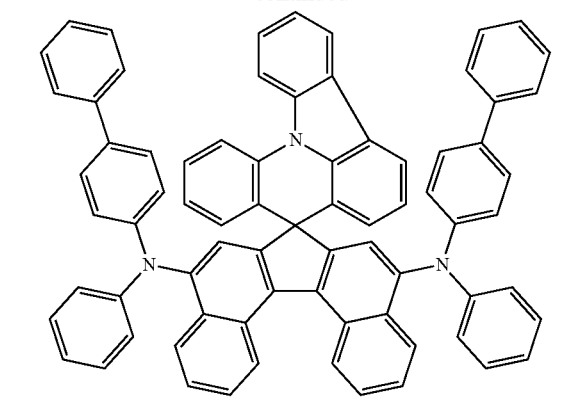
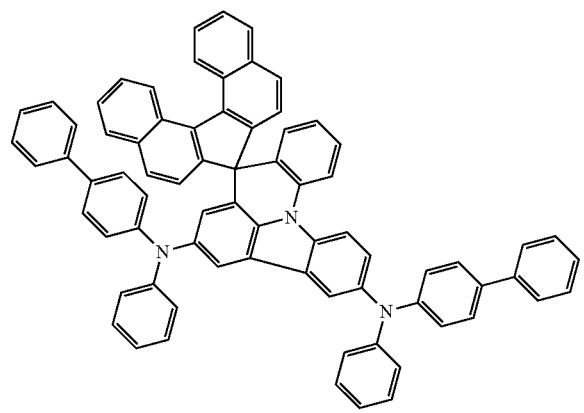
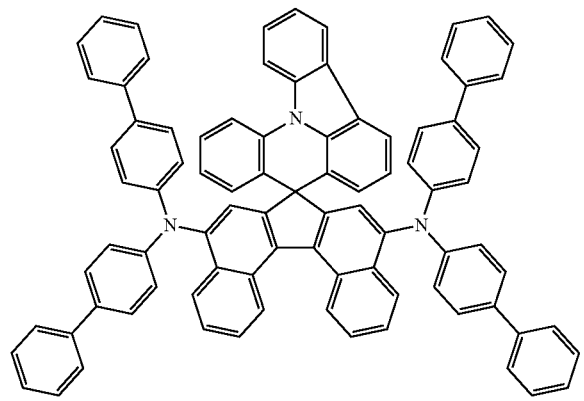
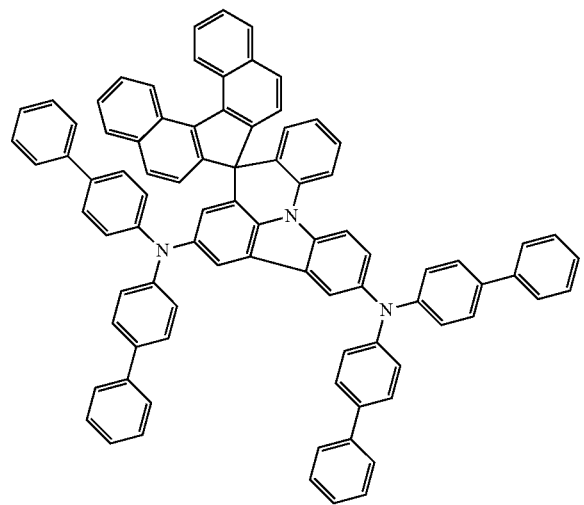
-continued
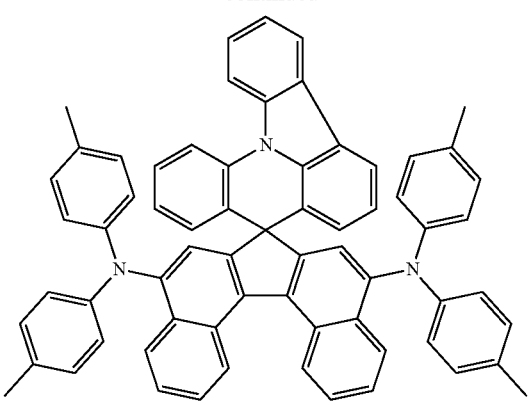
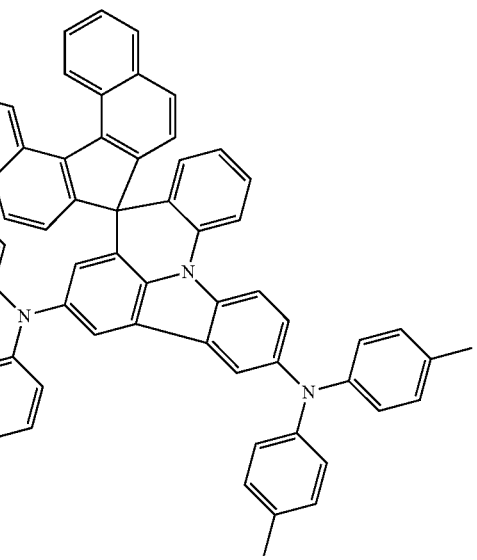
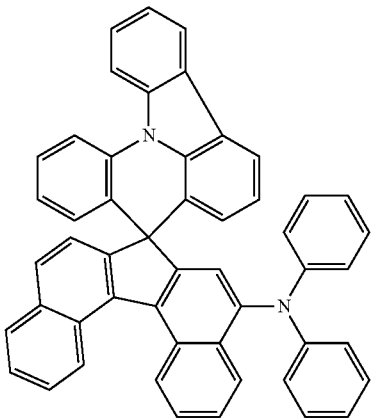

169
-continued
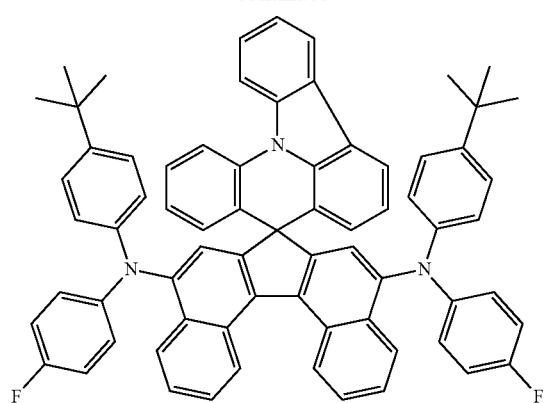
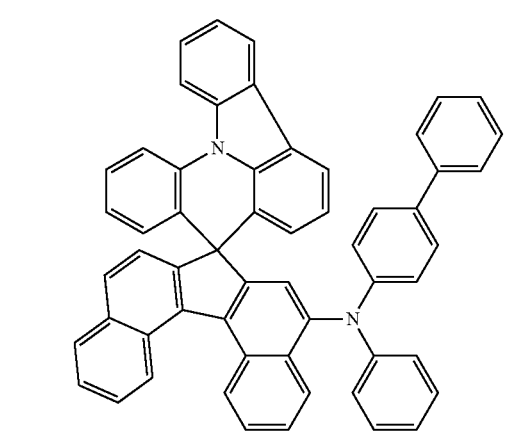
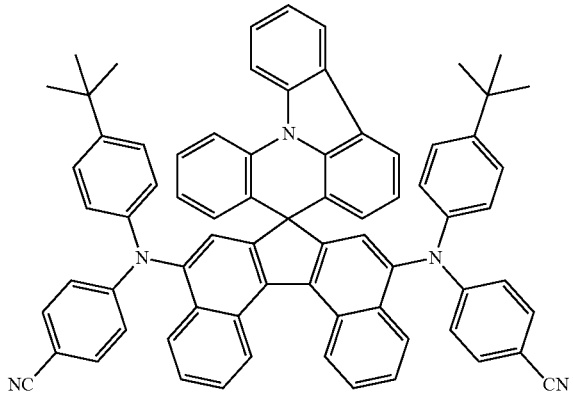
170
-continued
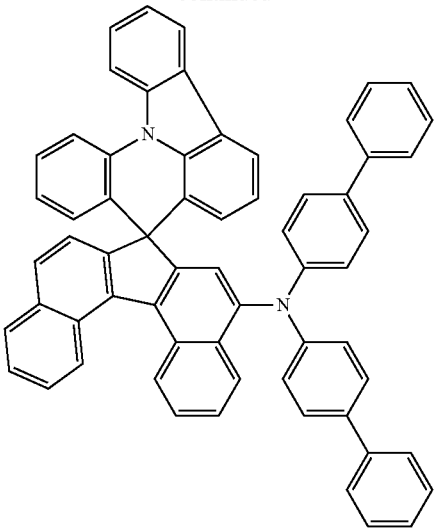
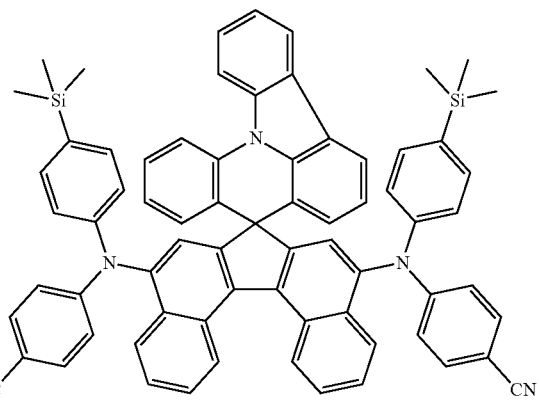
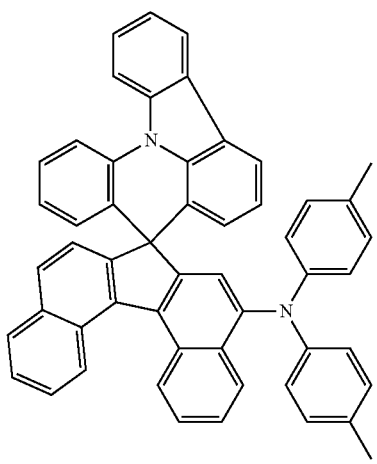

171
-continued
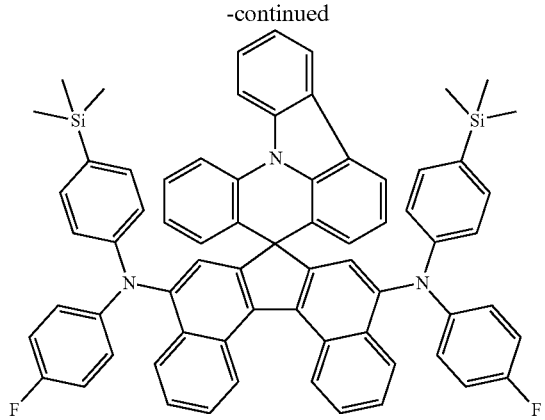
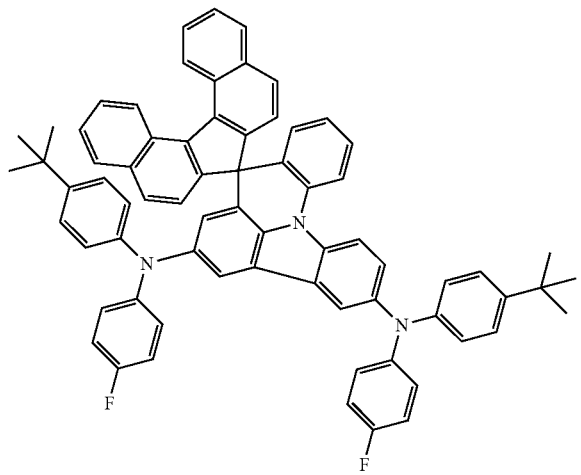
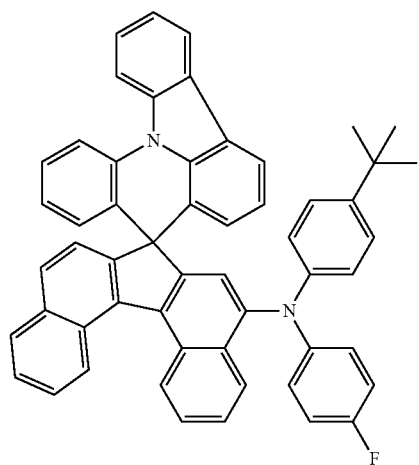
172
-continued
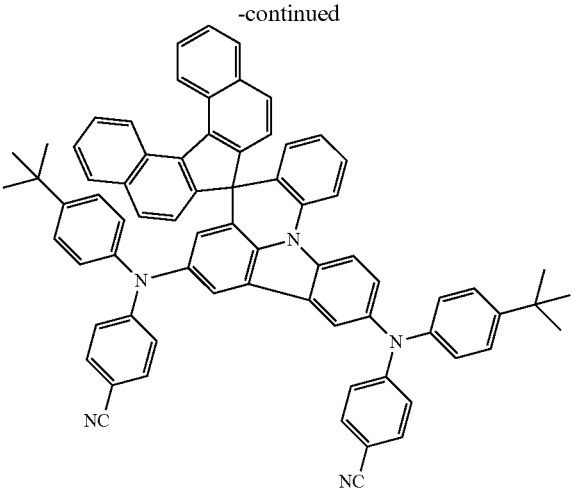
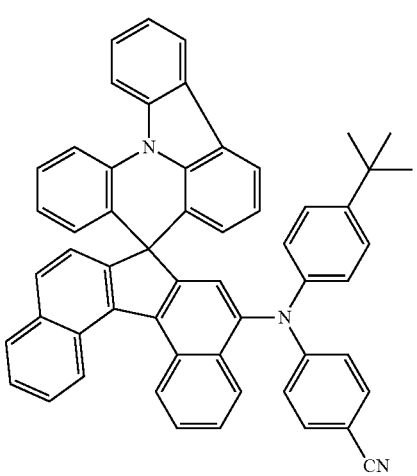
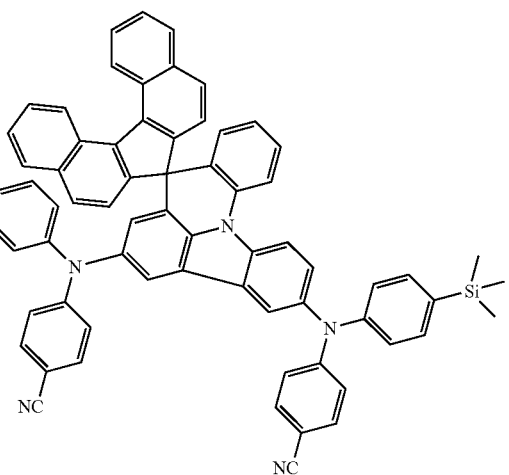

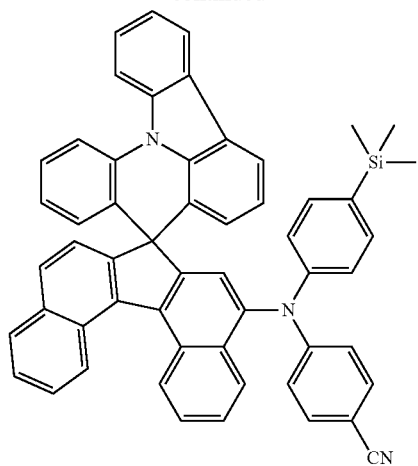
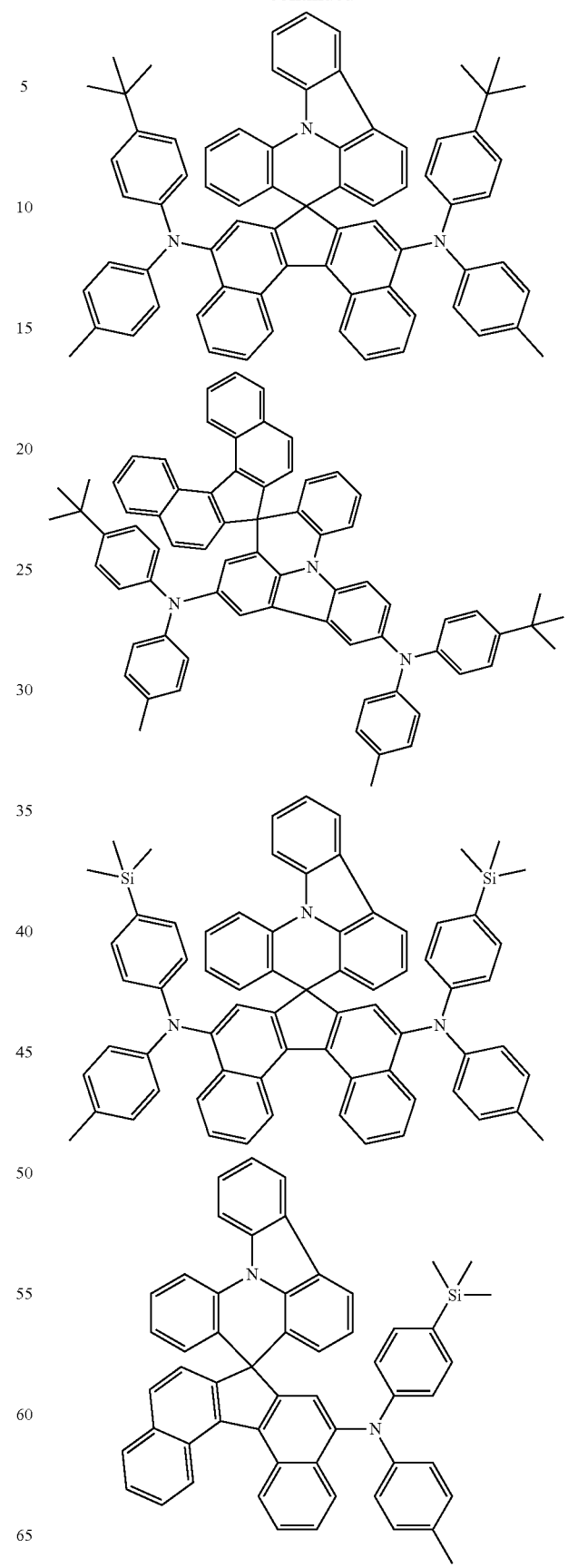

175
-continued
176
-continued
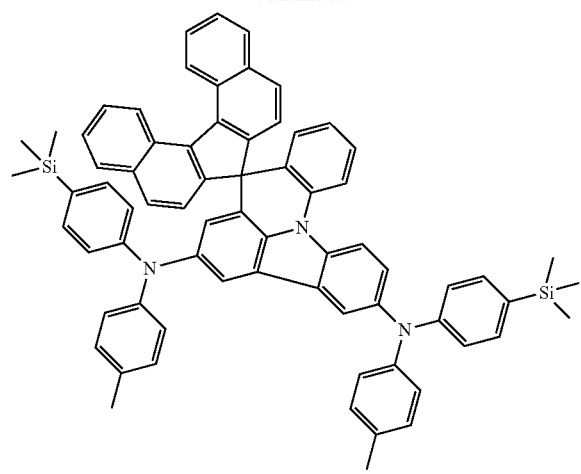
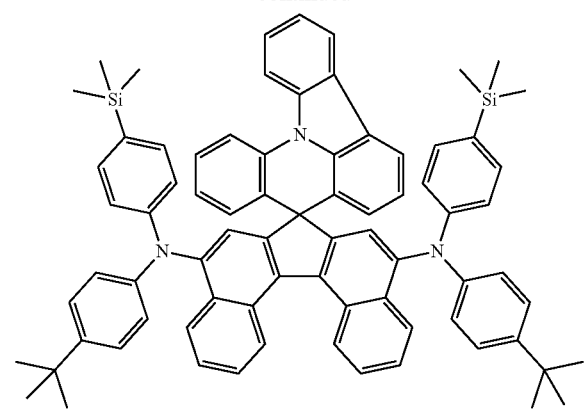
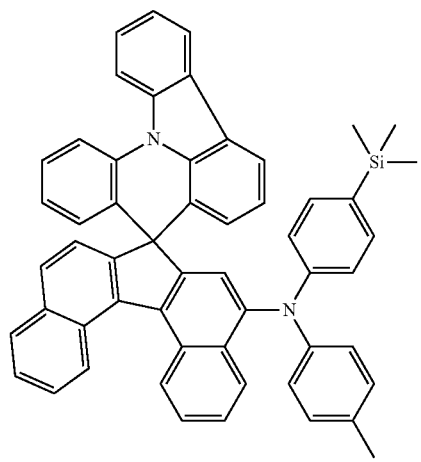
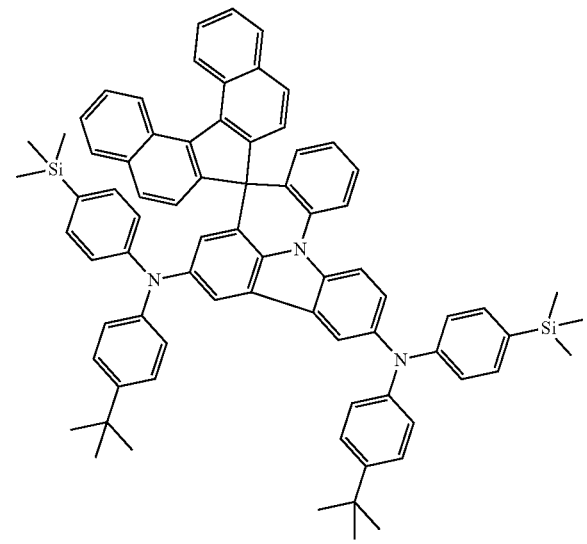
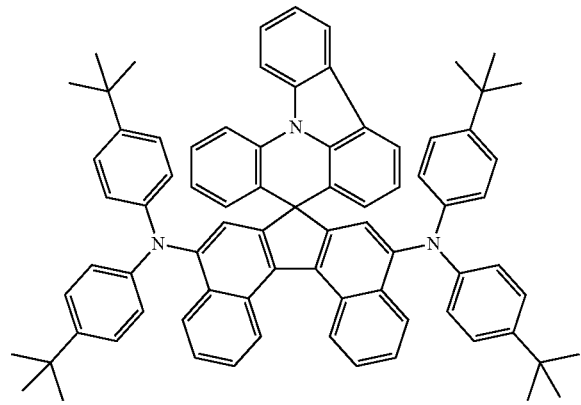

-continued
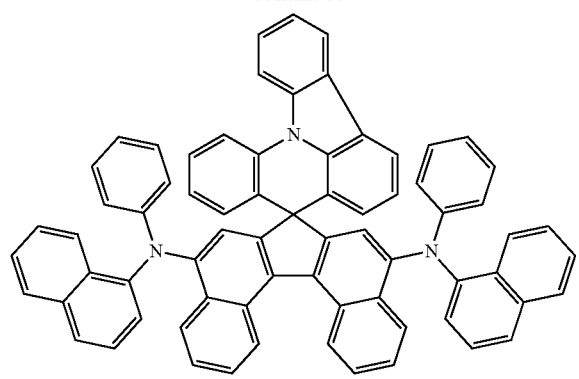
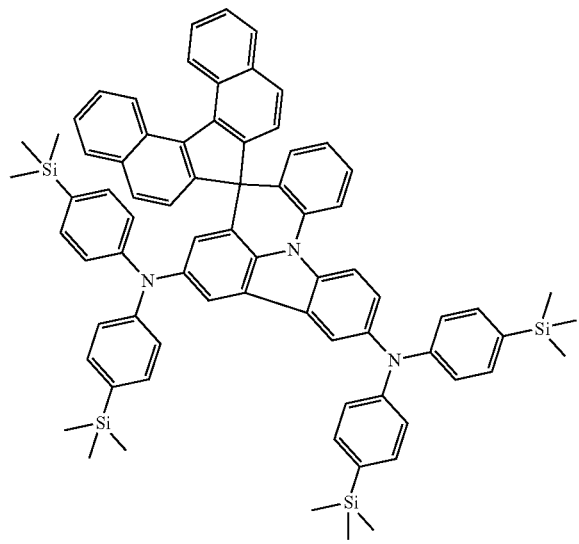
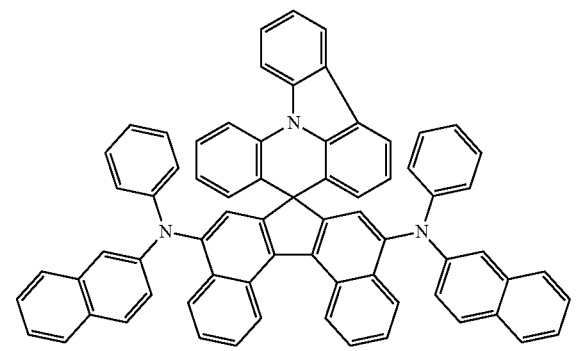
-continued
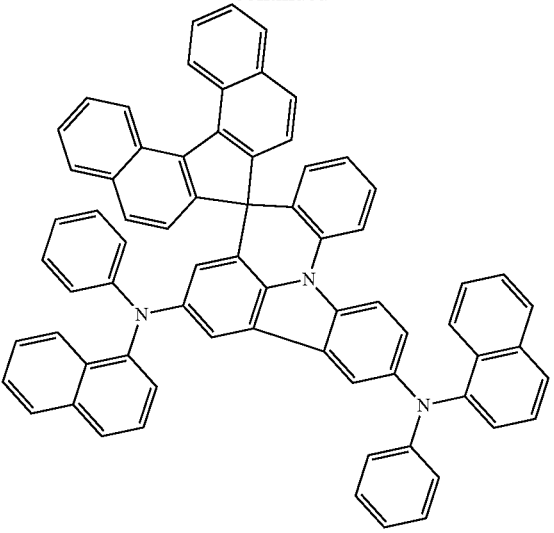
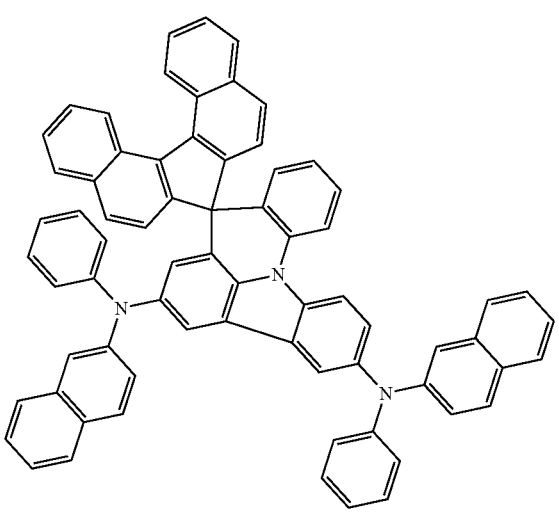

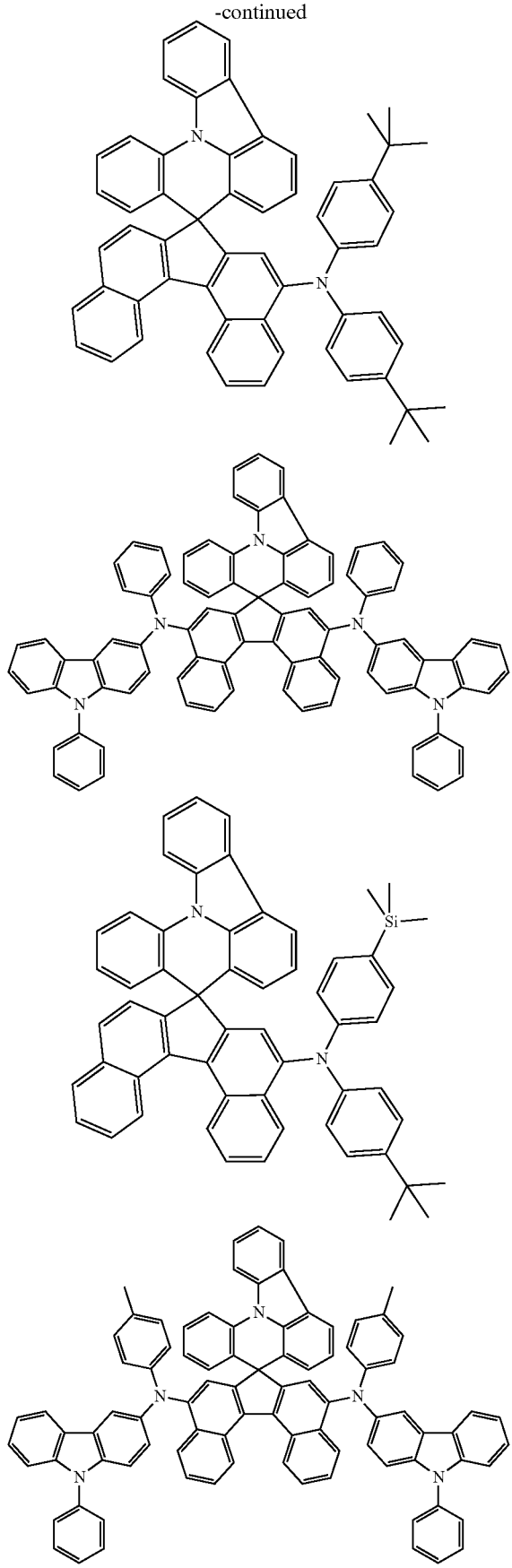
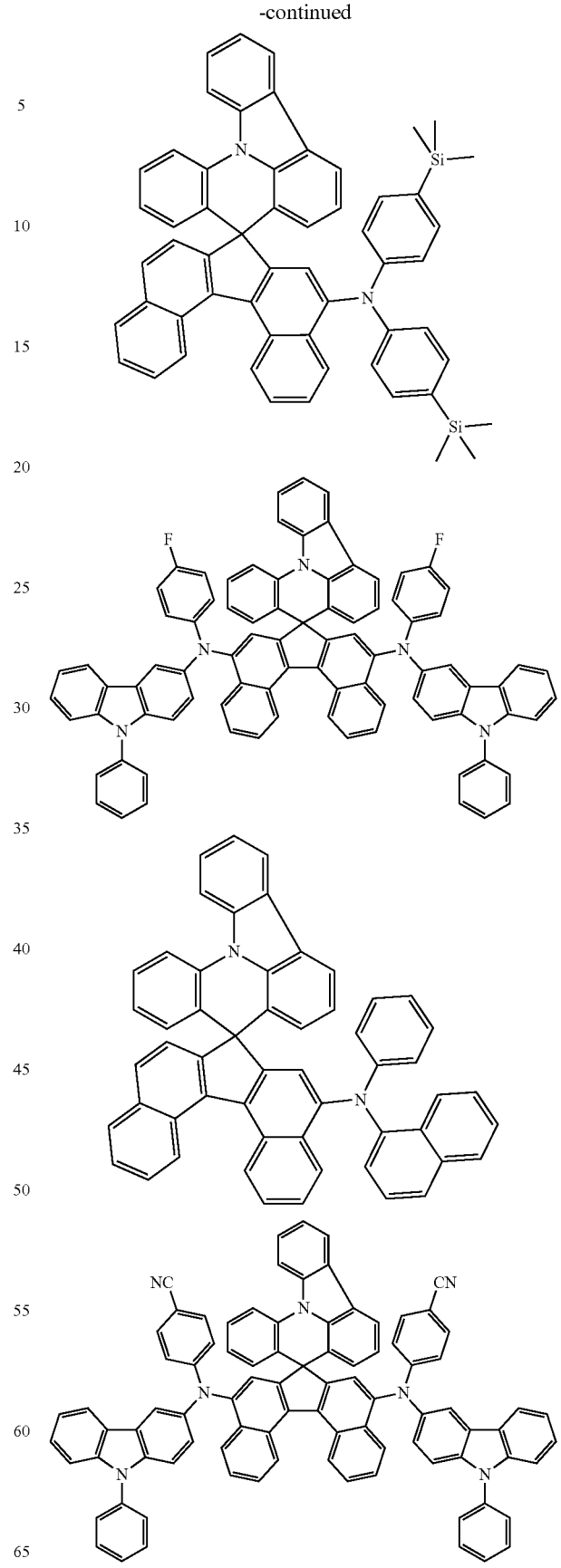

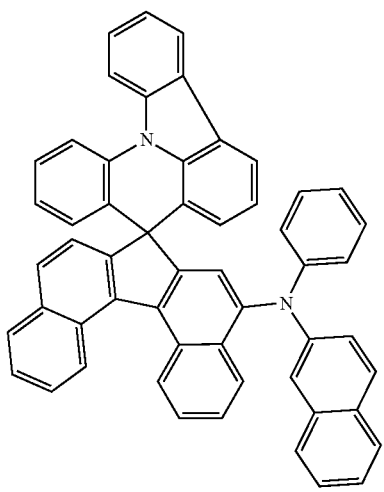
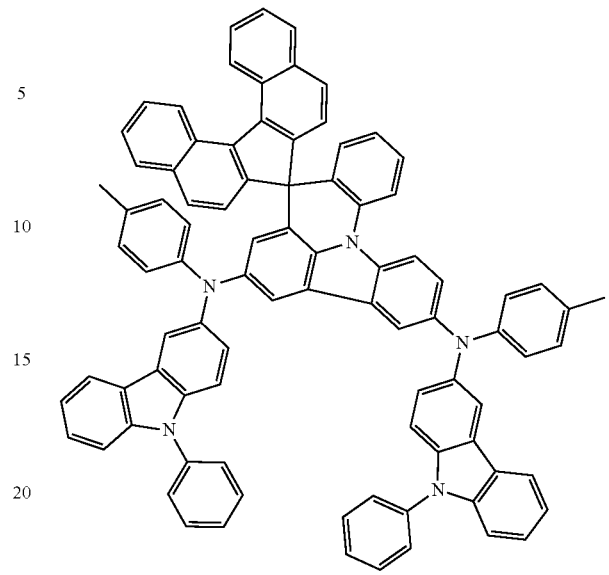
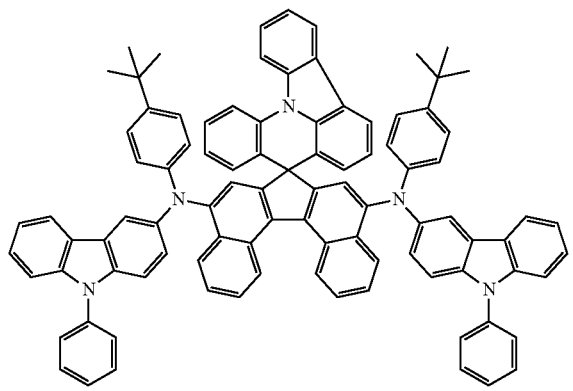
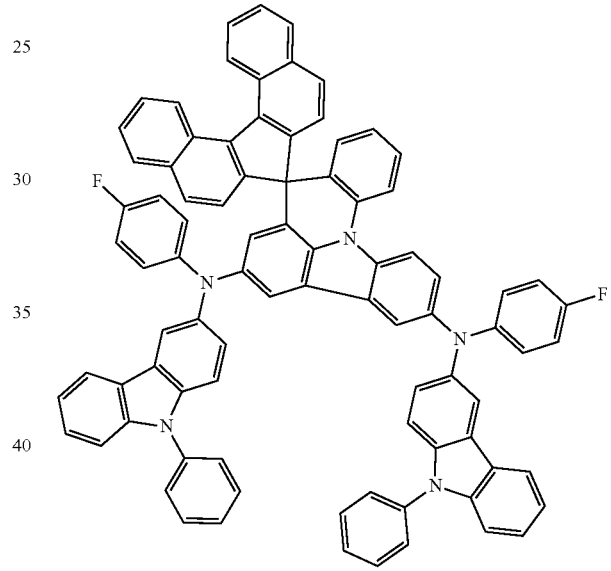
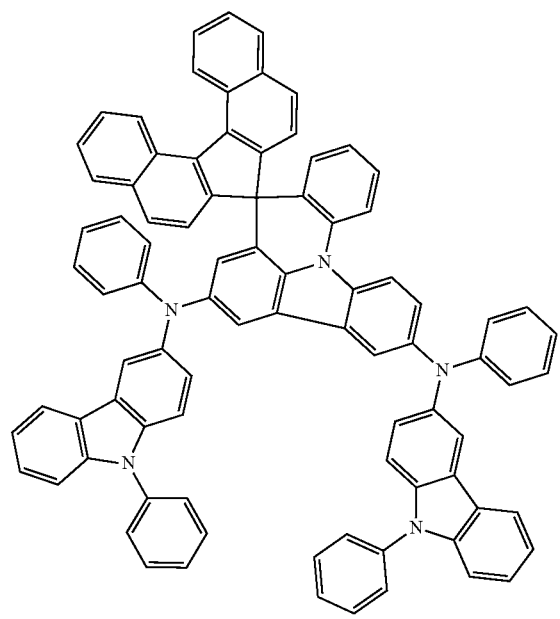

183
-continued
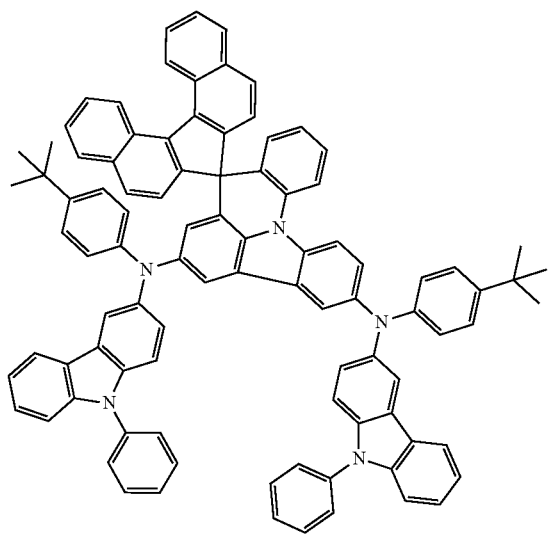
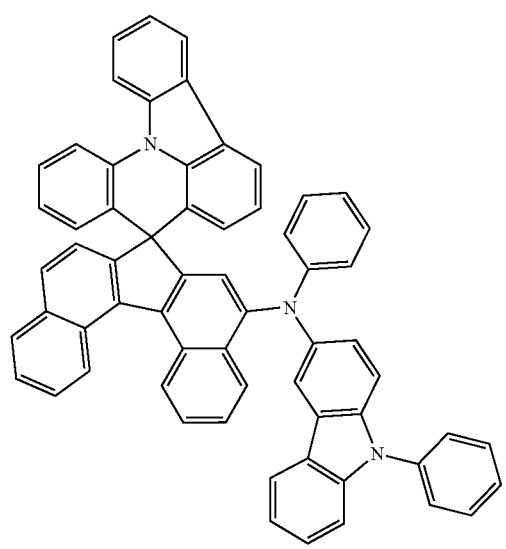
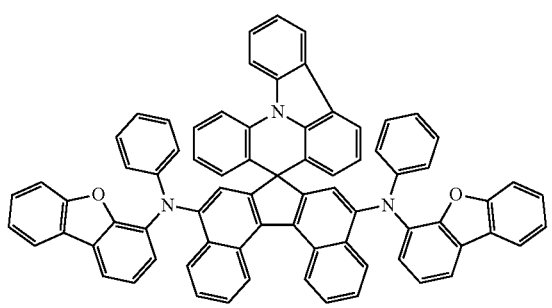
184
-continued
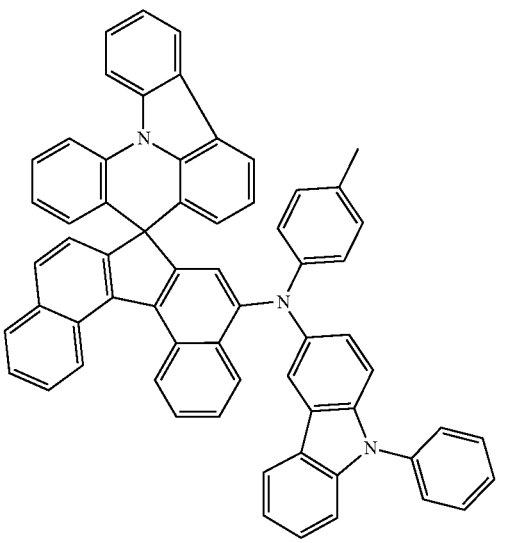
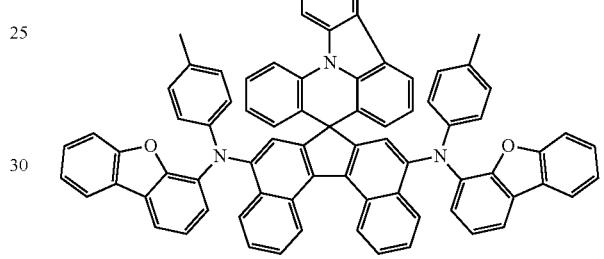
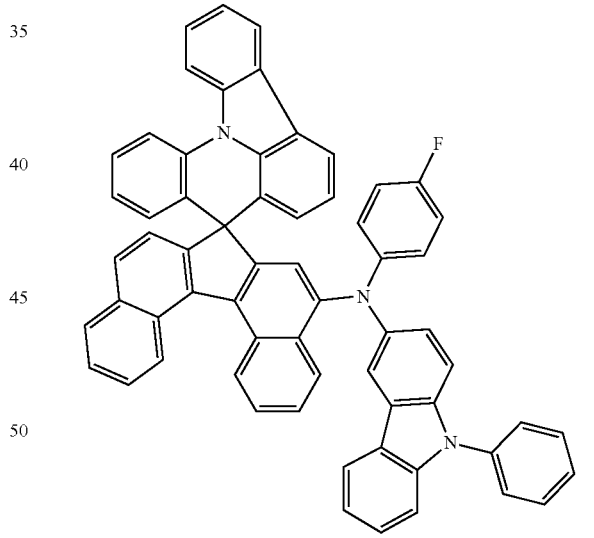
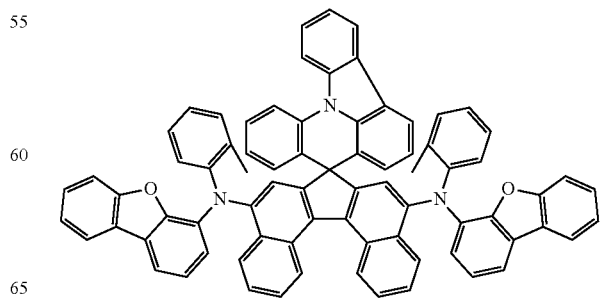

185
-continued
186
-continued
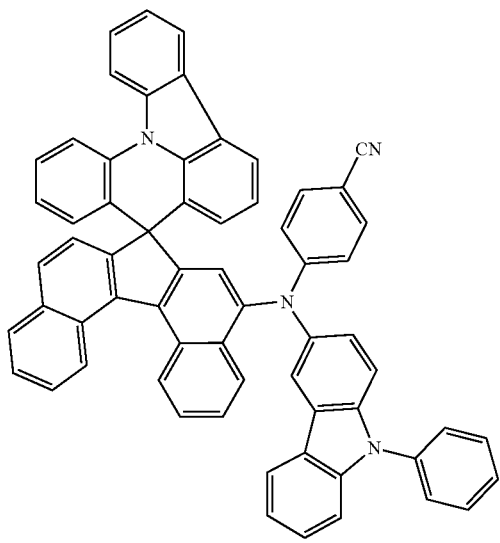
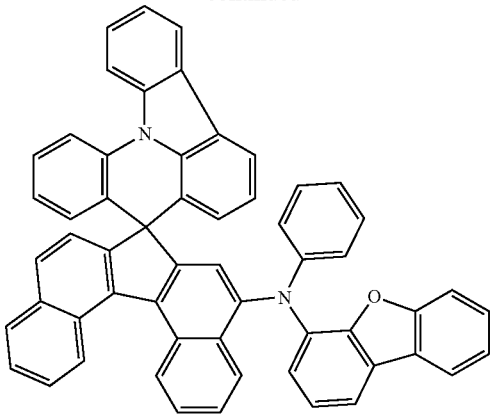
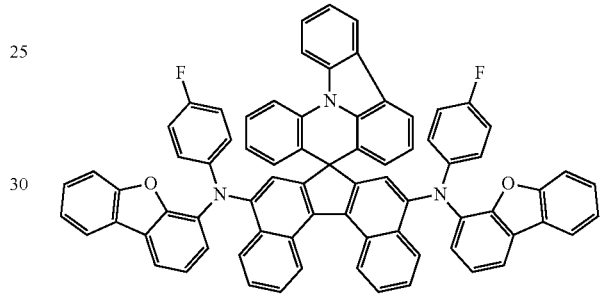
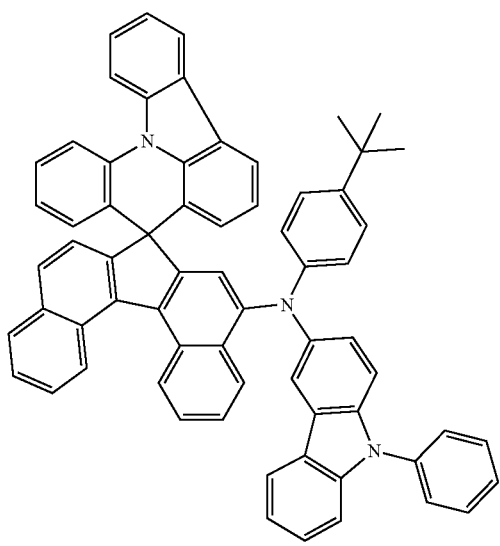
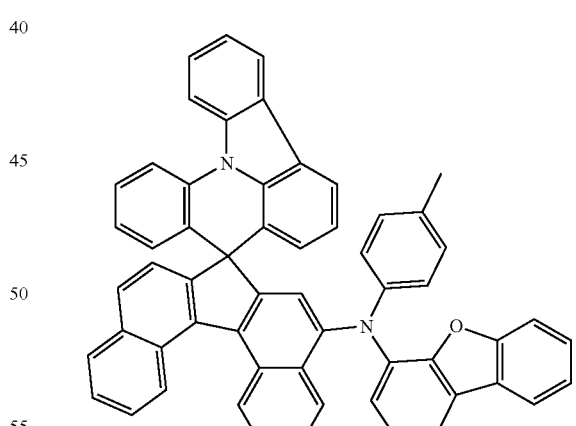
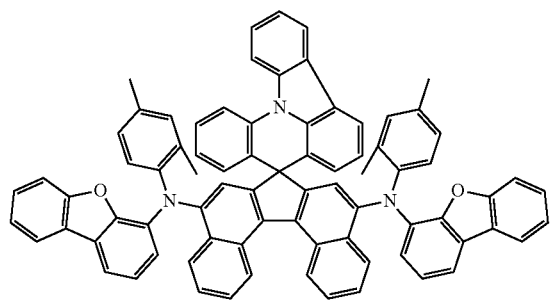
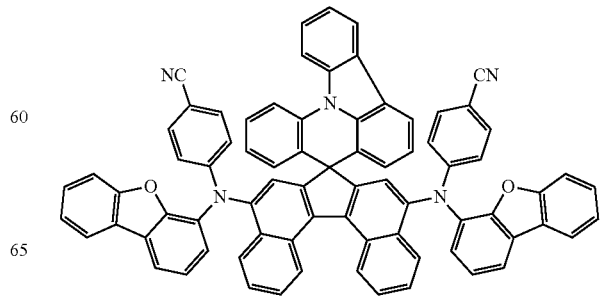

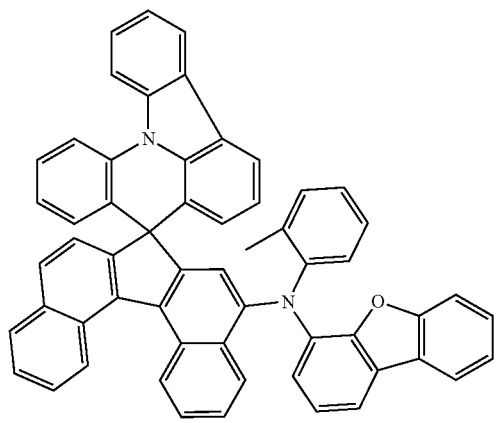
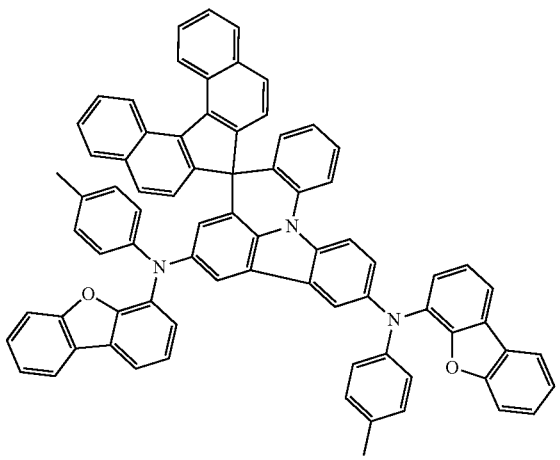
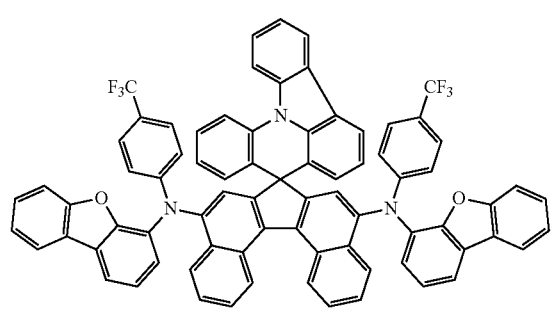
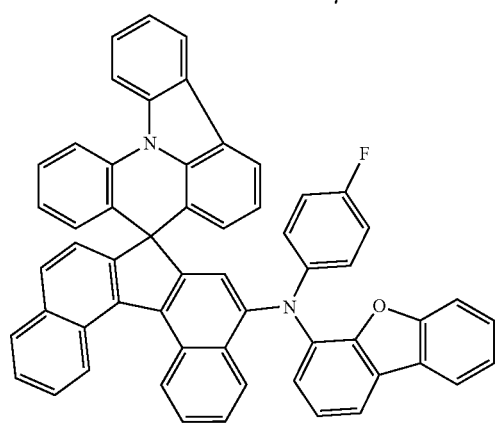
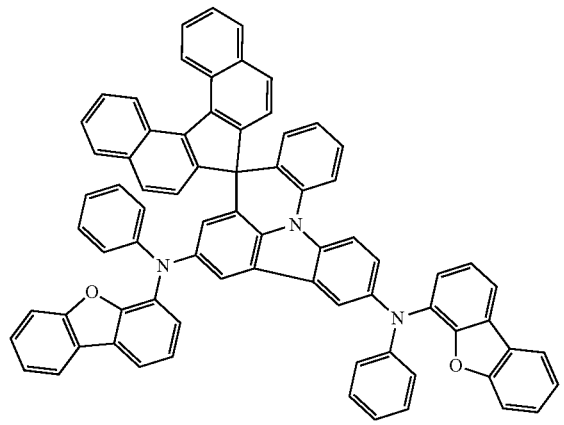
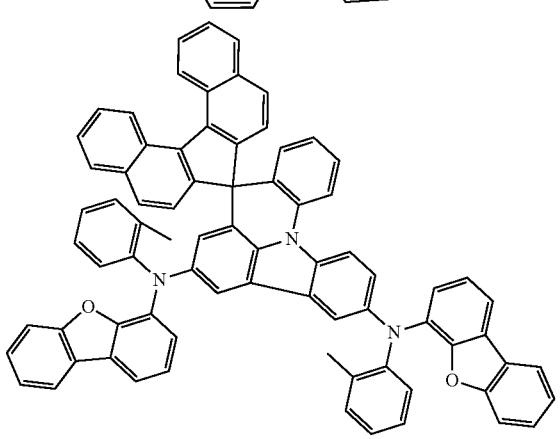
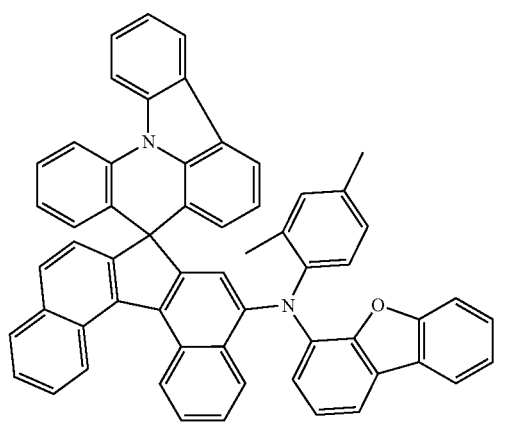
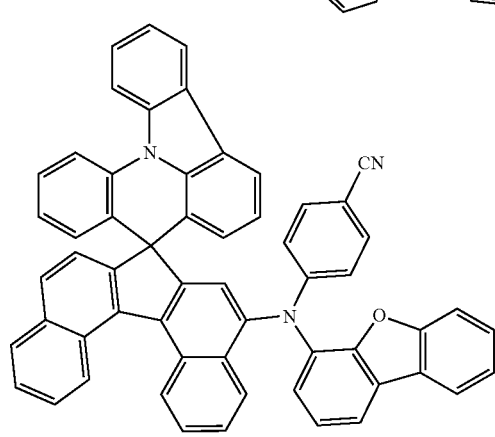

189
-continued
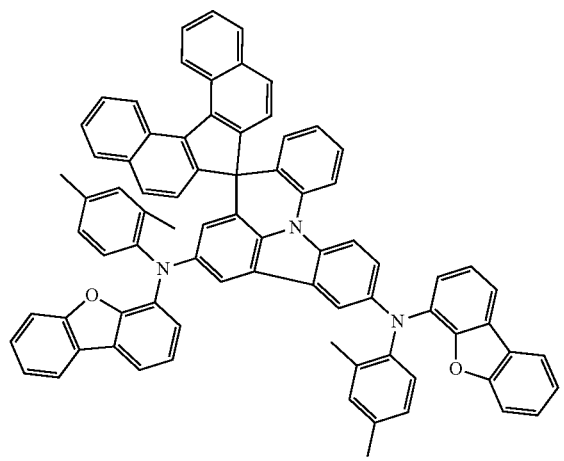
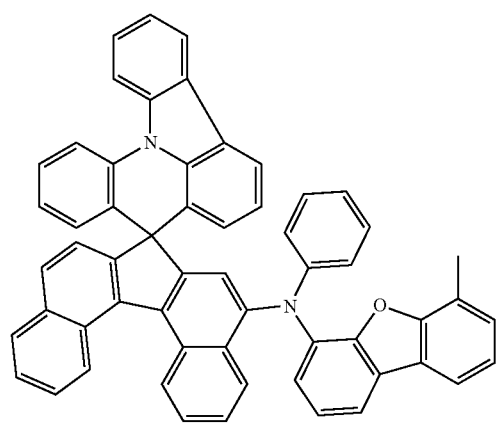
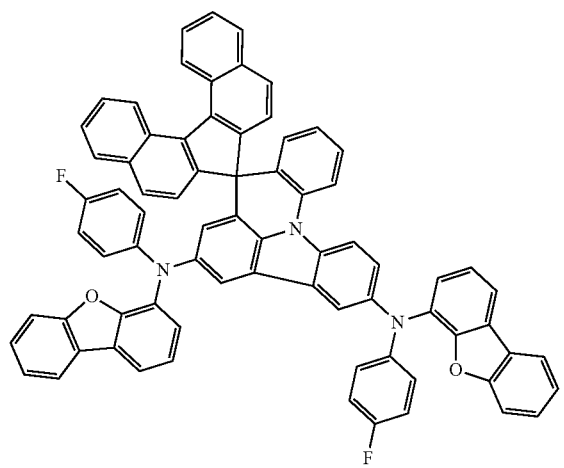
190
-continued
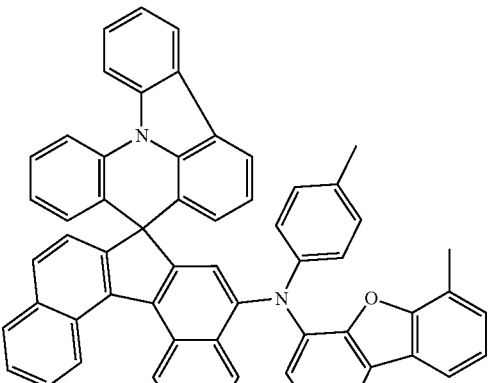
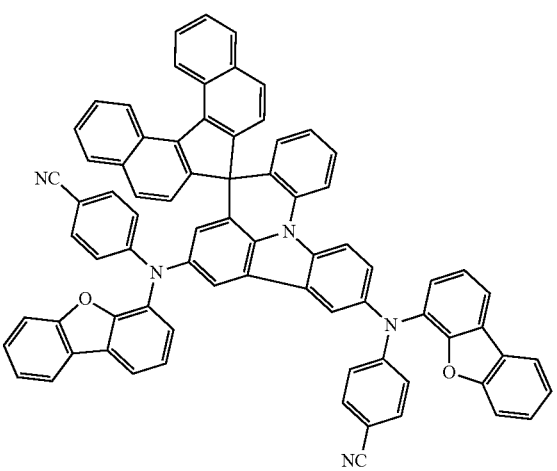
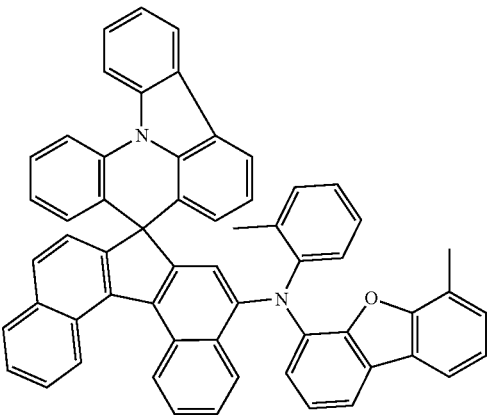
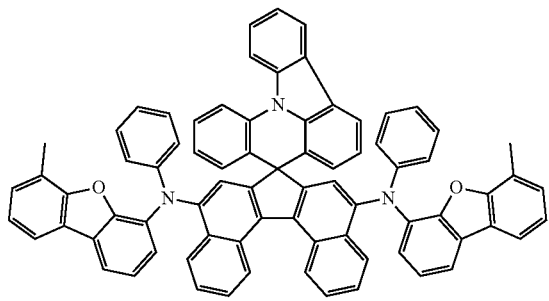

191
-continued
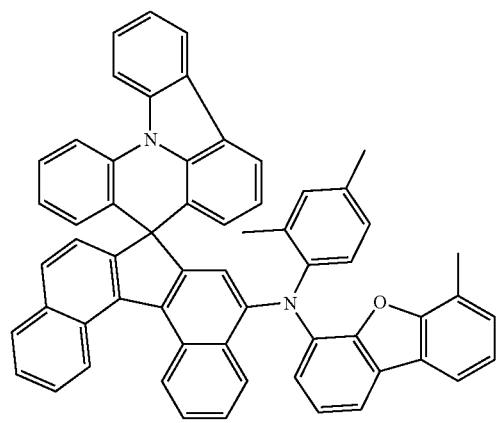
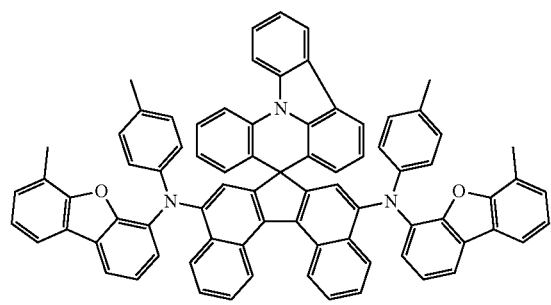
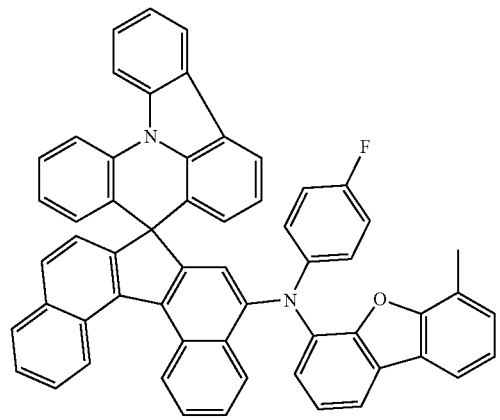
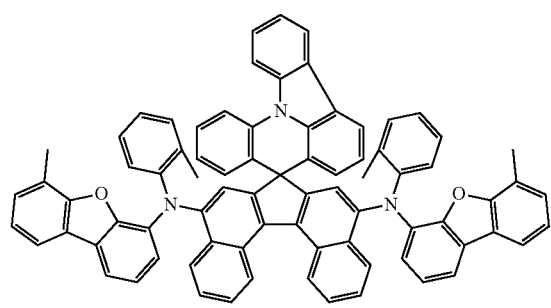
192
-continued
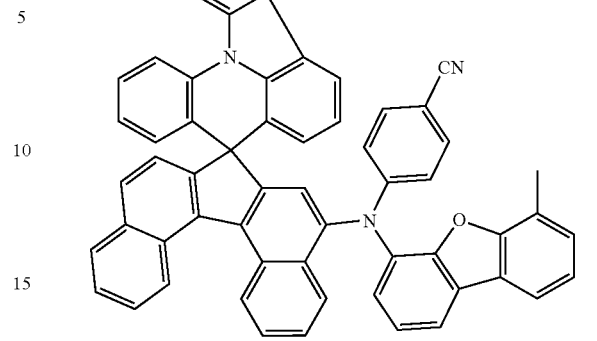
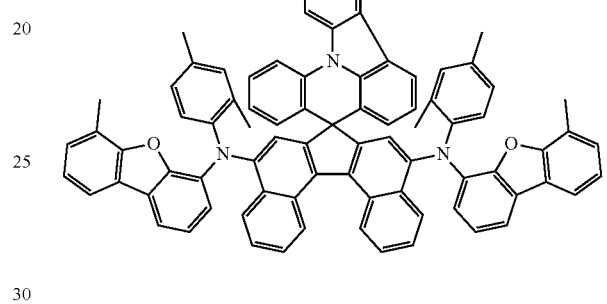
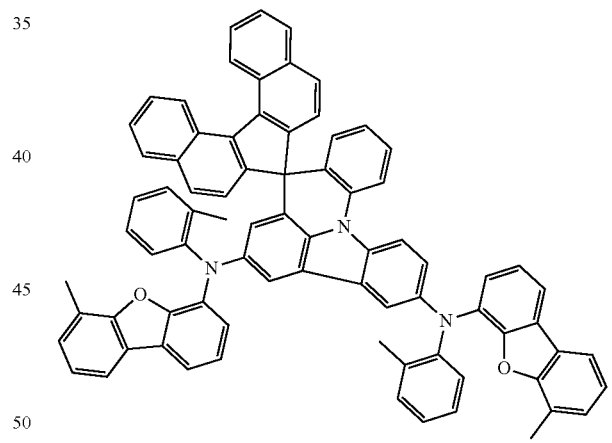
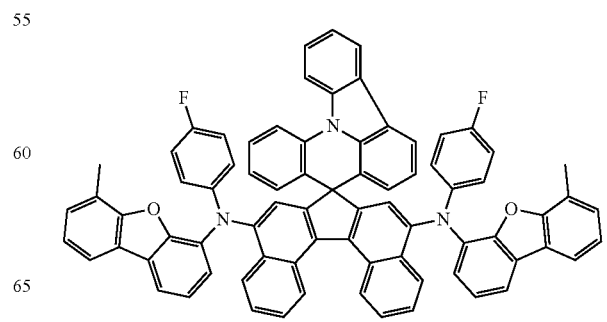

193
-continued
194
-continued
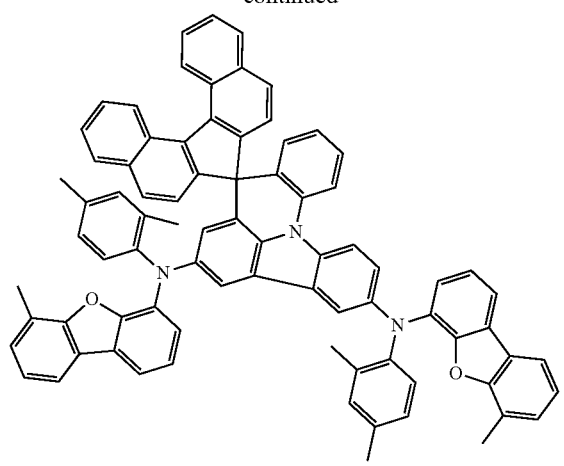
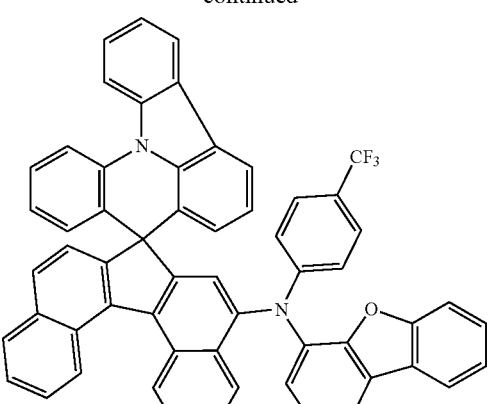
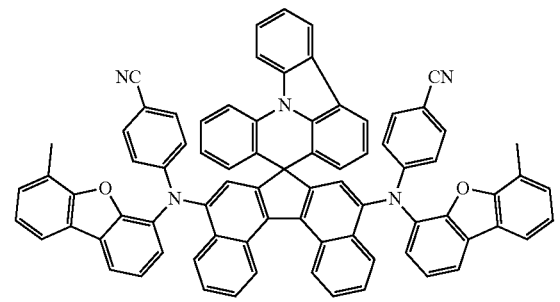
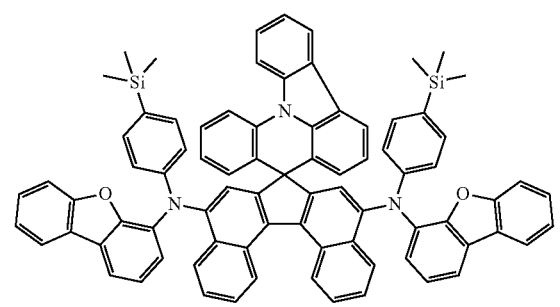
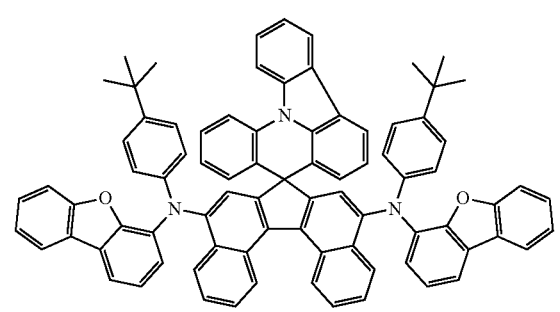

195
-continued
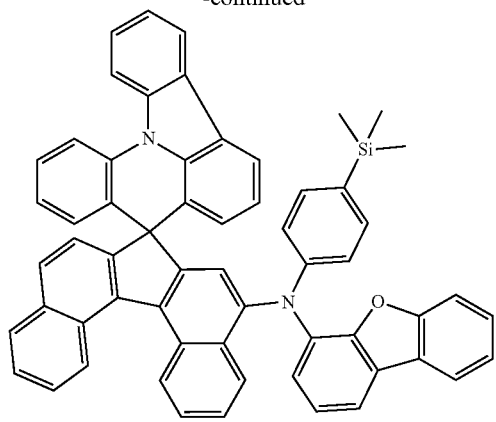
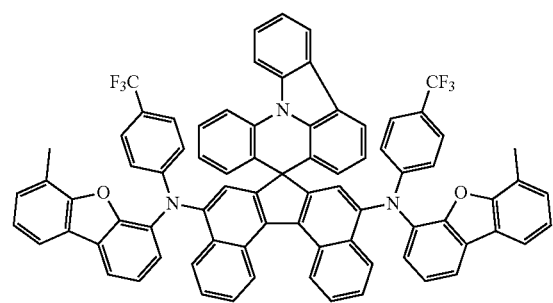
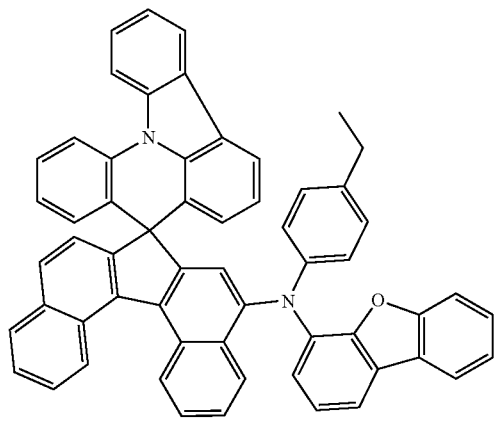
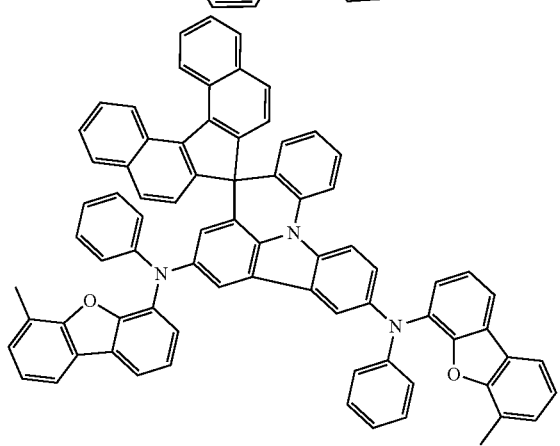
196
-continued
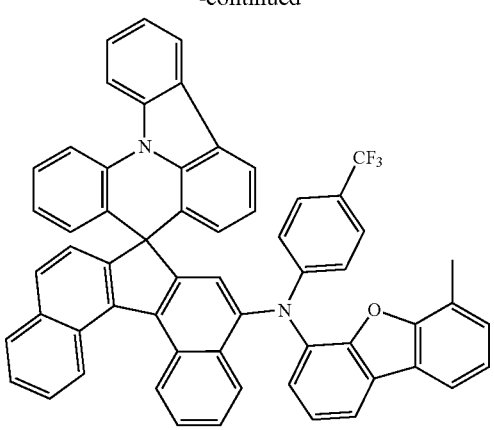
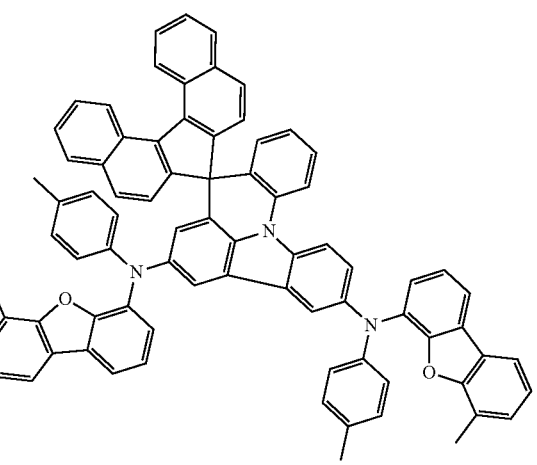
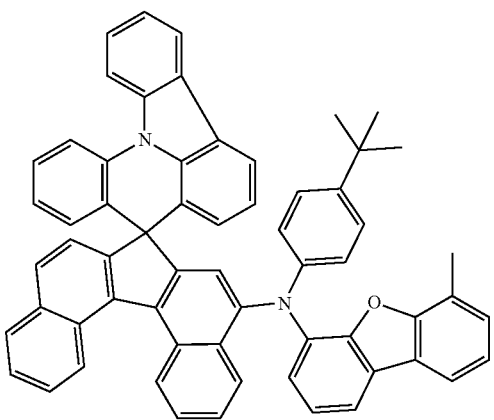

197
-continued
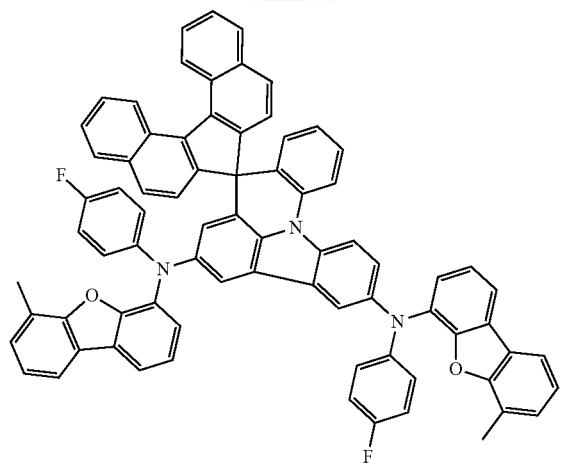
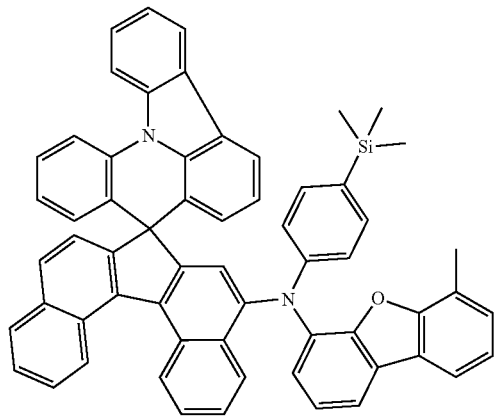
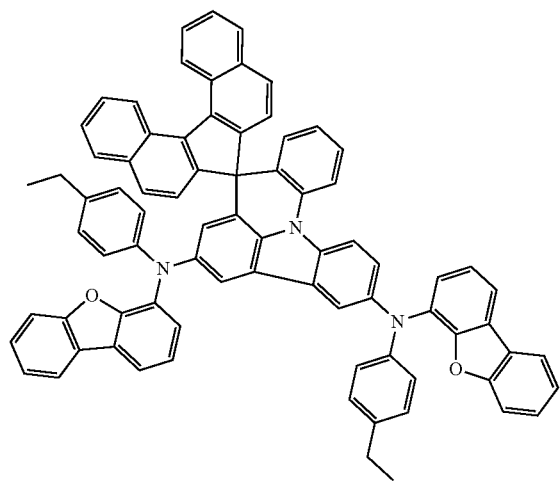
198
-continued
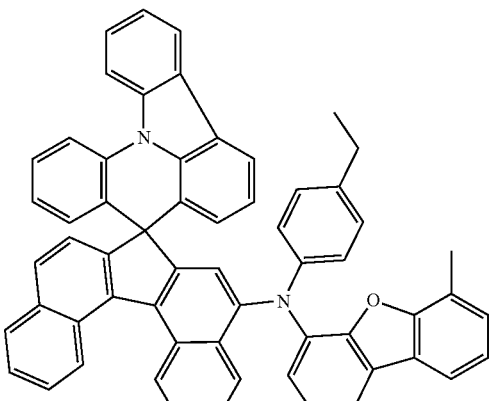
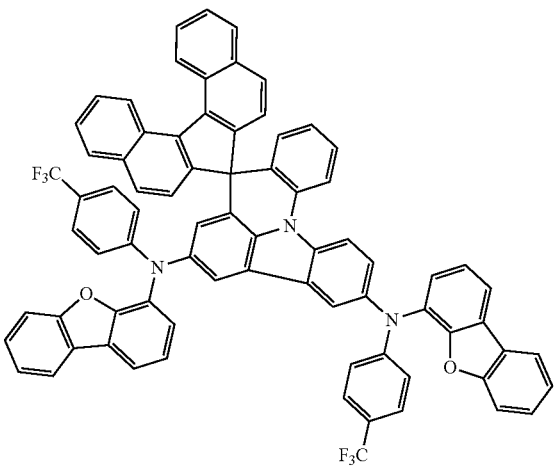
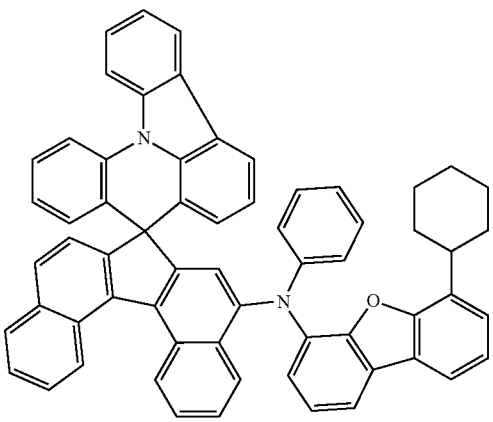

199
-continued
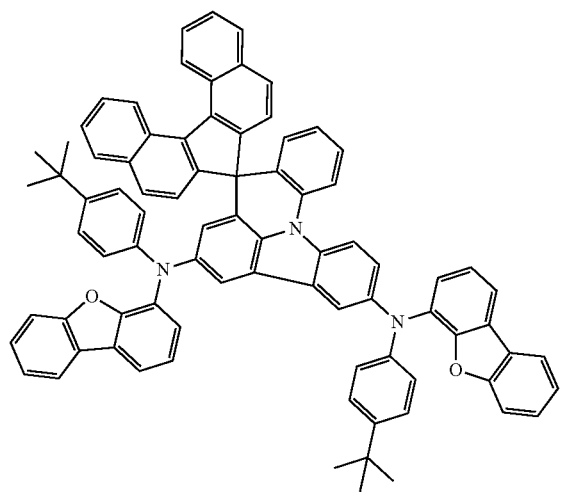
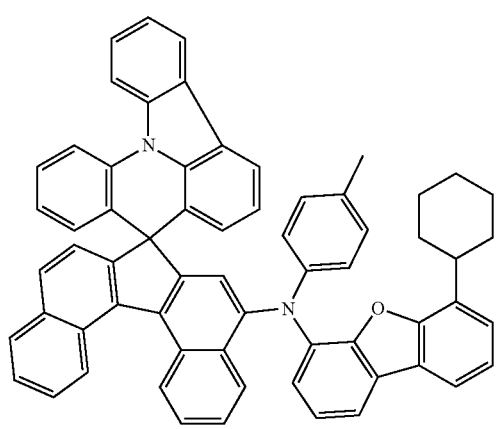
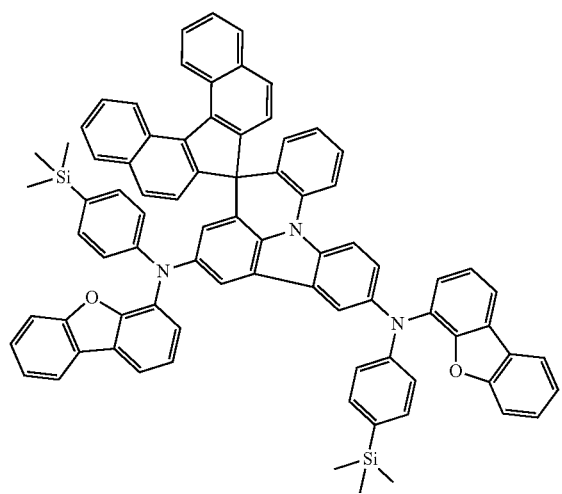
200
-continued
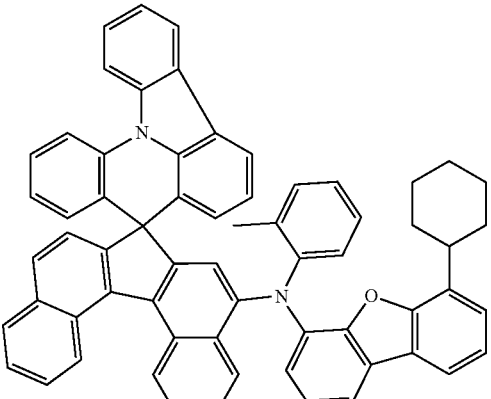
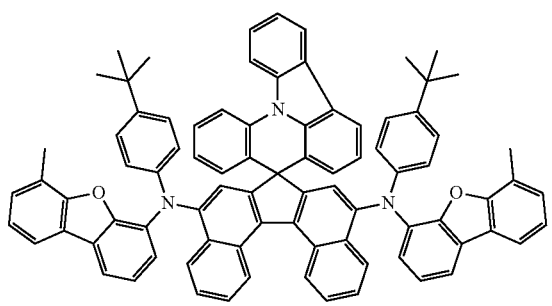
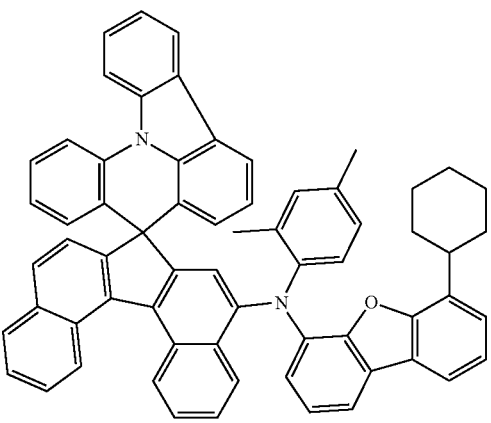
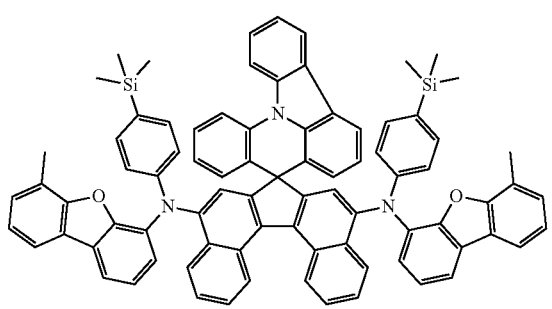

201
-continued
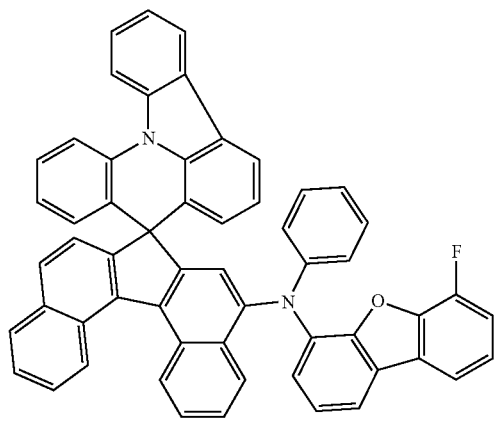
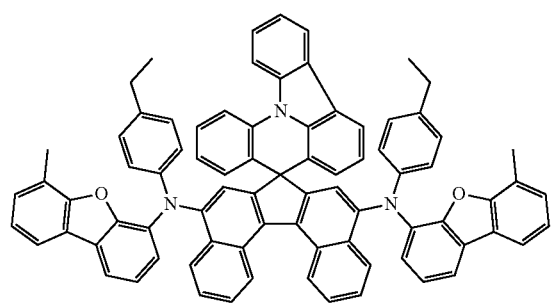
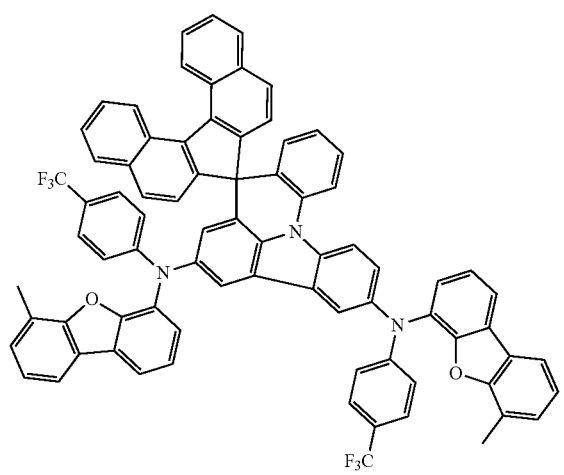
202
-continued
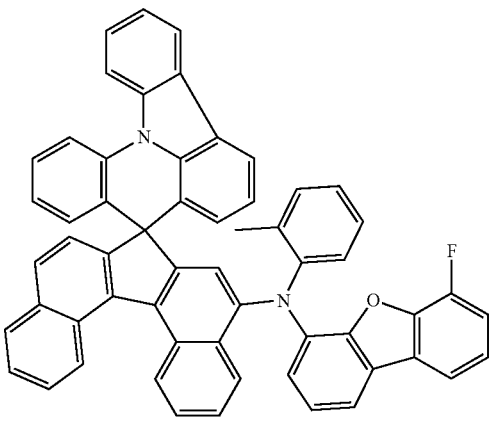
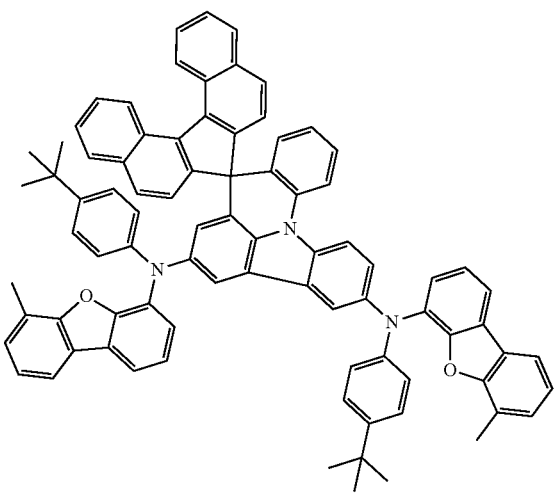
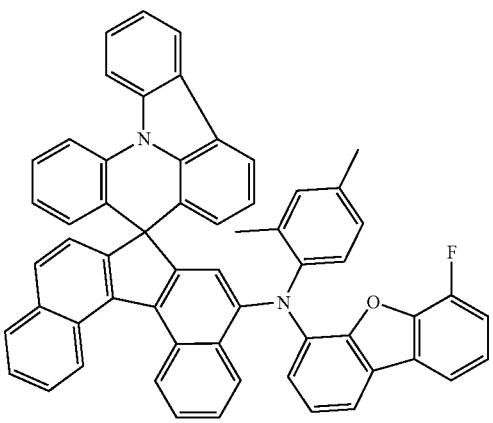

-continued
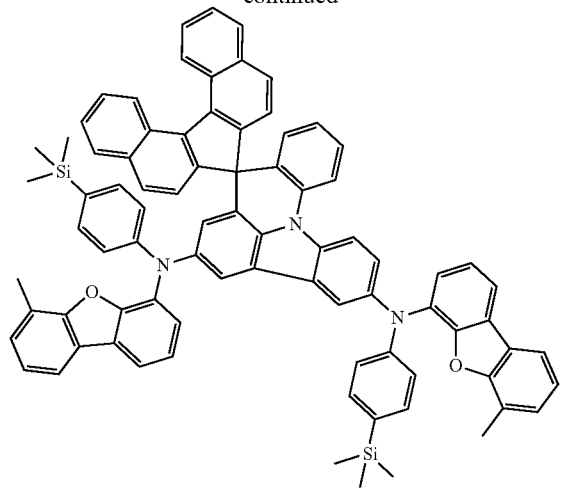
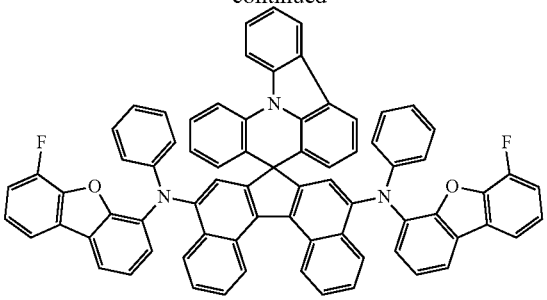
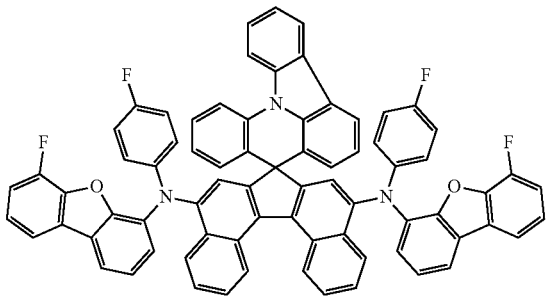
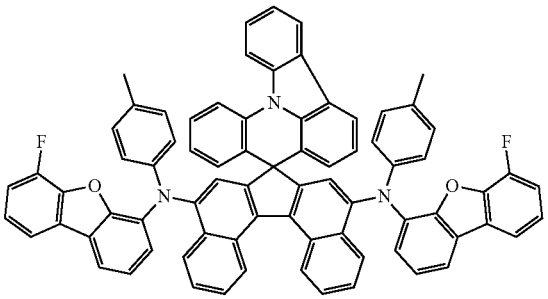
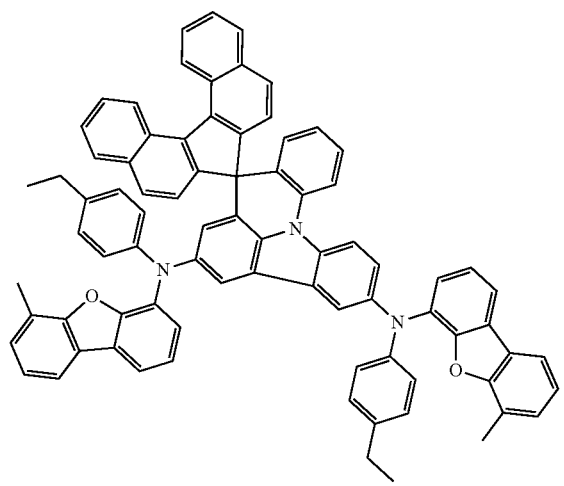
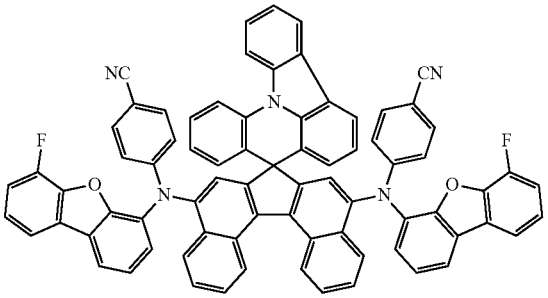
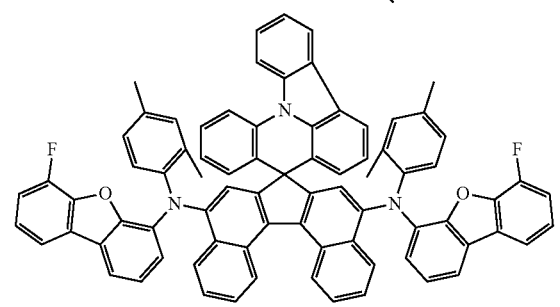
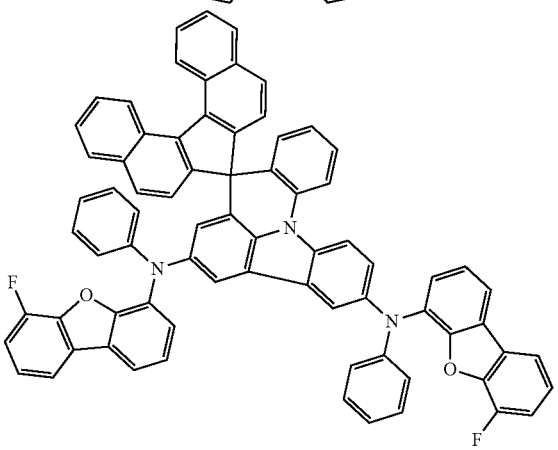

205
-continued
206
-continued
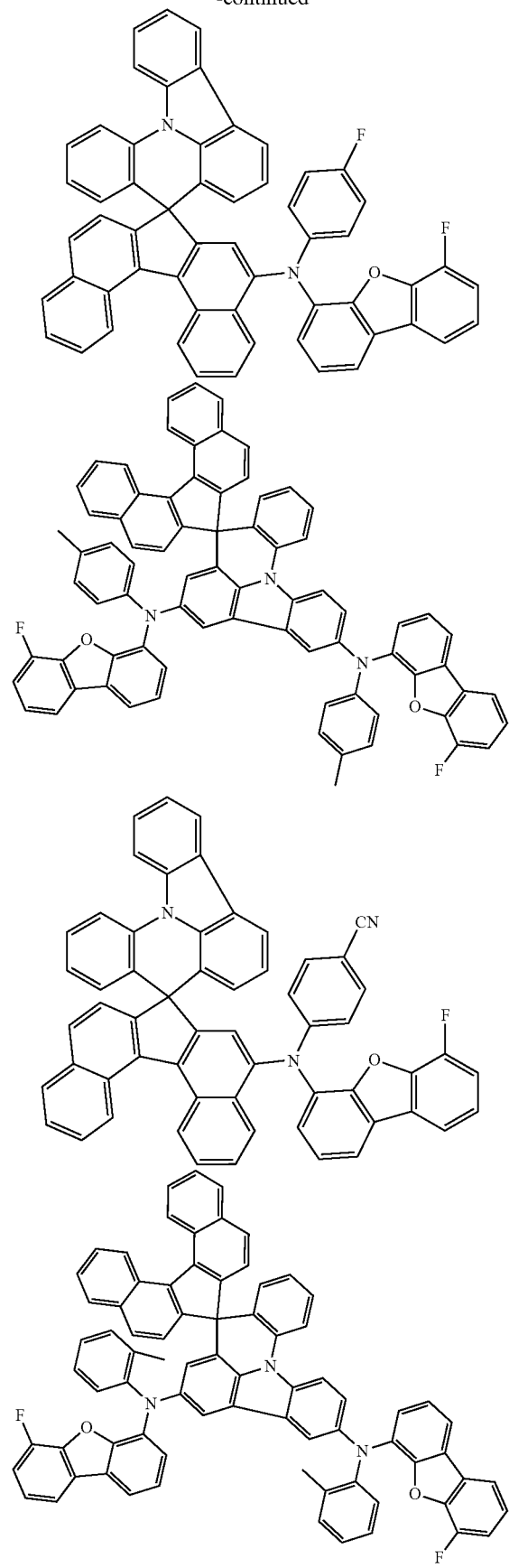
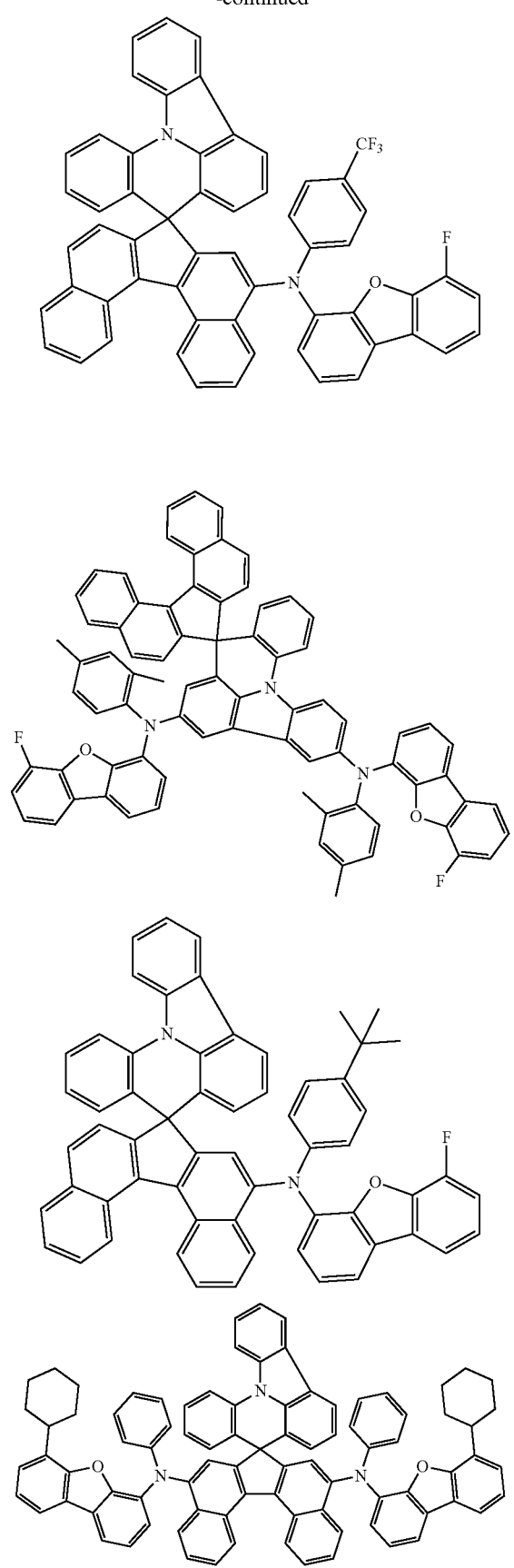

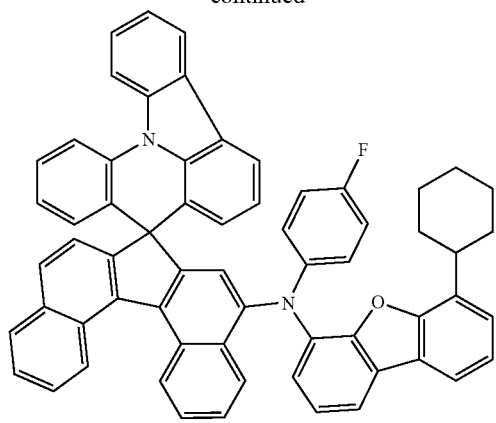
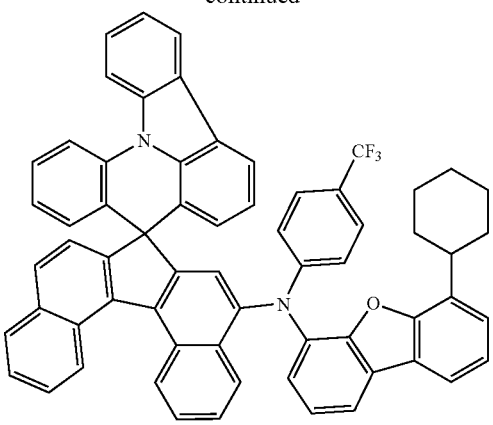
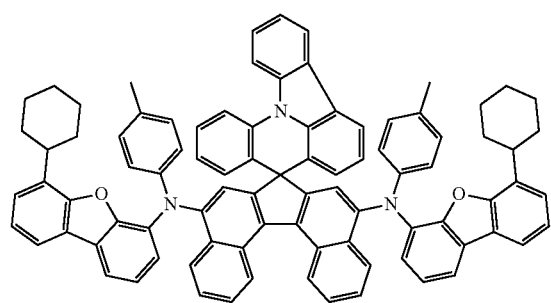
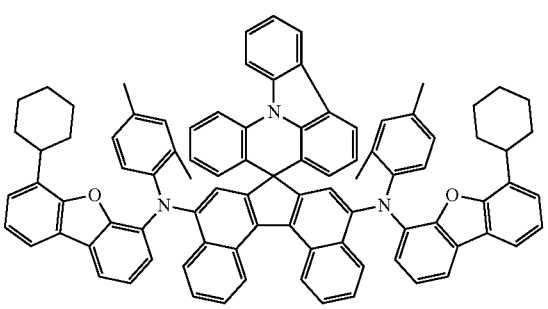
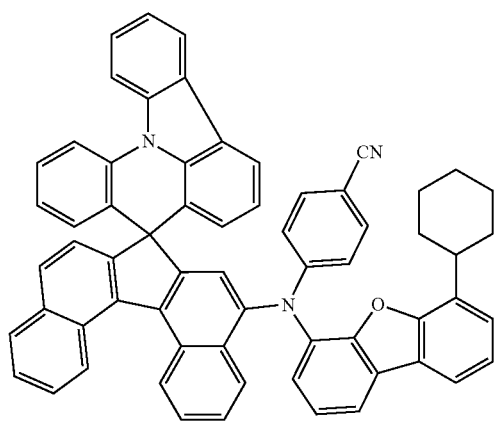
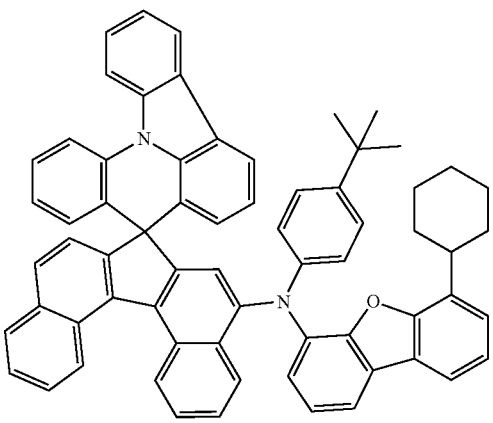
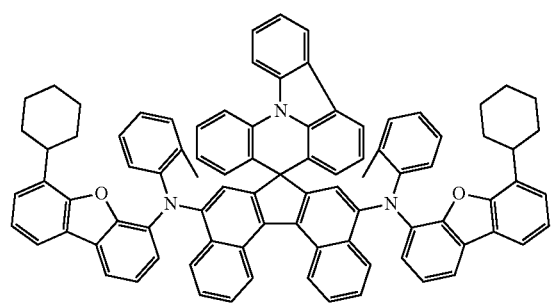
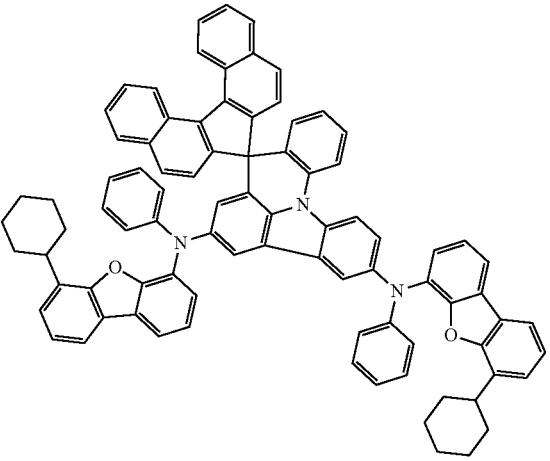

209
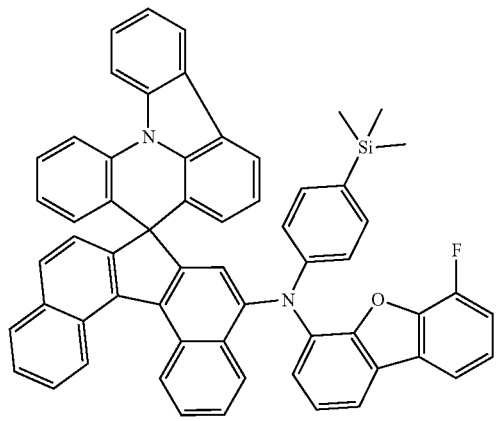
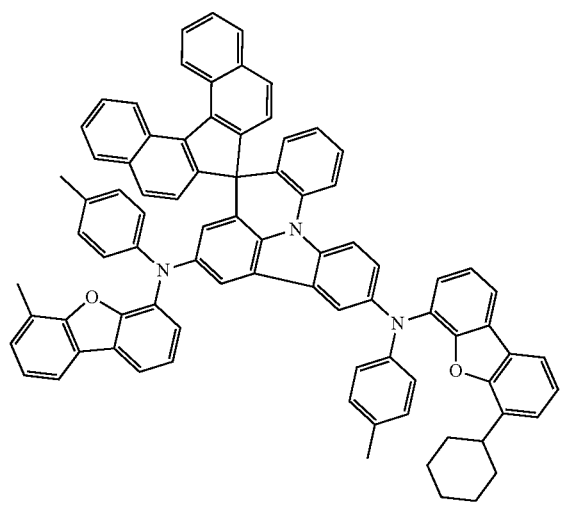
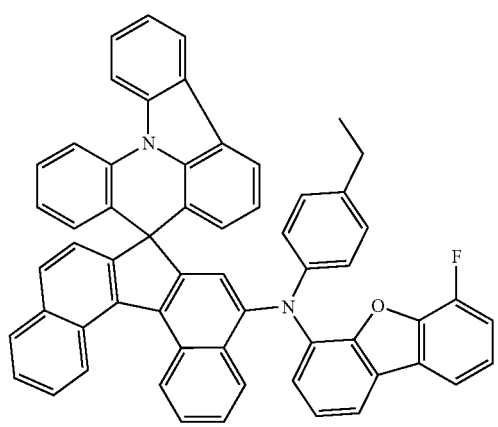
210
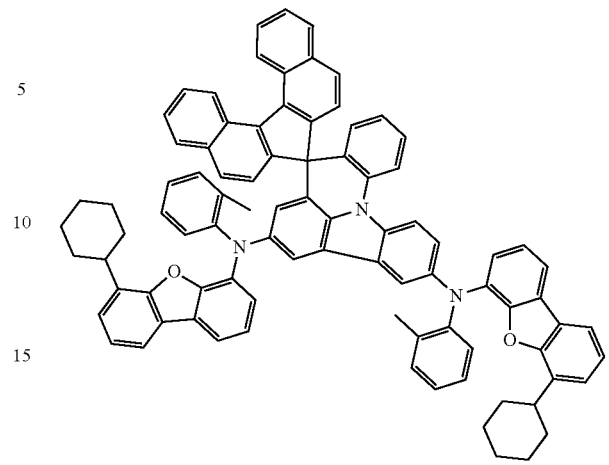
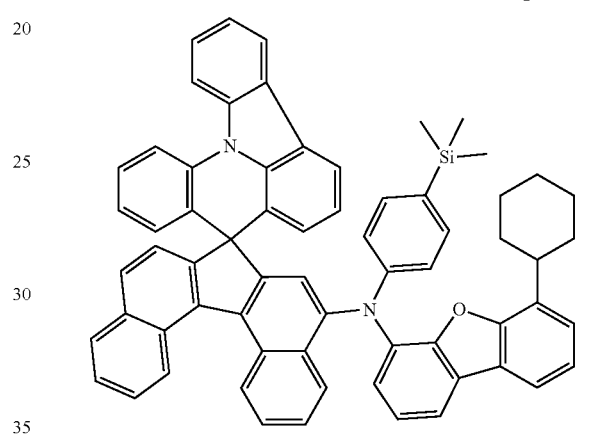
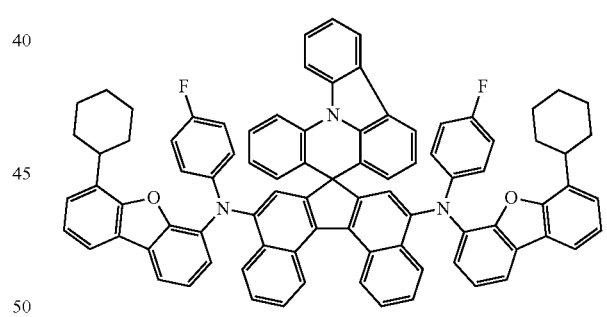

211
-continued
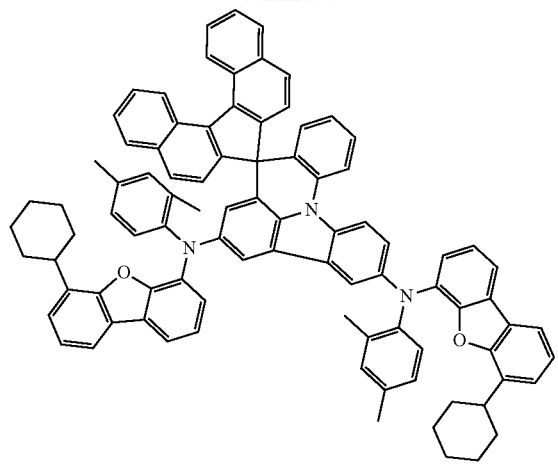
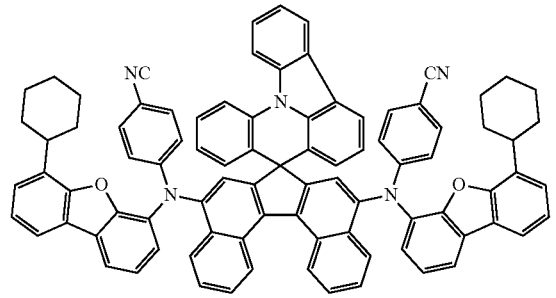
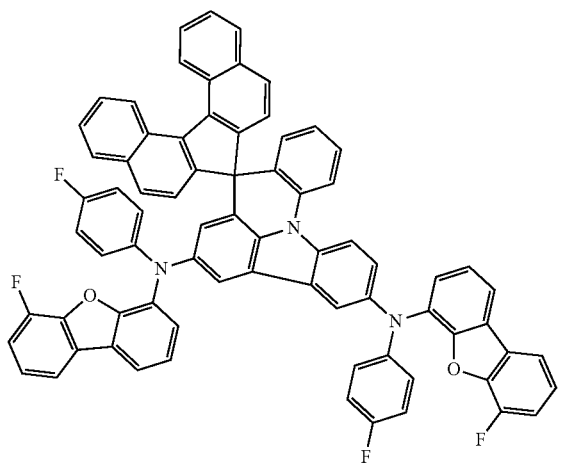
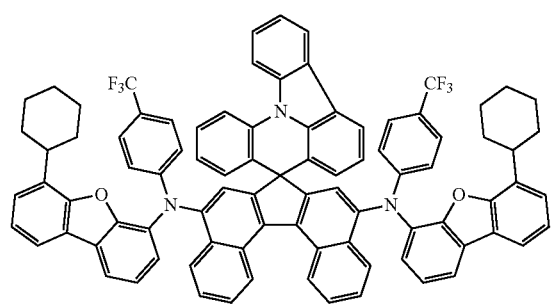
212
-continued
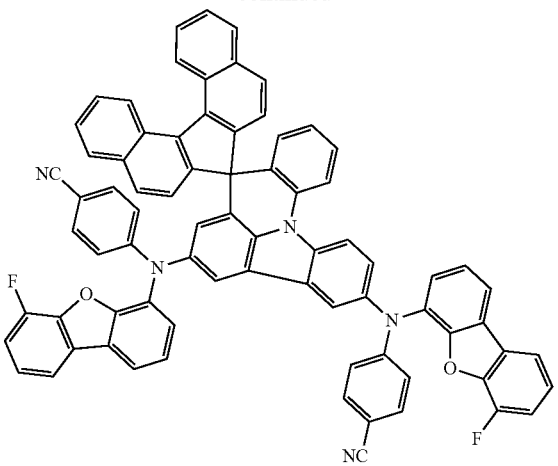
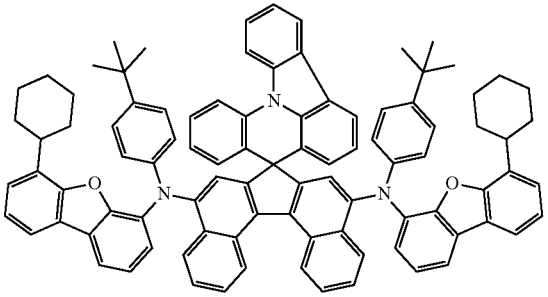
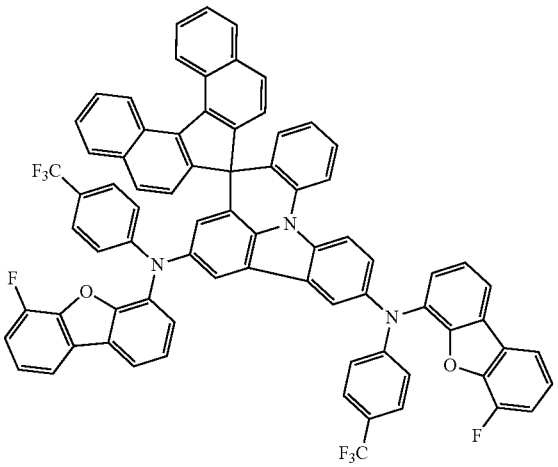
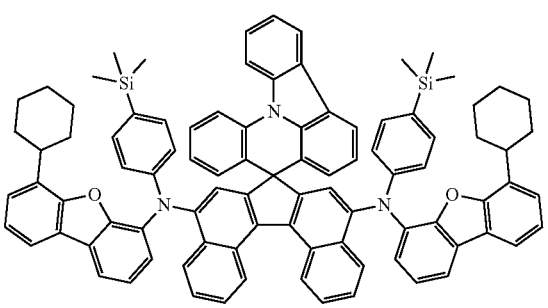

213
-continued
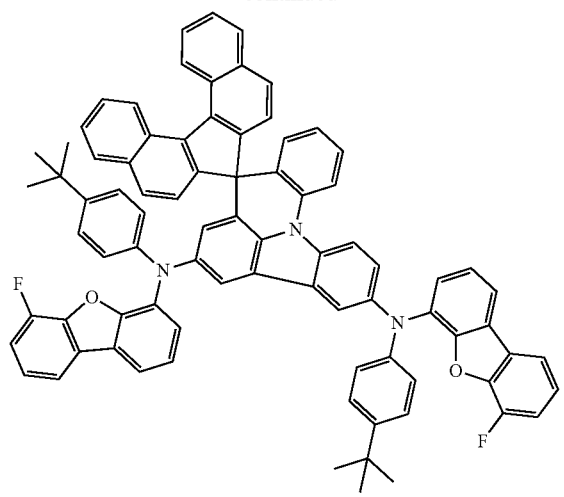
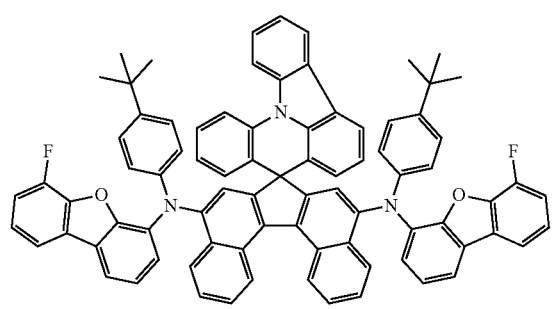
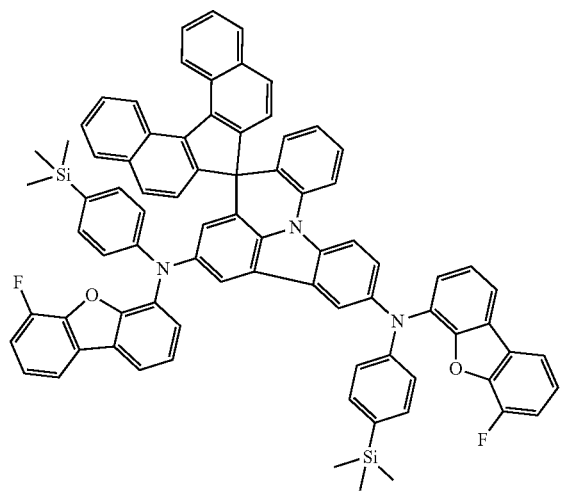
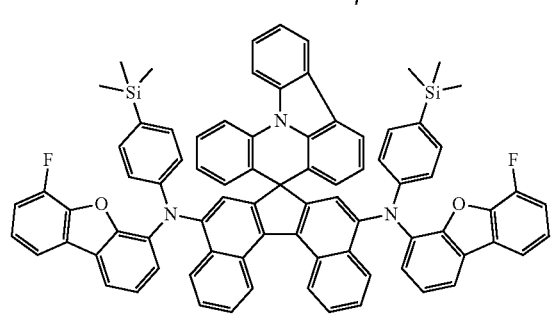
214
-continued
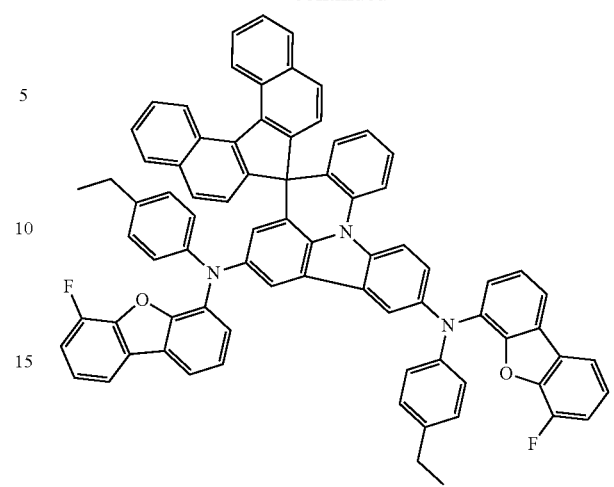
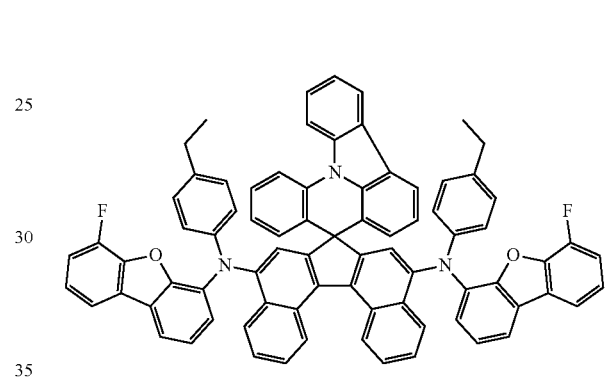
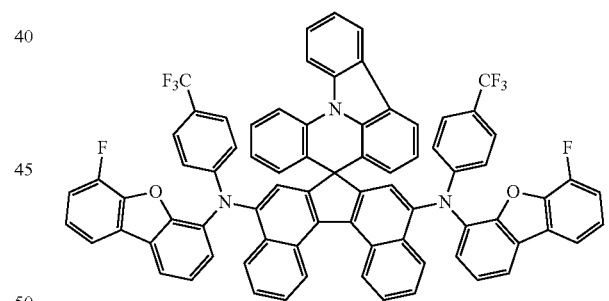
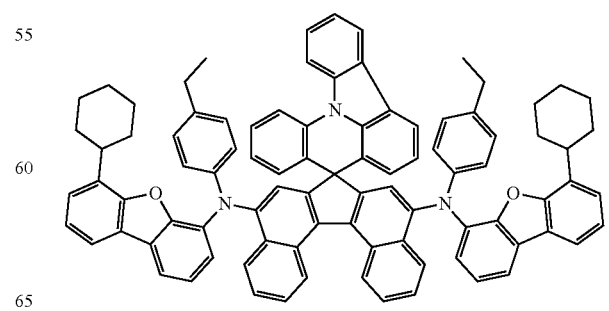

215
-continued
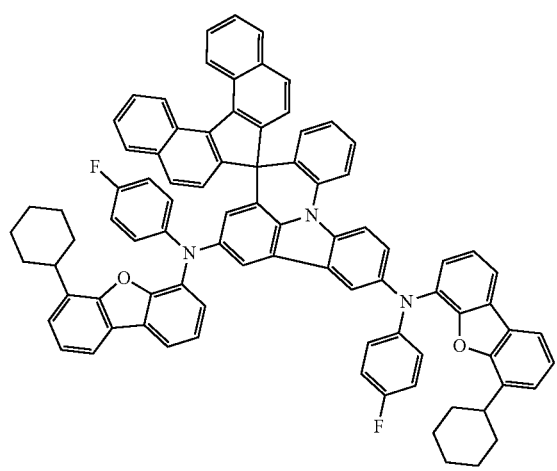
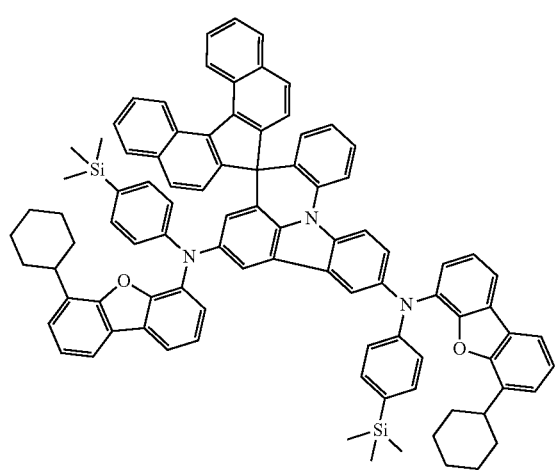
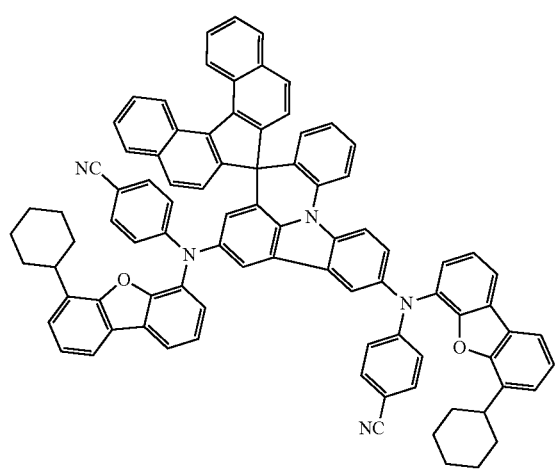
216
-continued
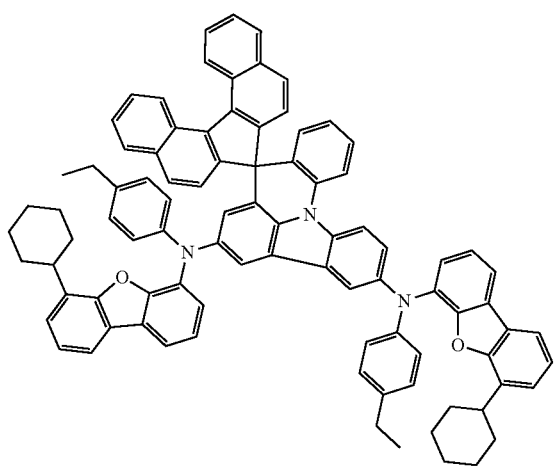
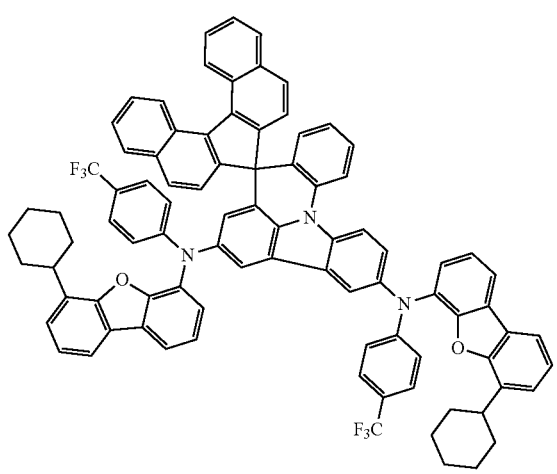
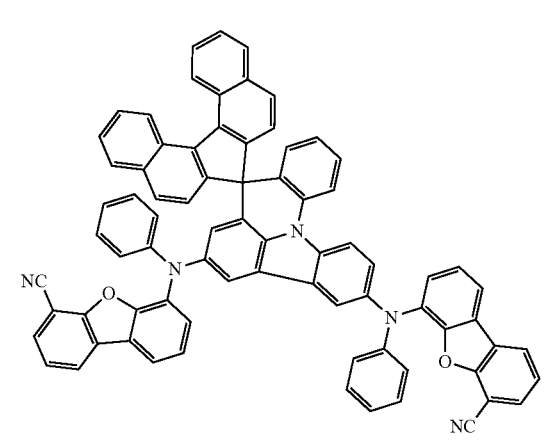

217
-continued
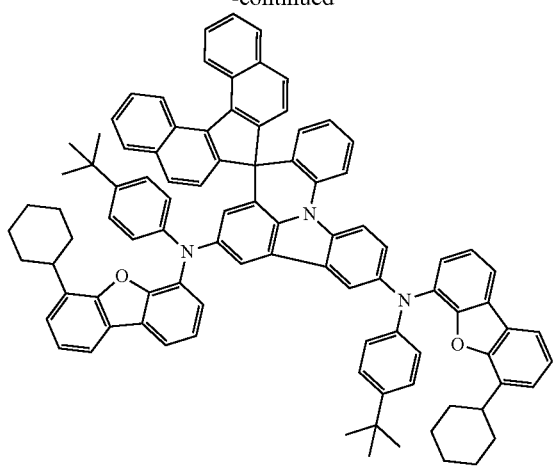
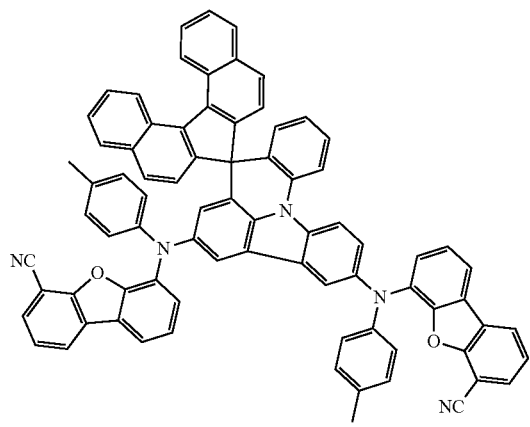
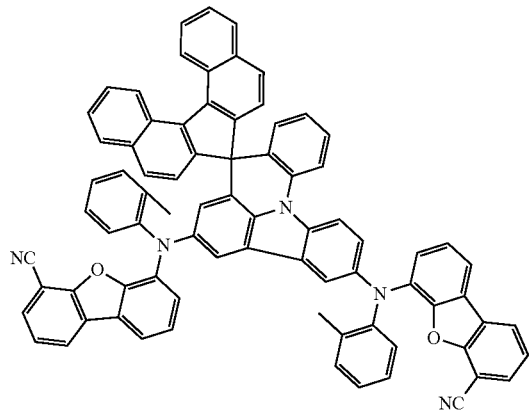
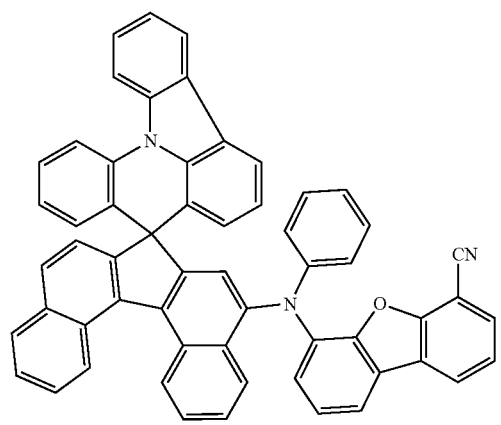
218
-continued
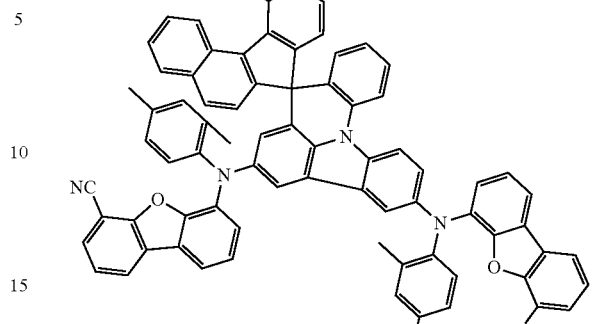
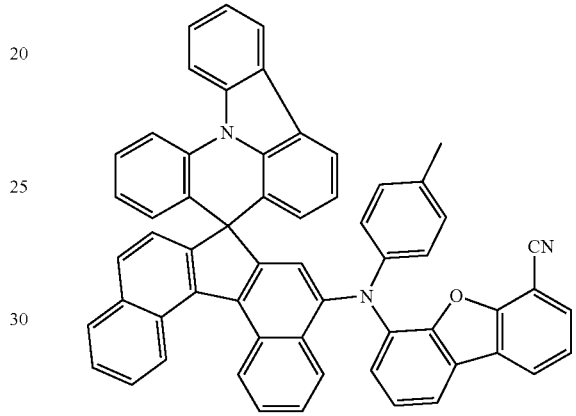
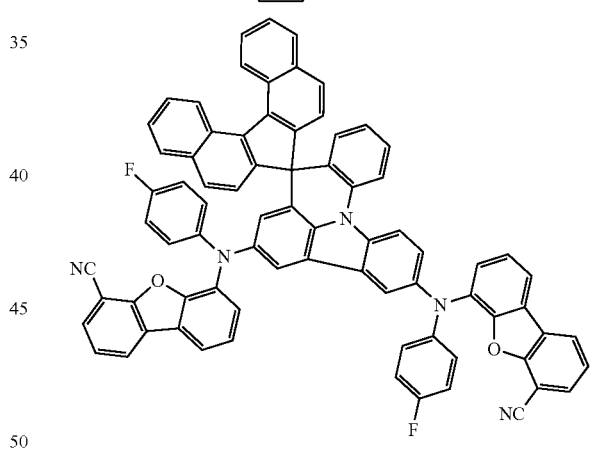
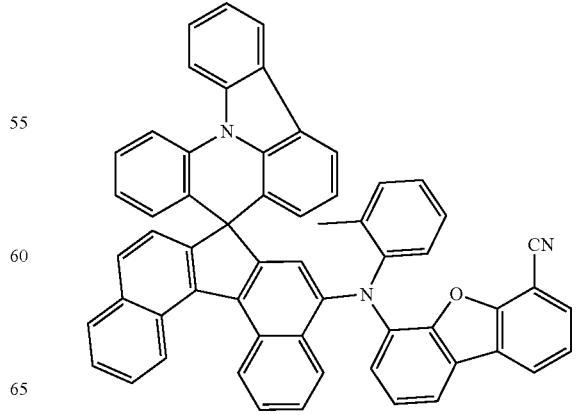

-continued
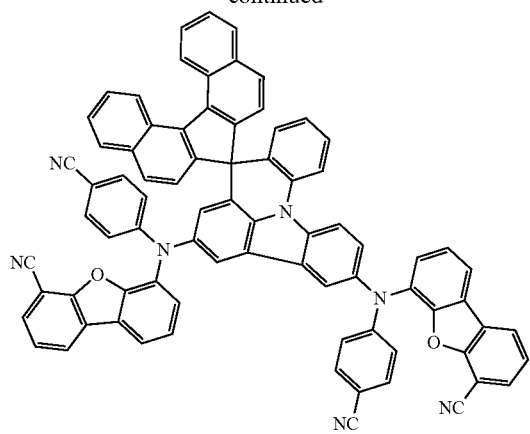
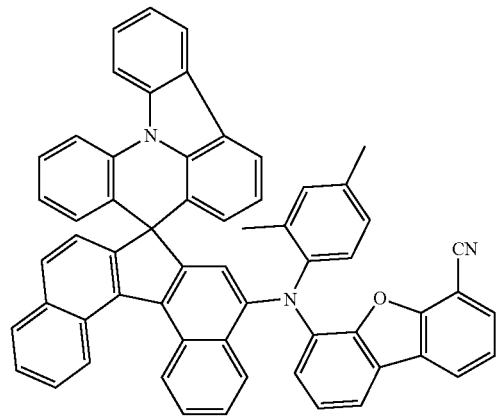
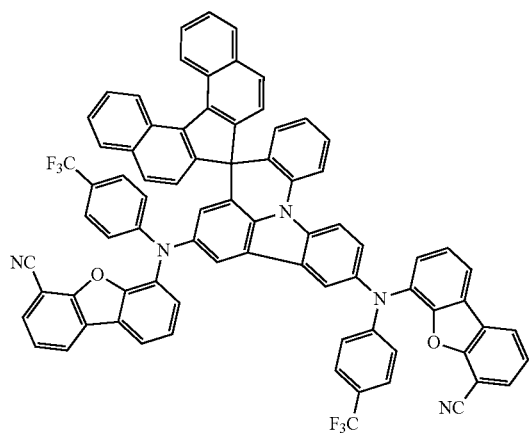
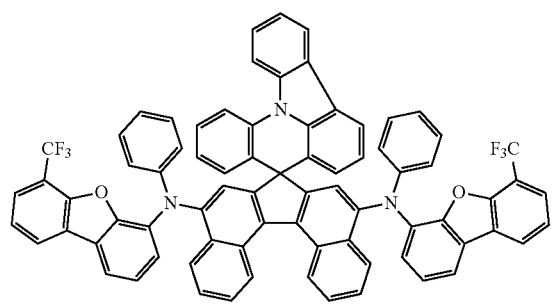
-continued
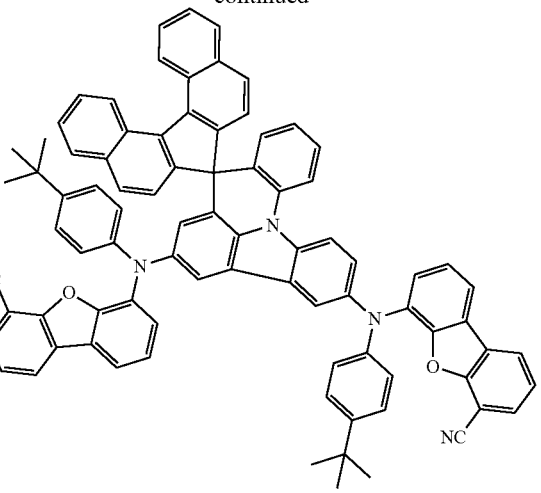
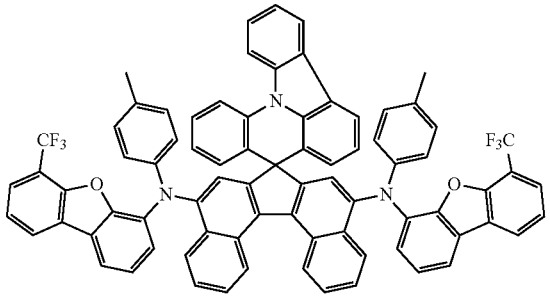
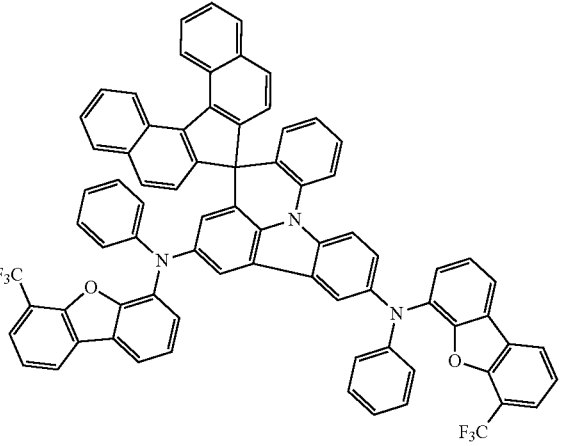
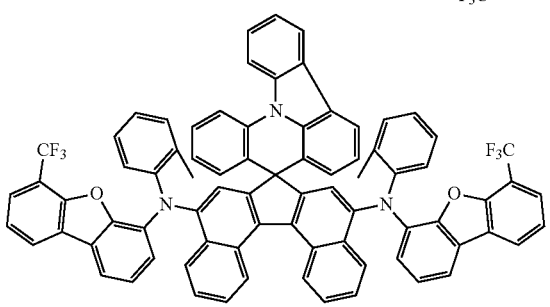

221
-continued
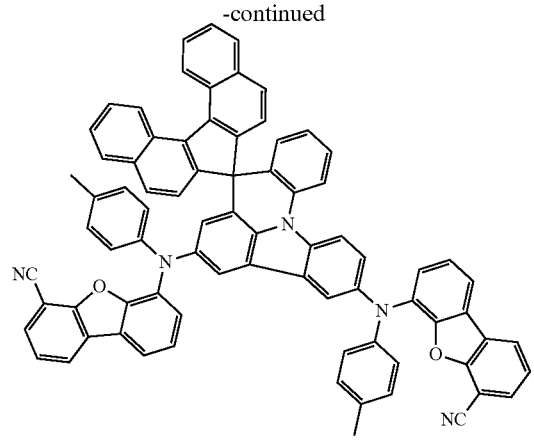
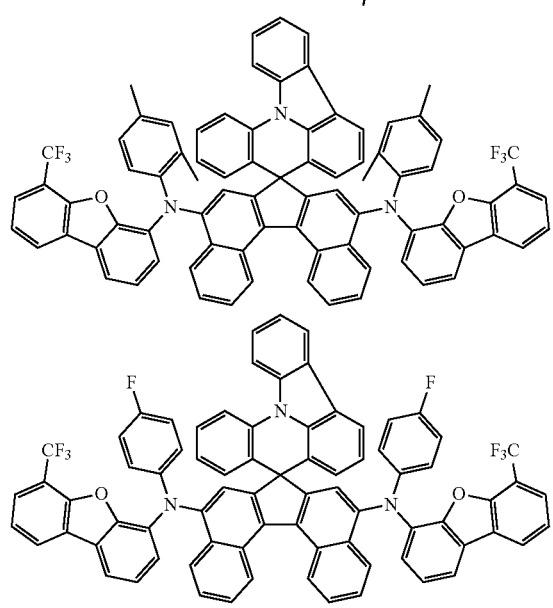
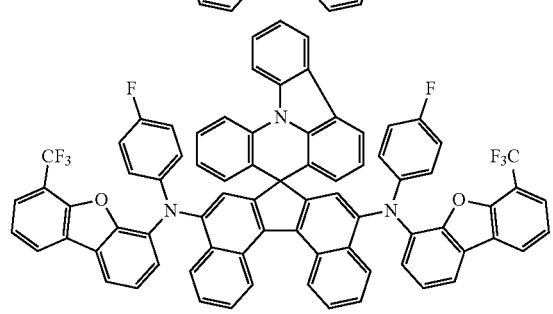
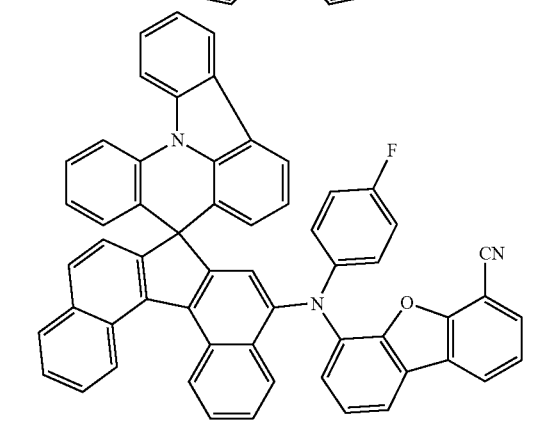
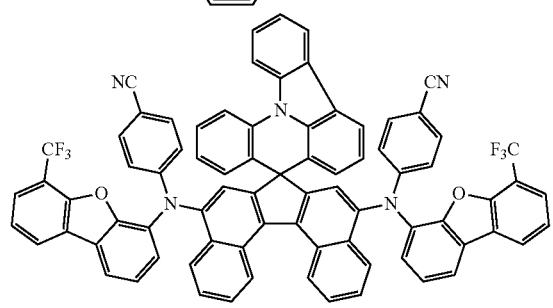
222
-continued
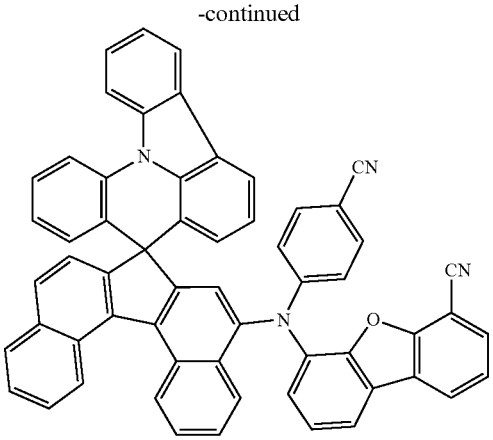
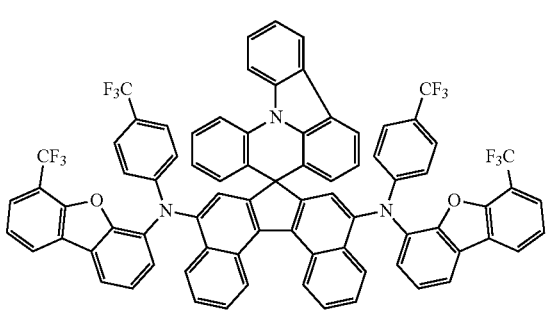
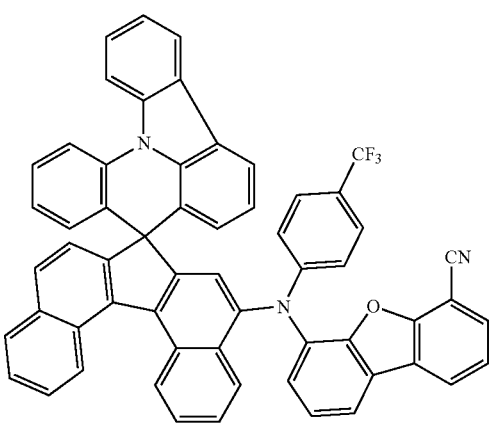
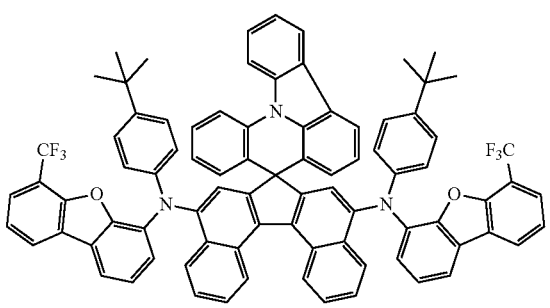

223
-continued
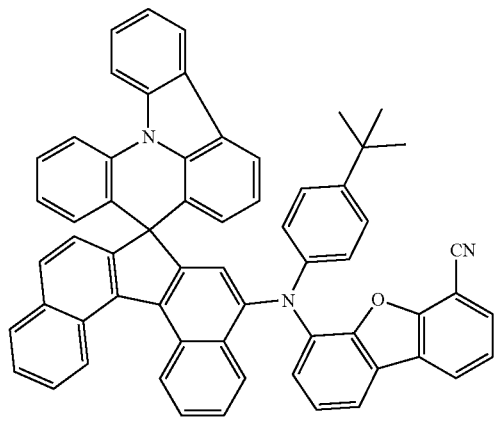
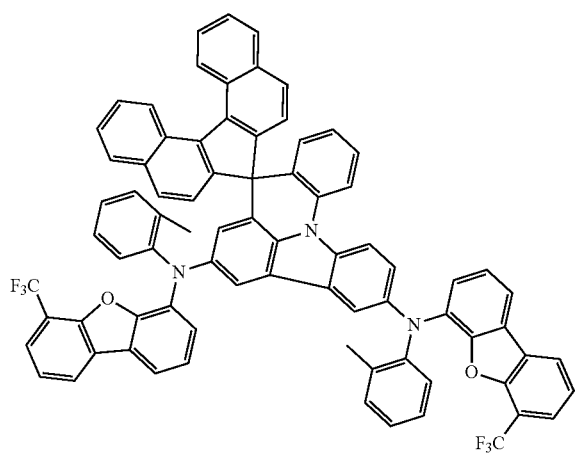
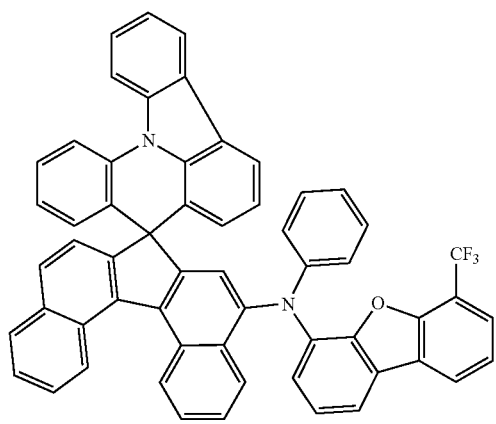
224
-continued
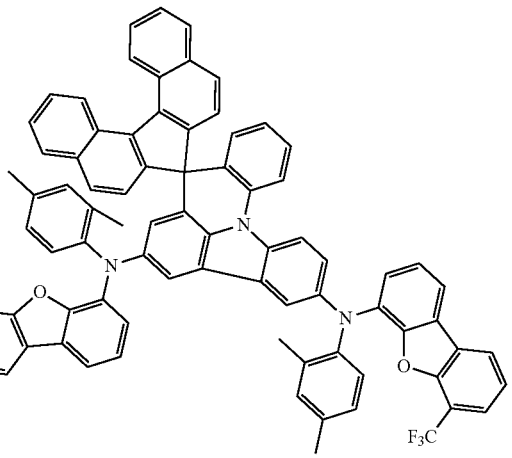
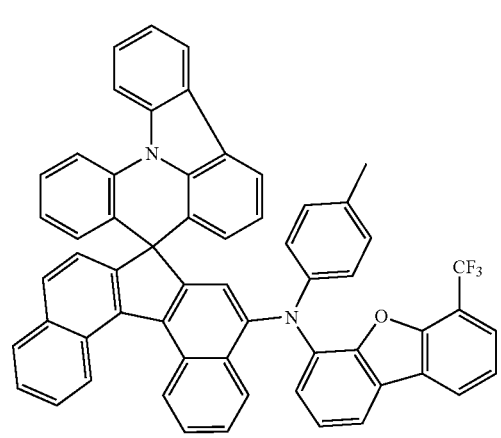
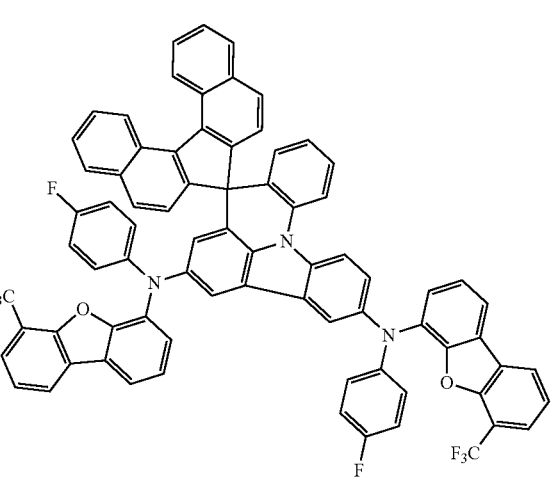

225
-continued
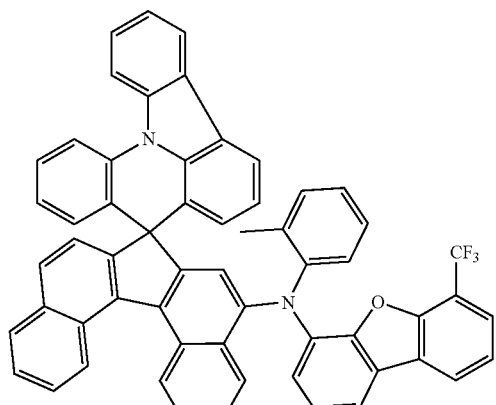
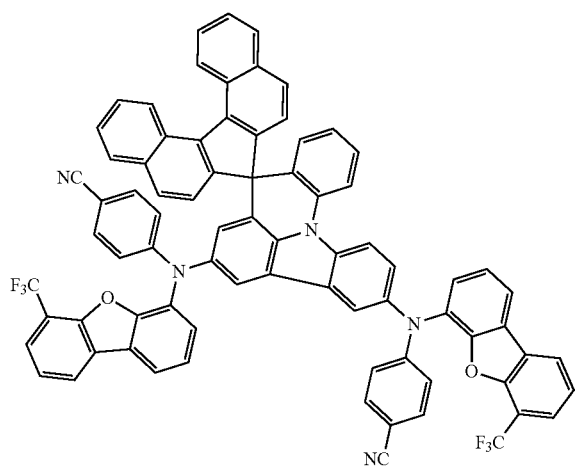
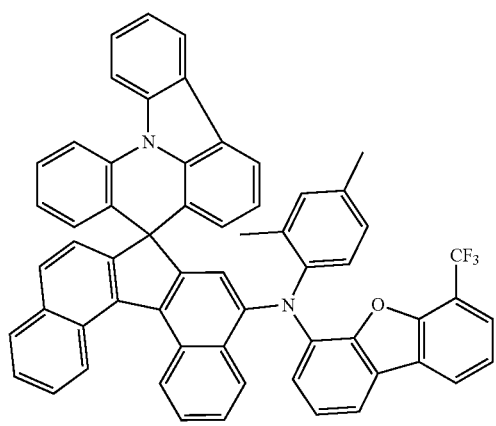
226
-continued
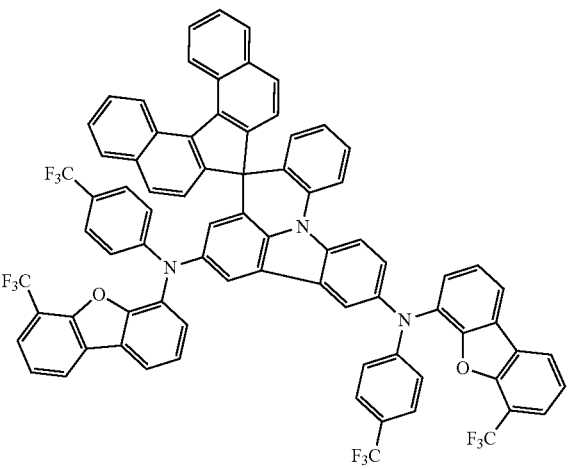
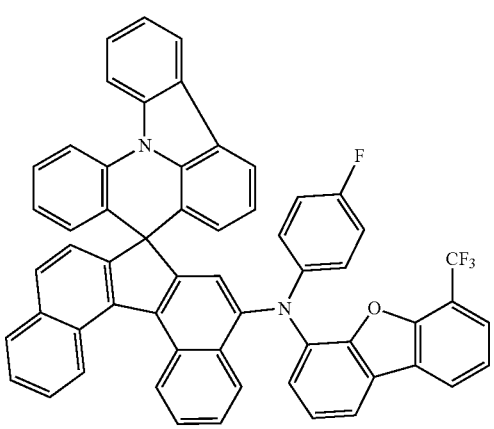
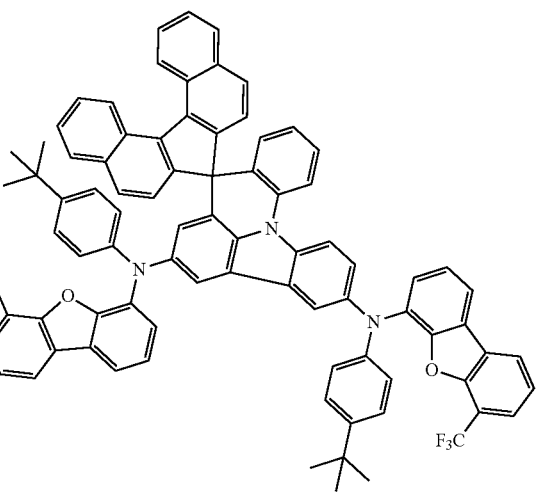

227
-continued
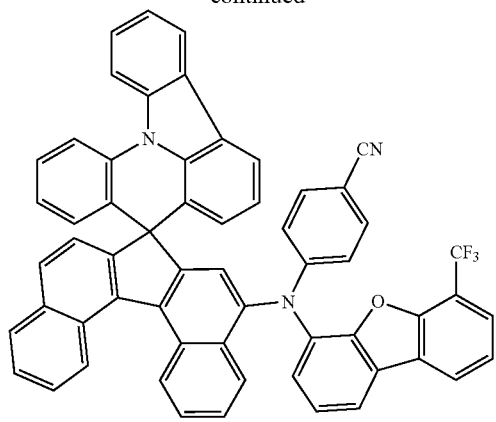
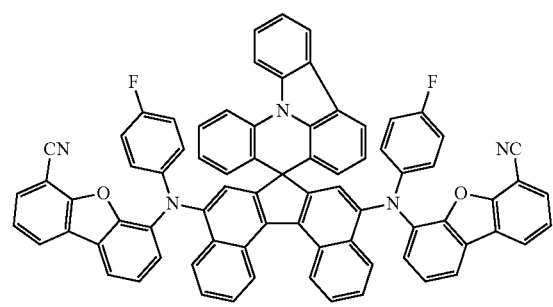
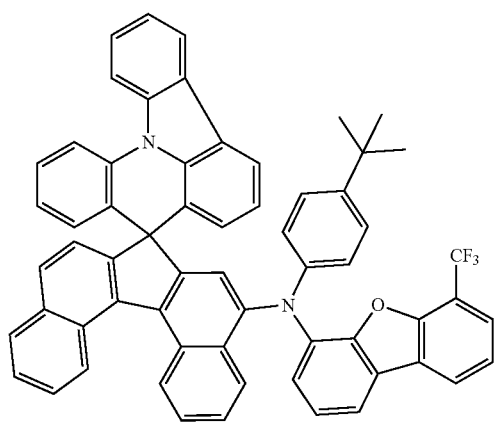
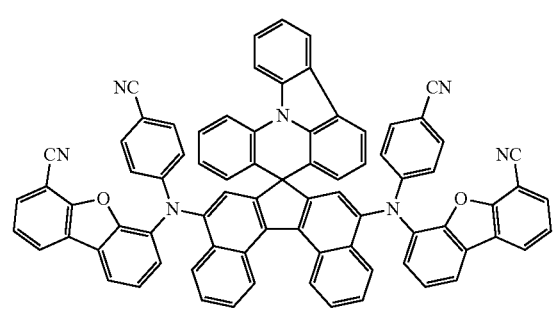
228
-continued
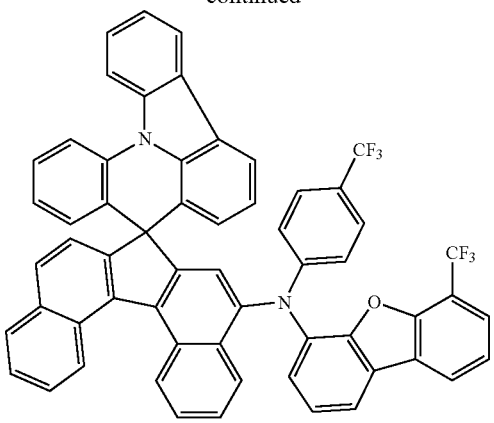
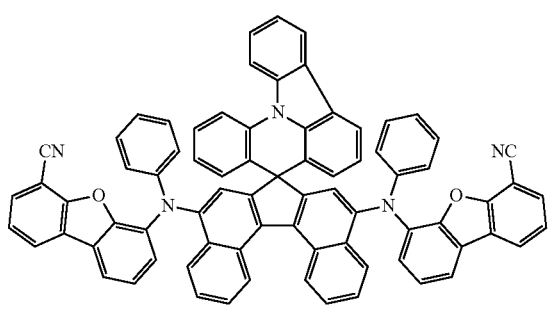
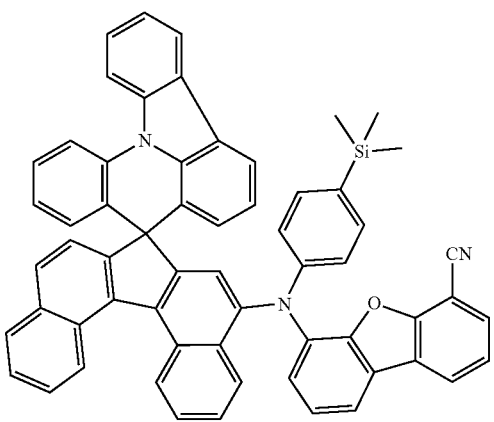
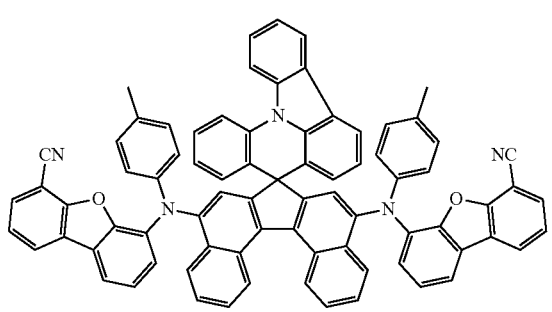

-continued
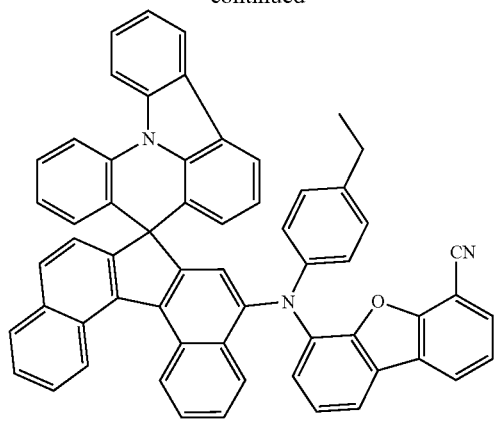
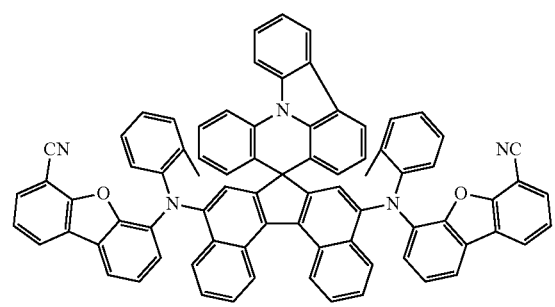
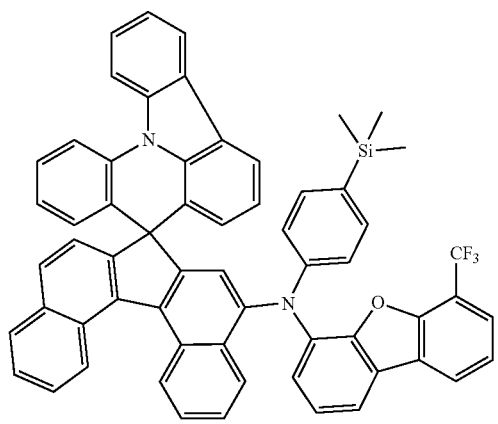
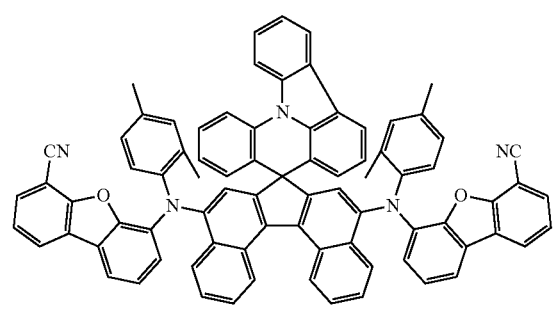
-continued
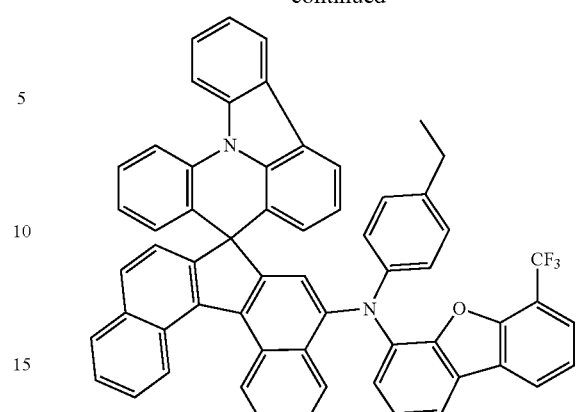
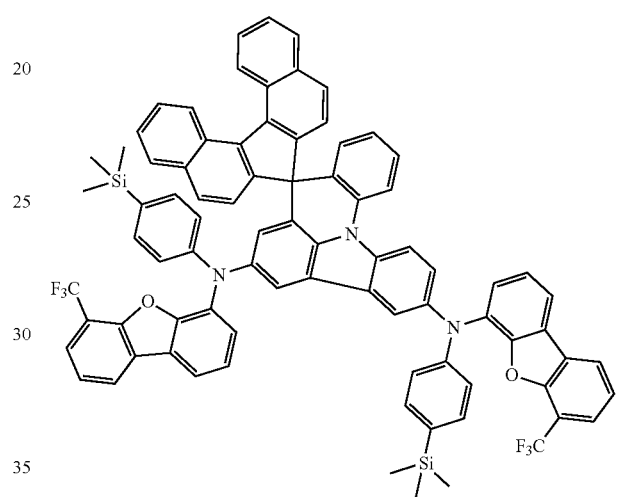
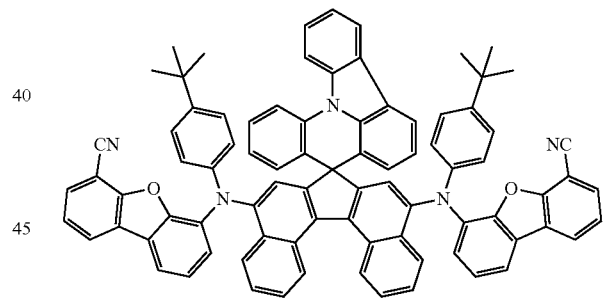
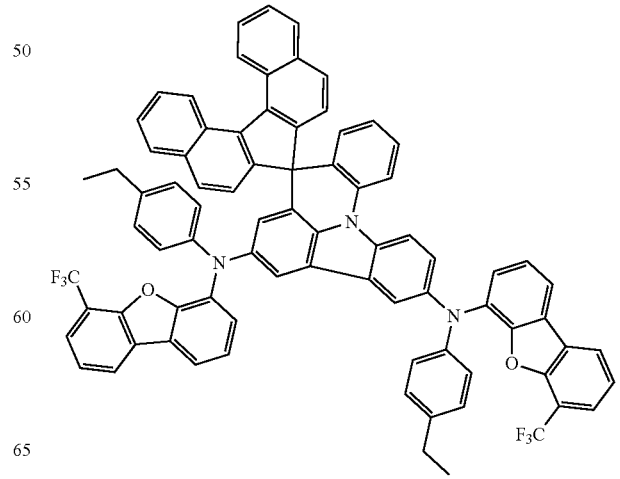

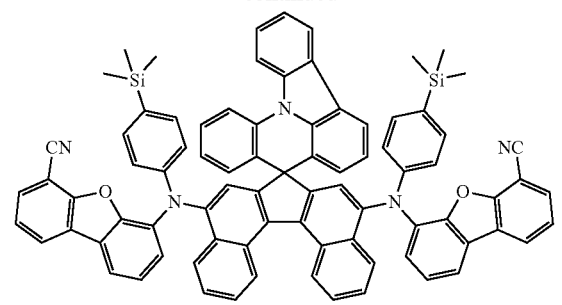
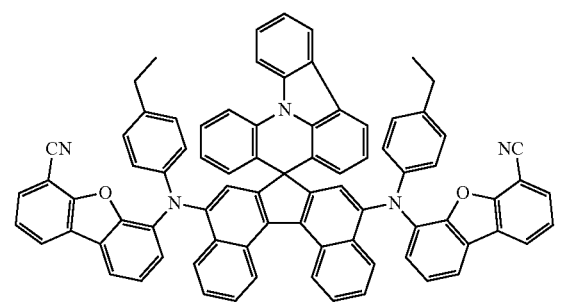
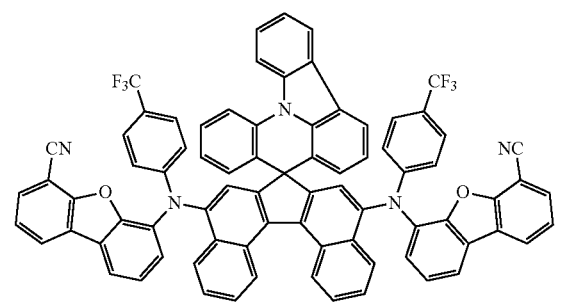
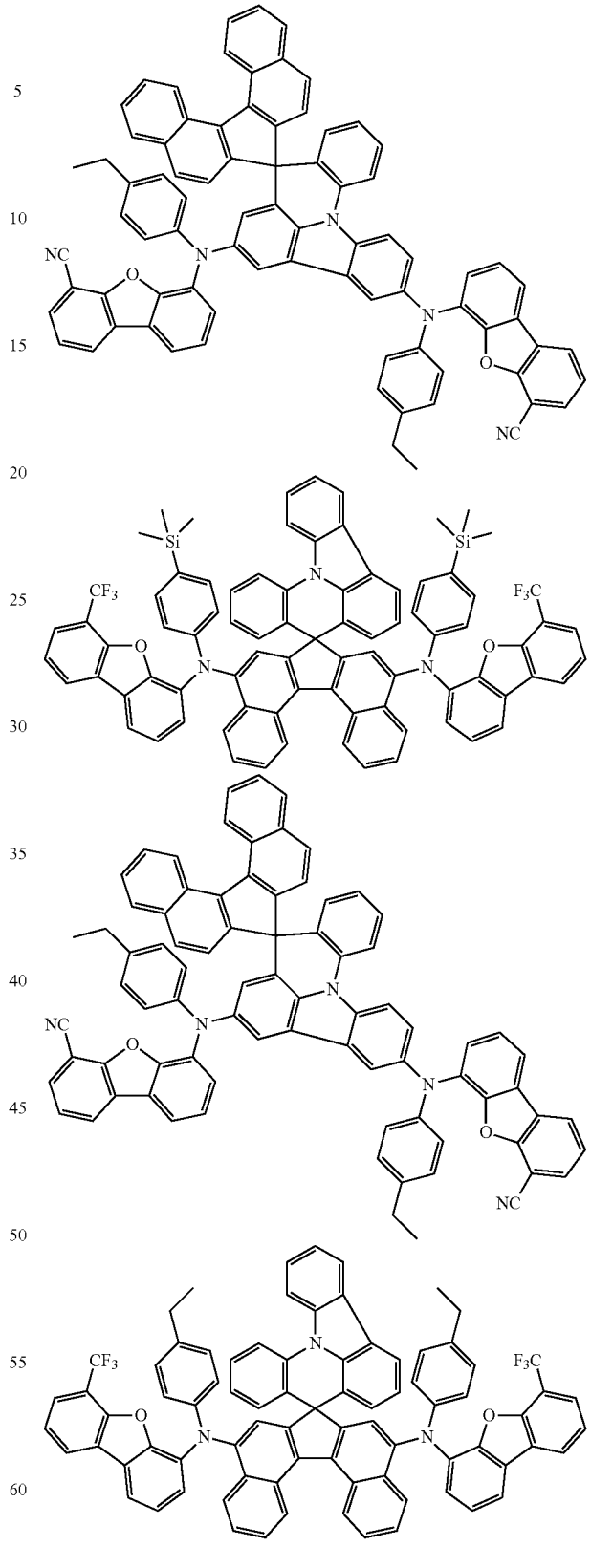
The compound according to one embodiment of the present specification may be prepared using preparation methods to be described below. Typical examples are described in the preparation examples to be described below, however, substituents may be added or excluded as necessary, and positions of the substituent may vary. In addition, based on technologies known in the art, starting materials, reaction materials, reaction conditions and the like may vary.

For example, the compound represented by Chemical Formula 1 may have its core structure prepared as in the following Reaction Formulae 1 to 5. Substituents may bond thereto using methods known in the art, and types, positions or the number of the substituents may vary depending on technologies known in the art. Substituents may bond as in the following Reaction Formulae 1 to 5, however, the reaction is not limited thereto.

[Reaction Formula 1]

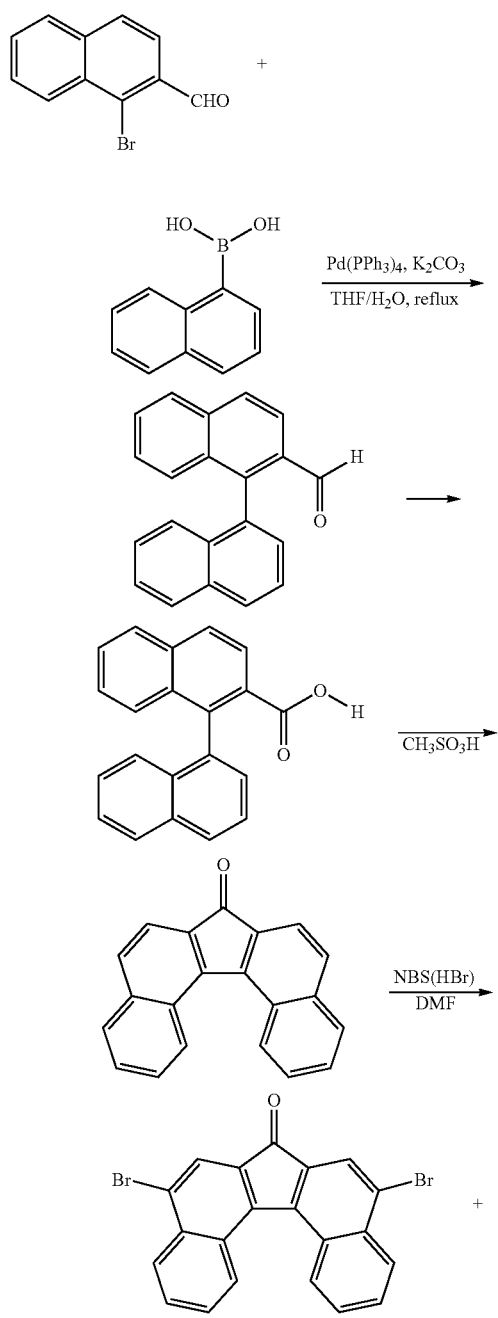

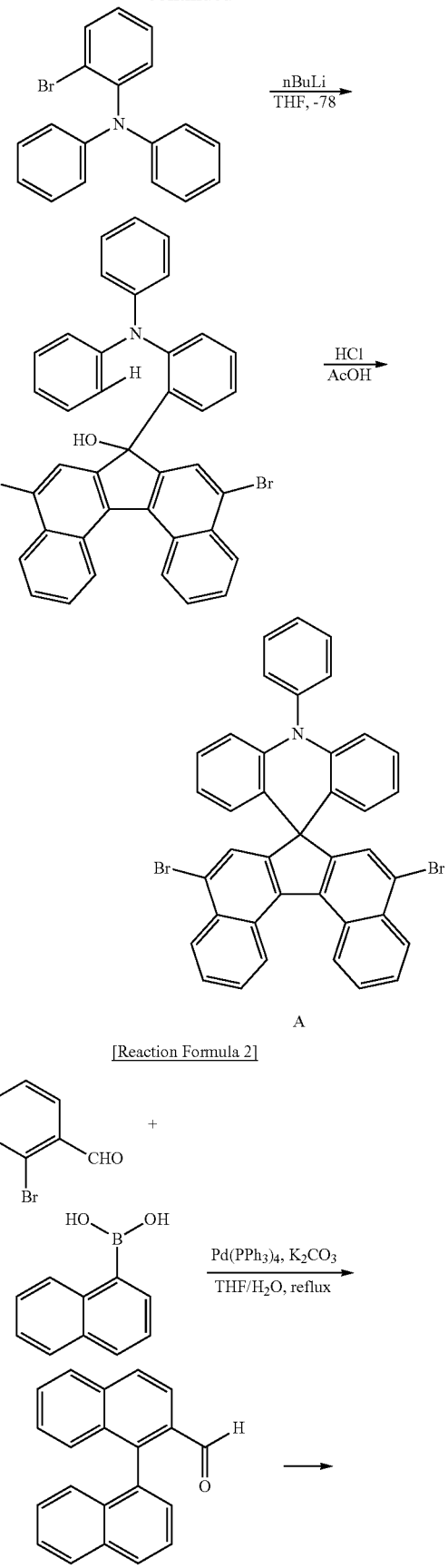

[Reaction Formula 2]

235
-continued
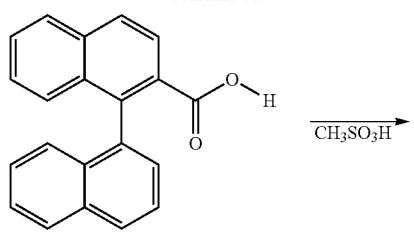
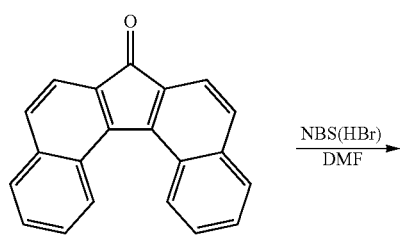
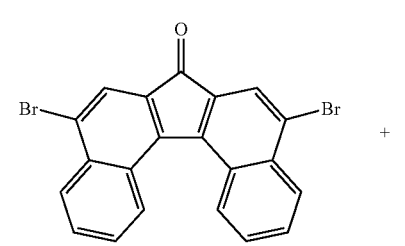
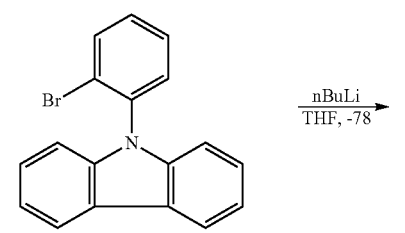
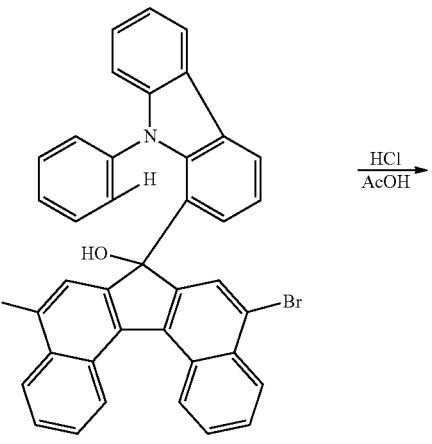
236
-continued
[Reaction Formula 3]

237
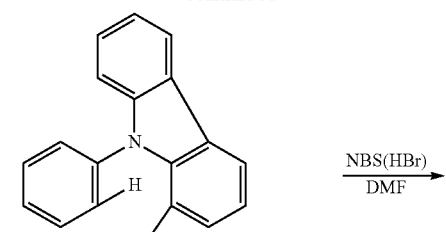
NBS(HBr) / DMF →
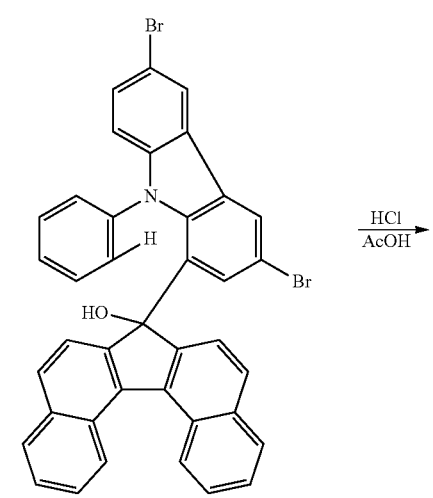
HCl / AcOH →
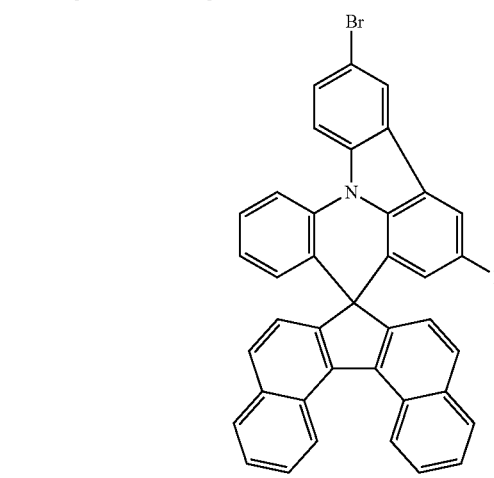
[Reaction Formula 4]
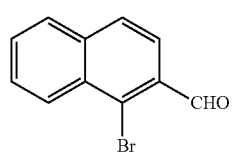 +
238
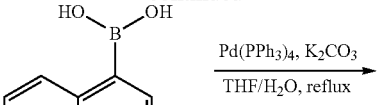
Pd(PPh₃)₄, K₂CO₃ / THF/H₂O, reflux →
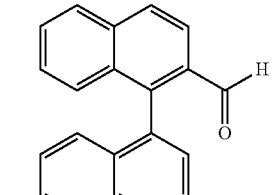
→
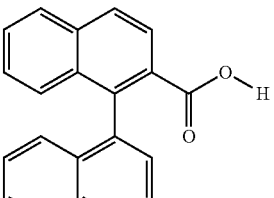
CH₃SO₃H →
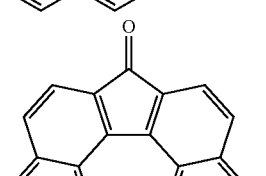
NBS(HBr) / DMF →
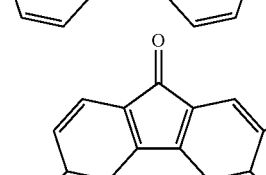
+
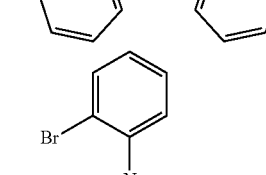
nBuLi / THF, -78 →
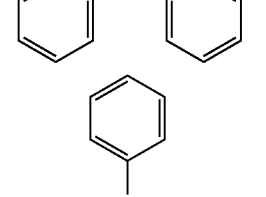
HCl / AcOH →
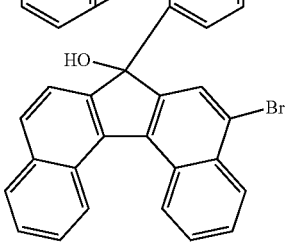

-continued

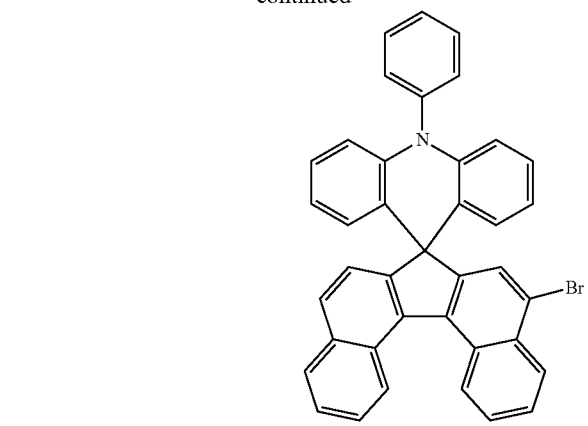

D

[Reaction Formula 5]

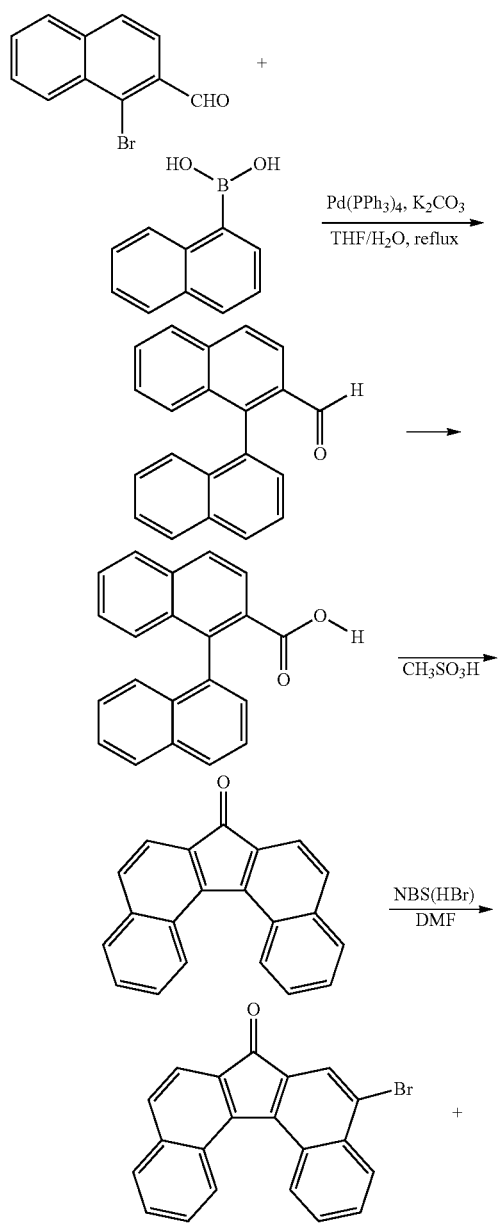

-continued

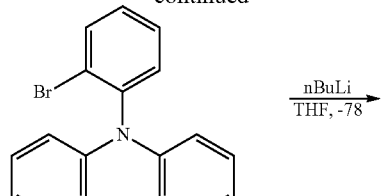

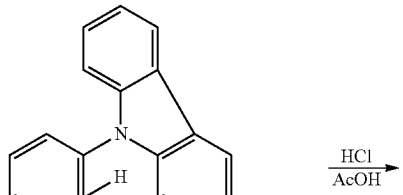

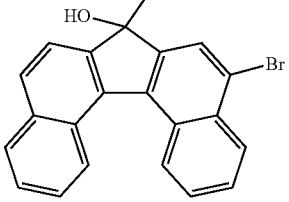

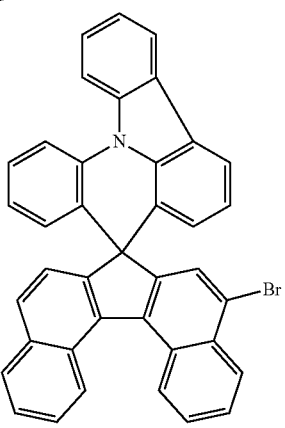

E

One embodiment of the present specification provides an organic electronic device comprising a first electrode; a second electrode provided opposite to the first electrode; and one or more organic material layers provided between the first electrode and the second electrode, wherein one or more layers of the organic material layers comprise the compound.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further comprised.

The organic material layer of the organic electronic device of the present specification may be formed in a single layer structure, but may be formed in a multilayer structure in which two or more organic material layers are laminated. For example, an organic light emitting device as a typical example of the organic electronic device of the present specification may have a structure comprising a hole injection layer, a hole transfer layer, a light emitting layer, an electron transfer layer, an electron injection layer, an electron blocking layer, a hole blocking layer and the like as the organic material layer. However, the structure of the organic electronic device is not limited thereto, and may comprise less numbers of organic material layers.

According to an exemplary embodiment of the present specification, the organic material layer comprises a light emitting layer, and the light emitting layer comprises the compound.

According to an exemplary embodiment of the present specification, the organic material layer comprises a hole injection layer or a hole transfer layer, and the hole injection layer or the hole transfer layer comprises the compound.

According to an exemplary embodiment of the present specification, the organic material layer comprises an electron injection layer, and the electron injection layer comprises the compound.

According to an exemplary embodiment of the present specification, the organic material layer comprises an electron blocking layer, and the electron blocking layer comprises the compound.

According to an exemplary embodiment of the present specification, the organic material layer comprises a hole injection layer, a hole transfer layer, or a layer carrying out hole injection and transfer at the same time, and the hole injection layer, the hole transfer layer, or the layer carrying out hole injection and transfer at the same time comprises the compound.

According to an exemplary embodiment of the present specification, the organic electronic device further comprises one, two or more layers selected from the group consisting of a light emitting layer, a hole injection layer, a hole transfer layer, an electron injection layer and an electron blocking layer.

According to an exemplary embodiment of the present specification, the organic electronic device may be selected from the group consisting of an organic light emitting device, an organic phosphorescent device, an organic solar cell, an organic photo conductor (OPC) and an organic transistor.

Hereinafter, an organic light emitting device will be illustrated.

According to an exemplary embodiment of the present specification, the organic light emitting device comprises a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers comprises the compound. According to an exemplary embodiment of the present specification, two or more may be selected from the group consisting of an electron transfer layer, an electron injection layer, a layer carrying out electron transfer and electron injection at the same time, and a hole blocking layer as the two or more organic material layers.

According to an exemplary embodiment of the present specification, the organic material layer comprises two or more electron transfer layers, and at least one of the two or more electron transfer layers comprises the compound. Specifically, According to an exemplary embodiment of the present specification, the compound may be comprised in one of the two or more electron transfer layers, or may be comprised in each of the two or more electron transfer layers.

In addition, when the compound is comprised in each of the two or more electron transfer layers According to an exemplary embodiment of the present specification, materials other than the compound may be the same as or different from each other.

According to an exemplary embodiment of the present specification, the organic material layer further comprises, in addition to the organic material layer comprising the compound, a hole injection layer or a hole transfer layer comprising a compound comprising an arylamine group, a carbazolyl group or a benzocarbazolyl group.

In another embodiment, the organic light emitting device may be an organic light emitting device having a structure in which an negative electrode, one or more organic material layers and a positive electrode are consecutively laminated on a substrate (normal type).

When the organic material layer comprising the compound of Chemical Formula 1 is an electron transfer layer, the electron transfer layer may further comprise an n-type dopant. As the n-type dopant, those known in the art may be used, and for example, metals or metal complexes may be used. According to one example, the electron transfer layer comprising the compound of Chemical Formula 1 may further comprise lithium quinolate (LiQ).

In another embodiment, the organic light emitting device may be an organic light emitting device having a reverse direction structure in which a positive electrode, one or more organic material layers and an negative electrode are consecutively laminated on a substrate (inverted type).

For example, structures of the organic light emitting device of the present specification may be as illustrated in FIG. 1 and FIG. 2, however, the structure is not limited thereto.

FIG. 1 illustrates a structure of the organic light emitting device (10) in which a first electrode (30), a light emitting layer (40) and a second electrode (50) are consecutively laminated on a substrate (20). FIG. 1 is an illustrative structure of the organic light emitting device according to one embodiment of the present specification, and other organic material layers may be further comprised.

FIG. 2 illustrates a structure of the organic light emitting device in which a first electrode (30), a hole injection layer (60), a hole transfer layer (70), an electron blocking layer (80), a light emitting layer (40), an electron transfer layer (90), an electron injection layer (100) and a second electrode (50) are consecutively laminated on a substrate (20). FIG. 2 is an illustrative structure of the organic light emitting device according to an embodiment of the present specification, and other organic material layers may be further comprised.

According to an exemplary embodiment of the present specification, the organic material layer comprises a light emitting layer, and the light emitting layer comprises the compound as a dopant material and comprises a compound represented by the following Chemical Formula 9 as a host material.

[Chemical Formula 9]

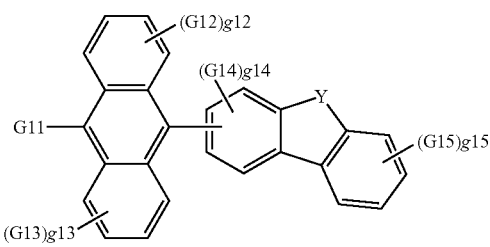

According to an exemplary embodiment of the present specification, Y is O or S.

According to an exemplary embodiment of the present specification, Y is O.

According to an exemplary embodiment of the present specification, Y is S.

According to an exemplary embodiment of the present specification, G11 is a substituted or unsubstituted aryl group.

According to an exemplary embodiment of the present specification, G11 is a substituted or unsubstituted phenyl group, a substituted or unsubstituted biphenyl group, a substituted or unsubstituted naphthyl group, a substituted or unsubstituted phenanthryl group, or a substituted or unsubstituted fluorenyl group.

According to an exemplary embodiment of the present specification, G11 is a phenyl group unsubstituted or substituted with an aryl group.

According to an exemplary embodiment of the present specification, G11 is a phenyl group unsubstituted or substituted with a phenyl group or a naphthyl group.

According to an exemplary embodiment of the present specification, G11 is a phenyl group.

According to an exemplary embodiment of the present specification, G11 is a biphenyl group.

According to an exemplary embodiment of the present specification, G11 is a naphthyl group unsubstituted or substituted with an aryl group.

According to an exemplary embodiment of the present specification, G11 is a naphthyl group unsubstituted or substituted with a phenyl group.

According to an exemplary embodiment of the present specification, G11 is a phenanthryl group.

According to an exemplary embodiment of the present specification, G12 to G15 are the same as or different from each other, and each independently hydrogen; deuterium; a halogen group; a nitrile group; a nitro group; a hydroxyl group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted phosphine oxide group; a substituted or unsubstituted amine group; a substituted or unsubstituted aryl group; or a substituted or unsubstituted heterocyclic group.

According to an exemplary embodiment of the present specification, G12 to G15 are each hydrogen.

According to an exemplary embodiment of the present specification, g12, g13 and g15 are each an integer of 1 to 4, g14 is an integer of 1 to 3, and when g12 to g15 are each 2 or greater, the two or more G12s to G15s are each the same as or different from each other.

According to an exemplary embodiment of the present specification, the compound represented by Chemical Formula 9 is any one selected from among the following compounds.

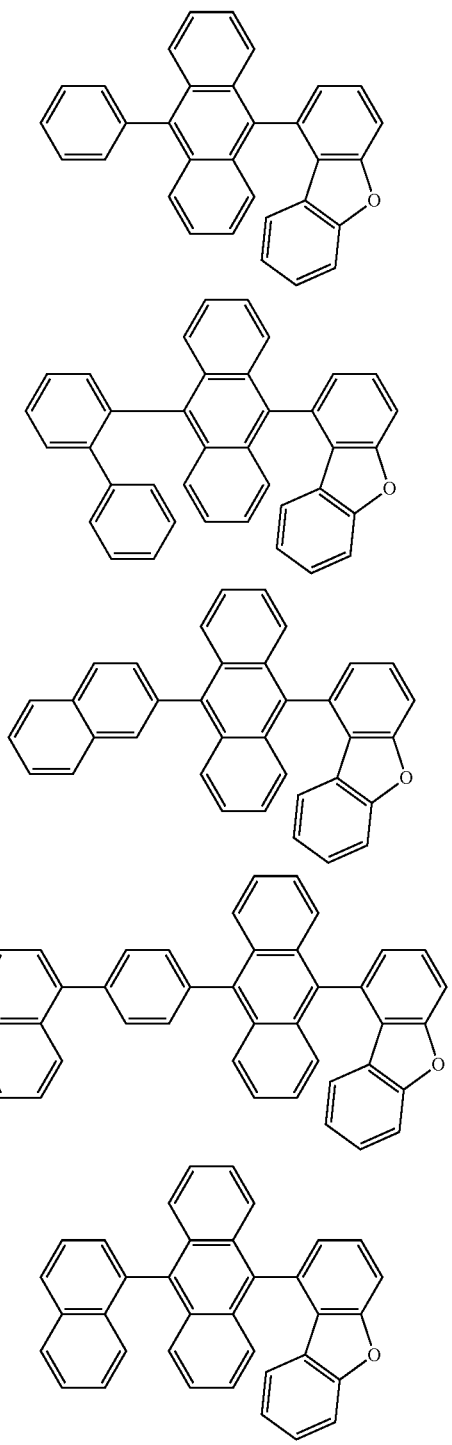

245
-continued
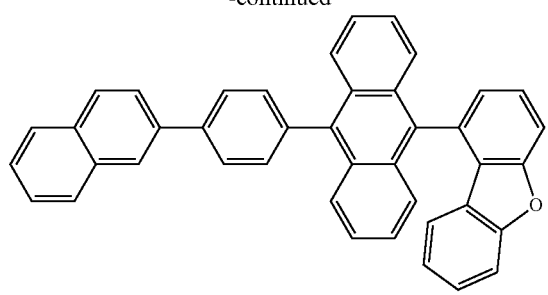
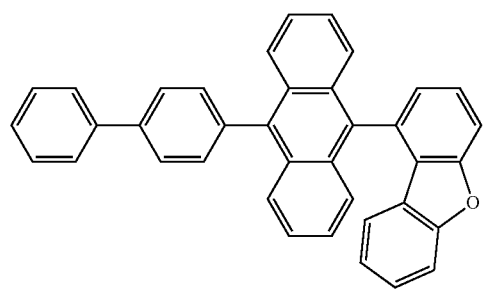
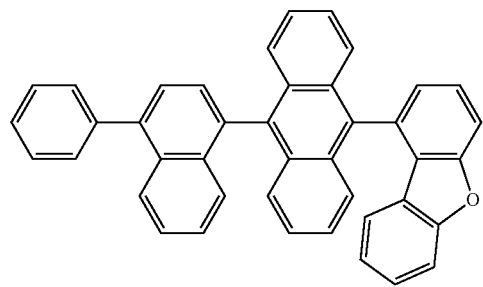
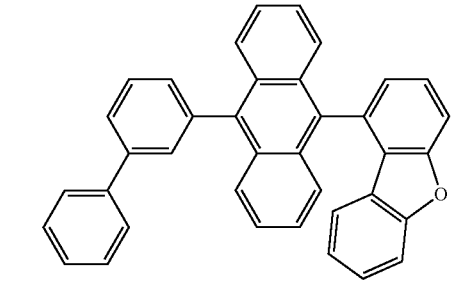
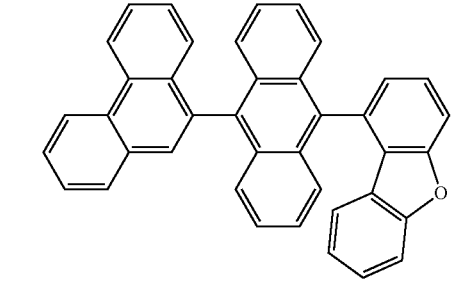
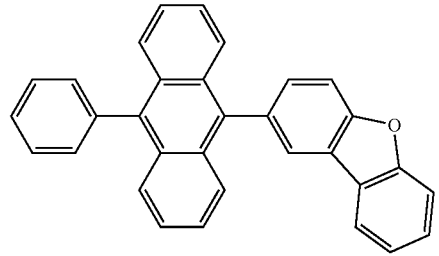
246
-continued
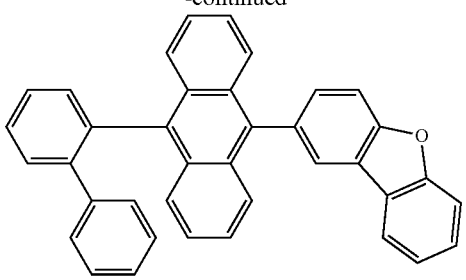
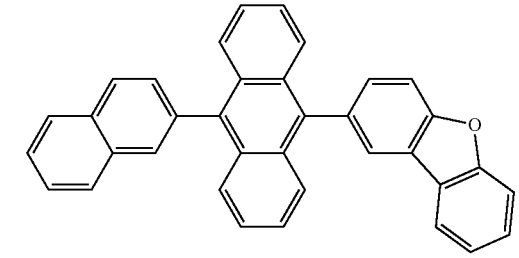
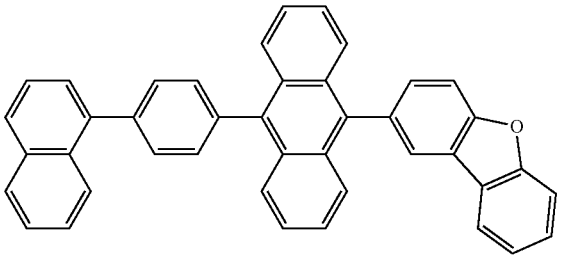
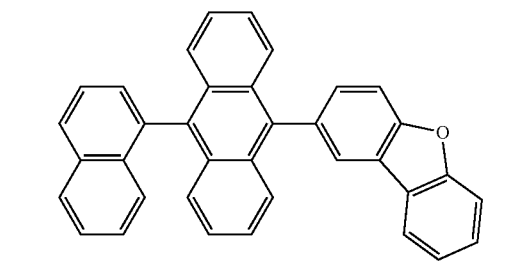
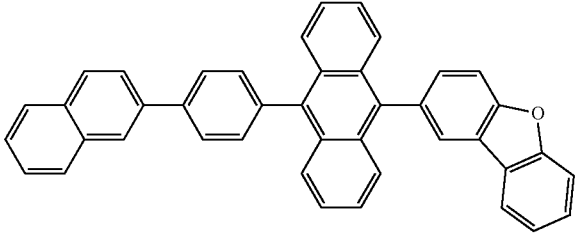
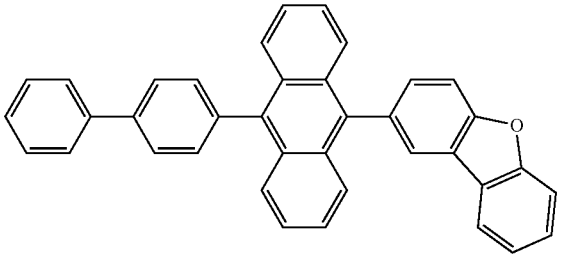

-continued
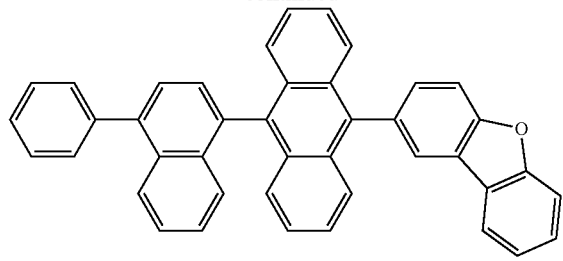
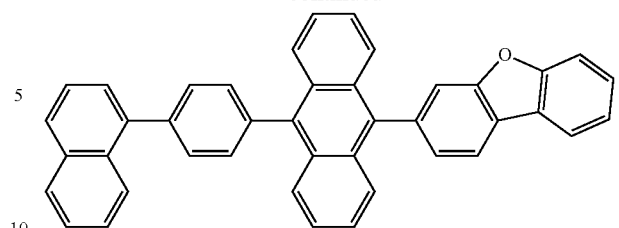
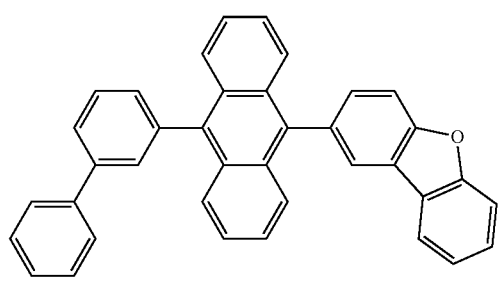
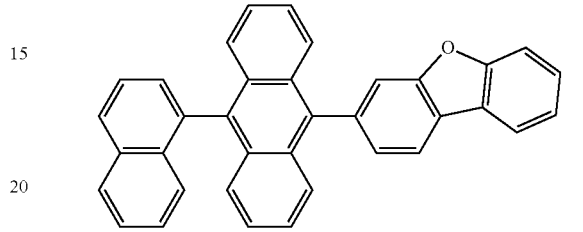
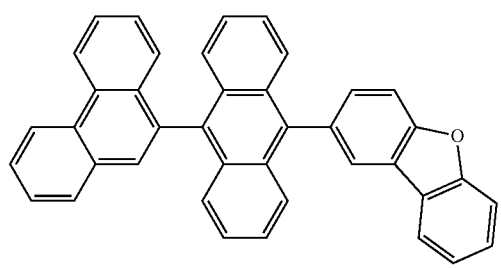
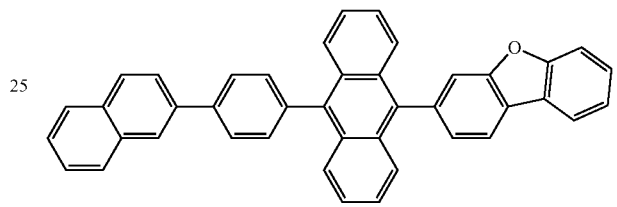
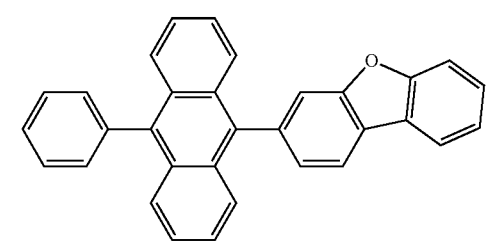
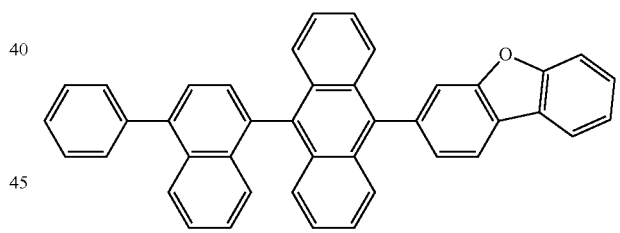
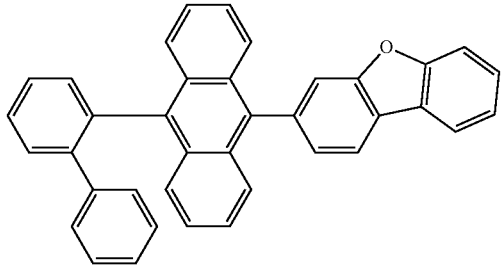
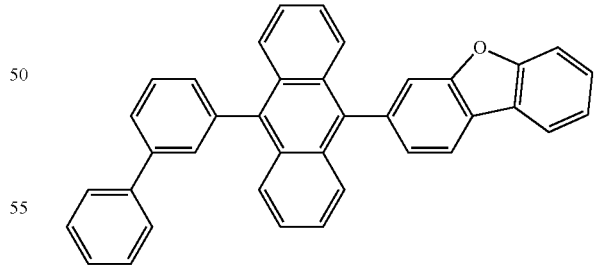
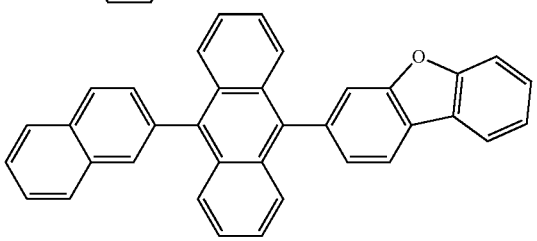
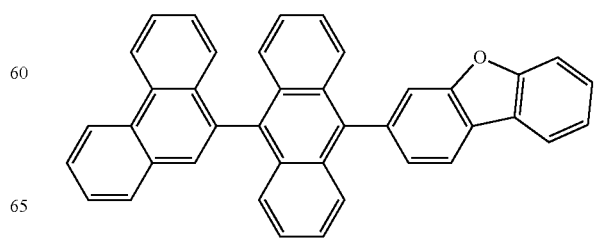

249
-continued
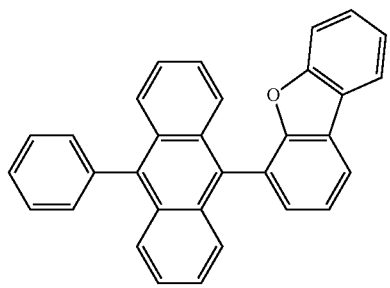
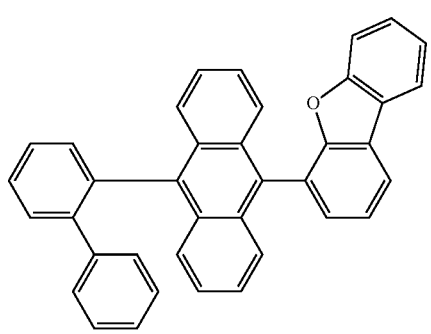
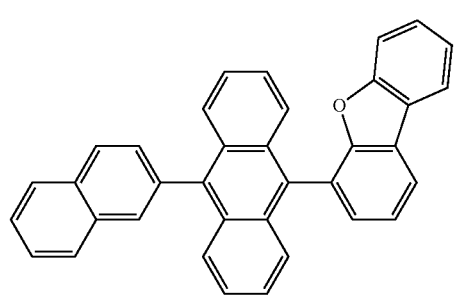
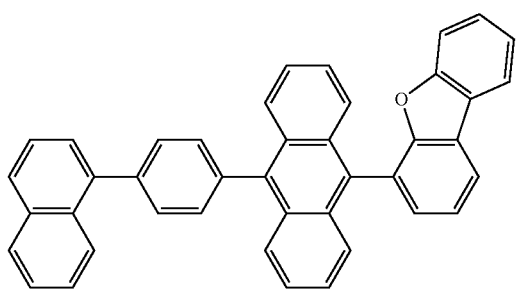
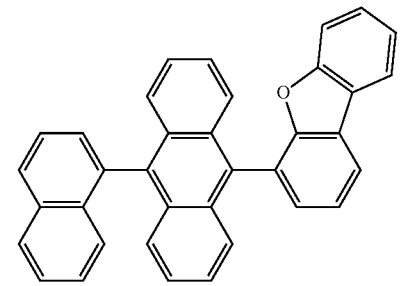
250
-continued
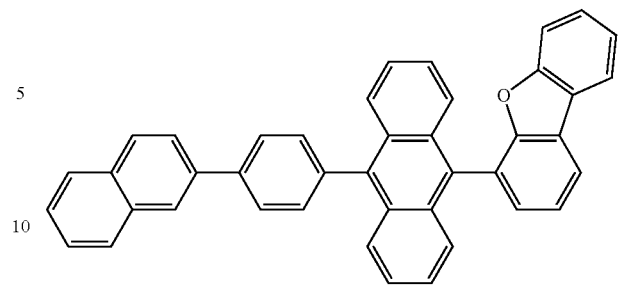
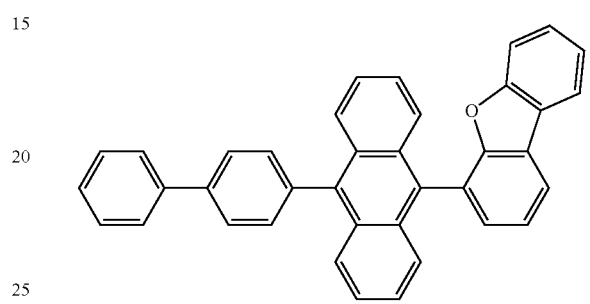
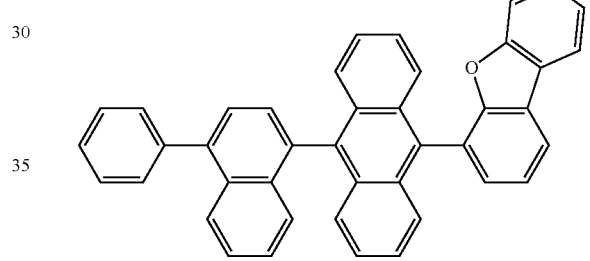
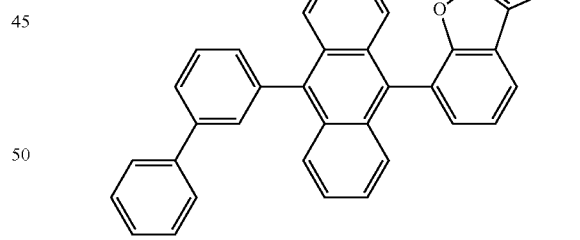
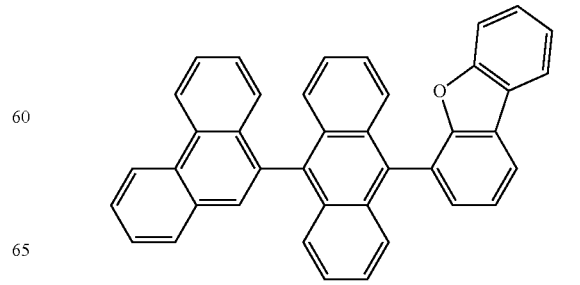

-continued
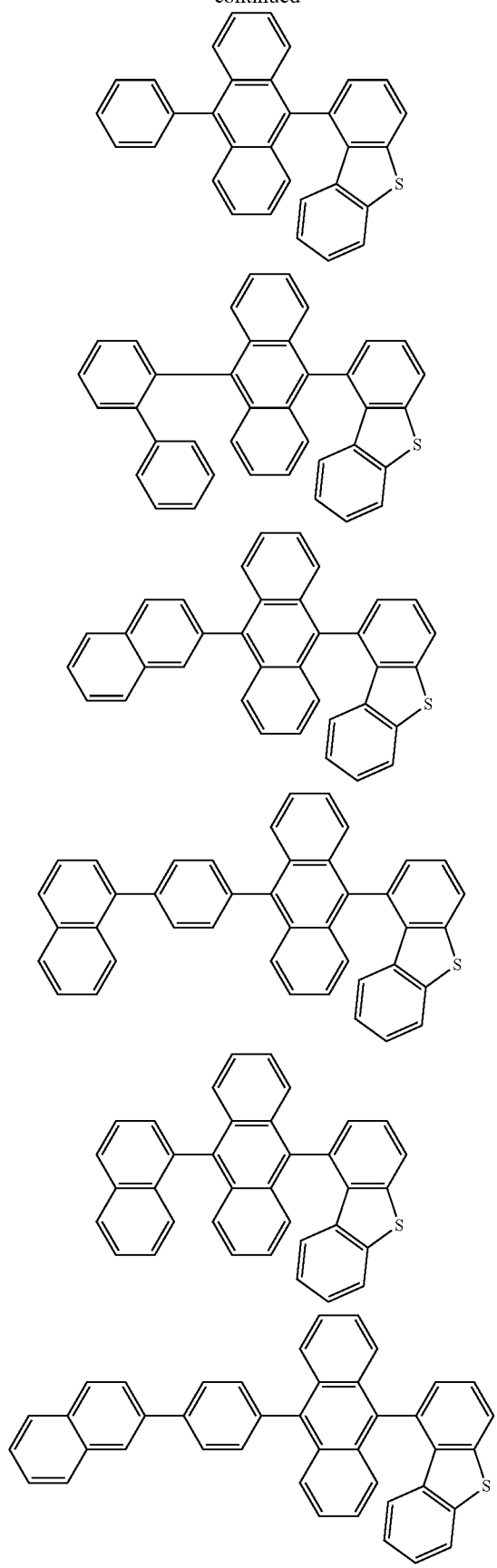
-continued
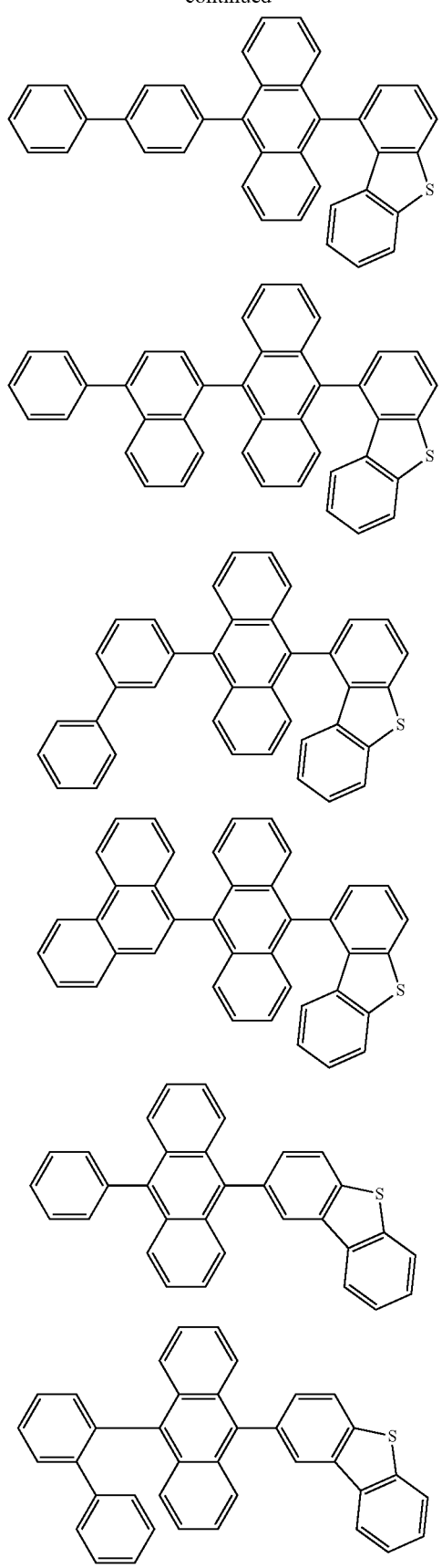

-continued
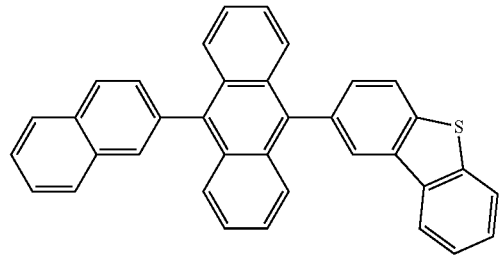
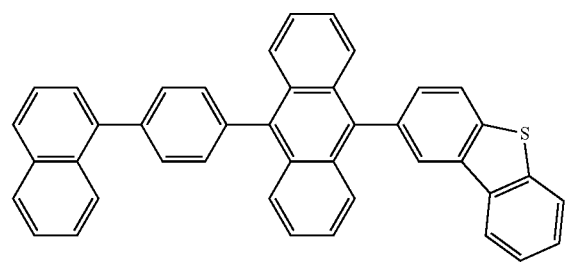
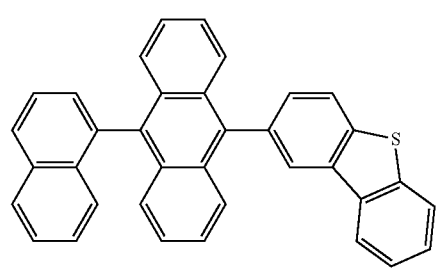
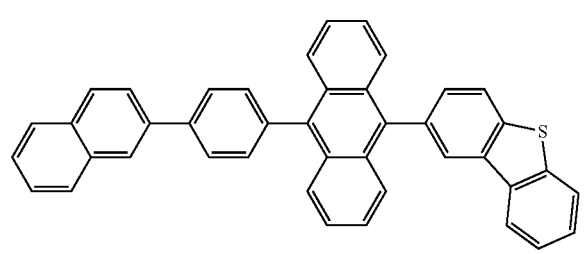
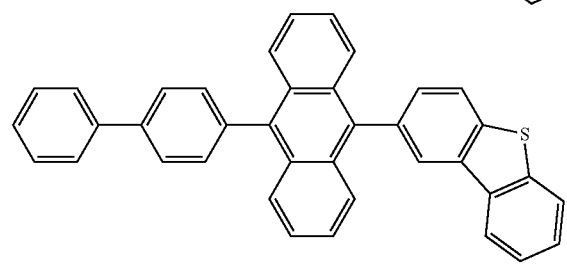
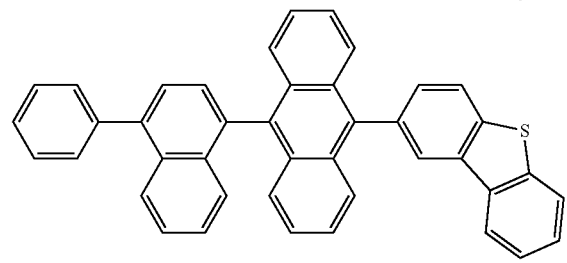
-continued
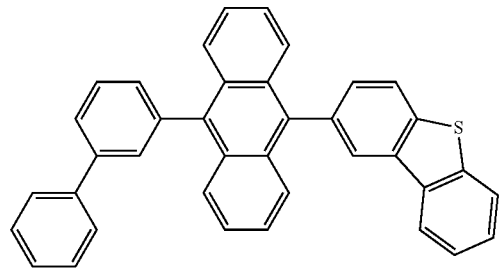
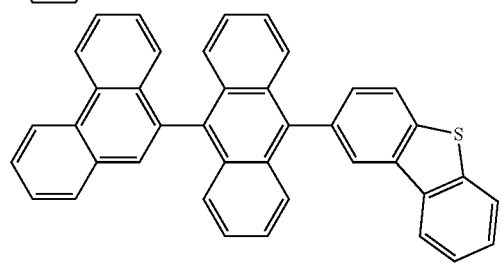
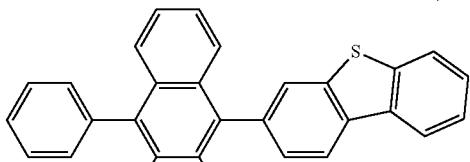
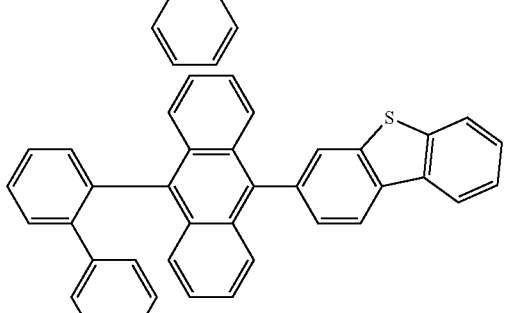
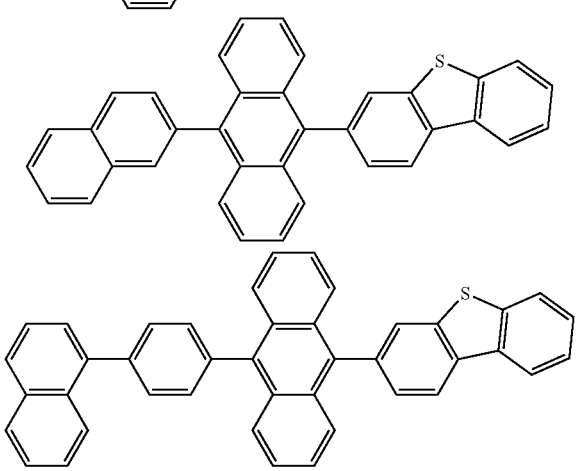
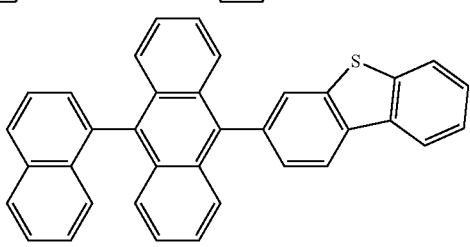

255
-continued
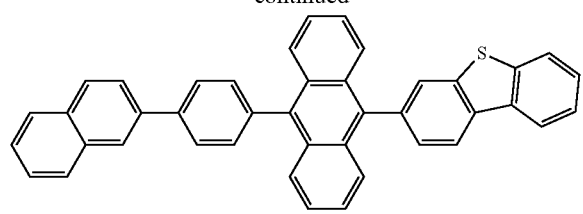
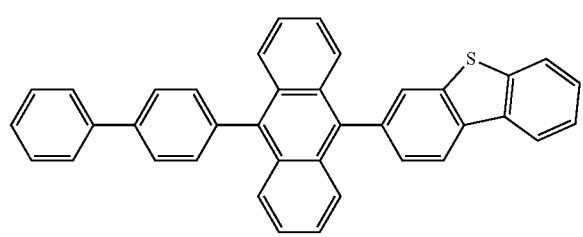
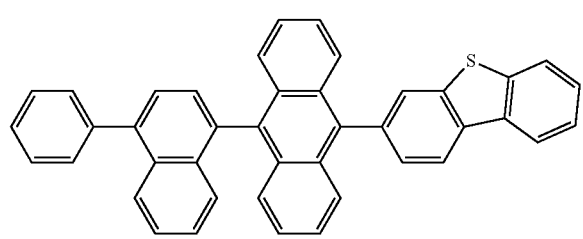
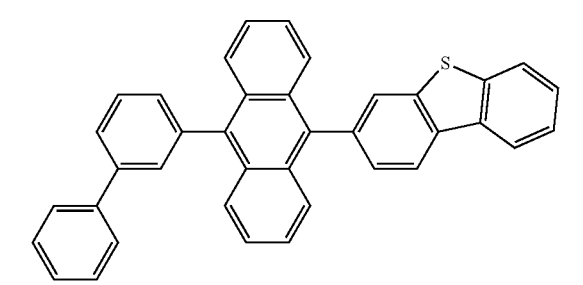
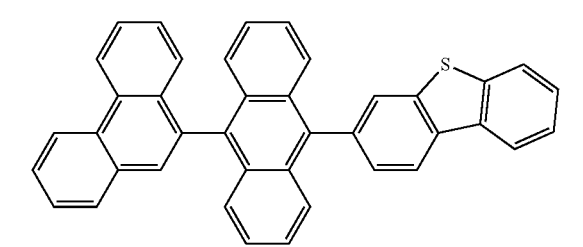
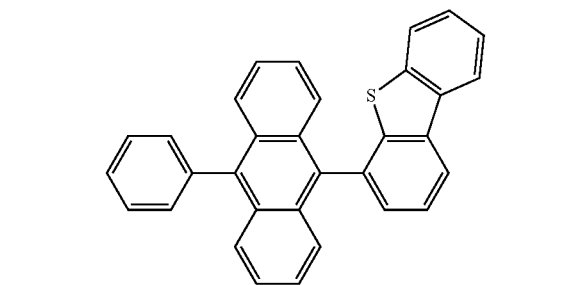
256
-continued
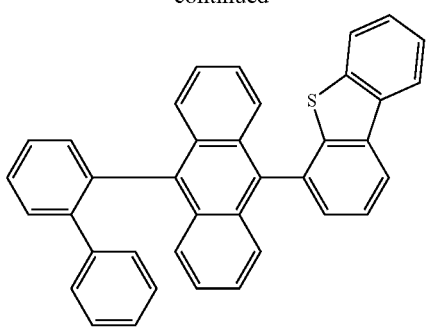
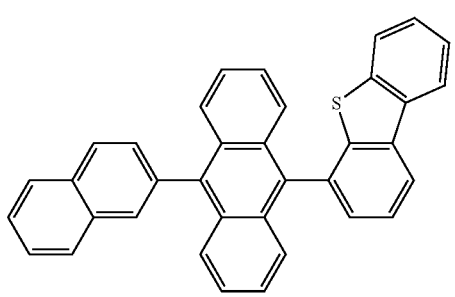
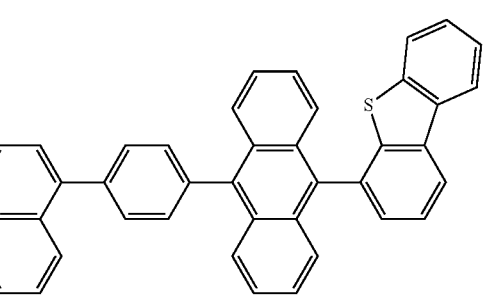
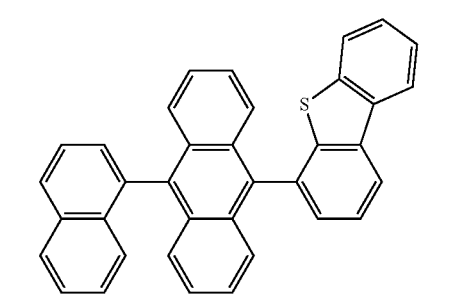
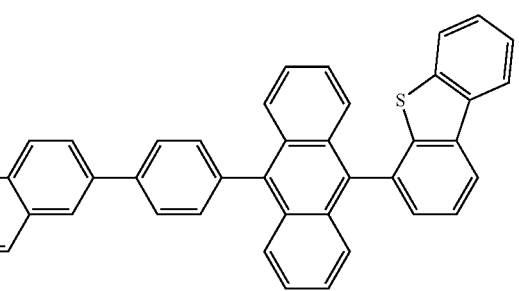

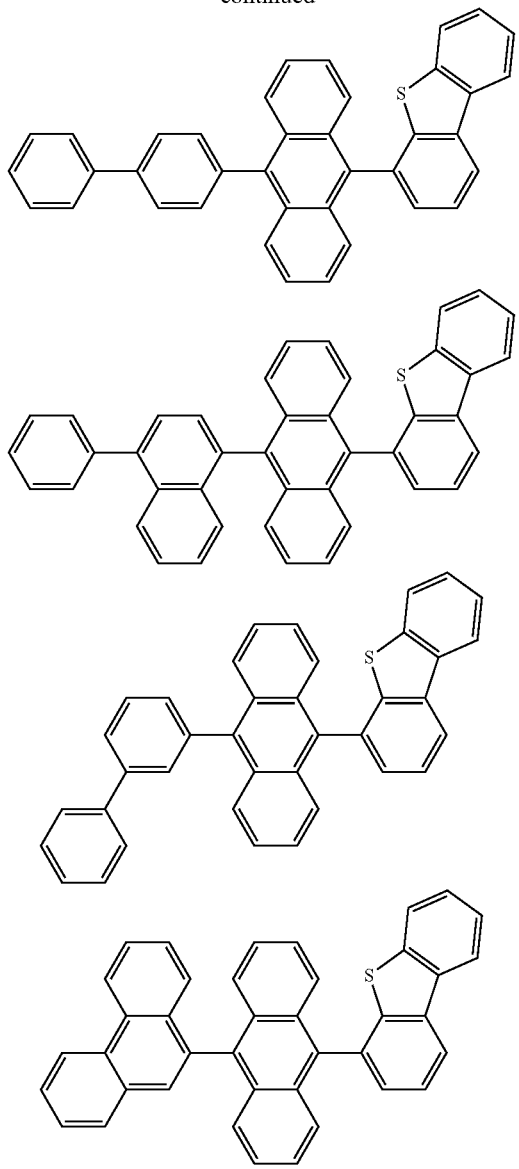

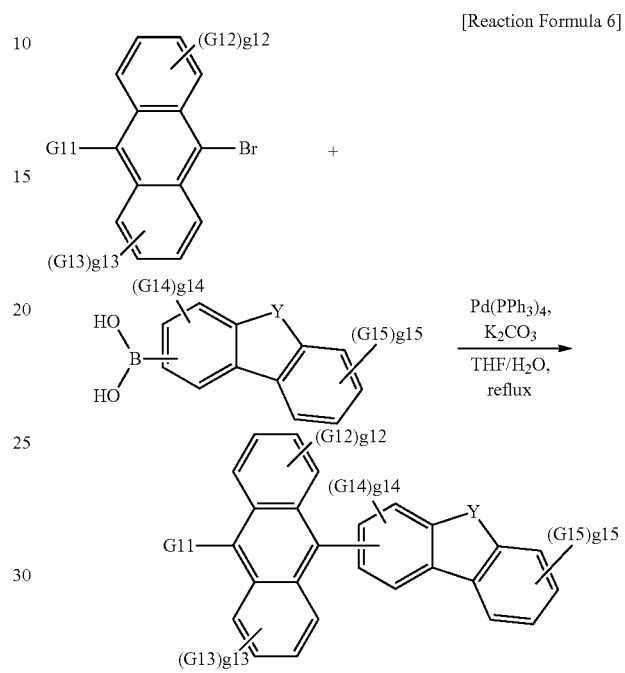

In Reaction Formula 6, G11 to G15 and g12 to g15 have the same definitions as in Chemical Formula 9.

The organic light emitting device of the present specification may be manufactured using materials and methods known in the art, except that one or more layers of the organic material layers comprise the compound, that is, the compound represented by Chemical Formula 1.

When the organic light emitting device comprises a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming a negative electrode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer thereon, and then depositing a material capable of being used as a positive electrode thereon. In addition to such a method, the organic light emitting device may also be manufactured by consecutively depositing a positive electrode material, an organic material layer and an negative electrode material on a substrate.

In addition, the compound represented by Chemical Formula 1 may be formed into an organic material layer using a solution coating method as well as a vacuum deposition method when manufacturing the organic light emitting According to an exemplary embodiment of the present specification, the organic material layer comprises a light emitting layer, and the light emitting layer comprises the compound represented by Chemical Formula 1 as a dopant material and comprises the compound represented by Chemical Formula 9 as a host material. Herein, a weight ratio of the compound represented by Chemical Formula 1 and the compound represented by Chemical Formula 9 (compound represented by Chemical Formula 1/compound represented by Chemical Formula 9) is from 0.005 to 0.10.

The compound represented by Chemical Formula 9 may be prepared using preparation methods to be described below. Typical examples are described in the preparation examples to be described below, however, substituents may be added or excluded as necessary, and positions of the substituent may vary. In addition, based on technologies known in the art, starting materials, reaction materials, reaction conditions and the like may vary.

For example, the compound represented by Chemical Formula 9 may have its core structure prepared as in the following Reaction Formula 6. Substituents may bond thereto using methods known in the art, and types, positions or the number of the substituents may vary depending on technologies known in the art. Substituents may bond as in the following Reaction Formula 6, however, the reaction is not limited thereto.

device. Herein, the solution coating method means spin coating, dip coating, doctor blading, inkjet printing, screen printing, a spray method, roll coating and the like, but is not limited thereto.

In addition to such a method, the organic light emitting device may also be manufactured by consecutively depositing a positive electrode material, an organic material layer and an negative electrode material on a substrate (International Patent Application Laid-Open Publication No. 2003/012890). However, the preparation method is not limited thereto.

According to an exemplary embodiment of the present specification, the first electrode is a negative electrode, and the second electrode is a positive electrode.

In another embodiment, the first electrode is a positive electrode, and the second electrode is a negative electrode.

As the negative electrode material, materials having large work function are normally preferred so that hole injection to an organic material layer is smooth. Specific examples of the negative electrode material capable of being used include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the positive electrode material, materials having small work function are normally preferred so that electron injection to an organic material layer is smooth. Specific examples of the positive electrode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al and the like, but are not limited thereto.

The light emitting layer may comprise a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

In the present specification, when the compound represented by Chemical Formula 1 is comprised in organic material layers other than the light emitting layer, or when an additional light emitting layer is provided, the light emitting material of the light emitting layer is preferably, as a material capable of emitting light in a visible light region by receiving holes and electrons from a hole transfer layer and an electron transfer layer, respectively, and binding the holes and the electrons, a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The hole injection layer is a layer that injects holes from an electrode, and the hole injection material is preferably a compound that has an ability to transfer holes, therefore, has a hole injection effect in an negative electrode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an negative electrode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an negative electrode or a hole injection layer, moving the holes to a light emitting layer, and having high mobility for the holes are suitable. Specific examples thereof comprise arylamine-based organic materials, conductive polymers, block copolymers having conjugated parts and non-conjugated parts together, and the like, but are not limited thereto.

The electron blocking layer is a layer capable of enhancing lifespan and efficiency of a device by preventing holes injected from a hole injection layer from passing through a light emitting layer and entering an electron injection layer, and as necessary, may be formed in an appropriate place between the light emitting layer and the electron injection layer using materials known in the art.

The hole blocking layer is a layer blocking holes from reaching a positive electrode and may generally be formed under the same condition as the hole injection layer. Specifically, oxadiazole derivatives, triazole derivatives, phenanthroline derivatives, aluminum complexes and the like are included, however, the hole blocking layer is not limited thereto.

The electron transfer layer is a layer that receives electrons from an electron injection layer and transfers the electrons to a light emitting layer, and as the electron transfer material, materials capable of favorably receiving electrons from a positive electrode, moving the electrons to a light emitting layer, and having high mobility for the electrons are suitable. Specific examples thereof include Al complexes of 8-hydroxyquinoline; complexes including Alq₃; organic radical compounds; hydroxyflavon-metal complexes, and the like, but are not limited thereto. The electron transfer layer may be used together with any desired positive electrode material as used in the art. Particularly, examples of the suitable positive electrode material include common materials that have small work function, and in which an aluminum layer or a silver layer follows. Specifically, the positive electrode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a positive electrode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyguinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

According to an exemplary embodiment of the present specification, the compound represented by Chemical Formula 1 may be comprised in an organic solar cell or an organic transistor in addition to the organic light emitting device.

The compound according to the present specification may also be used in an organic electronic device including an organic phosphorescent device, an organic solar cell, an organic photo conductor, an organic transistor and the like under a similar principle used in the organic light emitting device. For example, the organic solar cell may have a structure comprising a positive electrode, an negative electrode and a photoactive layer provided between the positive electrode and the negative electrode, and the photoactive layer may comprise the compound.

Hereinafter, the present specification will be described in detail with reference to examples, comparative examples and the like. However, the examples and the comparative examples according to the present specification may be modified to various different forms, and the scope of the present specification is not to be construed as being limited to the examples and the comparative examples described below. The examples and the comparative examples of the present specification are provided in order to more fully describe the present specification to those having average knowledge in the art.

EXAMPLE

Preparation Example 1

Synthesis of Compound 1

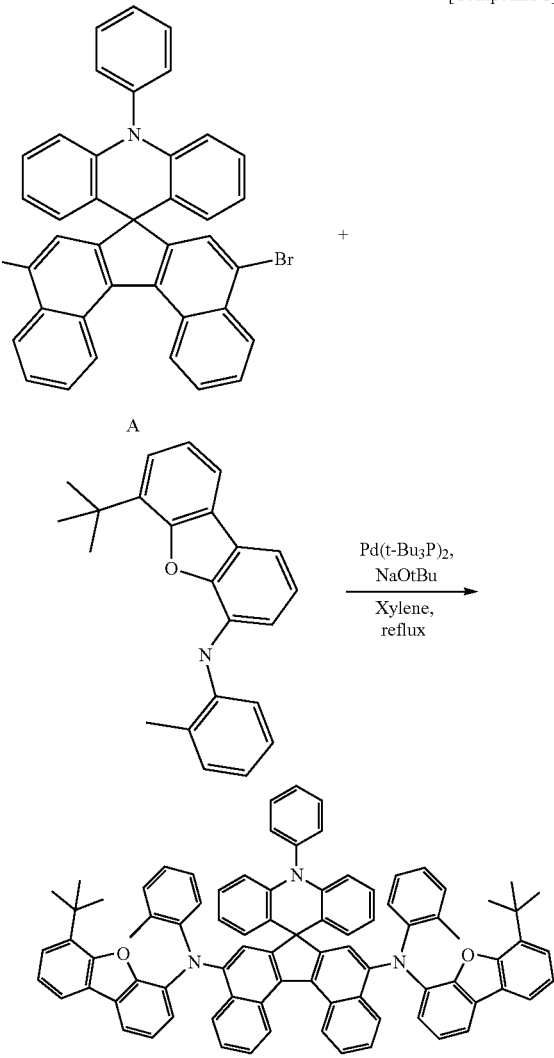

After completely dissolving Compound A (5.27 g, 7.95 mmol) and 6-(tert-butyl)-N-(o-tolyl)dibenzo[b,d]furane-4-amine (5.49 g, 16.69 mmol) in 160 ml of xylene in a 500 ml round bottom flask under nitrogen atmosphere, sodium-tert-butoxide (1.83 g, 19.08 mmol) and then bis(tri-tert-butylphosphine)palladium(0) (0.08 g, 0.16 mmol) were added thereto, and the result was heated and stirred for 9 hours. After lowering the temperature to room temperature, the result was filtered to remove salts, xylene was vacuum concentrated, and the result was columned using tetrahydrofuran:hexane=1:25 to prepare Compound 1 (5.12 g, purity: 99.99%, yield: 55%).

MS[M+H]⁺=1,162

263

Preparation Example 2

Synthesis of Compound 2

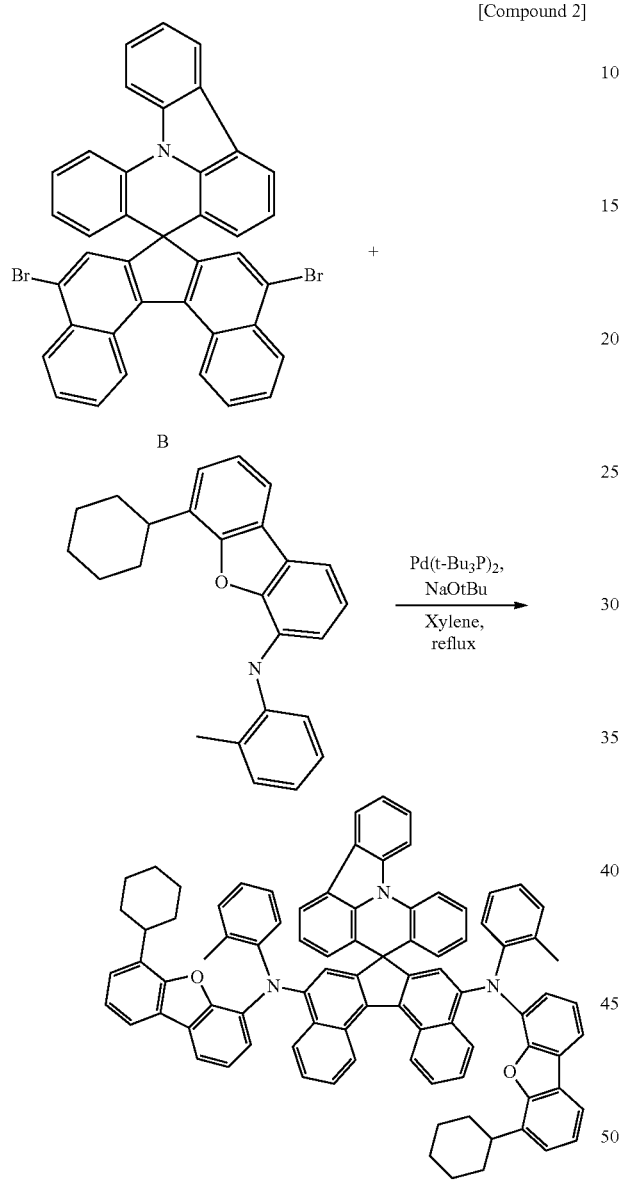

[Compound 2]

After completely dissolving Compound B (4.39 g, 6.64 mmol) and 6-cyclohexyl-N-(o-tolyl)dibenzo[b,d]furan-4-amine (4.95 g, 13.95 mmol) in 220 ml of xylene in a 500 ml round bottom dflask under nitrogen atmosphere, sodium-tert-butoxide (1.53 g, 15.94 mmol) and then bis(tri-tert-butylphosphine)palladium(0) (0.07 g, 0.13 mmol) were added thereto, and the result was heated and stirred for 6 hours. After lowering the temperature to room temperature, the result was filtered to remove salts, xylene was vacuum concentrated, and the result was columned using tetrahydrofuran:hexane=1:25 to prepare Compound 2 (3.24 g, purity: 99.99%, yield: 42%).

MS[M+H]$^+$=1,162

264

Preparation Example 3

Synthesis of Compound 3

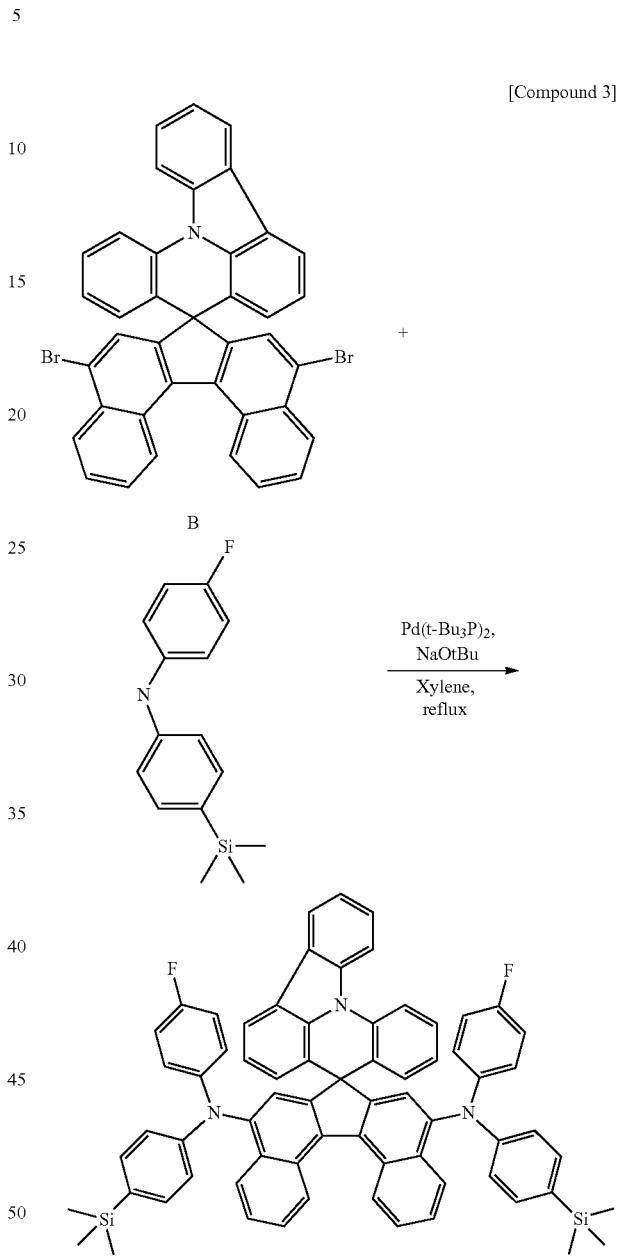

[Compound 3]

After completely dissolving Compound B (2.96 g, 4.48 mmol) and 4-fluoro-N-(4-(trimethylsilyl)phenyl)aniline (2.44 g, 9.40 mmol) in 150 ml of xylene in a 500 ml round bottom flask under nitrogen atmosphere, sodium-tert-butoxide (1.03 g, 10.75 mmol) and then bis(tri-tert-butylphosphine)palladium(0) (0.05 g, 0.09 mmol) were added thereto, and the result was heated and stirred for 7 hours. After lowering the temperature to room temperature, the result was filtered to remove salts, xylene was vacuum concentrated, and the result was columned using tetrahydrofuran:hexane=1:25 to prepare Compound 3 (2.17 g, purity: 99.99%, yield: 42%).

MS[M+H]$^+$=970

Preparation Example 4

Synthesis of Compound 4

[Compound 4]

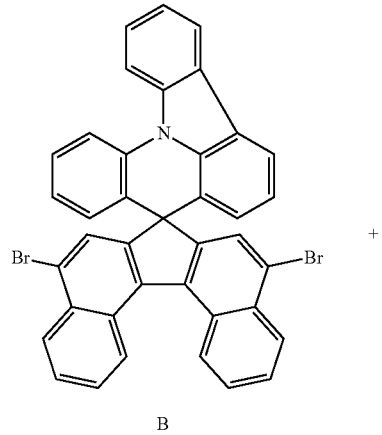

After completely dissolving Compound B (3.75 g, 5.67 mmol) and 6-(tert-butyl)-N-(o-tolyl)dibenzo[b,d]furan-4-amine (3.92 g, 11.91 mmol) in 170 ml of xylene in a 500 ml round bottom flask under nitrogen atmosphere, sodium-tert-butoxide (1.31 g, 13.62 mmol) and then bis(tri-tert-butylphosphine)palladium(0) (0.06 g, 0.11 mmol) were added thereto, and the result was heated and stirred for 8 hours. After lowering the temperature to room temperature, the result was filtered to remove salts, xylene was vacuum concentrated, and the result was columned using tetrahydrofuran:hexane=1:30 to prepare Compound 4 (4.78 g, purity: 99.99%, yield: 73%).

MS[M+H]$^+$=1,160

Preparation Example 5

Synthesis of Compound 5

[Compound 5]

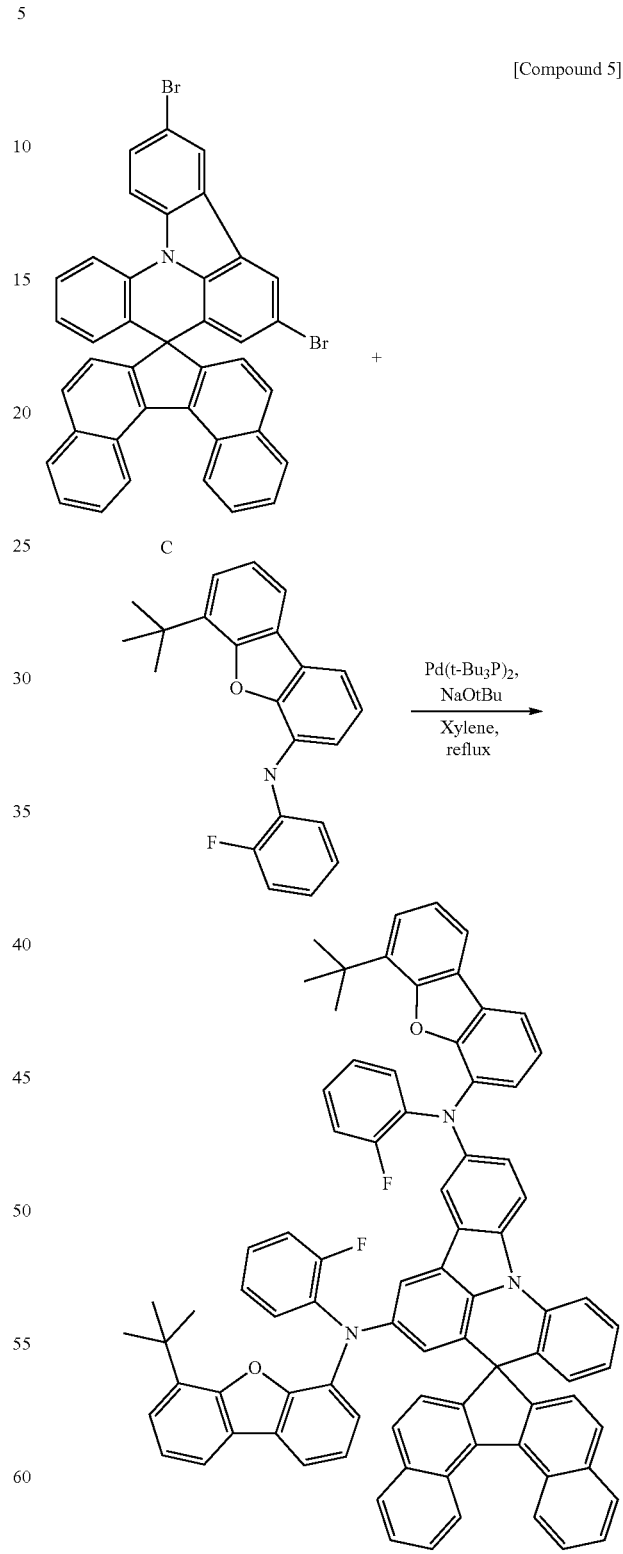

After completely dissolving Compound C (4.11 g, 6.22 mmol) and 6-(tert-butyl)-N-(2-fluorophenyl)dibenzo[b,d]furan-4-amine (4.35 g, 13.06 mmol) in 140 ml of xylene in a 500 ml round bottom flask under nitrogen atmosphere, sodium-tert-butoxide (1.43 g, 14.92 mmol) and then bis(tri-tert-butylphosphine)palladium(0) (0.06 g, 0.12 mmol) were added thereto, and the result was heated and stirred for 5 hours. After lowering the temperature to room temperature, the result was filtered to remove salts, xylene was vacuum concentrated, and the result was columned using tetrahydrofuran:hexane=1:30 to prepare Compound 5 (5.19 g, purity: 99.98%, yield: 71%).

MS[M+H]$^+$=1,168

Preparation Example 6

Synthesis of Compound 6

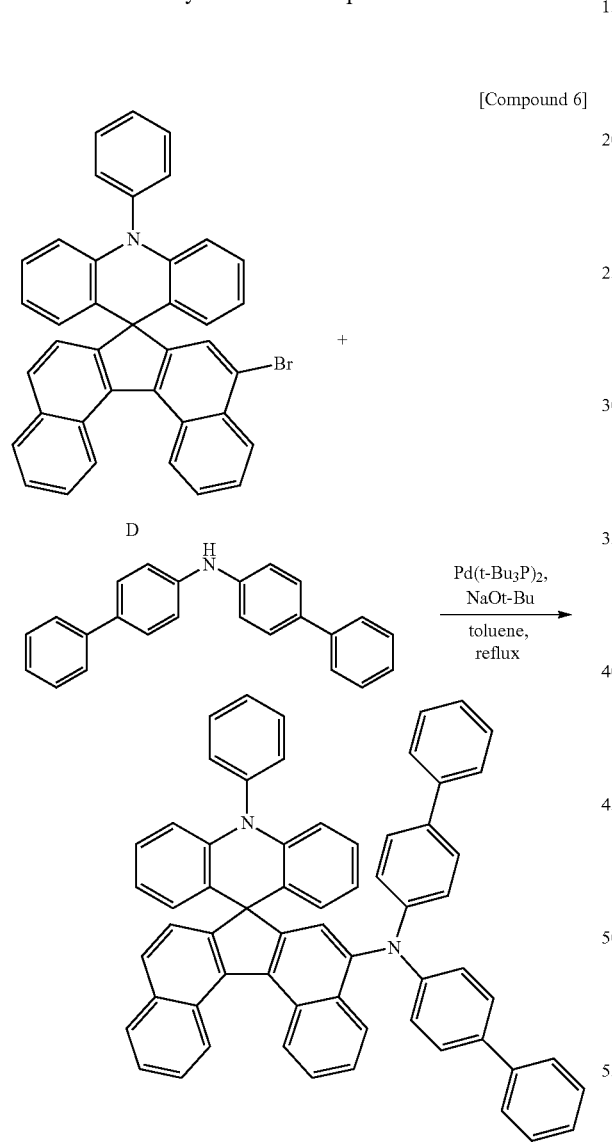

Preparation Example 7

Synthesis of Compound 7

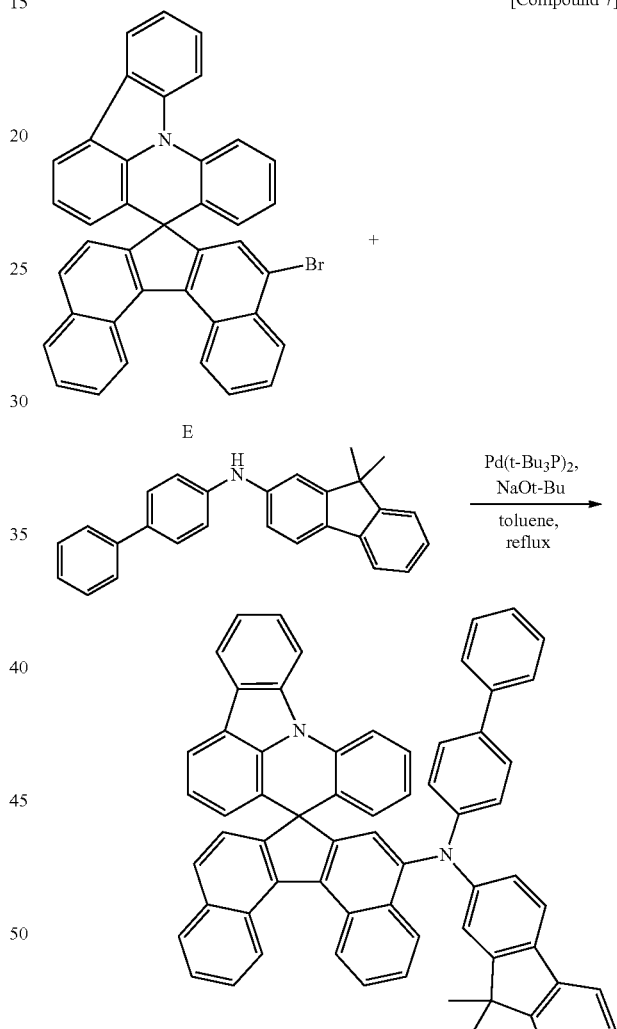

After introducing Compound D (7.45 g, 12.74 mmol), di([1,1'-biphenyl]-4-yl)amine (4.50 g, 14.01 mmol) and sodium-tert-butoxide (1.59 g, 16.56 mmol) to 220 ml of toluene in a 500 ml round bottom flask under nitrogen atmosphere, the temperature was raised while stirring the result. After raising the temperature and when the result started to reflux, bis(tri-tert-butylphosphine)palladium (0.07 g, 0.13 mmol) was slowly added dropwise thereto. After 4 hours, the reaction was terminated, the temperature was lowered to room temperature, and the result was concentrated under vacuum and recrystallized with 260 ml of ethyl acetate to prepare 7.96 g (yield: 76%) of Compound 6.

MS[M+H]$^+$=827

After introducing Compound E (8.29 g, 14.22 mmol), N-([1,1'-biphenyl]-4-yl)-9,9-dimethyl-9H-fluorene-2-amine (5.65 g, 15.64 mmol) and sodium-tert-butoxide (1.78 g, 18.49 mmol) to 220 ml of toluene in a 500 ml round bottom flask under nitrogen atmosphere, the temperature was raised while stirring the result. After raising the temperature and when the result started to reflux, bis(tri-tert-butylphosphine) palladium (0.07 g, 0.14 mmol) was slowly added dropwise thereto. After 4 hours, the reaction was terminated, the temperature was lowered to room temperature, and the result was concentrated under vacuum and recrystallized with 260 ml of ethyl acetate to prepare 7.96 g (yield: 76%) of Compound 7.

MS[M+H]$^+$=865

Preparation Example 8

Synthesis of Compound 8

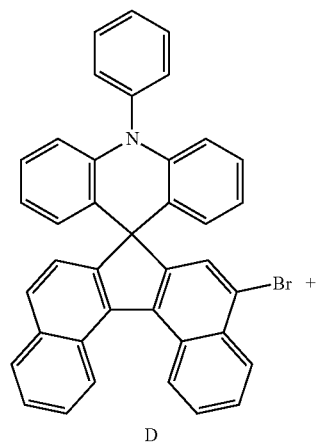

[Compound 8]

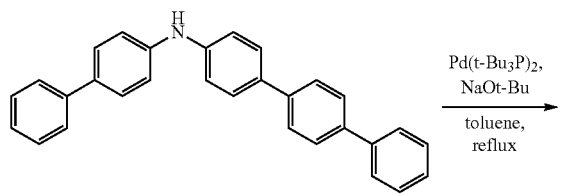

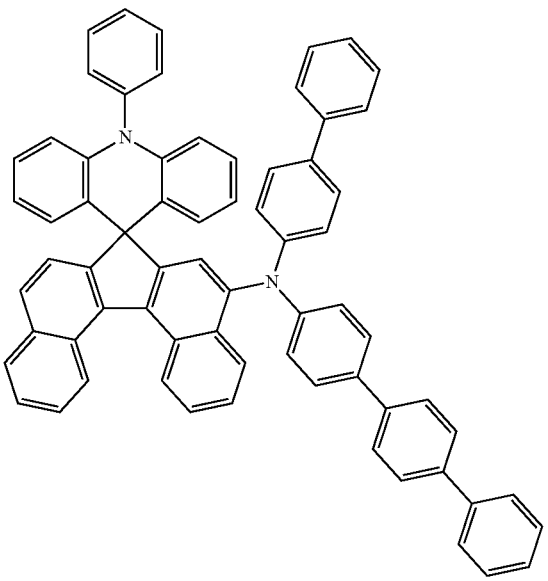

After introducing Compound D (6.64 g, 11.35 mmol), N-([1,1'-biphenyl]-4-yl)-[1,1':4',1''-terphenyl]-4-amine (4.96 g, 12.49 mmol) and sodium-tert-butoxide (1.42 g, 14.76 mmol) to 260 ml of toluene in a 500 ml round bottom flask under nitrogen atmosphere, the temperature was raised while stirring the result. After raising the temperature and when the result started to reflux, bis(tri-tert-butylphosphine)palladium (0.06 g, 0.11 mmol) was slowly added dropwise thereto. After 3 hours, the reaction was terminated, the temperature was lowered to room temperature, and the result was concentrated under vacuum and recrystallized with 210 ml of tetrahydrofuran to prepare 7.96 g (yield: 76%) of Compound 8.

MS[M+H]$^+$=903

Example 1

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

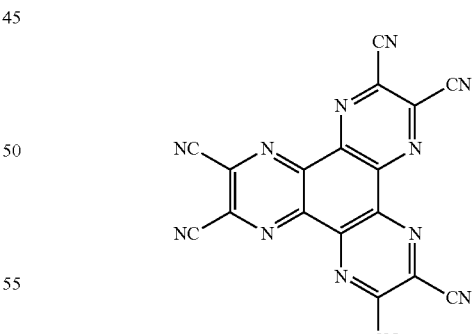

[HAT]

A hole transfer layer was formed on the hole injection layer by vacuum depositing the following compound N4,N4,N4',N4'-tetra([1,1'-biphenyl]-4-yl)-[1,1'-biphenyl]-4,4'-diamine (300 Å), a material transferring holes.

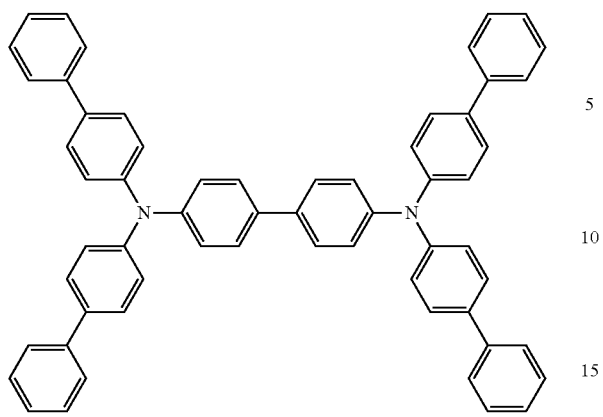

N⁴,N⁴,N⁴′,N⁴′-tetra([1,1′-biphenyl]-4-yl)-[1,1′-biphenyl]-4,4′-diamine

Subsequently, an electron blocking layer was formed on the hole transfer layer by vacuum depositing the following Compound EB1 to a film thickness of 100 Å.

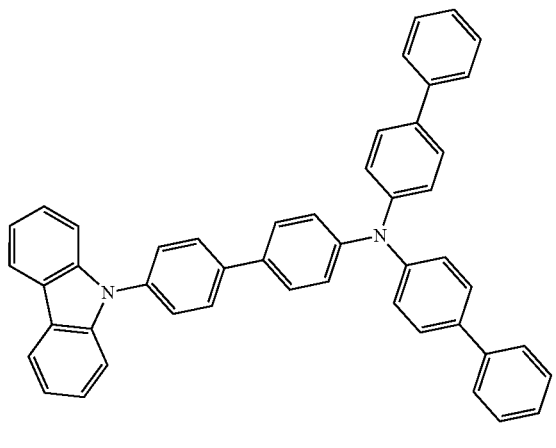

[EB 1]

Subsequently, a light emitting layer was formed on the electron blocking layer to a film thickness of 300 Å by vacuum depositing the following Compound BH and the following Compound 1 in a weight ratio of 25:1.

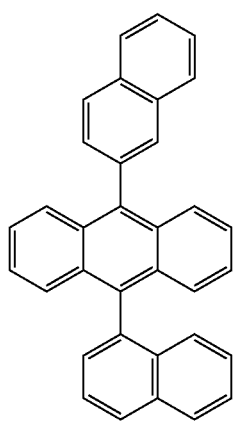

[BH]

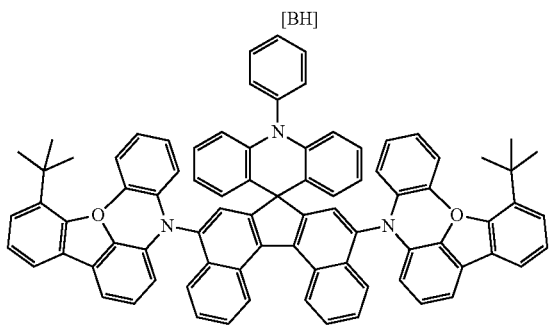

[Compound 1]

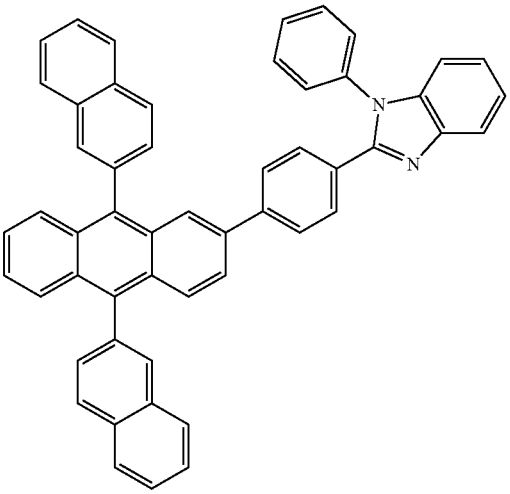

[ET1]

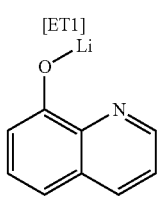

[LiQ]

On the light emitting layer, an electron injection and transfer layer was formed to a thickness of 300 Å by vacuum depositing Compound ET1 and the lithium quinolate (LiQ) compound in a weight ratio of 1:1. A positive electrode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the positive electrode at 0.3 Å/sec and 2 Å/sec, respectively, and the degree of vacuum during the deposition at $2\times10^{-7}$ torr to $5\times10^{-6}$ torr.

Example 1-2

An organic light emitting device was manufactured in the same manner as in Example 1-1 except that Compound 2 was used instead of Compound 1.

Example 1-3

An organic light emitting device was manufactured in the same manner as in Example 1-1 except that Compound 3 was used instead of Compound 1.

Example 1-4

An organic light emitting device was manufactured in the same manner as in Example 1-1 except that Compound 4 was used instead of Compound 1.

Example 1-5

An organic light emitting device was manufactured in the same manner as in Example 1-1 except that Compound 5 was used instead of Compound 1.

Comparative Example 1

An organic light emitting device was manufactured in the same manner as in Example 1-1 except that the following BD 1 was used instead of Compound 1.

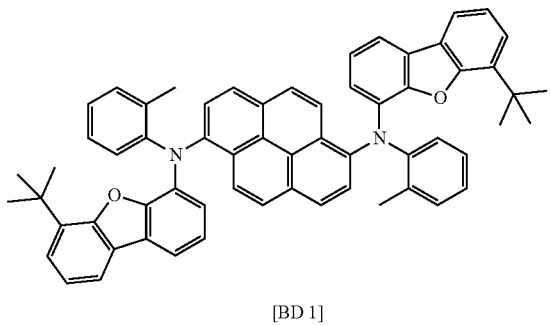 [SMILES: Cc1ccccc1N(c1ccc2ccc3c(N(c4ccccc4C)c4cccc5c4oc4c(C(C)(C)C)cccc45)ccc4ccc1c2c43)c1cccc2c1oc1c(C(C)(C)C)cccc12]

[BD 1]

Comparative Example 2

An organic light emitting device was manufactured in the same manner as in Example 1-1 except that the following BD 2 was used instead of Compound 1.

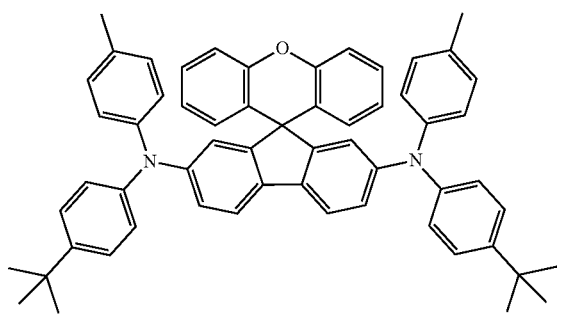

[BD 2]

Comparative Example 3

An organic light emitting device was manufactured in the same manner as in Example 1-1 except that the following BD 3 was used instead of Compound 1.

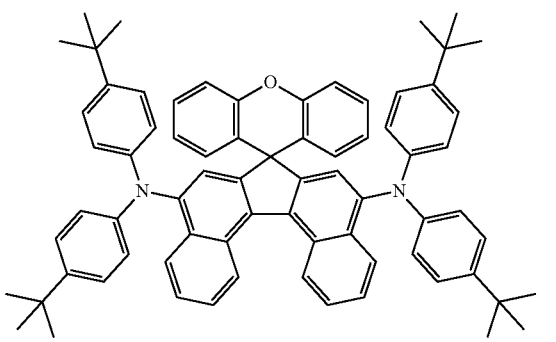

[BD 3]

When a current was applied to the organic light emitting devices manufactured in Examples 1-1 to 1-5 and Comparative Examples 1 to 3, a voltage, efficiency, a color coordinate and a lifespan were measured, and the results are shown in the following [Table 1]. T90 means time taken for the luminance decreasing to 90% of its initial luminance (5000 nit).

TABLE 1

| | Compound (Light Emitting Layer Dopant) | Voltage (V@10 mA/cm$^2$) | Efficiency (cd/A@10 mA/cm$^2$) | Color Coordinate (x, y) | T90 (hr) |
|---|---|---|---|---|---|
| Example 1-1 | Compound 1 | 4.31 | 6.48 | (0.141, 0.044) | 72 |
| Example 1-2 | Compound 2 | 4.43 | 6.21 | (0.142, 0.045) | 95 |
| Example 1-3 | Compound 3 | 4.45 | 6.18 | (0.141, 0.046) | 99 |
| Example 1-4 | Compound 4 | 4.40 | 6.20 | (0.141, 0.047) | 105 |
| Example 1-5 | Compound 5 | 4.46 | 6.28 | (0.141, 0.047) | 80 |
| Comparative Example 1 | BD 1 | 4.95 | 5.61 | (0.144, 0.046) | 51 |

TABLE 1-continued

| Compound (Light Emitting Layer Dopant) | Voltage (V@10 mA/cm²) | Efficiency (cd/A@10 mA/cm²) | Color Coordinate (x, y) | T90 (hr) |
|---|---|---|---|---|
| Comparative Example 2 BD 2 | 4.77 | 5.87 | (0.145, 0.041) | 56 |
| Comparative Example 3 BD 3 | 4.70 | 5.98 | (0.144, 0.040) | 54 |

As shown in Table 1, Examples 1-1 to 1-5 using the compound represented by Chemical Formula 1 of the present specification as a dopant of a light emitting layer exhibited low voltage, high efficiency and long lifespan properties compared to Comparative Examples 1 to 3, and were identified to be usable in an organic light emitting device.

Specifically, it was seen that Compound 1 having a Compound A core had an excellent low voltage property, and Compounds 2 to 4 having a Compound B core had an excellent long lifespan property. In addition, the compound represented by Chemical Formula 1 of the present specification was able to exhibit various color coordinates due to substituents such as a silyl group, fluorine, an aryl group and a heterocyclic group. Accordingly, it was seen that the compounds according to one embodiment of the present specification were capable of being used as various color coordinate light emitting materials applicable in industrial products using light.

Example 2

Example 2-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 100 Å.

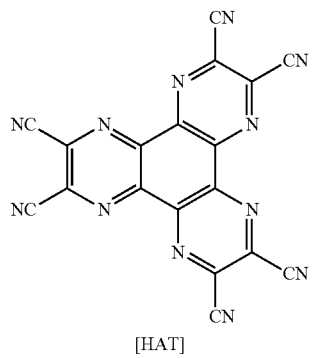

[HAT]

A hole transfer layer was formed on the hole injection layer by vacuum depositing the following Compound [HT 1] (1,150 Å), a material transferring holes.

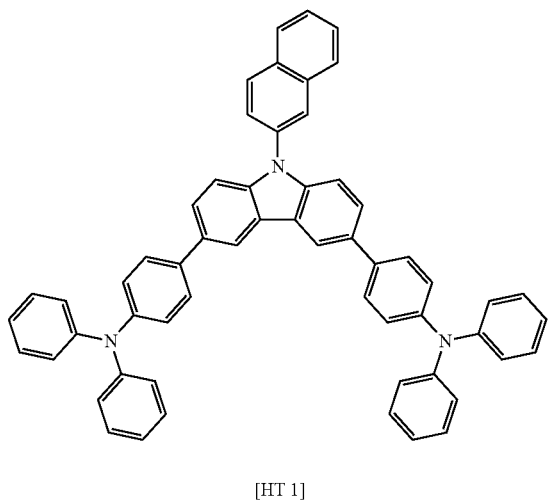

[HT 1]

Subsequently, an electron blocking layer was formed on the hole transfer layer to a film thickness of 100 Å by vacuum depositing the following Compound [EB 1].

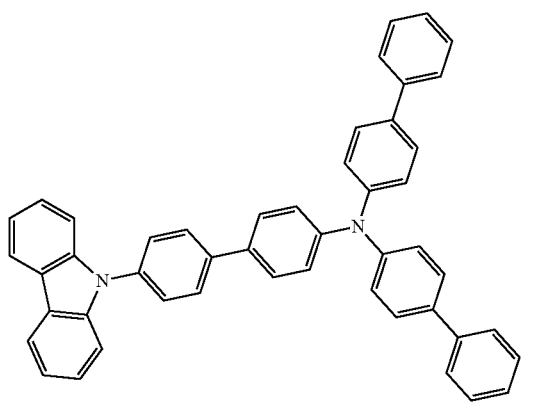

[EB 1]

Subsequently, a light emitting layer was formed on the electron blocking layer to a film thickness of 200 Å by vacuum depositing the following Compound BH 1 and the following Compound 1 in a weight ratio of 25:1.

[BH 1]
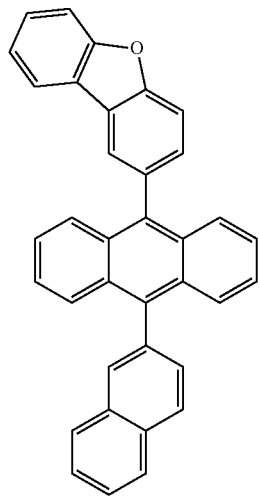
[Compound 1]
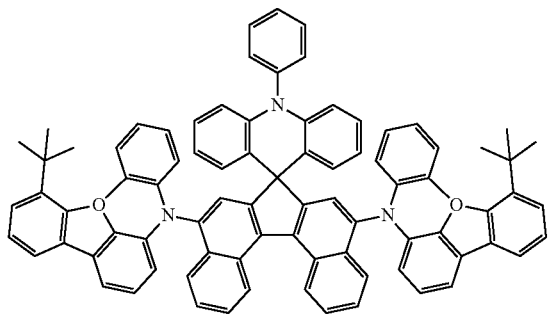
[HB 1]
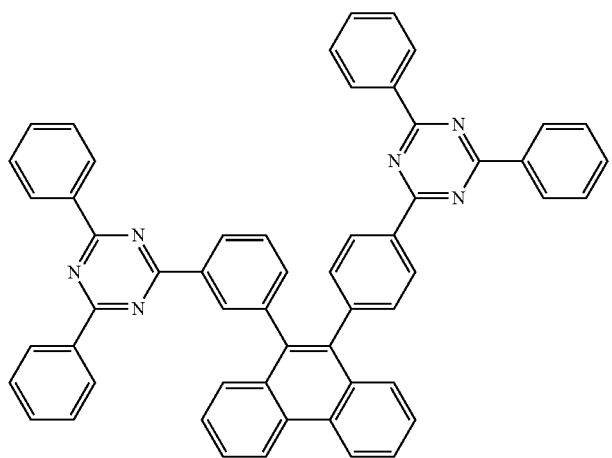
[ET 1]
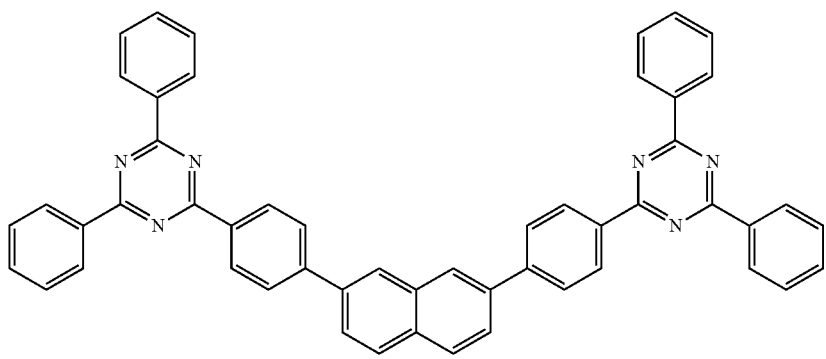
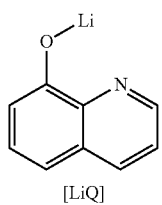
[LiQ]

A hole blocking layer was formed on the light emitting layer to a film thickness of 50 Å by vacuum depositing Compound HB 1.

Next, on the hole blocking layer, an electron injection and transfer layer was formed to a thickness of 310 Å by vacuum depositing Compound ET 1 and the lithium quinolate (LiQ) compound in a weight ratio of 1:1. A positive electrode was formed on the electron injection and transfer layer by depositing lithium fluoride (LiF) to a thickness of 12 Å and aluminum to a thickness of 1,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the positive electrode at 0.3 Å/sec and 2 Å/sec, respectively, and the degree of vacuum during the deposition at $2 \times 10^{-7}$ torr to $5 \times 10^{-6}$ torr.

Example 2-2

An organic light emitting device was manufactured in the same manner as in Example 2-1 except that Compound 2 was used instead of Compound 1.

Example 2-3

An organic light emitting device was manufactured in the same manner as in Example 2-1 except that Compound 3 was used instead of Compound 1.

Example 2-4

An organic light emitting device was manufactured in the same manner as in Example 2-1 except that Compound 4 was used instead of Compound 1.

Example 2-5

An organic light emitting device was manufactured in the same manner as in Example 2-1 except that Compound 5 was used instead of Compound 1.

Example 2-6

An organic light emitting device was manufactured in the same manner as in Example 2-1 except that the following Compound BH was used instead of BH 1.

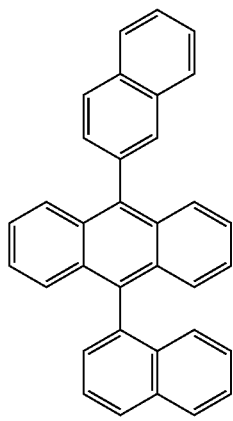

[BH]

When a current was applied to the organic light emitting devices manufactured in Examples 2-1 to 2-6, a voltage, efficiency, a color coordinate and a lifespan were measured, and the results are shown in the following [Table 2]. T90 means time taken for the luminance decreasing to 90% of its initial luminance (5000 nit).

TABLE 2

| | Compound (Light Emitting Layer Host) | Compound (Light Emitting Layer Dopant) | Voltage (V @ 10 mA/ cm$^2$) | Efficiency (cd/A @ 10 mA/ cm$^2$) | Color Coordinate (x, y) | T90 (hr) |
|---|---|---|---|---|---|---|
| Example 2-1 | BH 1 | Compound 1 | 4.31 | 6.35 | (0.141, 0.044) | 175 |
| Example 2-2 | BH 1 | Compound 2 | 4.37 | 6.18 | (0.142, 0.045) | 155 |
| Example 2-3 | BH 1 | Compound 3 | 4.42 | 6.15 | (0.141, 0.044) | 160 |
| Example 2-4 | BH 1 | Compound 4 | 4.43 | 6.13 | (0.141, 0.045) | 145 |
| Example 2-5 | BH 1 | Compound 5 | 4.41 | 6.21 | (0.141, 0.047) | 150 |
| Example 2-6 | BH | Compound 1 | 4.62 | 5.92 | (0.144, 0.046) | 130 |

As shown in Table 2, Examples 2-1 to 2-5 using the compound represented by Chemical Formula 1 of the present specification as a dopant of a light emitting layer and using the compound represented by Chemical Formula 9 of the present specification as a host of a light emitting layer exhibited low voltage, high efficiency and long lifespan properties compared to Example 2-6, and were identified to be usable in an organic light emitting device. Specifically, Examples 2-1 to 2-5 using the compound represented by Chemical Formula 9 of the present specification as a host of a light emitting layer had an increase in the lifespan by 10% to 30% compared to Example 2-6 using Compound BH that does not comprise a heteroaryl group. Accordingly, it was seen that the compounds according to one embodiment of the present specification were capable of being used as various color coordinate light emitting materials applicable in industrial products using light.

Hereinbefore, preferred embodiments of the present specification have been described, however, the present disclosure is not limited thereto, and various modifications may be made within the scope of the claims and the detailed descriptions of the disclosure, and the modifications are also included in the scope of the present disclosure.

The invention claimed is:
1. A compound represented by one of the following Chemical Formulae 2 to 8:
[Chemical Formula 2]
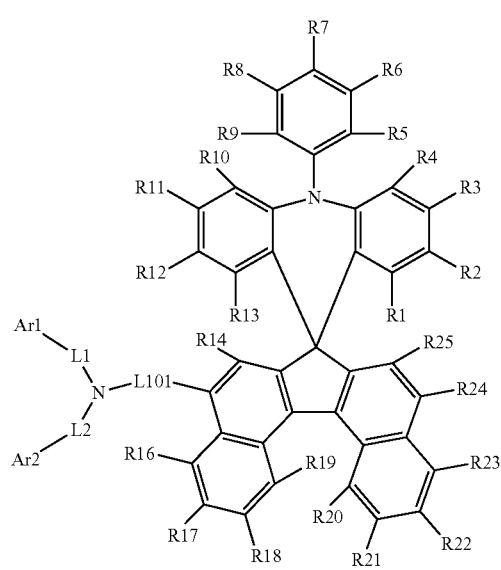
[Chemical Formula 3]
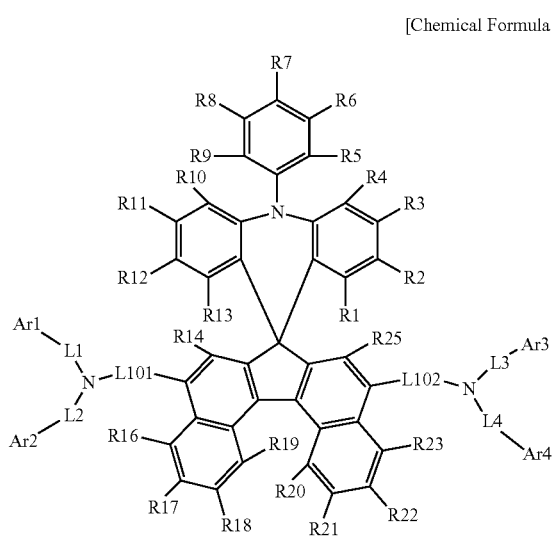
[Chemical Formula 4]
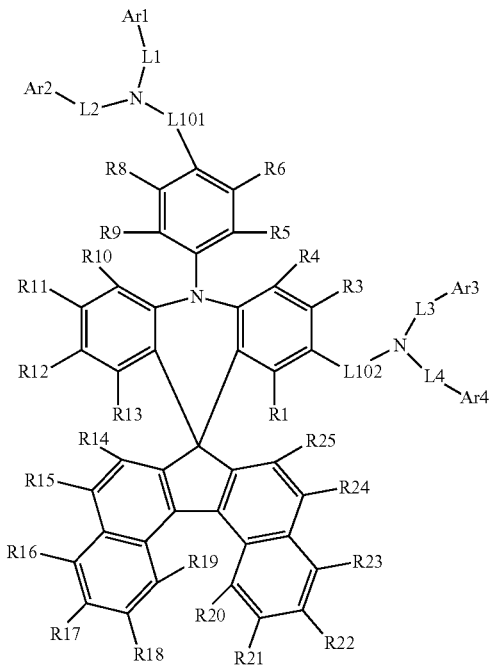
[Chemical Formula 5]
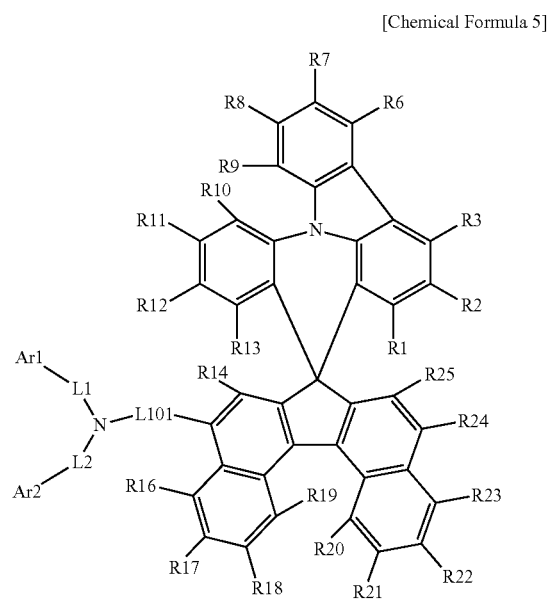

[Chemical Formula 6]

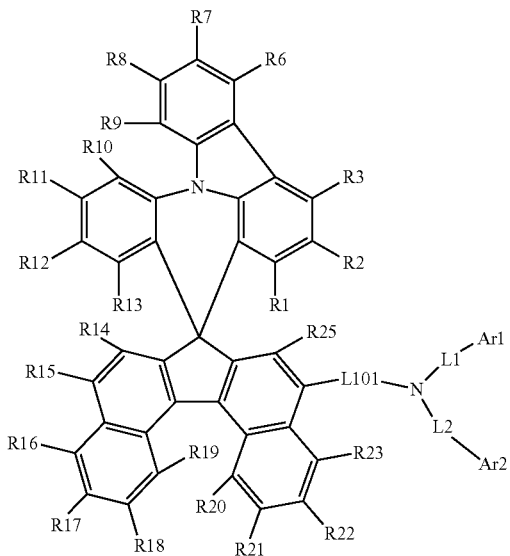

[Chemical Formula 7]

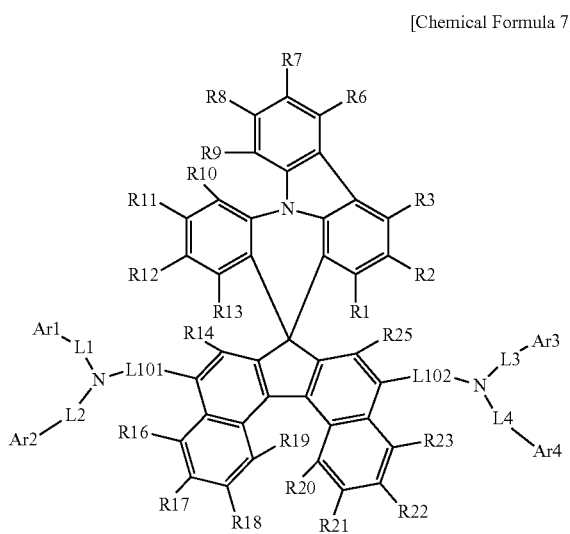

[Chemical Formula 8]

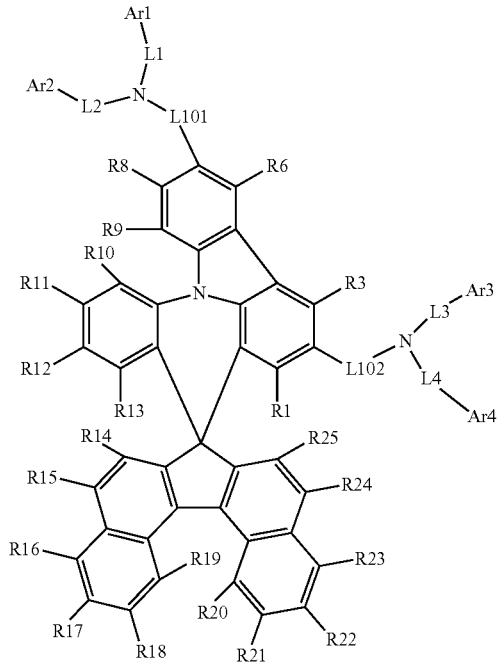

wherein, in Chemical Formulae 2 to 8,
R1 to R25 are hydrogen,
L101 and L102 are each independently a direct bond,
L1 to L4 are the same as or different from each other, and each independently a direct bond; a phenylene group; a biphenylene group; a naphthylene group; a fluorenylene group; a divalent carbazole group; a divalent dibenzofuran group; or a divalent dibenzothiophene group, and
Ar1 to Ar4 are the same as or different from each other, and each independently a methyl group; an ethyl group; a tert-butyl group; a cyclopentyl group; a cyclohexyl group; a phenyl group unsubstituted or substituted with fluorine, a trimethylsilyl group, a nitrile group, trifluoromethyl group, or a methyl group; a biphenyl group; a naphthyl group; an N-phenyl carbazole group; or a dibenzofuran group unsubstituted or substituted with fluorine, a trimethylsilyl group, a nitrile group, trifluoromethyl group, or a methyl group.

2. The compound of claim 1, wherein any one or more of Ar1 and Ar2 are the following Chemical Formula 1A:

[Chemical Formula 1A]

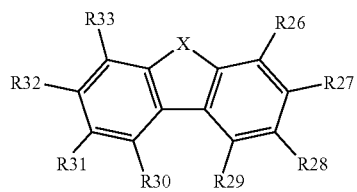

wherein, in Chemical Formula 1A,
X is O or NR,
R is a phenyl group; and R26 to R29 are hydrogen; with the proviso that when X is NR, R26 to R29 are the same as or different from each other, and each independently hydrogen; fluorine; a nitrile group; a methyl group; a trifluoromethyl group; a trimethylsilyl group; with the proviso that when X is O, and any one of R30 to R33 bonds to L1 or L2 of Chemical Formulae 2 to 8, and groups that do not bond to L1 or L2 of Chemical Formulae 2 to 8 among R30 to R33 are hydrogen.

3. The compound of claim 1, wherein Chemical Formula 1 is any one selected from the following compounds:

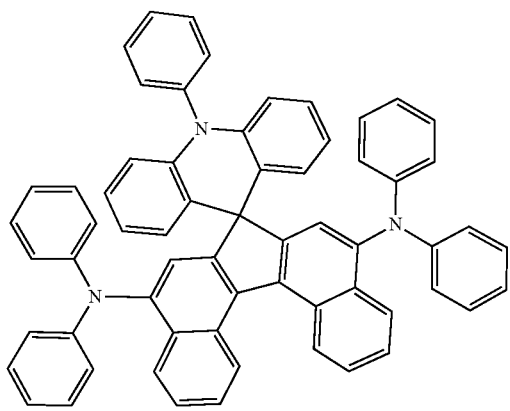

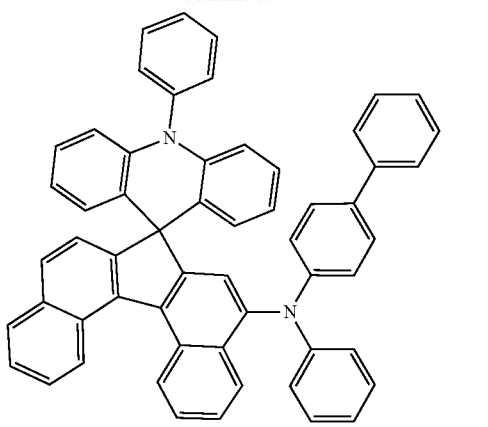

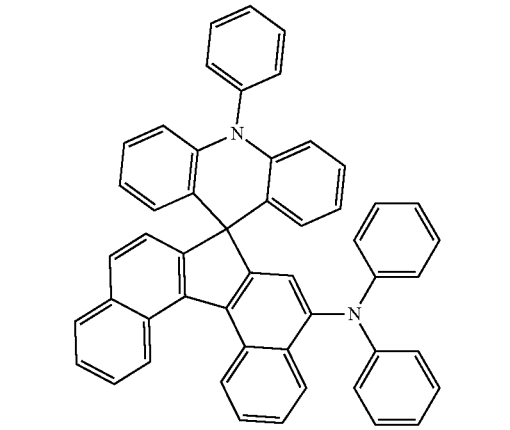

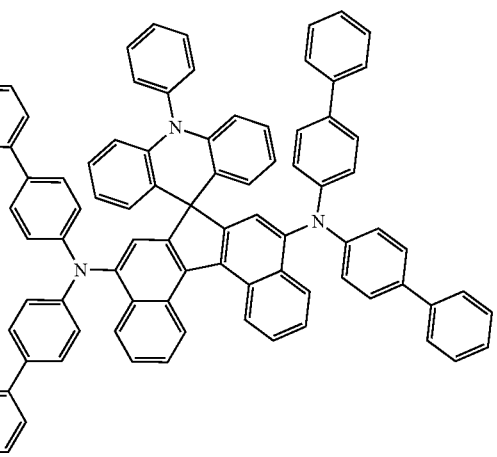

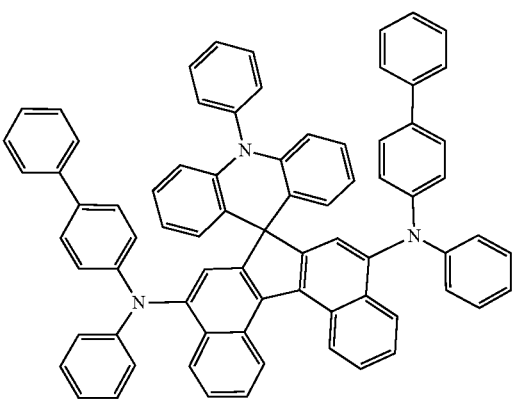

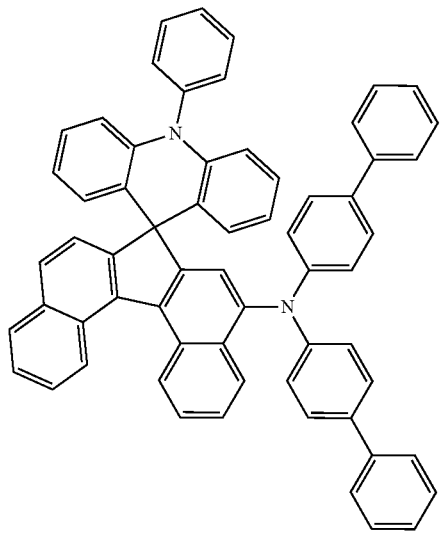

287
-continued
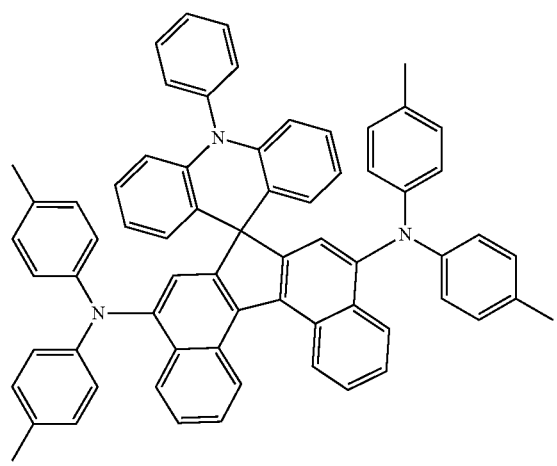
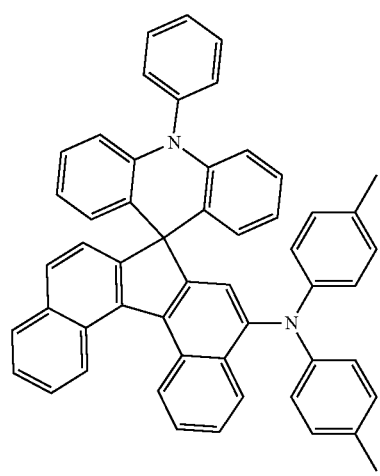
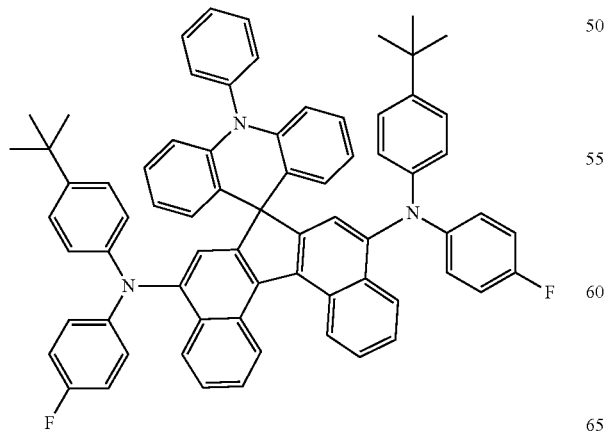
288
-continued
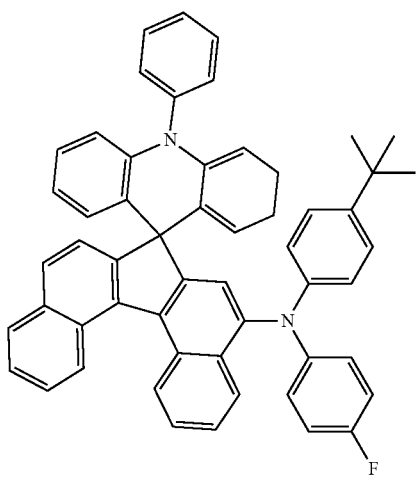
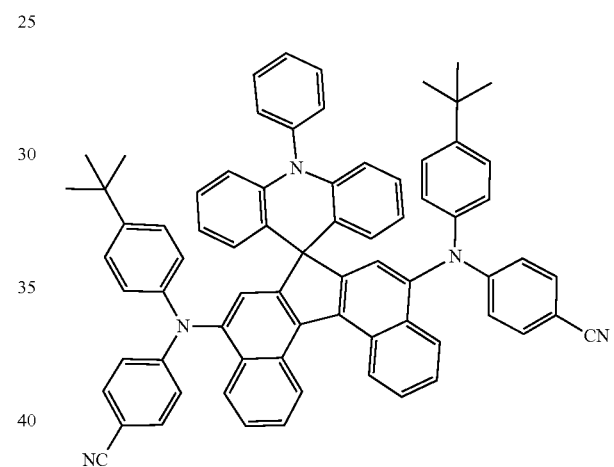
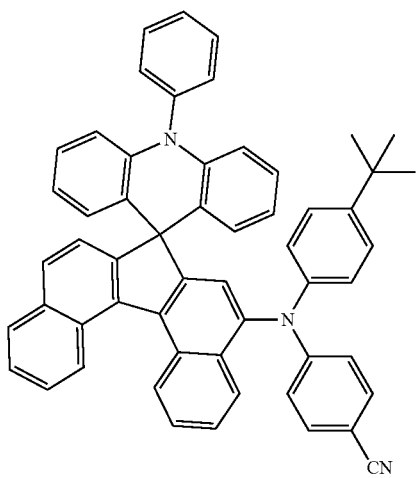

289
-continued
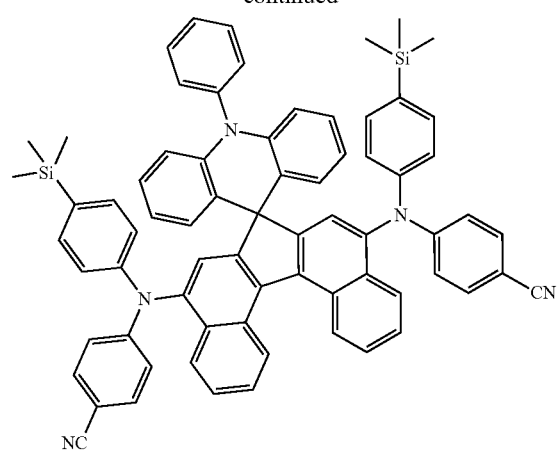
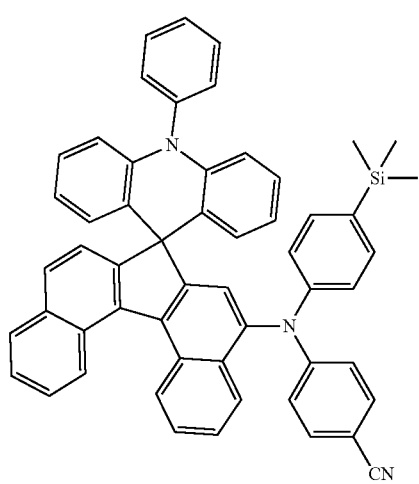
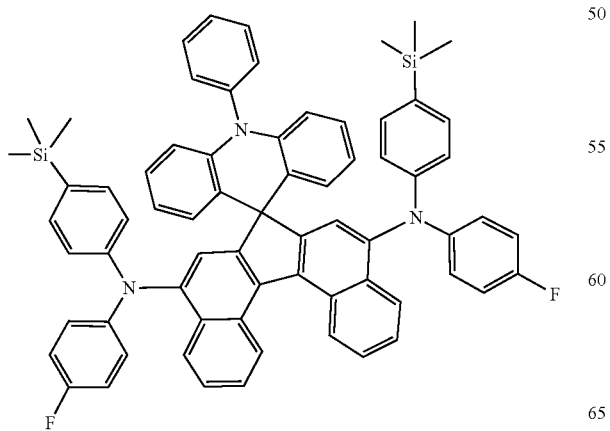
290
-continued
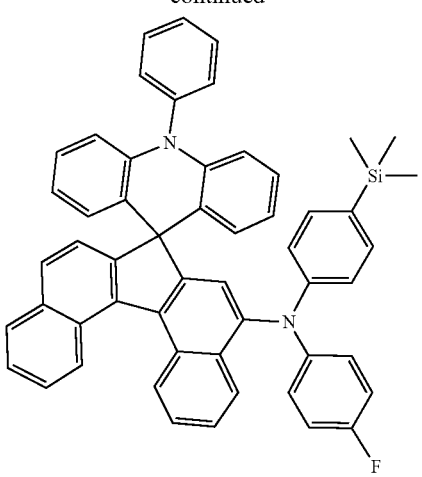
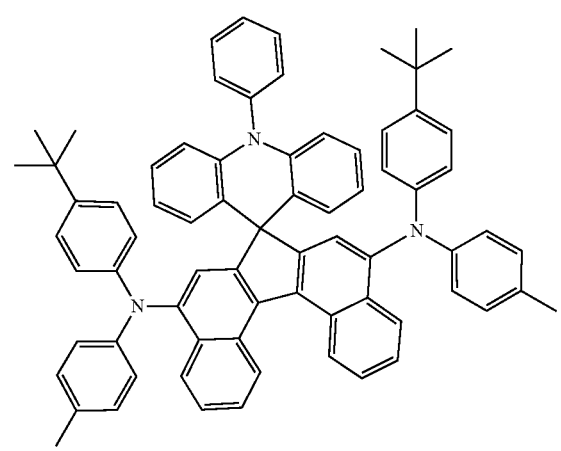
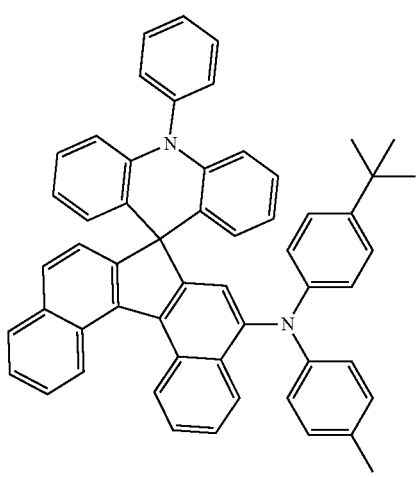

291
-continued
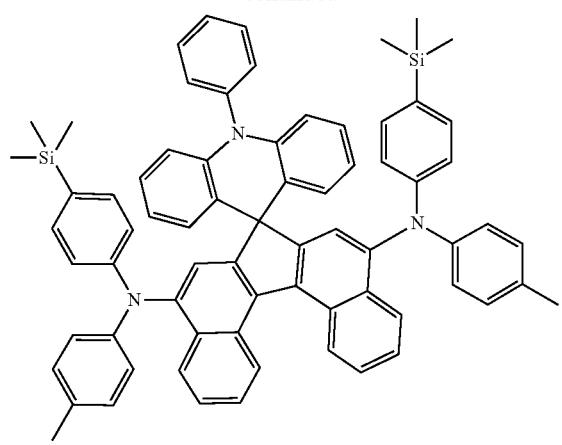
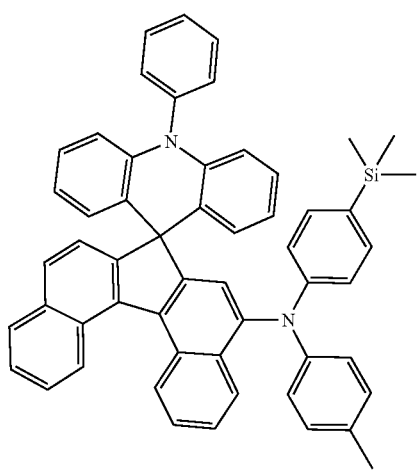
292
-continued
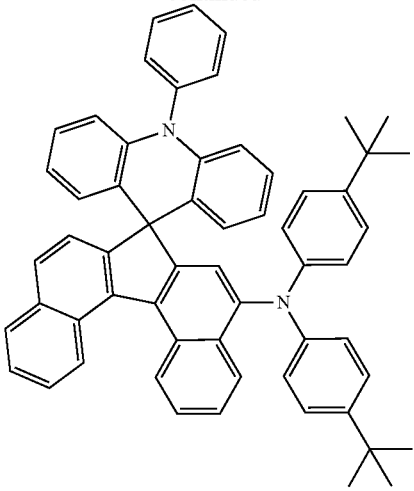
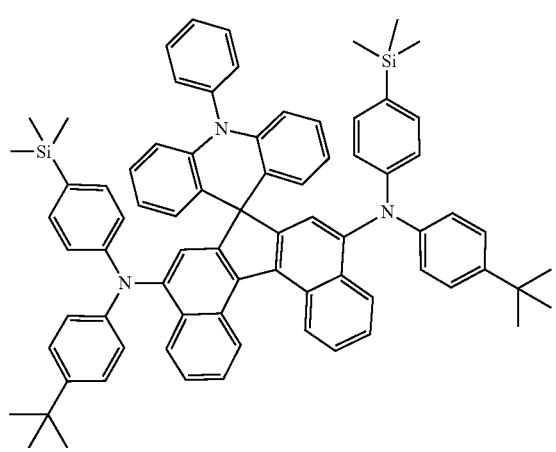
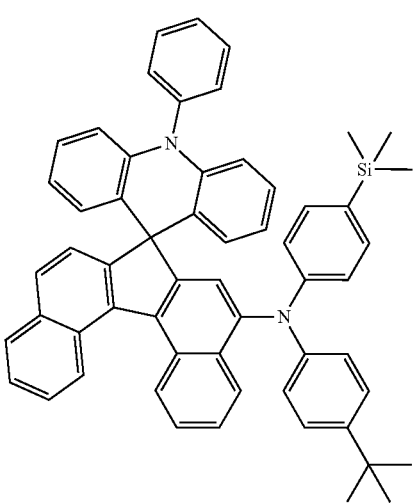

293
-continued
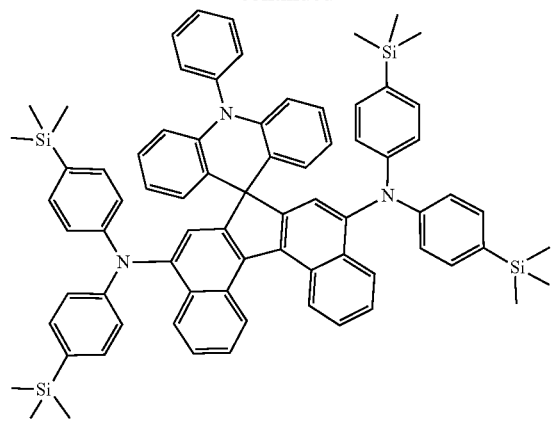
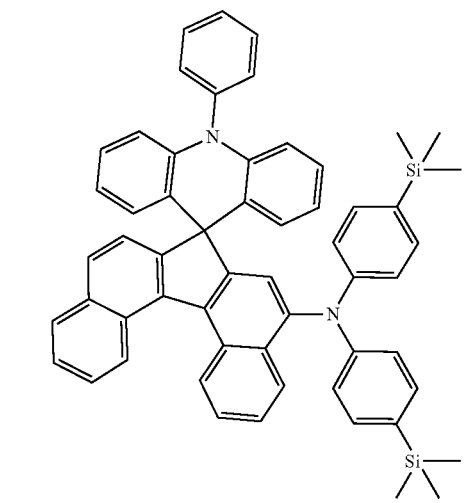
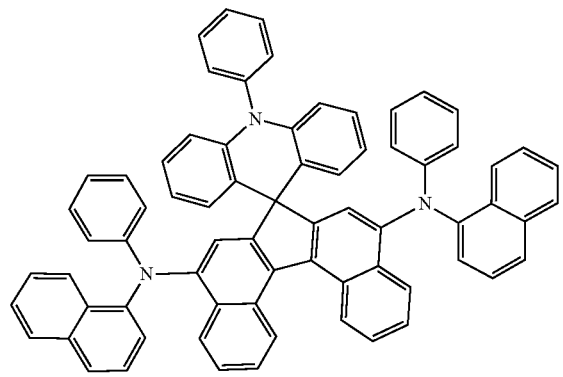
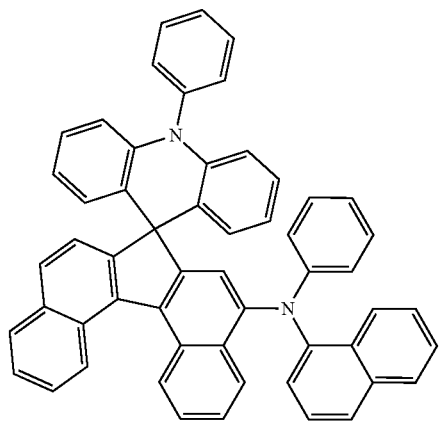
294
-continued
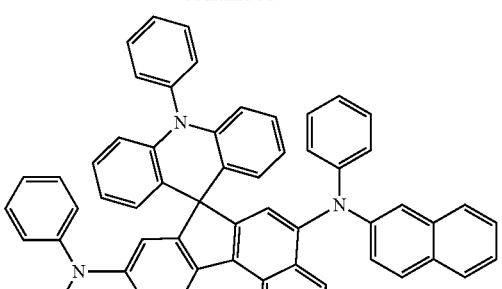
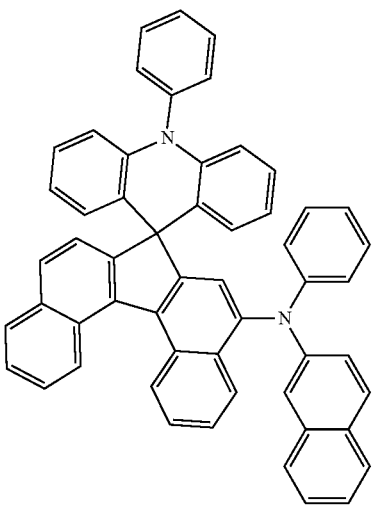
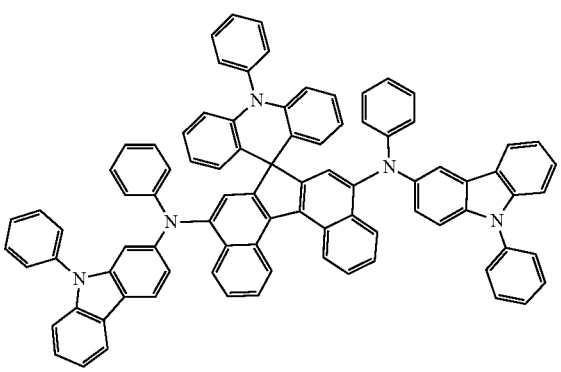

295
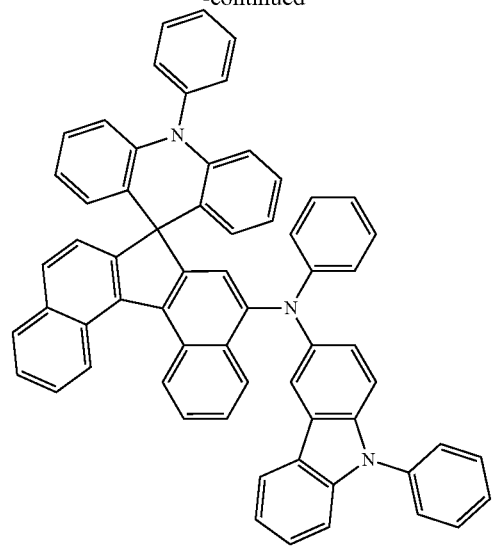
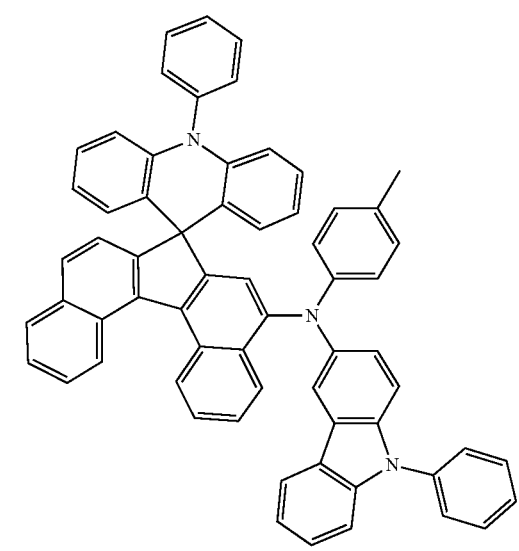
296
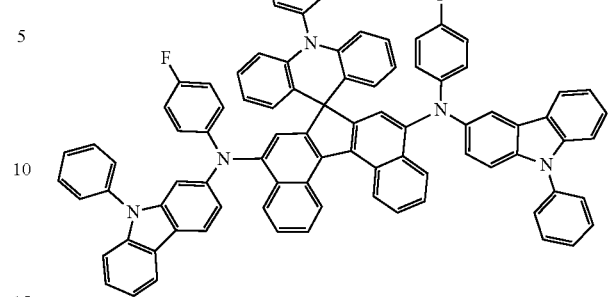
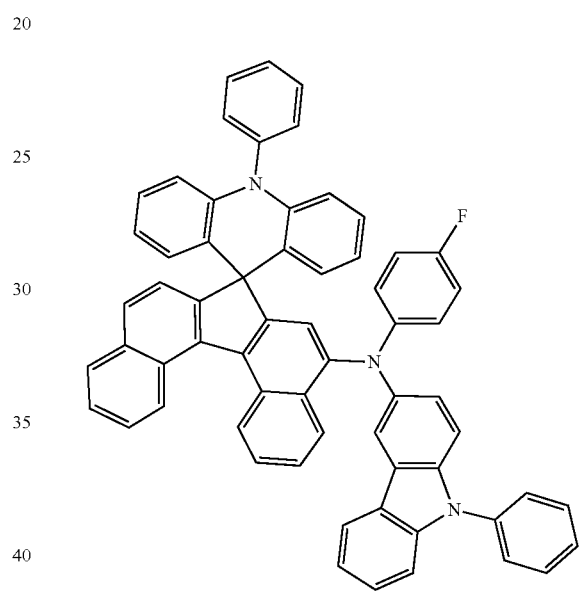
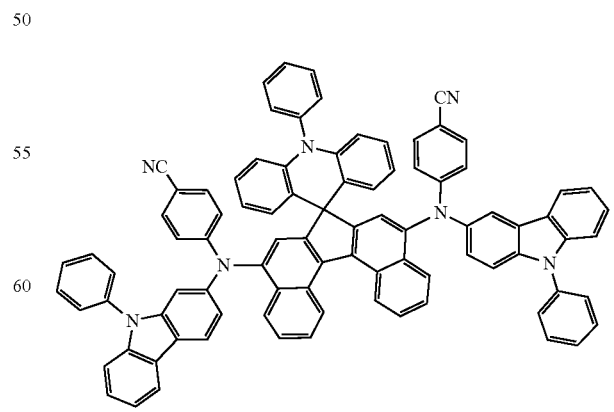

297
-continued
298
-continued
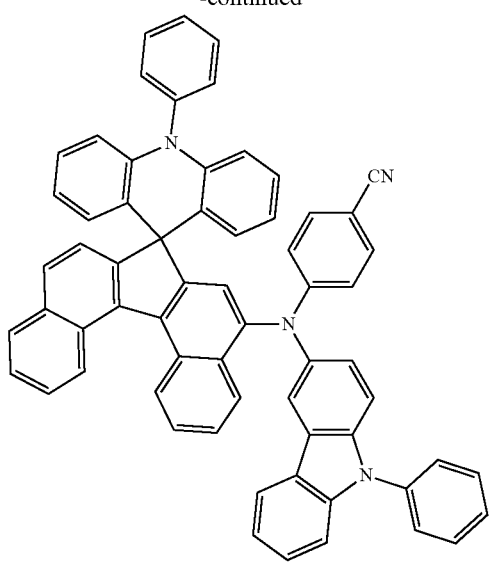
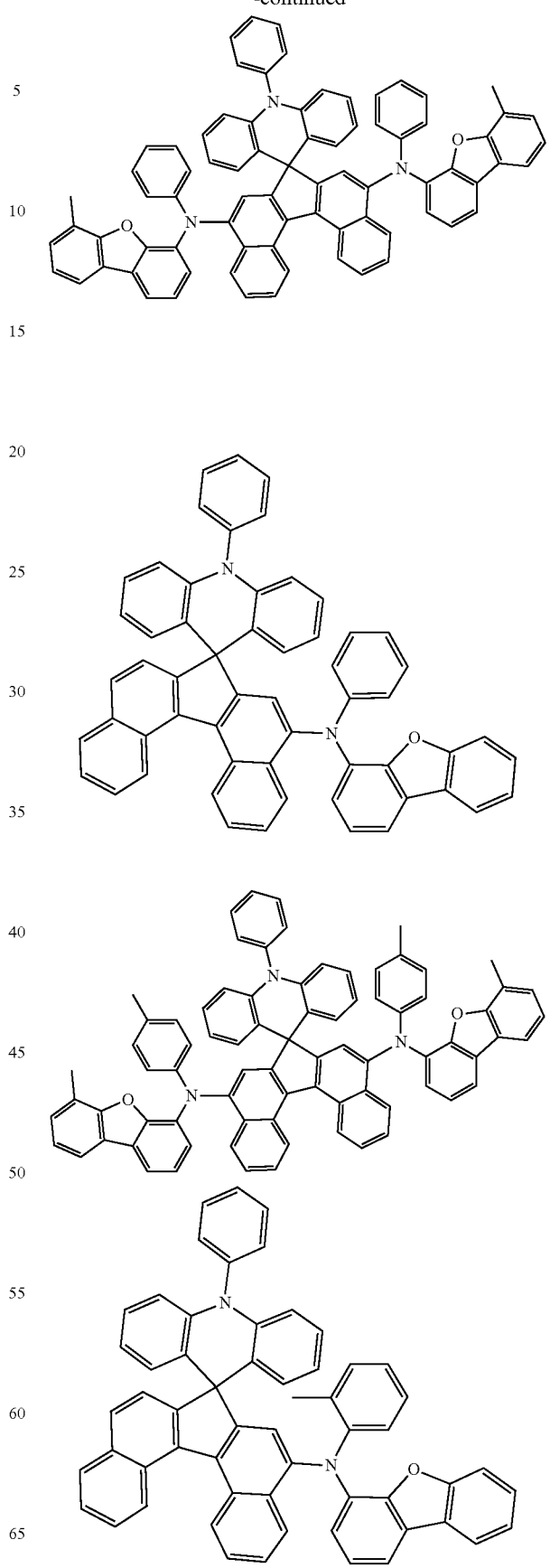

299
-continued
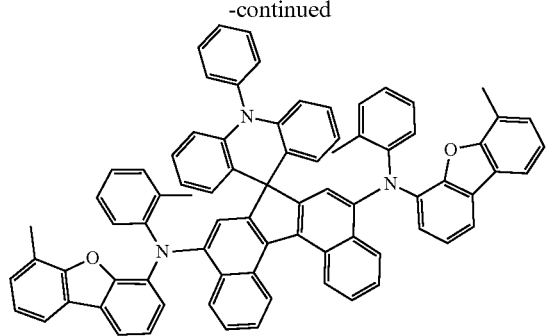
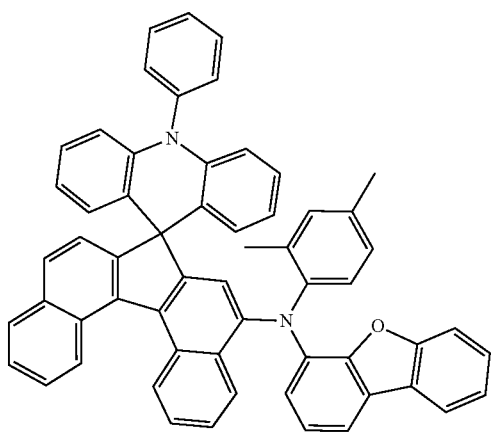
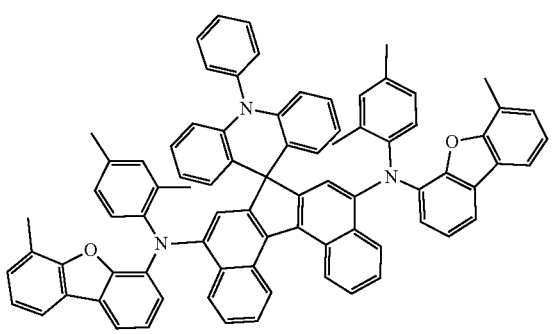
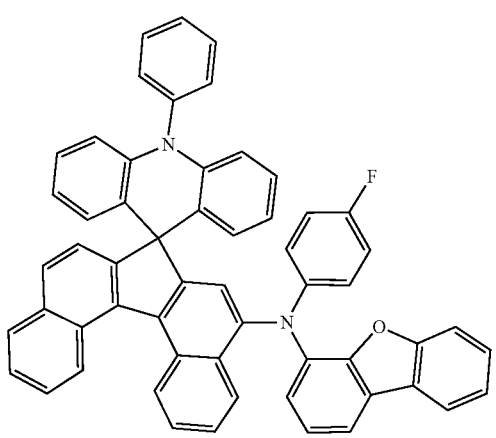
300
-continued
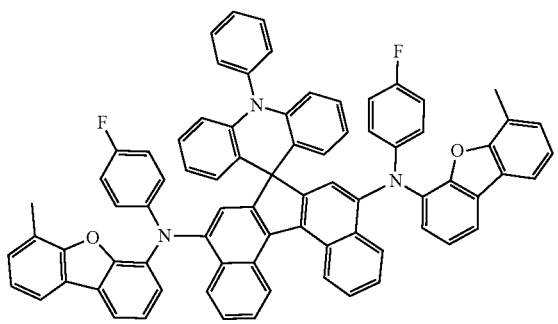
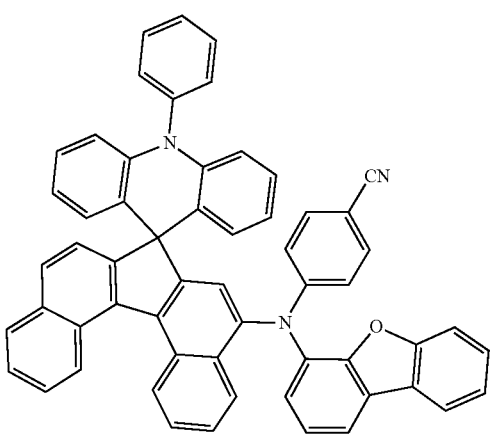
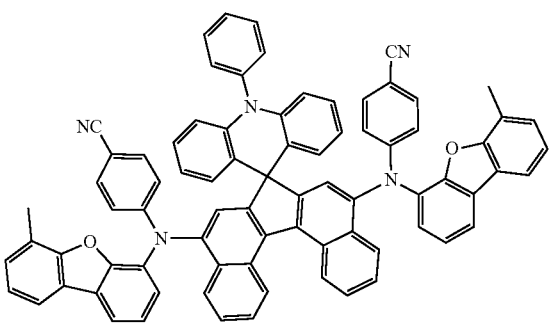
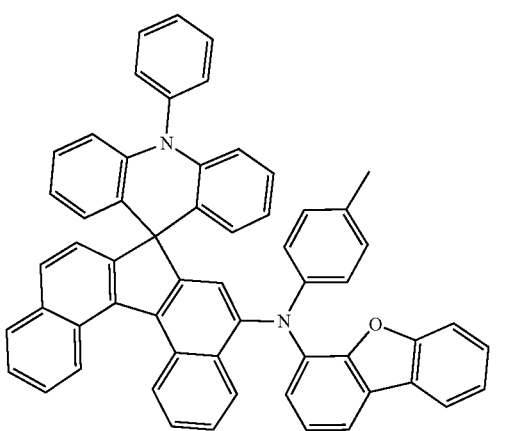

301
-continued
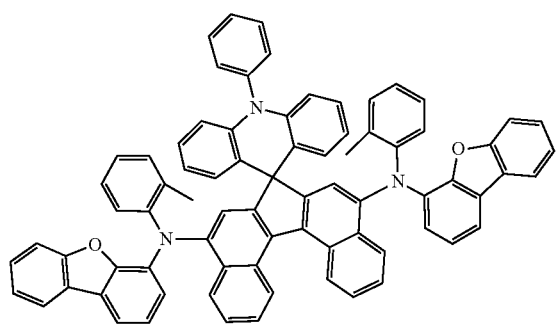
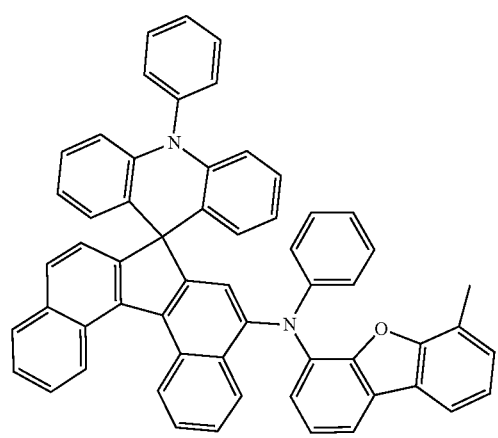
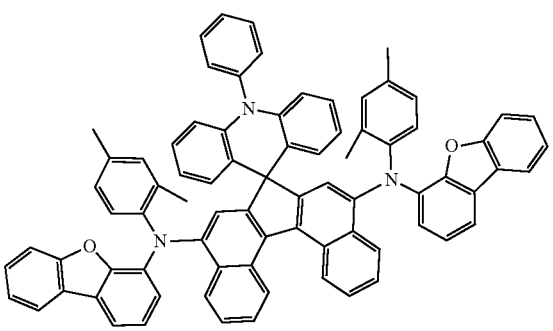
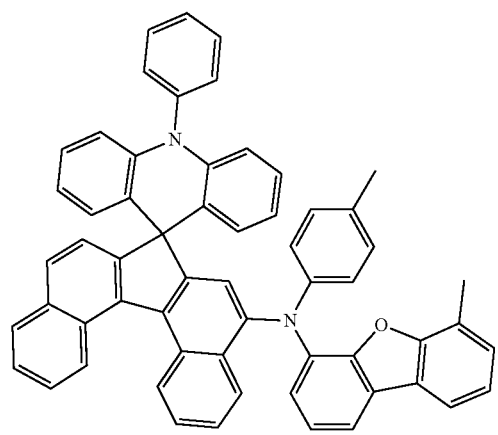
302
-continued
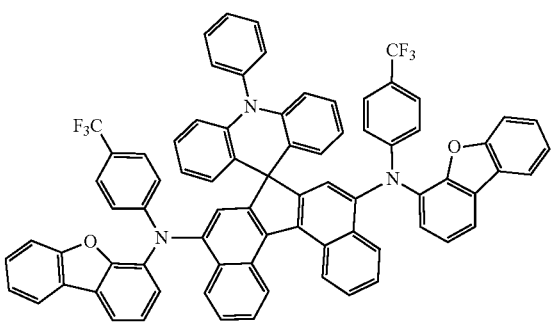
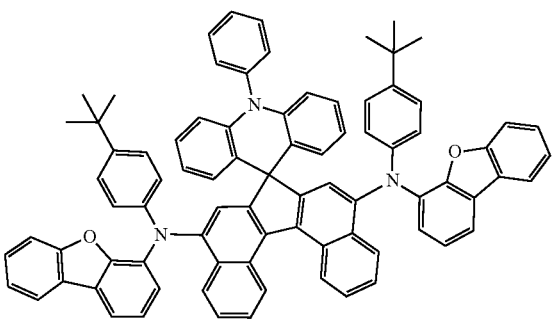
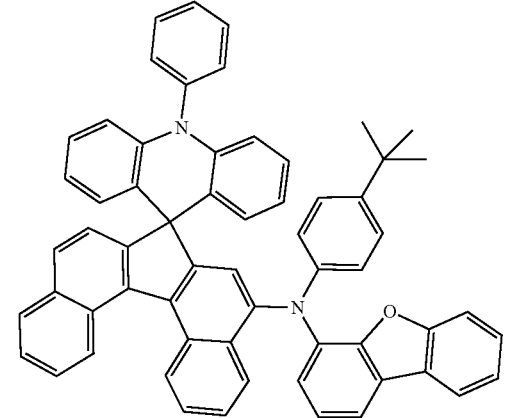

303
-continued
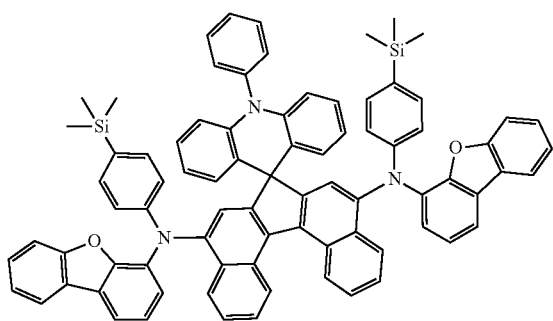
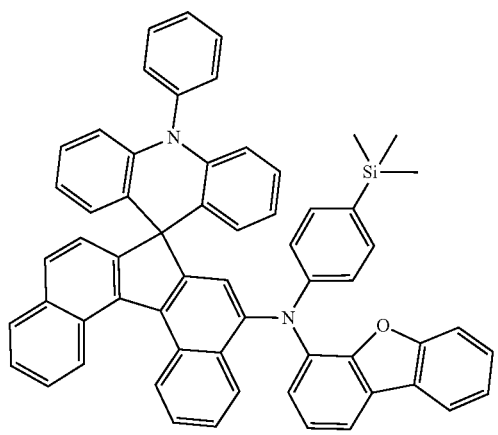
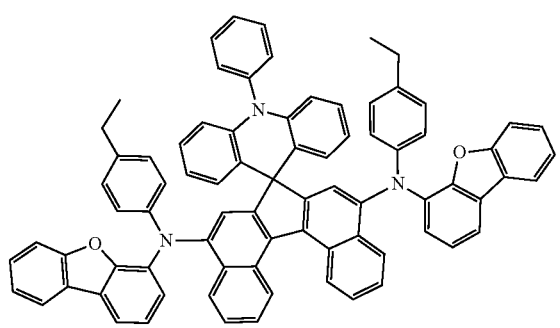
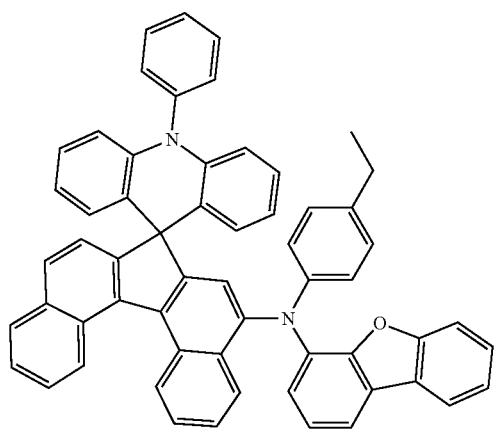
304
-continued
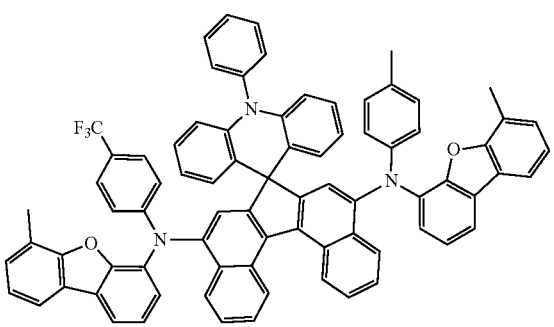
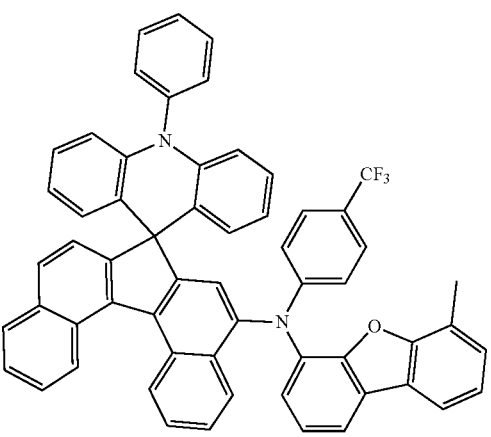
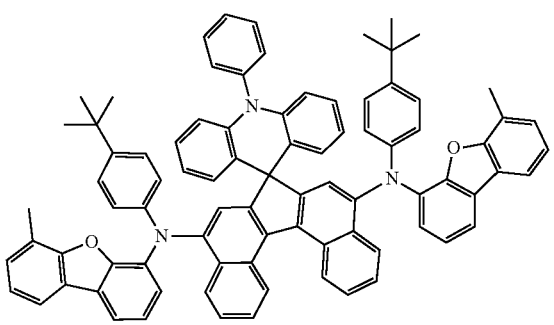
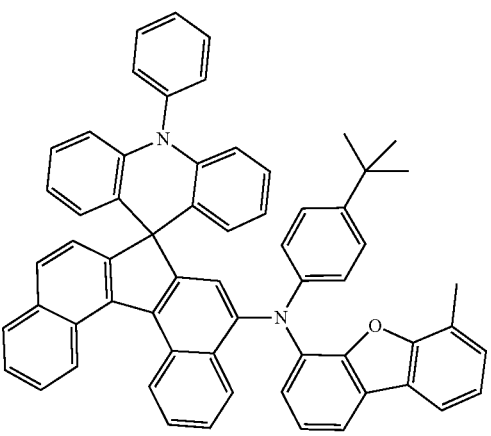

305
-continued
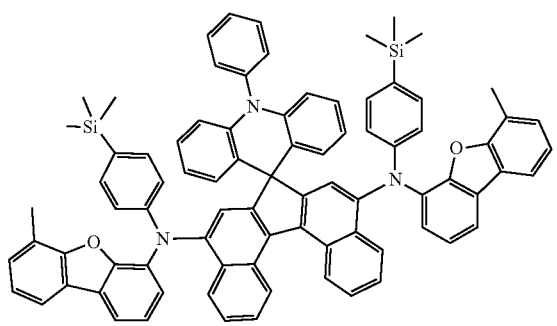
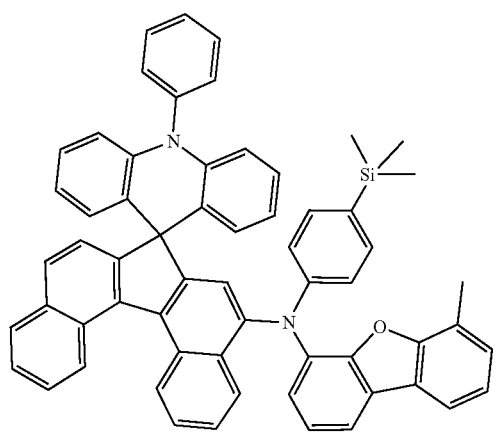
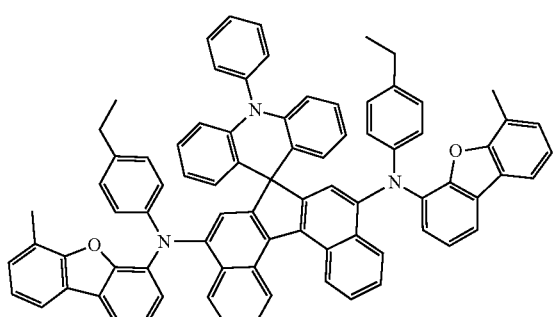
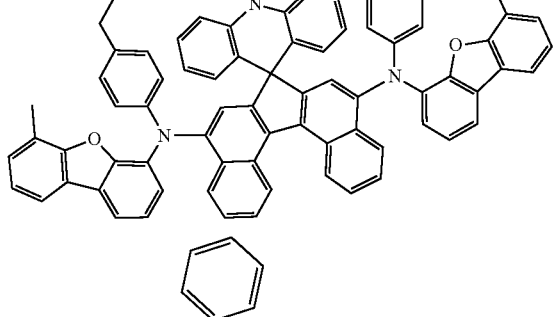
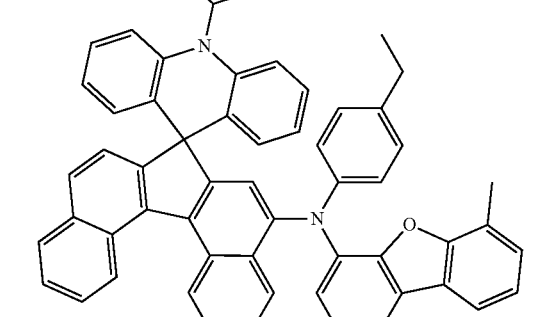
306
-continued
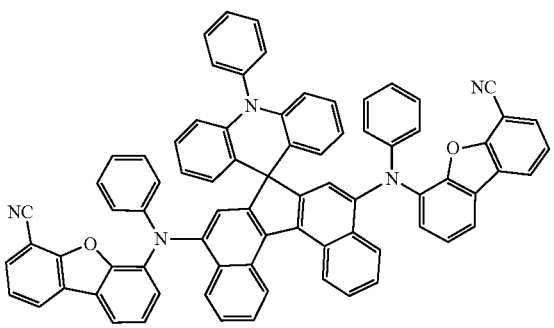
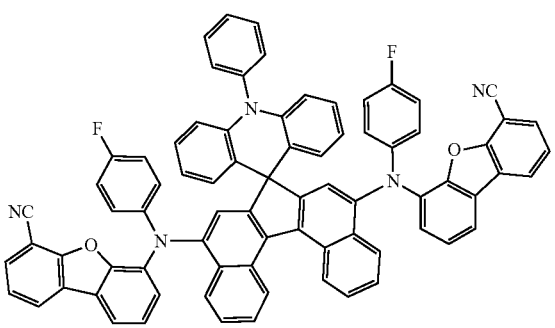
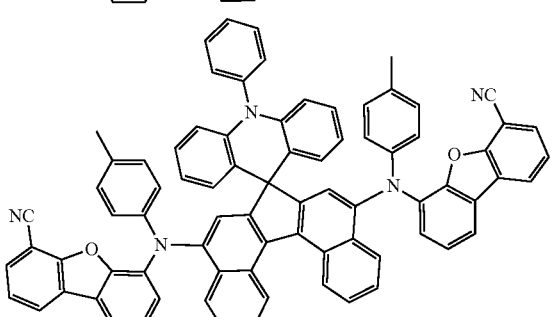
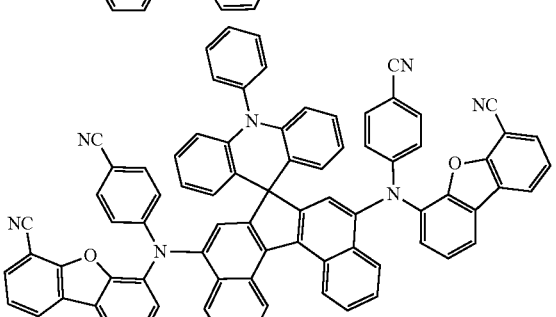
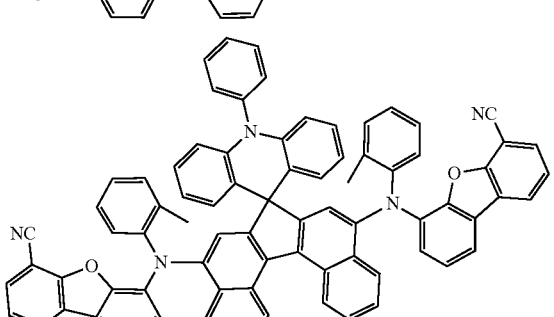

307
-continued
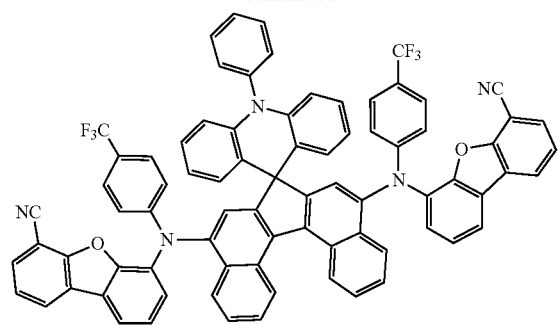
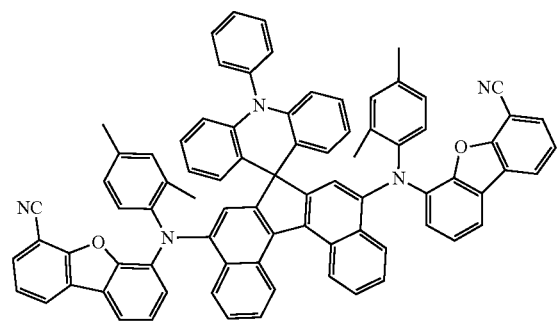
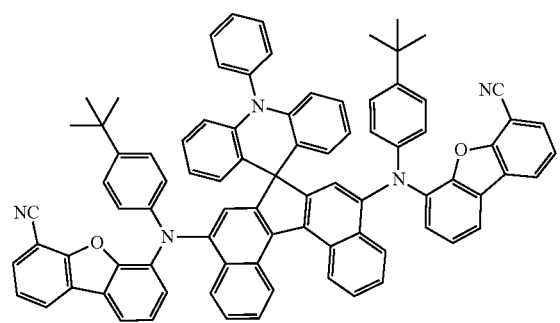
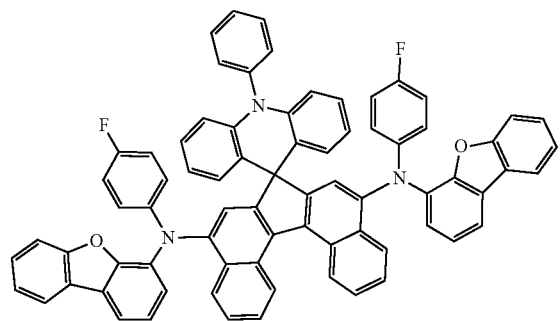
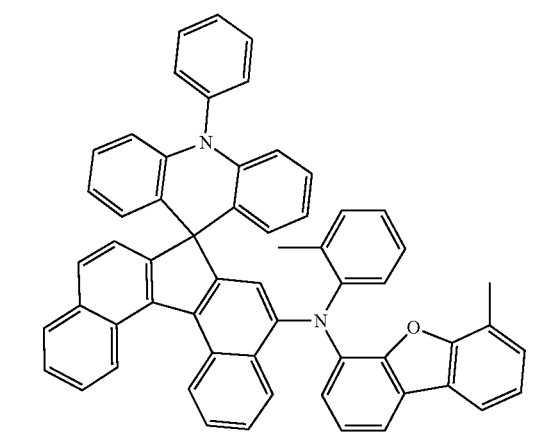
308
-continued
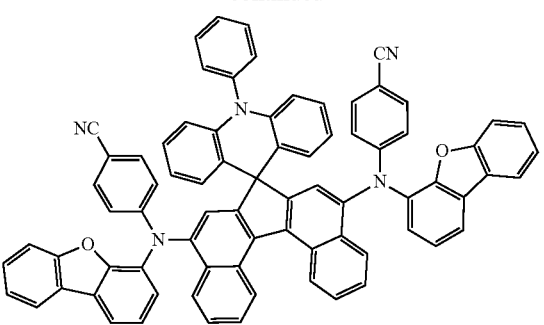
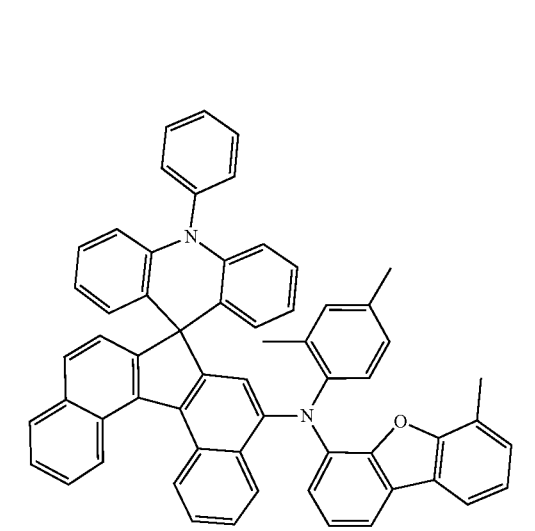
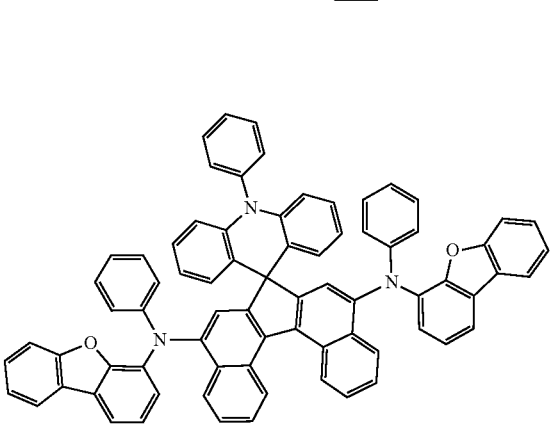
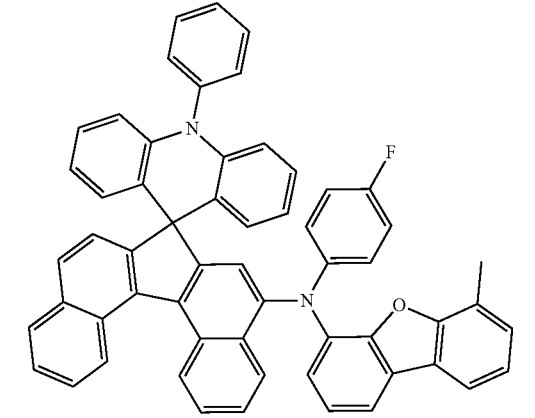

309 -continued 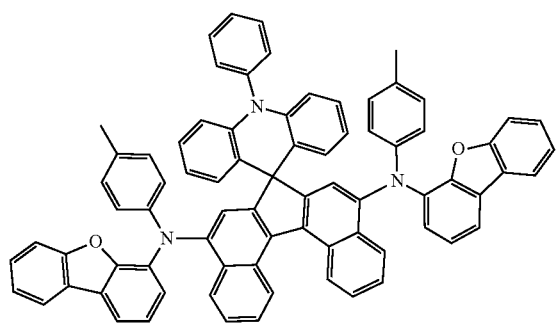
310 -continued 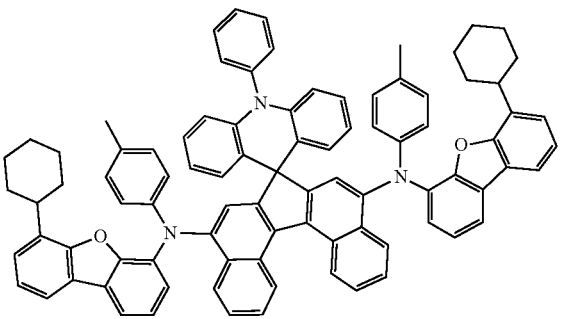
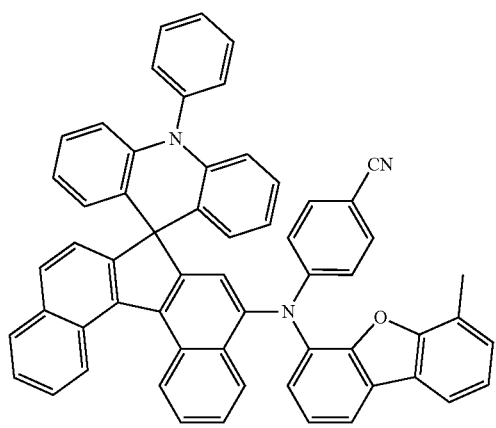
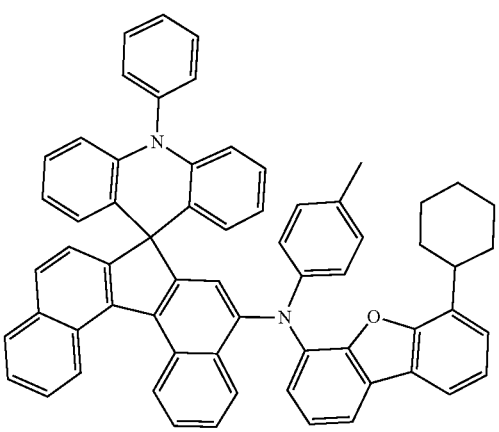
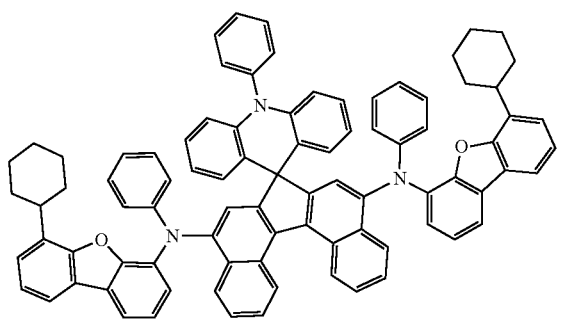
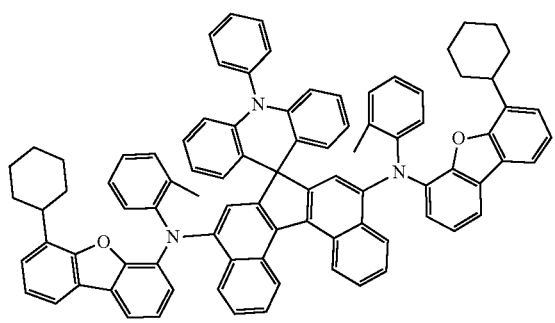
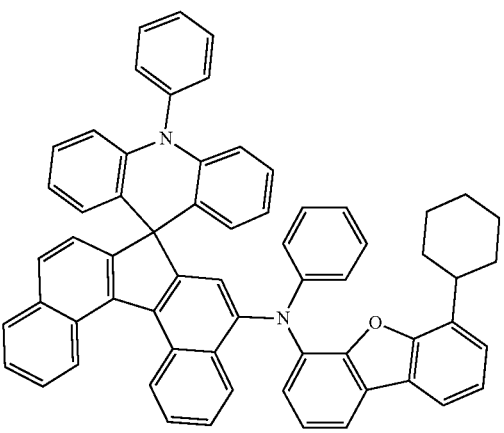
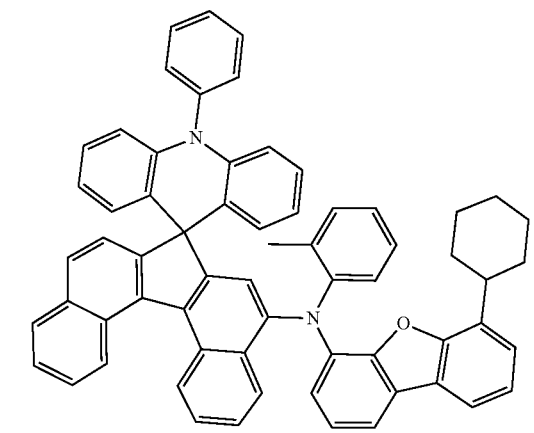

311
-continued
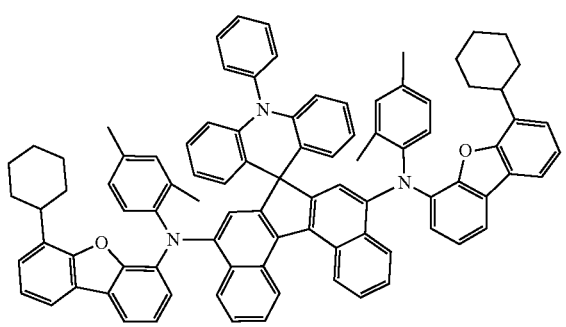
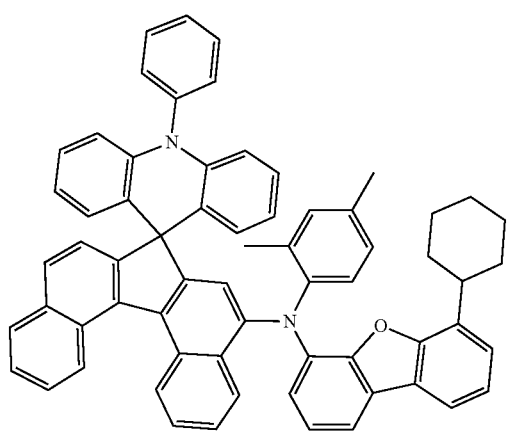
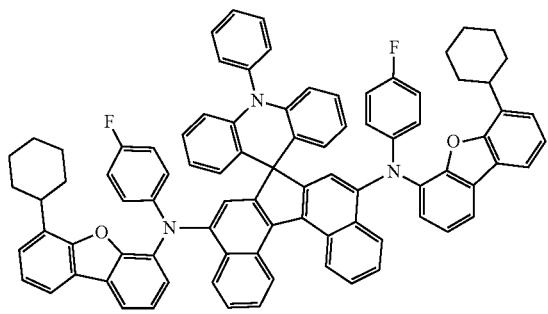
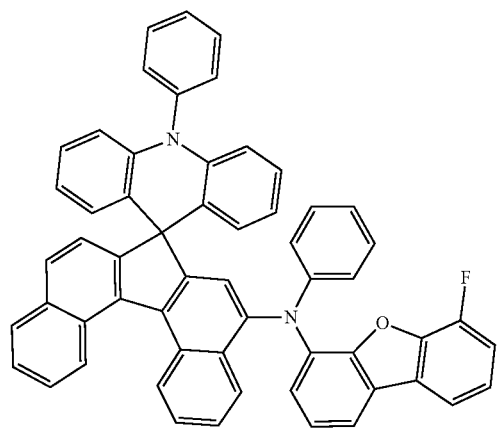
312
-continued
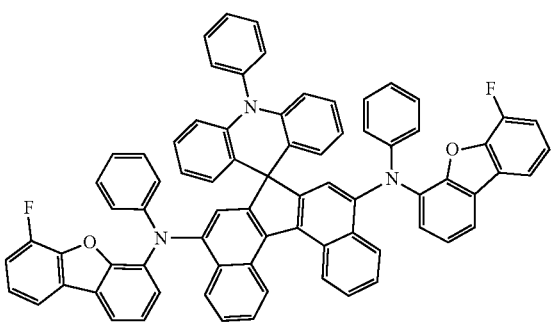
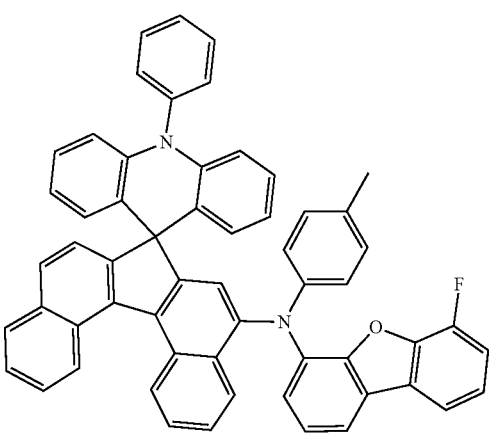
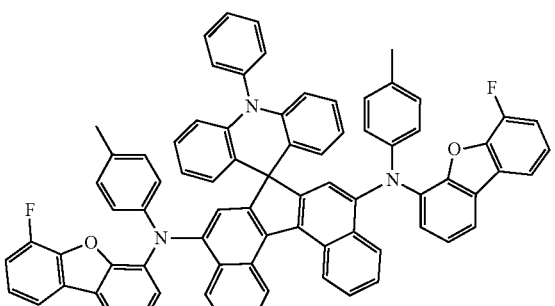
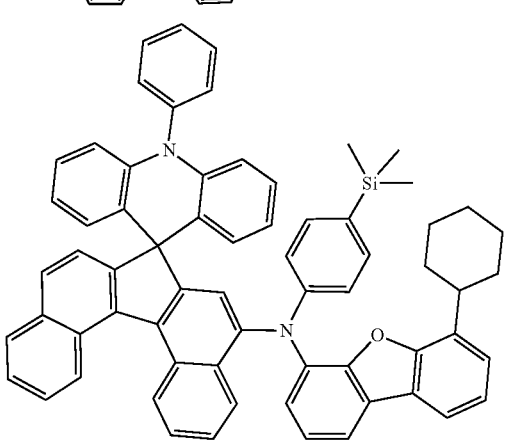

313
-continued
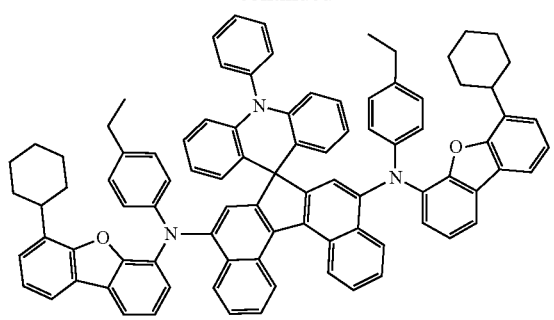
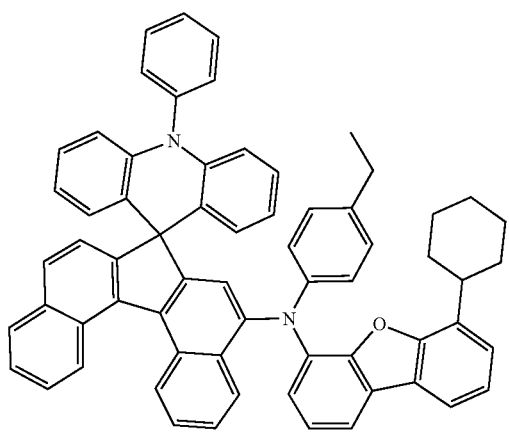
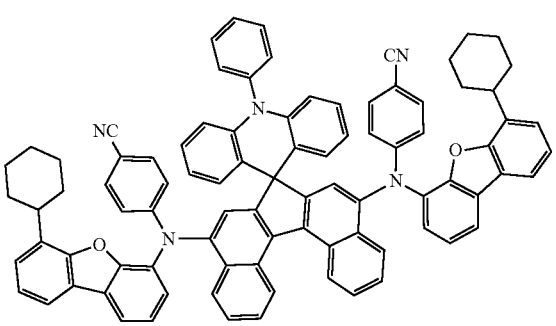
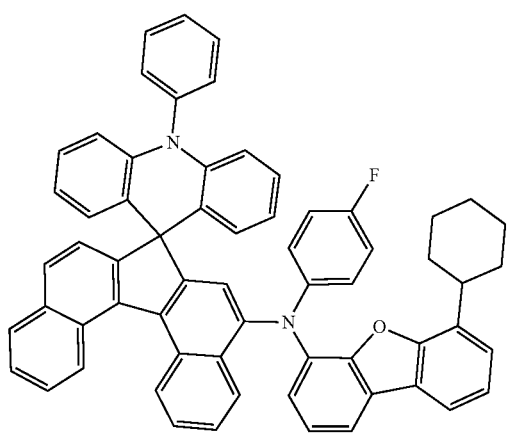
314
-continued
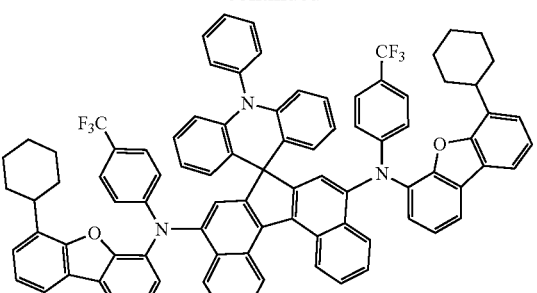
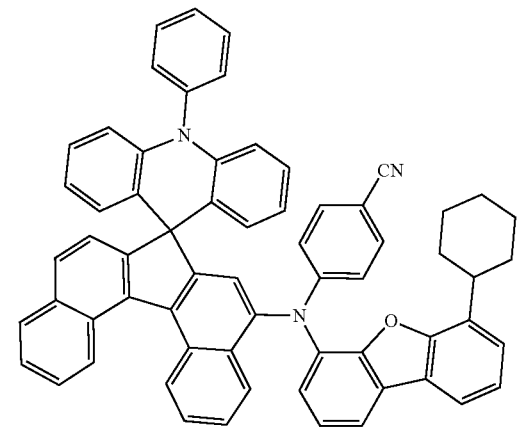
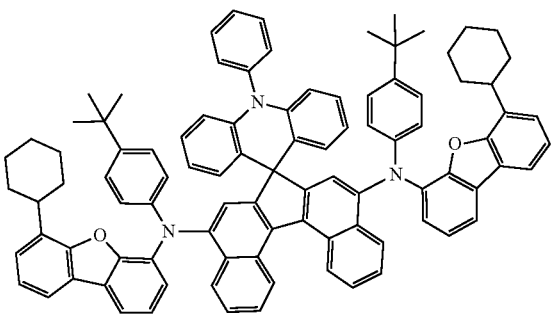
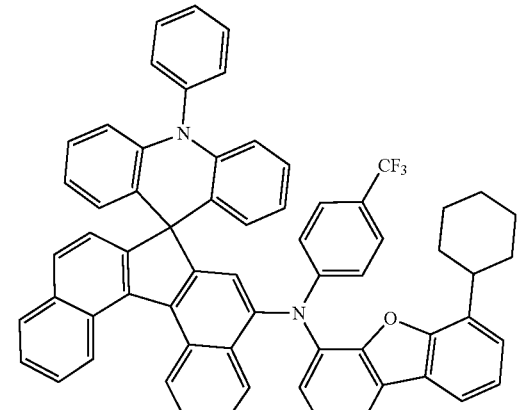

315
-continued
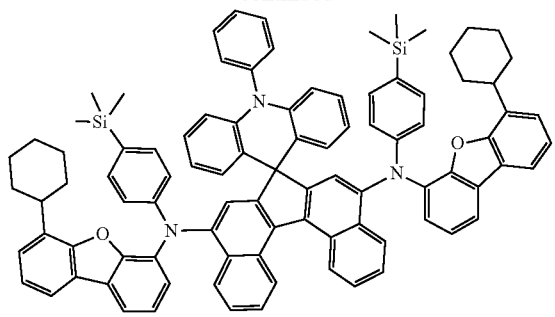
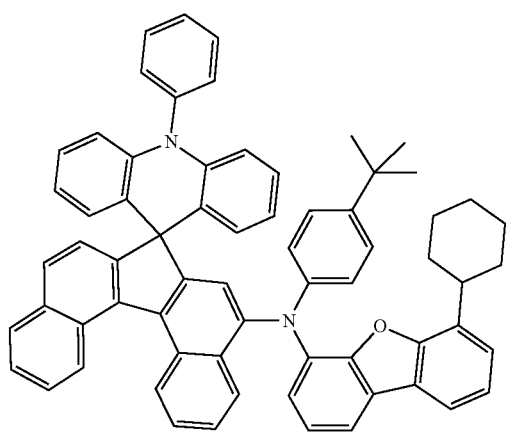
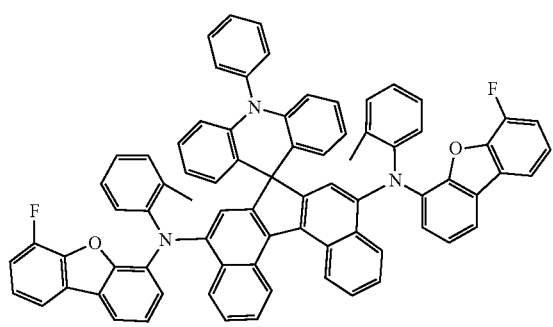
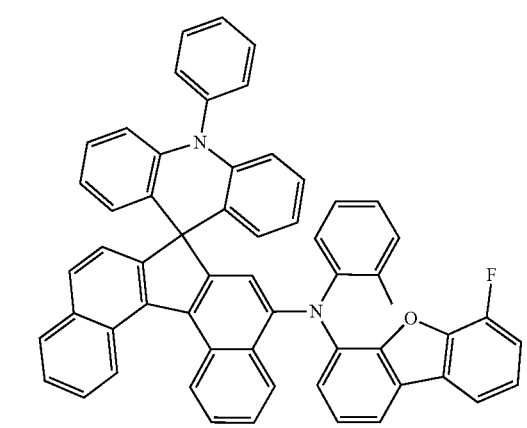
316
-continued
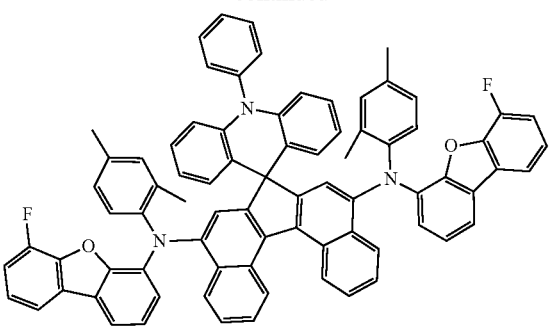
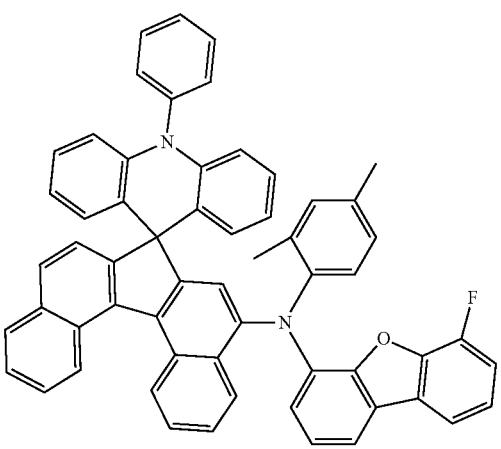
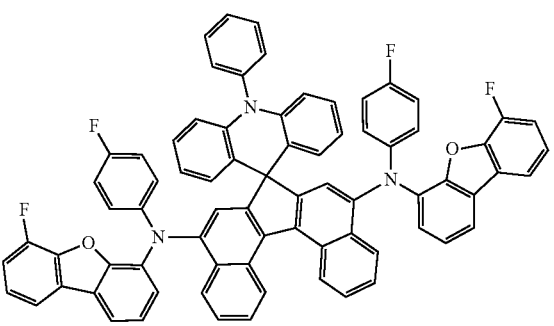
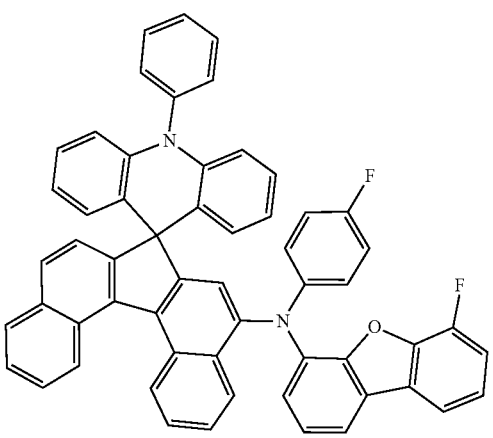

317
-continued
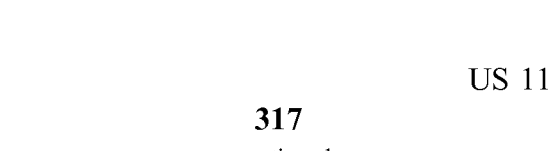
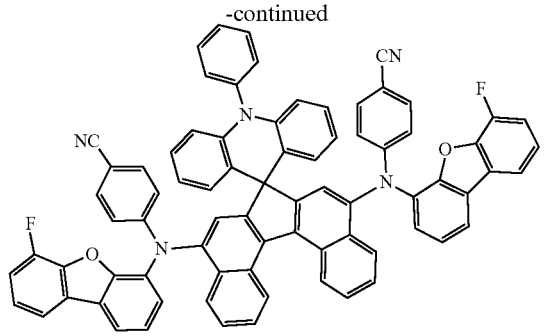
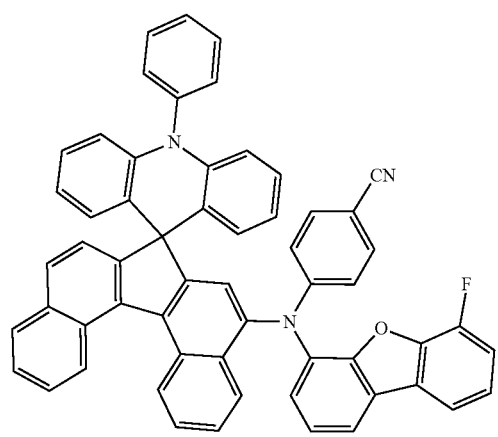
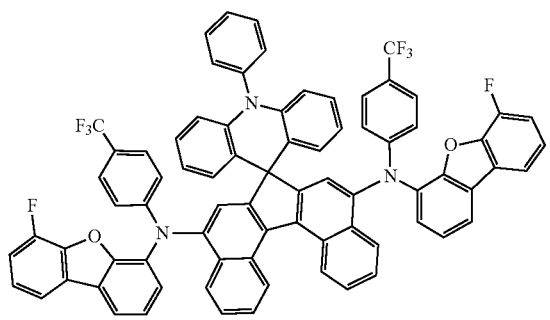
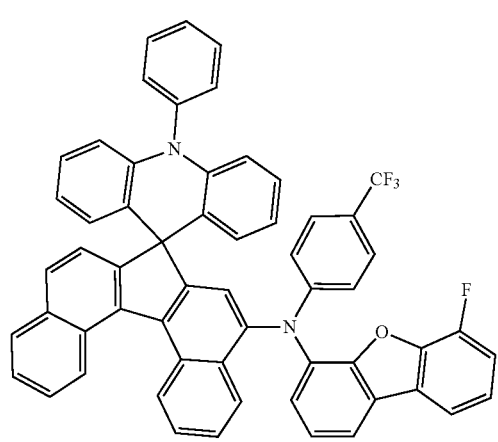
318
-continued
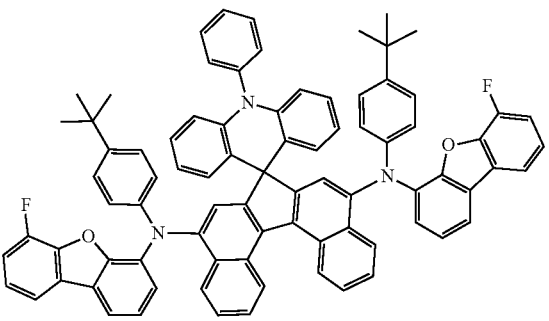
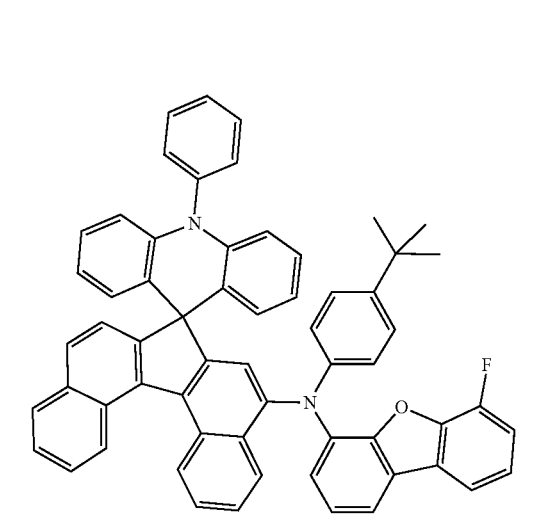
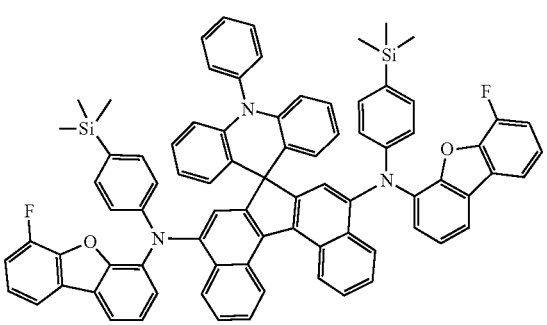
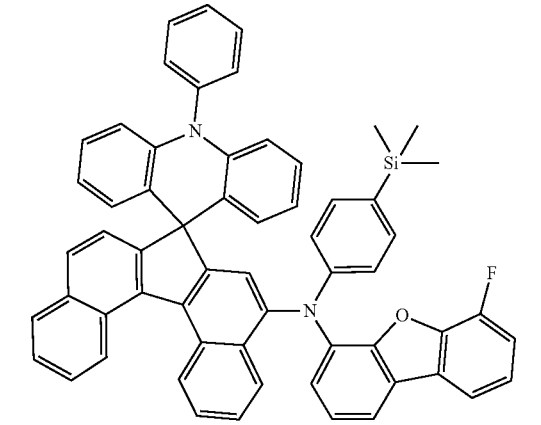

319
-continued
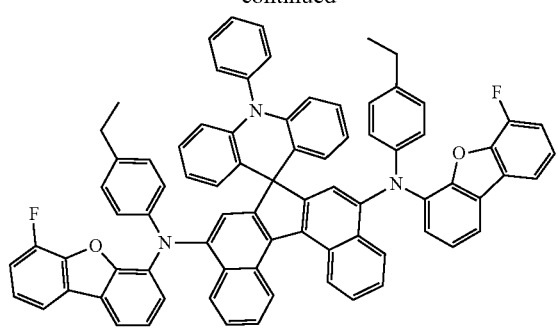
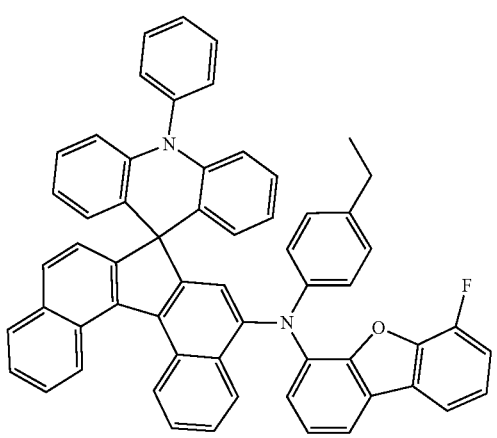
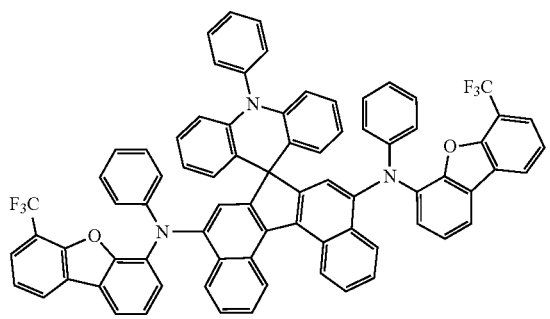
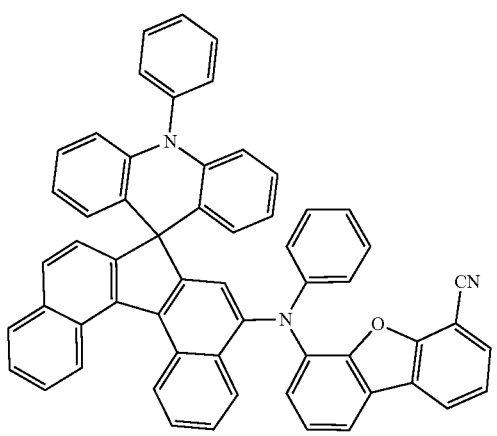
320
-continued
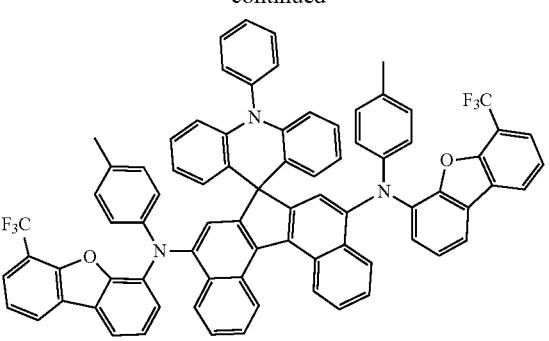
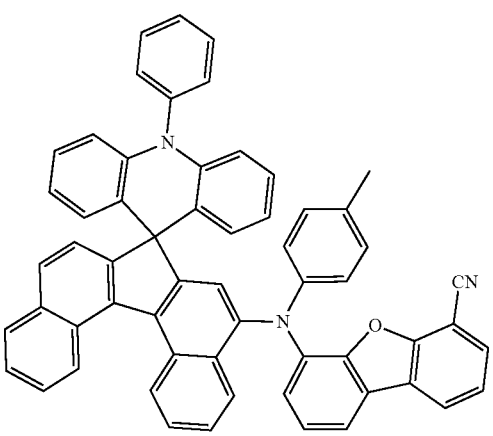
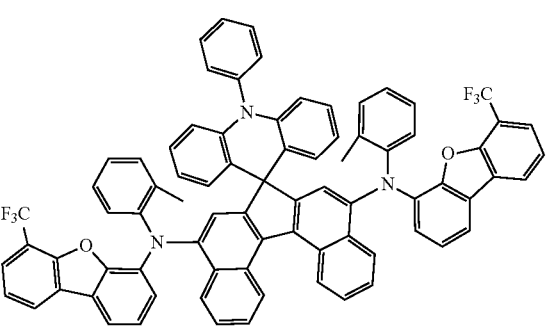
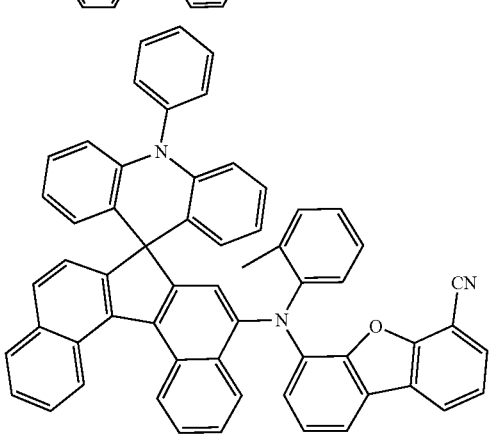

321
-continued
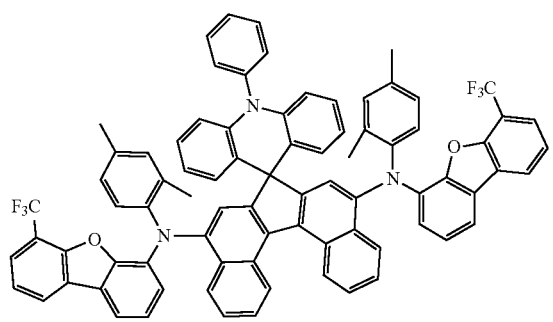
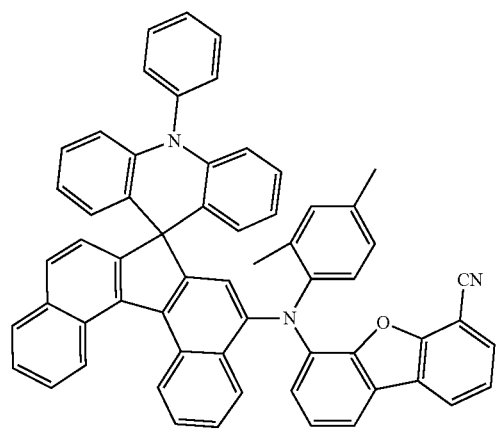
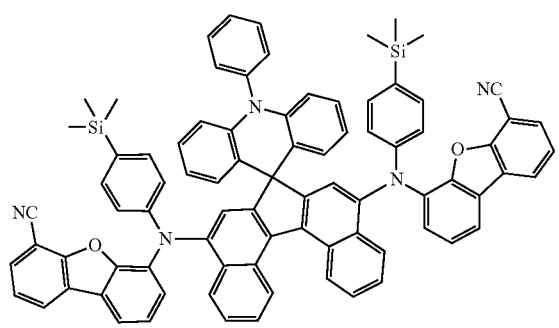
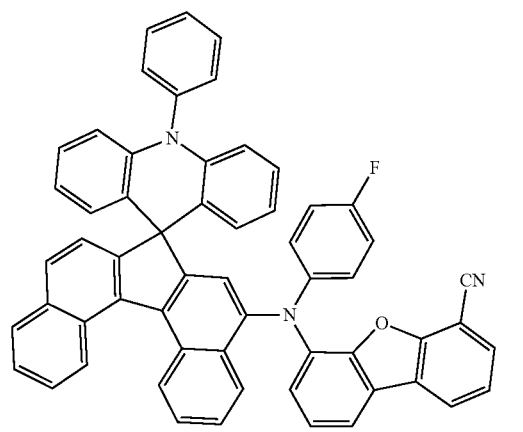
322
-continued
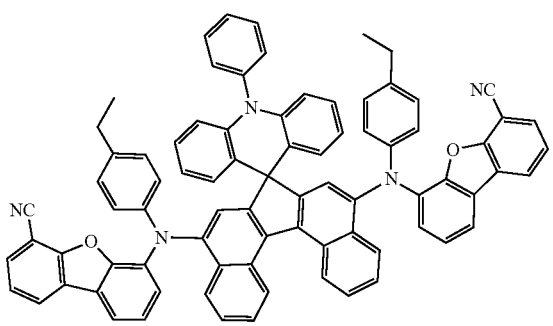
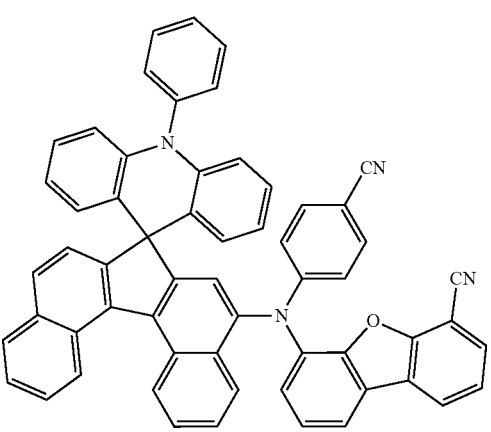
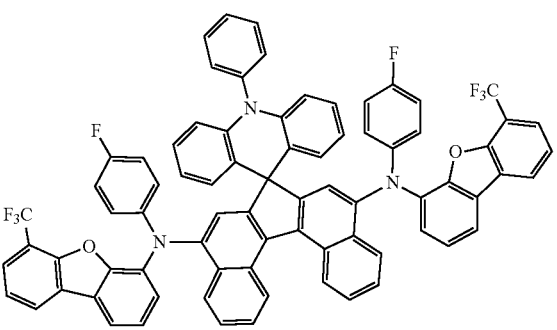
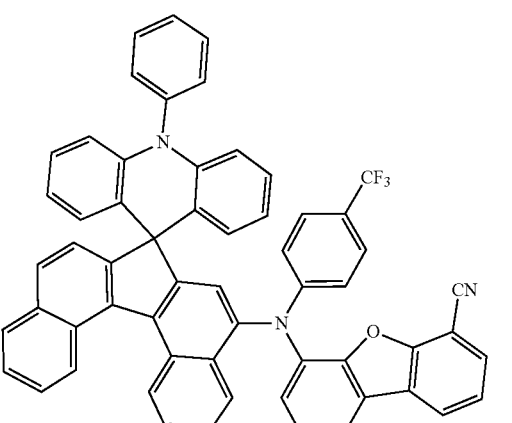

323
-continued
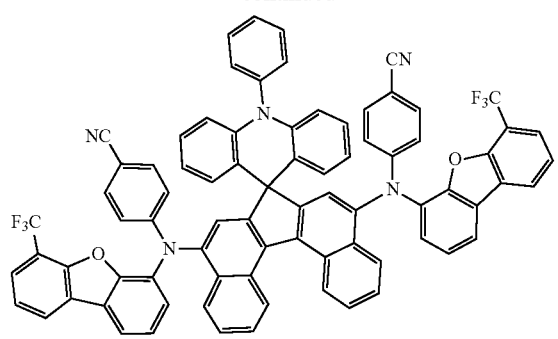
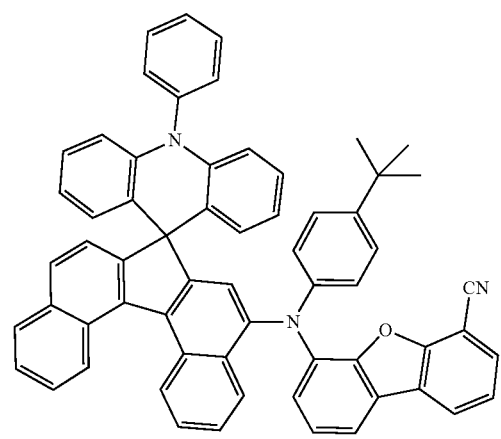
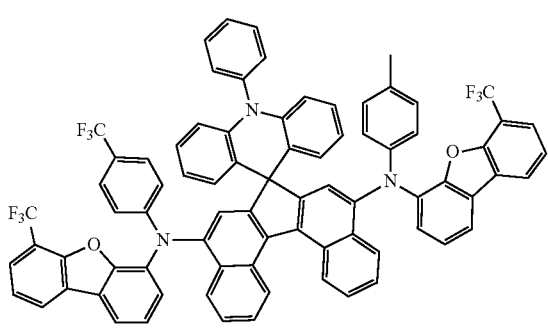
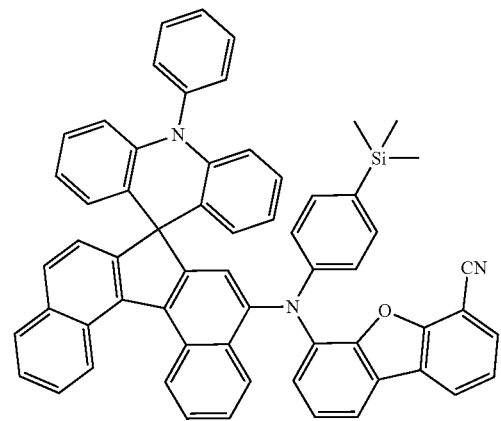
324
-continued
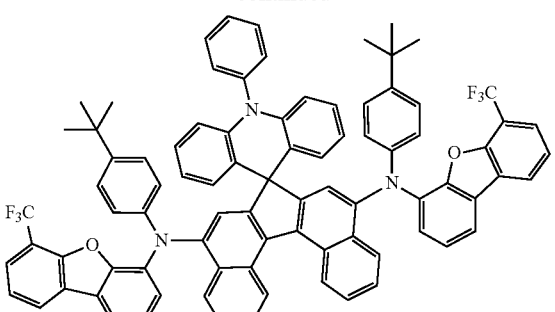
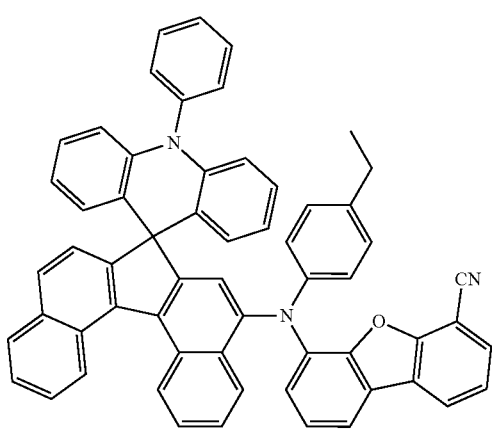
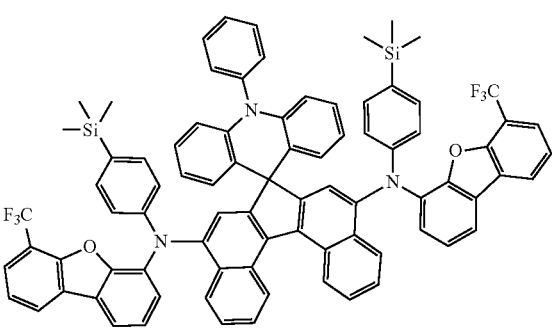
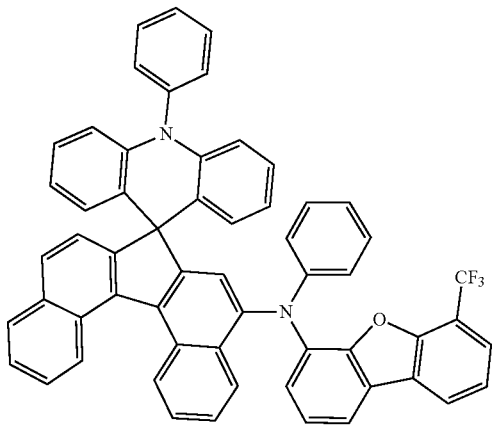

325
-continued
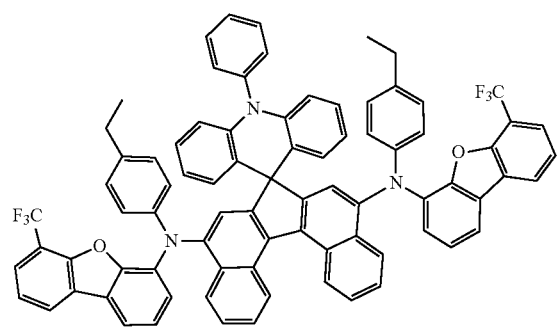
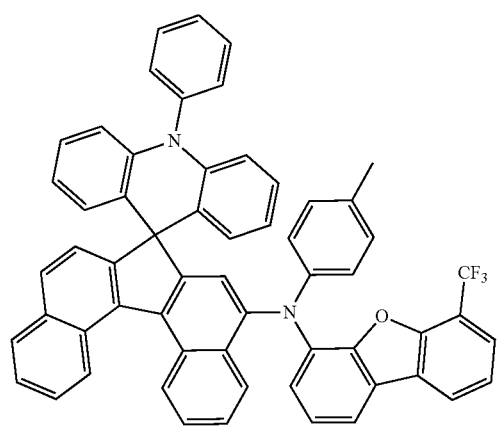
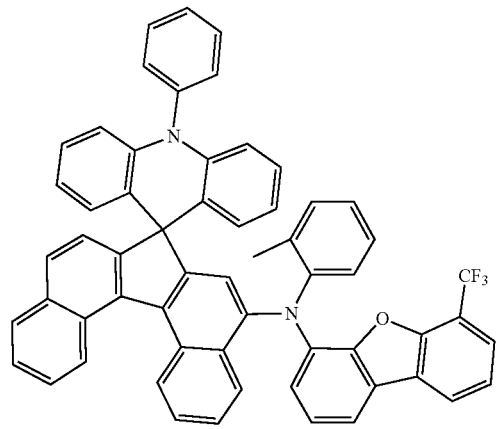
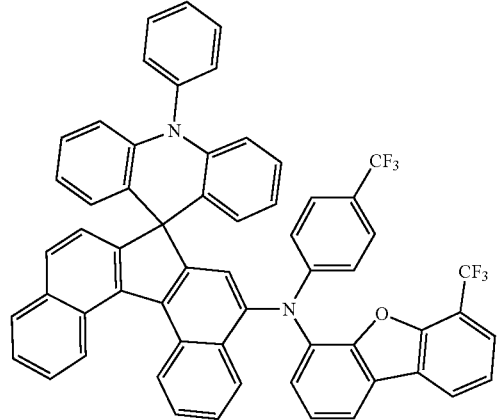
326
-continued
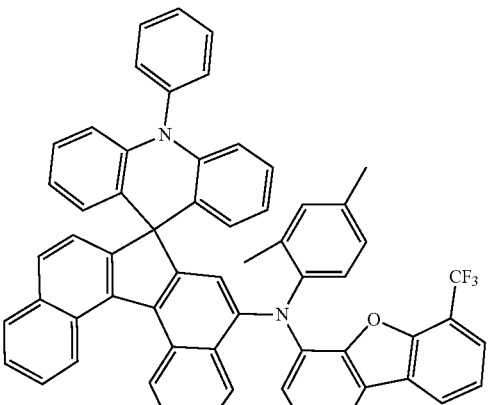
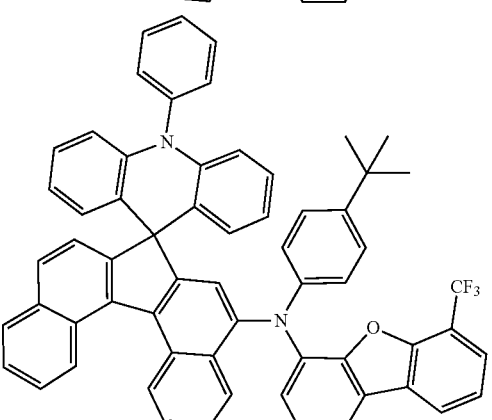
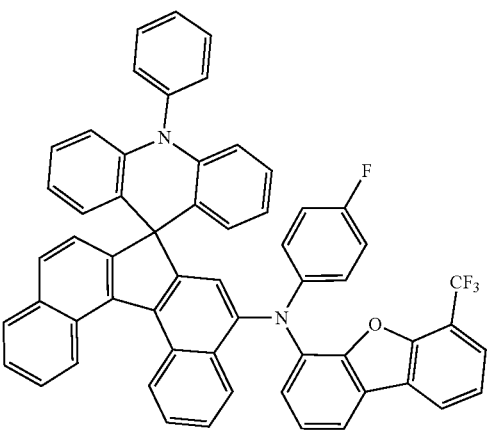
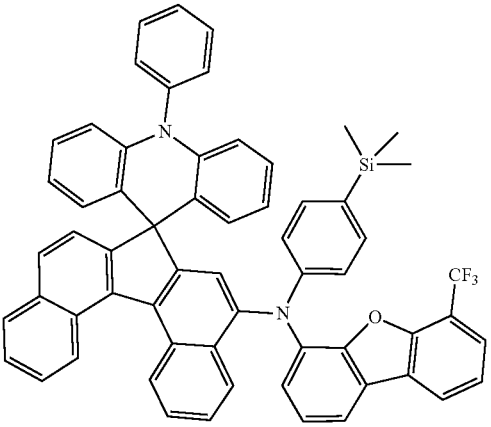

327
-continued
328
-continued
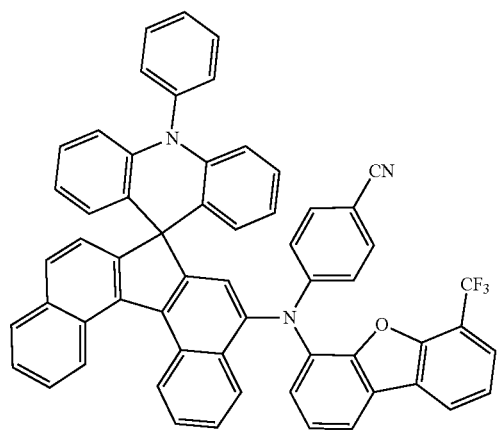
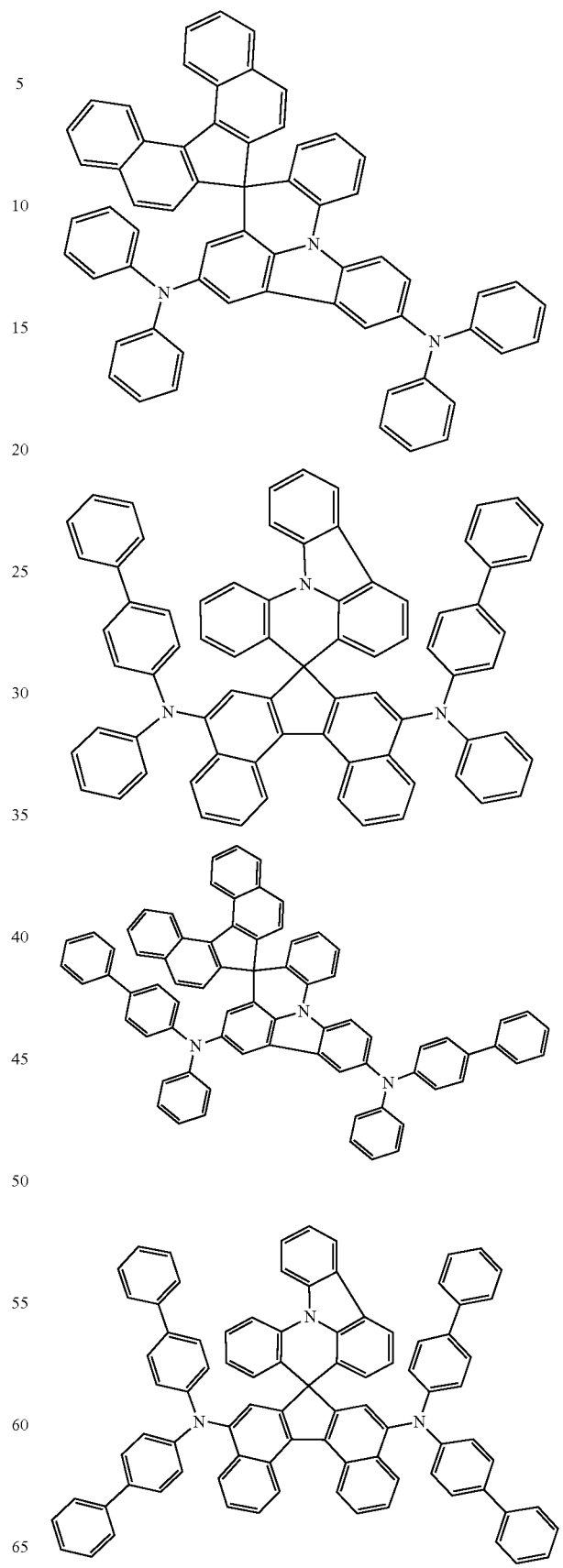

329
-continued
330
-continued
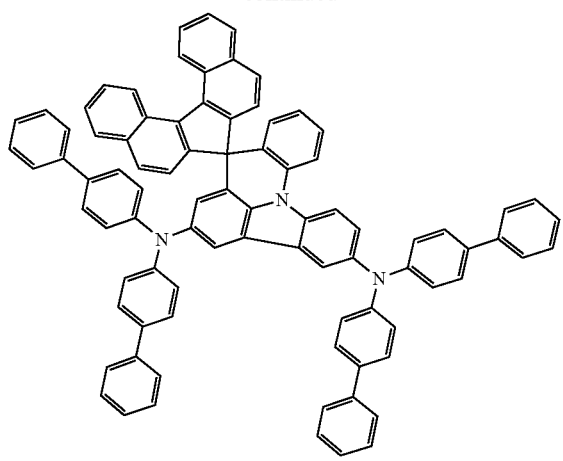
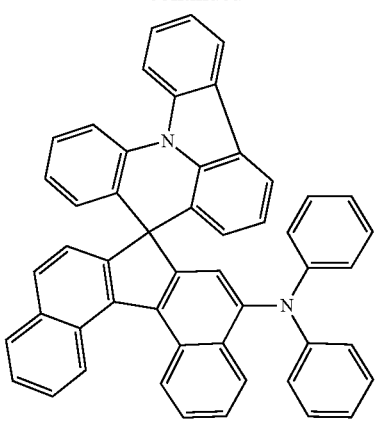
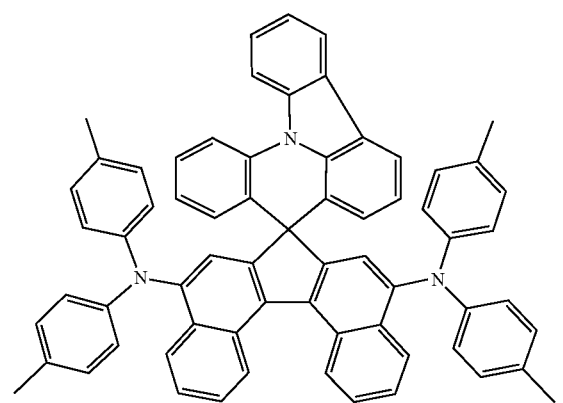
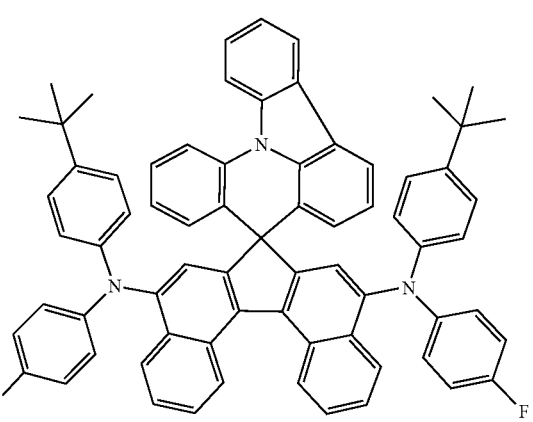
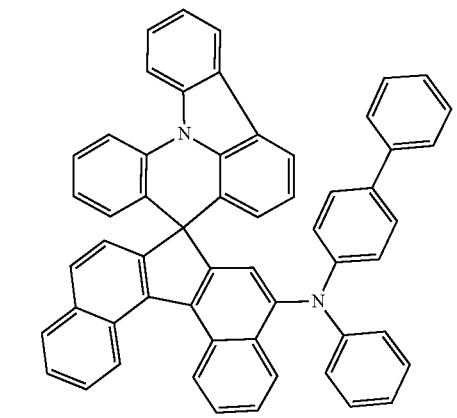
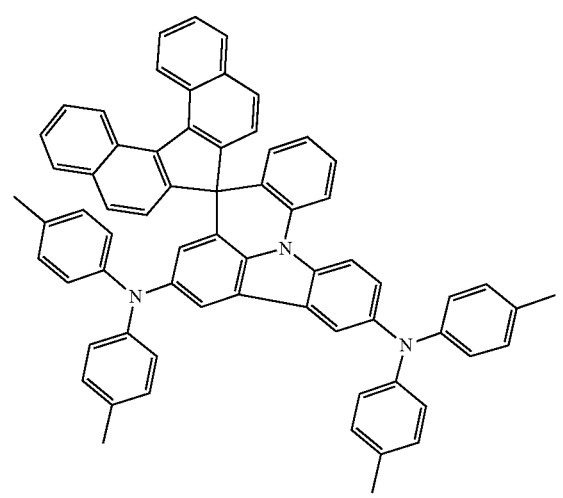
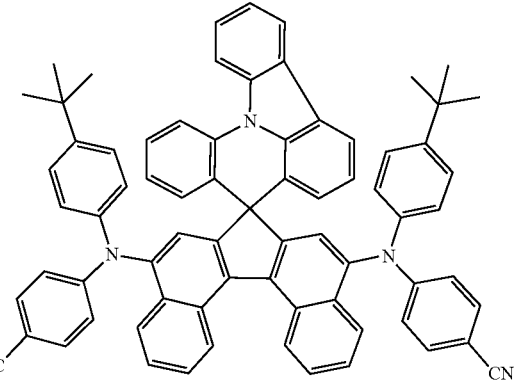

331
-continued
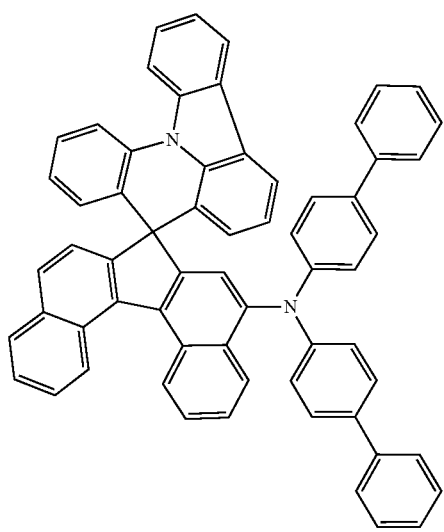
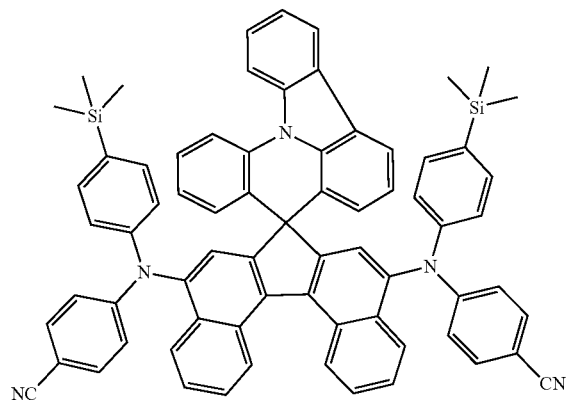
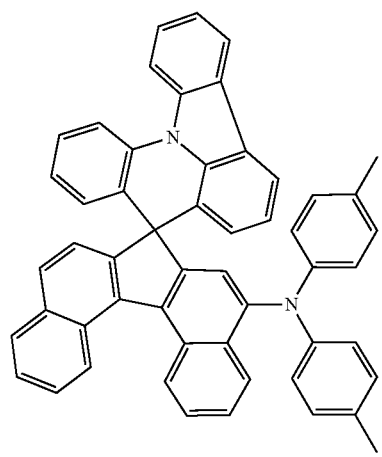
332
-continued
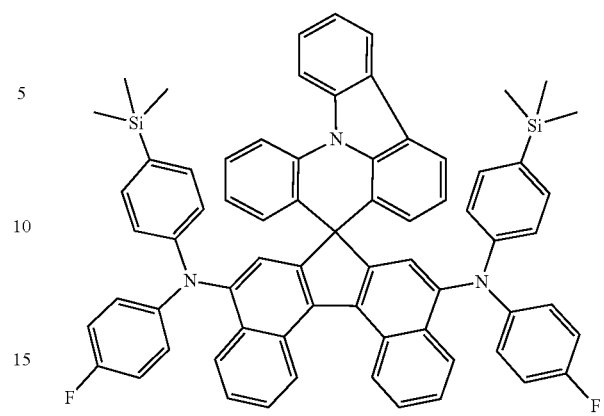
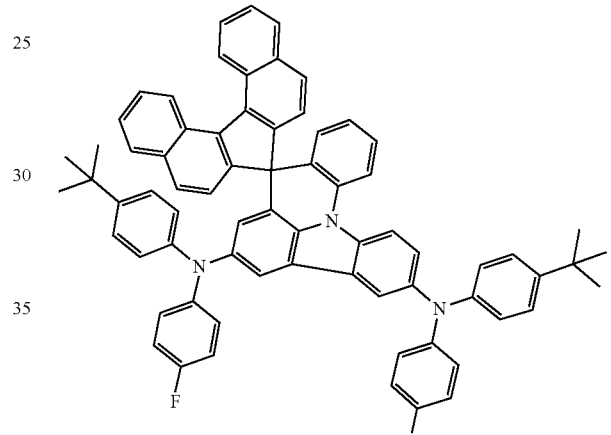
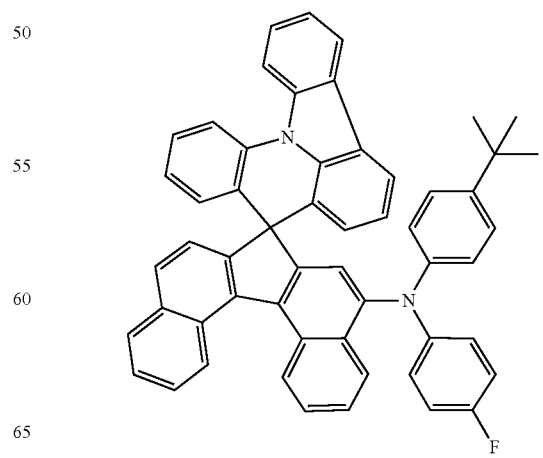

333
-continued
334
-continued
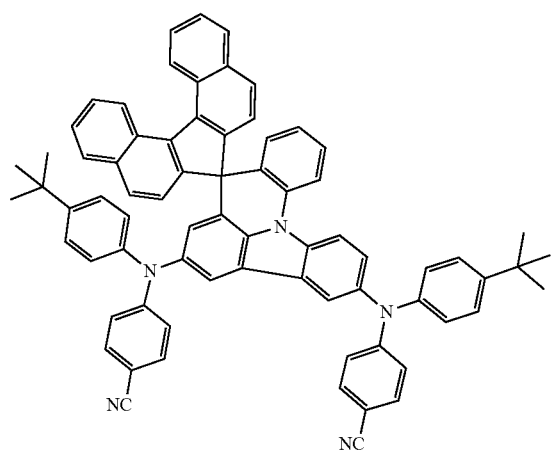
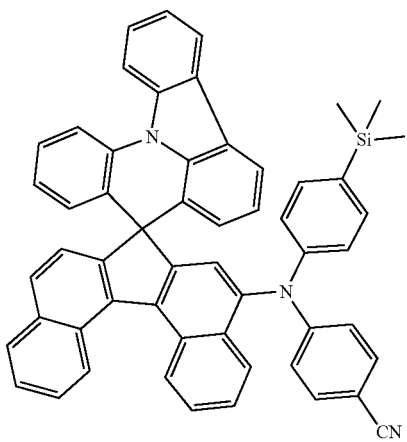
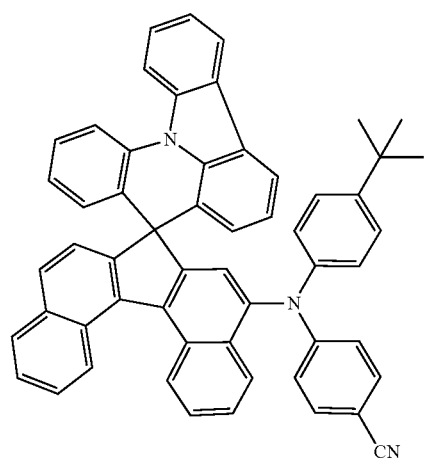
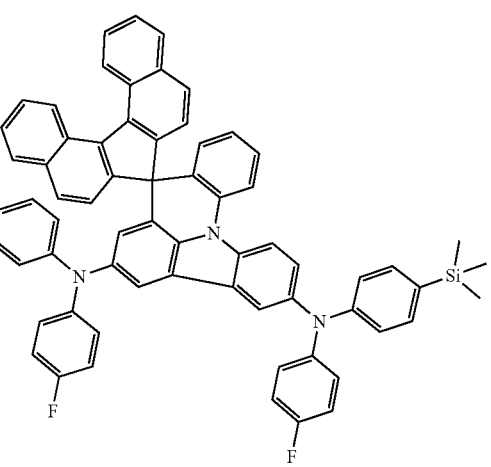
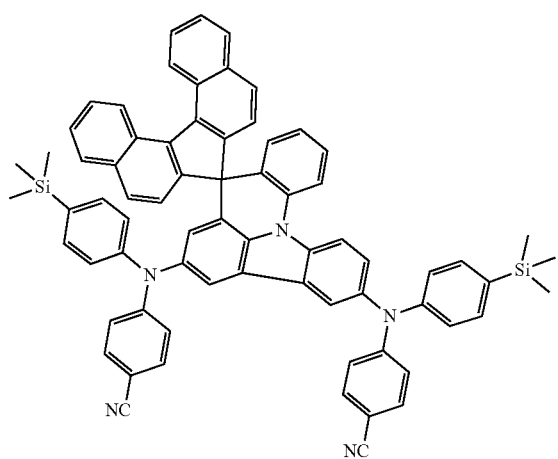
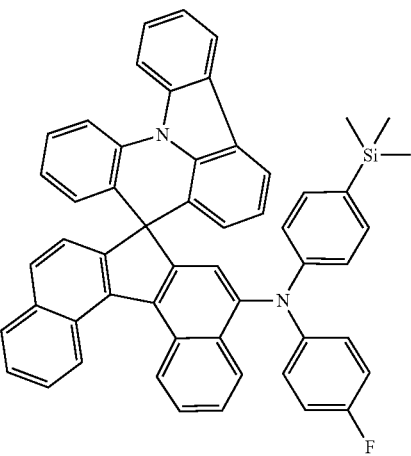

335
-continued
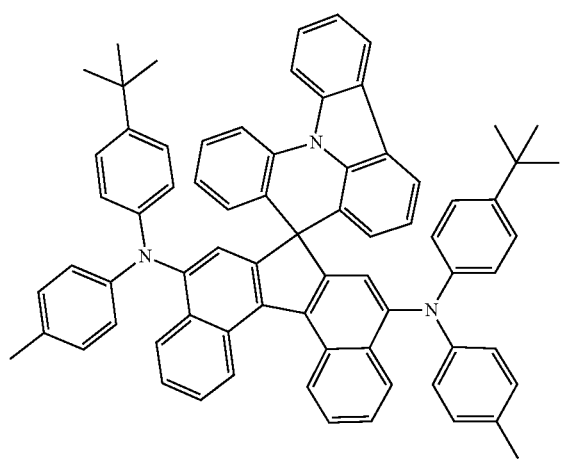
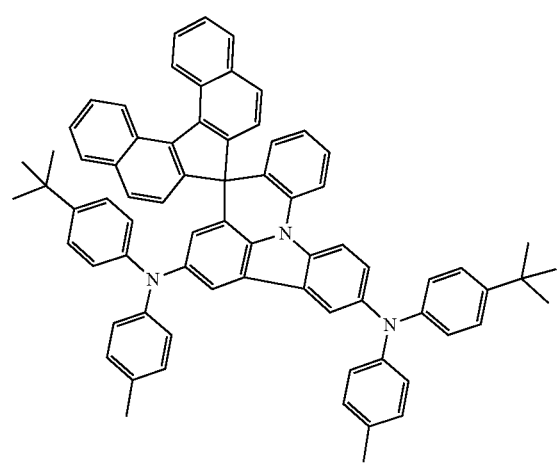
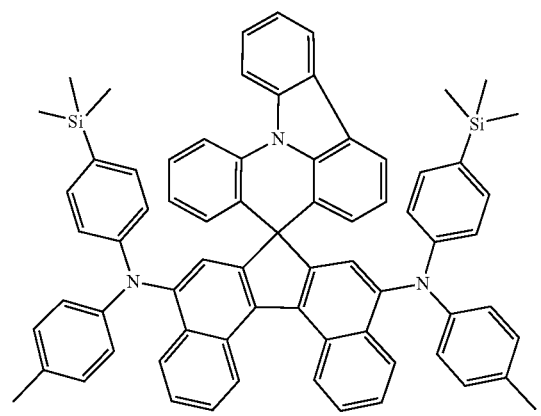
336
-continued
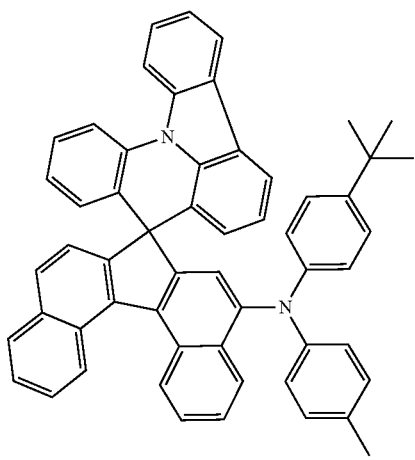
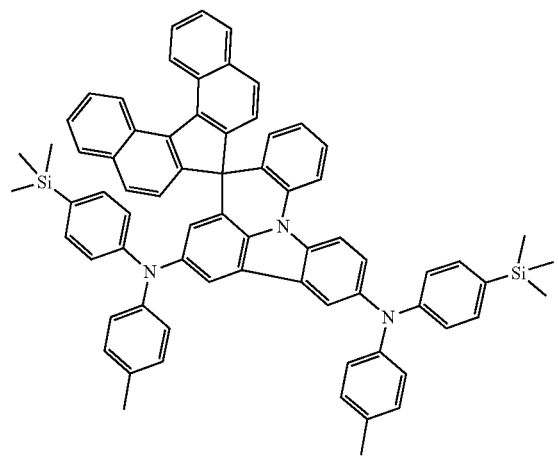
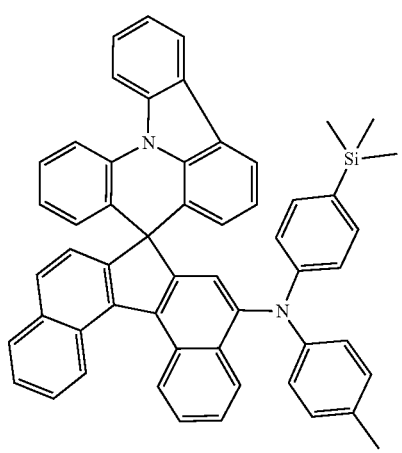

337
-continued
338
-continued
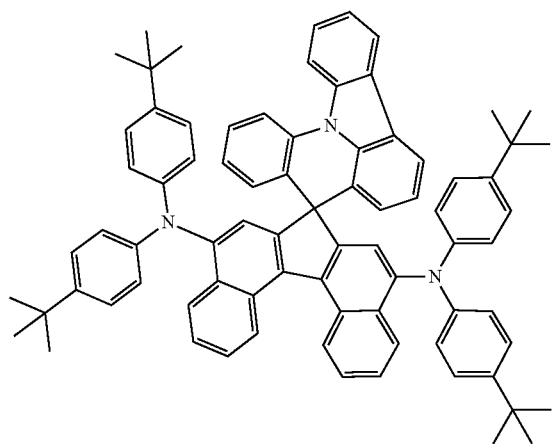
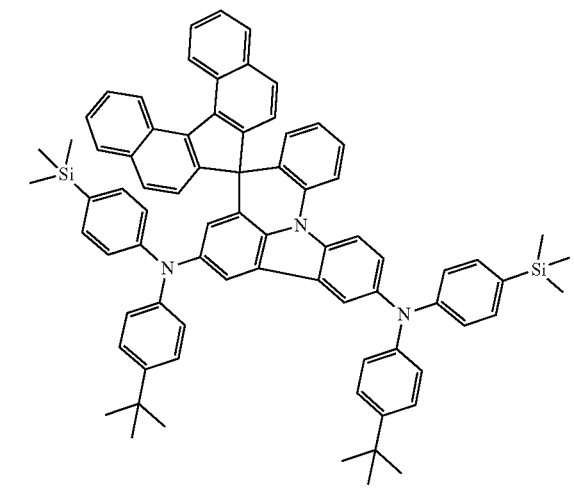
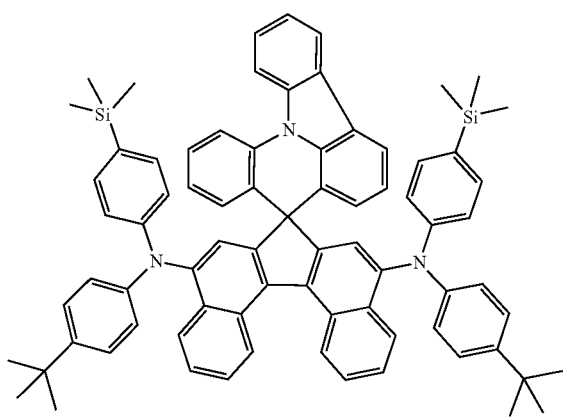
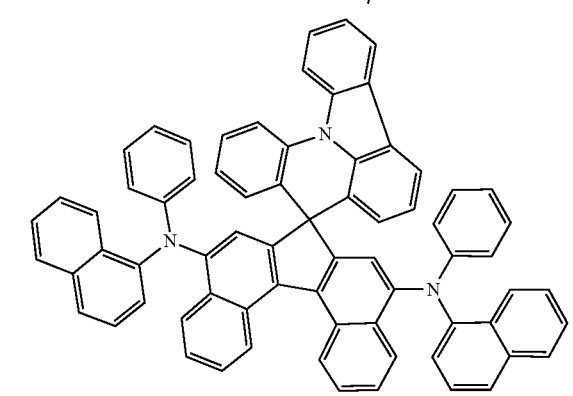
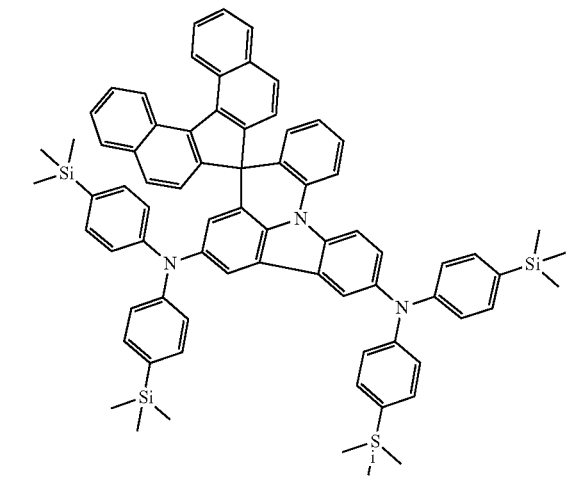
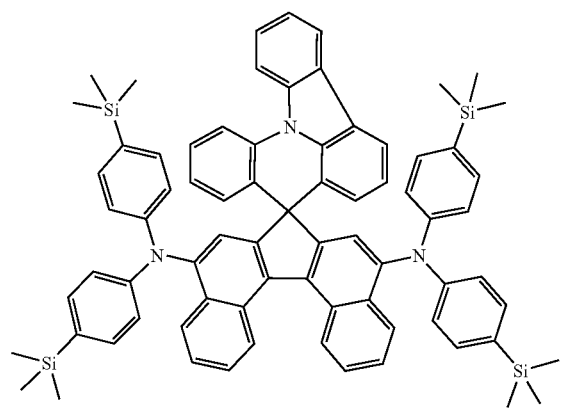
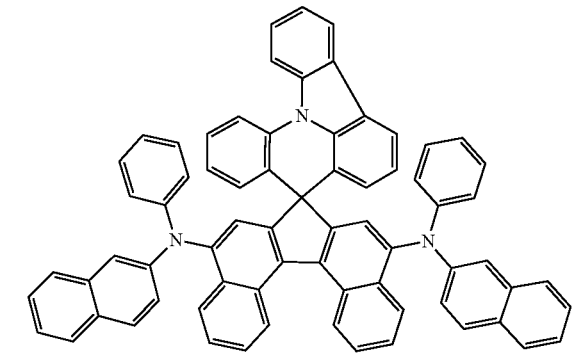

339
-continued
340
-continued
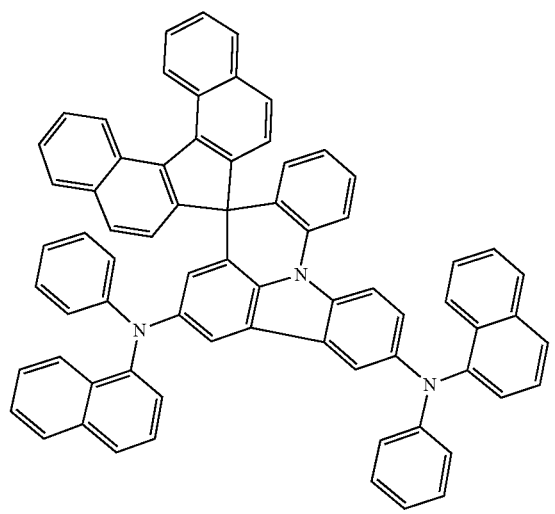
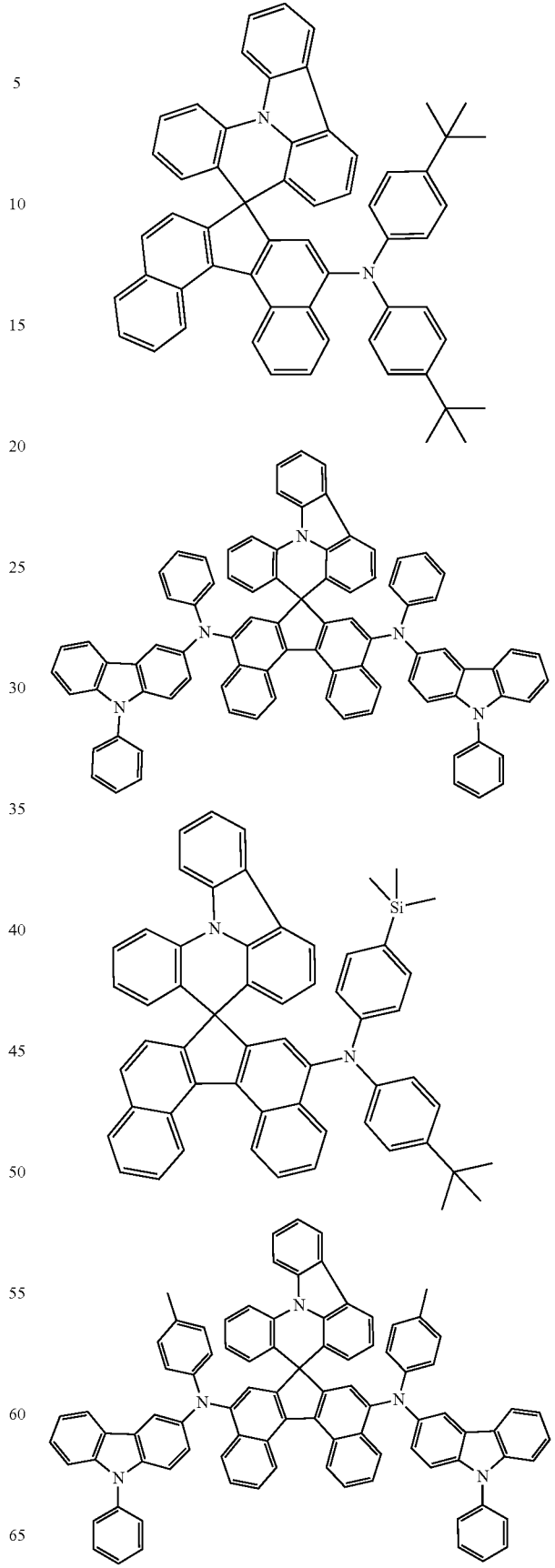

341
-continued
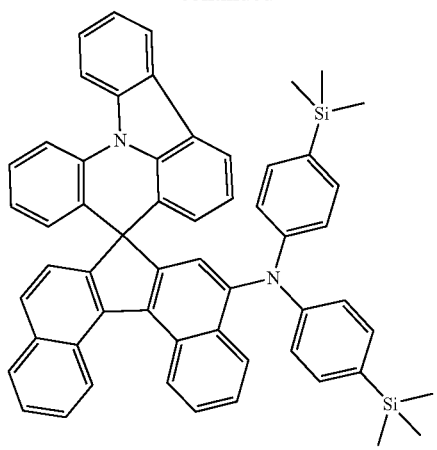
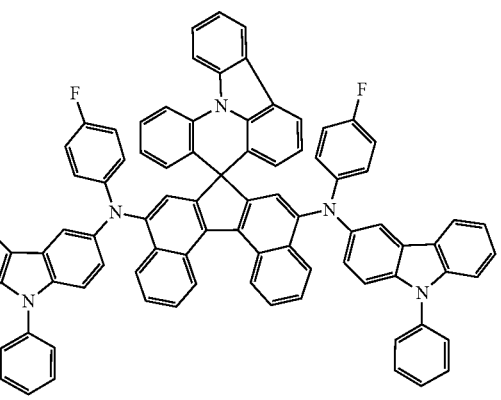
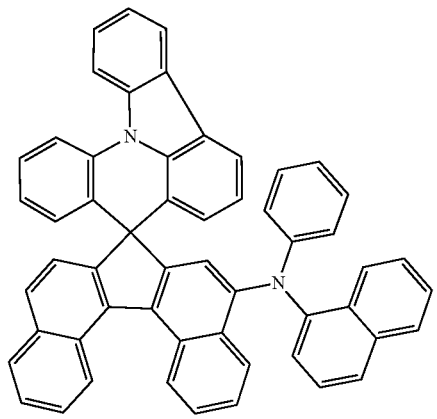
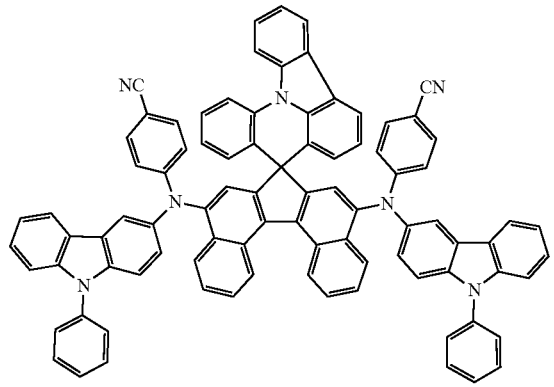
342
-continued
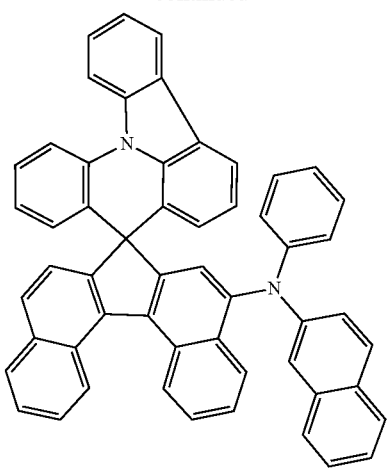
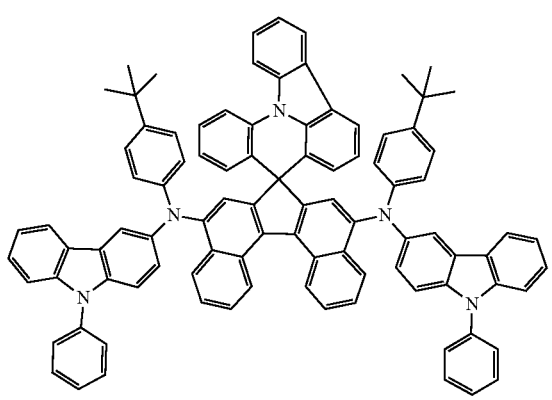
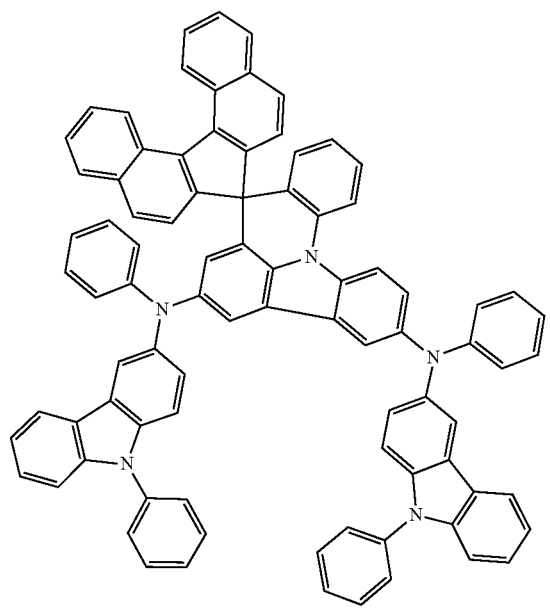

343
-continued
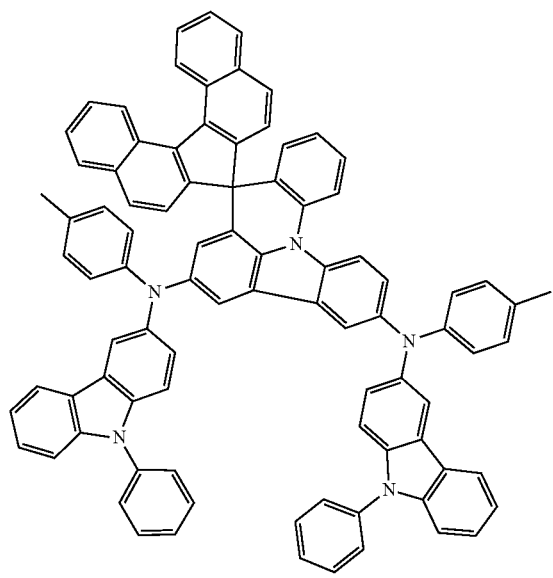
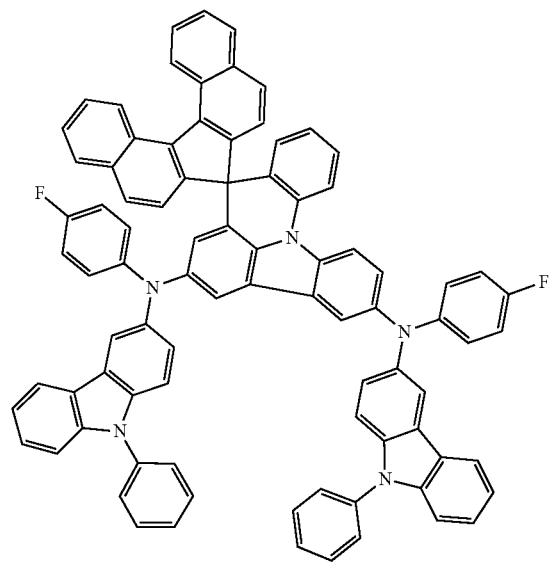
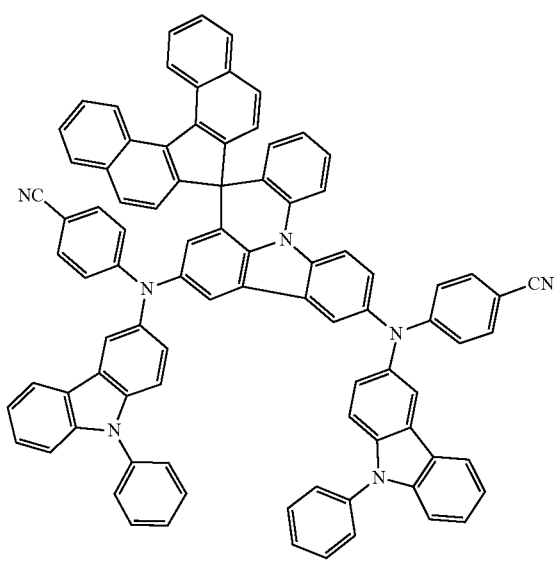
344
-continued
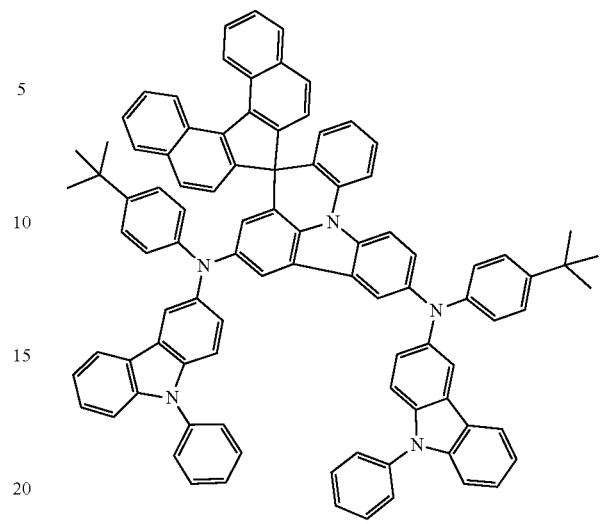
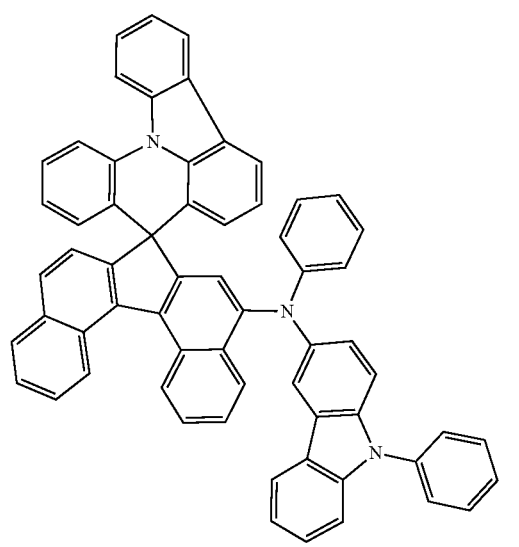
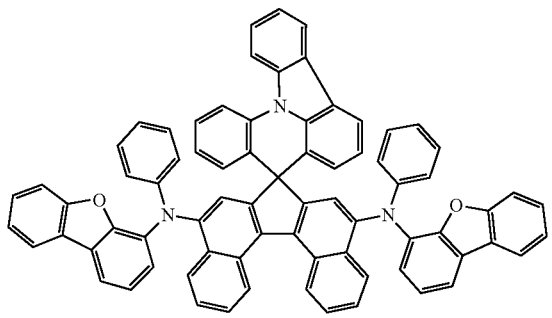

345
-continued
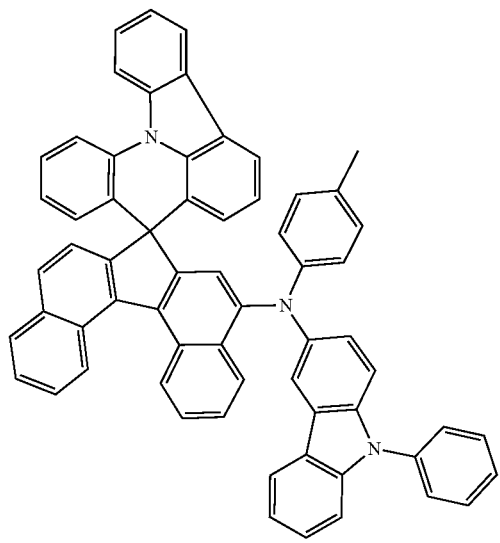
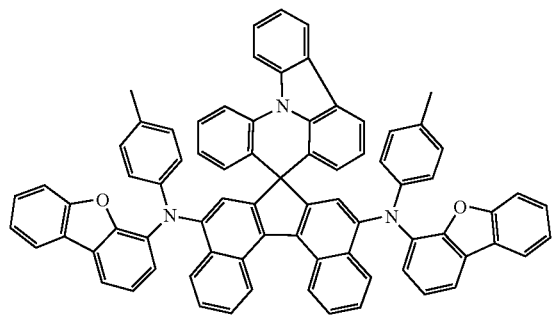
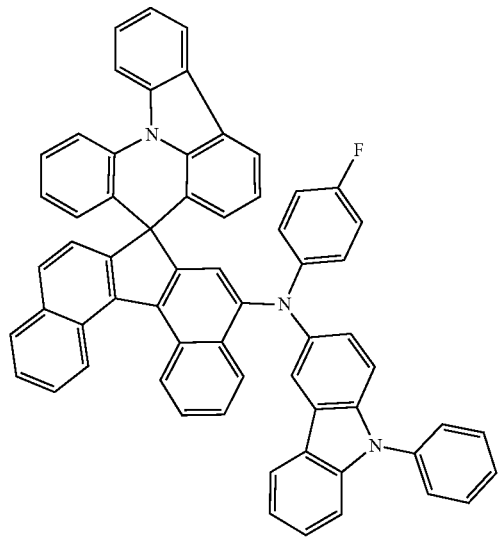
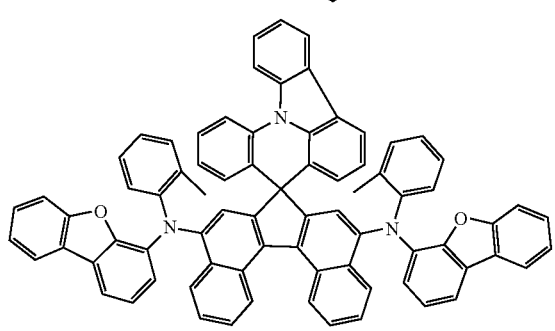
346
-continued
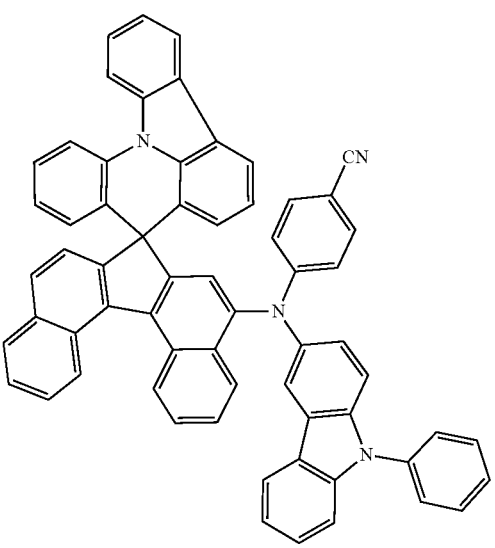
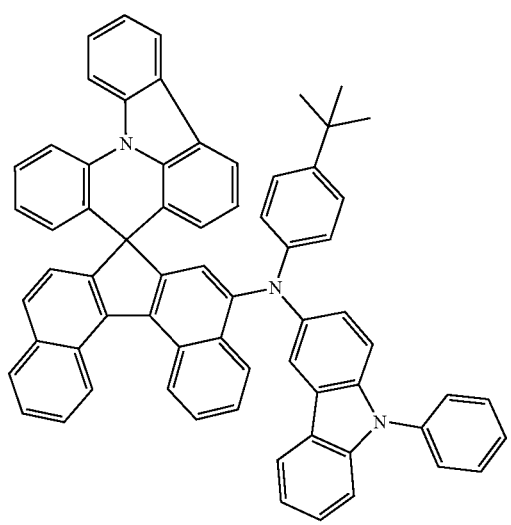
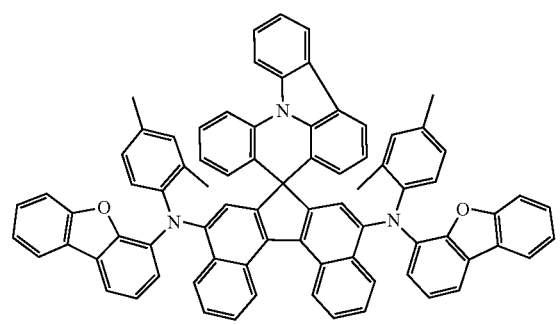

347
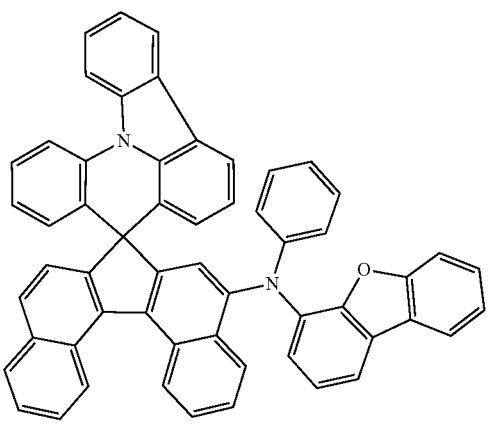
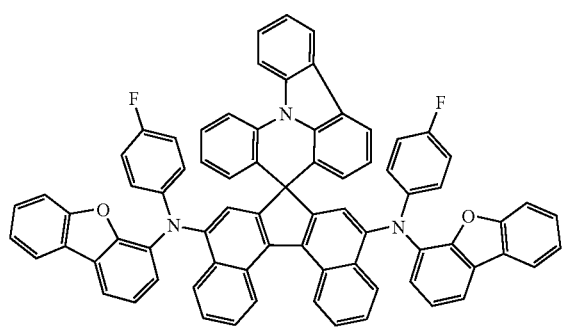
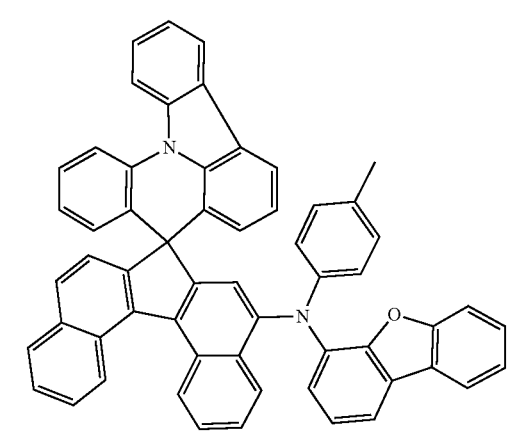
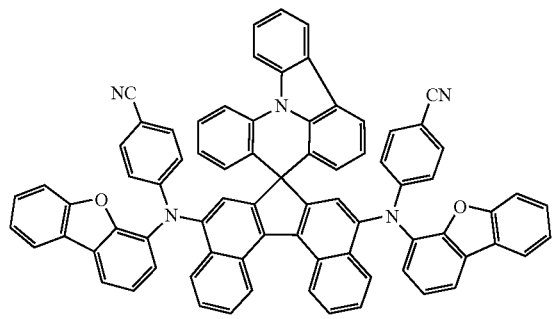
348
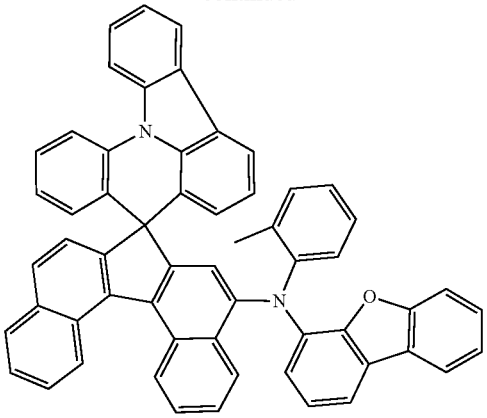
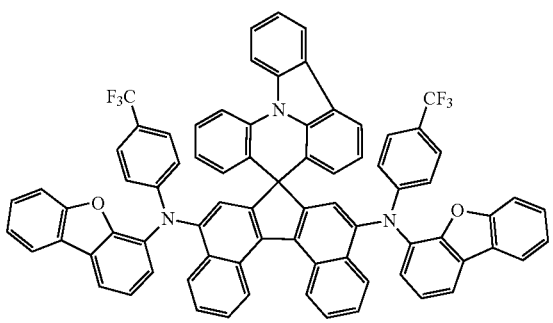
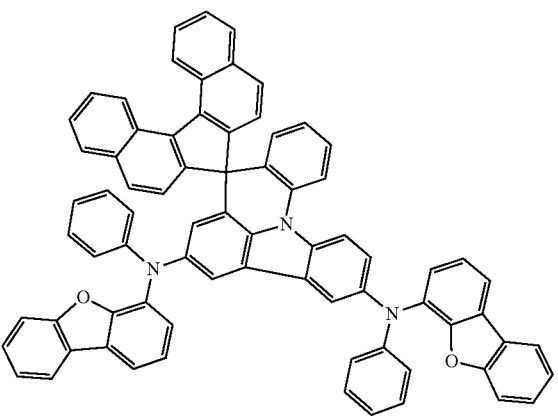
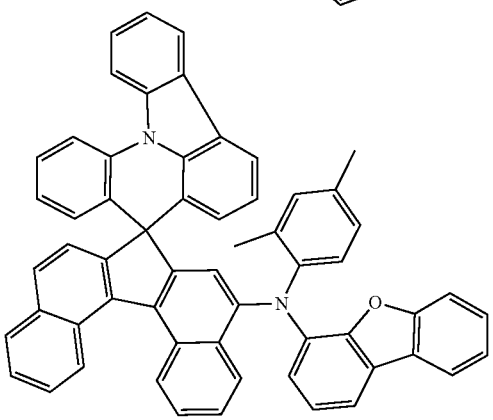

349
-continued
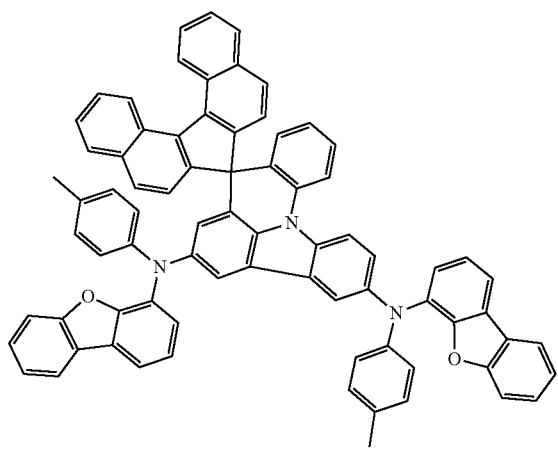
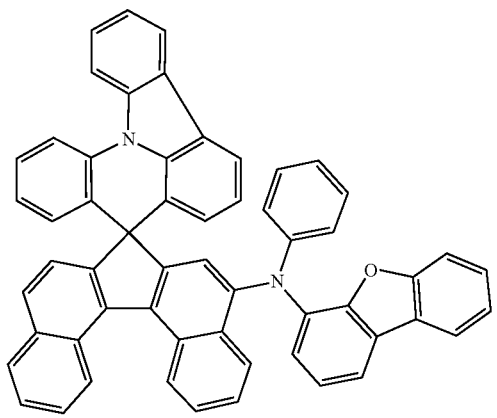
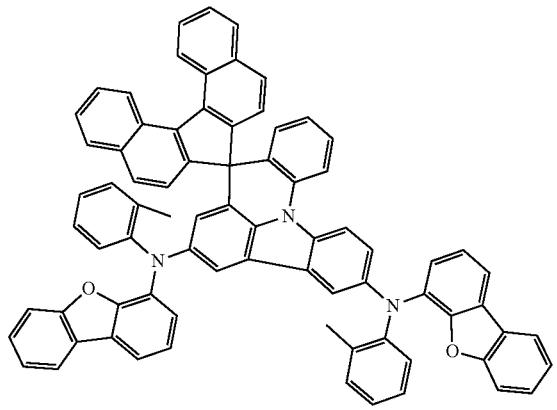
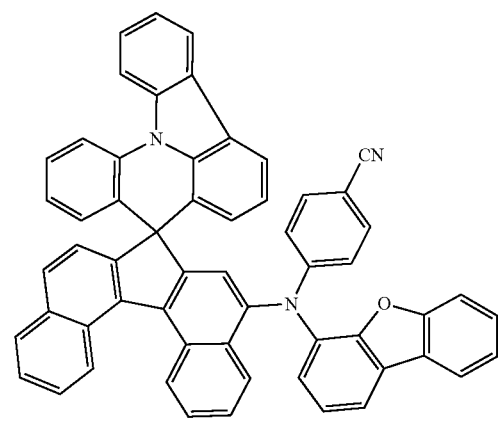
350
-continued
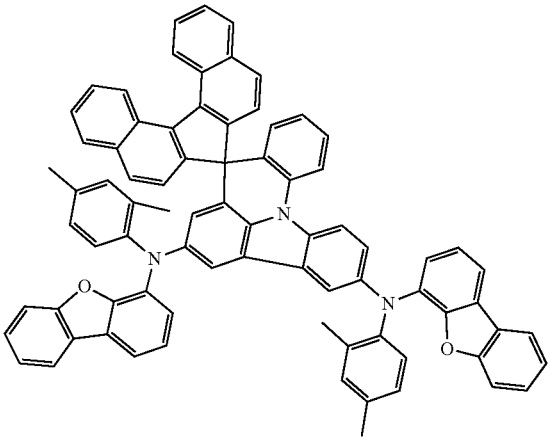
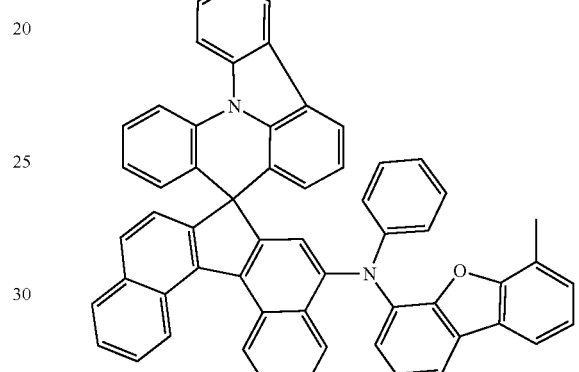
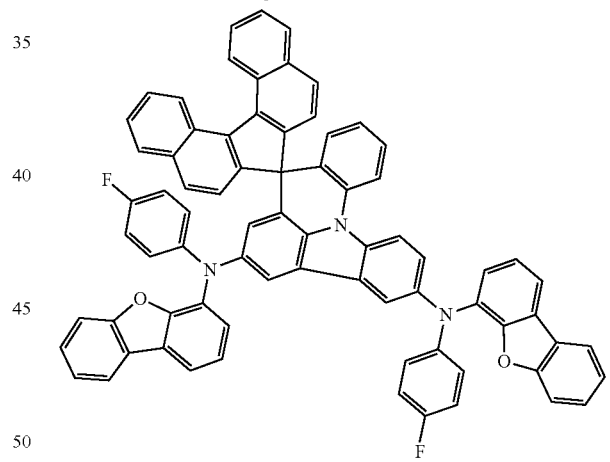
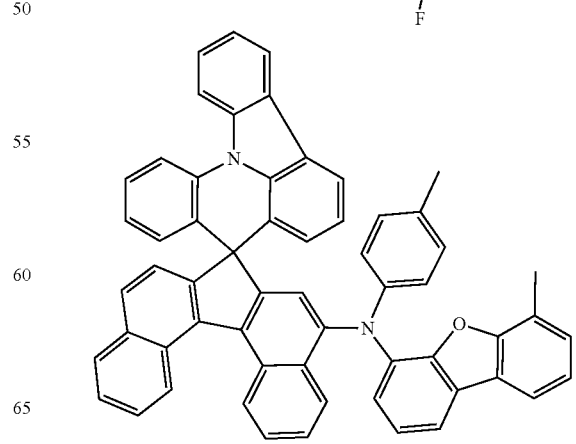

351
-continued
352
-continued
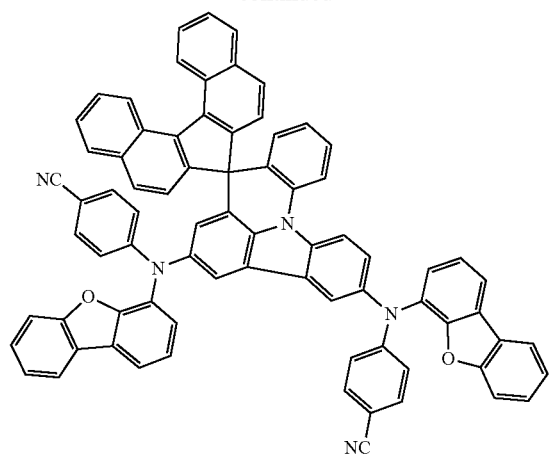
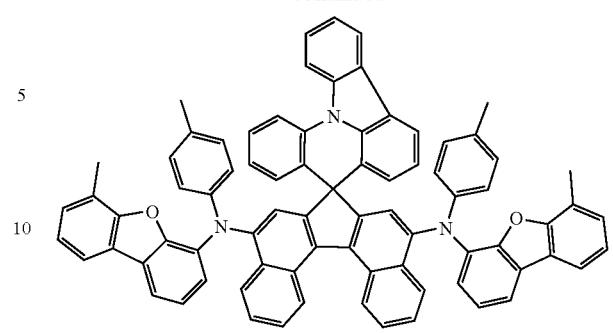
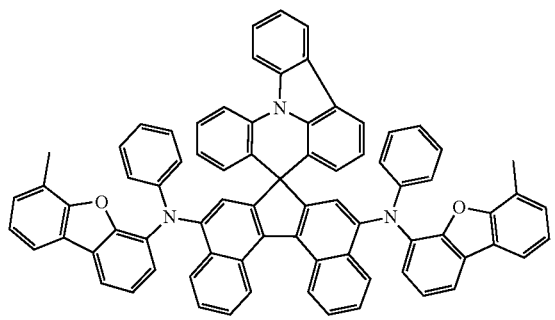
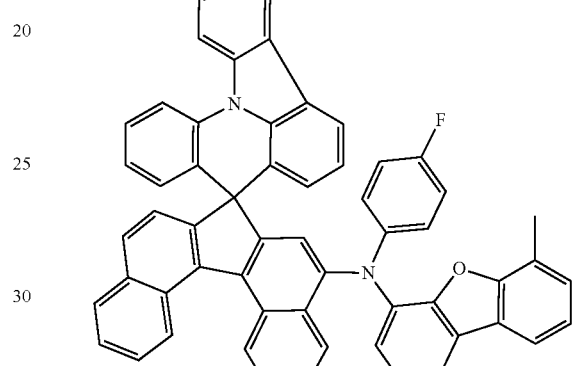
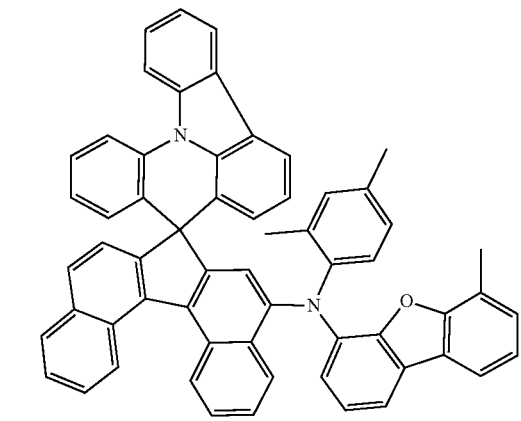
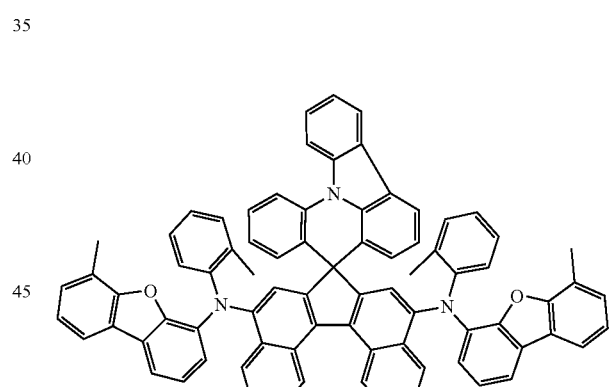
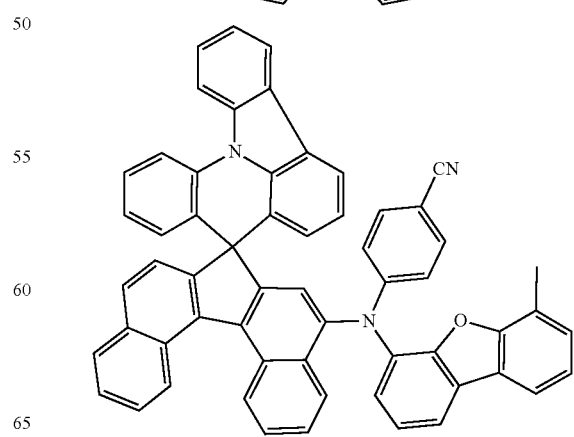

353
-continued
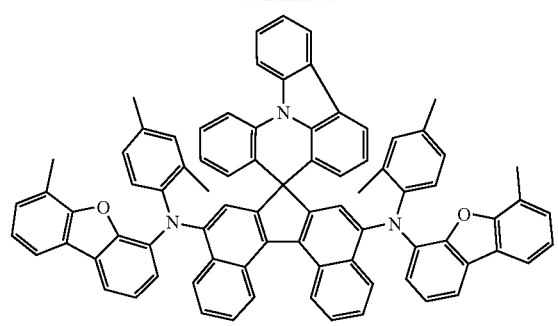
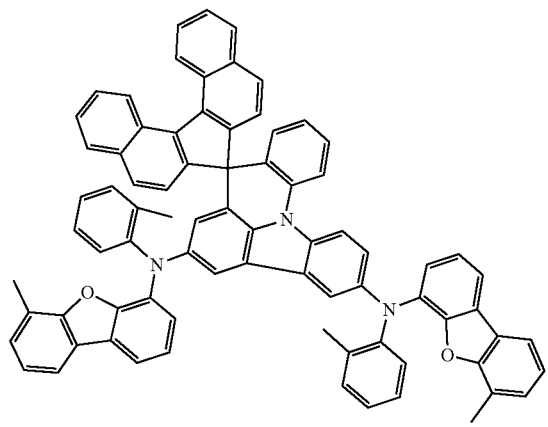
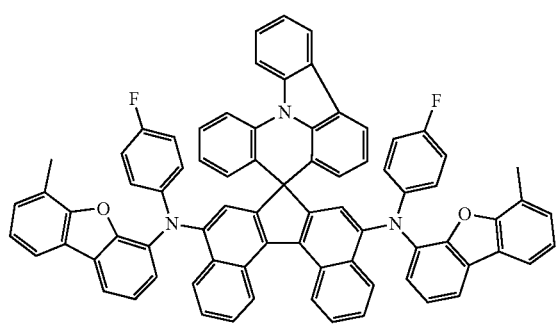
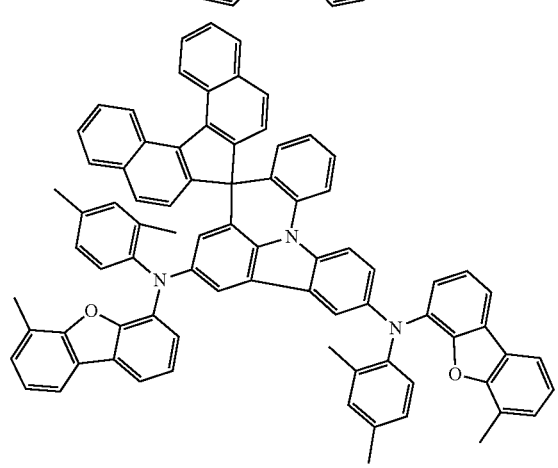
354
-continued
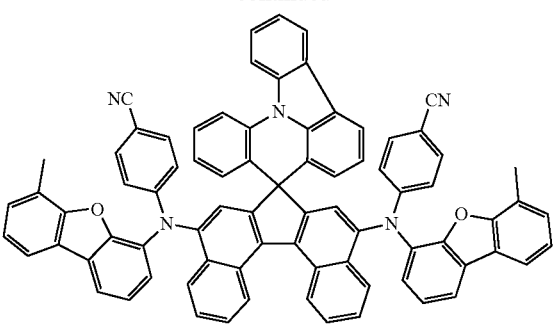
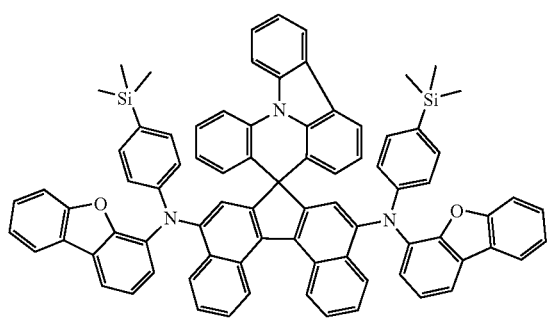
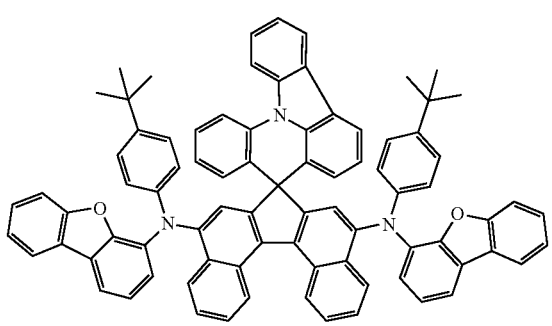
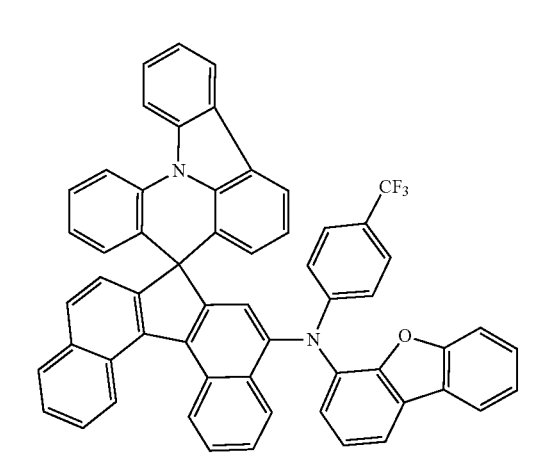

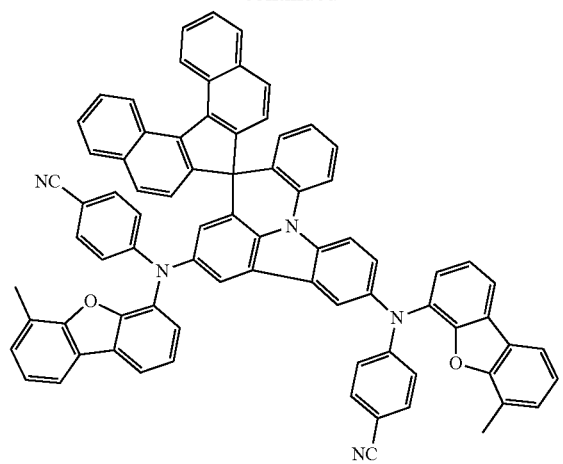
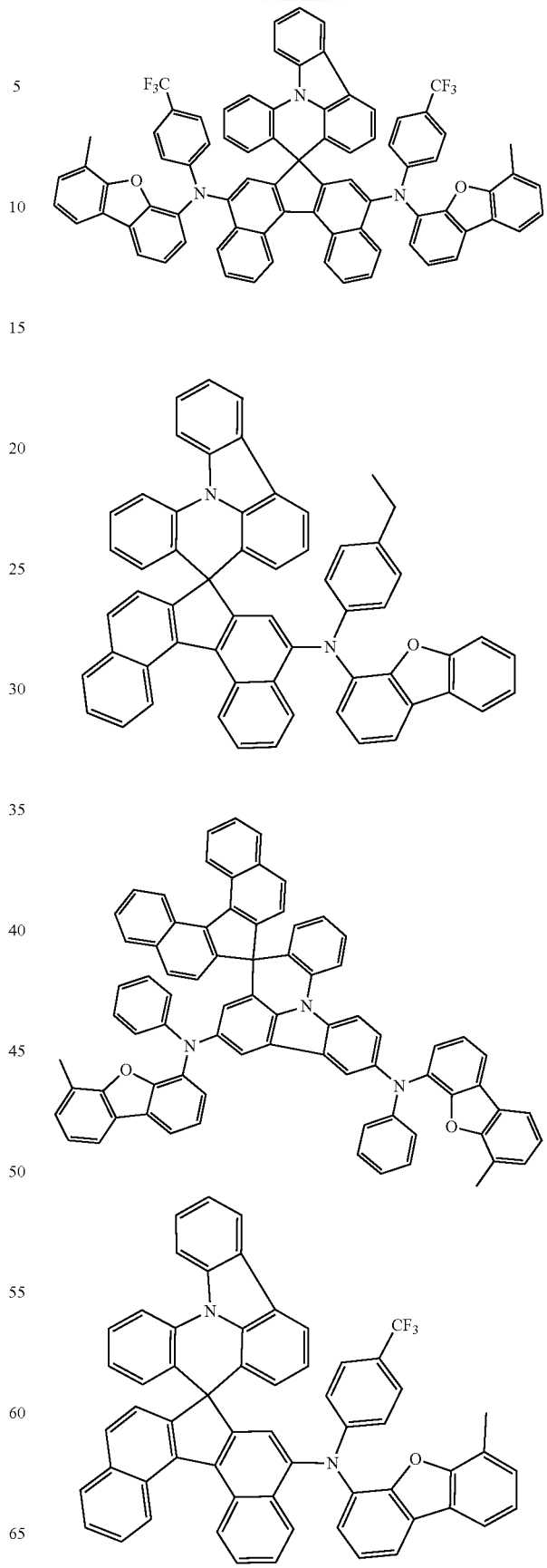

357
-continued
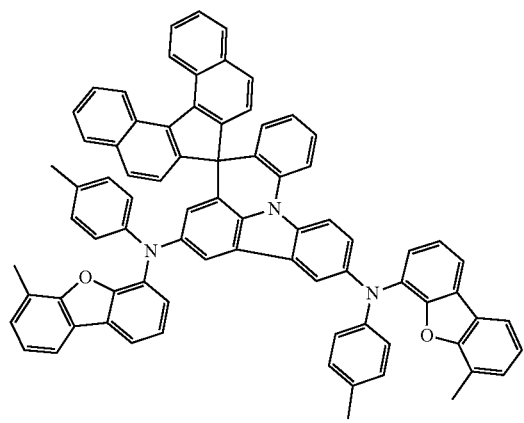
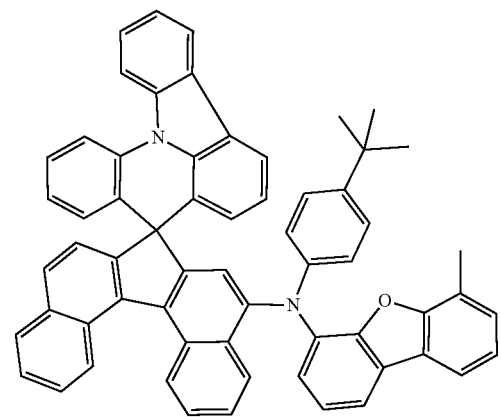
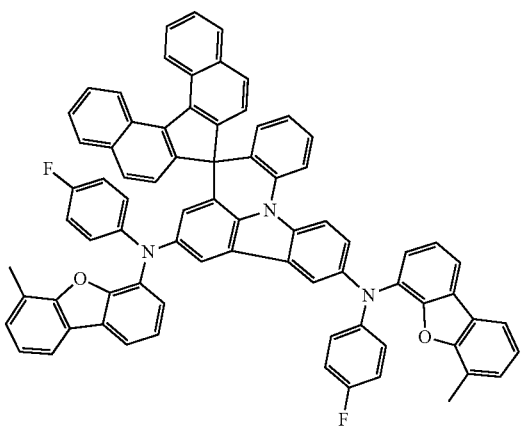
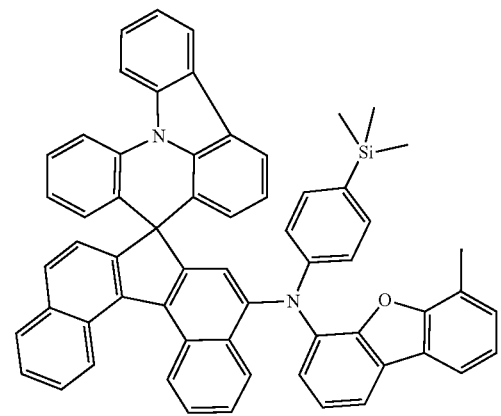
358
-continued
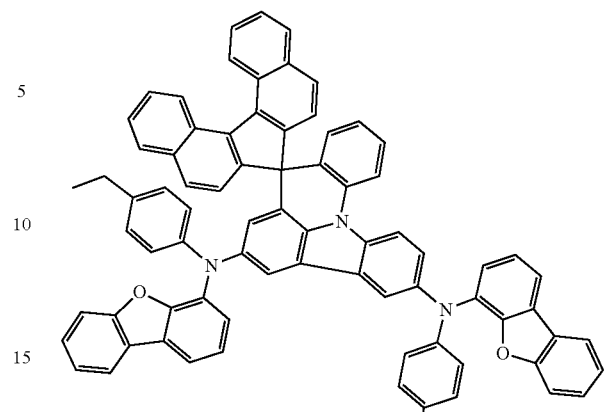
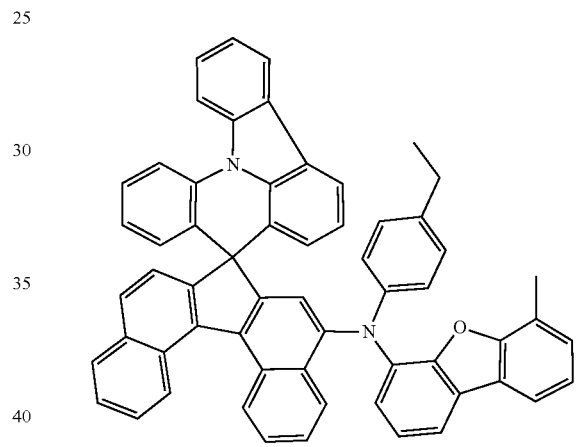
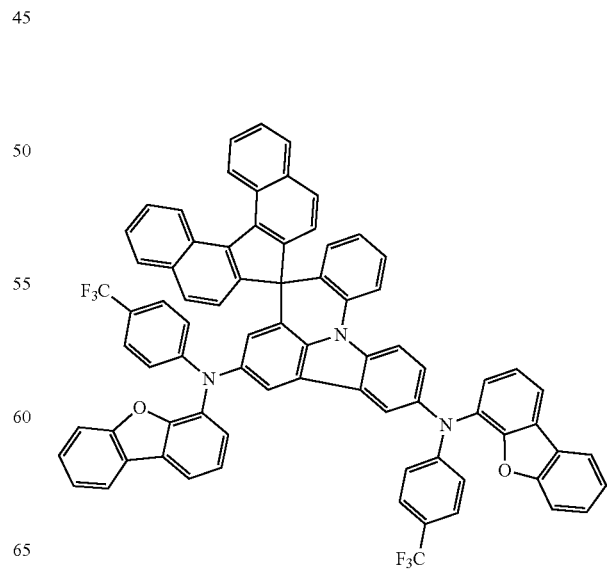

359
-continued
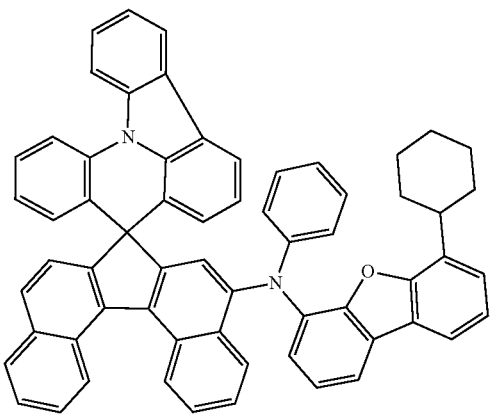
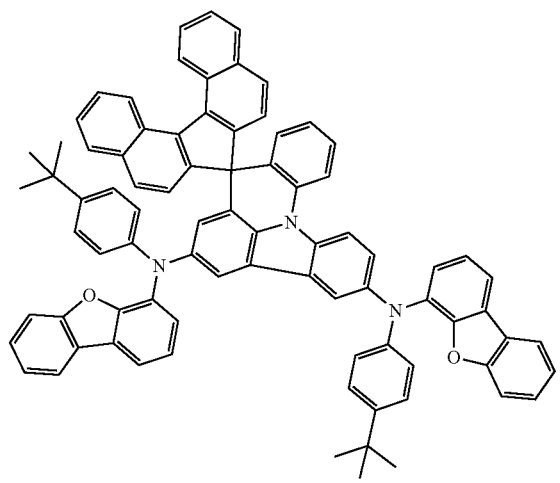
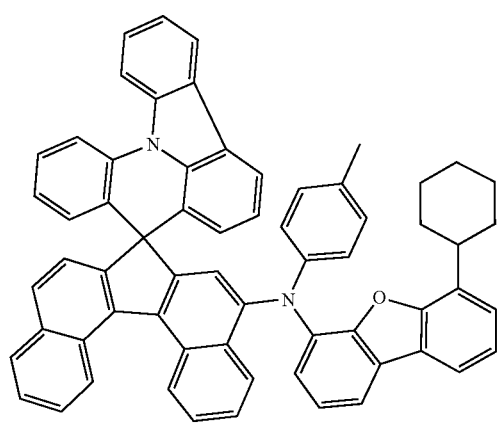
360
-continued
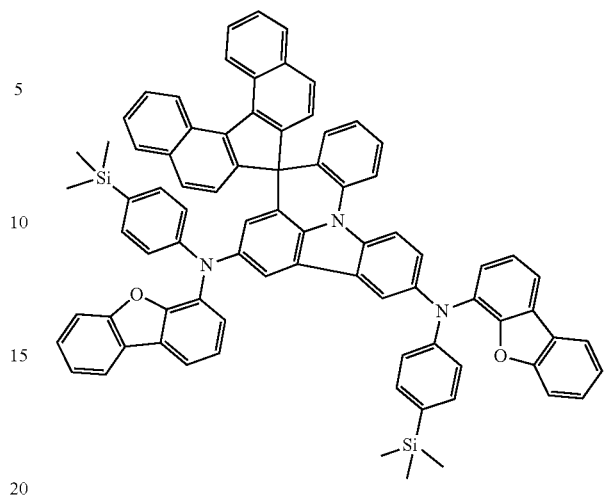
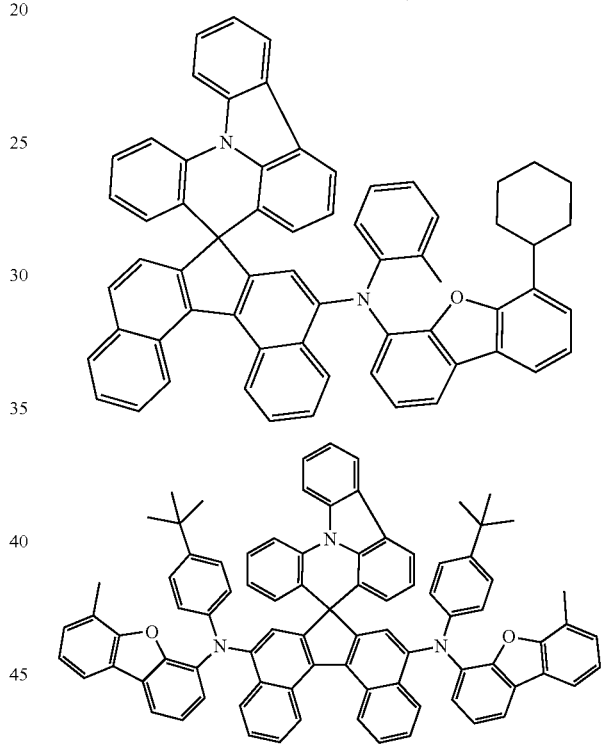
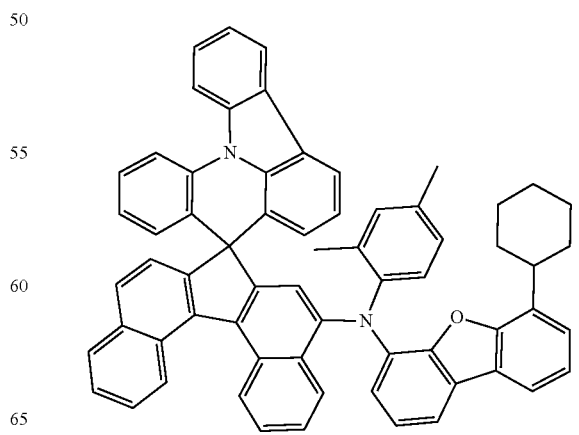

361
-continued
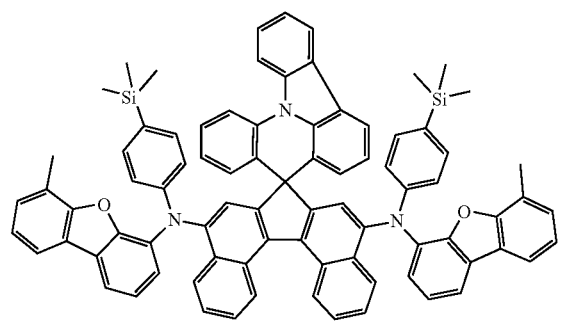
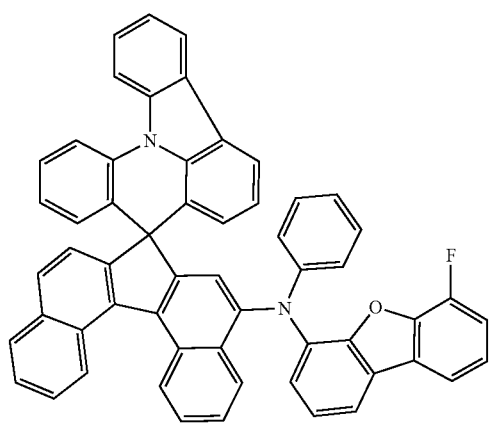
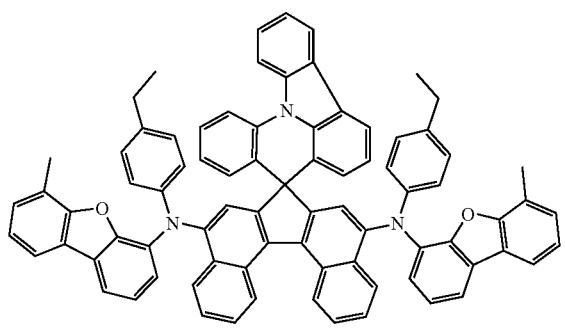
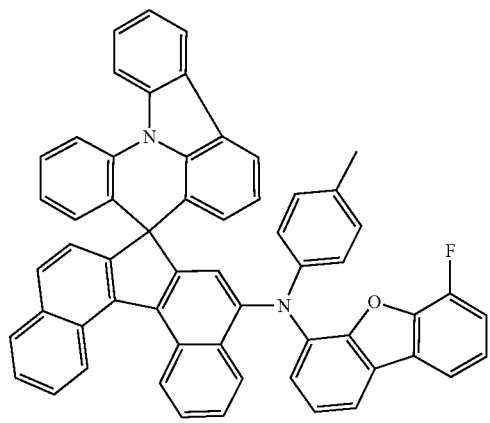
362
-continued
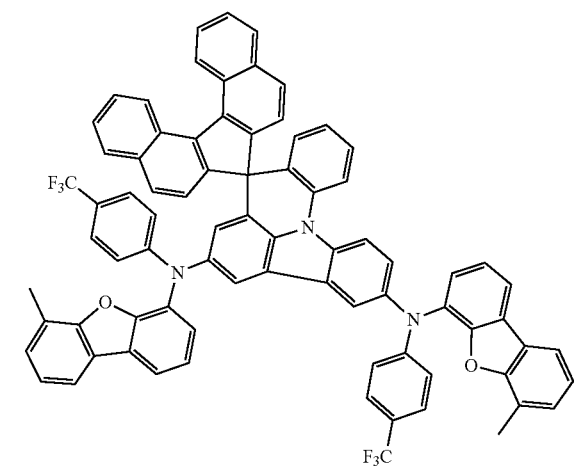
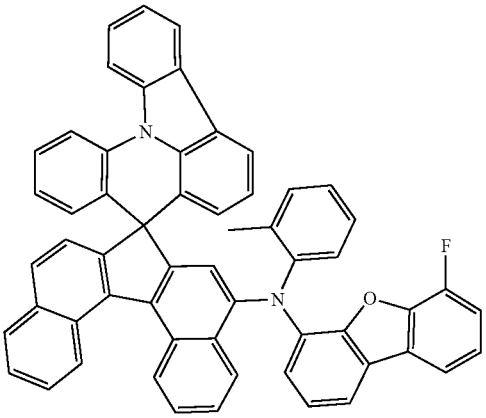
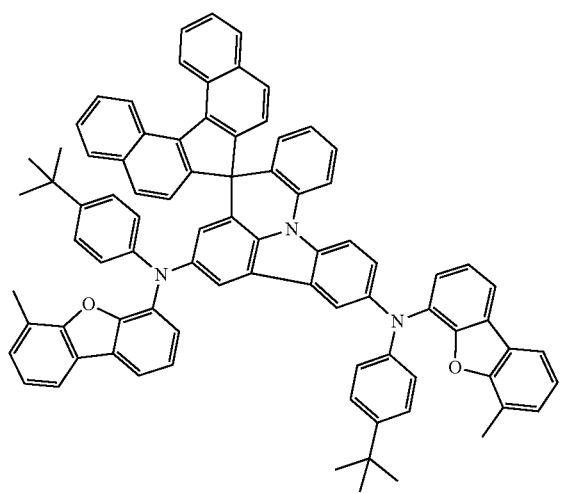

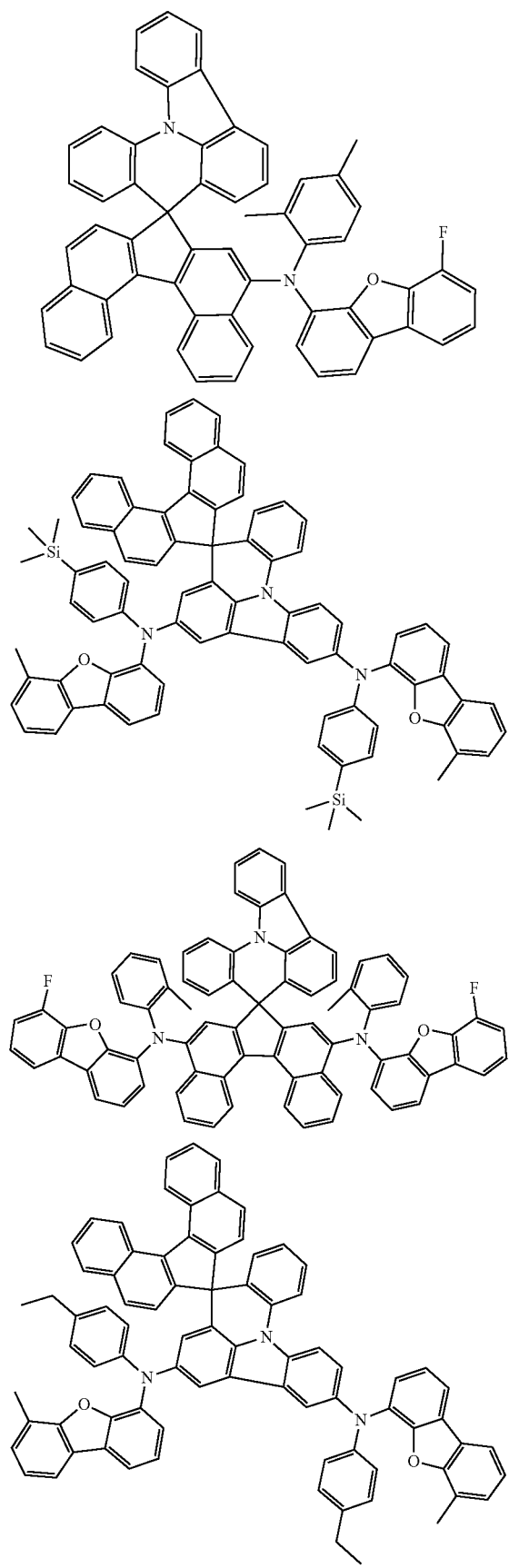
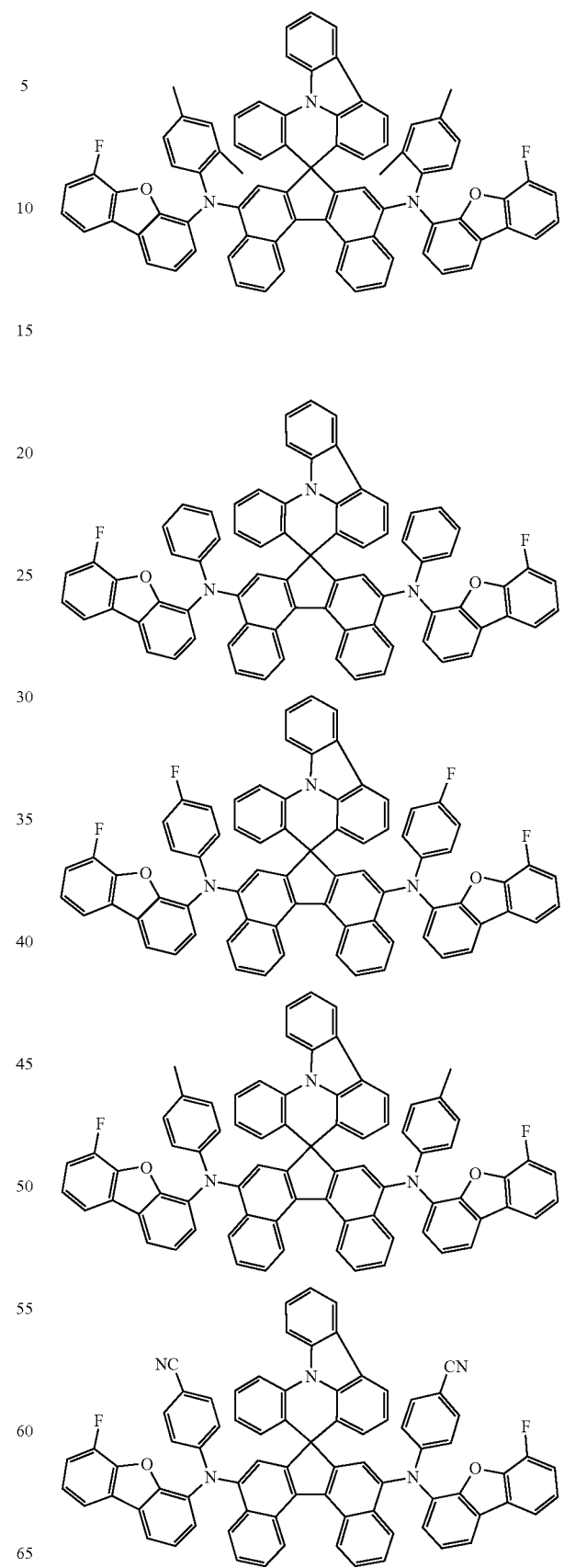

365
-continued
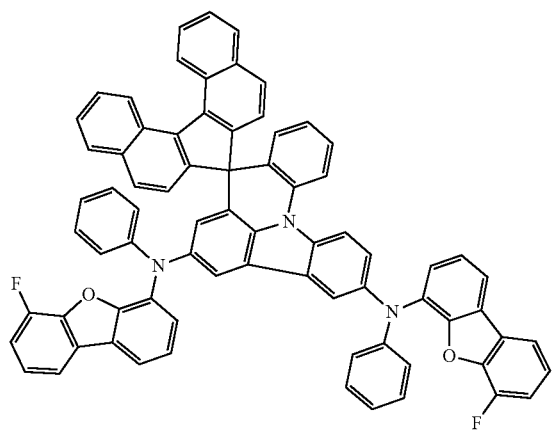
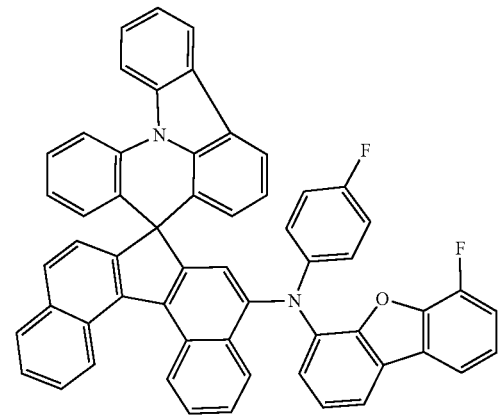
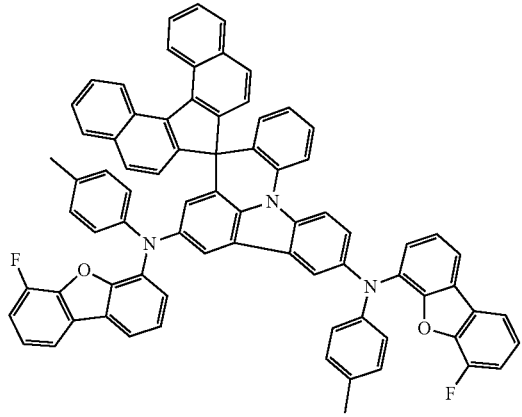
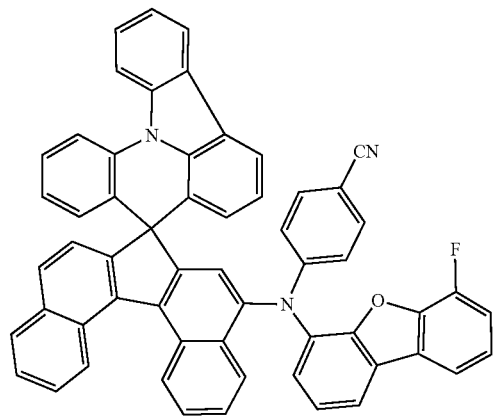
366
-continued
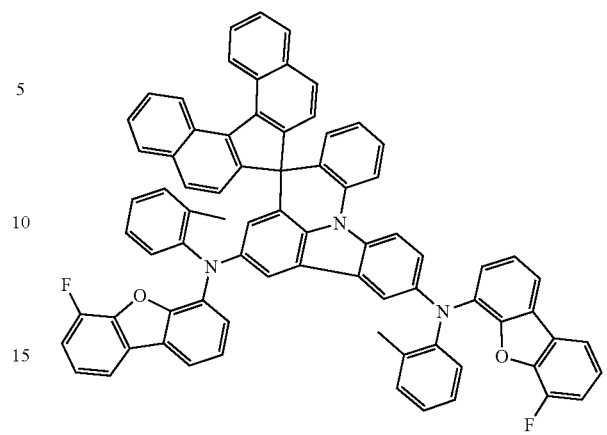
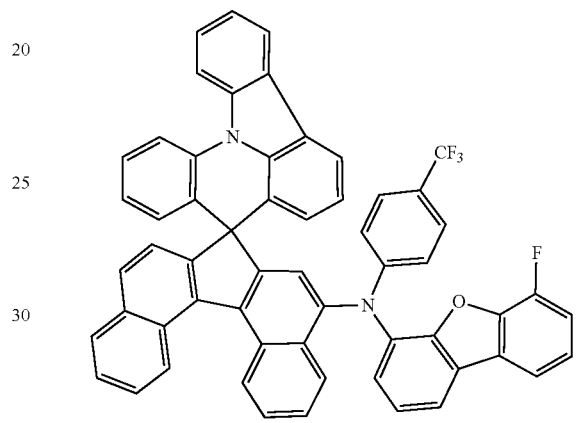
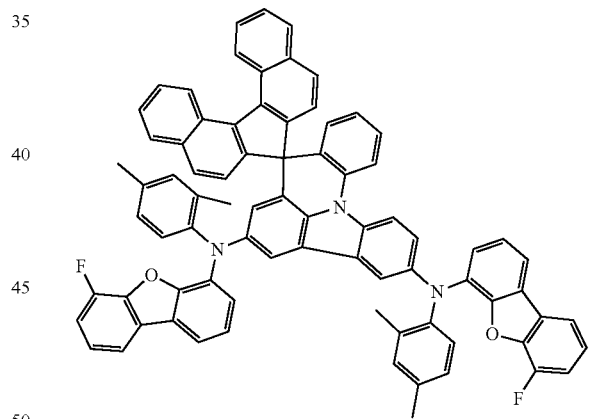
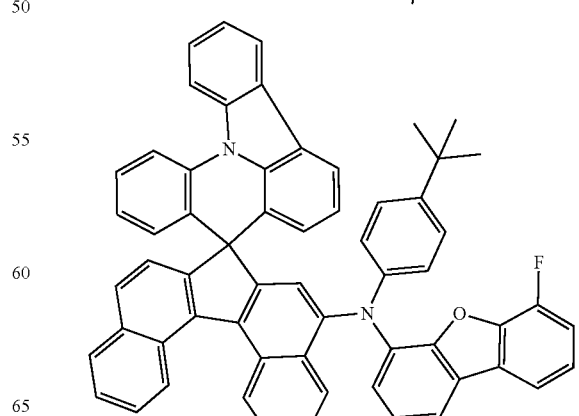

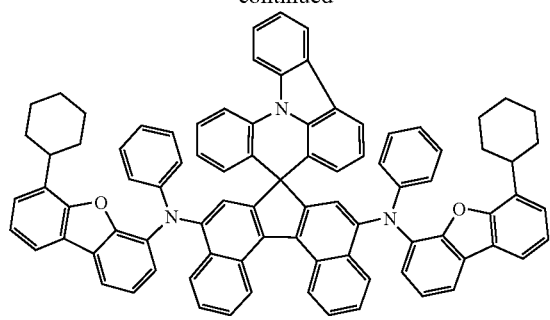
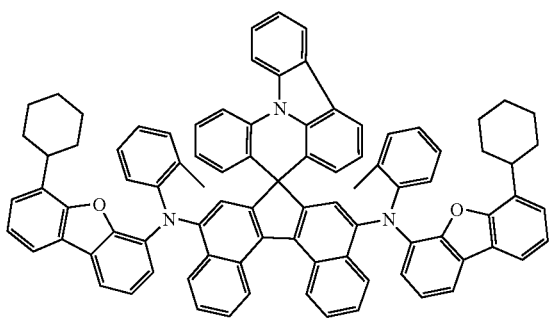
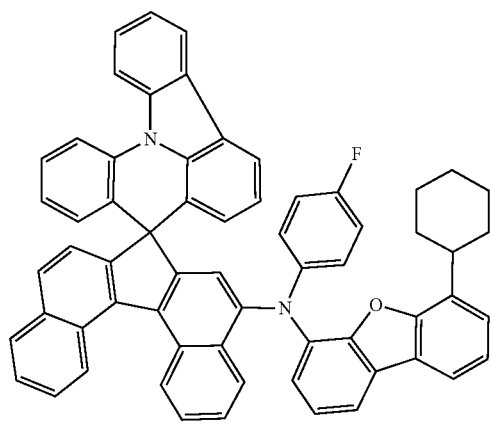
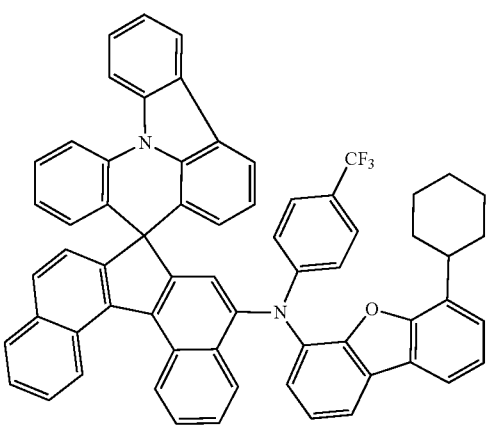
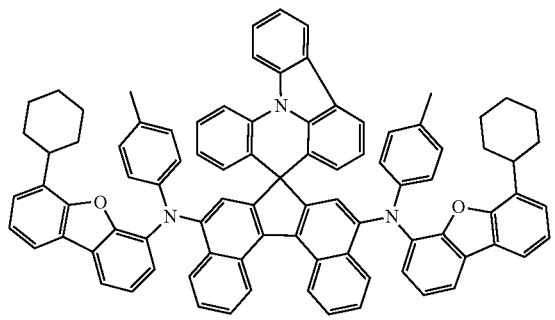
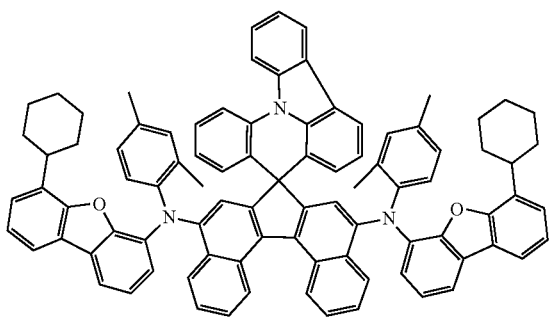
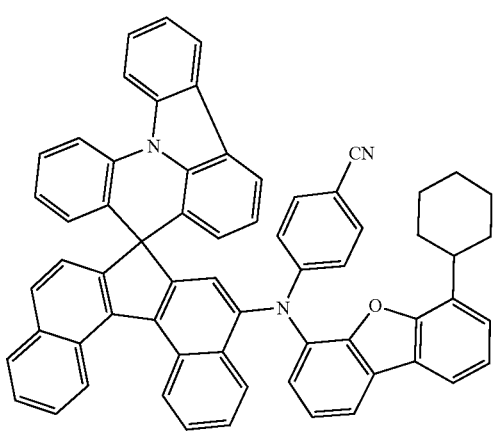
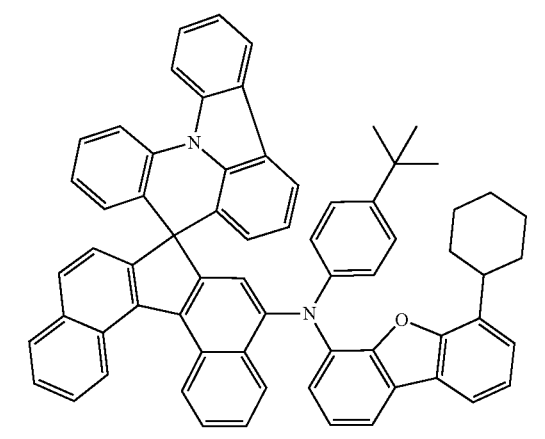

369
-continued
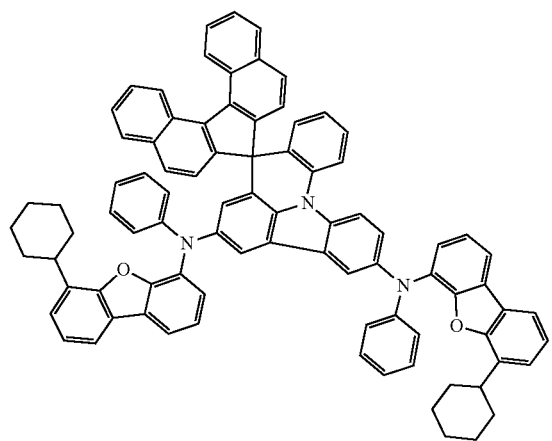
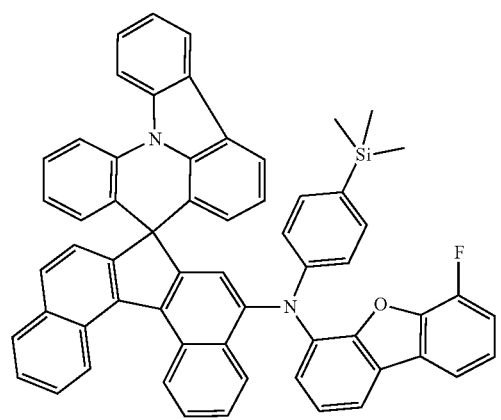
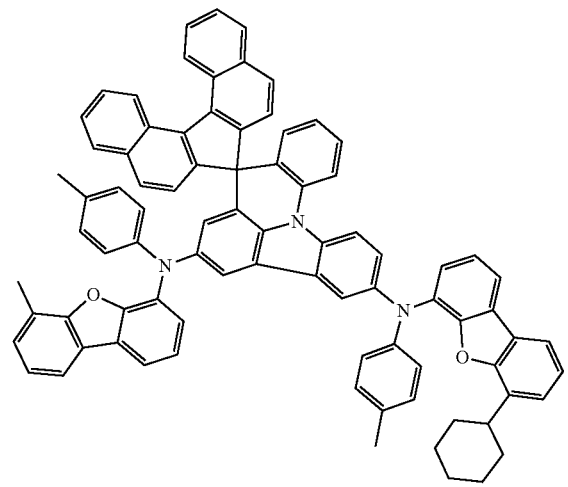
370
-continued
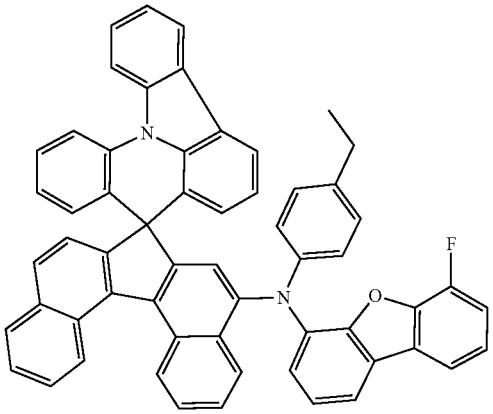
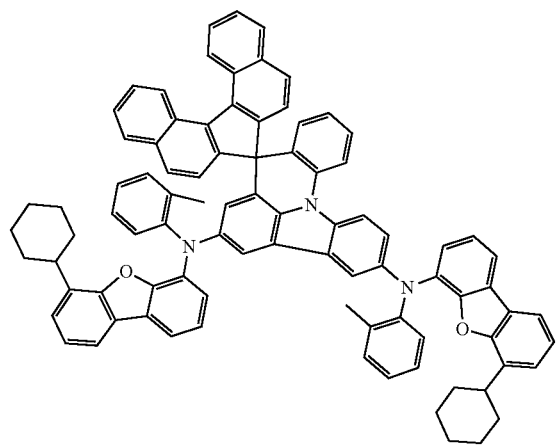
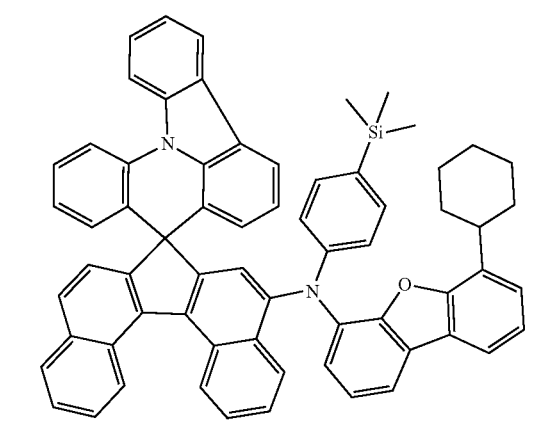
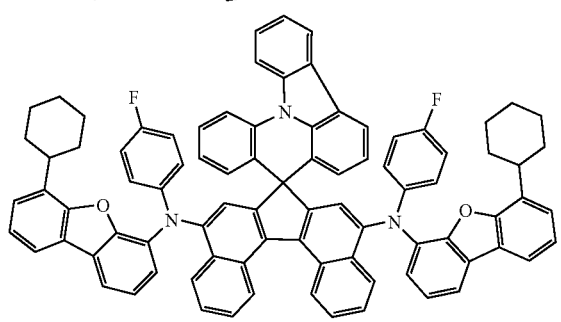

371
-continued
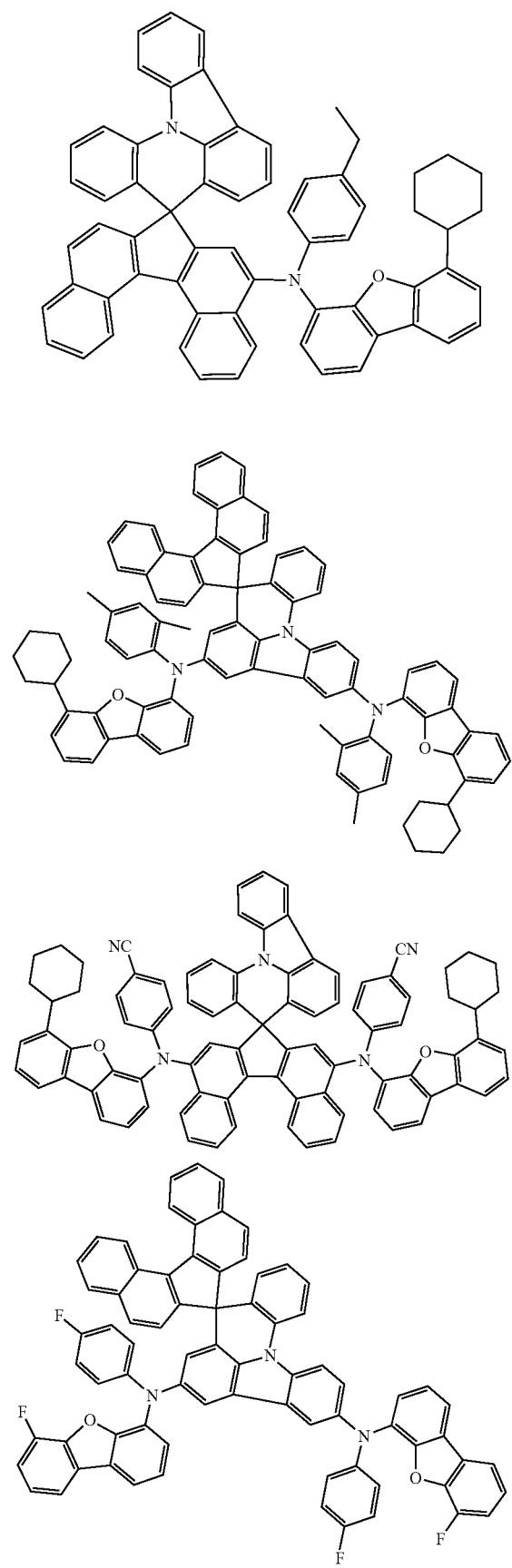
372
-continued
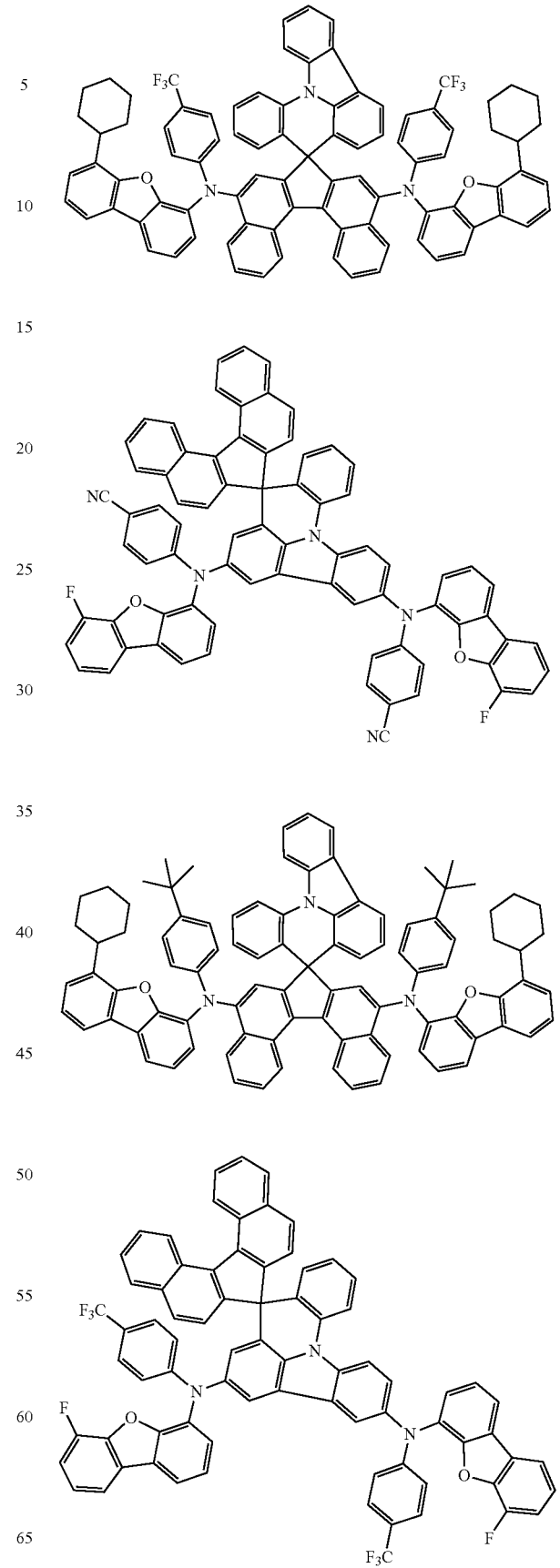

373
-continued
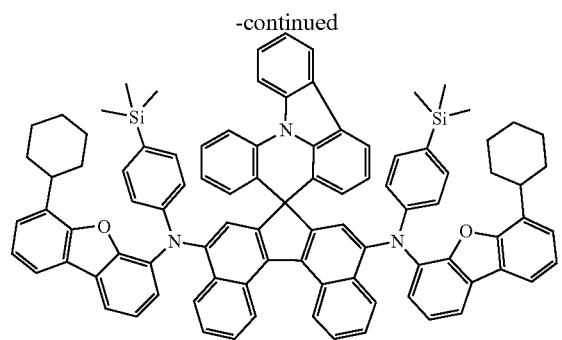
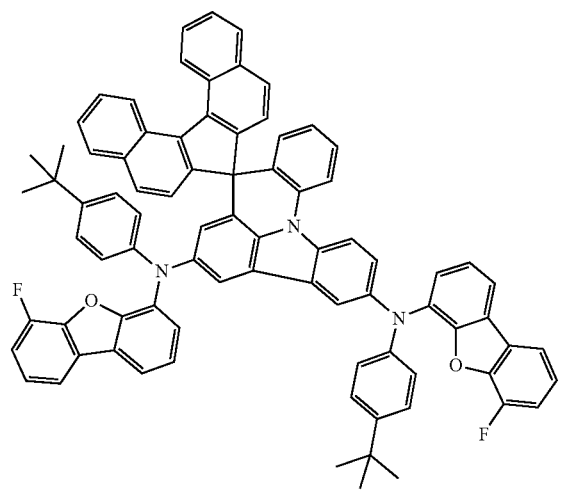
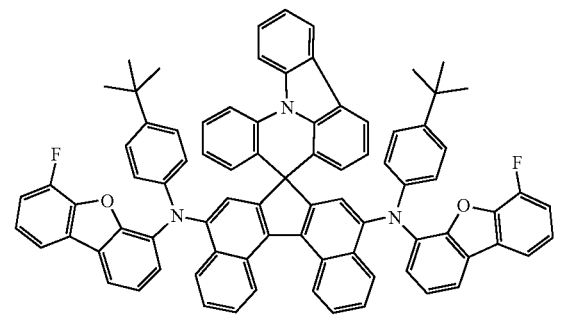
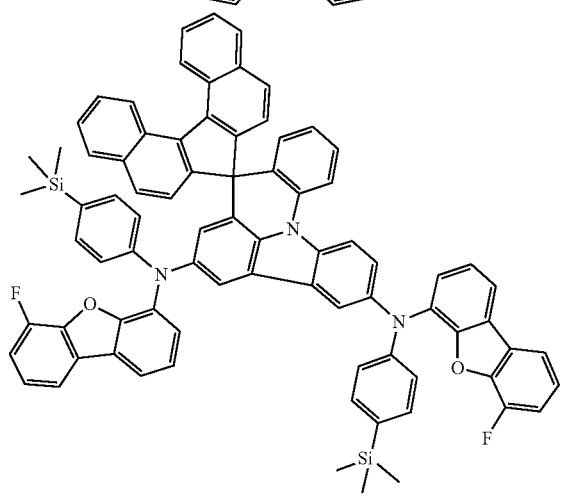
374
-continued
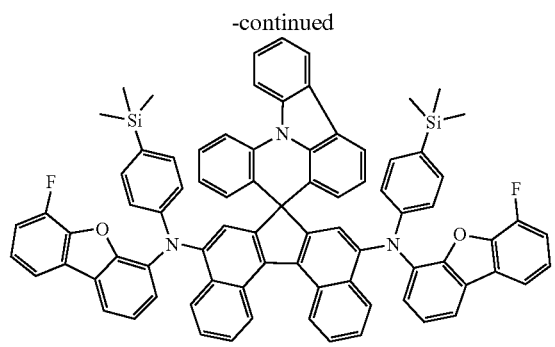
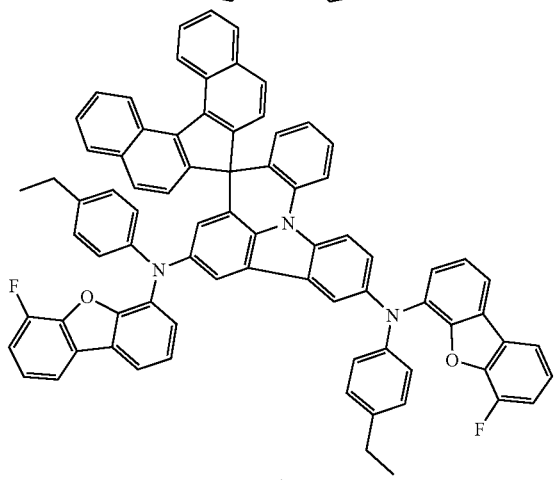
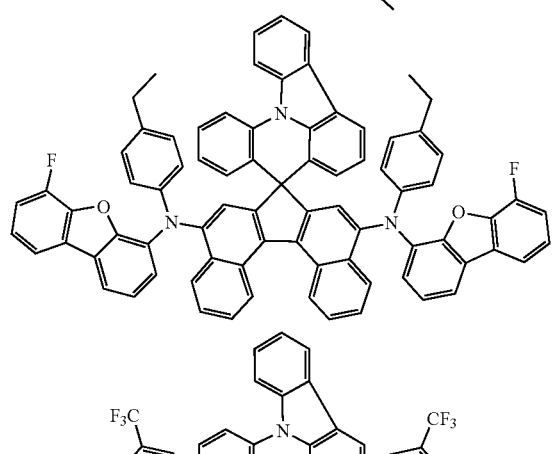
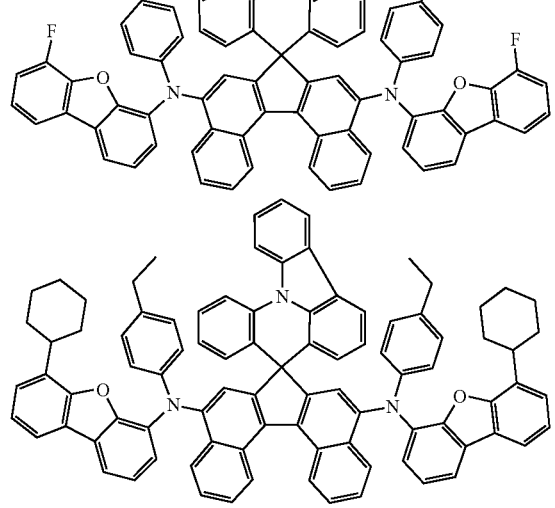

375
-continued
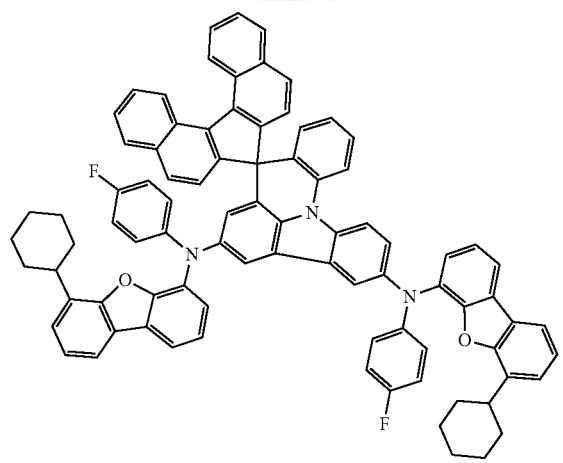
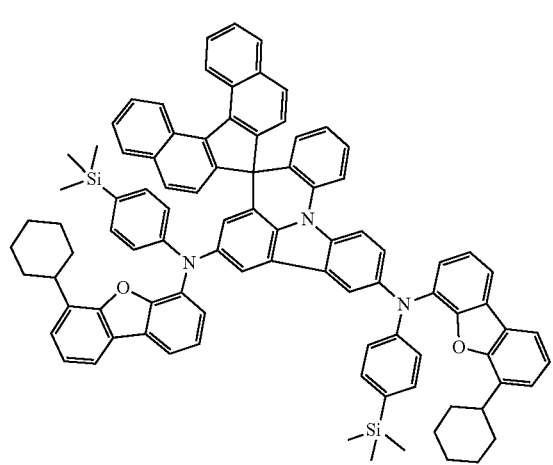
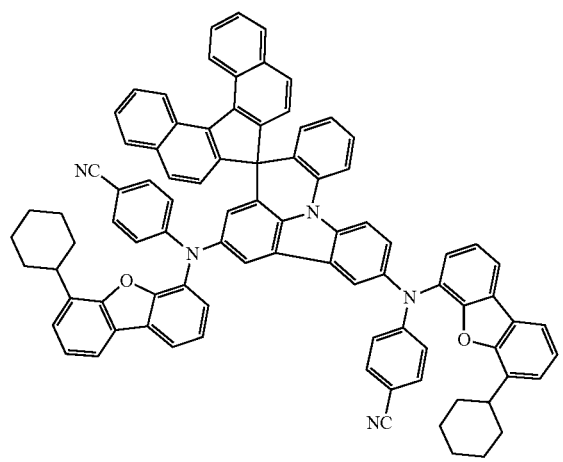
376
-continued
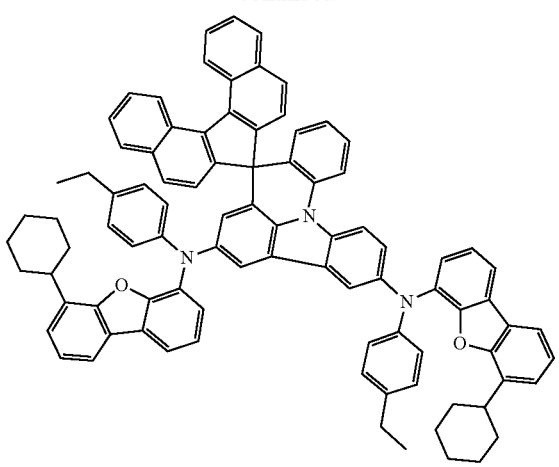
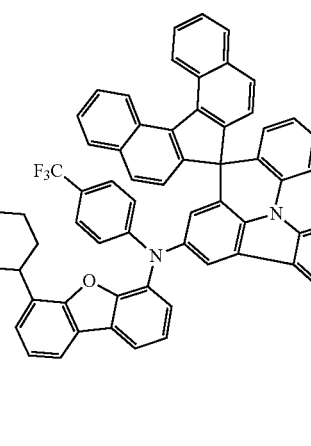
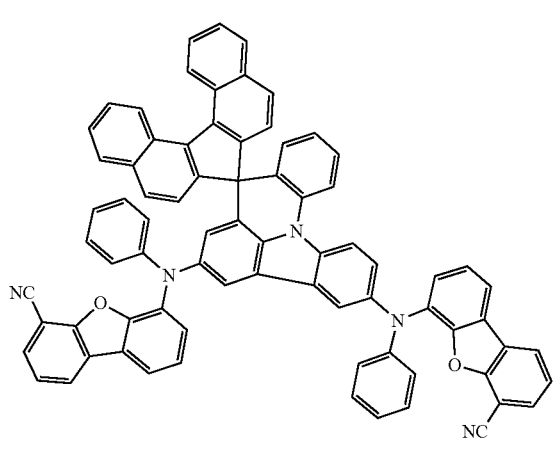

-continued
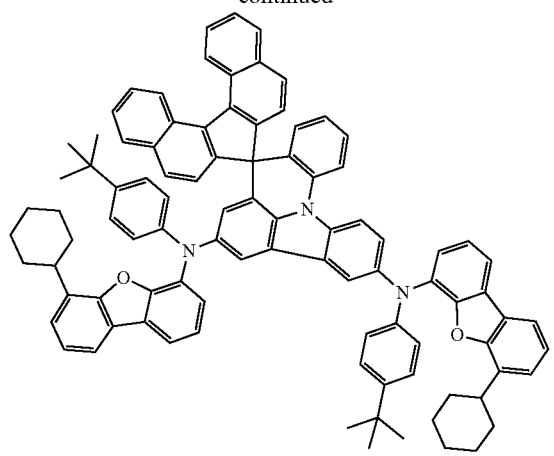
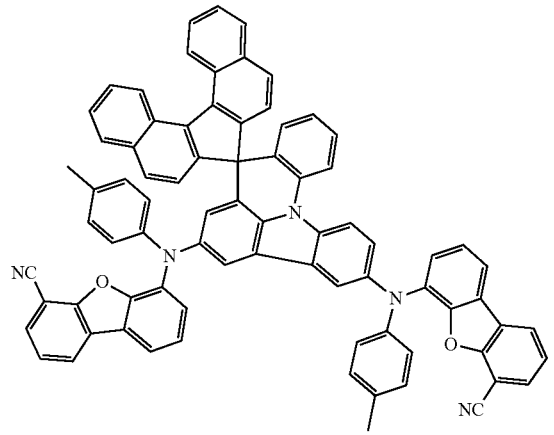
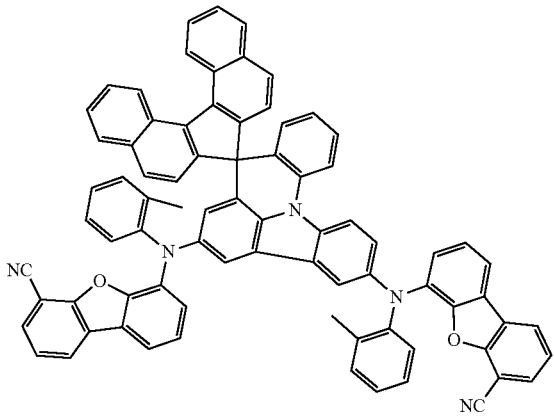
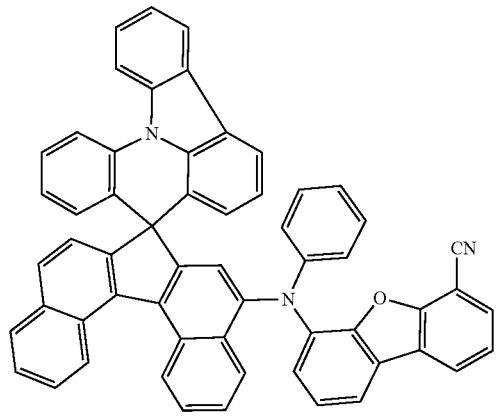
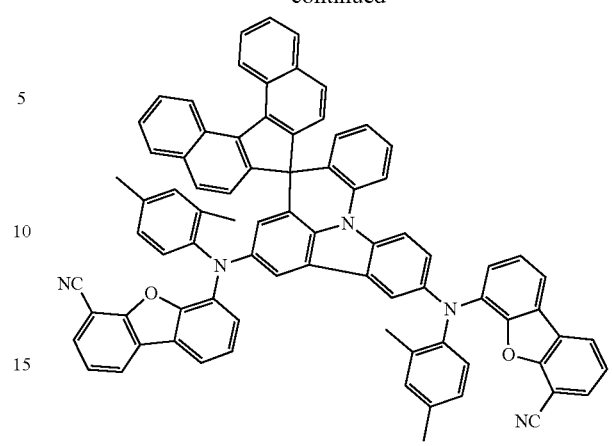
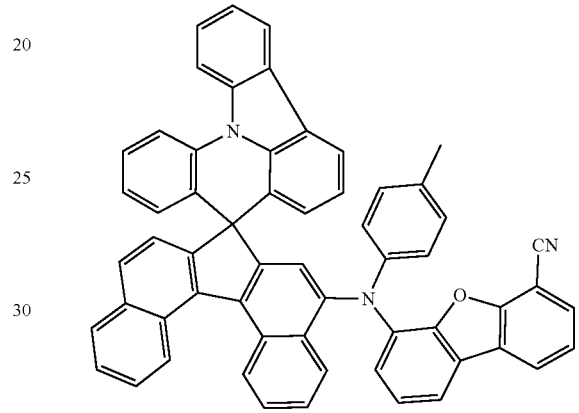
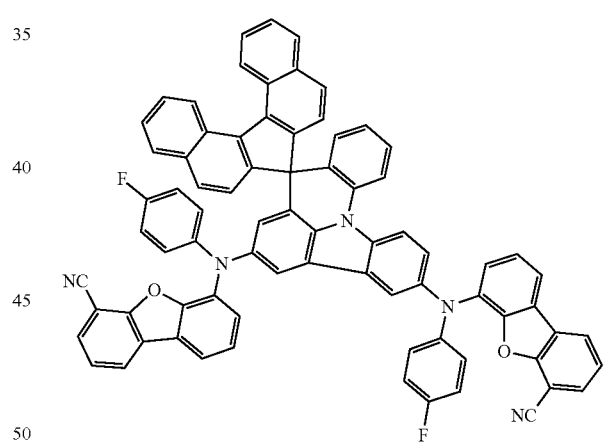
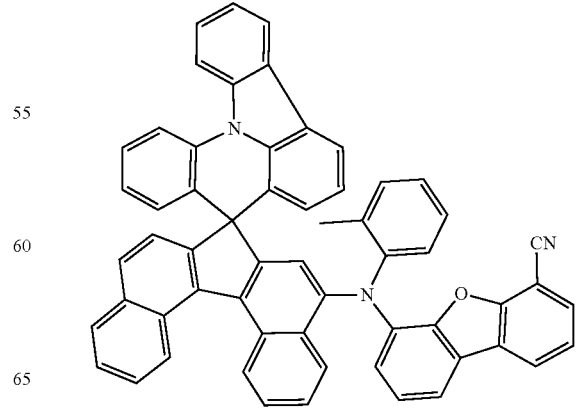

379
-continued
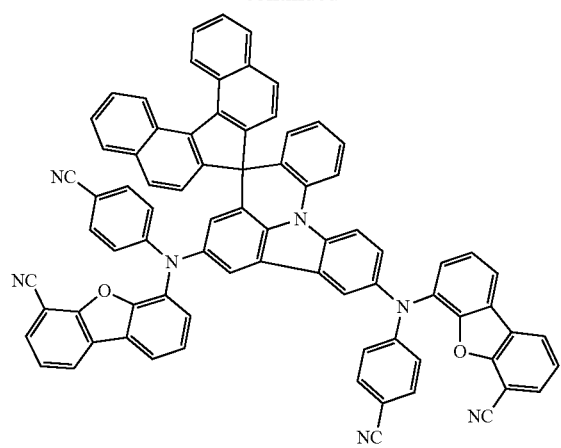
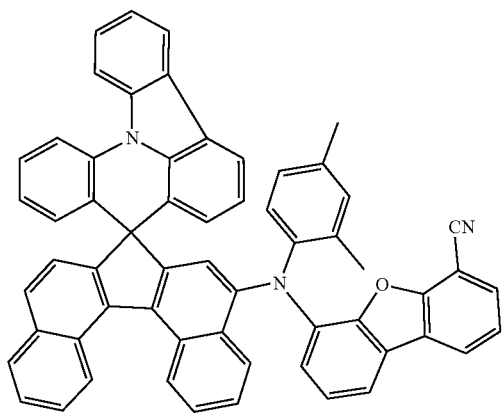
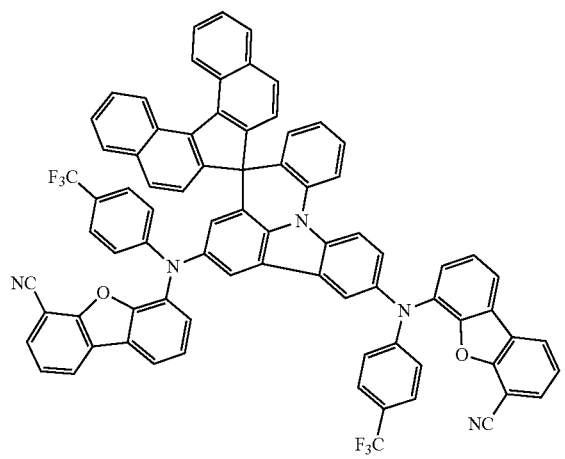
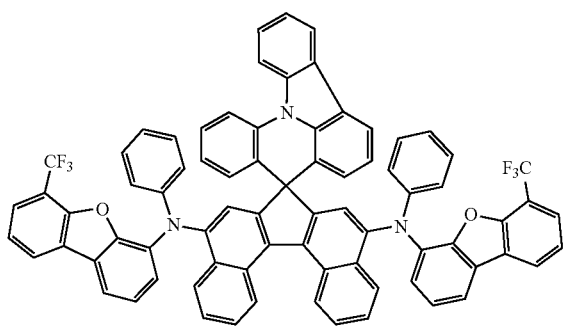
380
-continued
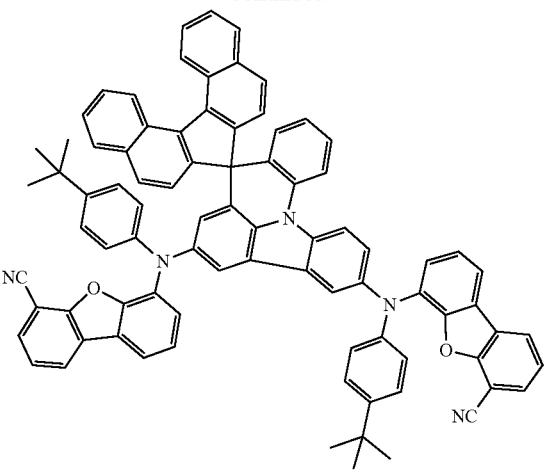
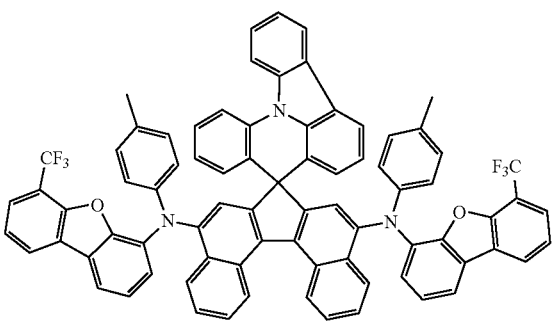
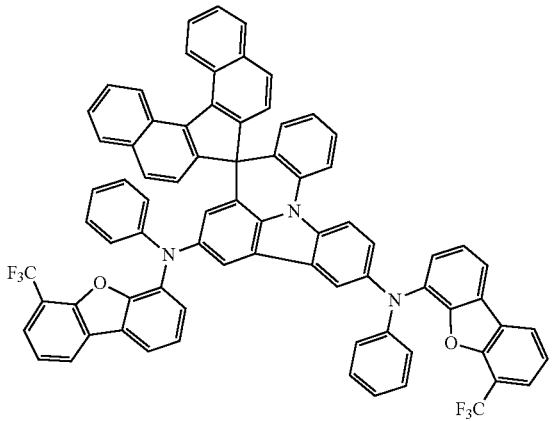
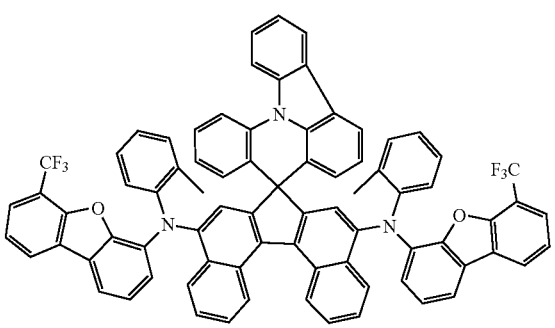

381
-continued
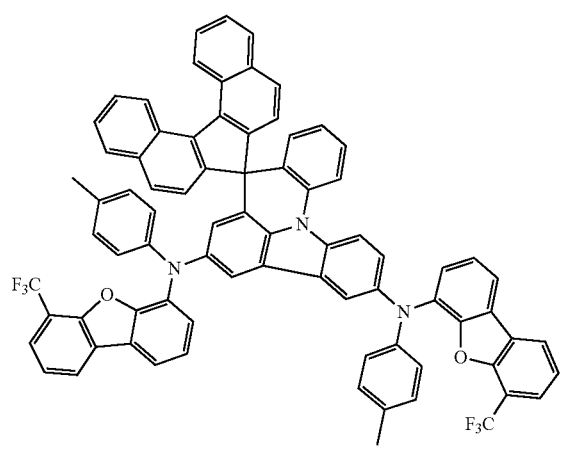
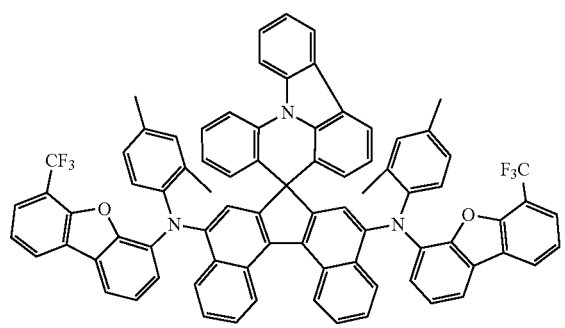
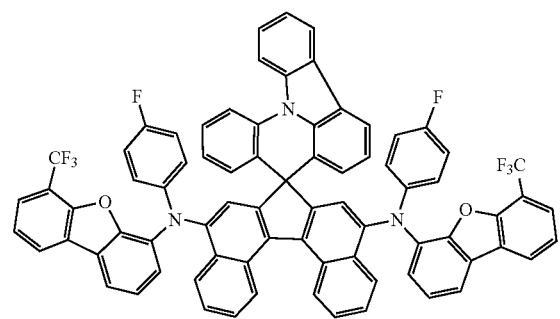
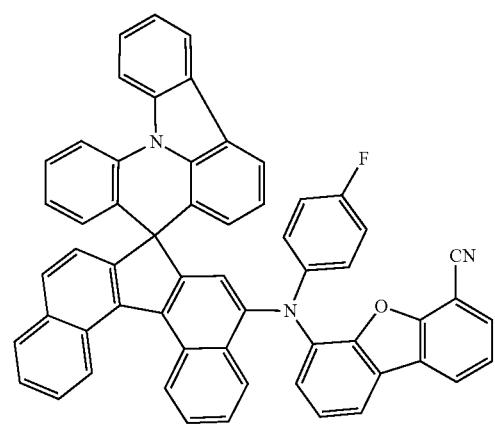
382
-continued
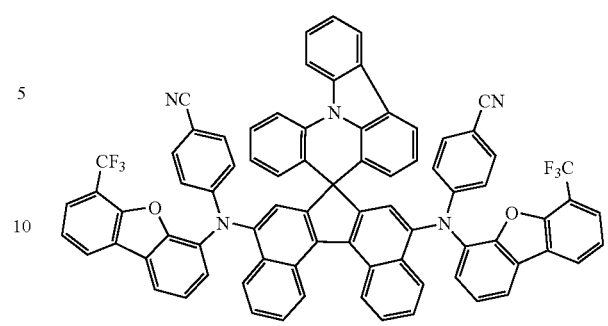
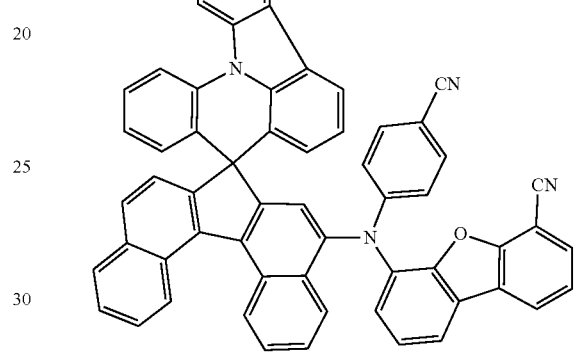
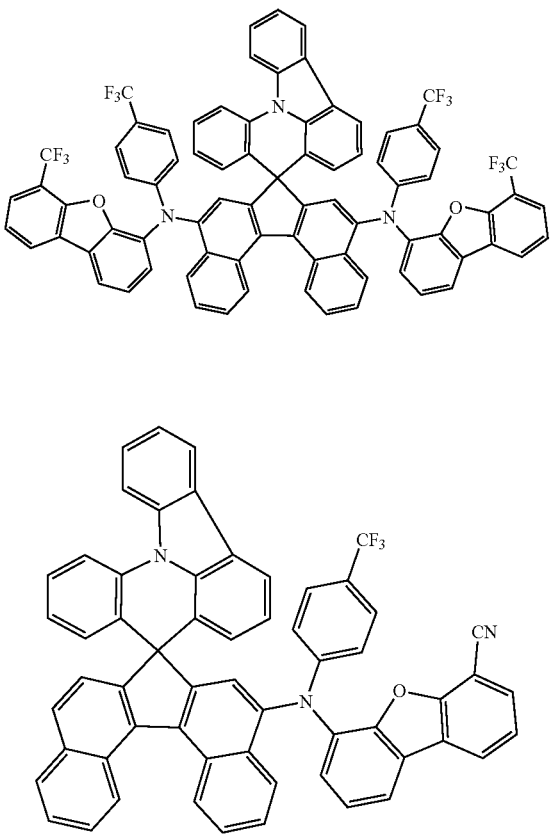

383
-continued
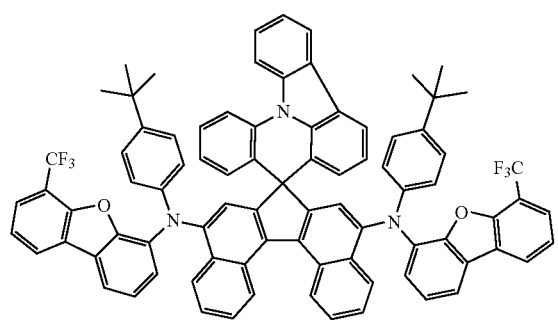
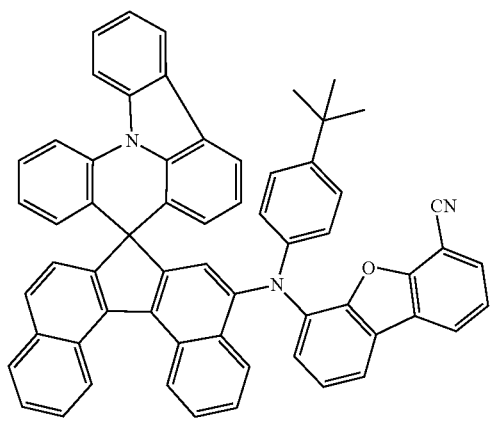
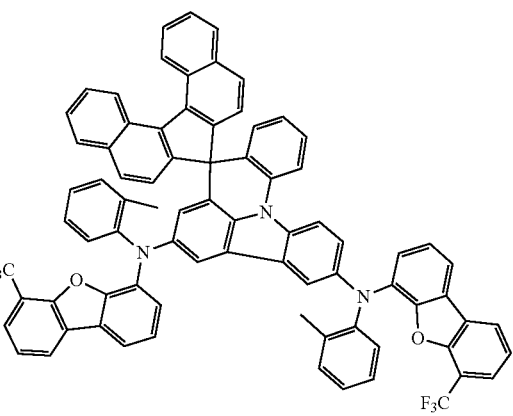
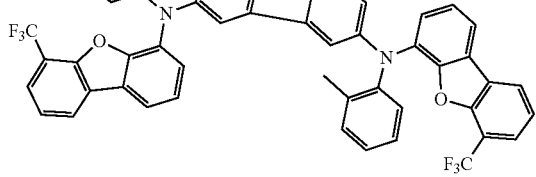
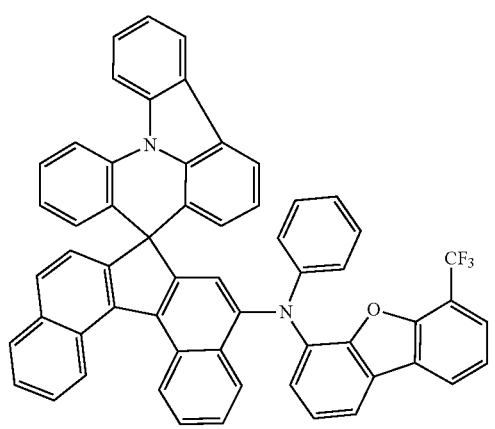
384
-continued
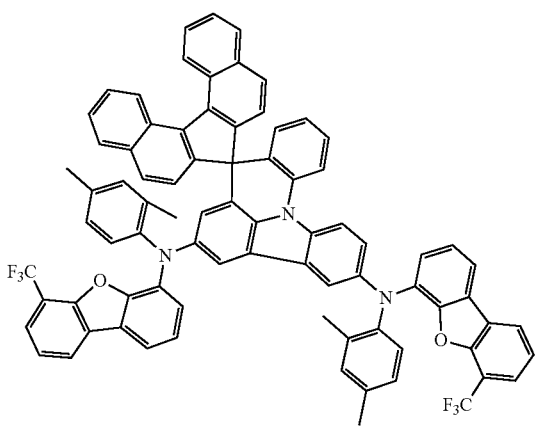
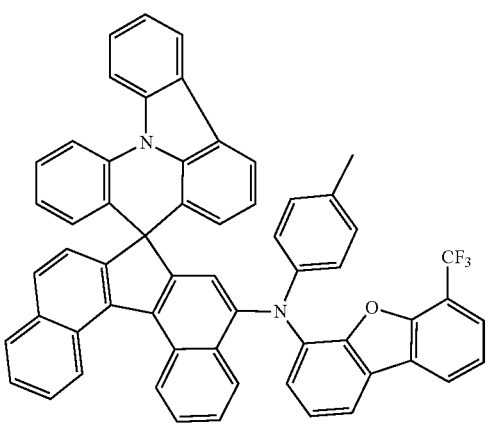
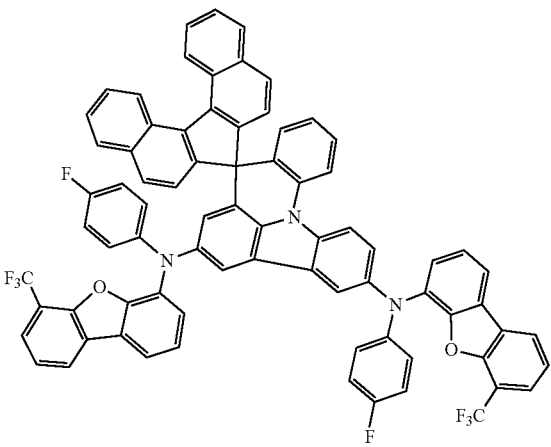
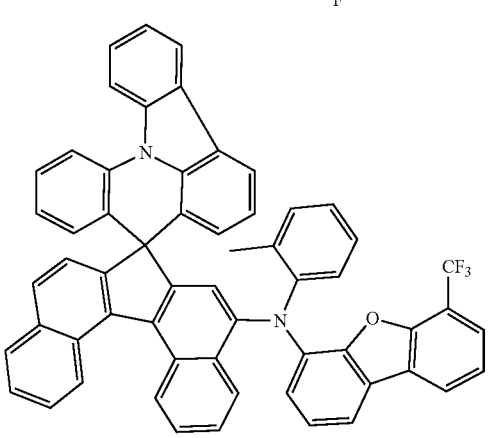

385
-continued
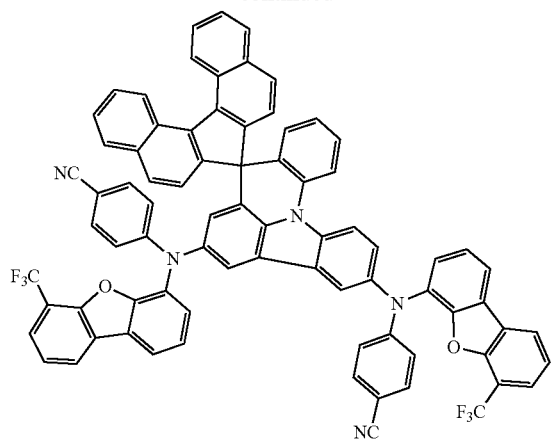
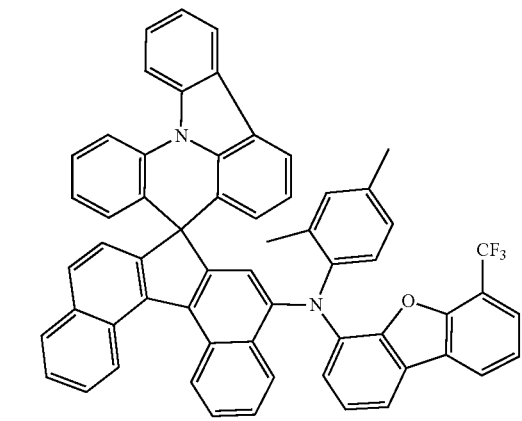
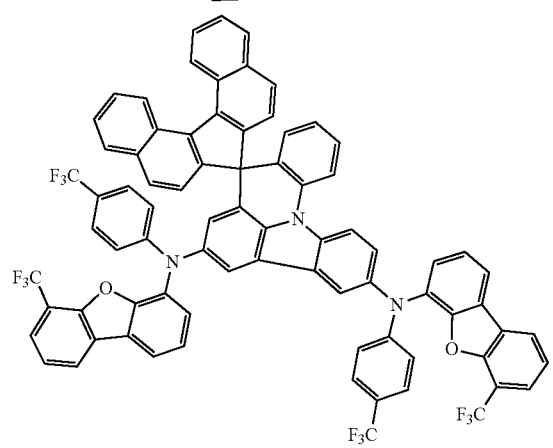
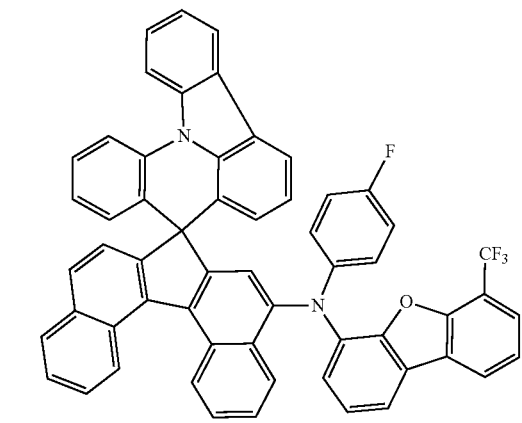
386
-continued
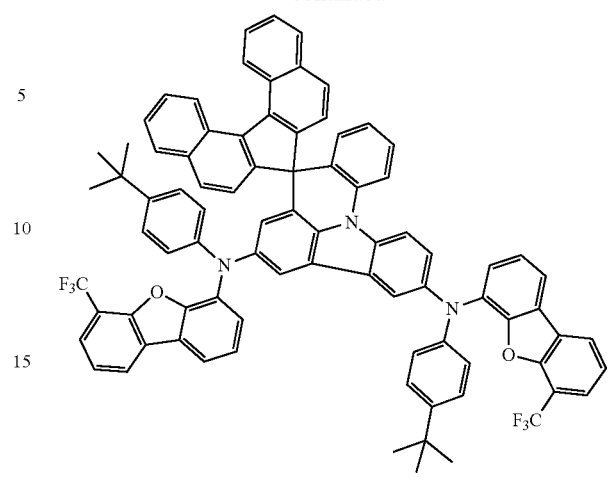
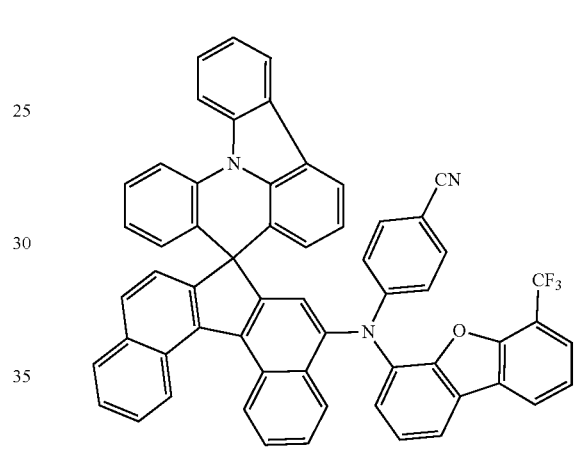
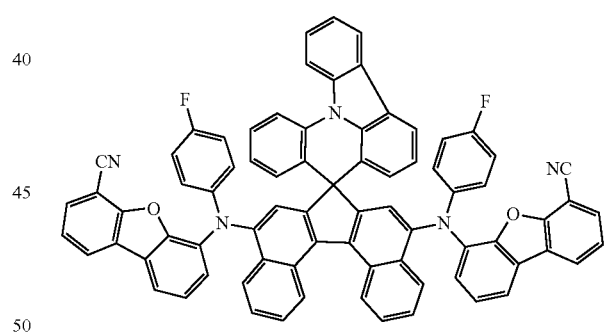
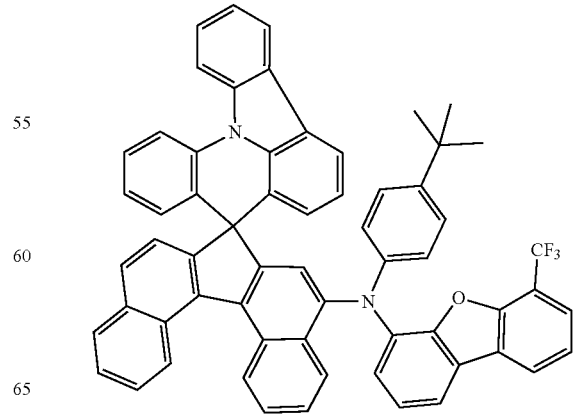

387
-continued
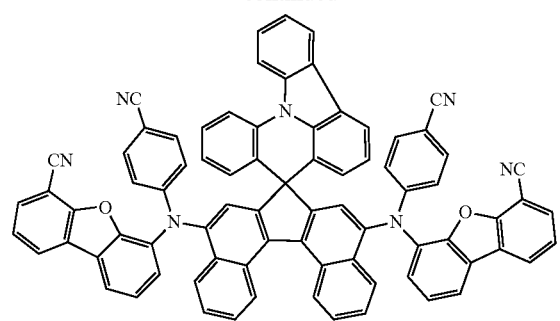
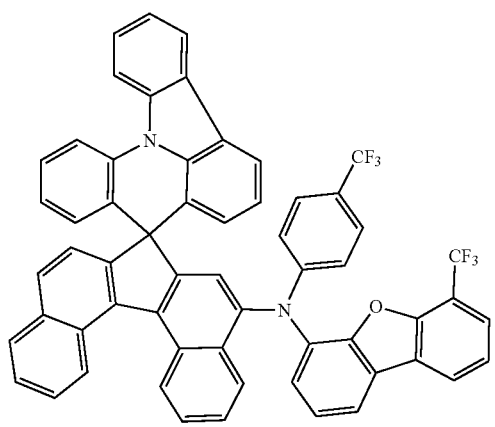
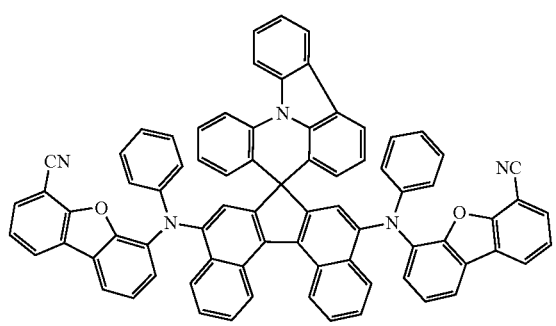
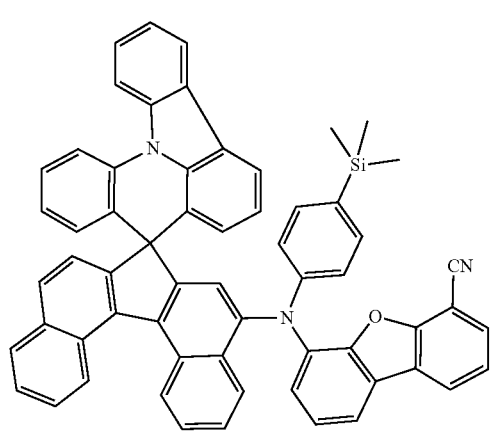
388
-continued
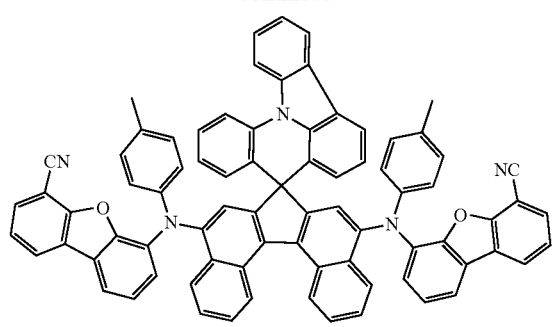
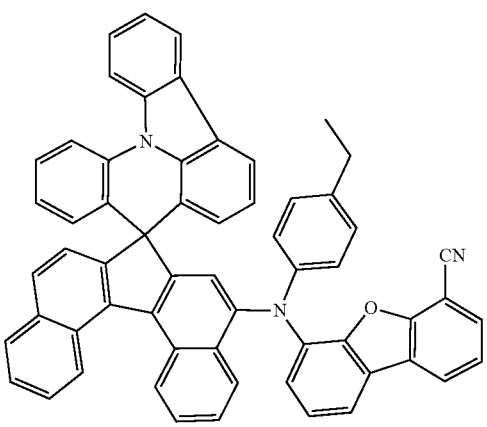
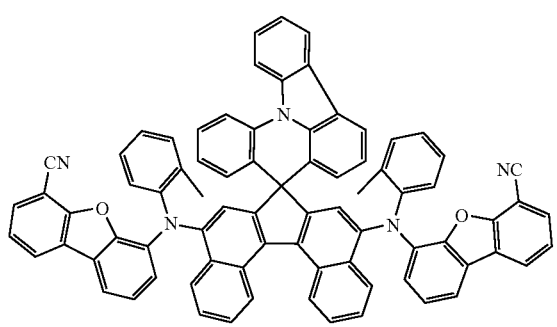
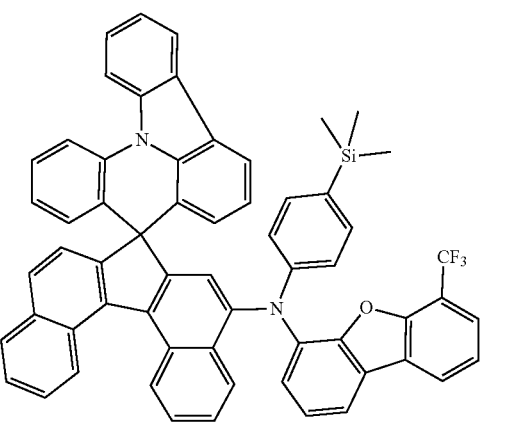

389
-continued
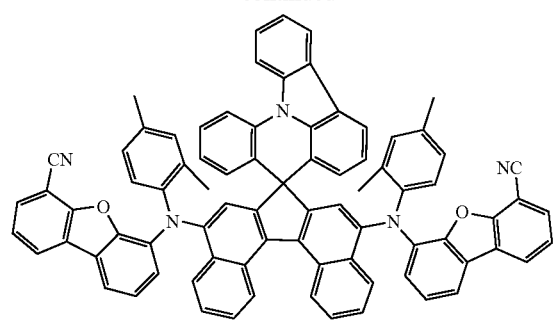
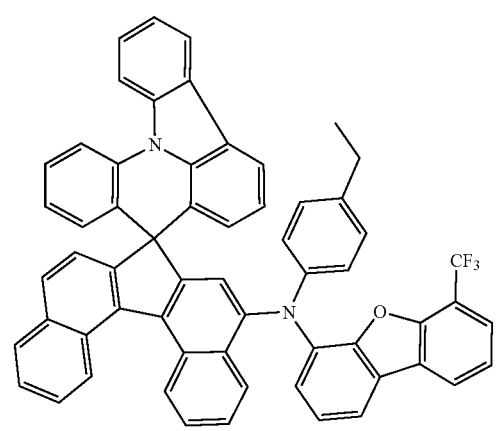
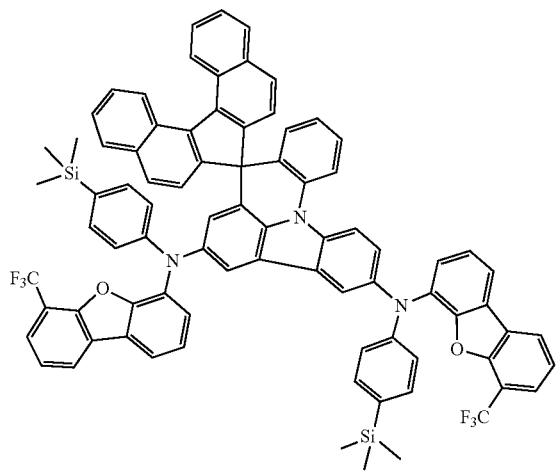
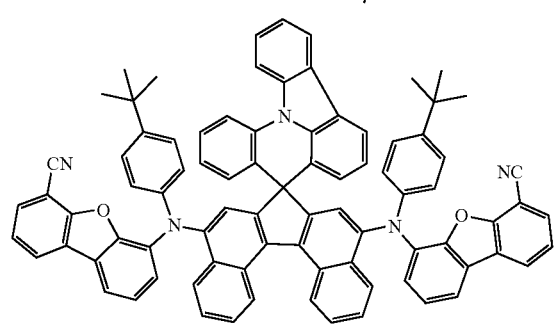
390
-continued
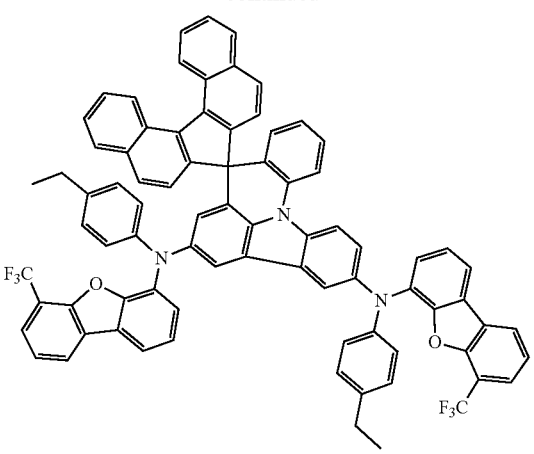
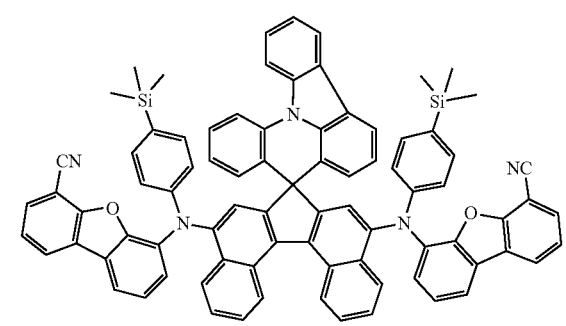
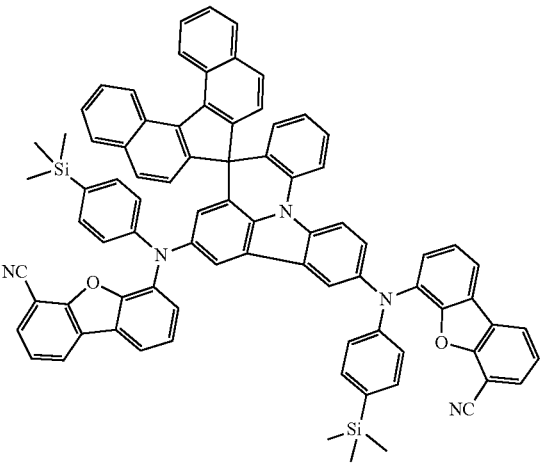
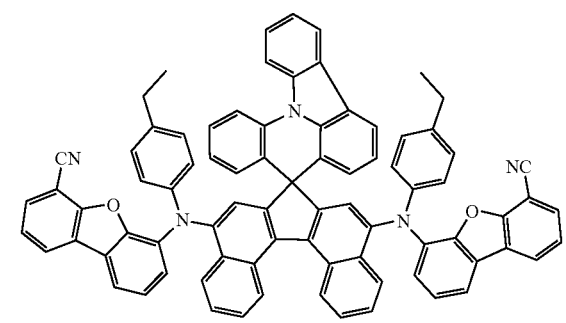

391
-continued

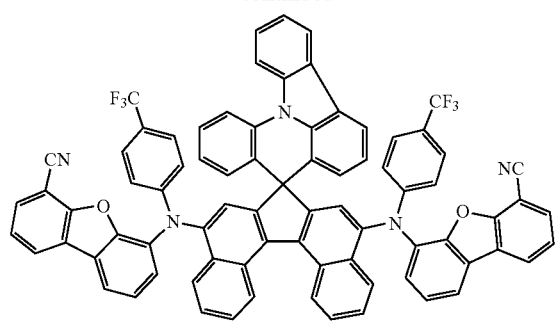

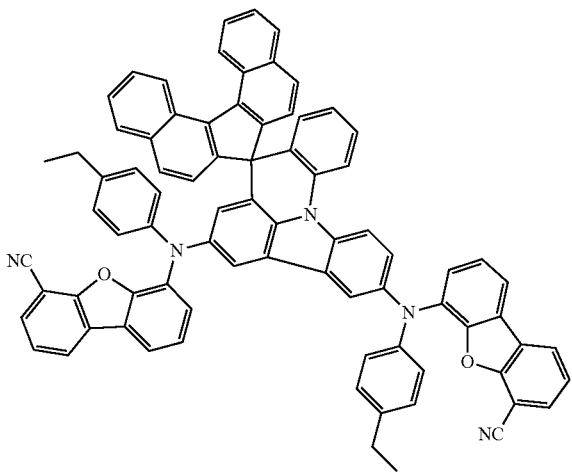

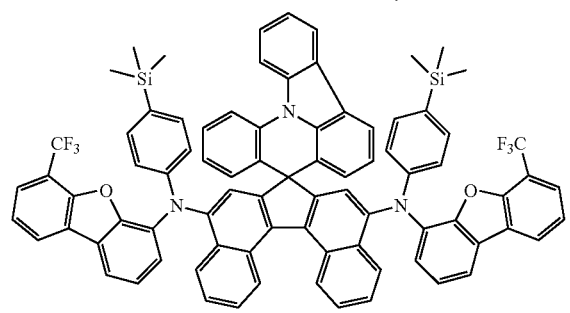

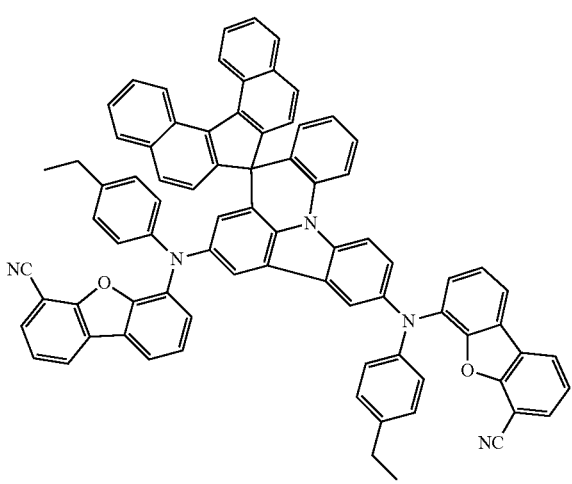

392
-continued

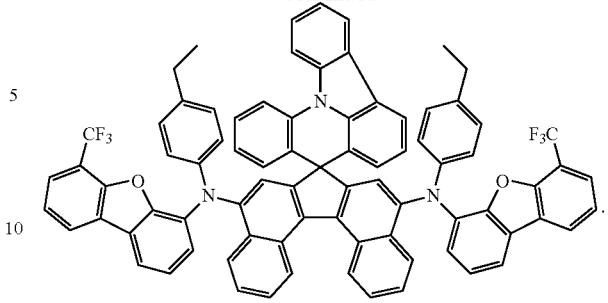

4. An organic electronic device comprising:
a first electrode;
a second electrode disposed to face the first electrode; and
an organic material layer having one or more layers disposed between the first electrode and the second electrode,
wherein one or more layers of the organic material layer comprise the compound of claim 1.

5. The organic electronic device of claim 4, wherein the organic material layer comprises a light emitting layer, and the light emitting layer comprises the compound.

6. The organic electronic device of claim 4, wherein the organic material layer comprises an electron injection layer, and the electron injection layer comprises the compound.

7. The organic electronic device of claim 4, wherein the organic material layer comprises an electron blocking layer, and the electron blocking layer comprises the compound.

8. The organic electronic device of claim 4, wherein the organic material layer comprises a hole injection layer, a hole transfer layer, or a layer carrying out hole injection and transfer at the same time, and the hole injection layer, the hole transfer layer, or the layer carrying out hole injection and transfer at the same time comprises the compound.

9. The organic electronic device of claim 4, further comprising one, two or more layers selected from the group consisting of a light emitting layer, a hole injection layer, a hole transfer layer, an electron injection layer and an electron blocking layer.

10. The organic electronic device of claim 4, which is selected from the group consisting of an organic light emitting device, an organic phosphorescent device, an organic solar cell, an organic photo conductor (OPC) and an organic transistor.

11. An organic electronic device comprising:
a first electrode;
a second electrode disposed to face the first electrode; and
an organic material layer having one or more layers disposed between the first electrode and the second electrode,
wherein one or more layers of the organic material layer comprise a compound represented by the following Chemical Formula 1,
wherein the organic material layer comprises a light emitting layer, and the light emitting layer comprises the compound as a dopant material and comprises a compound represented by the following Chemical Formula 9 as a host material:

[Chemical Formula 1]

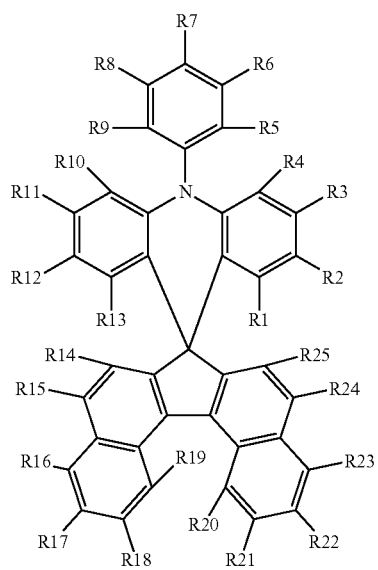

in Chemical Formula 1,
at least one of R1 to R25 is

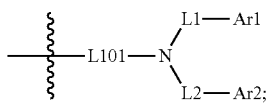

L101, L1, and L2 are the same as or different from each other, and each independently a direct bond; a substituted or unsubstituted arylene group; or a substituted or unsubstituted divalent heterocyclic group;

Ar1 and Ar2 are the same as or different from each other, and each independently hydrogen; deuterium; a halogen group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group;

groups that are not

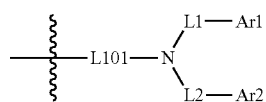

among R1 to R25 are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heterocyclic group, or bond to adjacent groups to form a substituted or unsubstituted ring; and

means a site bonding to other substituents or bonding sites,

[Chemical Formula 9]

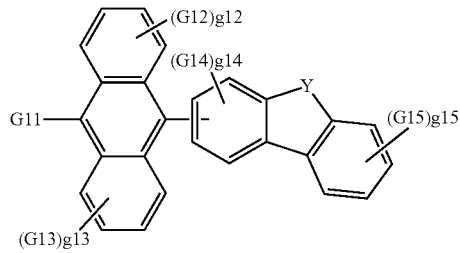

in Chemical Formula 9,

Y is O or S,

G11 is a substituted or unsubstituted aryl group,

G12 to G15 are the same as or different from each other, and each independently hydrogen; deuterium; a halogen group; a nitrile group; a nitro group; a hydroxyl group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted phosphine oxide group; a substituted or unsubstituted amine group; a substituted or unsubstituted aryl group; or a substituted or unsubstituted heterocyclic group, g12, g13 and g15 are each an integer of 1 to 4, g14 is an integer of 1 to 3, and when g12 to g15 are each 2 or greater, the two or more G12s to G15s are each the same as or different from each other.

12. The organic electronic device of claim 11, wherein the compound represented by Chemical Formula 9 is any one selected from the following compounds:

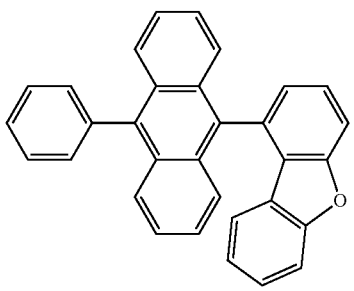

395
-continued
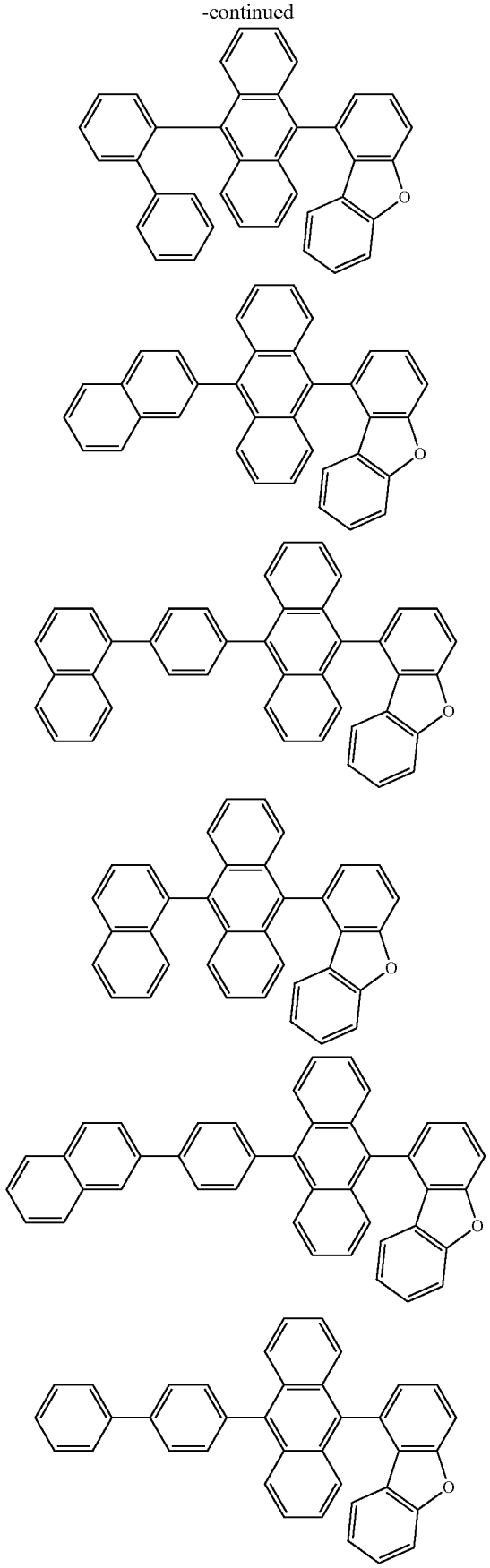
396
-continued
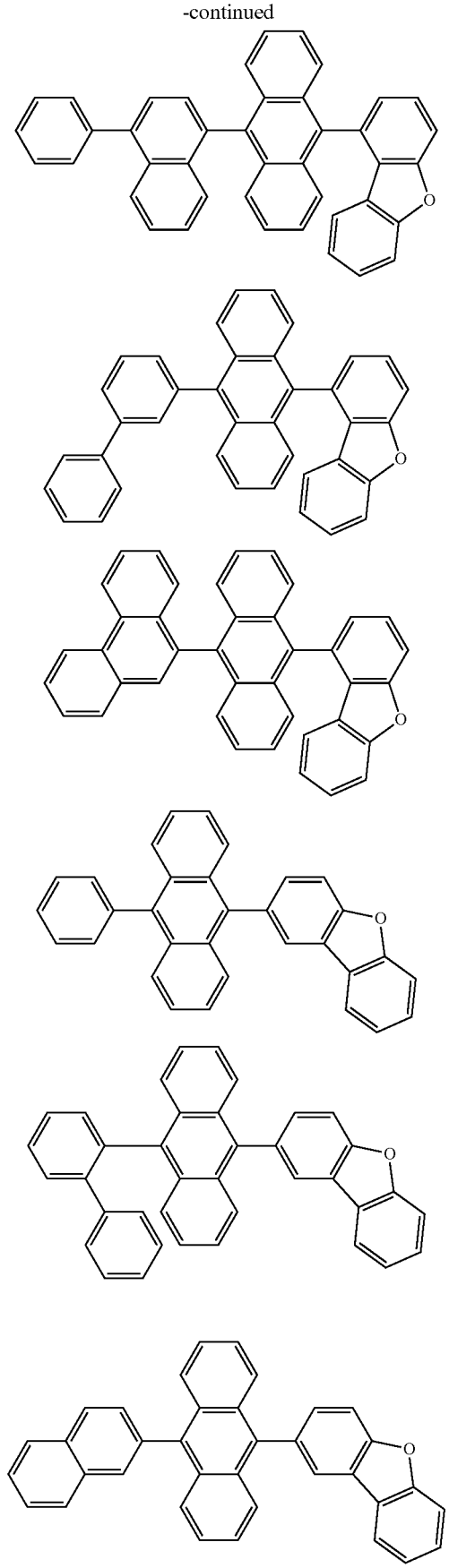

397
-continued
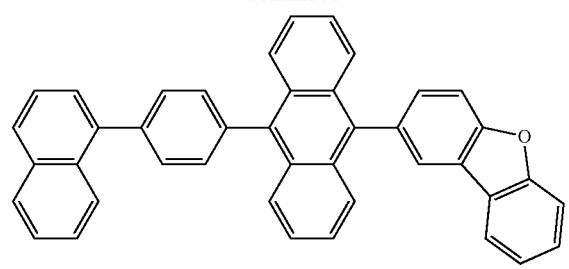
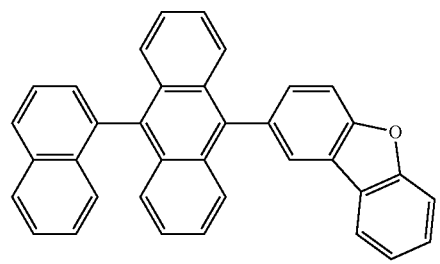
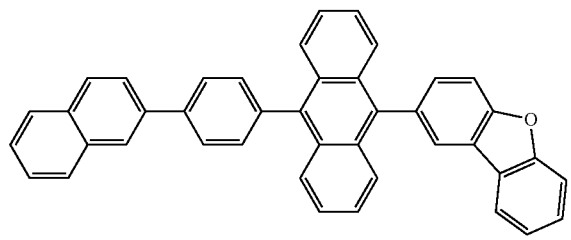
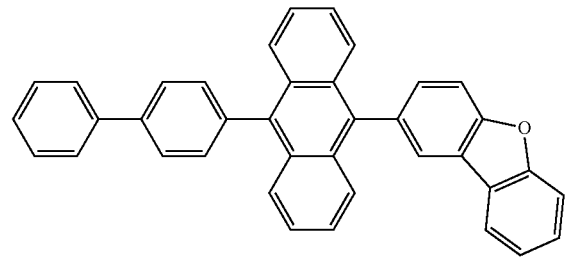
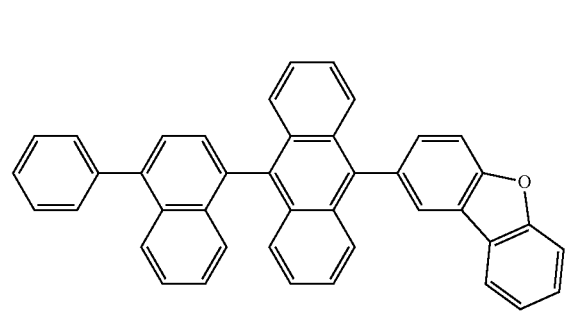
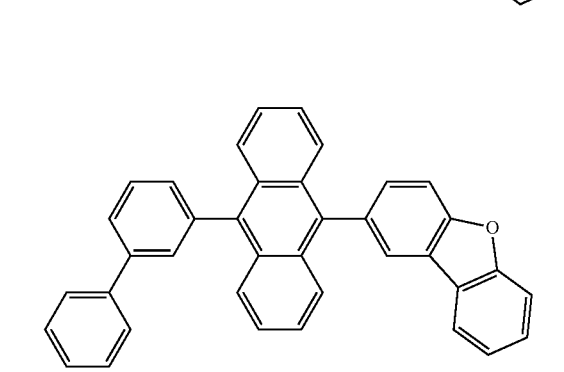
398
-continued
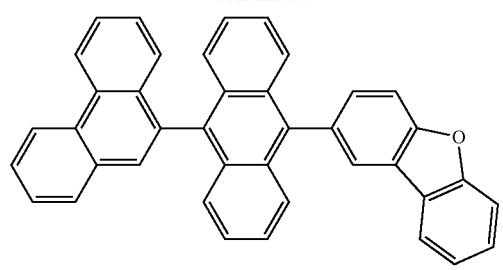
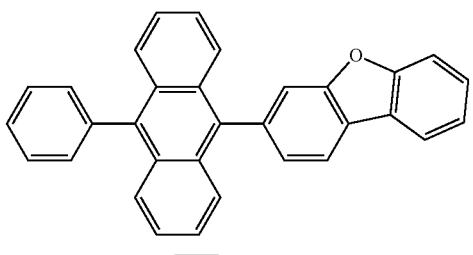
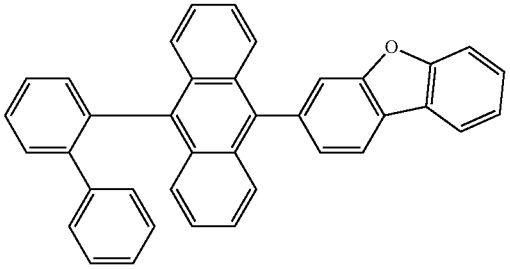
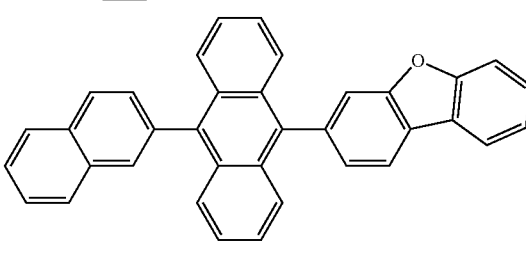
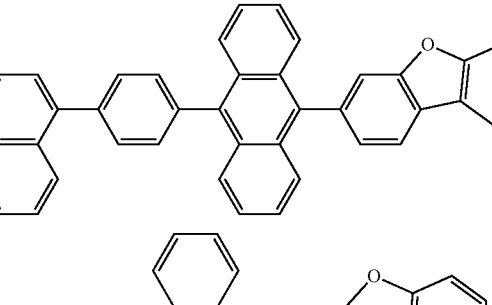
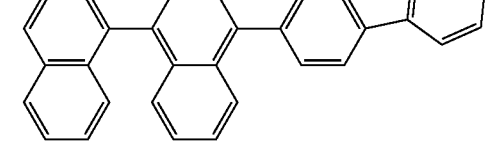
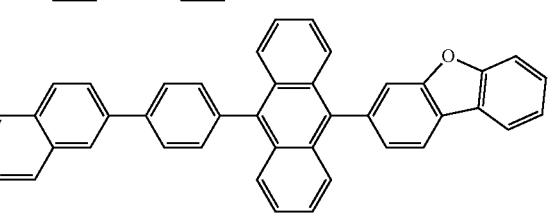

399
-continued
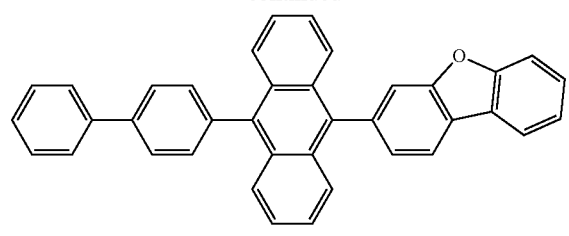
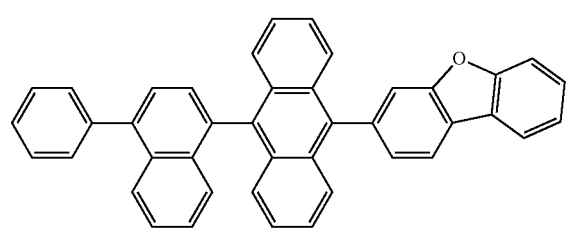
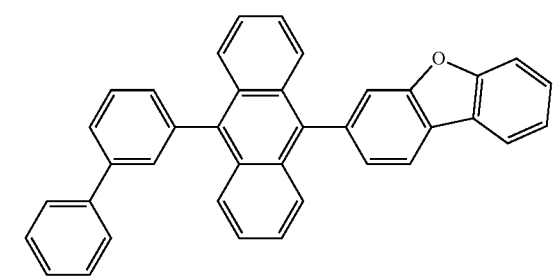
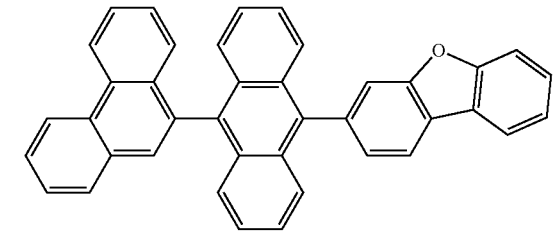
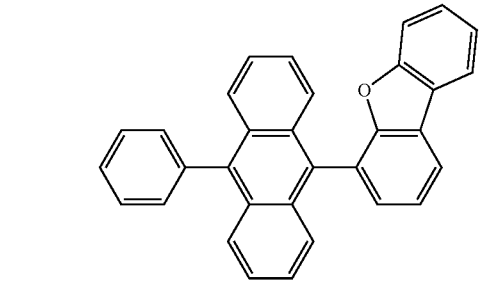
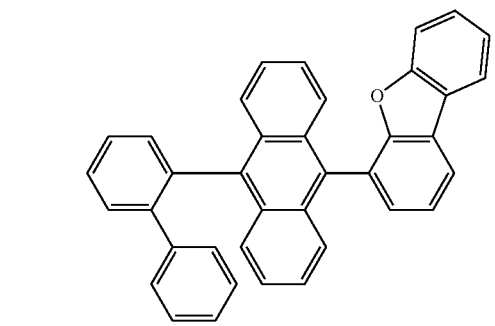
400
-continued
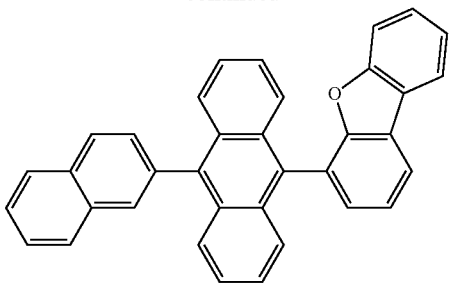
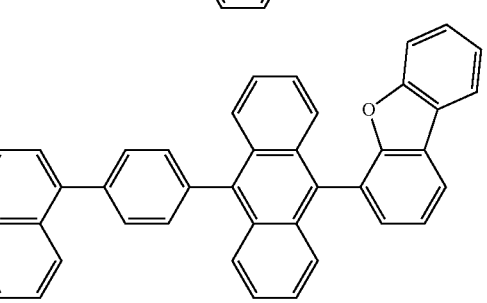
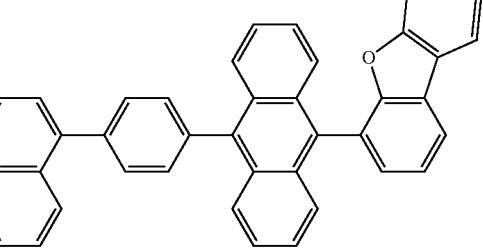
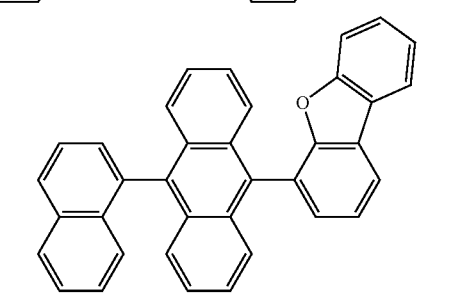
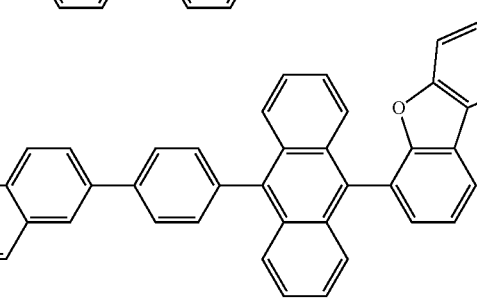
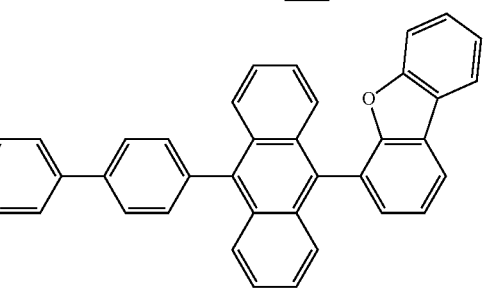
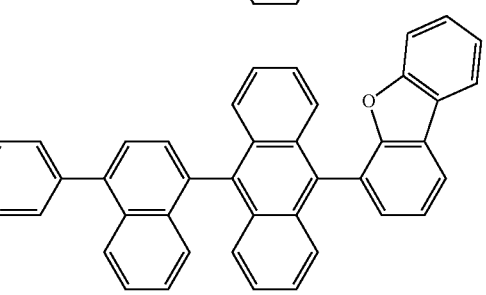

401
-continued
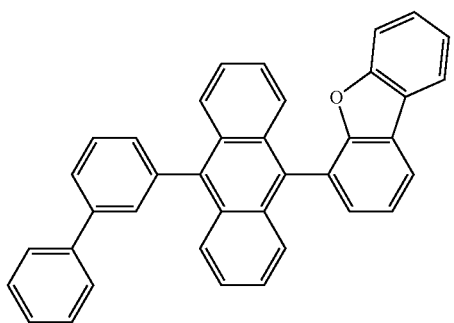
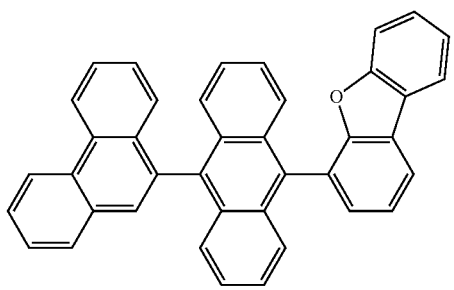
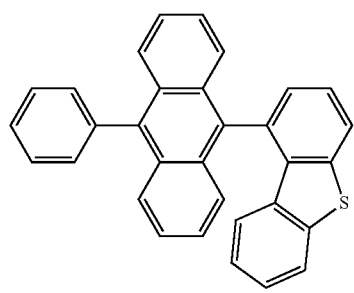
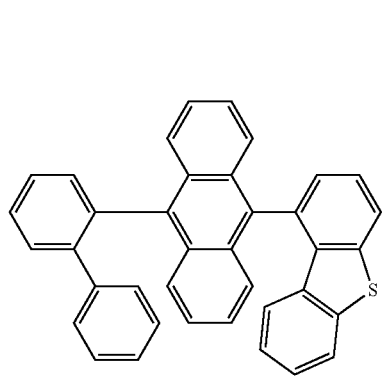
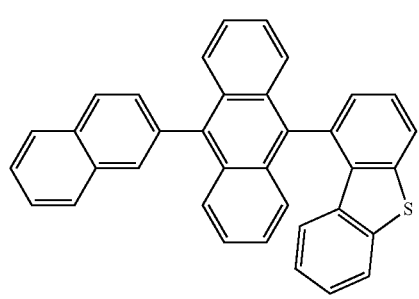
402
-continued
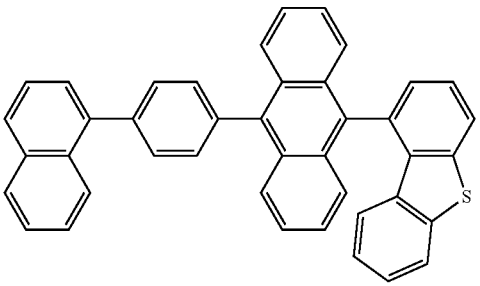
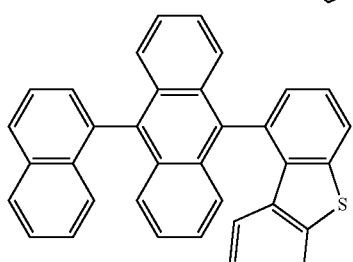
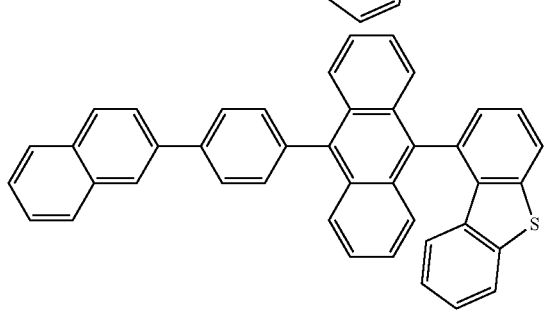
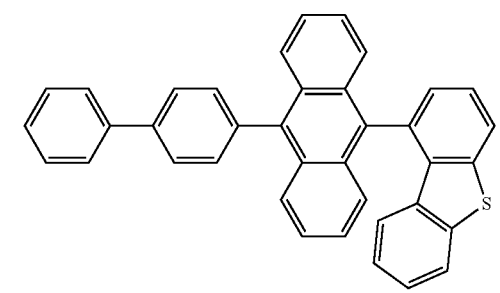
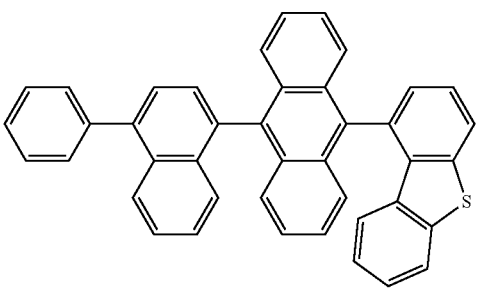
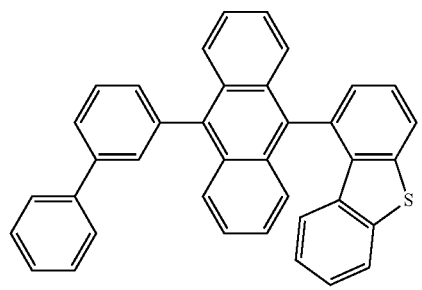

403
-continued
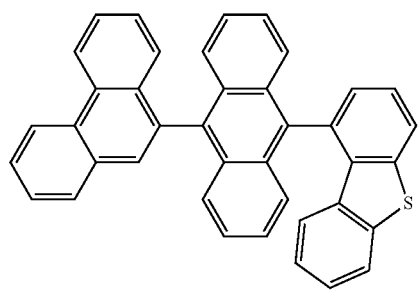
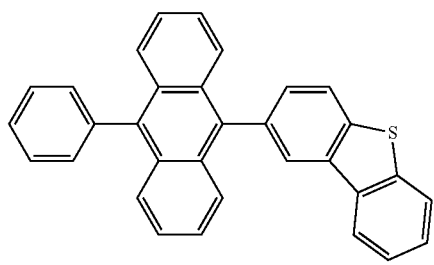
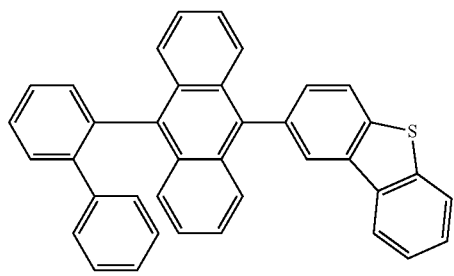
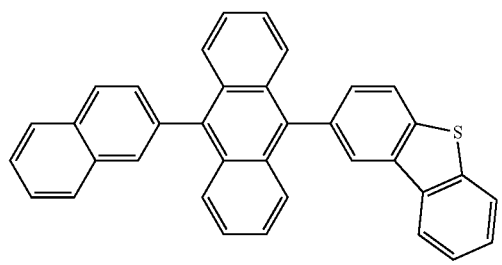
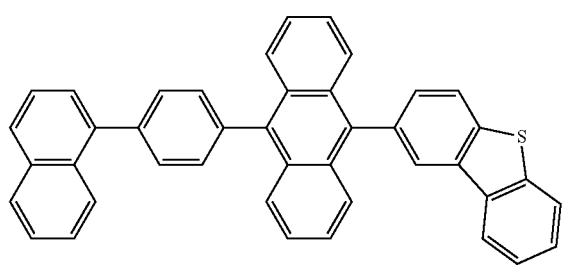
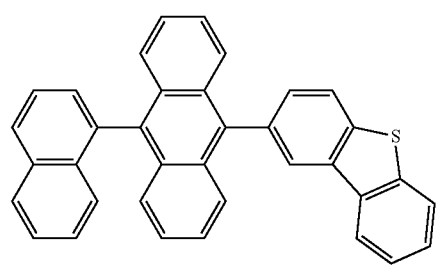
404
-continued
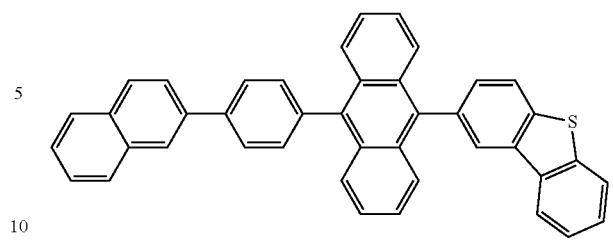
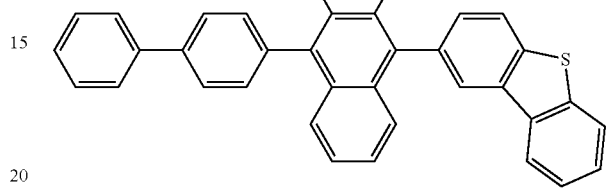
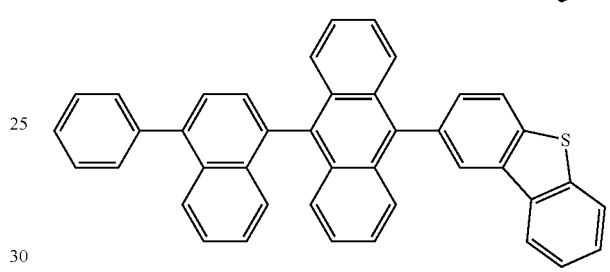
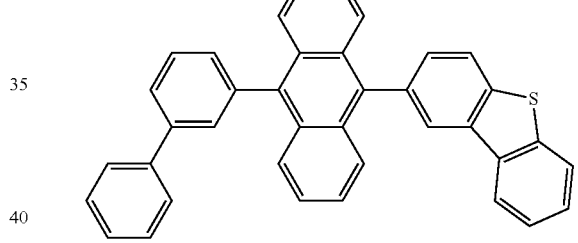
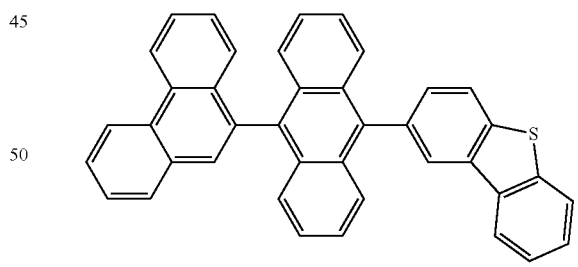
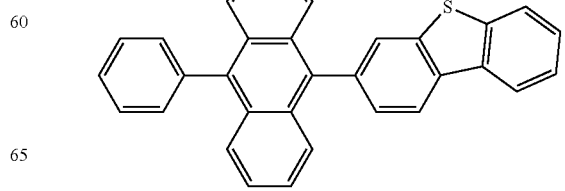

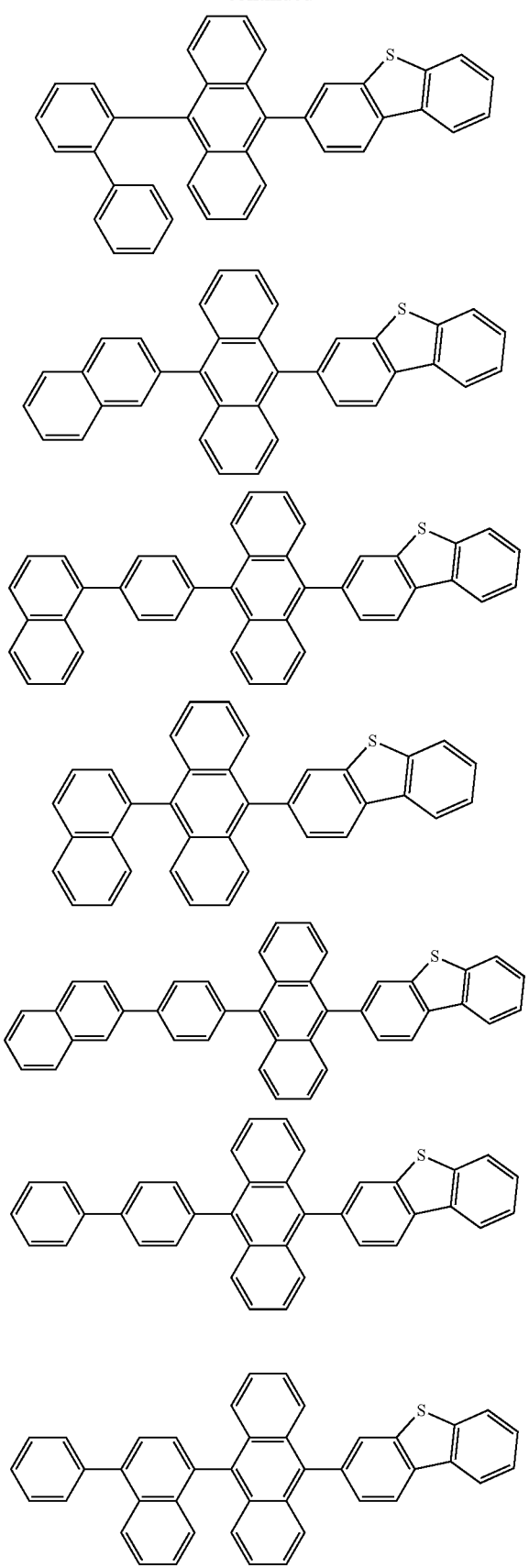

407
-continued
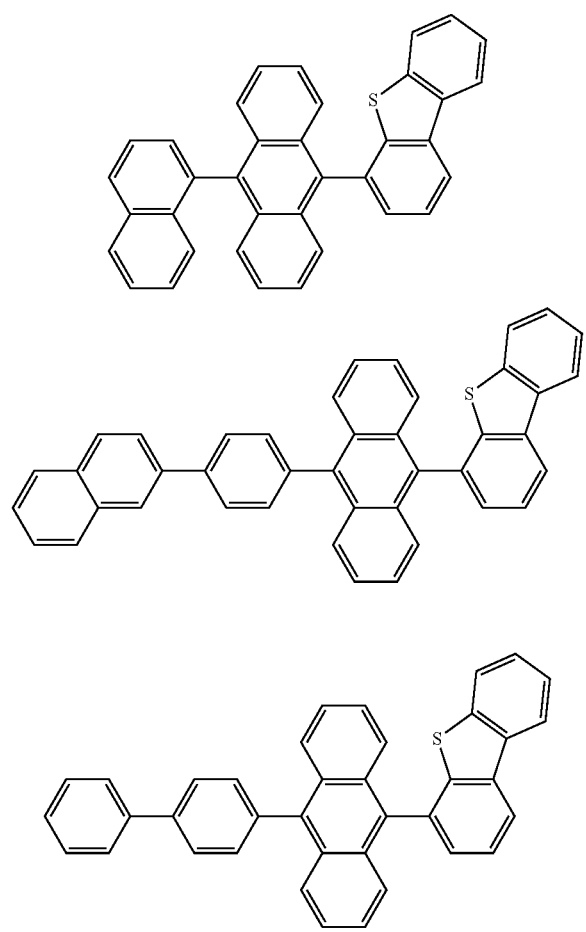
408
-continued
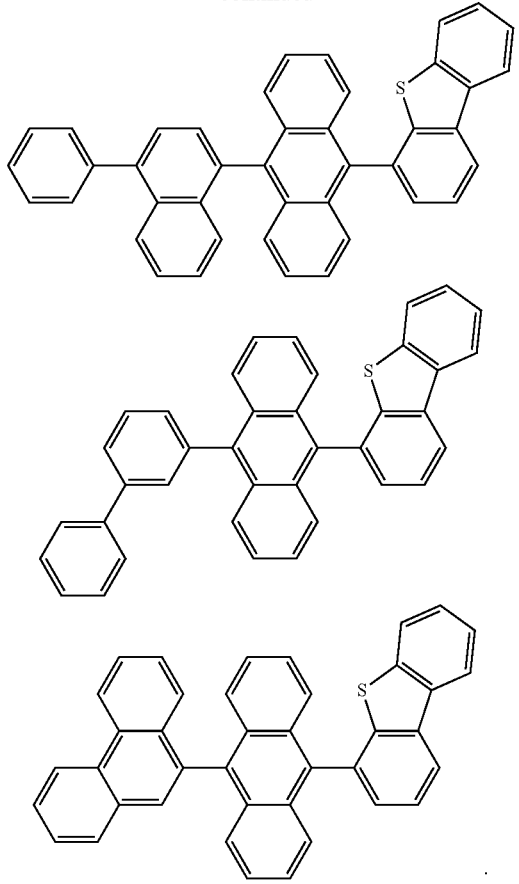
* * * * *